United States Patent
Jun et al.

(10) Patent No.: US 9,887,372 B2
(45) Date of Patent: Feb. 6, 2018

(54) AMINE-BASED COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Mieun Jun, Yongin-si (KR); Soobyung Ko, Yongin-si (KR); Haejin Kim, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 49 days.

(21) Appl. No.: 15/167,779

(22) Filed: May 27, 2016

(65) Prior Publication Data

US 2016/0365521 A1    Dec. 15, 2016

(30) Foreign Application Priority Data

Jun. 11, 2015 (KR) .................. 10-2015-0082568
Apr. 15, 2016 (KR) .................. 10-2016-0046496

(51) Int. Cl.

| C07C 13/48 | (2006.01) |
|---|---|
| C07D 401/00 | (2006.01) |
| C07F 7/00 | (2006.01) |
| C07F 7/08 | (2006.01) |
| H01L 51/00 | (2006.01) |
| H01L 27/32 | (2006.01) |
| C09K 11/06 | (2006.01) |
| H01L 51/50 | (2006.01) |

(52) U.S. Cl.
CPC ........ H01L 51/0094 (2013.01); C07F 7/0816 (2013.01); C09K 11/06 (2013.01); H01L 27/3211 (2013.01); H01L 51/006 (2013.01); H01L 51/0058 (2013.01); H01L 51/0059 (2013.01); H01L 51/0061 (2013.01); H01L 51/0073 (2013.01); C09K 2211/1007 (2013.01); C09K 2211/1011 (2013.01); C09K 2211/1014 (2013.01); C09K 2211/1088 (2013.01); C09K 2211/1096 (2013.01); H01L 51/5012 (2013.01); H01L 51/5056 (2013.01)

(58) Field of Classification Search
CPC .... C09K 2211/1007; C09K 2211/1011; C09K 2211/1088; C09K 2211/1104; C09K 2211/1096
See application file for complete search history.

(56) References Cited

U.S. PATENT DOCUMENTS

| 7,053,255 B2 | 5/2006 | Ikeda et al. |
|---|---|---|
| 7,233,019 B2 | 6/2007 | Ionkin et al. |
| 2005/0064233 A1* | 3/2005 | Matsuura .............. C07C 13/567 428/690 |
| 2006/0052641 A1* | 3/2006 | Funahashi ............. C09K 11/06 564/426 |
| 2008/0100208 A1* | 5/2008 | Shin ....................... C07C 13/62 313/504 |
| 2011/0006289 A1 | 1/2011 | Mizuki et al. |

FOREIGN PATENT DOCUMENTS

| KR | 10-2005-0086518 A | 8/2005 |
|---|---|---|
| KR | 10-2006-0006760 A | 1/2006 |
| KR | 10-2008-0039763 A | 5/2008 |
| KR | 10-2009-0111355 A | 10/2009 |
| KR | 10-2010-0097182 A | 9/2010 |
| KR | 10-2012-0116837 A | 10/2012 |
| KR | 10-2012-0116881 | * 10/2012 |
| KR | 10-2012-0116881 A | 10/2012 |
| KR | 10-2014-0143672 A | 12/2014 |

* cited by examiner

*Primary Examiner* — Robert Harlan
(74) *Attorney, Agent, or Firm* — Lewis Rocca Rothgerber Christie LLP

(57) ABSTRACT

According to one or more embodiments, an organic light-emitting device may include: a first electrode; a second electrode facing the first electrode, and an organic layer between the first electrode and the second electrode, the organic layer including an emission layer, wherein the organic layer includes an amine-based compound represented by Formula 1:

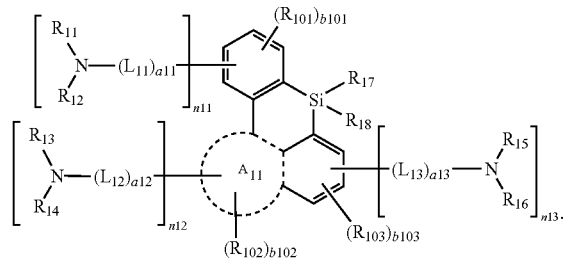

Formula 1

20 Claims, 3 Drawing Sheets

AMINE-BASED COMPOUND AND ORGANIC LIGHT-EMITTING DEVICE INCLUDING THE SAME

CROSS-REFERENCE TO RELATED APPLICATIONS

This application claims priority to and the benefits of Korean Patent Application No. 10-2015-0082568, filed on Jun. 11, 2015, in the Korean Intellectual Property Office, and Korean Patent Application No. 10-2016-0046496, filed on Apr. 15, 2016, in the Korean Intellectual Property Office, the disclosures of both of which are incorporated herein in their entireties by reference.

BACKGROUND

1. Field

One or more embodiments of the present disclosure relate to an amine-based compound and an organic light-emitting device including the same.

2. Description of the Related Art

Organic light-emitting devices are self-emission devices that have wide viewing angles, high contrast ratios, short response times, and/or excellent brightness, driving voltage, and/or response speed characteristics, and may produce full-color images.

For example, an organic light-emitting device may include a first electrode on a substrate, and a hole transport region, an emission layer, an electron transport region, and a second electrode, which are sequentially positioned on the first electrode. Holes provided from the first electrode may move toward the emission layer through the hole transport region, and electrons provided from the second electrode may move toward the emission layer through the electron transport region. Carriers, such as holes and electrons, may then recombine in the emission layer to produce excitons. These excitons may transition from an excited state to a ground state, to thereby generate light.

SUMMARY

An aspect according to one or more embodiments of the present disclosure is directed toward an amine-based compound and an organic light-emitting device including the same.

Additional aspects will be set forth in part in the description which follows and, in part, will be apparent from the description, or may be learned by practice of the presented embodiments.

According to one or more embodiments, an amine-based compound is represented by Formula 1:

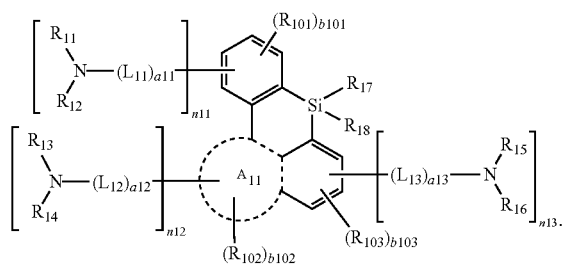

Formula 1

In Formula 1, $A_{11}$ may be selected from a $C_6$-$C_{20}$ carbocyclic group and a $C_1$-$C_{20}$ heterocyclic group, $L_{11}$ to $L_{13}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 to a13 may each independently be selected from 0, 1, 2, 3, 4, and 5, $R_{11}$ to $R_{16}$ may each independently be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, n11 to n13 may each independently be selected from 0, 1, and 2, wherein a sum of n11 to n13 may be selected from 1, 2, 3, 4, 5, and 6, $R_{17}$, $R_{18}$, and $R_{101}$ to $R_{103}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b101 and b103 may each independently be selected from 1, 2, 3, and 4, b102 may be selected from 1, 2, 3, 4, 5, 6, 7, and 8, and $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

According to one or more embodiments, an organic light-emitting device may include: a first electrode; a second electrode facing the first electrode, and an organic layer between the first electrode and the second electrode, the organic layer including an emission layer, wherein the organic layer includes the amine-based compound of Formula 1.

According to one or more embodiments, an organic light-emitting device may include: a substrate divided into and defined by a first sub-pixel region, a second sub-pixel region, and a third sub-pixel region; a plurality of first electrodes respectively patterned according to the first sub-pixel region, the second sub-pixel region, and the third sub-pixel region; a second electrode facing the plurality of first electrodes; and an organic layer between each of the plurality of first electrodes and the second electrode, the organic layer including an emission layer, wherein the organic layer includes the amine-based compound of Formula 1.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
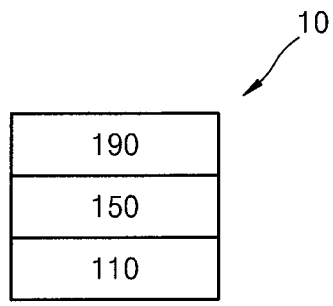
FIG. 1 is a schematic view of a structure of an organic light-emitting device according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments of the present disclosure are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As the inventive concept allows for various changes and numerous embodiments, particular embodiments will be illustrated in the drawings and described in more detail in the written description. Effects, features, and a method of achieving the inventive concept will be obvious by referring to exemplary embodiments of the inventive concept with reference to the accompanying drawings. The inventive concept may, however, be embodied in many different forms and should not be construed as being limited to the embodiments set forth herein.

Hereinafter, the inventive concept will be described in more detail by explaining exemplary embodiments of the inventive concept with reference to the accompanying drawings. Like reference numerals in the drawings denote like elements, and thus their description will not be repeated.

In the embodiments described in the present specification, an expression used in the singular encompasses the expression of the plural, unless it has a clearly different meaning in the context.

In the present specification, it is to be understood that the terms such as "including," "having," and/or "comprising" are intended to indicate the presence of the stated features or components, and are not intended to preclude the presence or addition of one or more other features or components.

It will be understood that when a layer, region, or component is referred to as being "on" or "onto" another layer, region, or component, it may be directly or indirectly formed on the other layer, region, or component. That is, for example, intervening layer(s), region(s), or component(s) may be present.

Sizes of components in the drawings may be exaggerated for convenience of explanation. In other words, since sizes and thicknesses of components in the drawings are arbitrarily illustrated for convenience of explanation, the following embodiments of the present disclosure are not limited thereto.

The expression that "(an organic layer) includes an amine-based compound" used herein may include a case in which "(an organic layer) includes one amine-based compound represented by Formula 1" and a case in which "(an organic layer) includes two or more different amine-based compounds represented by Formula 1".

The term "organic layer" used herein may refer to a single layer and/or a plurality of layers between the first electrode and the second electrode of an organic light-emitting device. The "organic layer" may include, in addition to an organic compound, a metal-containing organometallic complex.

The amine-based compound may be represented by Formula 1:

Formula 1

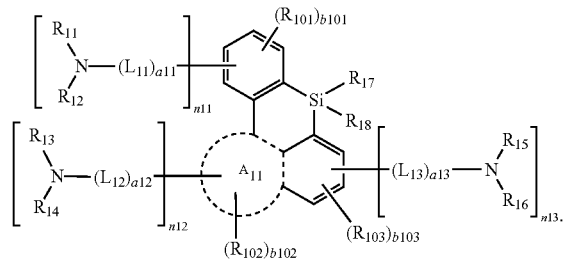

In Formula 1, $A_{11}$ may be selected from a $C_6$-$C_{20}$ carbocyclic group and a $C_1$-$C_{20}$ heterocyclic group. In Formula 1, $A_{11}$ may be a ring condensed through a 6-membered ring therebetween. In Formula 1, a bond shared between $A_{11}$ and the 6-membered ring may be a single bond or a double bond.

For example, $A_{11}$ in Formula 1 may be selected from a $C_6$-$C_{15}$ carbocyclic group and a $C_1$-$C_{15}$ heterocyclic group, but embodiments of the present disclosure are not limited thereto.

In various embodiments, in Formula 1, $A_{11}$ may be selected from a benzene group, a naphthalene group, a fluorene group, a phenanthrene group, an anthracene group, a triphenylene group, a pyrene group, a chrysene group, a furan group, a thiophene group, a pyridine group, a pyrazine group, a pyrimidine group, a pyridazine group, a quinoline group, an isoquinoline group, a quinoxaline group, a quinazoline group, a benzofuran group, a benzothiophene group, a dibenzofuran group, and a dibenzothiophene group, but embodiments of the present disclosure are not limited thereto.

In various embodiments, $A_{11}$ in Formula 1 may be selected from a benzene group, a naphthalene group, a phenanthrene group, an anthracene group, a triphenylene group, a pyrene group, and a chrysene group, but embodiments of the present disclosure are not limited thereto.

In various embodiments, $A_{11}$ in Formula 1 may be selected from a benzene group, a naphthalene group, and a phenanthrene group, but embodiments of the present disclosure are not limited thereto.

In various embodiments, $A_{11}$ in Formula 1 may be selected from groups represented by Formulae 9-1 to 9-4, but embodiments of the present disclosure are not limited thereto:

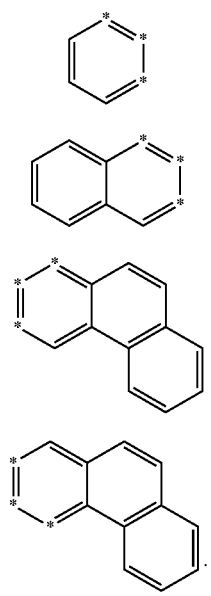

9-1

9-2

9-3

9-4

In Formulae 9-1 to 9-4,
* indicates the carbon atom of Formula 1.

In Formula 1, $L_{11}$ to $L_{13}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, in Formula 1, $L_{11}$ to $L_{13}$ may each independently be selected from the group consisting of:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but embodiments of the present disclosure are not limited thereto.

In various embodiments, in Formula 1, $L_{11}$ to $L_{13}$ may each independently be selected from the group consisting of:

a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group; and a phenylene group, a naphthylene group, a fluorenylene group, a phenanthrenylene group, an anthracenylene group, a triphenylenylene group, a pyrrolylene group, a thiophenylene group, a furanylene group, a pyridinylene group, a pyrazinylene group, a pyrimidinylene group, an indolylene group, a quinolinylene group, an isoquinolinylene group, a benzoquinolinylene group, a naphthyridinylene group, a quinoxalinylene group, a quinazolinylene group, a cinnolinylene group, a carbazolylene group, a phenanthridinylene group, a benzimidazolylene group, a benzofuranylene group, a benzothiophenylene group, a triazolylene group, a dibenzofuranylene group, and a dibenzothiophenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

In various embodiments, in Formula 1, $L_{11}$ to $L_{13}$ may each independently be a group selected from groups represented by Formulae 3-1 to 3-43, but embodiments of the present disclosure are not limited thereto:

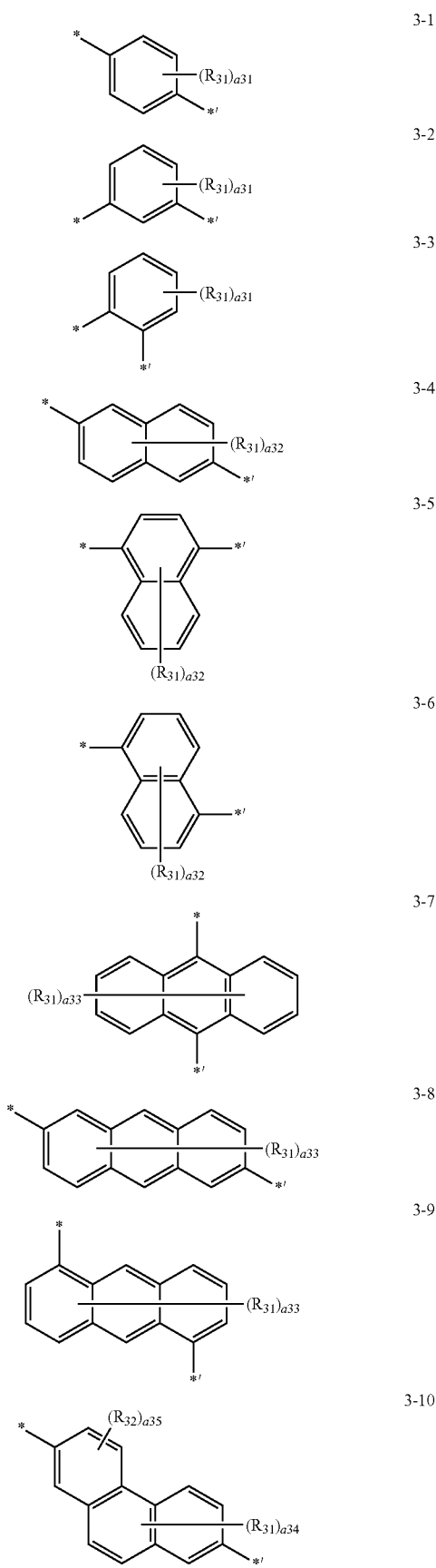

-continued
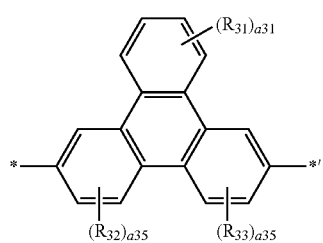
3-11
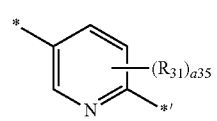
3-12
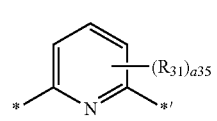
3-13
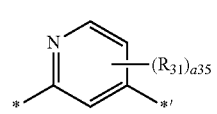
3-14
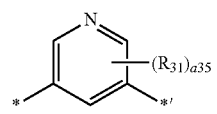
3-15
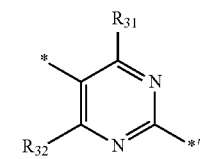
3-16
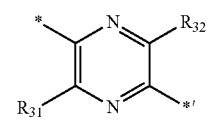
3-17
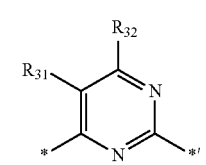
3-18
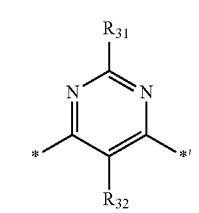
3-19
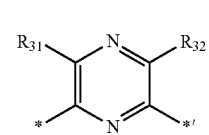
3-20
-continued
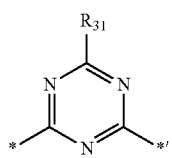
3-21
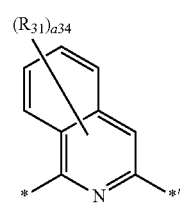
3-22
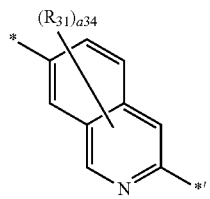
3-23
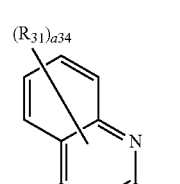
3-24
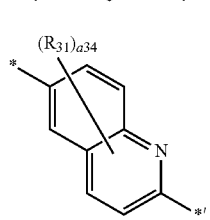
3-25
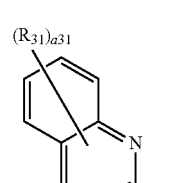
3-26
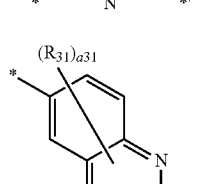
3-27
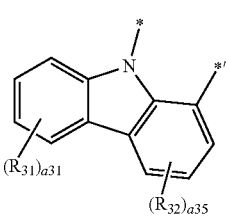
3-28

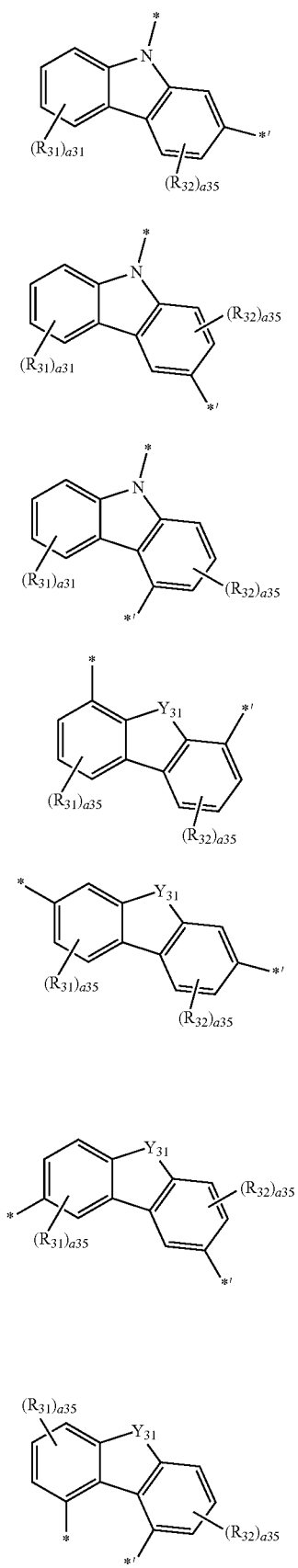
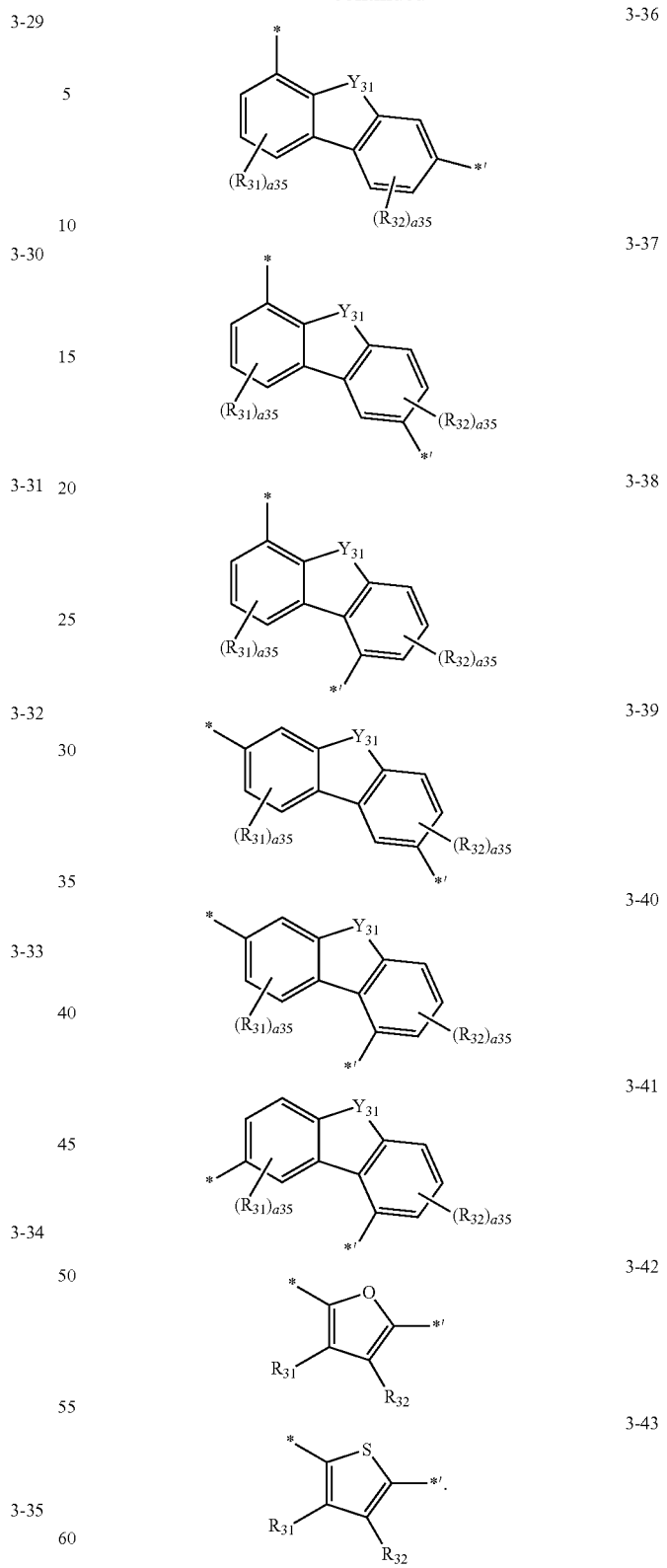
In Formulae 3-1 to 3-43,
Y$_{31}$ may be selected from C(R$_{33}$)(R$_{34}$), N(R$_{33}$), oxygen (O), and sulfur (S),
R$_{31}$ to R$_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzo-fluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a31 may be selected from 1, 2, 3, and 4, a32 may be selected from 1, 2, 3, 4, 5, and 6, a33 may be selected from 1, 2, 3, 4, 5, 6, 7, and 8, a34 may be selected from 1, 2, 3, 4, and 5, a35 may be selected from 1, 2, and 3, and

* and *' may each independently indicate a binding site to a neighboring atom.

In various embodiments, in Formula 1, $L_{11}$ to $L_{13}$ may each independently be a group selected from groups represented by Formulae 3-1 to 3-43, and $Y_{31}$ may be selected from $C(R_{33})(R_{34})$, $N(R_{33})$, O, and S, wherein $R_{31}$ to $R_{34}$ may each independently be selected from hydrogen, deuterium, —F, —Cl, —Br, —I, a methyl group, an ethyl group, a tert-butyl group, a methoxy group, an ethoxy group, a tert-butoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

In various embodiments, in Formula 1, $L_{11}$ to $L_{13}$ may each independently be a group selected from groups represented by Formulae 4-1 to 4-56, but embodiments of the present disclosure are not limited thereto:

4-1

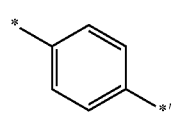

4-2

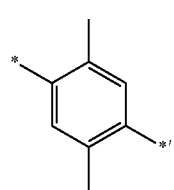

4-3

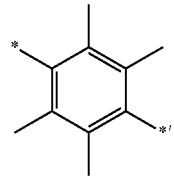

-continued 4-4

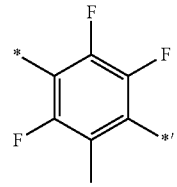

4-5

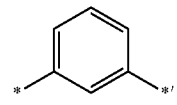

4-6

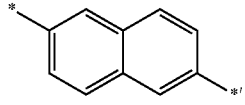

4-7

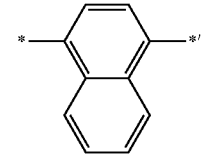

4-8

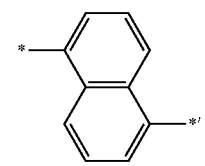

4-9

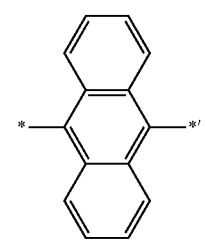

4-10

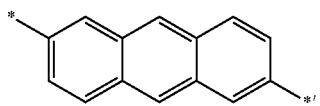

4-11

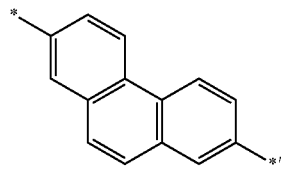

4-12

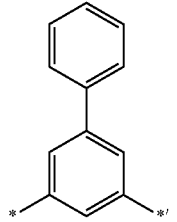

-continued 4-13

4-14

4-15

4-16

4-17

4-18

4-19

4-20

4-21

4-22

4-23

-continued 4-24

4-25

4-26

4-27

4-28

4-29

4-30

4-31

4-32

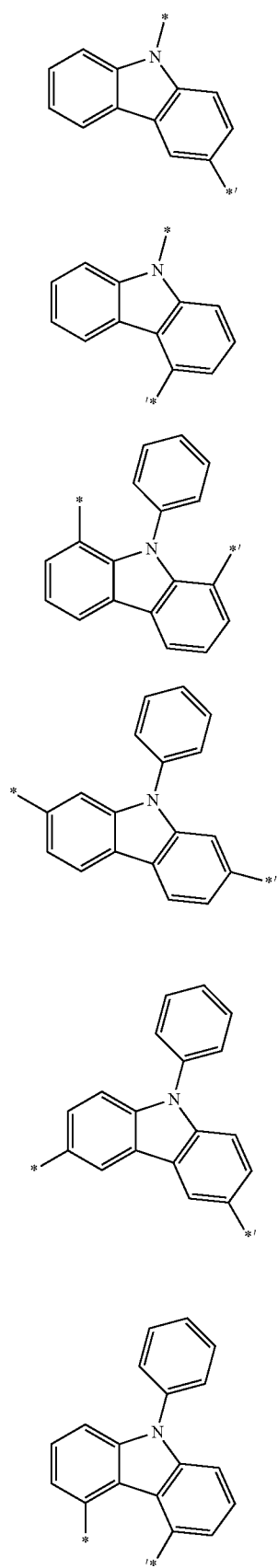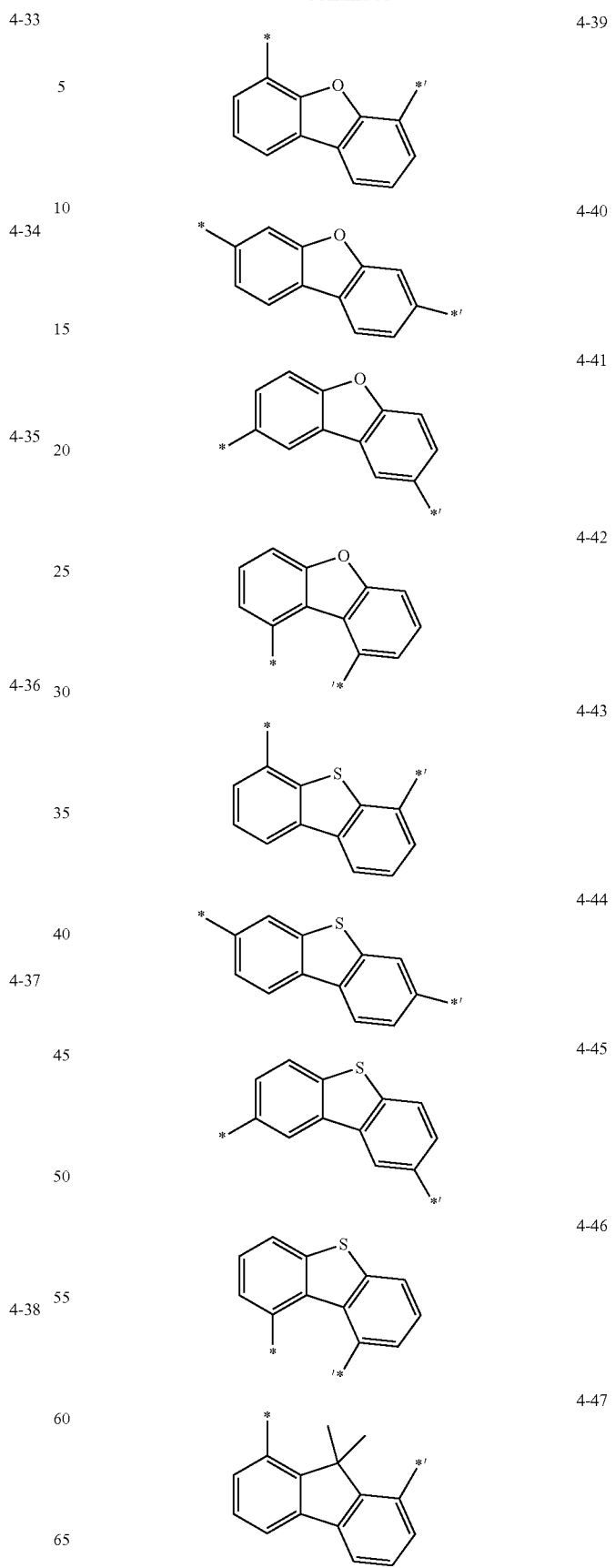

-continued 4-48
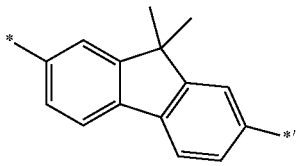

4-49
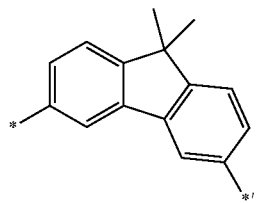

4-50
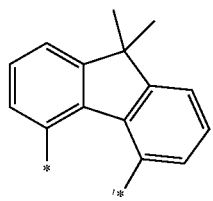

4-51
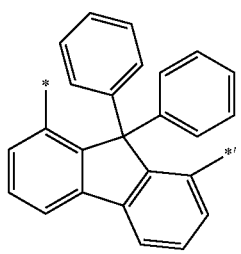

4-52
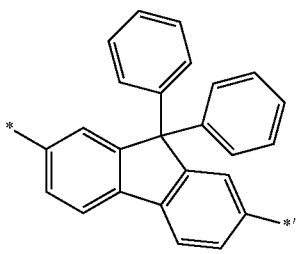

4-53
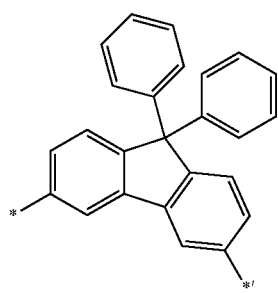

-continued 4-54

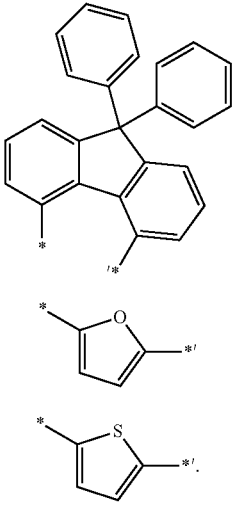

4-55

4-56

In Formulae 4-1 to 4-56,

* and *' may each independently indicate a binding site to a neighboring atom.

In Formula 1, a11 indicates the number of $L_{11}$(s), and may be selected from 0, 1, 2, 3, 4, and 5. When a11 is 0, $(L_{11})_{a11}$ is a single bond, and when a11 is 2 or more, 2 or more $L_{11}$(s) may be identical to or different from each other.

In Formula 1, a12 indicates the number of $L_{12}$(s), and may be selected from 0, 1, 2, 3, 4, and 5. When a12 is 0, $(L_{12})_{a12}$ is a single bond, and when a12 is 2 or more, 2 or more $L_{12}$(s) may be identical to or different from each other.

In Formula 1, a13 indicates the number of $L_{13}$(s), and may be selected from 0, 1, 2, 3, 4, and 5. When a13 is 0, $(L_{13})_{a13}$ is a single bond, and when a13 is 2 or more, 2 or more $L_{13}$(s) may be identical to or different from each other.

For example, in Formula 1, a11 to a13 may each independently be selected from 0, 1, and 2, but embodiments of the present disclosure are not limited thereto.

In various embodiments, in Formula 1, the sum of a11 to a13 may be selected from 0, 1, and 2, but embodiments of the present disclosure are not limited thereto.

In Formula 1, $R_{11}$ to $R_{16}$ may each independently be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 1, $R_{11}$ to $R_{16}$ may each independently be selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), and —B($Q_{31}$)($Q_{32}$); and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with a $C_1$-$C_{20}$ alkyl group that is substituted with at least one selected from deuterium, —F, —Cl, —Br, —I, a cyano group, and a nitro group, wherein $Q_{31}$ to $Q_{33}$ may each independently be selected from a $C_1$-$C_{60}$ alkyl group, a $C_6$-$C_{60}$ aryl group, a biphenyl group, and a terphenyl group, but embodiments of the present disclosure are not limited thereto.

In various embodiments, in Formula 1, $R_{11}$ to $R_{16}$ may each independently be selected from the group consisting of:

a phenyl group, a biphenyl group, a terphenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group;

a phenyl group, a biphenyl group, a terphenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, a dibenzosilolyl group, and —Si($Q_{31}$)($Q_{32}$)($Q_{33}$); and a phenyl group, a biphenyl group, a terphenyl group, a naphthyl group, a fluorenyl group, a phenanthrenyl group, an anthracenyl group, a triphenylenyl group, a pyrrolyl group, a thiophenyl group, a furanyl group, a pyridinyl group, a pyrazinyl group, a pyrimidinyl group, a quinolinyl group, an isoquinolinyl group, a carbazolyl group, a naphthyridinyl group, a quinoxalinyl group, a quinazolinyl group, a cinnolinyl group, a phenanthridinyl group, an acridinyl group, a phenanthrolinyl group, a phenazinyl group, a benzofuranyl group, a benzothiophenyl group, a triazinyl group, a dibenzofuranyl group, a dibenzothiophenyl group, and a dibenzosilolyl group, each substituted with a $C_1$-$C_{20}$ alkyl group that is substituted with at least one selected from deuterium, —F, —Cl, —Br, —I, a cyano group and a nitro group, wherein $Q_{31}$ to $Q_{33}$ may each independently be selected from a $C_1$-$C_{20}$ alkyl group, a $C_6$-$C_{60}$ aryl group, a biphenyl group, and a terphenyl group, but embodiments of the present disclosure are not limited thereto.

In various embodiments, in Formula 1, $R_{11}$ to $R_{16}$ may each independently be selected from the group consisting of:

a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, and a dibenzosilolyl group; and a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, —$CD_3$, —$CF_3$, a $C_1$-$C_{20}$ alkoxy group, a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, a dibenzosilolyl group, and —Si($Q_{31}$)($Q_{32}$)($Q_{33}$), wherein $Q_{31}$ to $Q_{33}$ may each independently be selected from a methyl group, an ethyl group, a tert-butyl group, a phenyl group, a biphenyl group, a terphenyl group, and a naphthyl group, but embodiments of the present disclosure are not limited thereto.

In various embodiments, in Formula 1, $R_{11}$ to $R_{16}$ may each independently be a group selected from groups represented by Formulae 5-1 to 5-32, but embodiments of the present disclosure are not limited thereto:

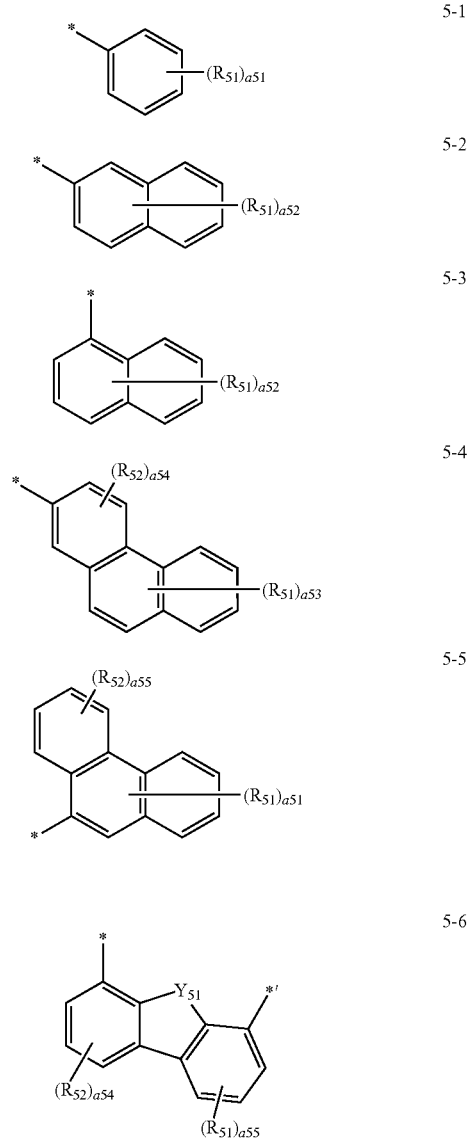

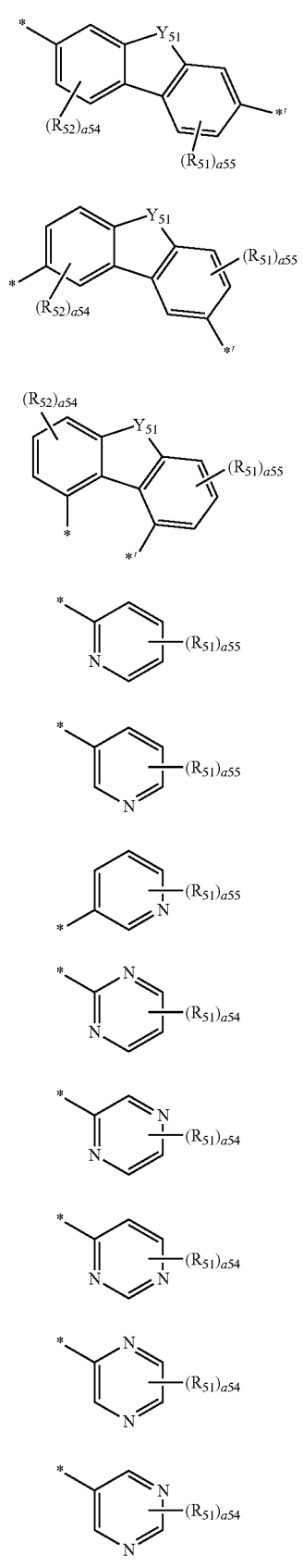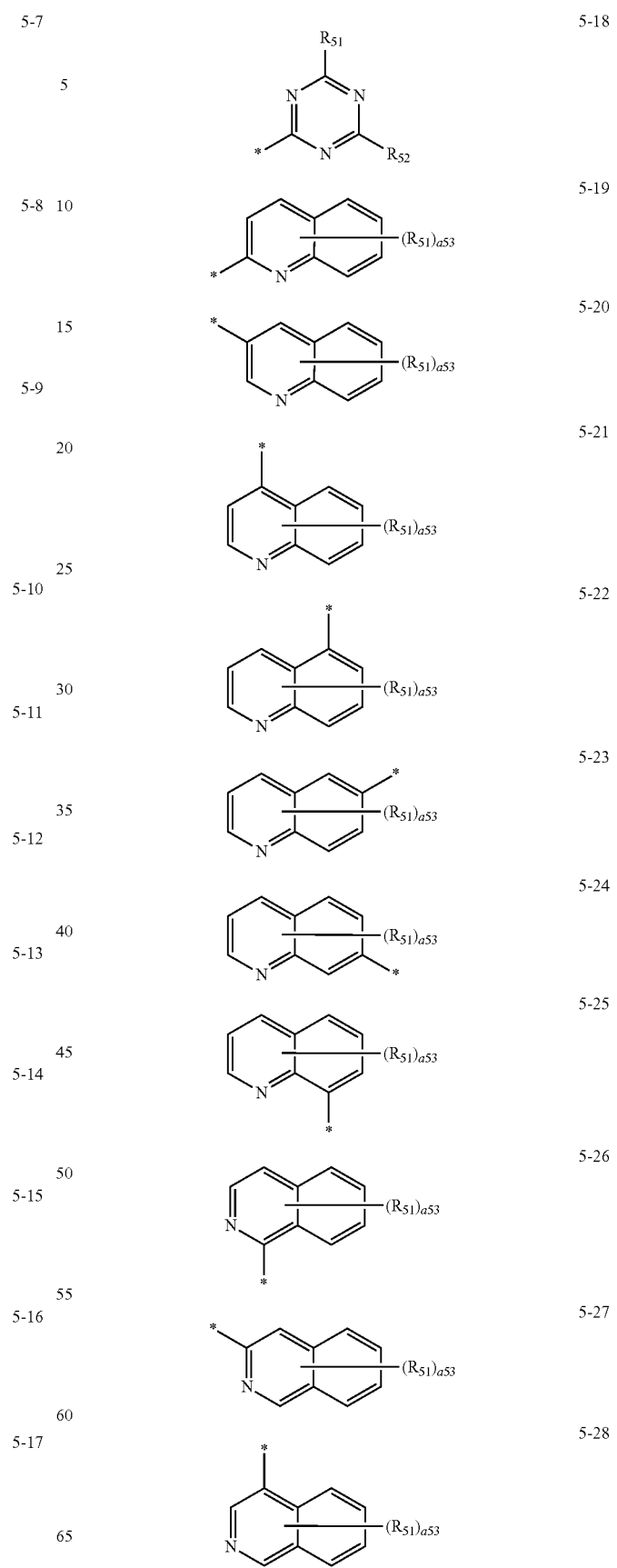

-continued

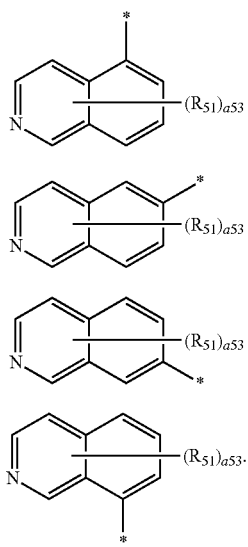

5-29
5-30
5-31
5-32

In Formulae 5-1 to 5-32, $Y_{51}$ may be selected from $C(R_{53})(R_{54})$, $Si(R_{53})(R_{54})$, $N(R_{53})$, O, and S, and $R_{51}$ to $R_{54}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, —$CD_3$, —$CF_3$, a $C_1$-$C_{20}$ alkoxy group, a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, a dibenzosilolyl group, and —$Si(Q_{31})(Q_{32})(Q_{33})$, wherein $Q_{31}$ to $Q_{33}$ may each independently be selected from a methyl group, an ethyl group, a tert-butyl group, a phenyl group, a biphenyl group, a terphenyl group, and a naphthyl group, a51 may be selected from 1, 2, 3, 4, and 5,
a52 may be selected from 1, 2, 3, 4, 5, 6, and 7,
a53 may be selected from 1, 2, 3, 4, 5, and 6,
a54 may be selected from 1, 2, and 3,
a55 may be selected from 1, 2, 3, and 4, and
* indicates a binding site to a neighboring atom.

In various embodiments, in Formula 1, $R_{11}$ to $R_{16}$ may each independently be a group selected from groups represented by Formulae 6-1 to 6-195, but embodiments of the present disclosure are not limited thereto:

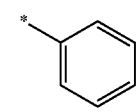

6-1

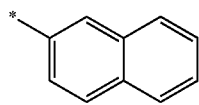

6-2

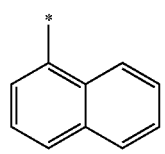

6-3

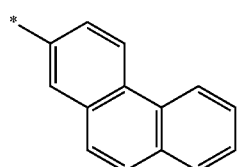

6-4

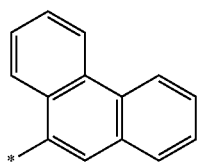

6-5

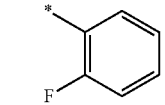

6-6

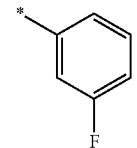

6-7

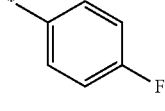

6-8

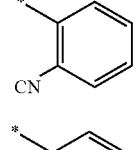

6-9

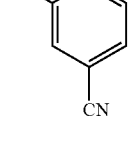

6-10

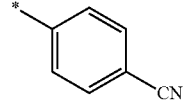

6-11

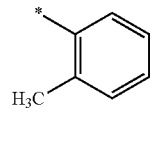

6-12

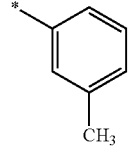

6-13

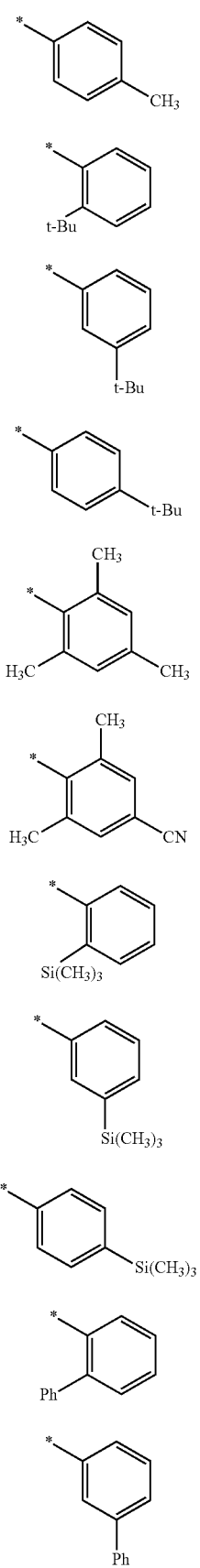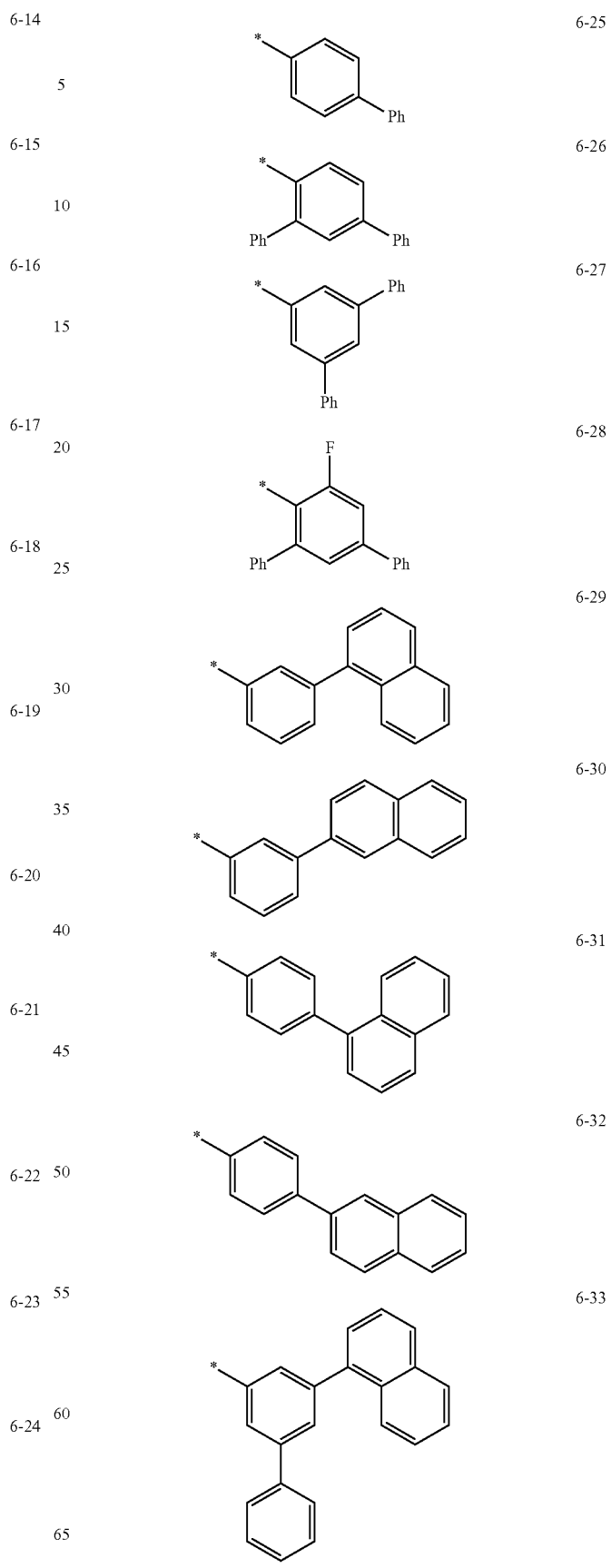

-continued
6-34
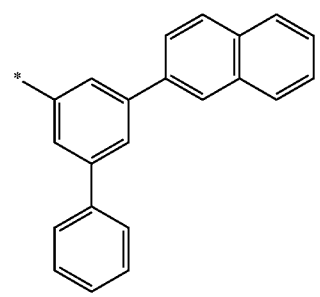
6-35
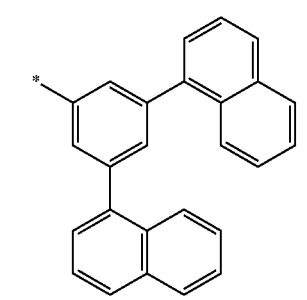
6-36
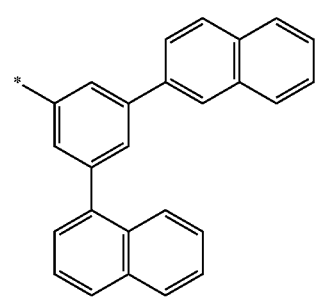
6-37
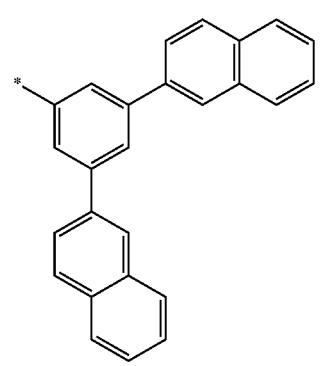
6-38
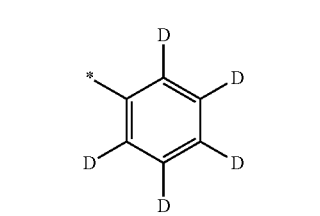
6-39
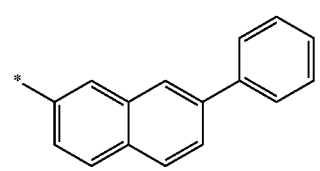
-continued
6-40
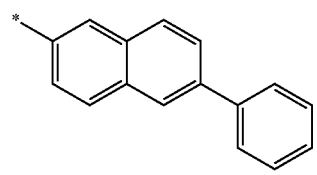
6-41
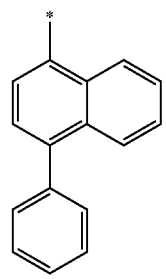
6-42
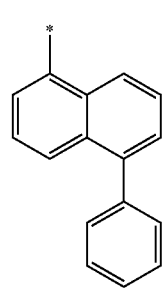
6-43
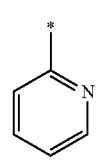
6-44
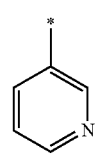
6-45
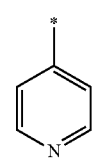
6-46
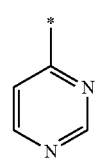
6-47
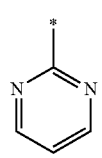

6-48 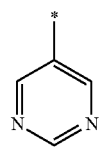
6-49 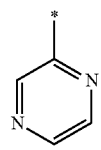
6-50 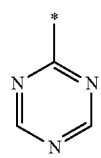
6-51 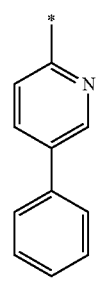
6-52 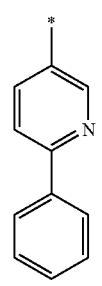
6-53 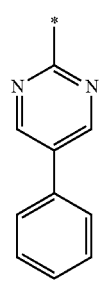
6-54 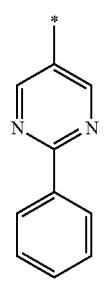
6-55 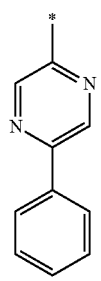
6-56 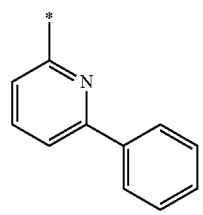
6-57 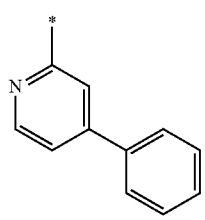
6-58 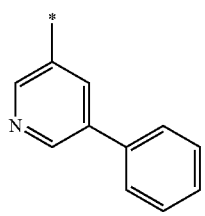
6-59 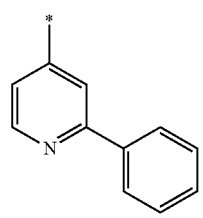
6-60 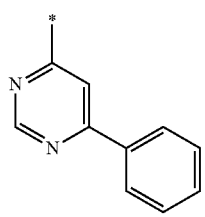
6-61 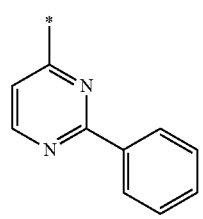

6-62 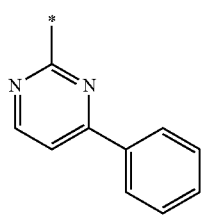
6-63 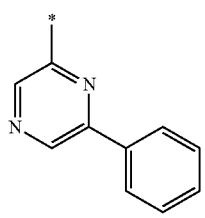
6-64 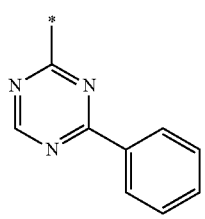
6-65 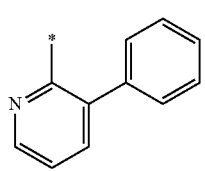
6-66 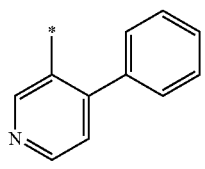
6-67 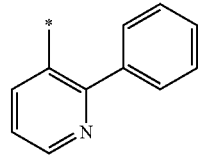
6-68 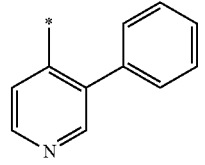
6-69 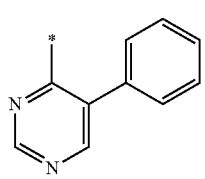
6-70 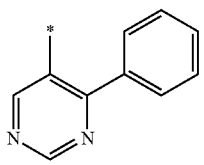
6-71 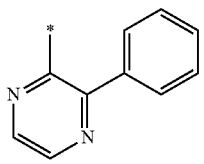
6-72 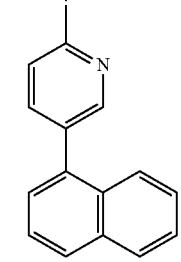
6-73 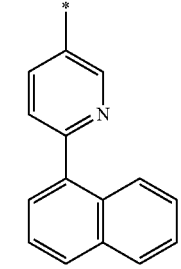
6-74 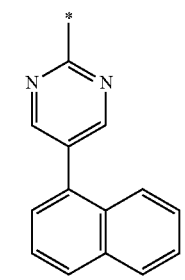
6-75 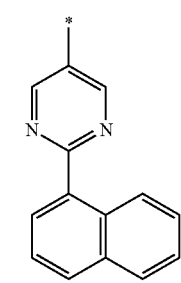

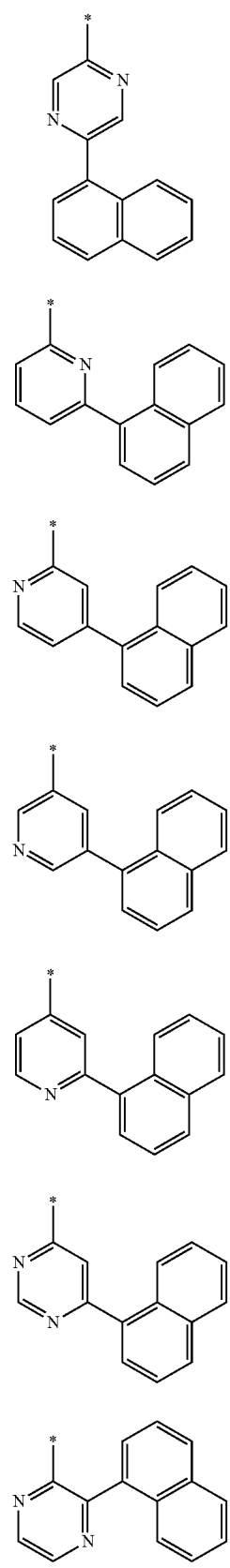

6-87
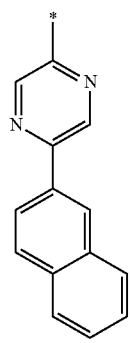
6-88
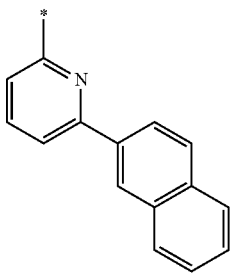
6-89
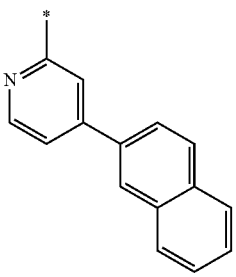
6-90
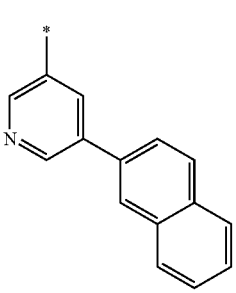
6-91
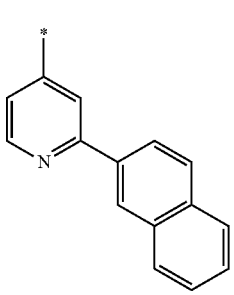
6-92
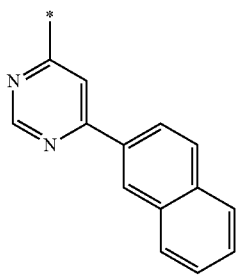
6-92
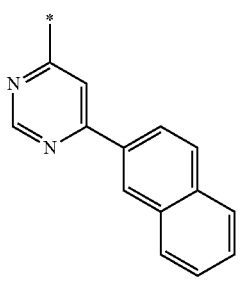
6-93
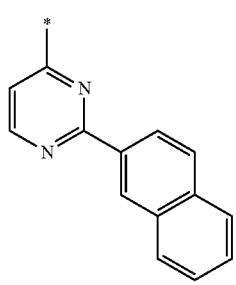
6-94
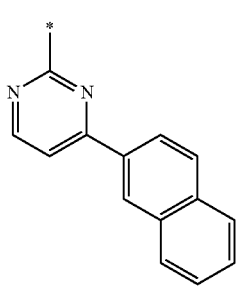
6-95
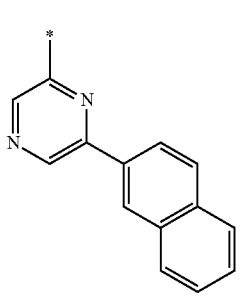

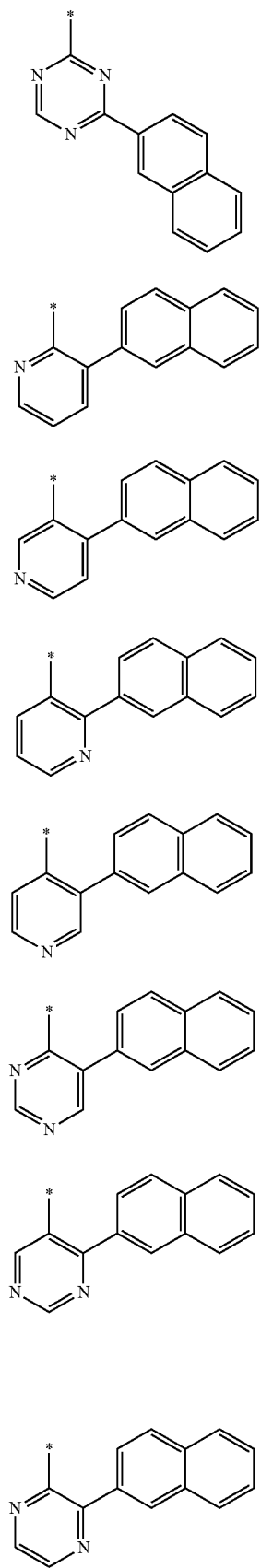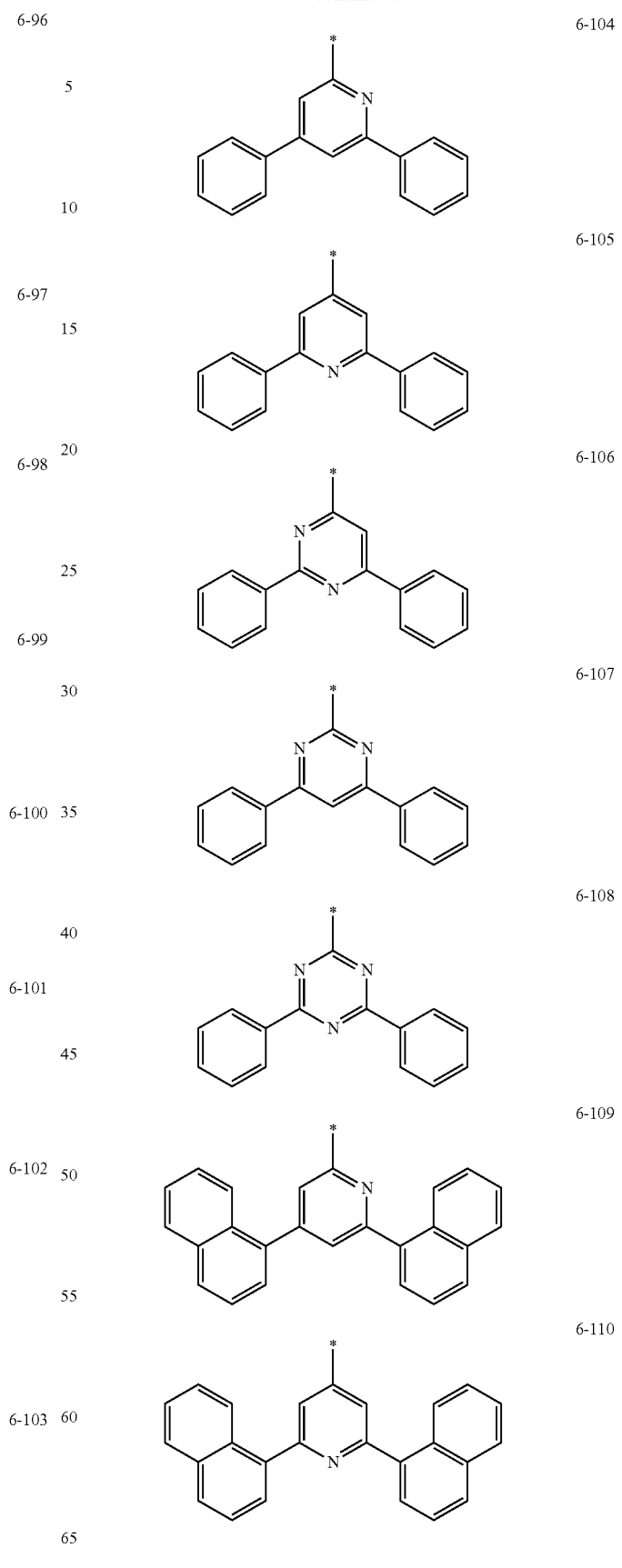

6-111
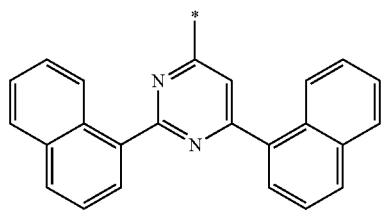
6-112
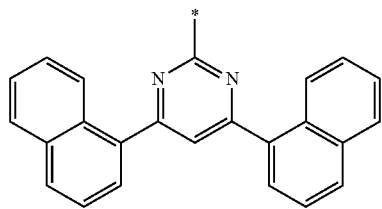
6-113
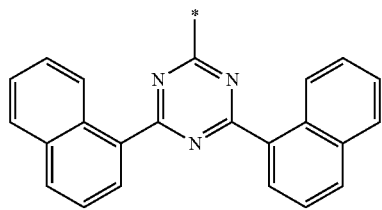
6-114
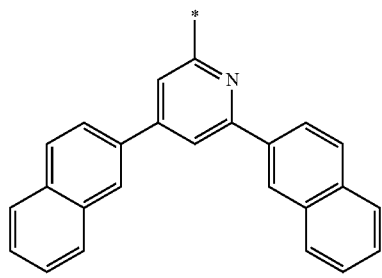
6-115
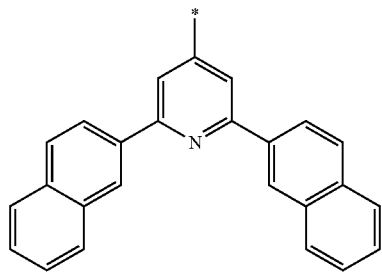
6-116
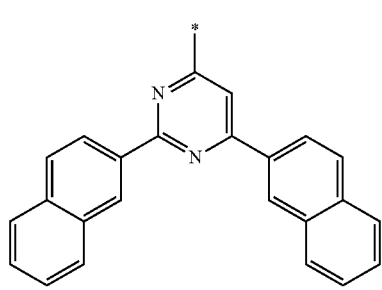
6-117
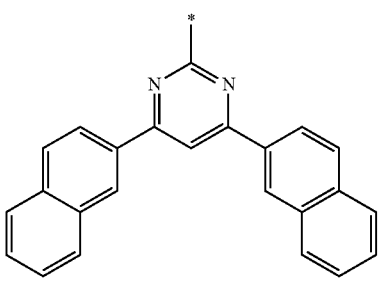
6-118
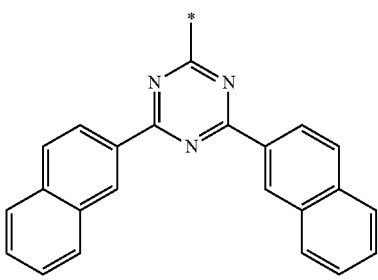
6-119
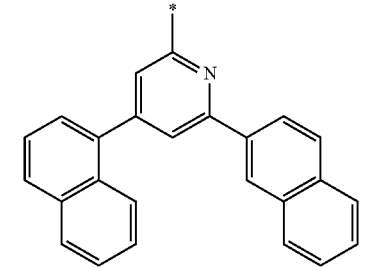
6-120
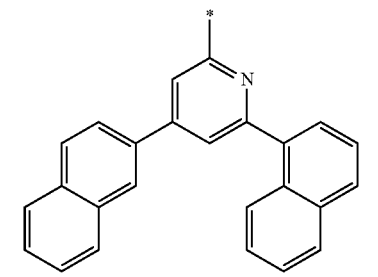
6-121
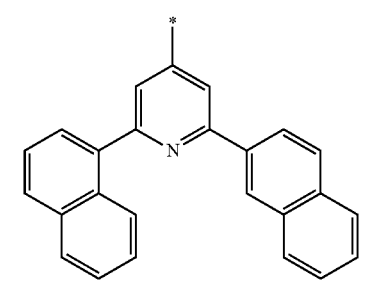

6-122 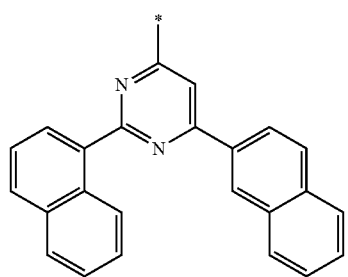
6-123 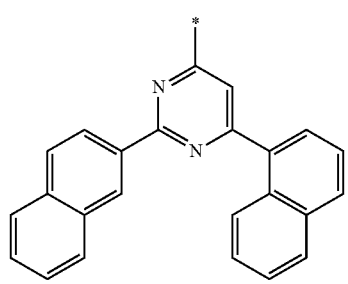
6-124 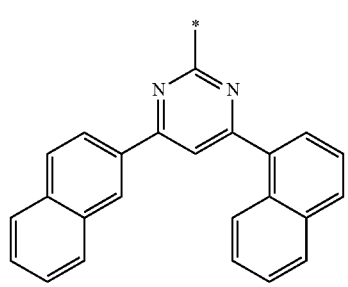
6-125 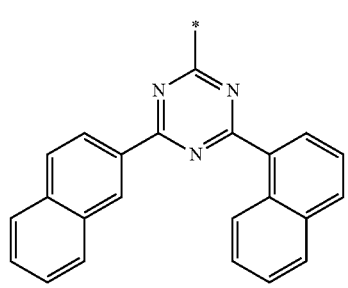
6-126 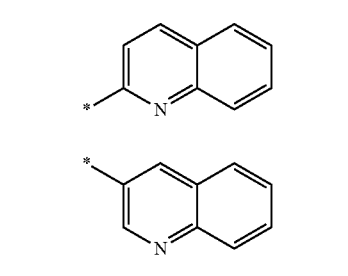
6-127 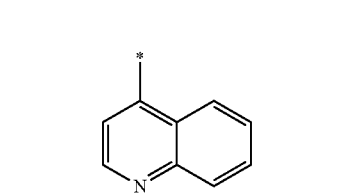
6-128 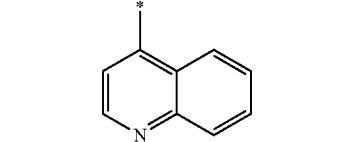
6-129 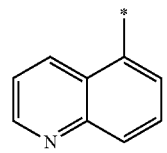
6-130 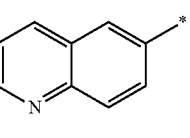
6-131 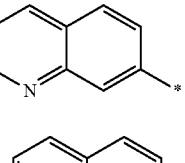
6-132 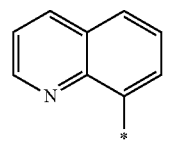
6-133 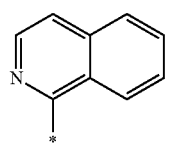
6-134 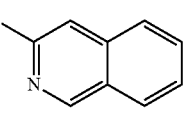
6-135 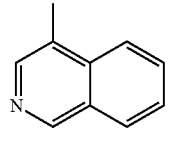
6-136 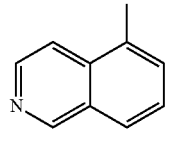
6-137 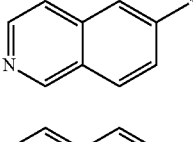
6-138 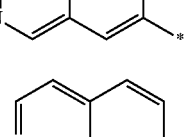
6-139 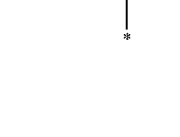

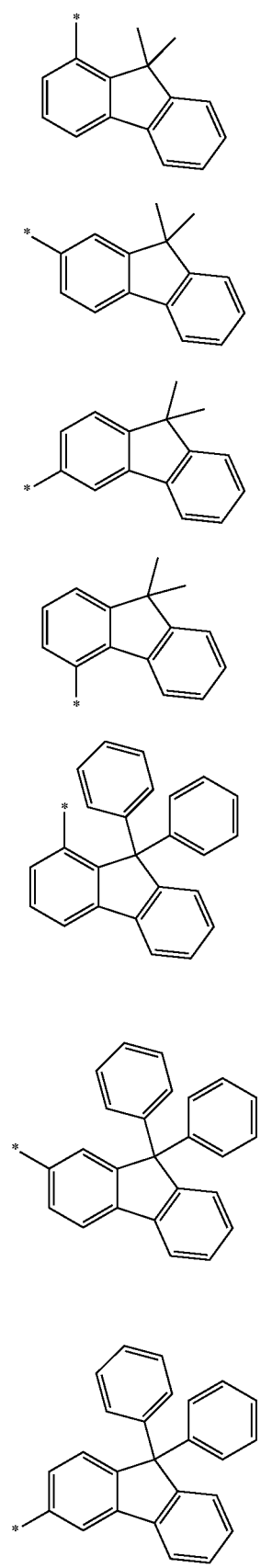
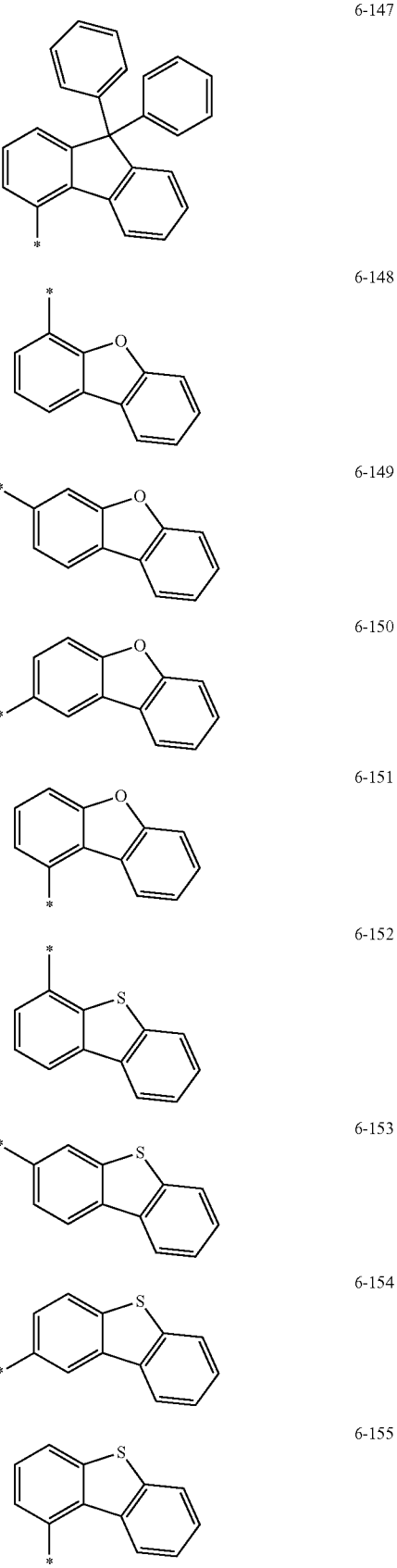

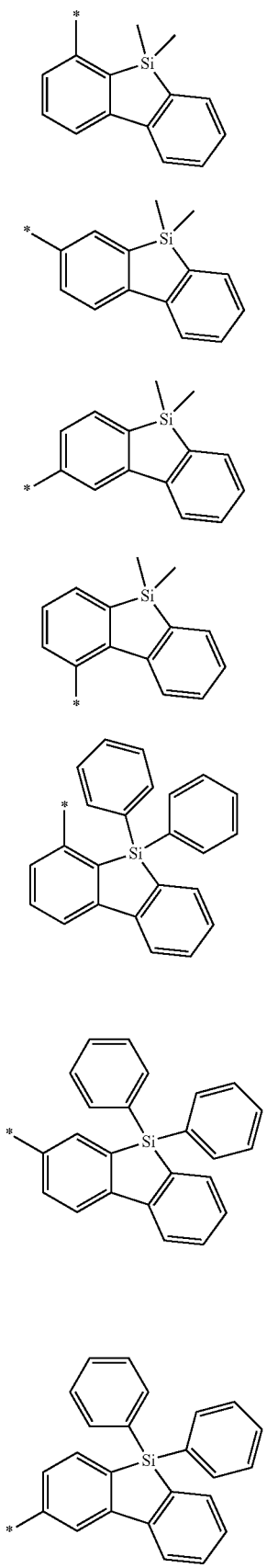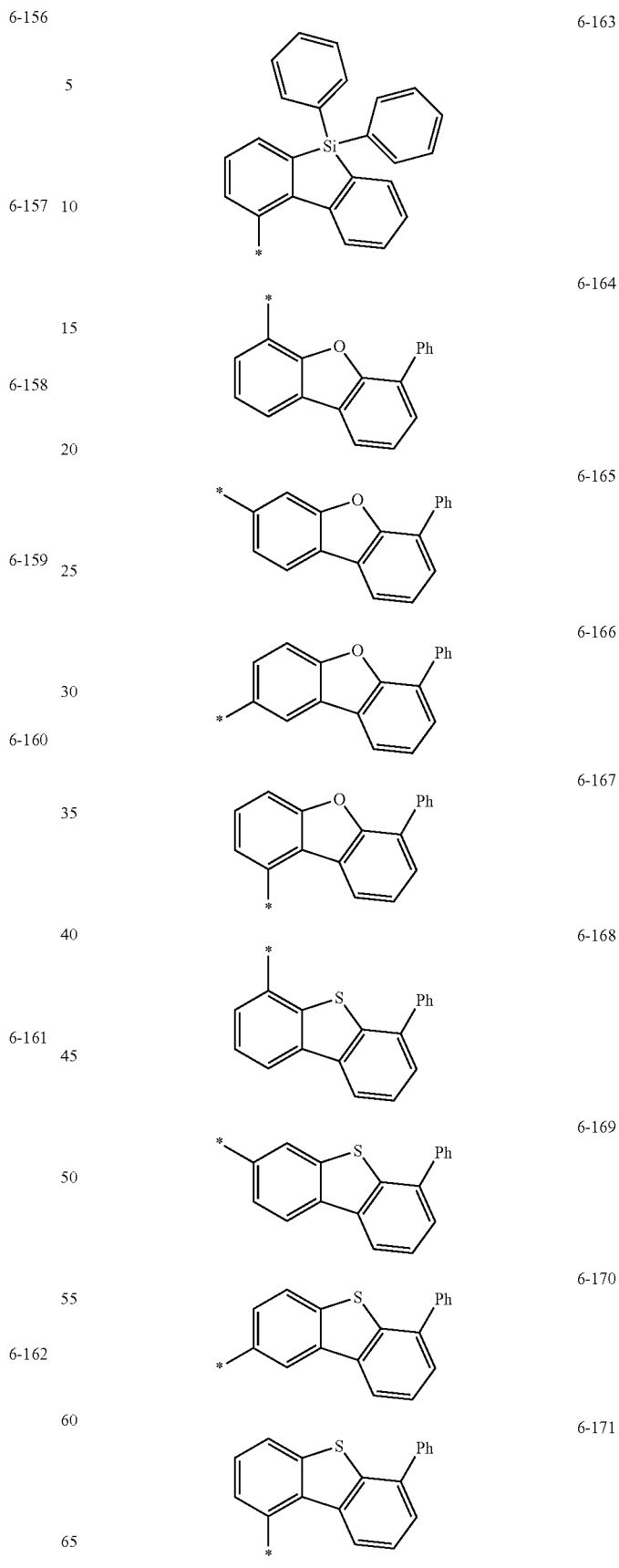

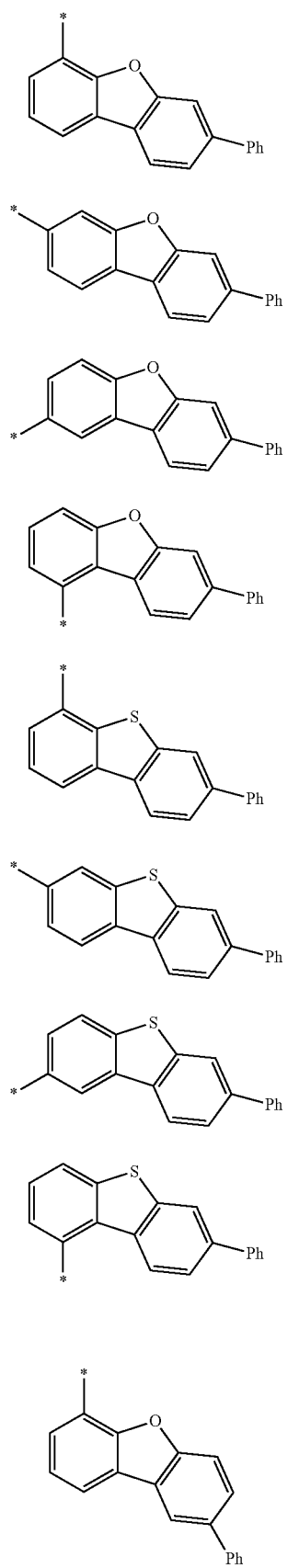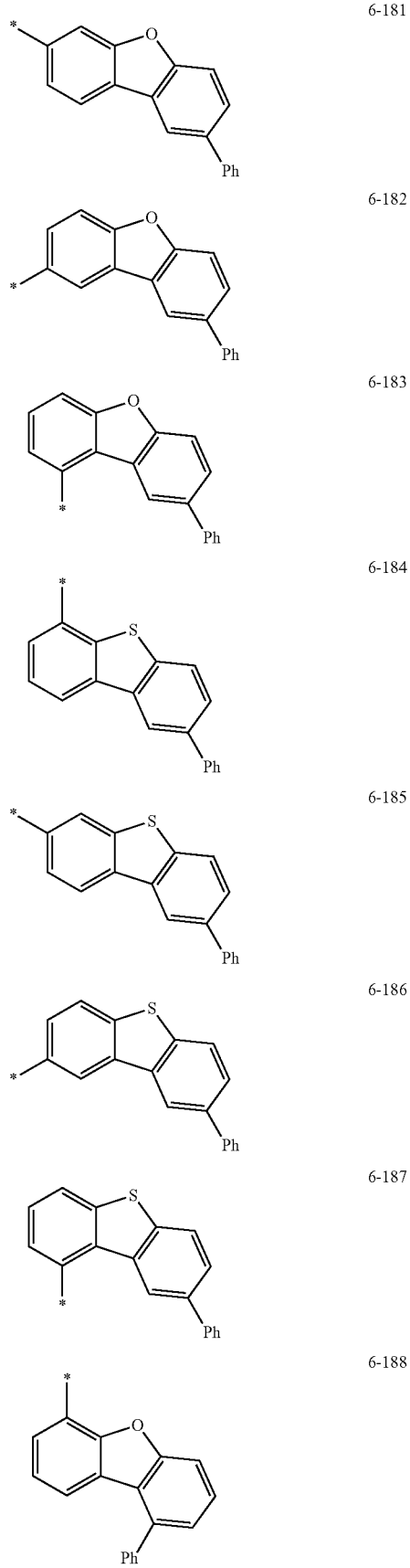

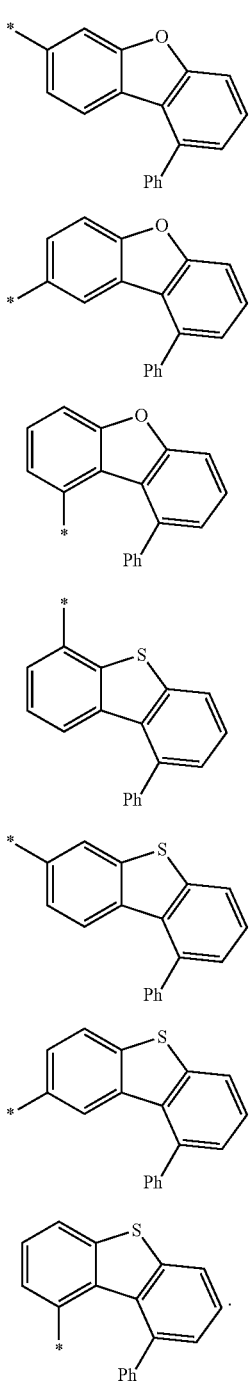

In Formulae 6-1 to 6-195,
t-Bu indicates a tert-butyl group,
Ph indicates a phenyl group, and
* indicates a binding site to a neighboring atom.

In various embodiments, in Formula 1,
there may be a case where $R_{11}=R_{12}=R_{13}=R_{14}=R_{15}=R_{16}$, a case where $R_{11}=R_{13}=R_{15}$, $R_{14}=R_{12}=R_{16}$, and $R_{11}\neq R_{14}$, or a case where $R_{11}\neq R_{12}\neq R_{13}\neq R_{14}\neq R_{15}\neq R_{16}$, but embodiments of the present disclosure are not limited thereto.

In Formula 1, n11 to n13 may each independently be selected from 0, 1, and 2, wherein the sum of n11 to n13 may be selected from 1, 2, 3, 4, 5, and 6.

For example, in Formula 1, n11 to n13 may each independently be selected from 0 and 1, but embodiments of the present disclosure are not limited thereto.

In various embodiments, in Formula 1, the sum of n11 to n13 may be selected from 1, 2, 3, and 4, but embodiments of the present disclosure are not limited thereto.

In various embodiments, in Formula 1, the sum of n11 to n13 may be selected from 1 and 2, but embodiments of the present disclosure are not limited thereto.

In various embodiments, in Formula 1, the sum of n11 to n13 may be 2, but embodiments of the present disclosure are not limited thereto.

In Formula 1, $R_{17}$, $R_{18}$, and $R_{101}$ to $R_{103}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

For example, in Formula 1, $R_{17}$, $R_{18}$, and $R_{101}$ to $R_{103}$ may each independently be selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_1$-$C_{60}$ alkoxy group, a cyclopentyl group, and a cyclohexyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group, each substituted with a $C_1$-$C_{60}$ alkyl group; and $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, wherein $Q_1$ to $Q_3$ may each independently be selected from a $C_1$-$C_{20}$ alkyl group, a phenyl group, a biphenyl group, a terphenyl group, and a naphthyl group, but embodiments of the present disclosure are not limited thereto.

In various embodiments, in Formula 1, $R_{17}$, $R_{18}$, and $R_{101}$ to $R_{103}$ may each independently be selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_1$-$C_{60}$ alkoxy group, a cyclopentyl group, and a cyclohexyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group, each substituted with at least one selected from a methyl group, an ethyl group, an n-propyl group, an iso-propyl group, an n-butyl group, a sec-butyl group, an iso-butyl group, and a tert-butyl group; and $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, wherein $Q_1$ to $Q_3$ may each independently be selected from a $C_1$-$C_{20}$ alkyl group, a phenyl group, a biphenyl group, a terphenyl group, and a naphthyl group, but embodiments of the present disclosure are not limited thereto.

In various embodiments, in Formula 1, $R_{17}$ and $R_{18}$ may each independently be selected from a methyl group, an ethyl group, an n-propyl group, an iso-propyl group, an n-butyl group, a sec-butyl group, an iso-butyl group, a tert-butyl group, a cyclopentyl group, a cyclohexyl group, a phenyl group, a biphenyl group, a terphenyl group, and a naphthyl group, but embodiments of the present disclosure are not limited thereto.

In various embodiments, in Formula 1, $R_{17}$ and $R_{18}$ may each independently be a methyl group, but embodiments of the present disclosure are not limited thereto.

In various embodiments, in Formula 1, $R_{101}$ to $R_{103}$ may each independently be selected from hydrogen, deuterium, —F, a hydroxyl group, a cyano group, a methyl group, an ethyl group, an n-propyl group, an iso-propyl group, an n-butyl group, a sec-butyl group, an iso-butyl group, a tert-butyl group, a cyclopentyl group, a cyclohexyl group, a phenyl group, a biphenyl group, a terphenyl group, a naphthyl group, a fluorenyl group, a phenyl group substituted with a methyl group, a fluorenyl group substituted with a methyl group, a pyridinyl group, a pyrazinyl group, a pyrimidinyl group, a quinolinyl group, an isoquinolinyl group, a carbazolyl group, a triazinyl group, $-Si(CH_3)_3$, and $-Si(Ph)_3$, but embodiments of the present disclosure are not limited thereto.

In various embodiments, in Formula 1, $R_{101}$ to $R_{103}$ may be hydrogen, but embodiments of the present disclosure are not limited thereto.

For example, the amine-based compound of Formula 1 may be represented by one of Formulae 1-1 to 1-3, but embodiments of the present disclosure are not limited thereto:

Formula 1-1

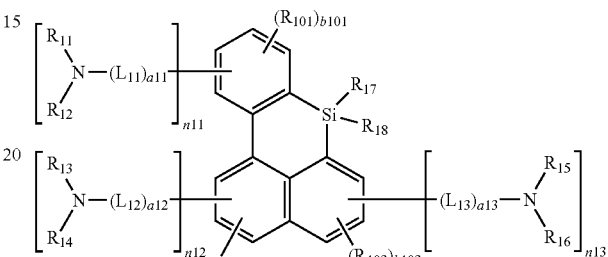

Formula 1-2

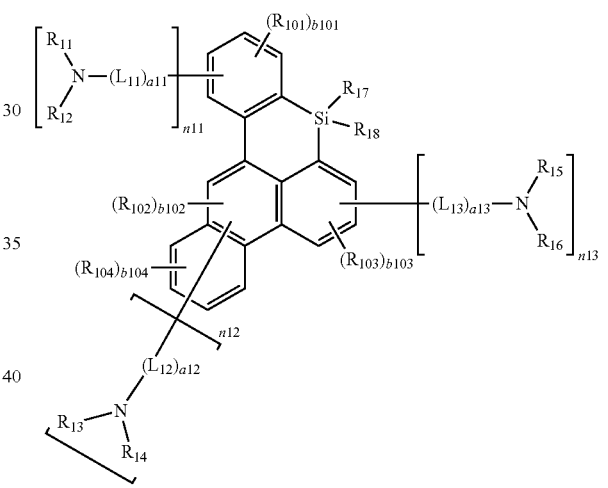

Formula 1-3

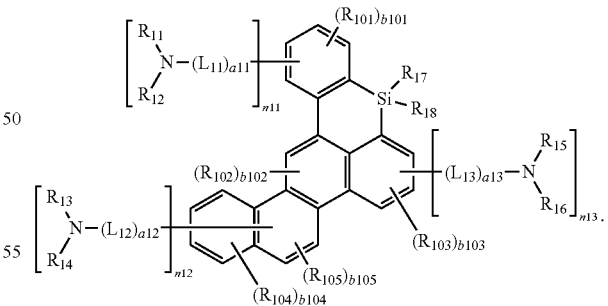

In Formulae 1-1 to 1-3, $L_{11}$ to $L_{13}$, a11 to a13, $R_{11}$ to $R_{18}$, n11 to n13, $R_{101}$ to $R_{103}$, and b101 to b103 may each independently be the same as respectively described herein in connection with Formula 1, $R_{104}$ and $R_{105}$ may each independently be the same as described herein in connection with $R_{101}$ in Formula 1, and b104 and b105 may each independently be the same as described herein in connection with b101 in Formula 1.

In various embodiments, the amine-based compound of Formula 1 may be represented by one of Formulae 1-11 to 1-19, but embodiments of the present disclosure are not limited thereto:
Formula 1-11
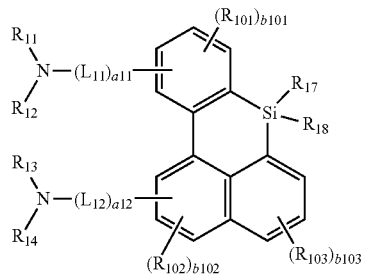
Formula 1-12
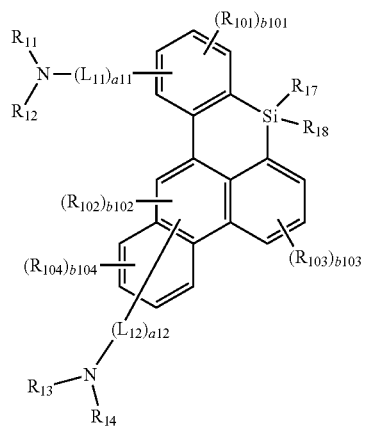
Formula 1-13
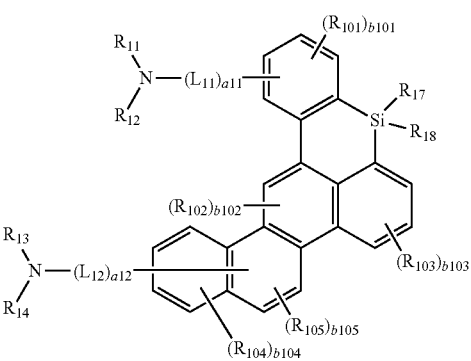
Formula 1-14
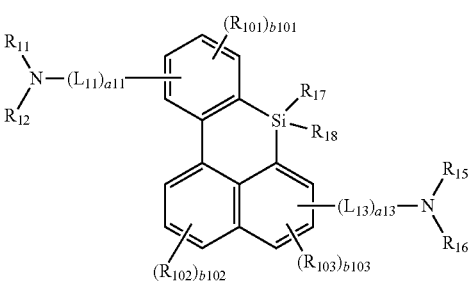
Formula 1-15
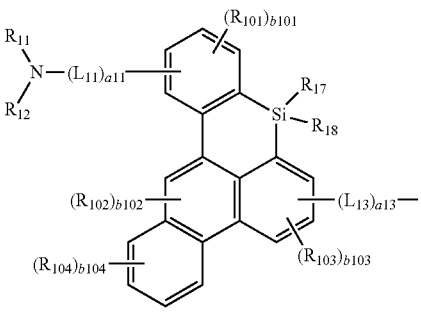
Formula 1-16
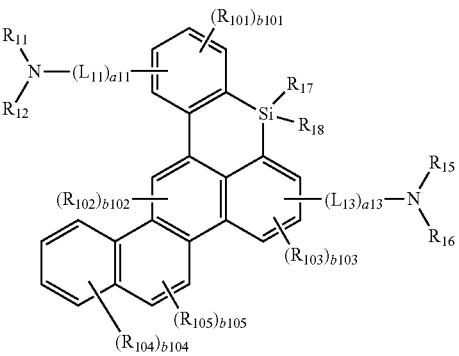
Formula 1-17
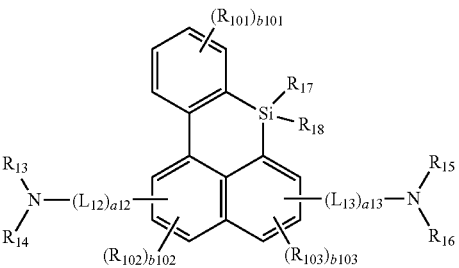
Formula 1-18
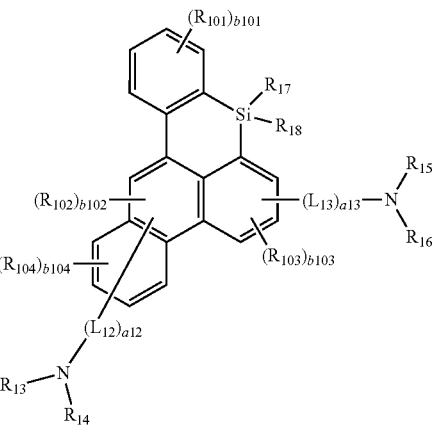

-continued

Formula 1-19

[Chemical structure diagram showing Formula 1-19 with substituents $(R_{101})_{b101}$, $(R_{102})_{b102}$, $(R_{103})_{b103}$, $(R_{104})_{b104}$, $(R_{105})_{b105}$, $R_{13}$, $R_{14}$, $R_{15}$, $R_{16}$, $R_{17}$, $R_{18}$, $(L_{12})_{a12}$, $(L_{13})_{a13}$]

In Formulae 1-11 to 1-19, $L_{11}$ to $L_{13}$, a11 to a13, $R_{11}$ to $R_{16}$, $R_{17}$, $R_{18}$, $R_{101}$ to $R_{103}$, and b101 to b103 may each independently be the same as respectively described herein in connection with Formula 1, $R_{104}$ and $R_{105}$ may each independently be the same as described herein in connection with $R_{101}$ in Formula 1, and b104 and b105 may each independently be the same as described herein in connection with b101 in Formula 1.

For example, in Formulae 1-11 to 1-13,
a11 and a12 may be both 0,
a11 may be 0, and a12 may be 1 or 2,
a11 may be 1 or 2, and a12 may be 0,
a11 and a12 may be both 1,
a11 may be 1, and a12 may be 2,
a11 may be 2, and a12 may be 1, or
a11 and a12 may be both 2.

For example, in Formulae 1-14 to 1-16,
a11 and a13 may be both 0,
a11 may be 0, and a13 may be 1 or 2,
a11 may be 1 or 2, and a13 may be 0,
a11 and a13 may be both 1,
a11 may be 1, and a13 may be 2,
a11 may be 2, and a13 may be 1, or
a11 and a13 may be both 2.

For example, in Formulae 1-17 to 1-19,
a12 and a13 may be both 0,
a12 may be 0, and a13 may be 1 or 2,
a12 may be 1 or 2, and a13 may be 0,
a12 and a13 may be both 1,
a12 may be 1, and a13 may be 2,
a12 may be 2, and a13 may be 1, or
a12 and a13 may be both 2.

In various embodiments, in Formulae 1-11 to 1-13, there may be a case where $R_{11}=R_{12}=R_{13}=R_{14}$;
a case where $R_{11}=R_{13}$, $R_{12}=R_{14}$, and $R_{12}\neq R_{13}$;
a case where $R_{11}=R_{13}$, $R_{12}\neq R_{14}$, and $R_{12}\neq R_{13}$; or
a case where $R_{11}\neq R_{12}\neq R_{13}\neq R_{14}$.

In various embodiments, in Formulae 1-14 to 1-16, there may be a case where $R_{11}=R_{12}=R_{15}=R_{16}$;
a case where $R_{11}=R_{15}$, $R_{12}=R_{16}$, and $R_{12}\neq R_{15}$;
a case where $R_{11}=R_{15}$, $R_{12}\neq R_{16}$, and $R_{12}\neq R_{15}$; or
a case where $R_{11}\neq R_{12}\neq R_{15}\neq R_{16}$.

In various embodiments, in Formulae 1-17 to 1-19, there may be a case where $R_{13}=R_{14}=R_{15}=R_{16}$;
a case where $R_{13}=R_{15}$, $R_{14}=R_{16}$, and $R_{14}\neq R_{15}$;
a case where $R_{13}=R_{15}$, $R_{14}\neq R_{16}$, and $R_{14}\neq R_{15}$; or
a case where $R_{13}\neq R_{14}\neq R_{15}\neq R_{16}$.

In various embodiments, the amine-based compound of Formula 1 may be represented by one of Formulae 1-21 to 1-23, but embodiments of the present disclosure are not limited thereto:

Formula 1-21

[Chemical structure diagram for Formula 1-21]

Formula 1-22

[Chemical structure diagram for Formula 1-22]

Formula 1-23

[Chemical structure diagram for Formula 1-23]

In Formulae 1-21 to 1-23, $L_{11}$, $L_{12}$, a11, a12, $R_{11}$ to $R_{14}$, $R_{17}$, $R_{18}$, $R_{101}$ to $R_{103}$, and b101 to b103 may each independently be the same as respectively described herein in connection with Formula 1, $R_{104}$ and $R_{105}$ may each independently be the same as described herein in connection with $R_{101}$ in Formula 1, and b104 and b105 may each independently be the same as described herein in connection with b101 in Formula 1.

In various embodiments, the amine-based compound of Formula 1 may be one selected from Compounds 1 to 437, but embodiments of the present disclosure are not limited thereto:
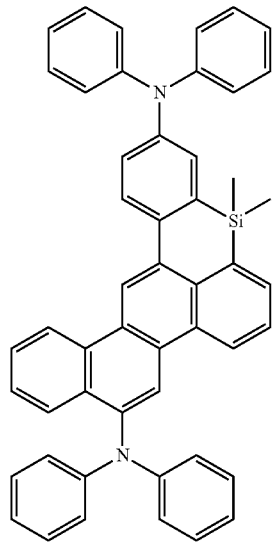
1
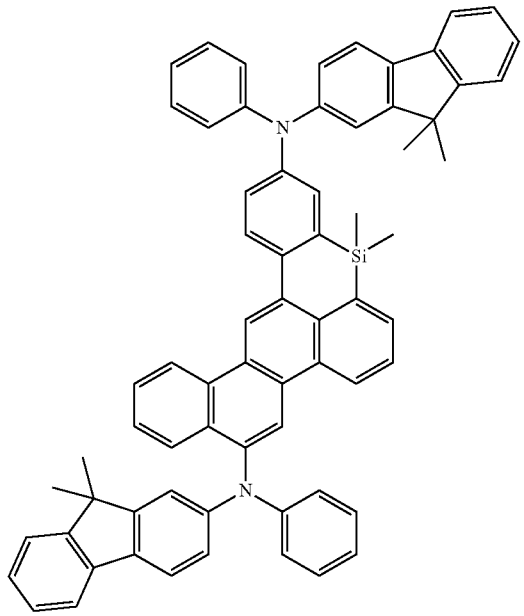
2
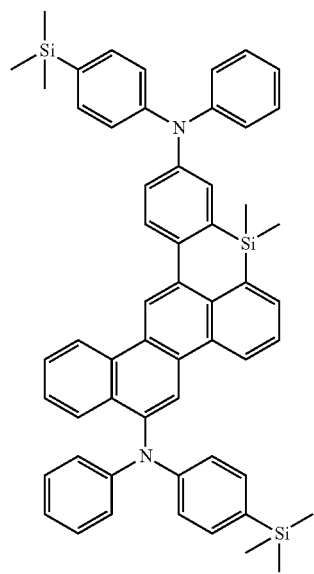
3
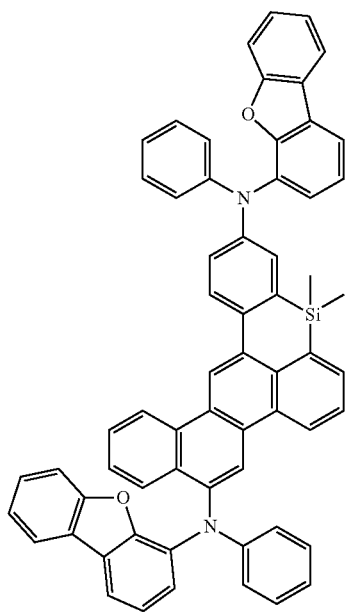
4

-continued
| 5 | 6 |
|---|---|
| 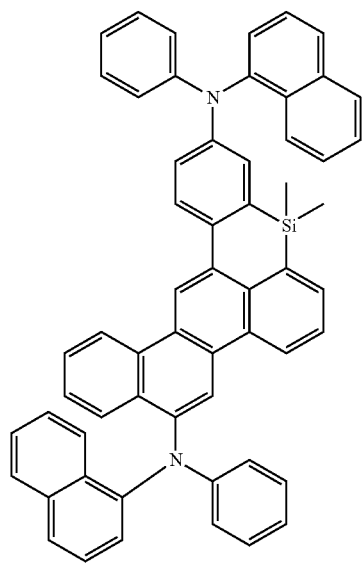 | 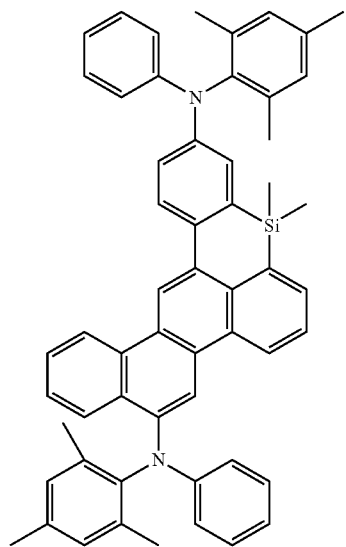 |
| 7 | 8 |
| 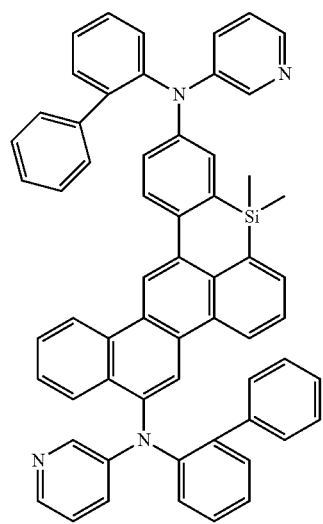 | 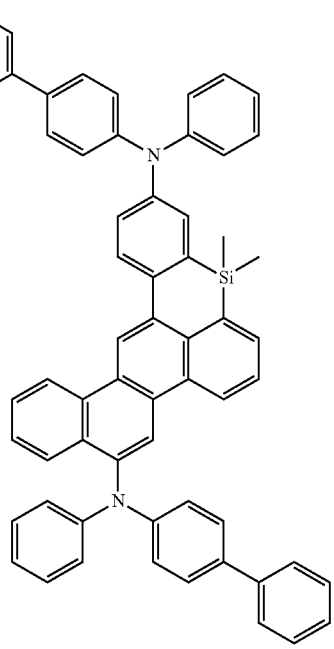 |

-continued
9
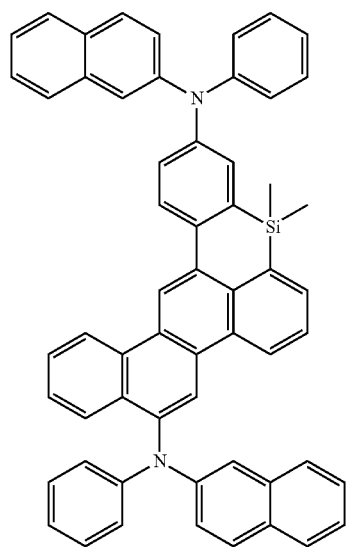
10
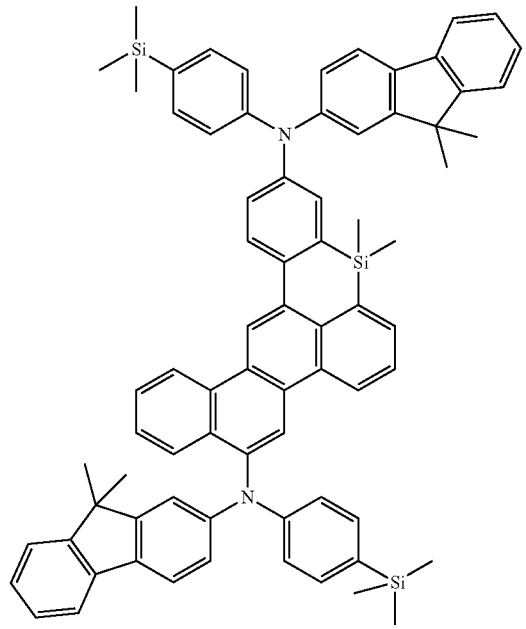
11
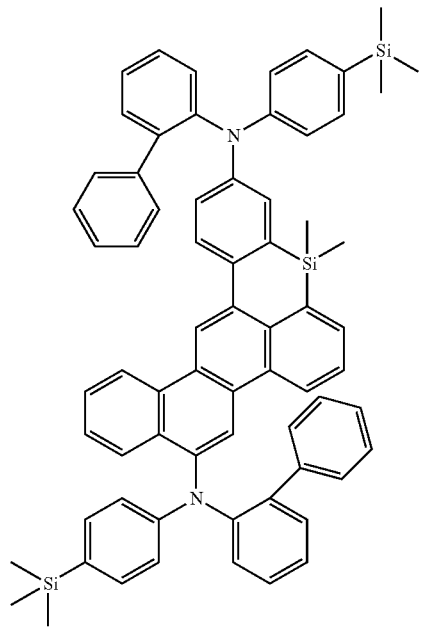
12
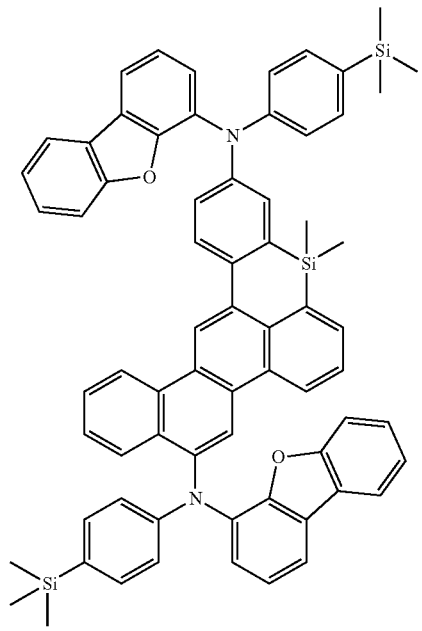

13
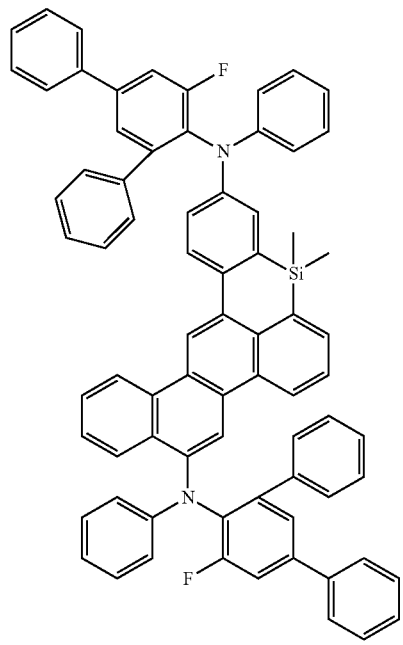
14
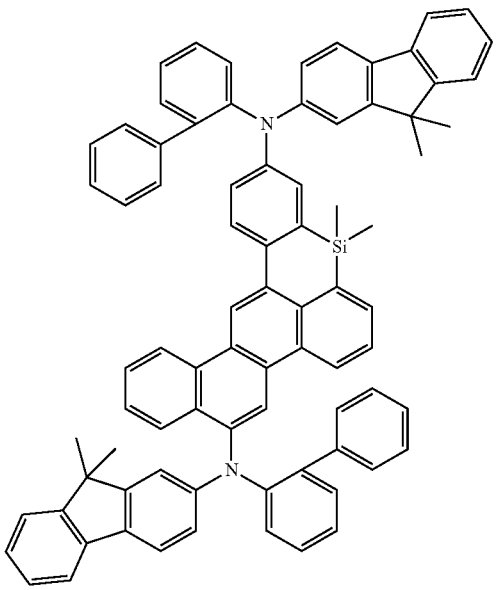
15
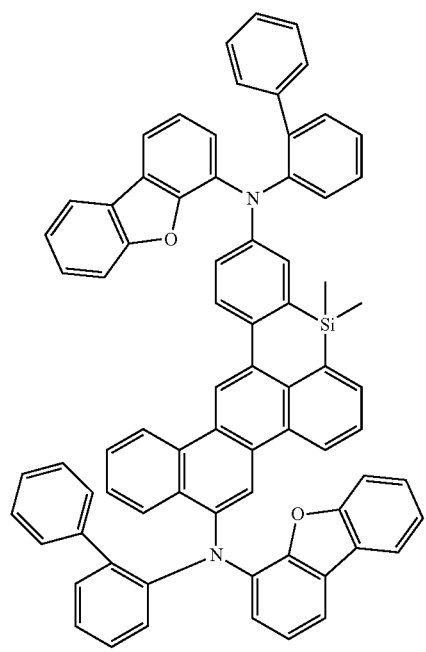
16
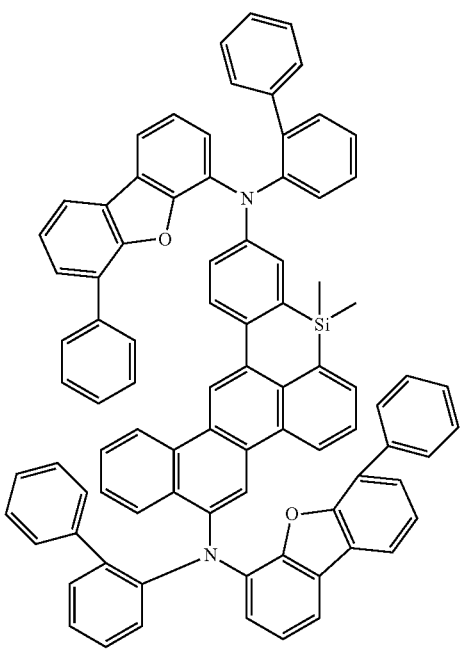

-continued
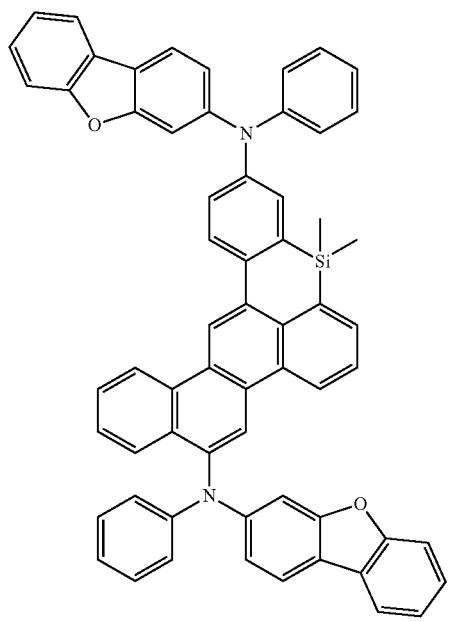
17
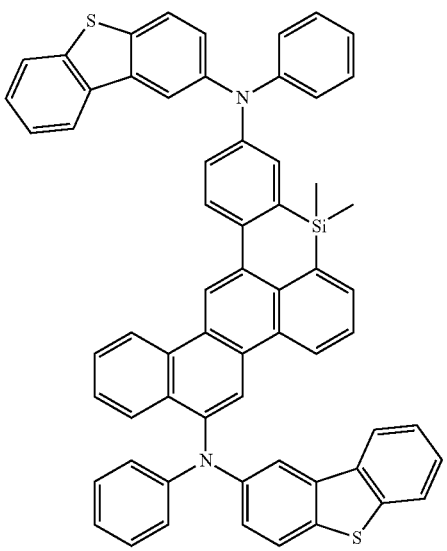
18
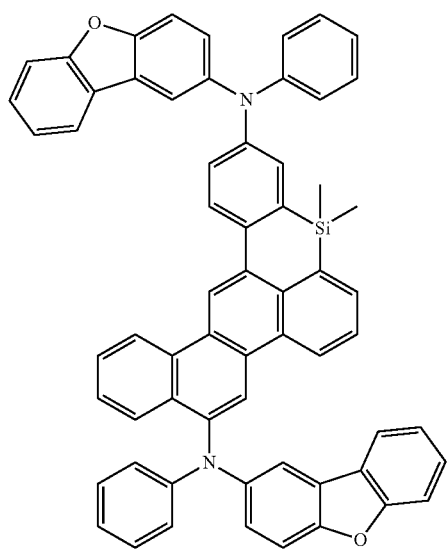
19
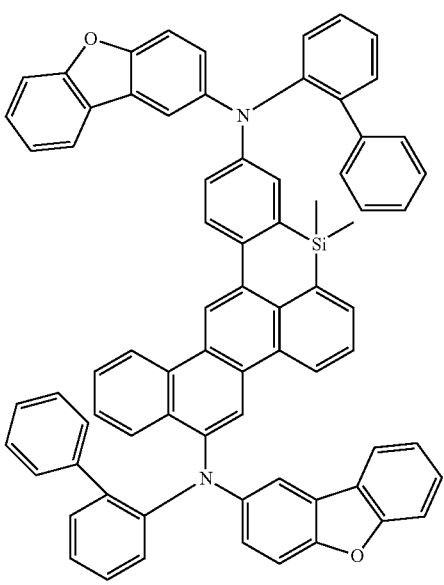
20

-continued
21
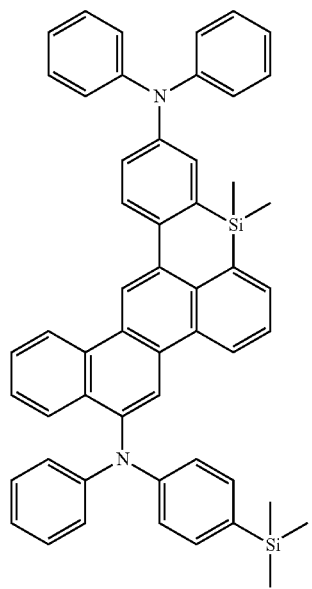
22
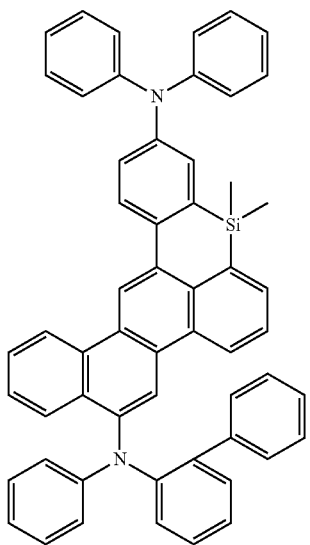
23
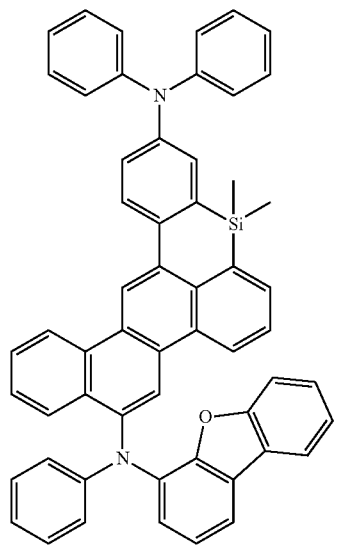
24
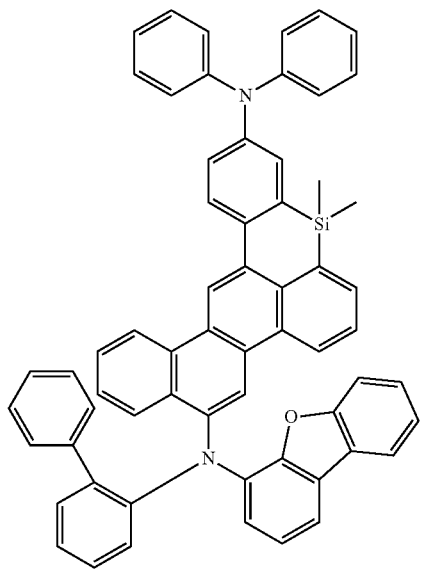

-continued
25
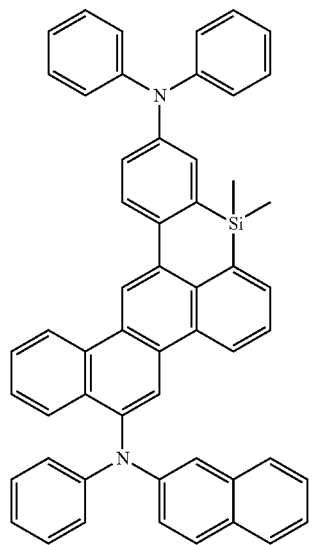
26
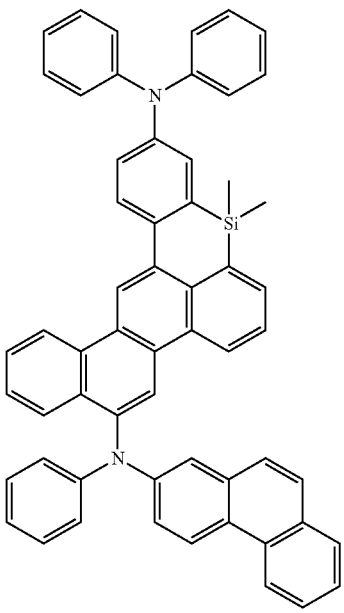
27
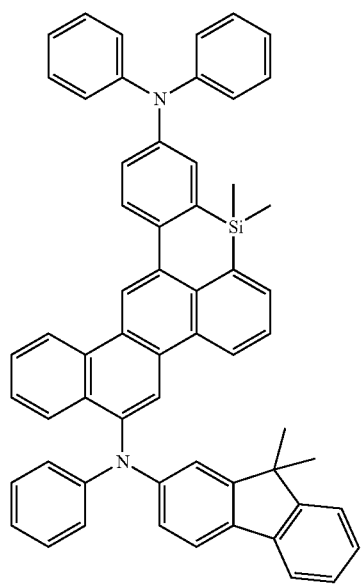
28
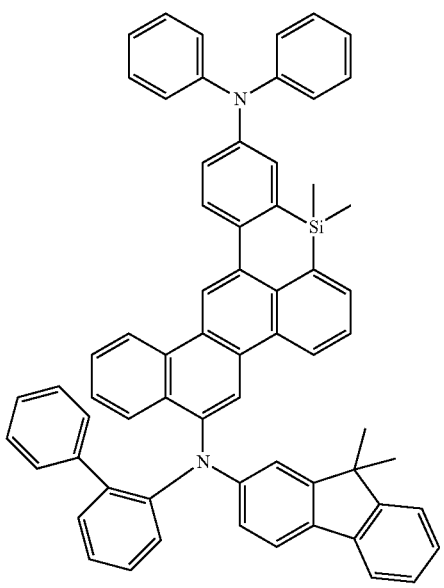

-continued
29
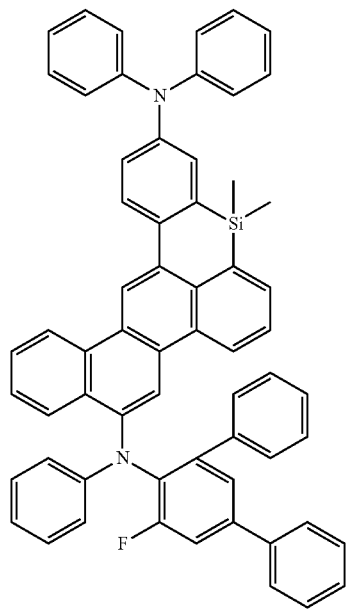
30
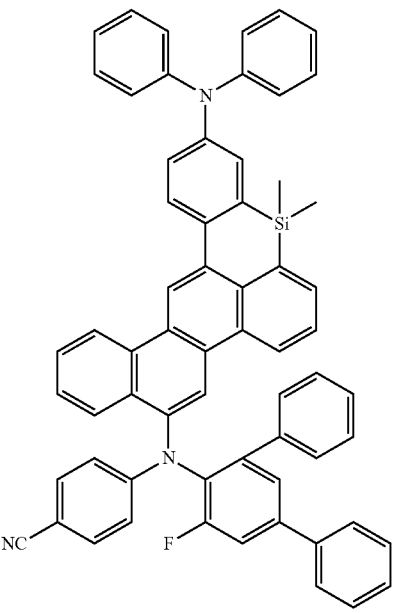
31
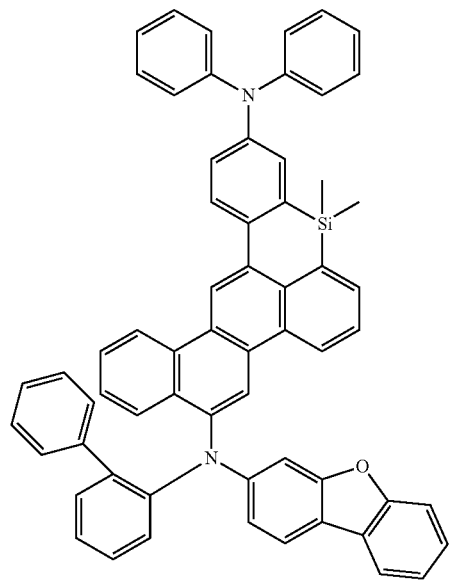
32
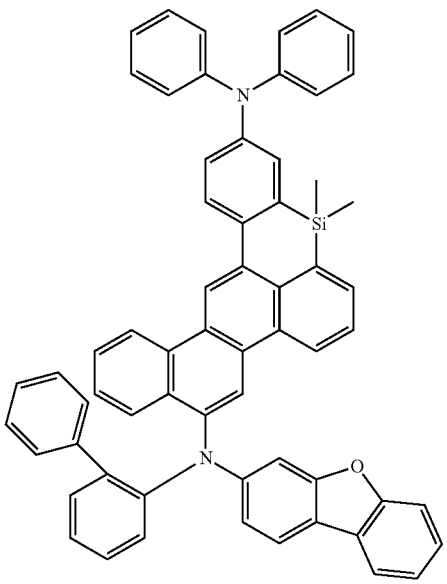

-continued
33
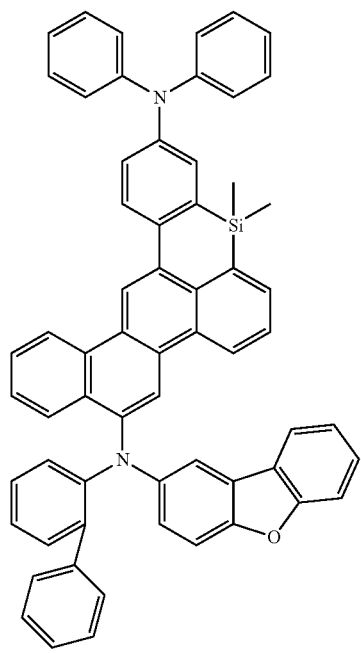
34
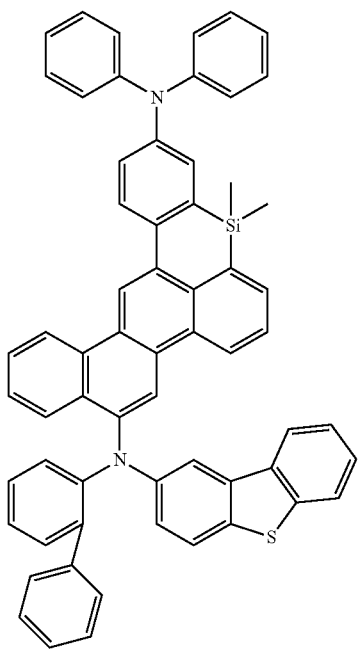
35
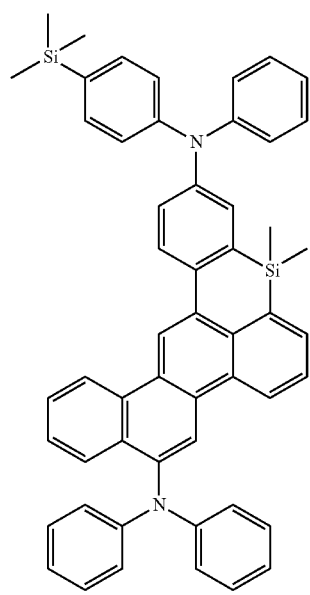
36
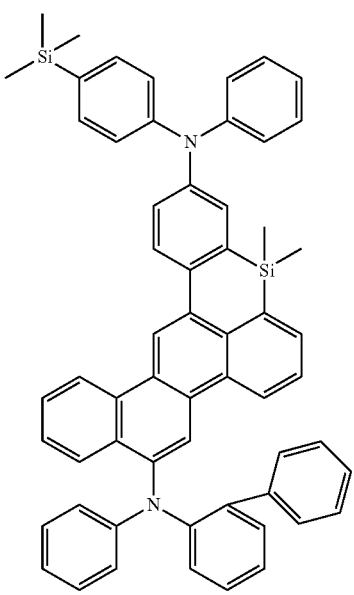

-continued
37
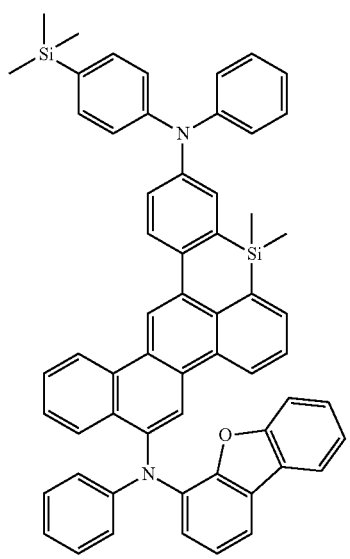
38
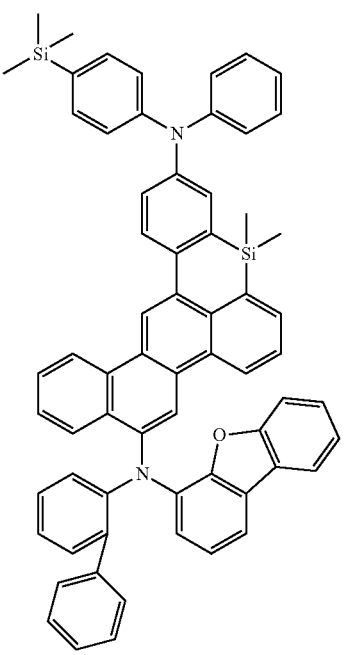
39
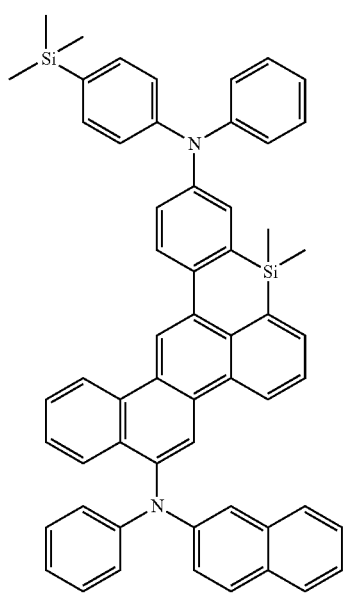
40
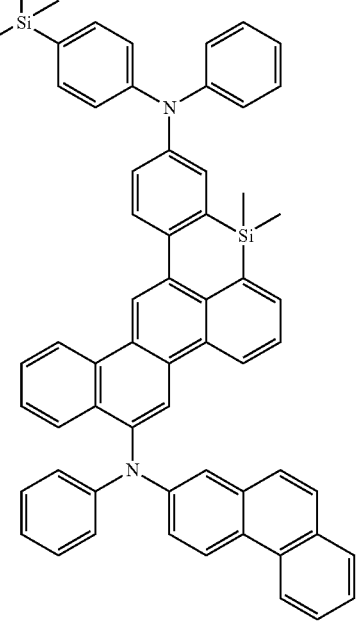

-continued
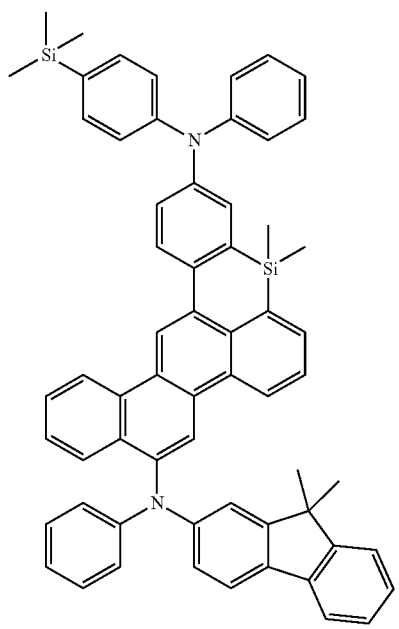
41
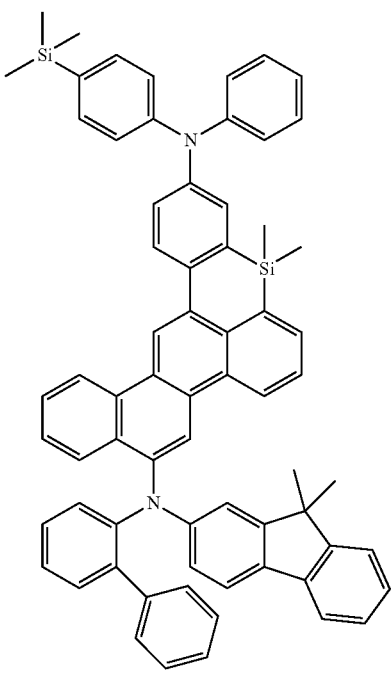
42
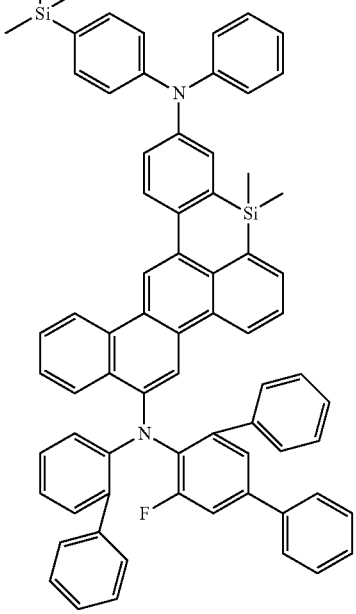
43
44

-continued
45
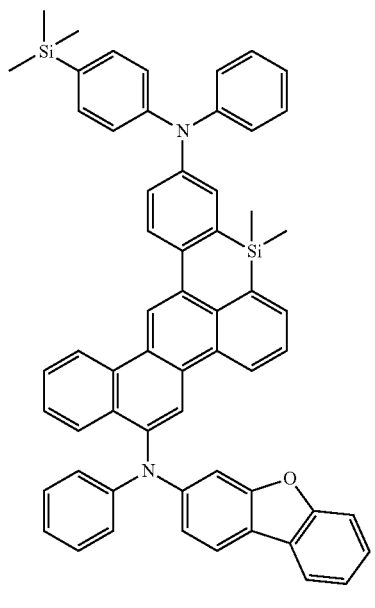
46
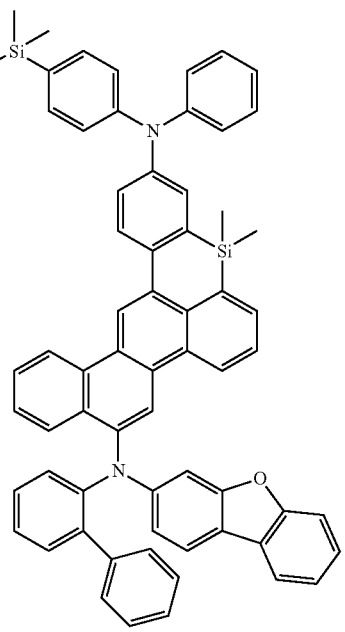
47
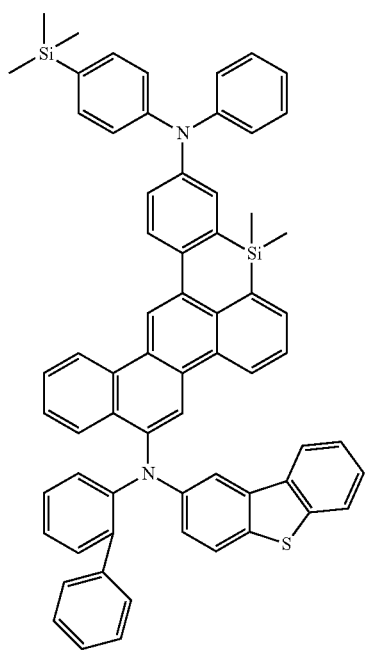
48
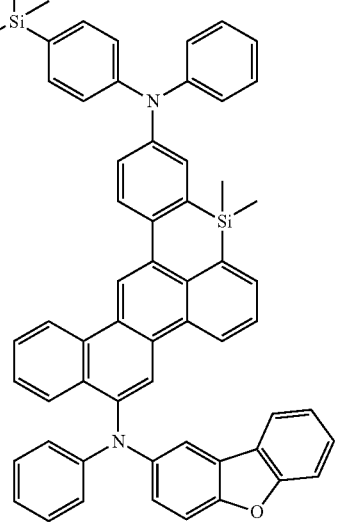

-continued
49
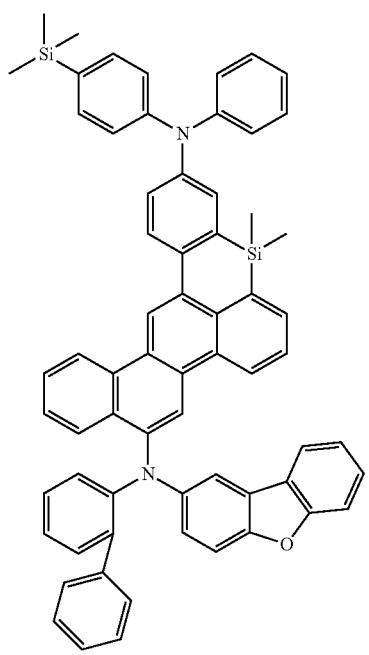
50
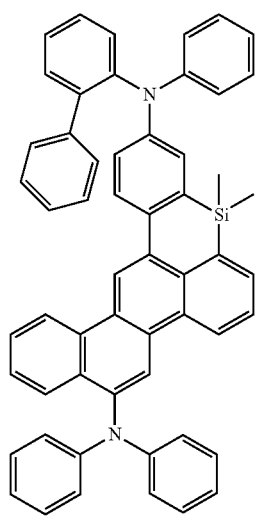
51
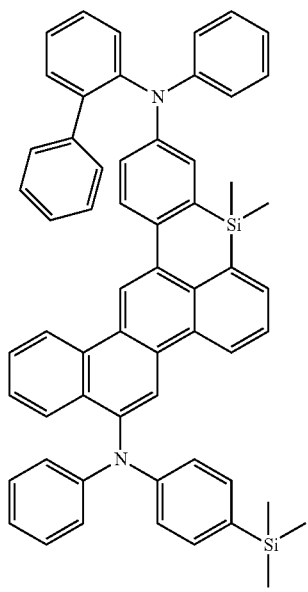
52
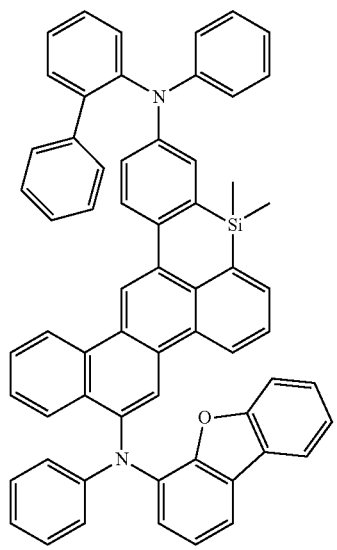

-continued
53
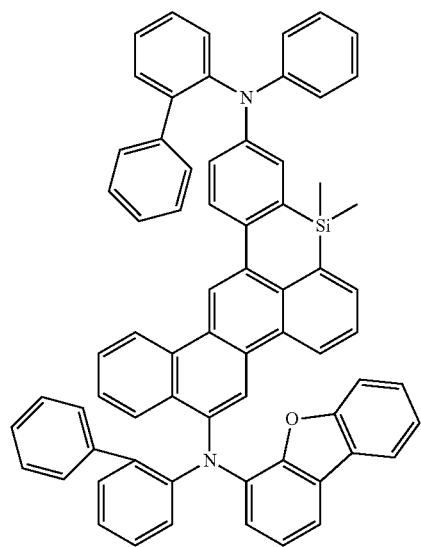
54
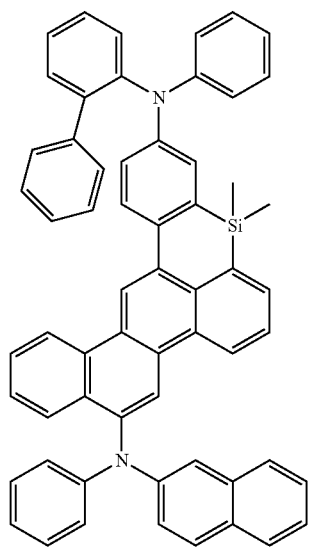
55
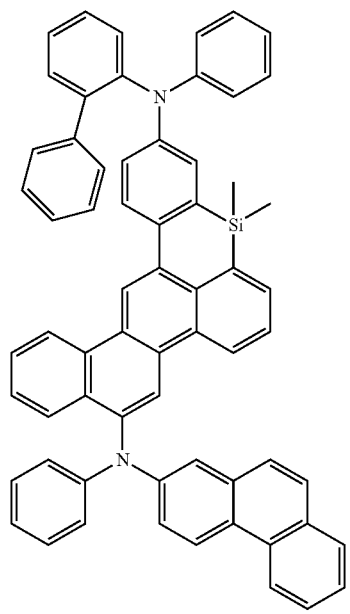
56
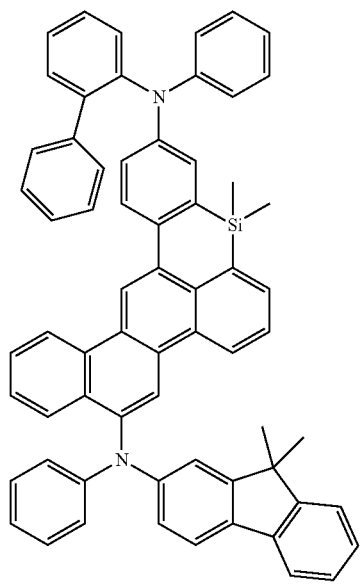

-continued
57
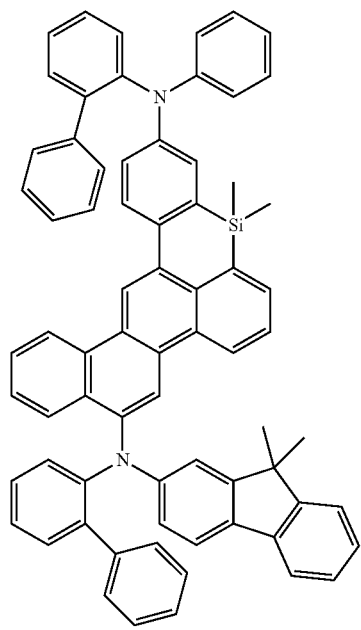
58
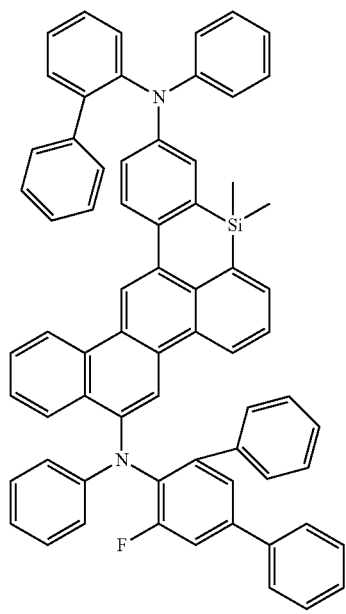
59
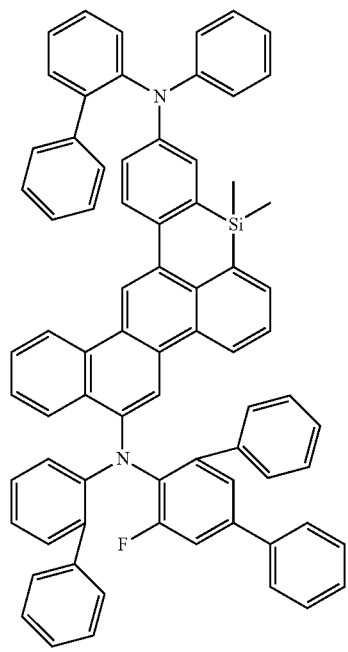
60
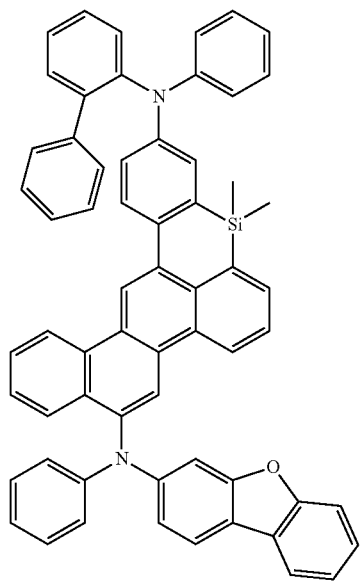

-continued
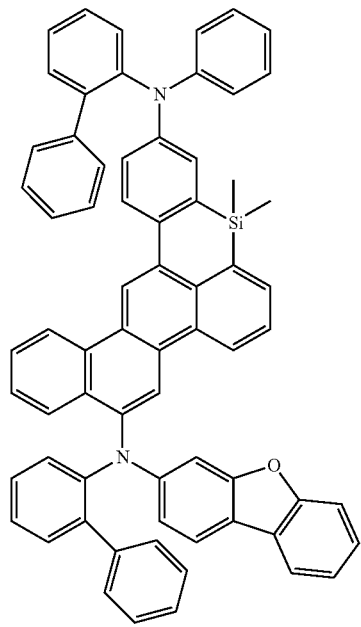
61
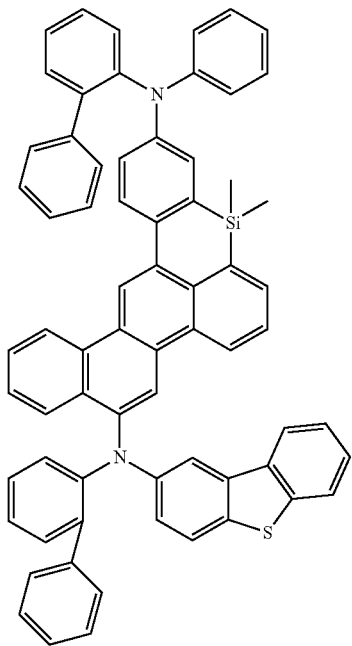
62
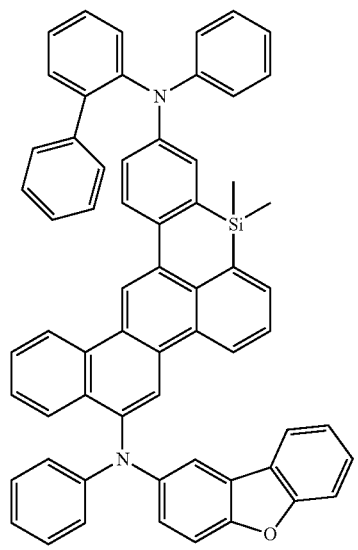
63
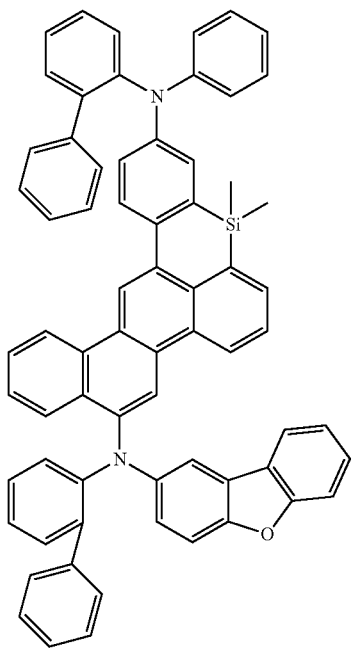
64

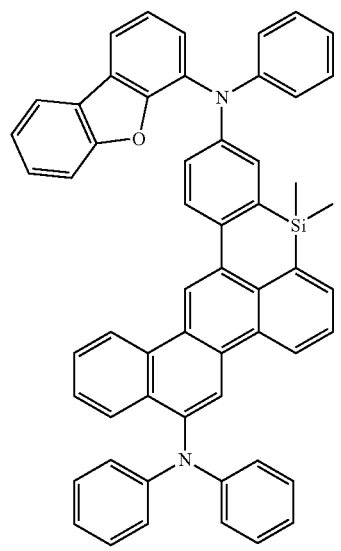
65
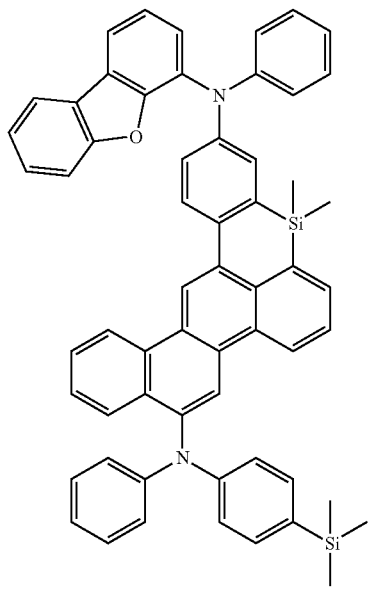
66
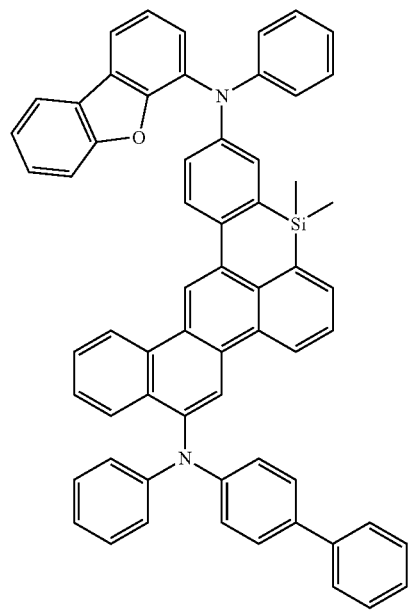
67
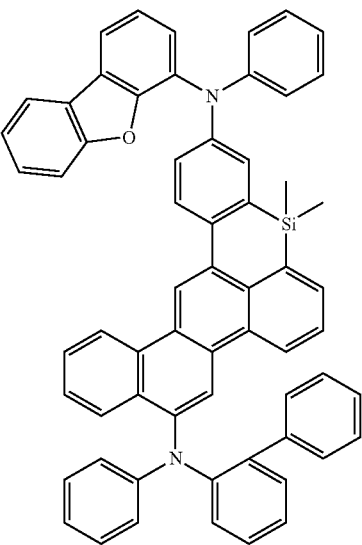
68

95
96
-continued
69
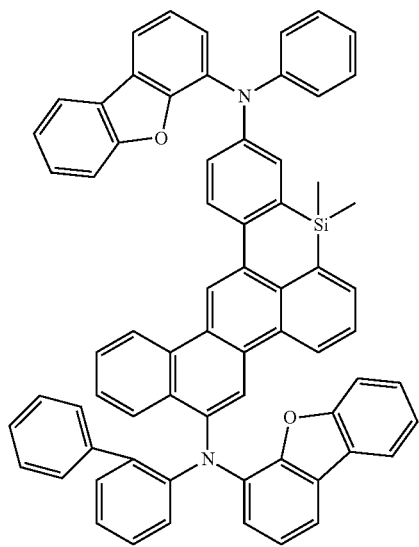
70
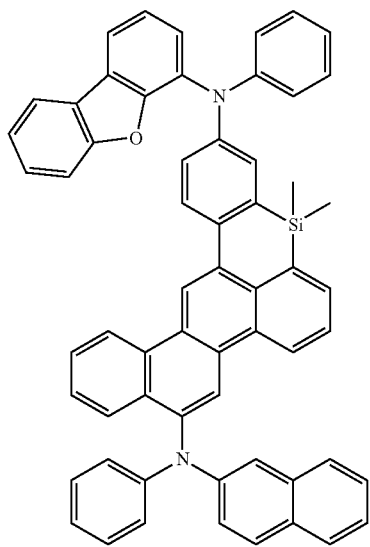
71
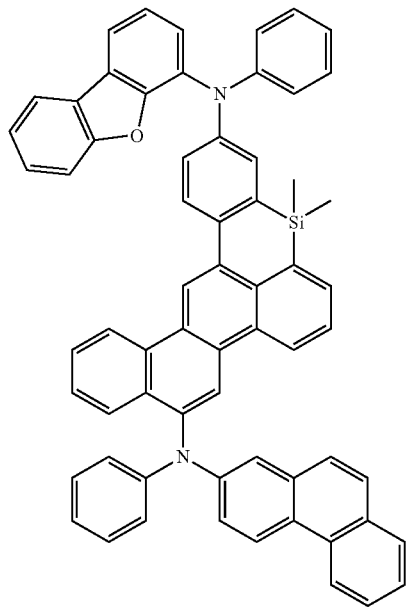
72
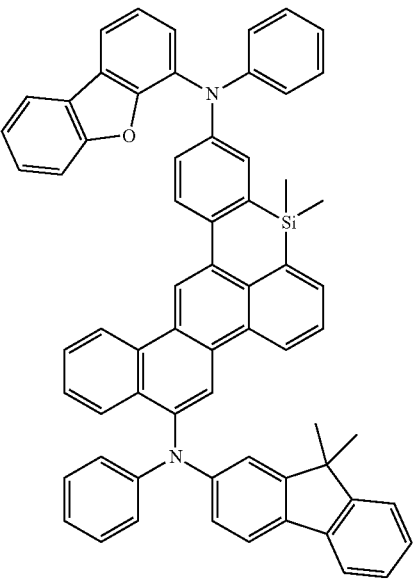

-continued
73
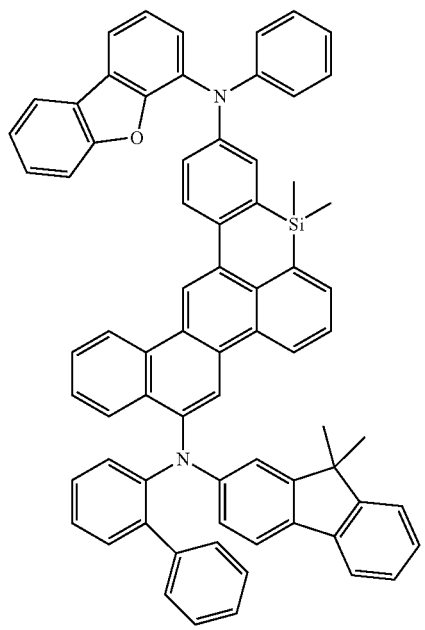
74
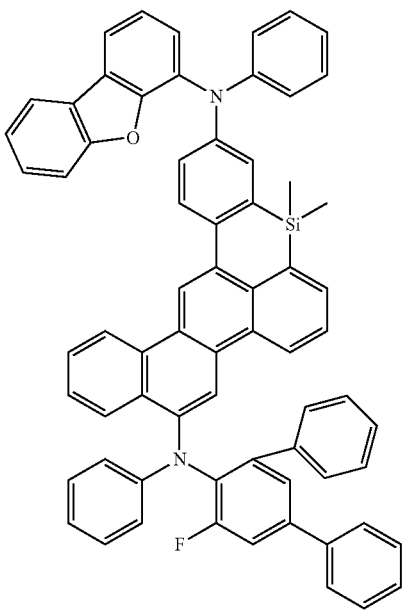
75
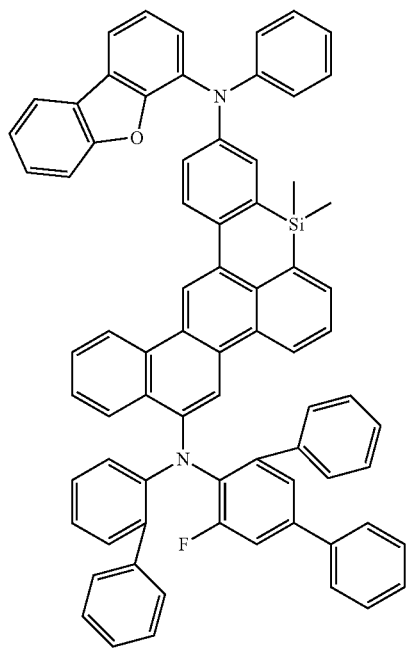
76
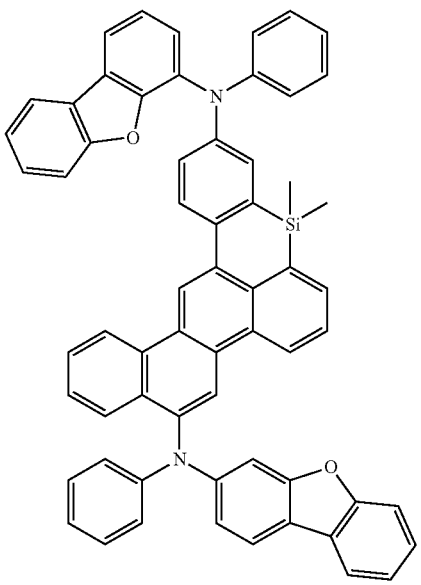

-continued
77
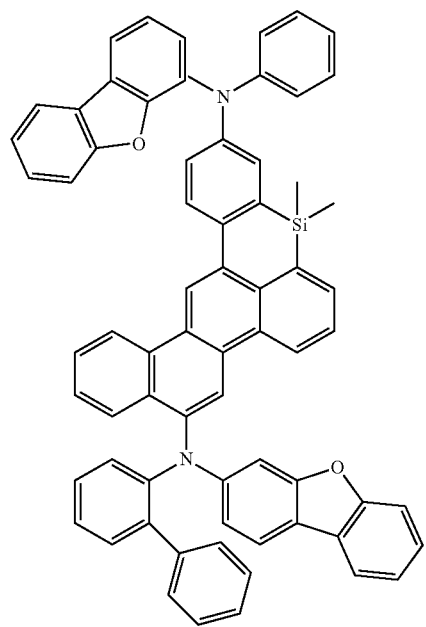
78
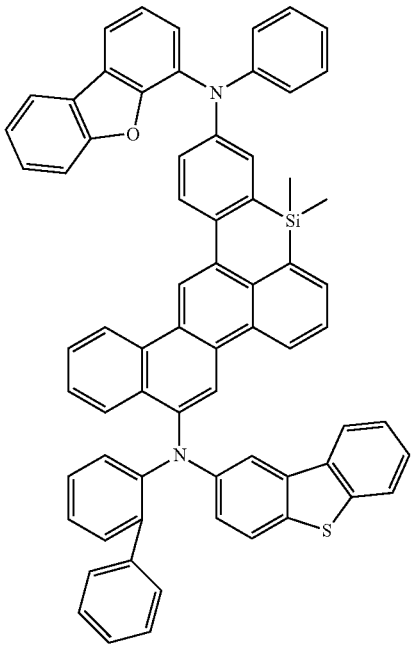
79
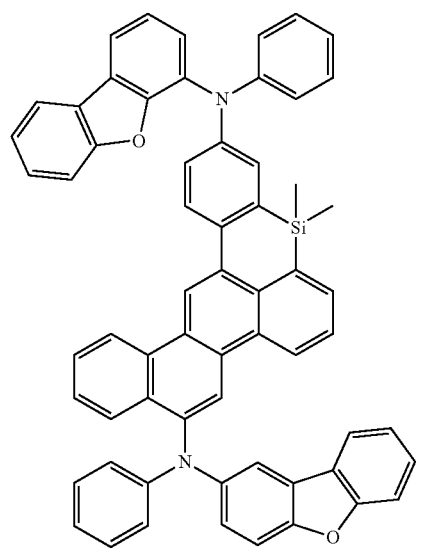
80
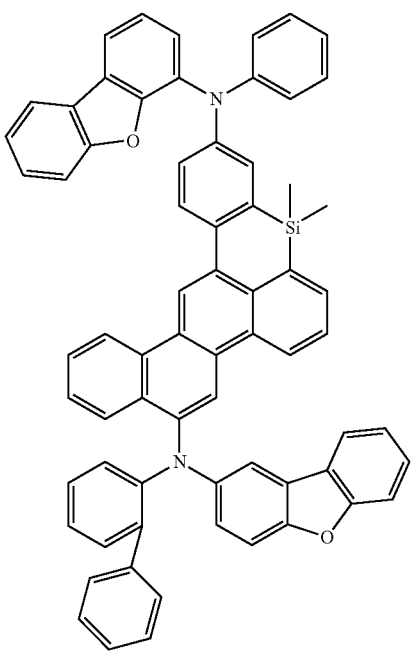

101
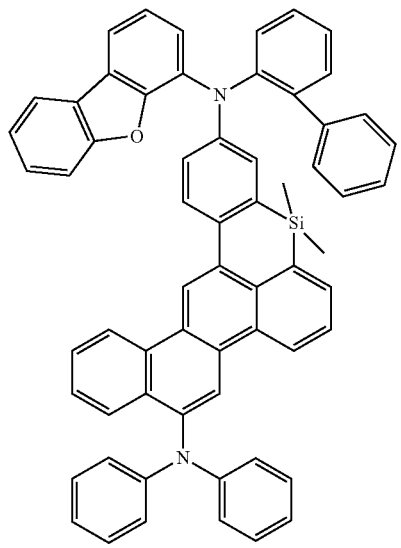
81
102
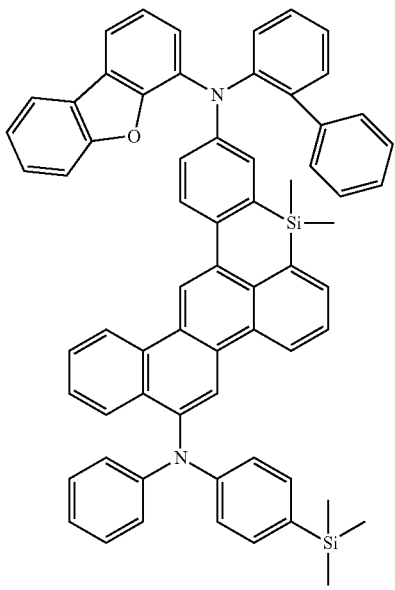
82
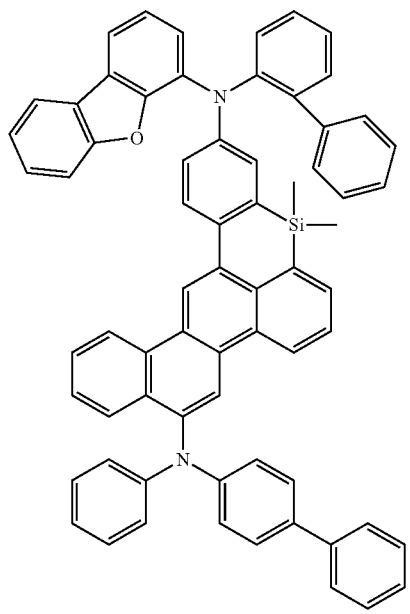
83
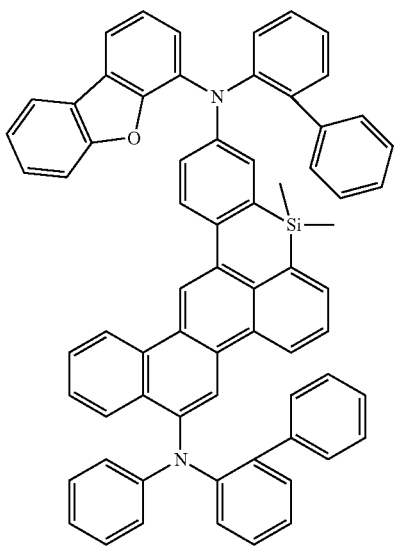
84

-continued
103
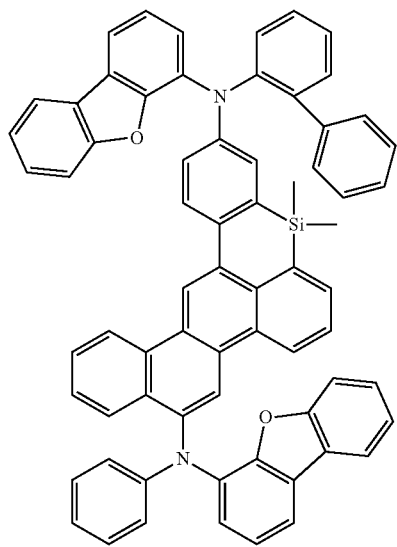
85
104
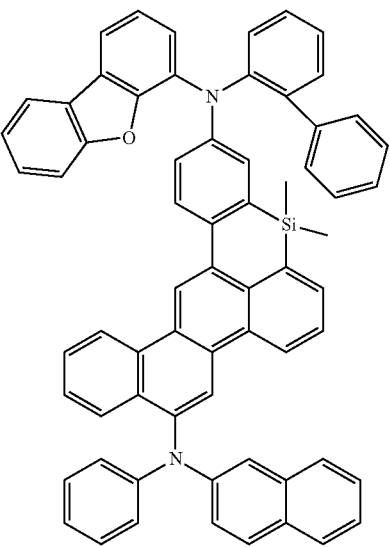
86
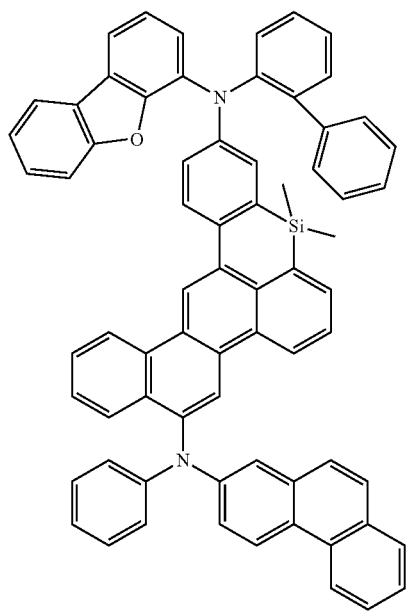
87
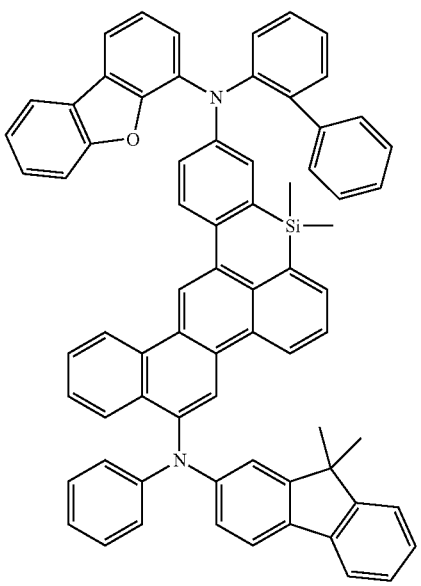
88

-continued
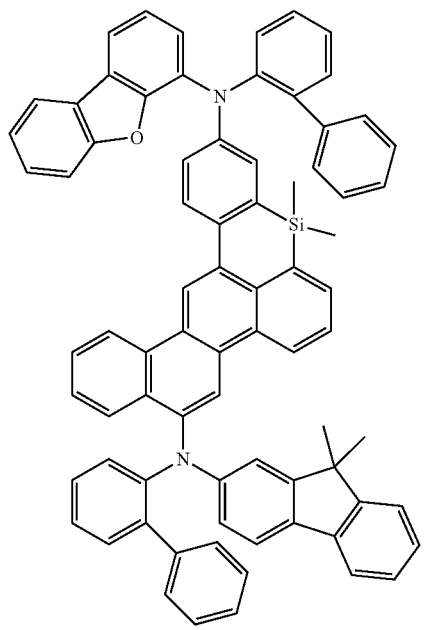
89
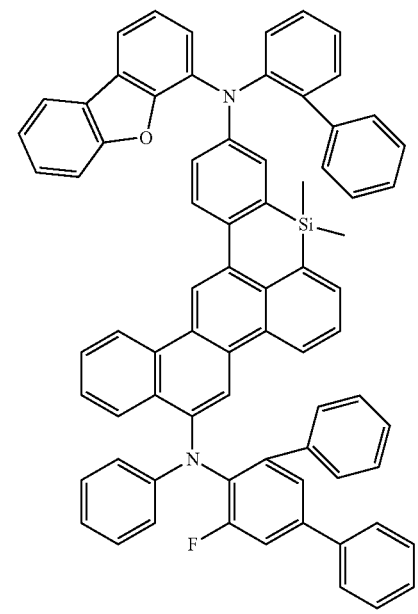
90
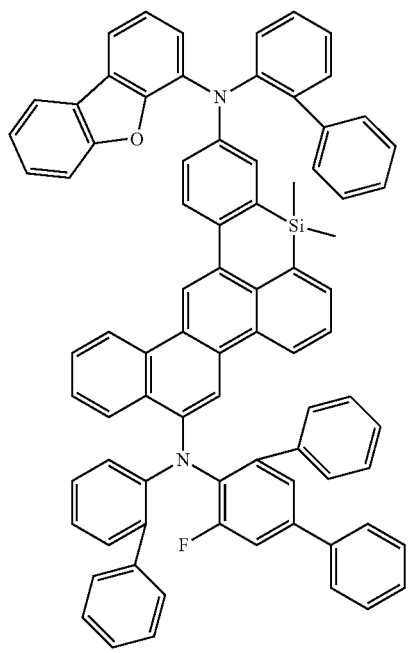
91
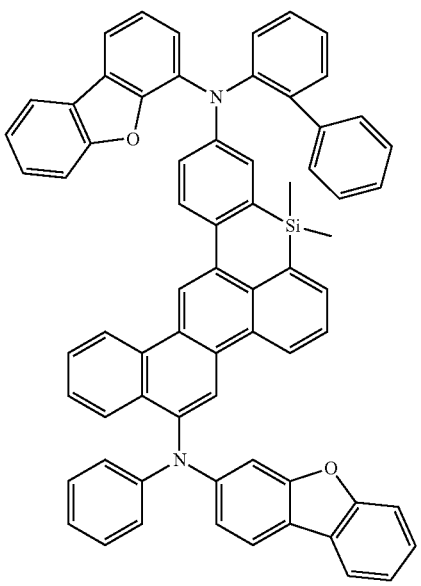
92

-continued
93
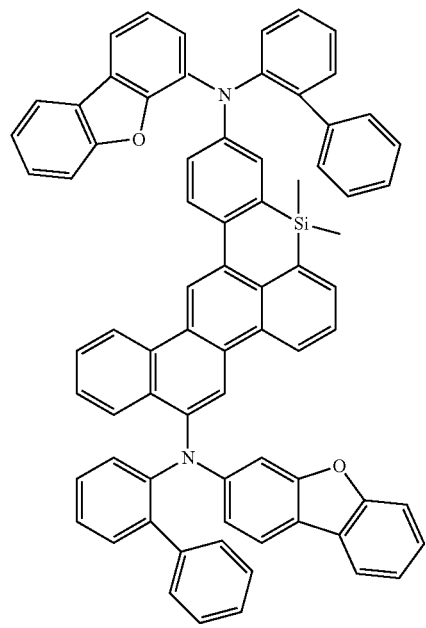
94
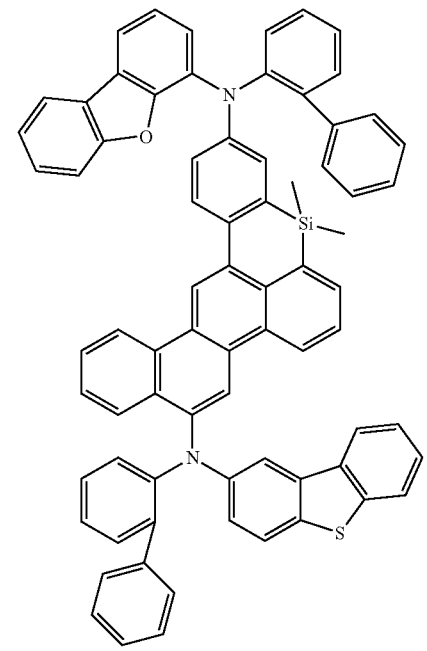
95
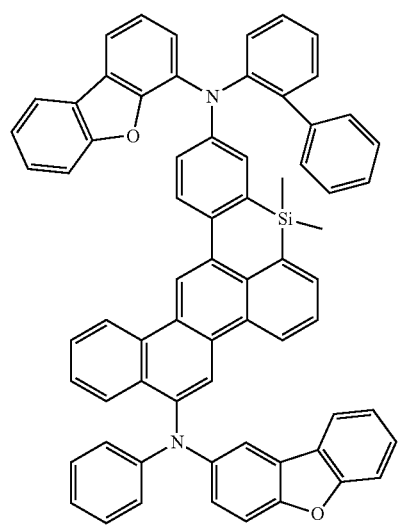
96
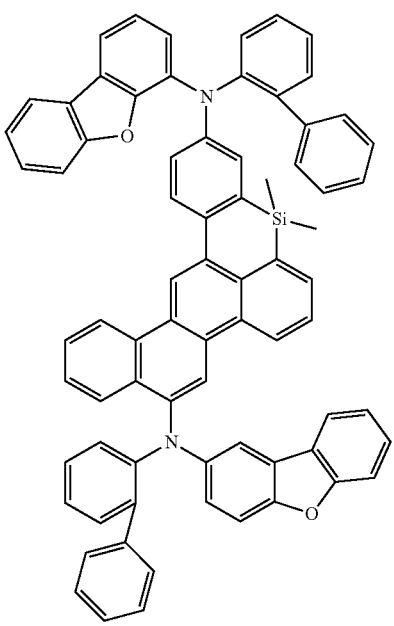

-continued
97
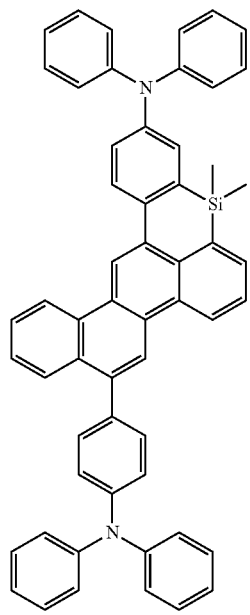
98
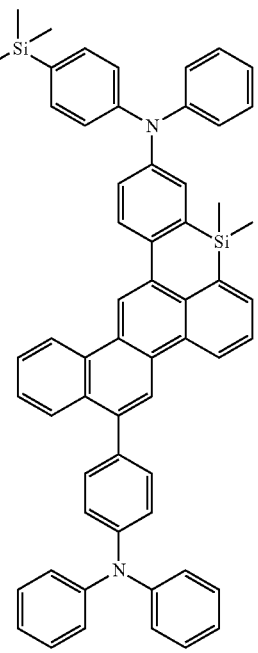
99
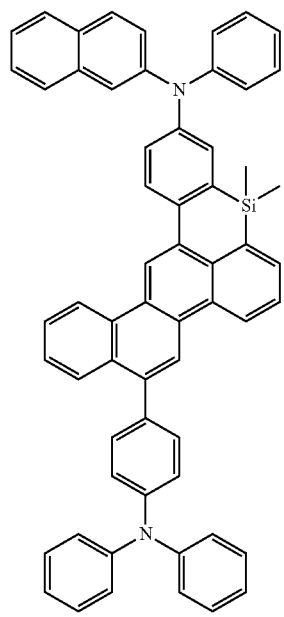
100
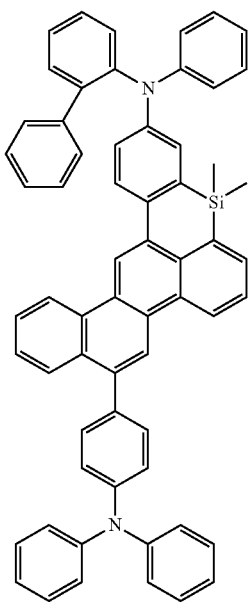

-continued
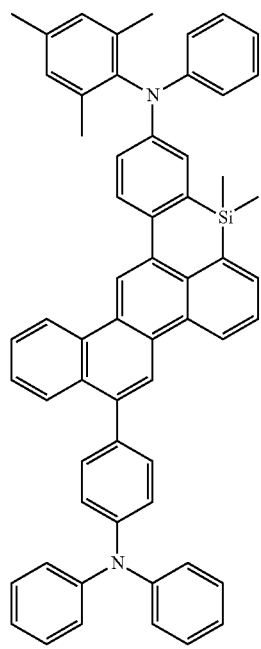
101
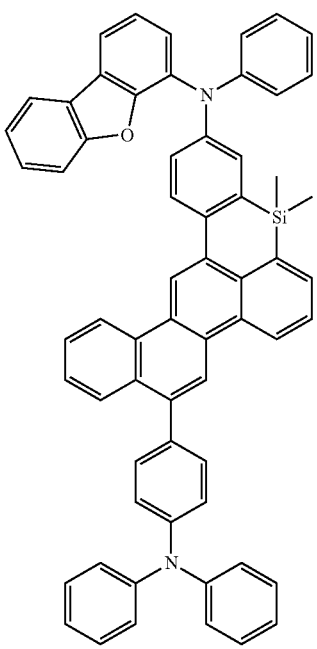
102
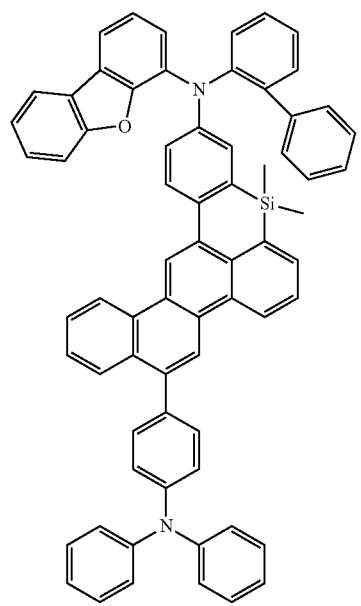
103
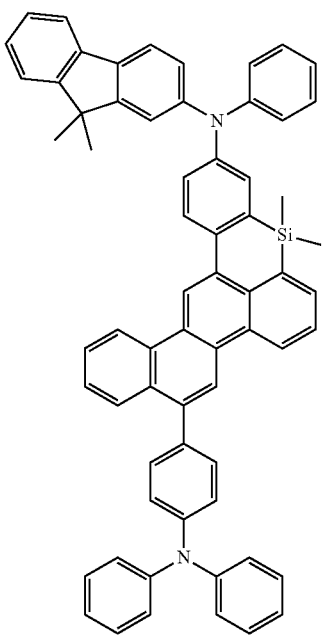
104

-continued
105
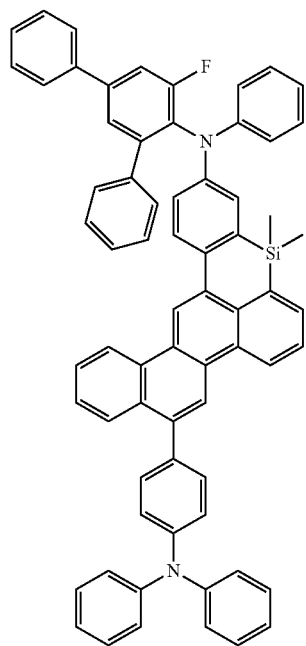
106
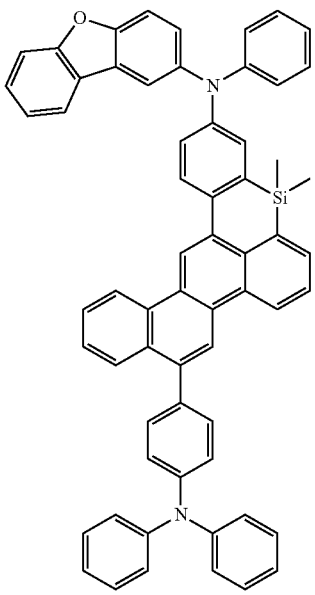
107
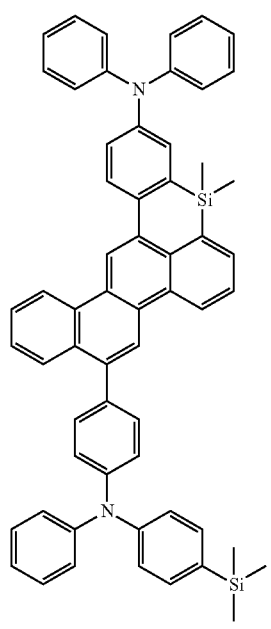
108
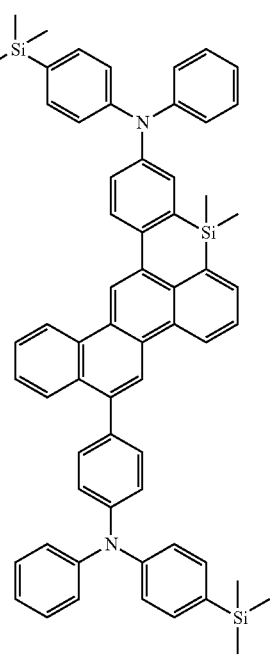

-continued
109
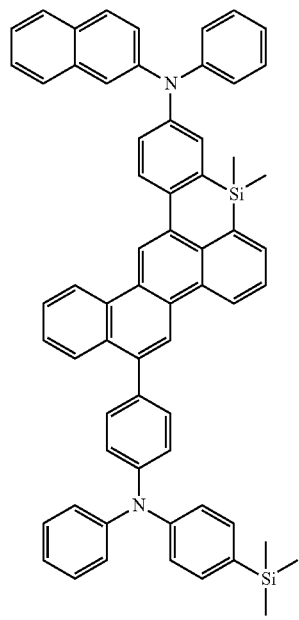
110
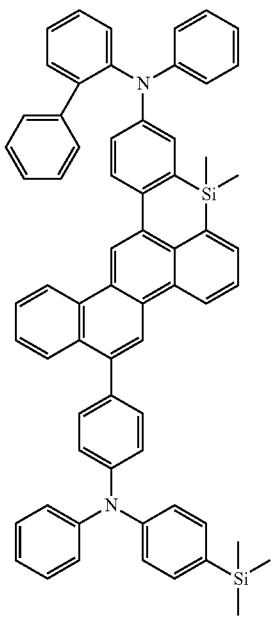
111
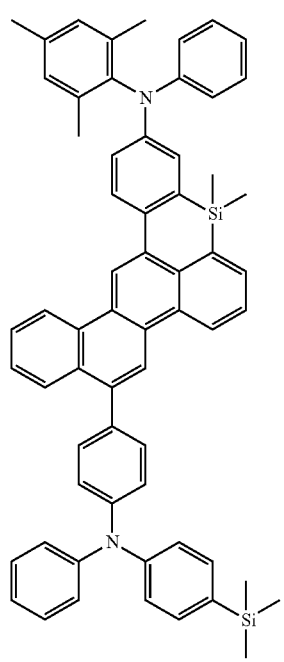
112
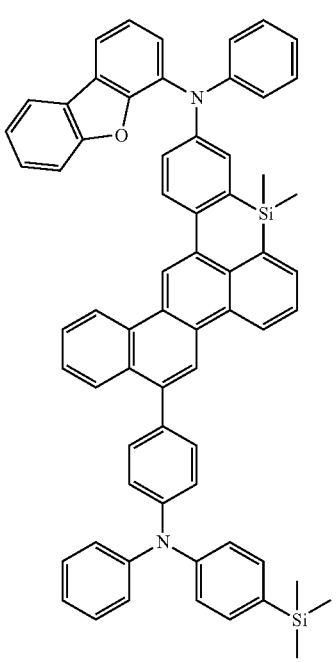

-continued
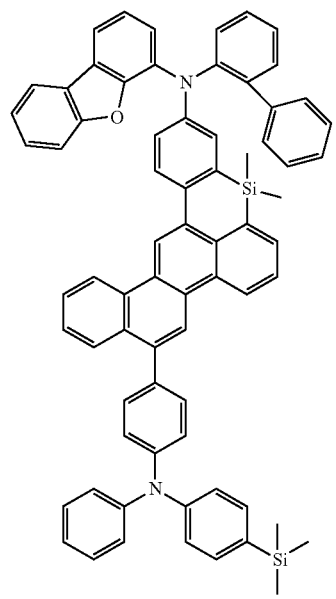
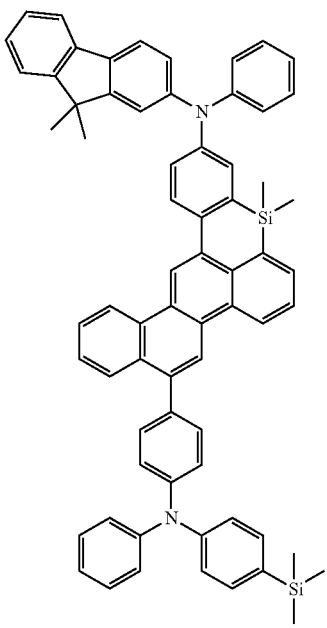
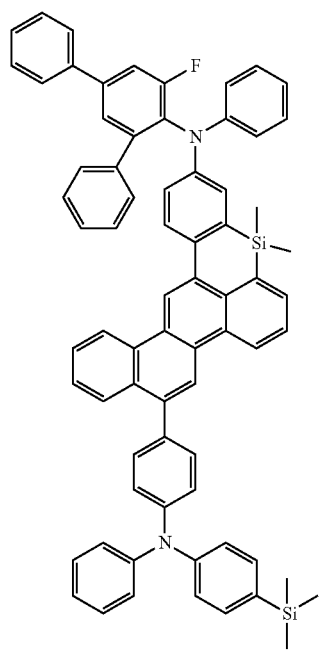

-continued
117
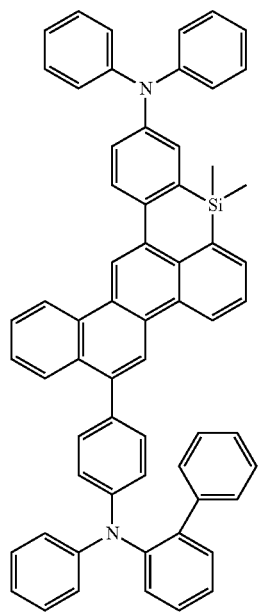
118
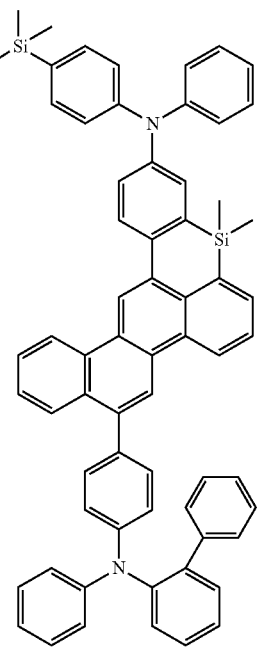
119
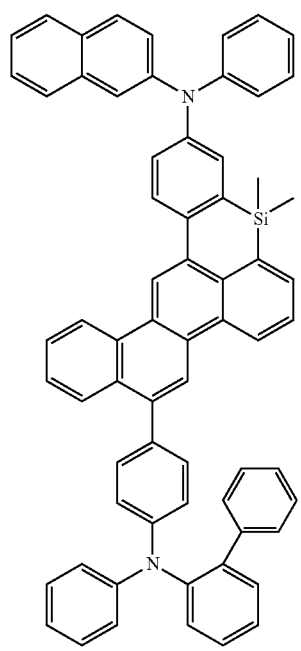
120
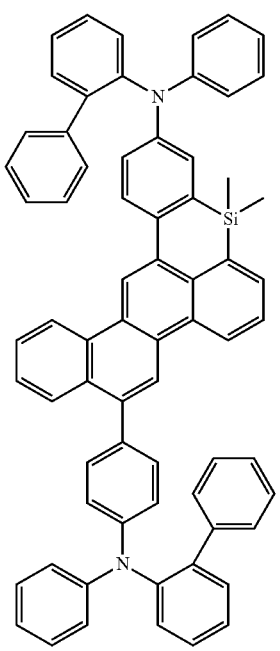

-continued
121
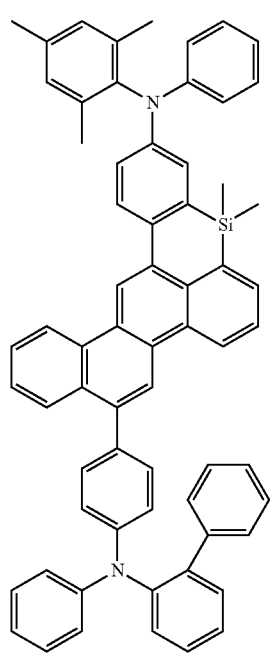
122
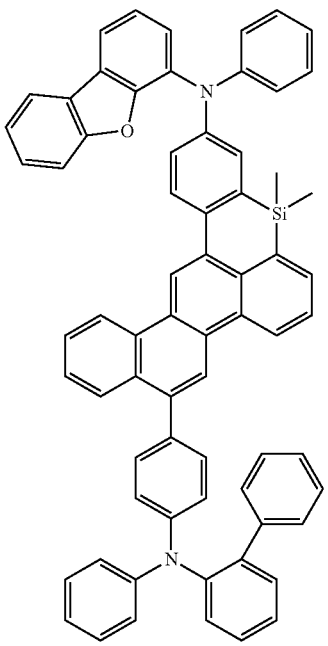
123
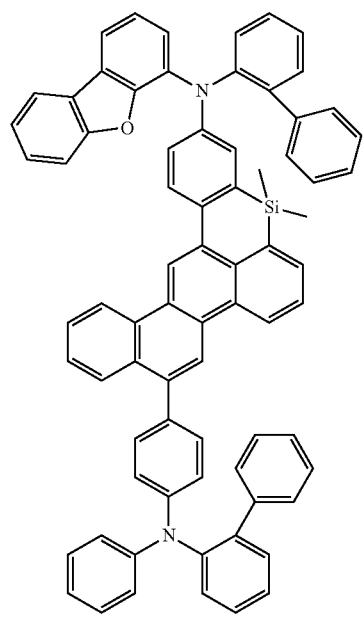
124
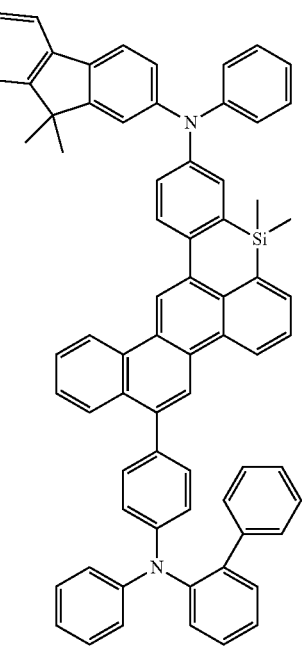

123
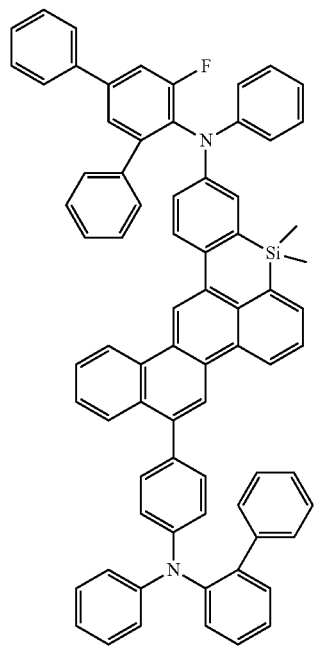
124
-continued
125
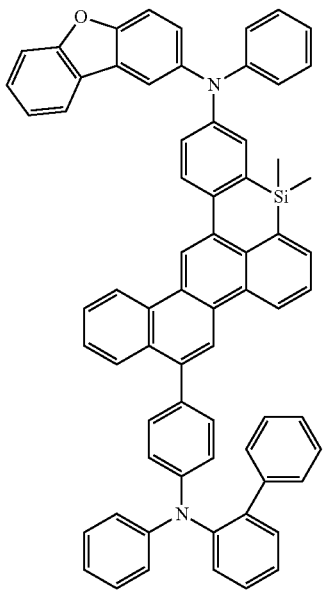
126
127
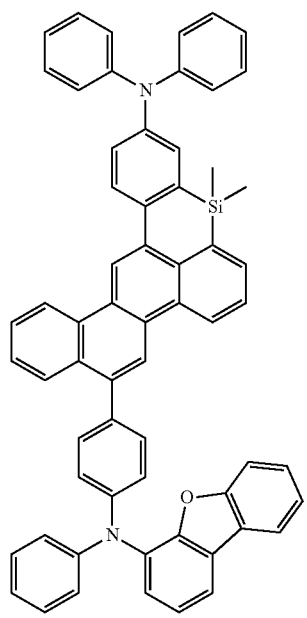
128
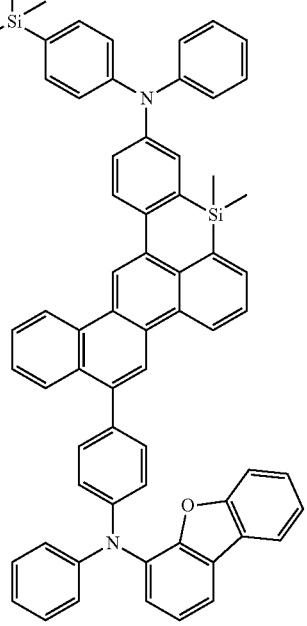

-continued
125
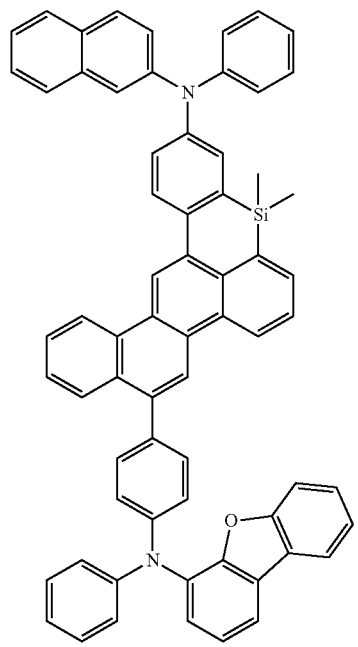
129
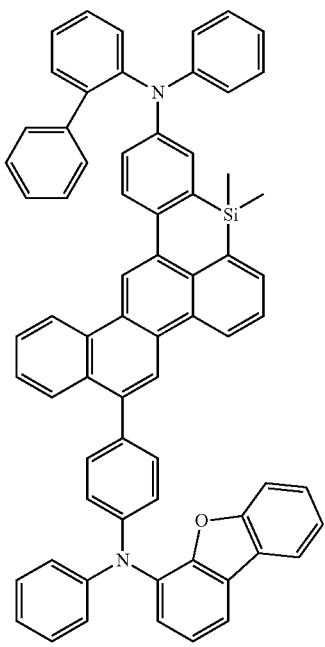
126
130
131
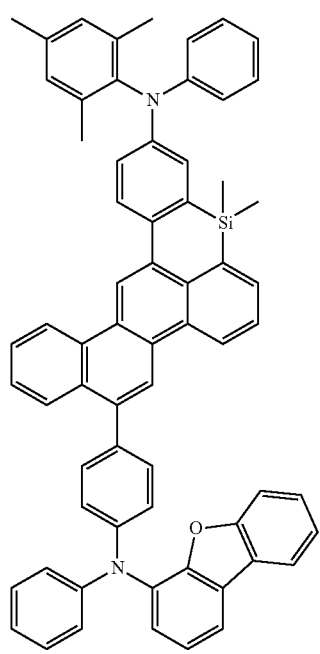
132
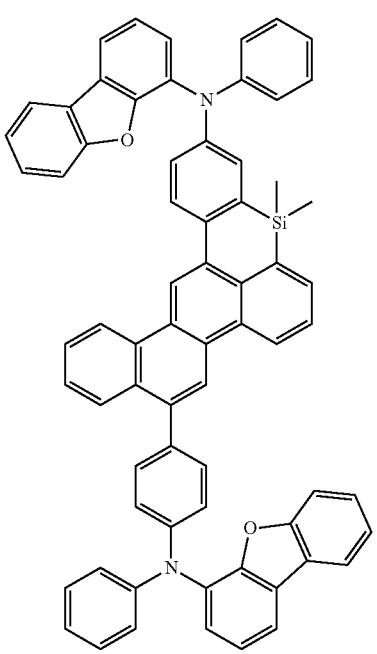

127 128
-continued
133 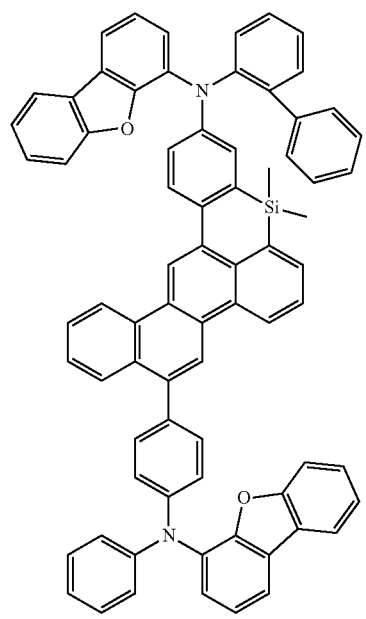 134 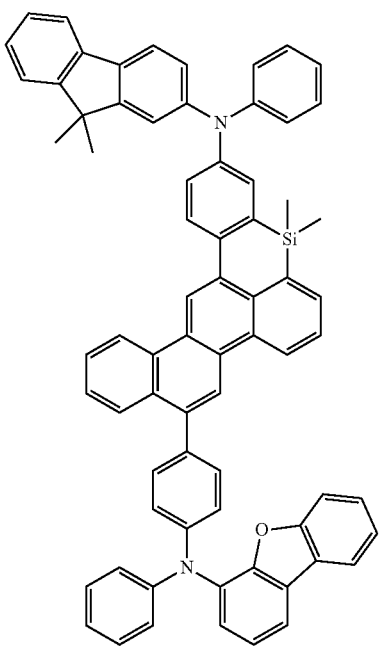
135 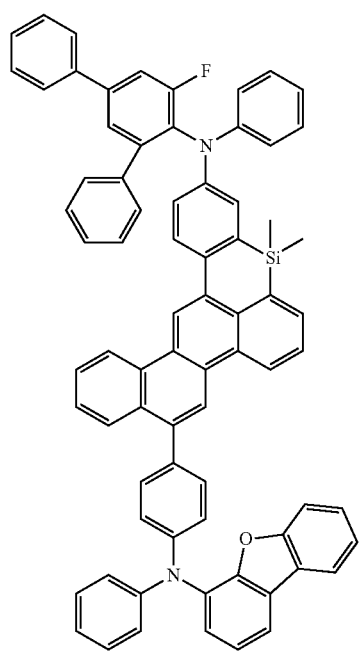 136 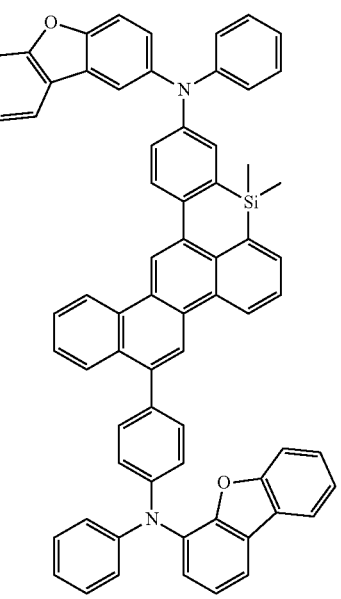

-continued
129
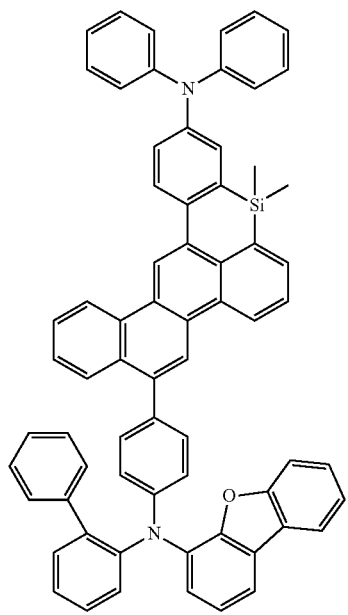
137
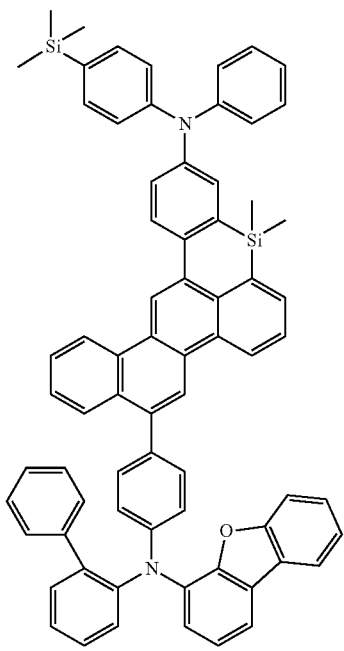
138
139
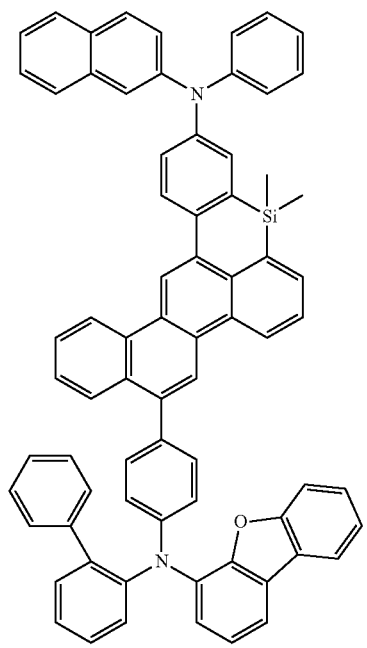
140
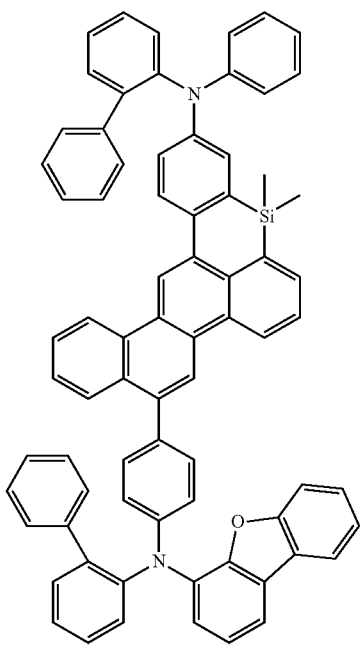

-continued
131
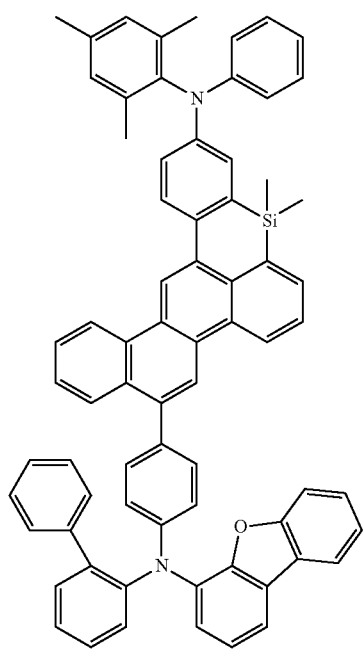
141
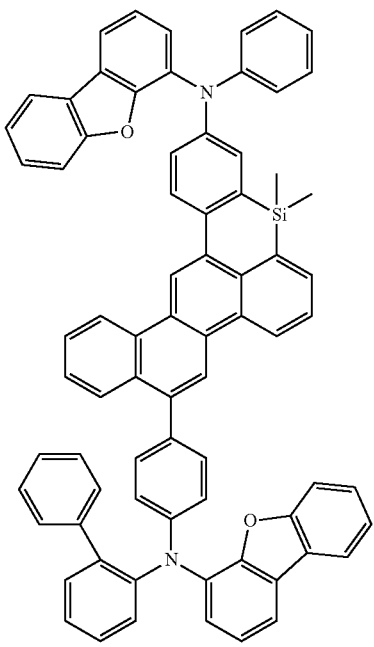
142
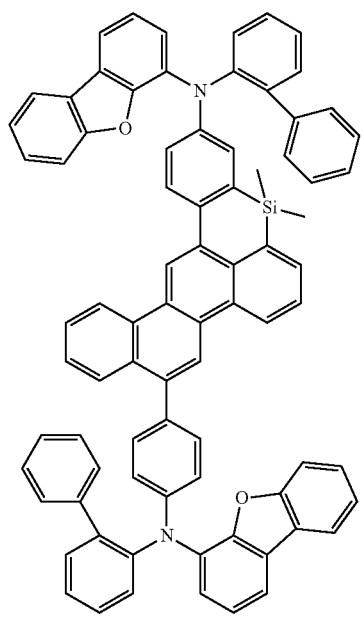
143
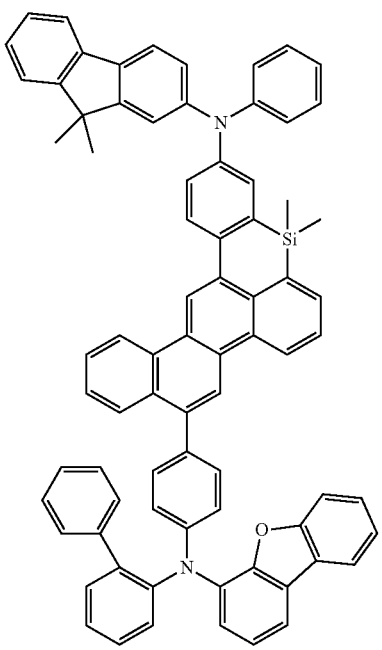
144

-continued
145
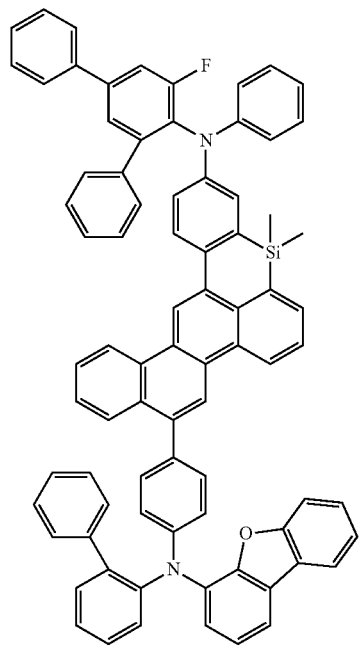
146
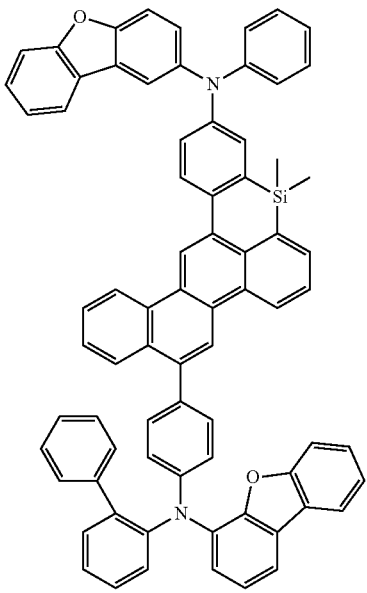
147
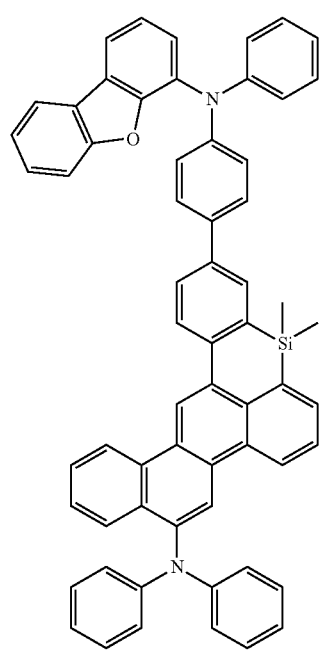
148
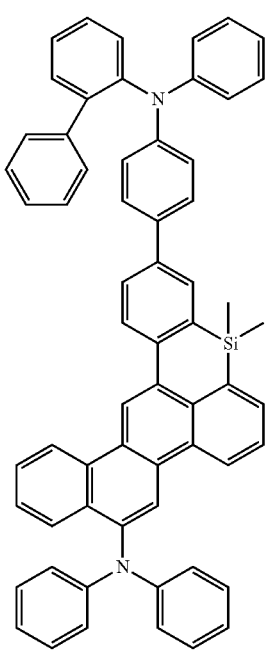

-continued
135
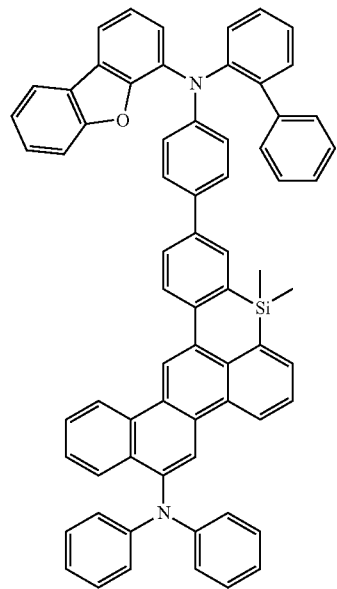
149
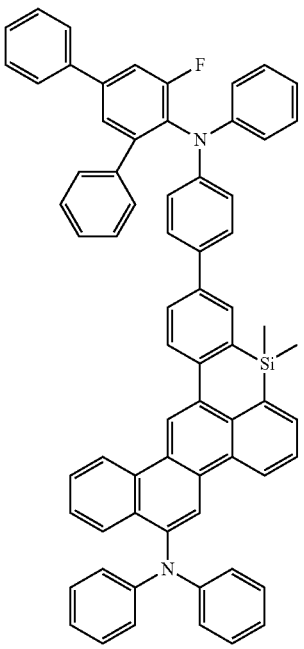
136
150
151
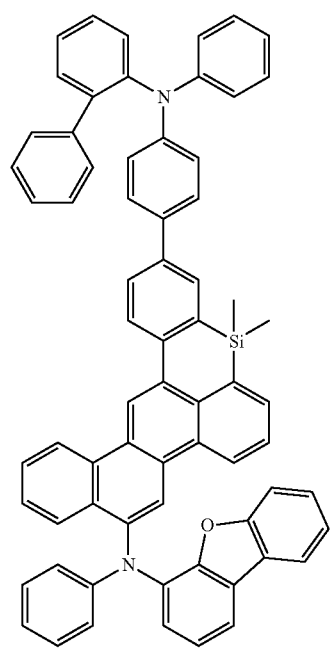
152
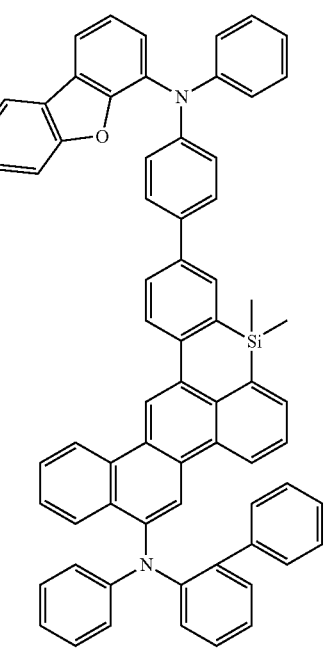

-continued
153
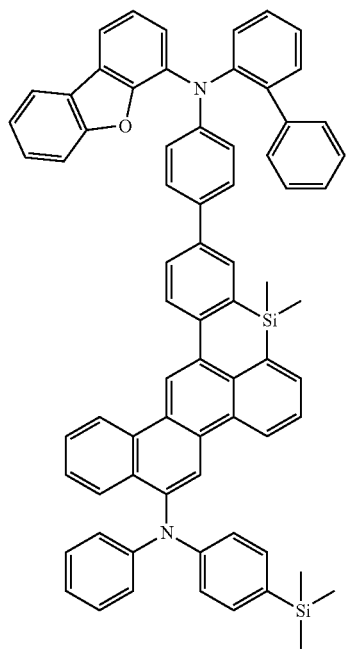
154
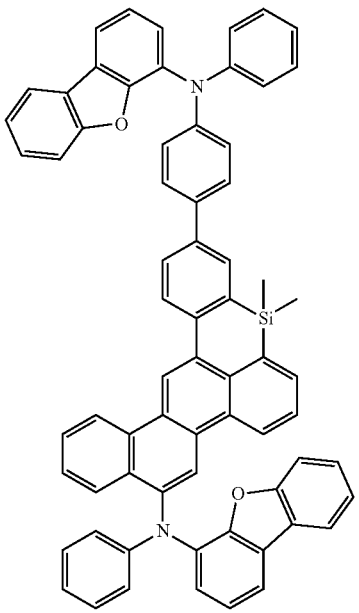
155
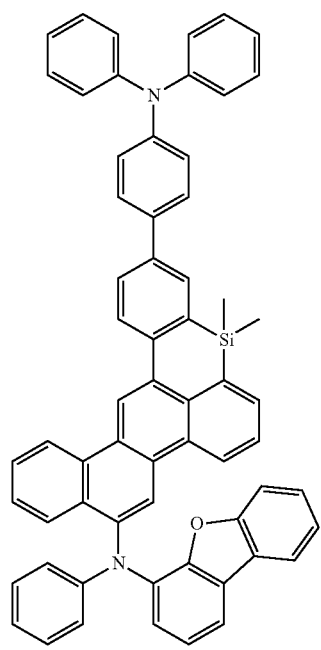
156
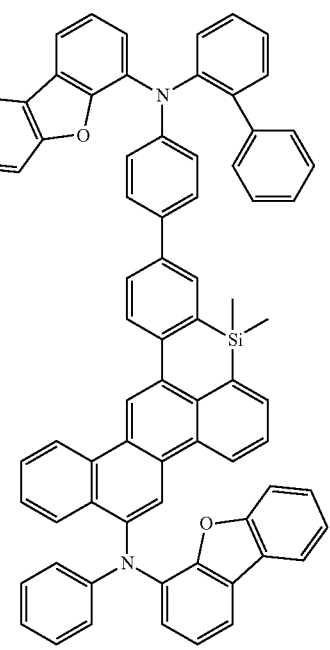

-continued
157 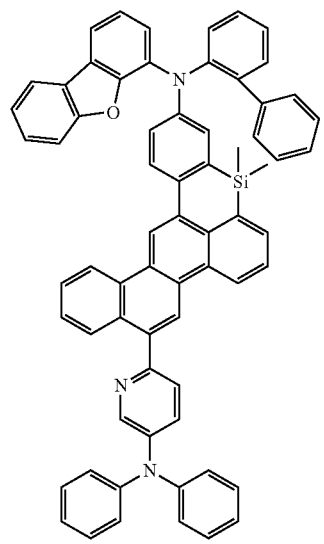
158 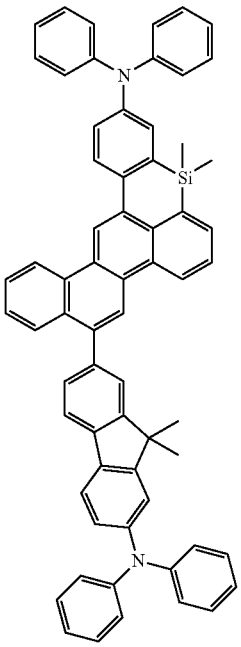
159 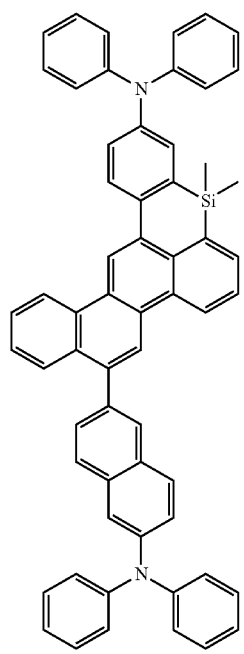
160 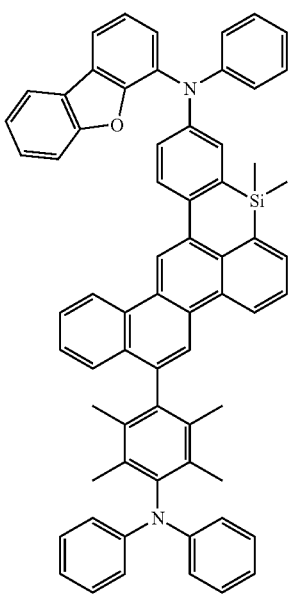

-continued
161
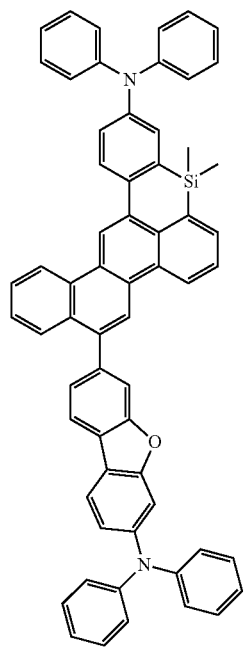
162
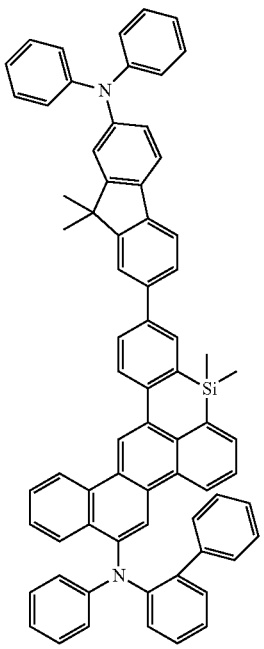
163
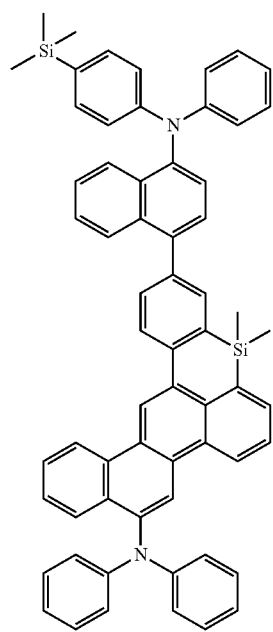
164
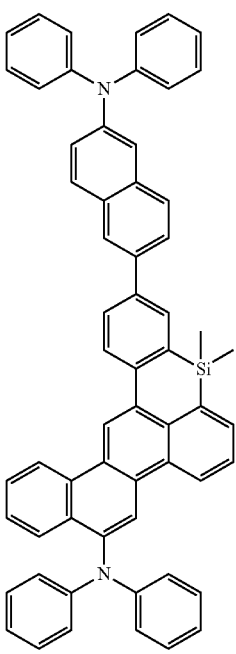

165
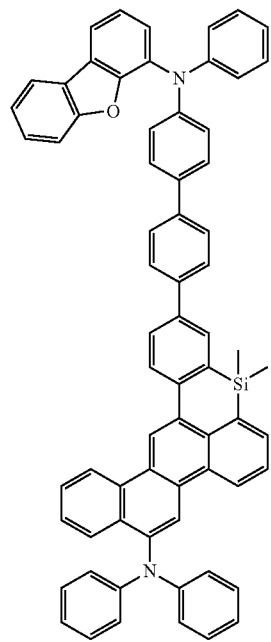
166
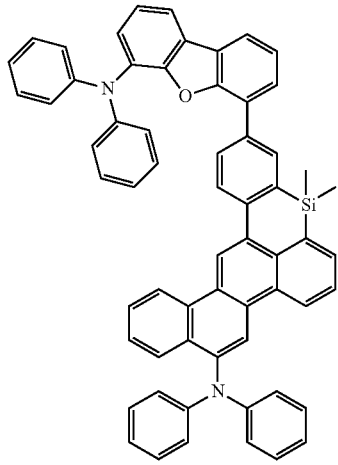
167
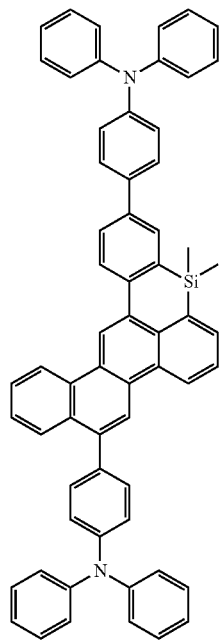
168
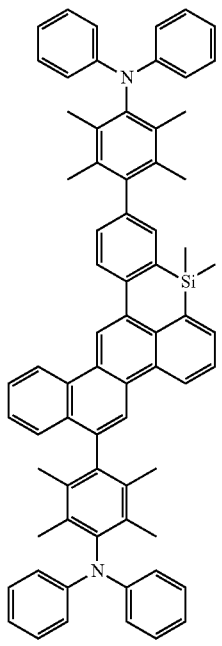

-continued
169
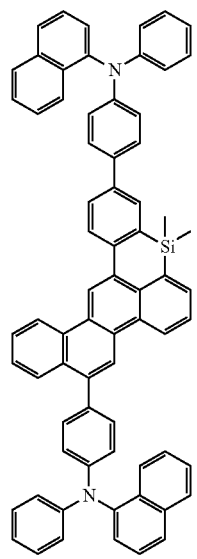
170
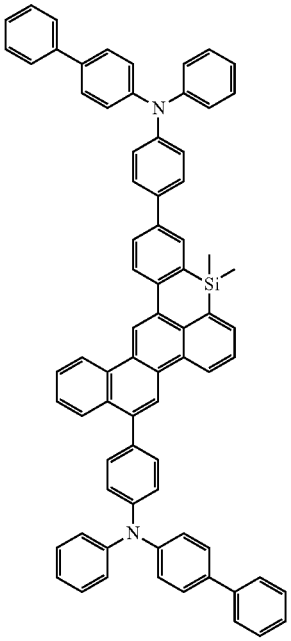
171
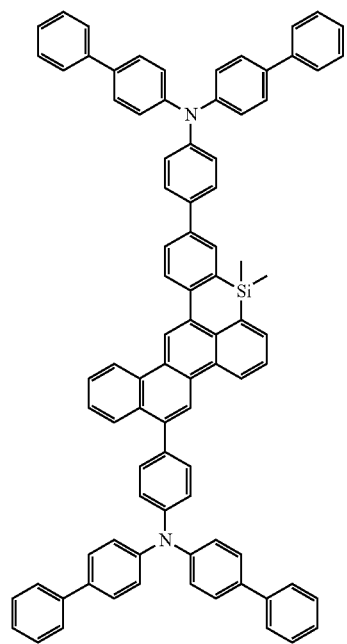
172
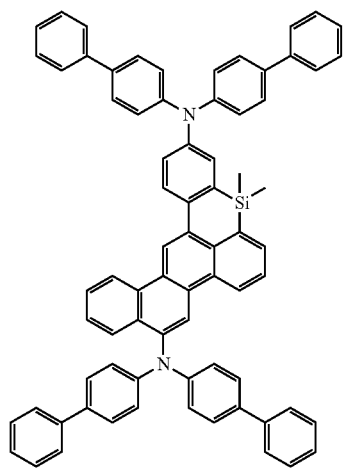

147 148
-continued
173 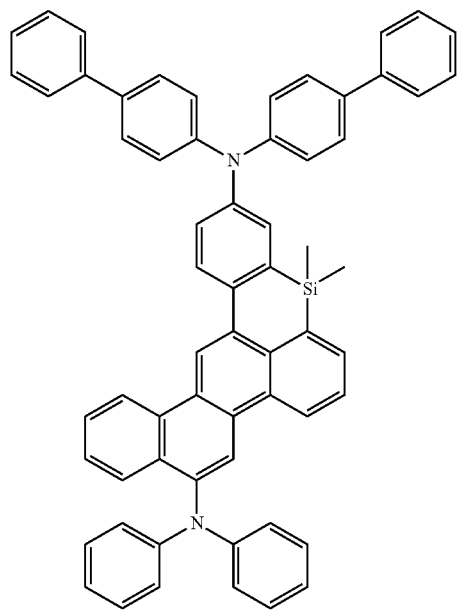 174 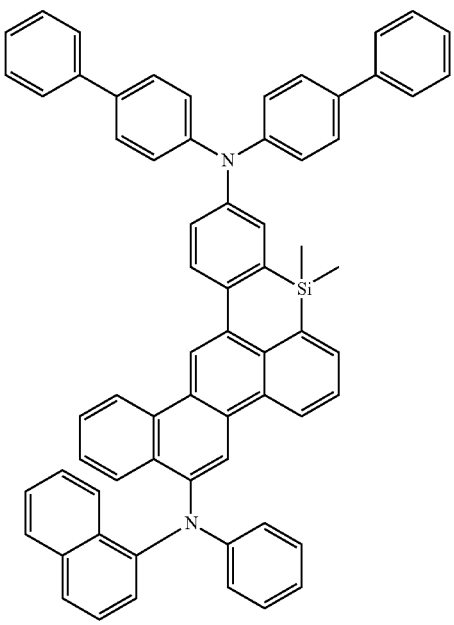
175 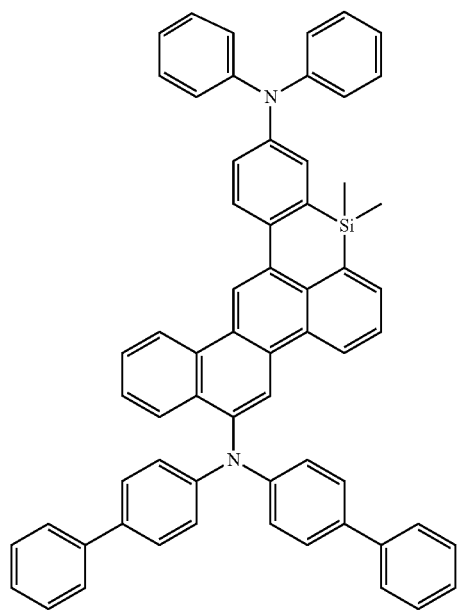 176 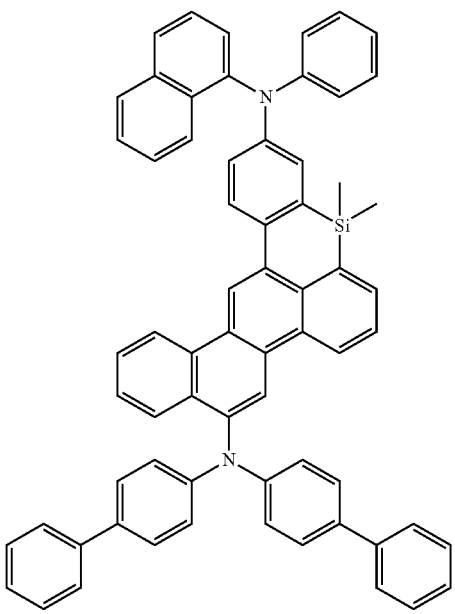

-continued
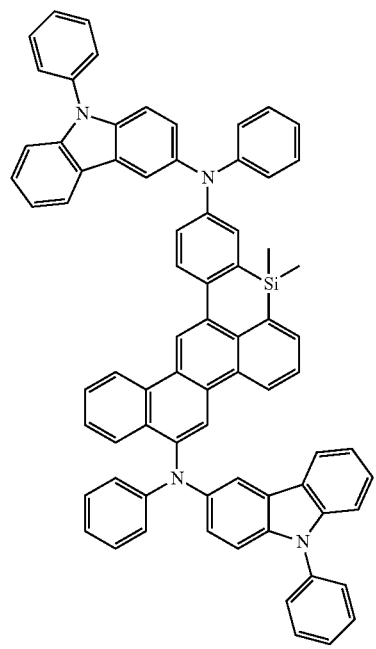
177
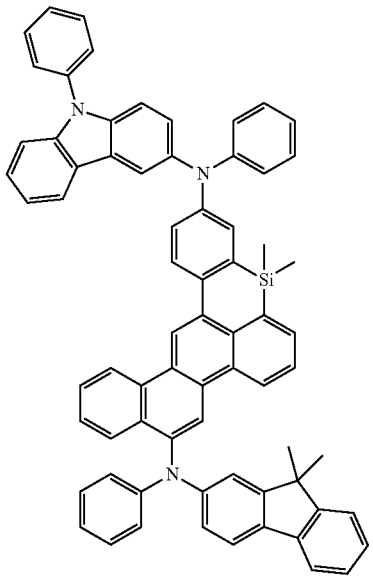
178
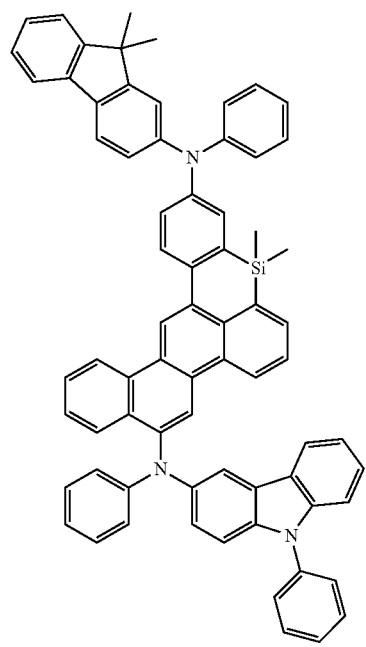
179
180

-continued
181 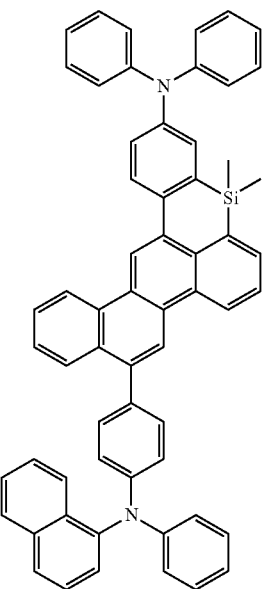
182 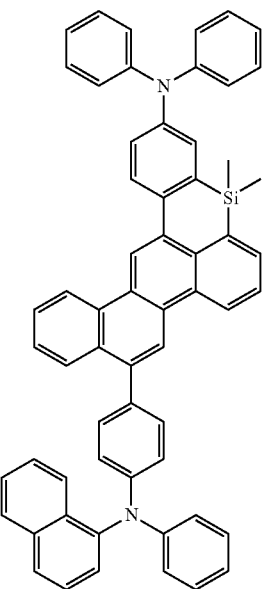
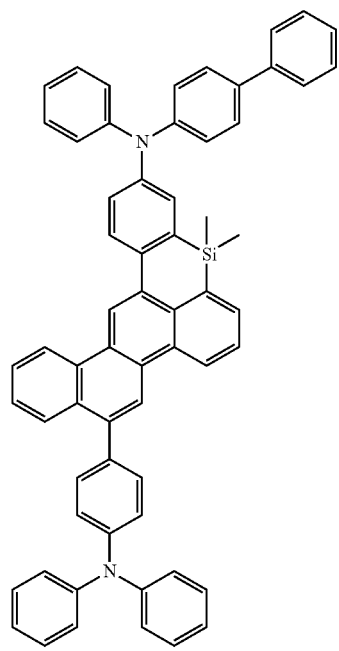
183 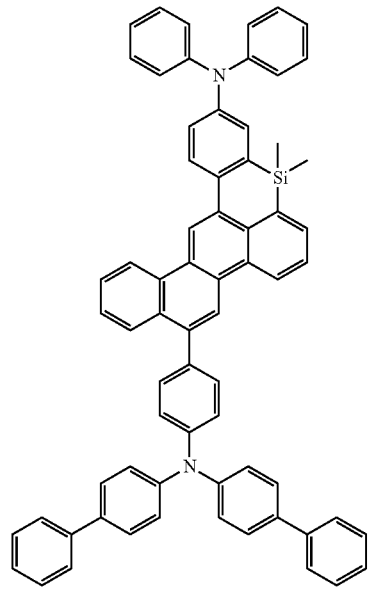
184 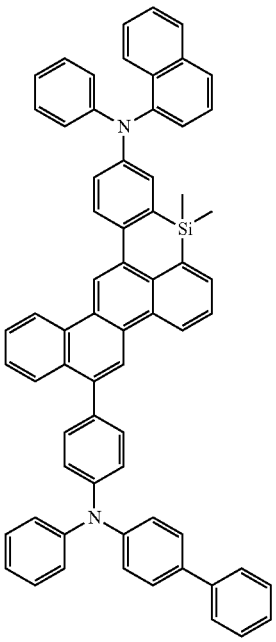

-continued
153
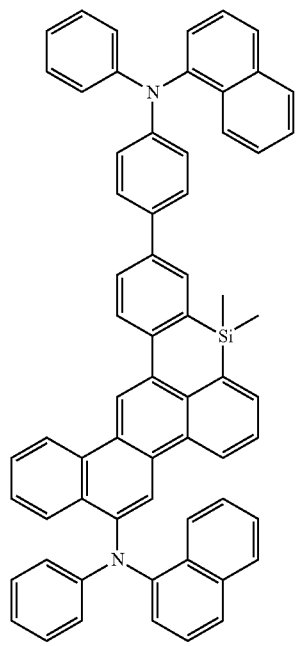
185
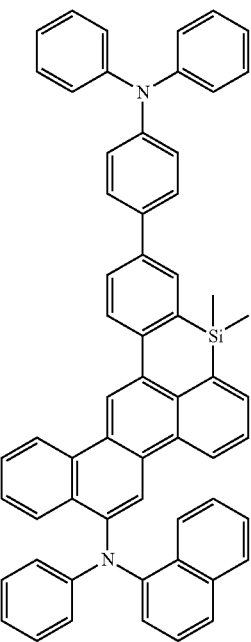
186
187
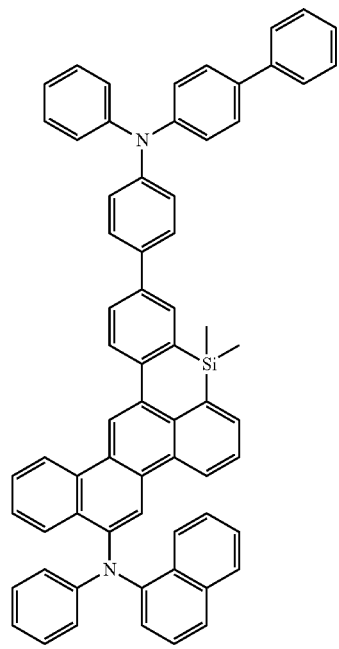
188

-continued
| 189 | 190 |
|---|---|
| 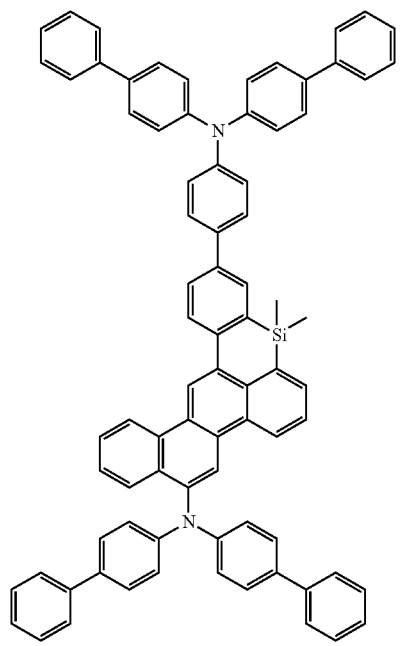 | 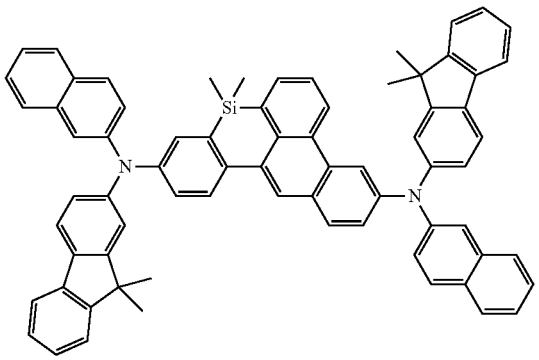 |
| 191 | 192 |
| 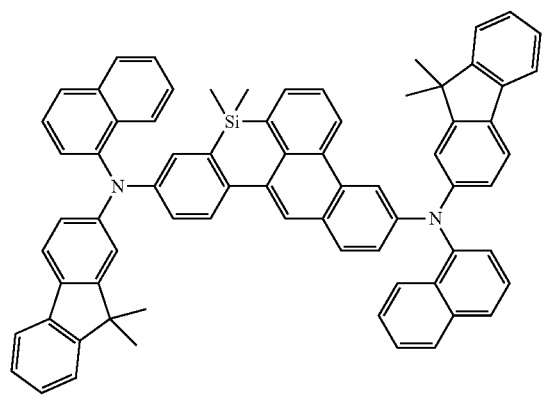 | 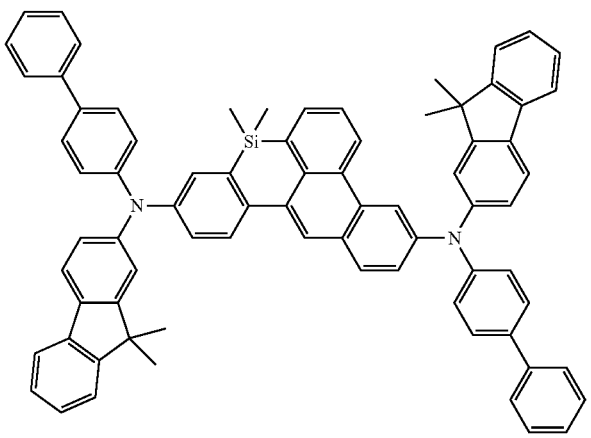 |
| 193 | 194 |
| 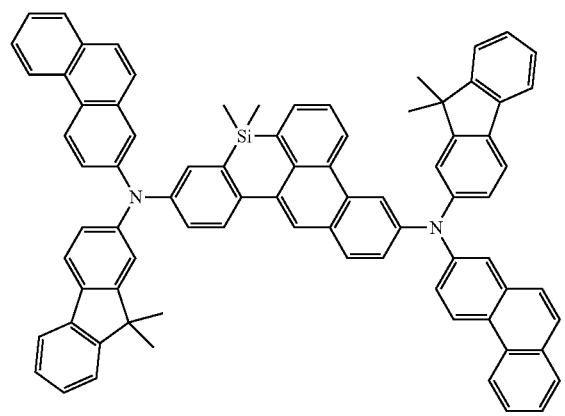 | 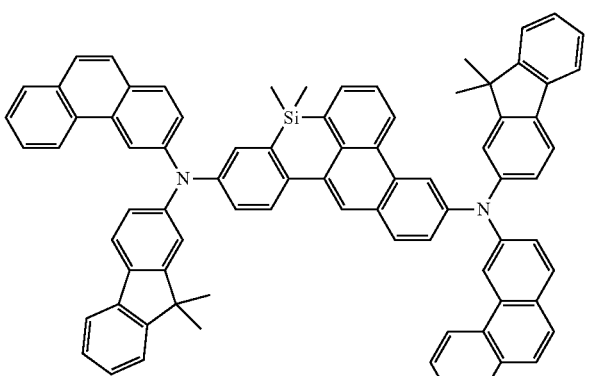 |

-continued
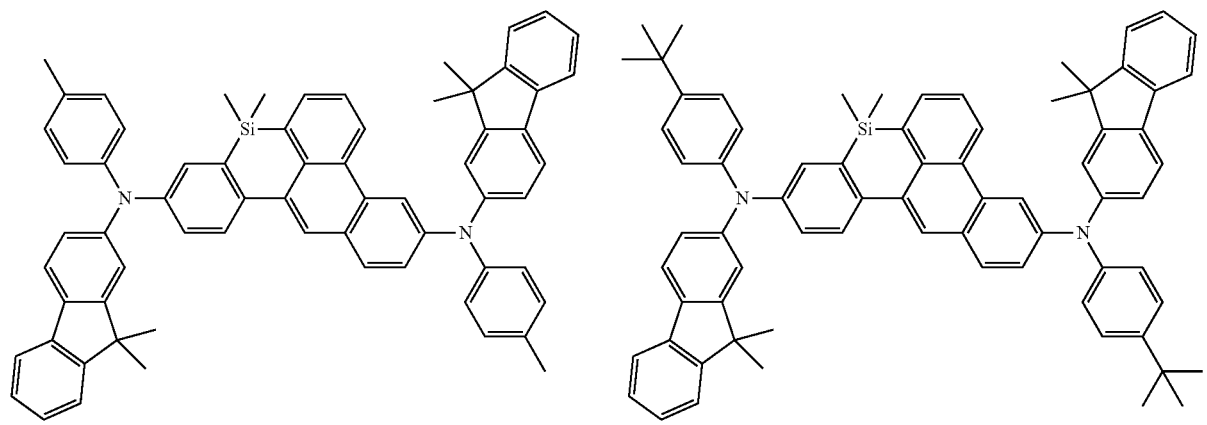
195
196
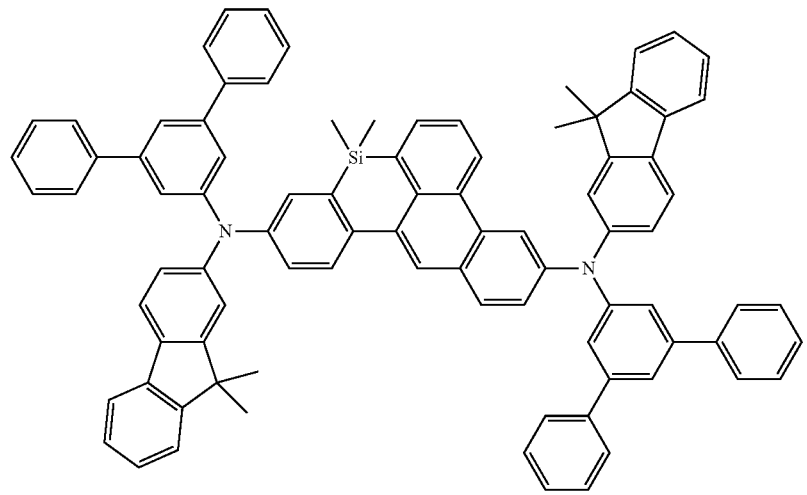
197
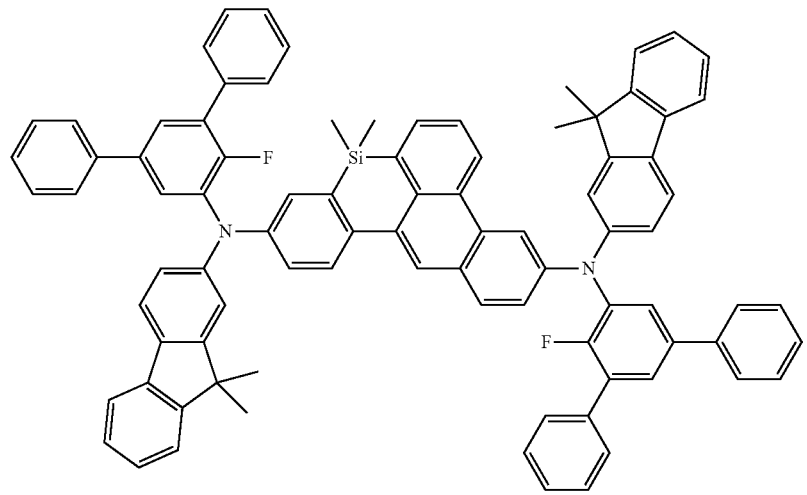
198

199
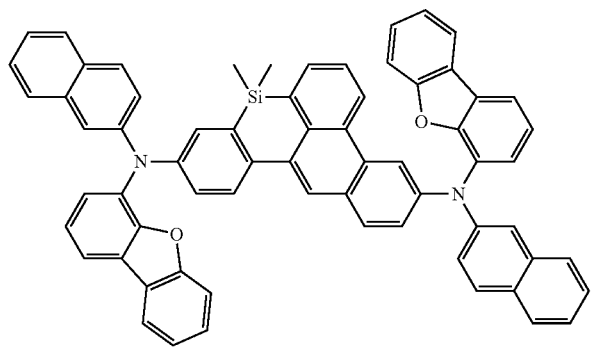
200
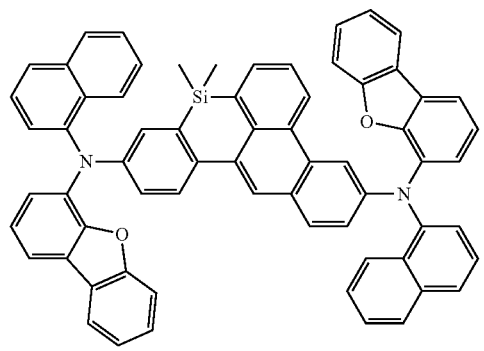
201
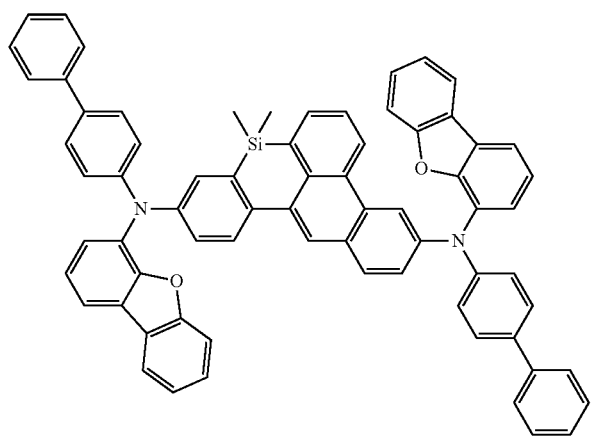
202
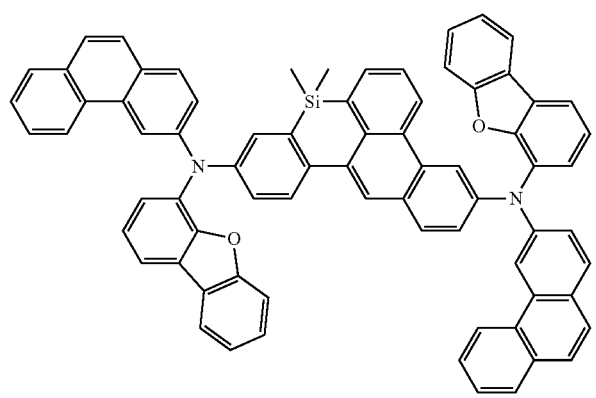
203
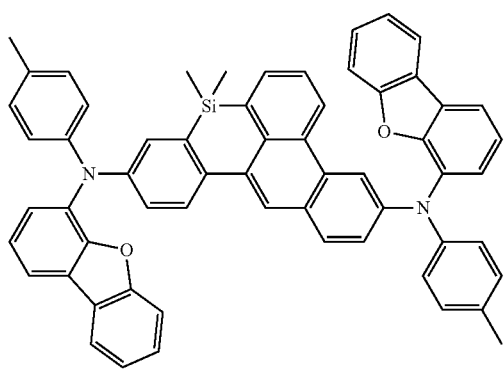
204
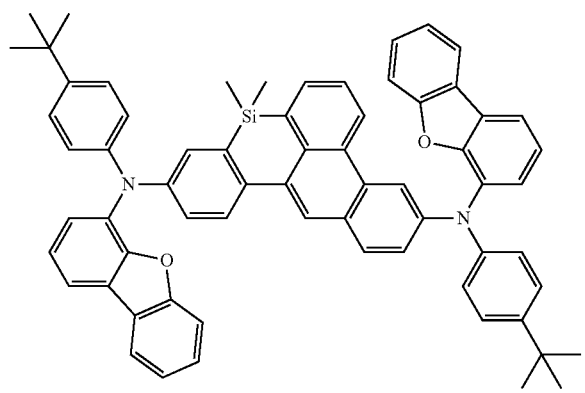

205
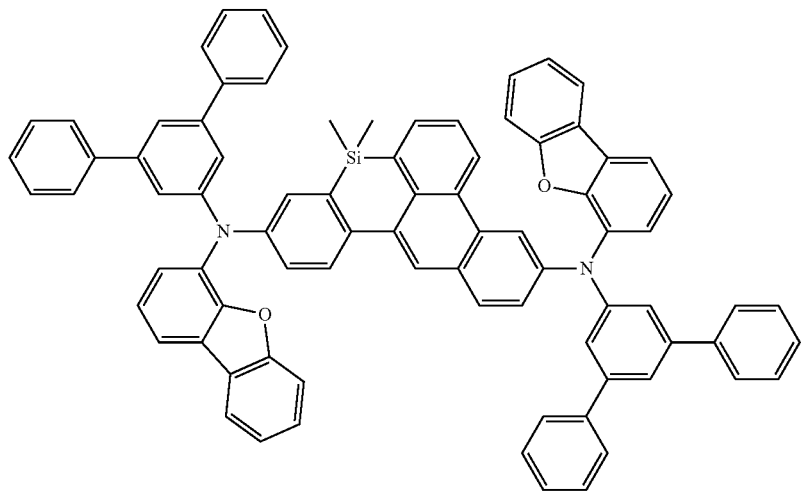
206
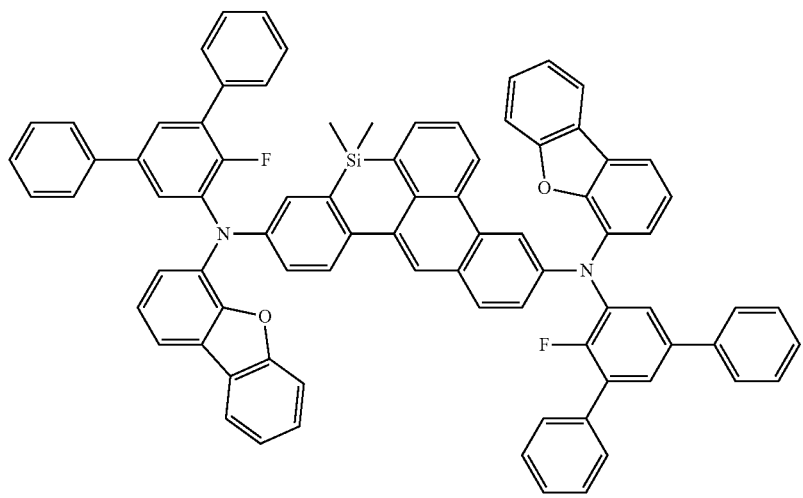
207
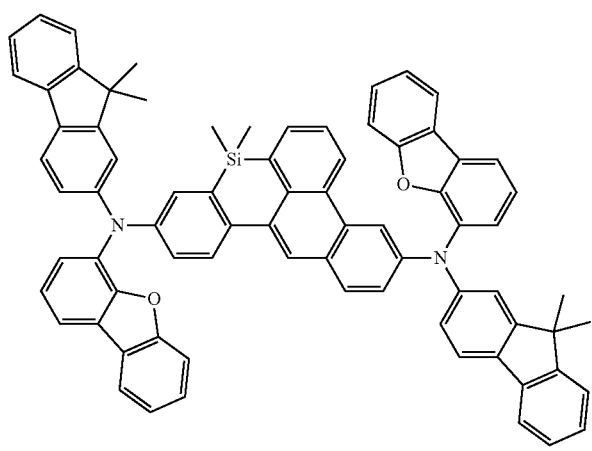

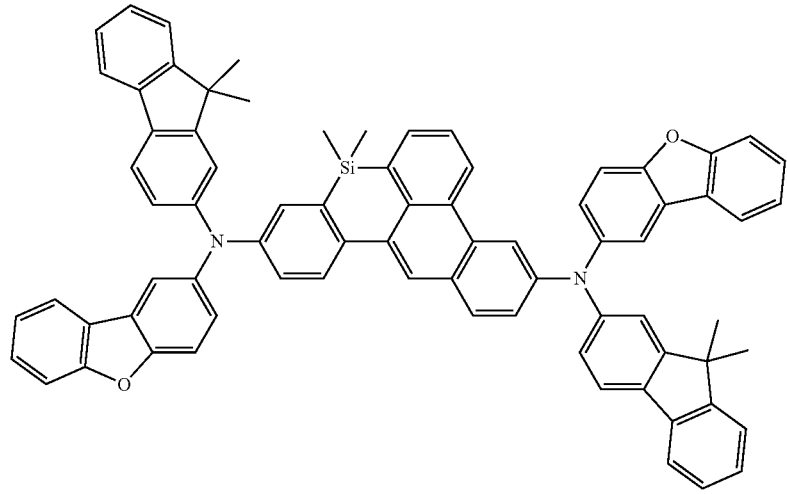
208
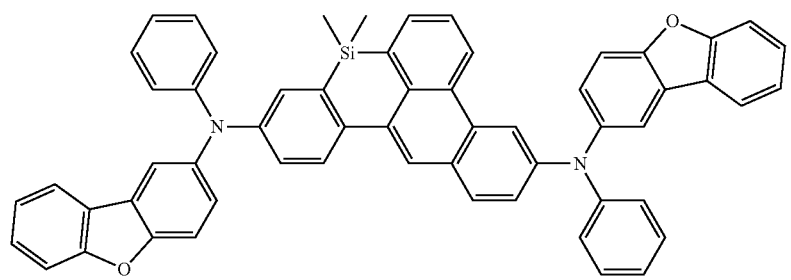
209
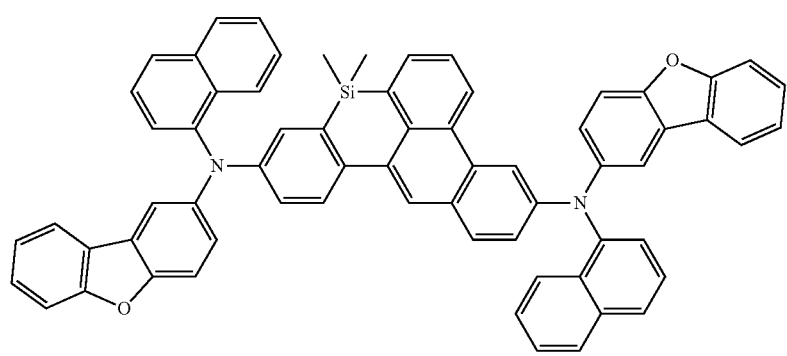
210
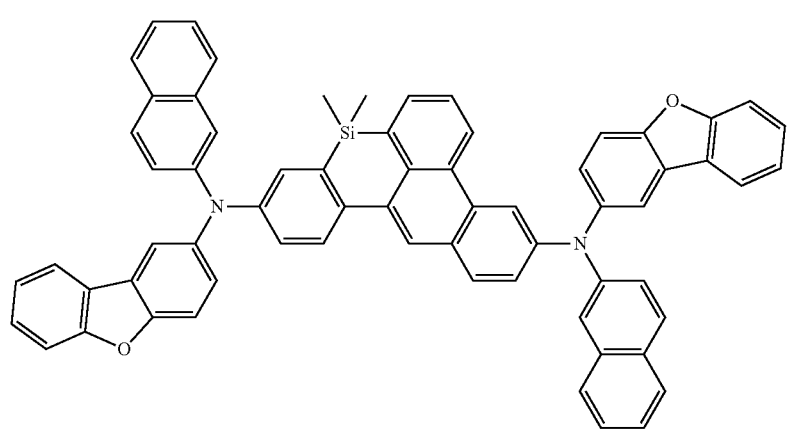
211

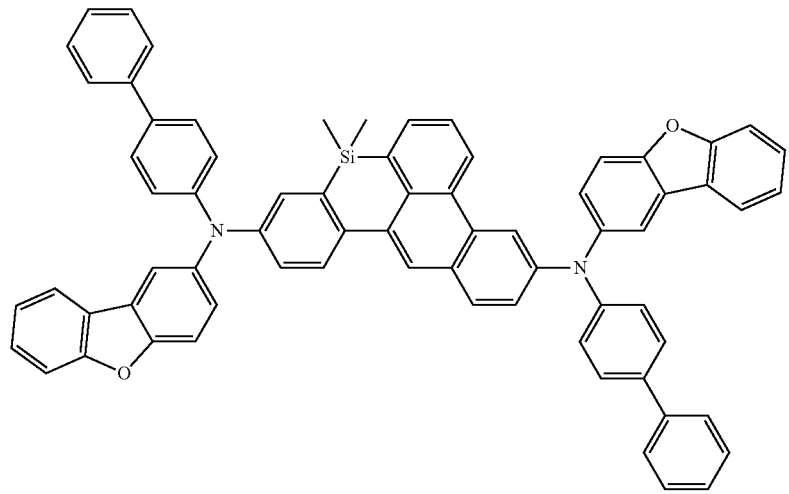
212
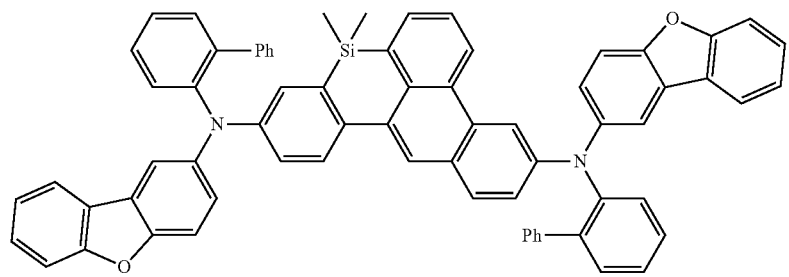
213
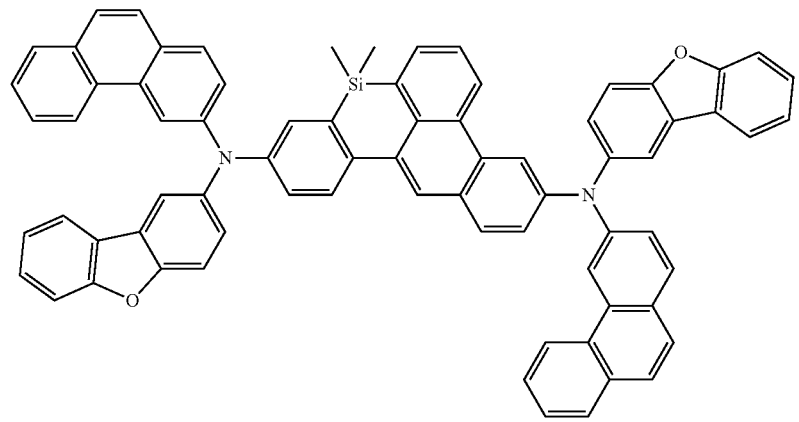
214
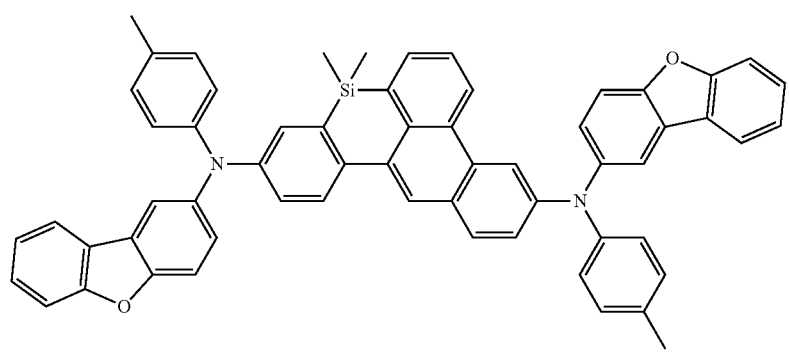
215

216
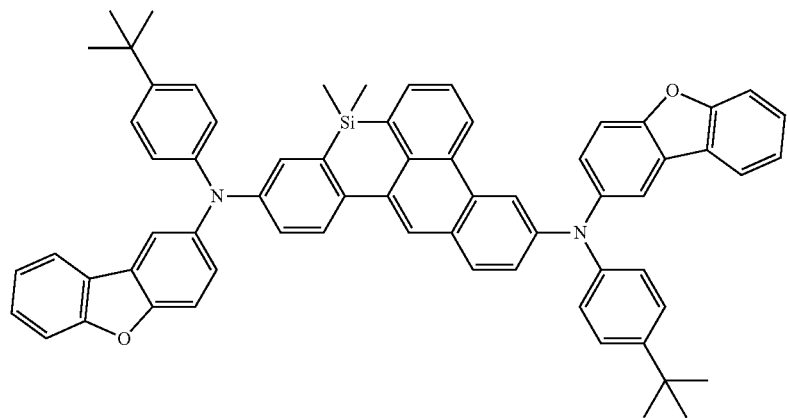
217
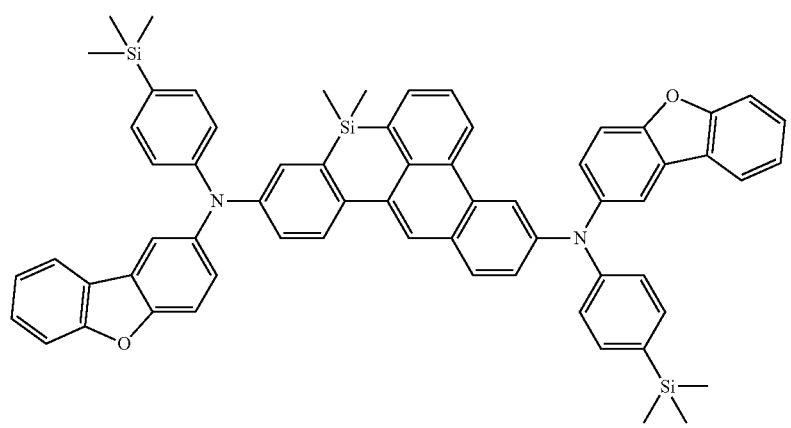
218
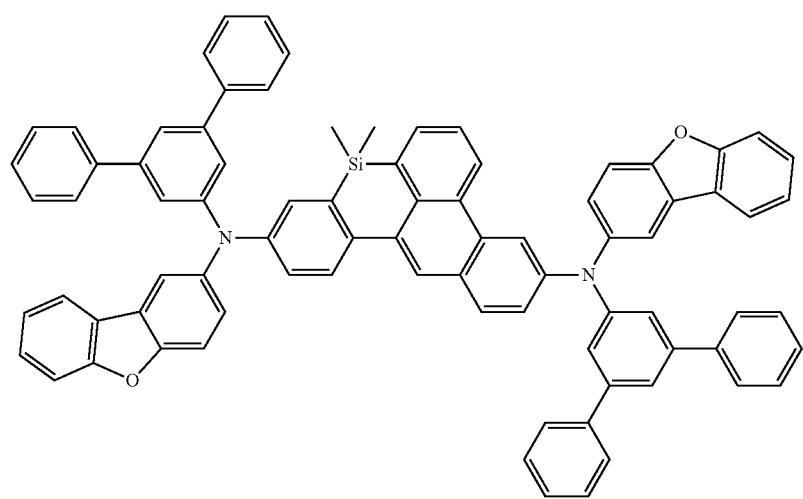

-continued
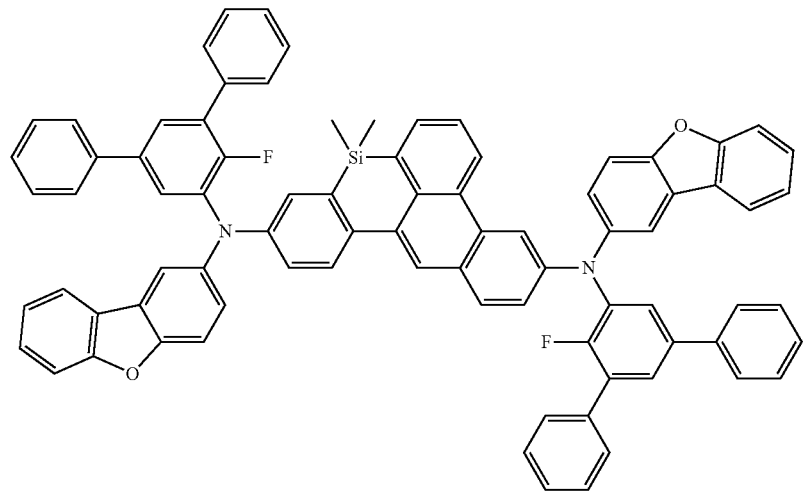
219
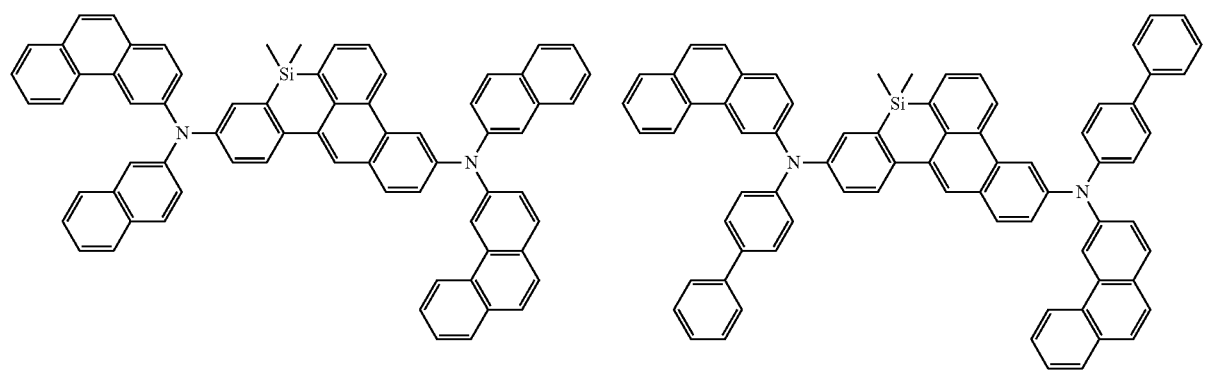
220 221
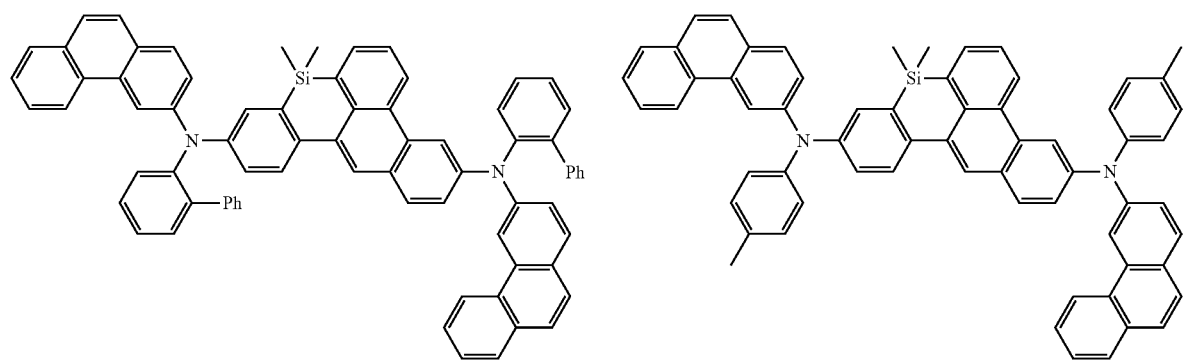
222 223
224 225

171  172
226 227
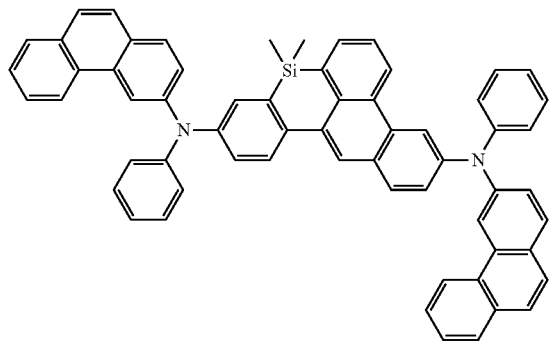
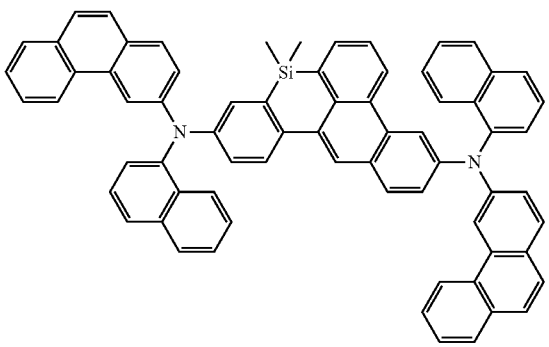
228
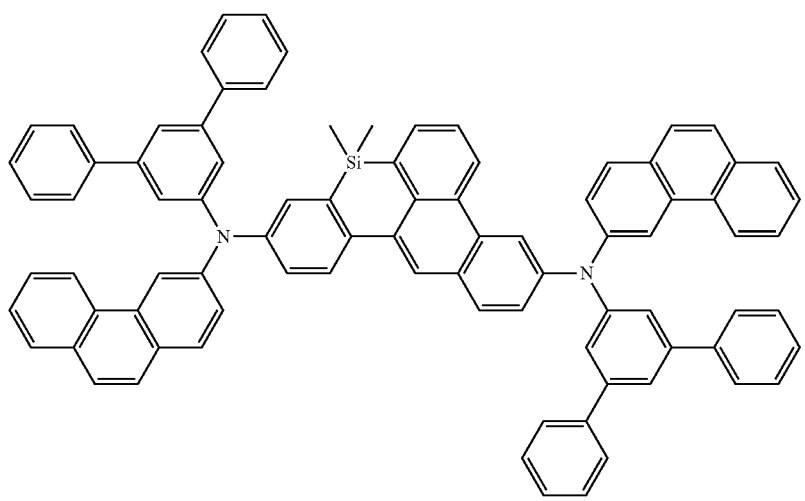
229
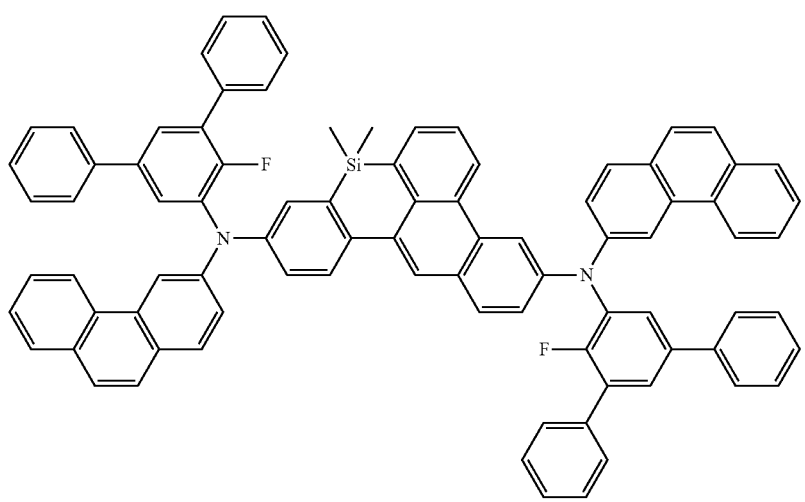

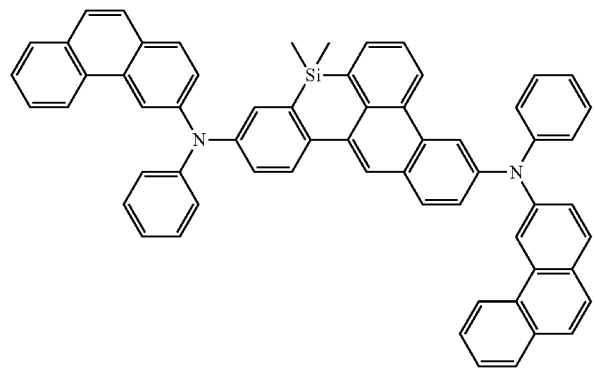
230
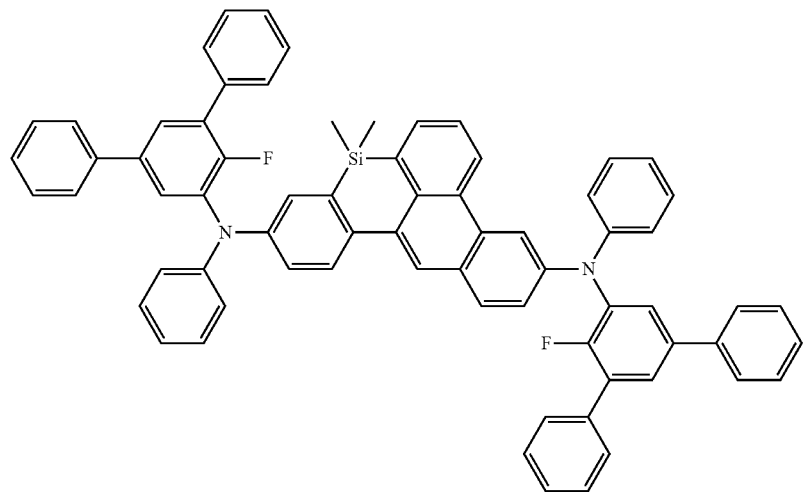
231
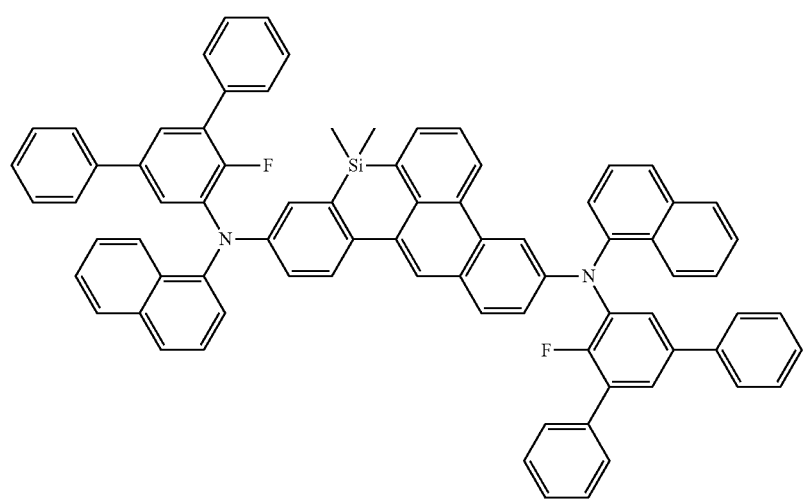
232

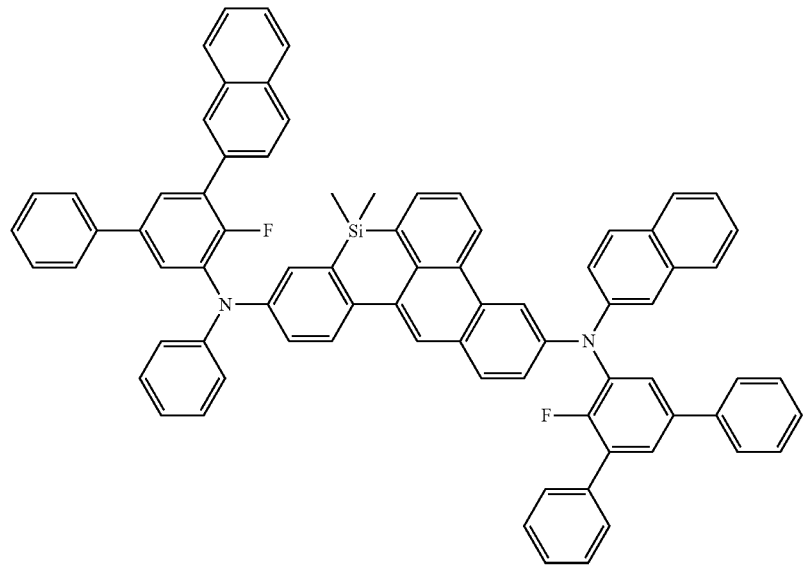
233
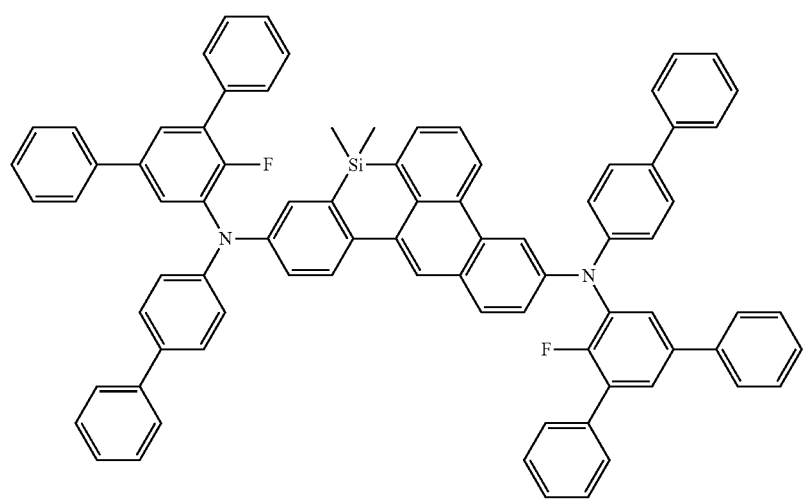
234
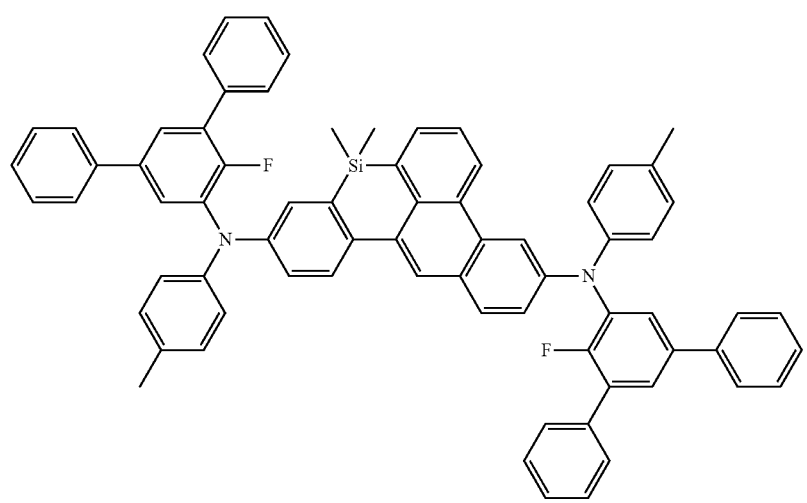
235

236
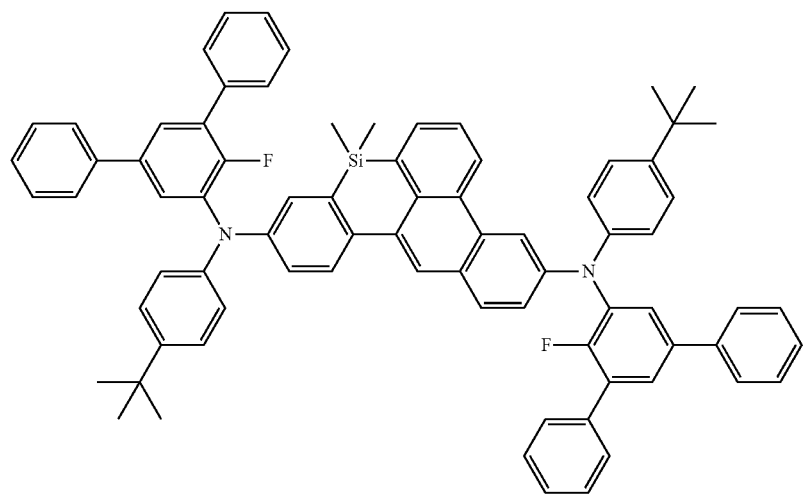
237
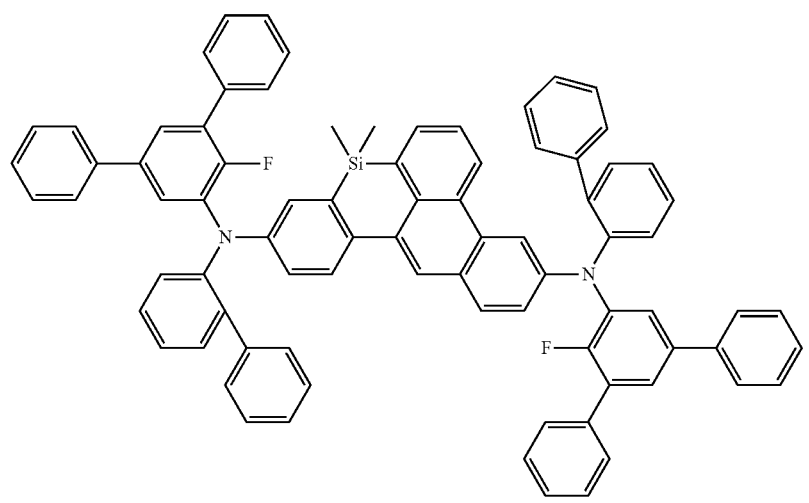
238
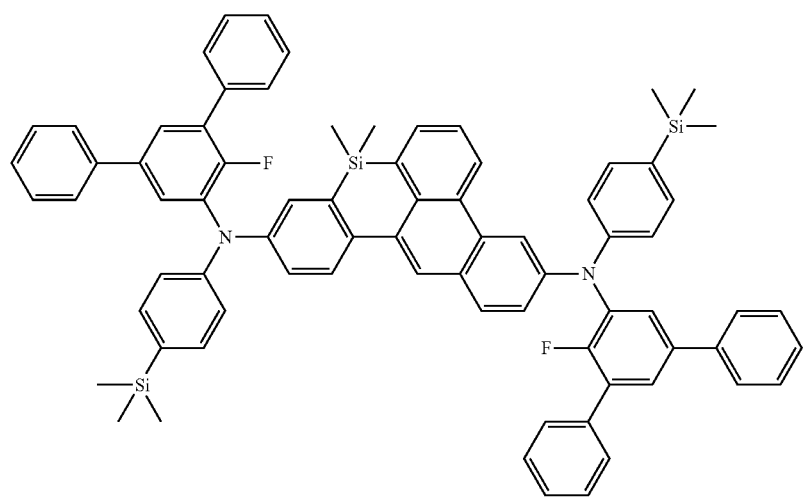

-continued
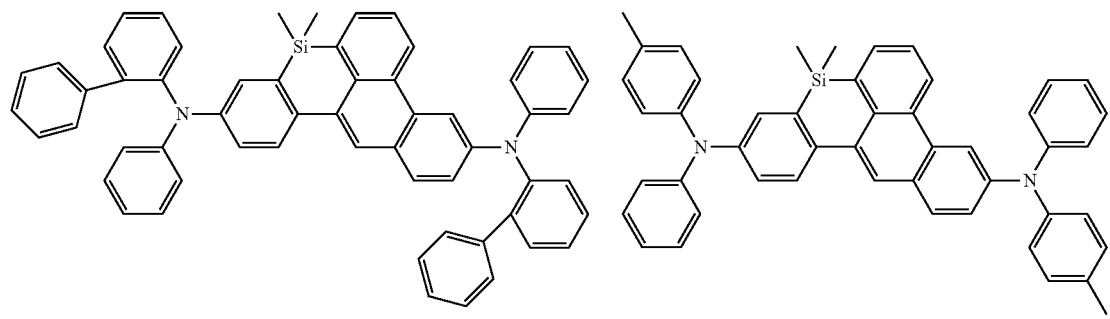
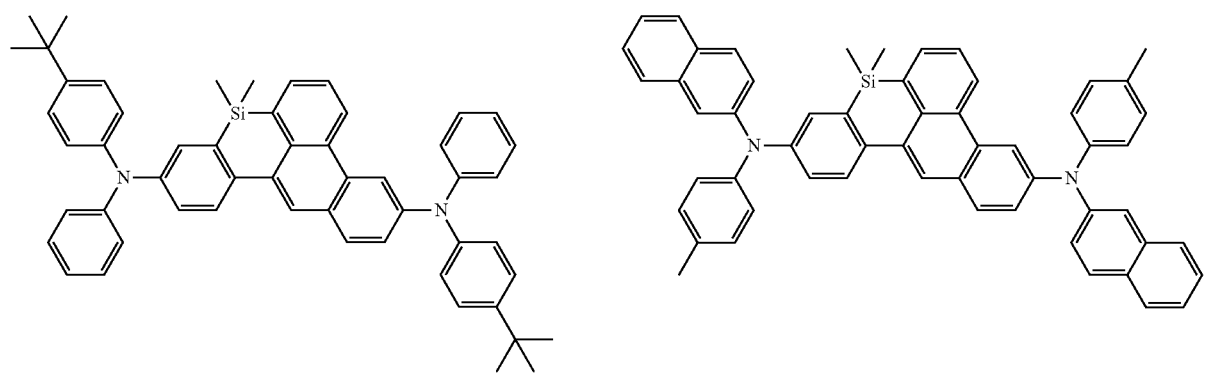
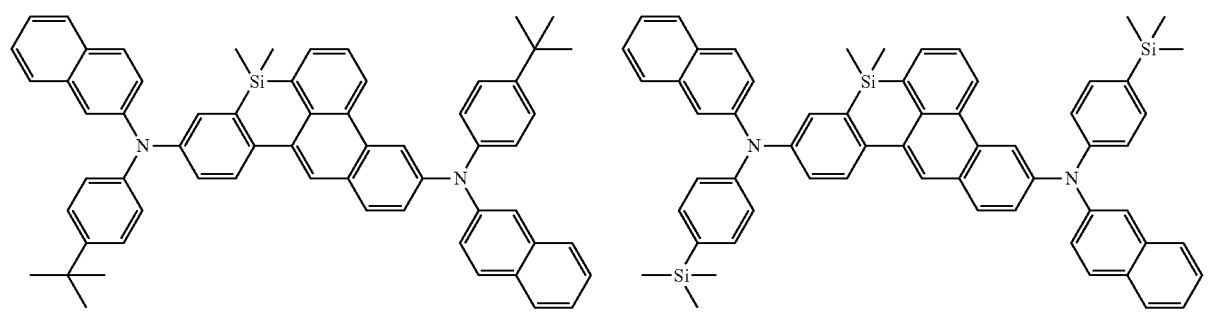
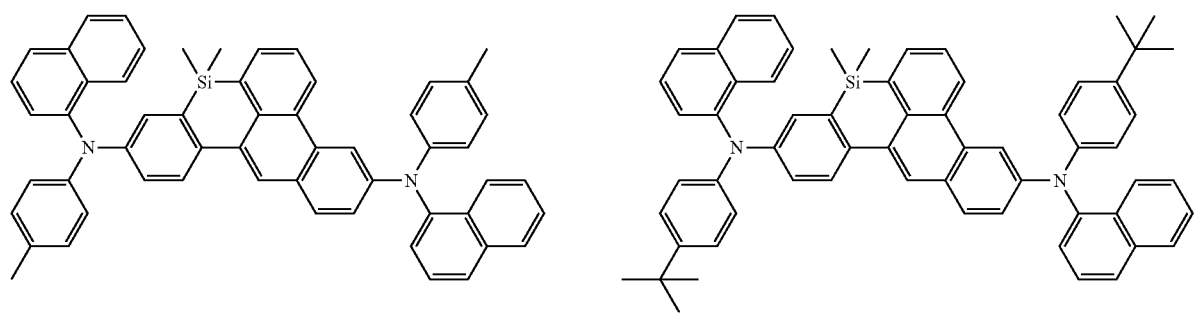

-continued
247
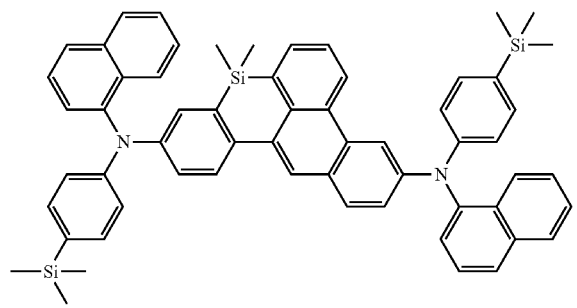
248
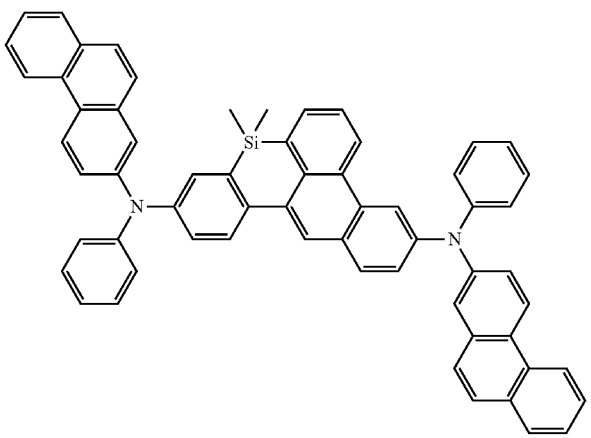
249
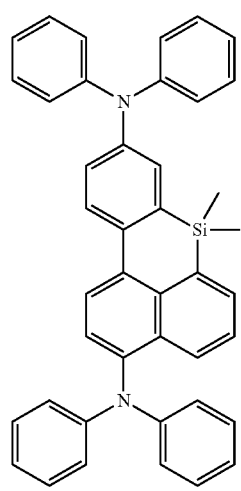
250
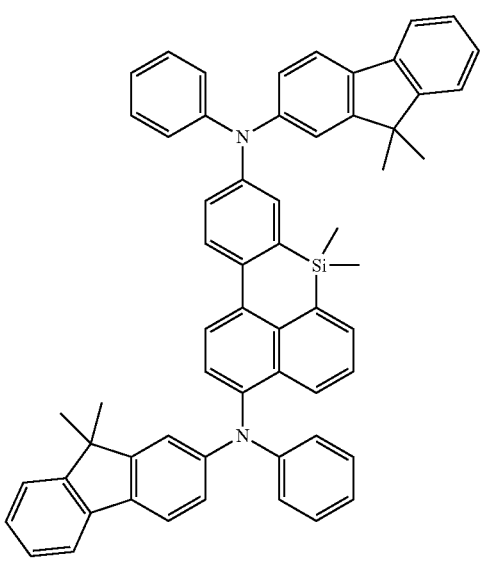
251
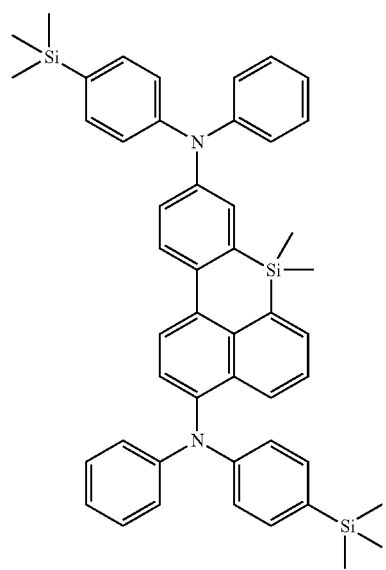
252
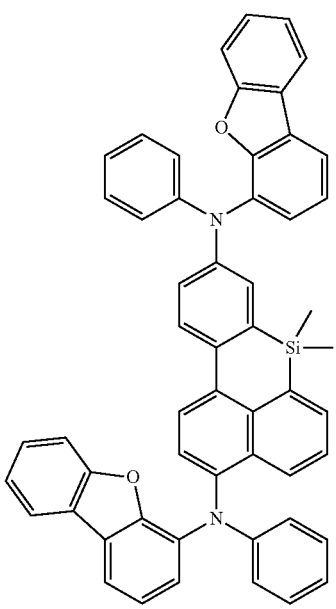

-continued
| 253 | 254 |
|---|---|
| 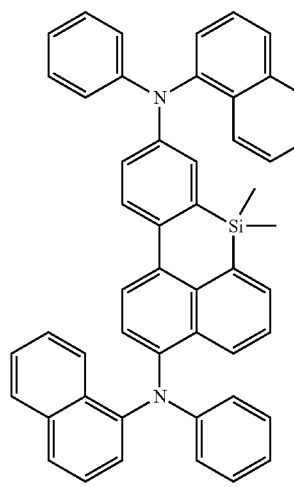 | 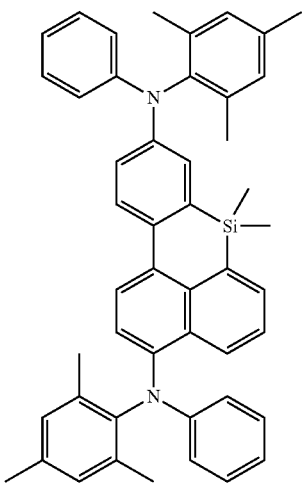 |
| 255 | 256 |
| 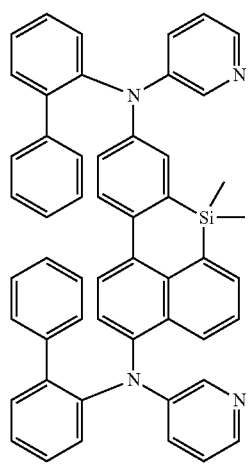 | 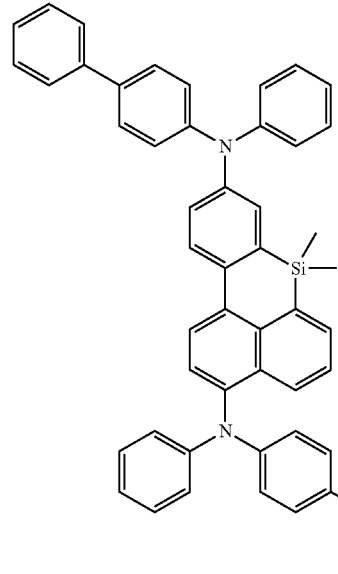 |
| 257 | 258 |
| 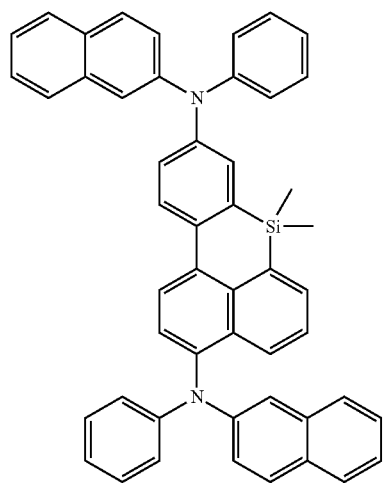 | 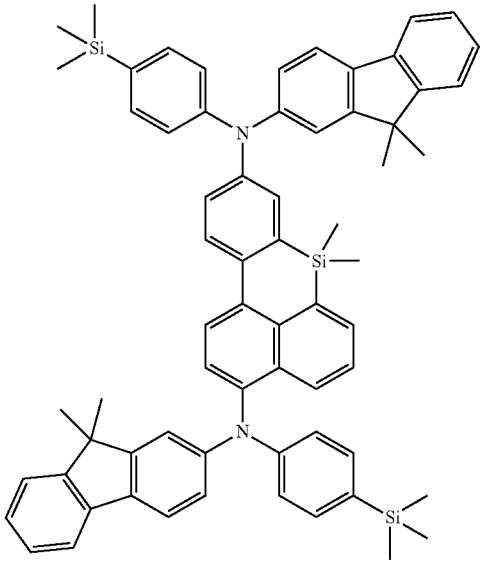 |

-continued
259 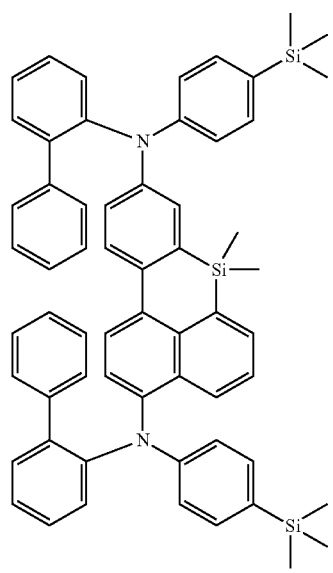 260 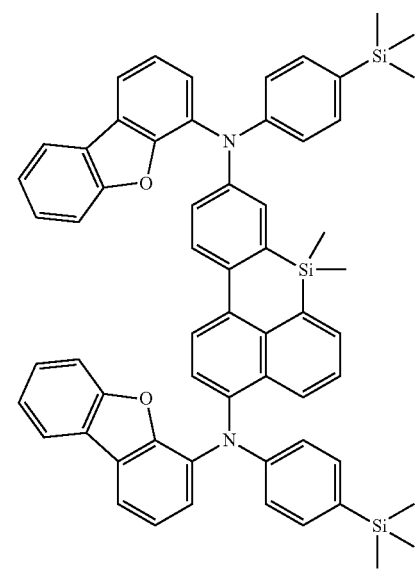
261 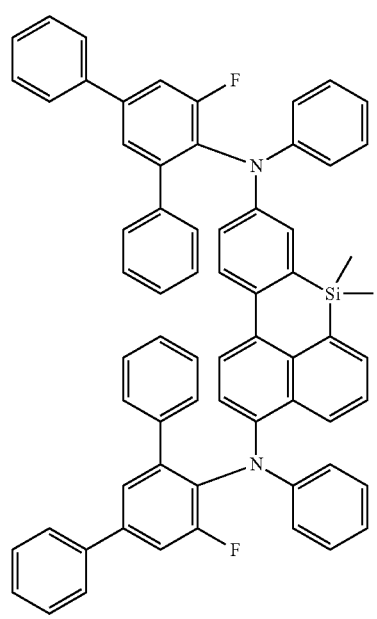 262 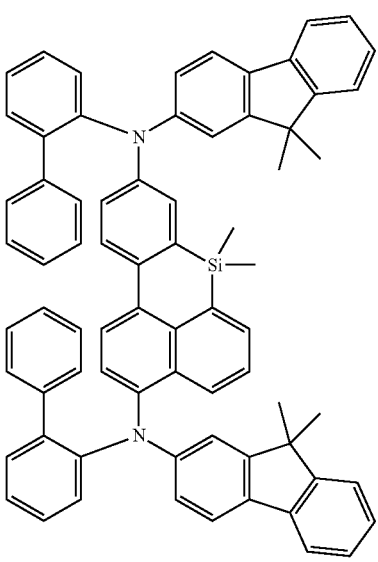

-continued
263 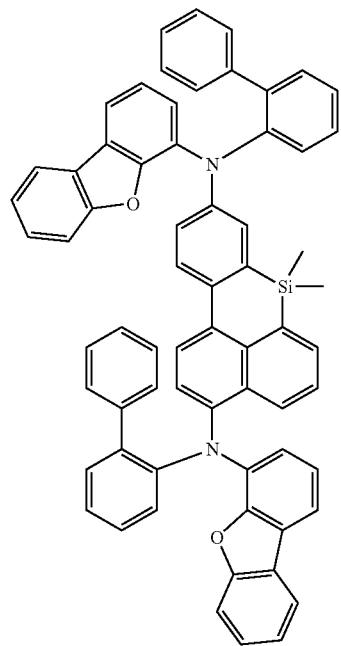
264 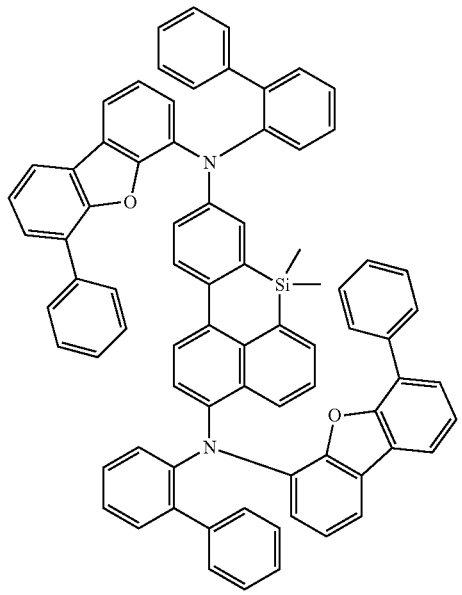
265 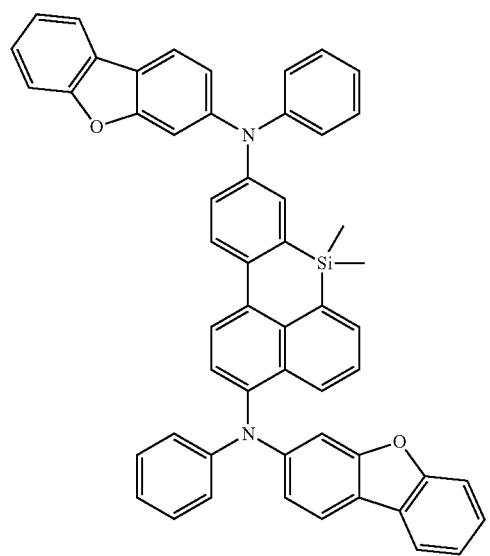
266 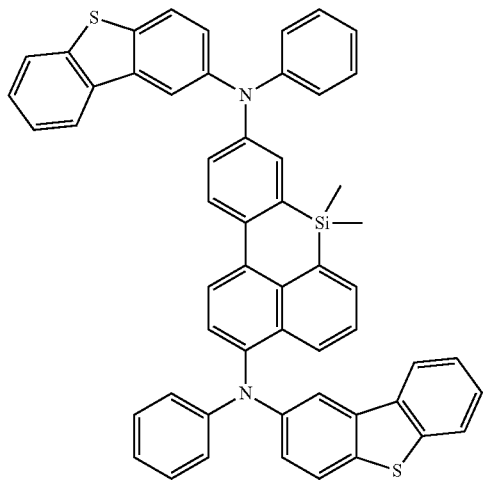

-continued
267
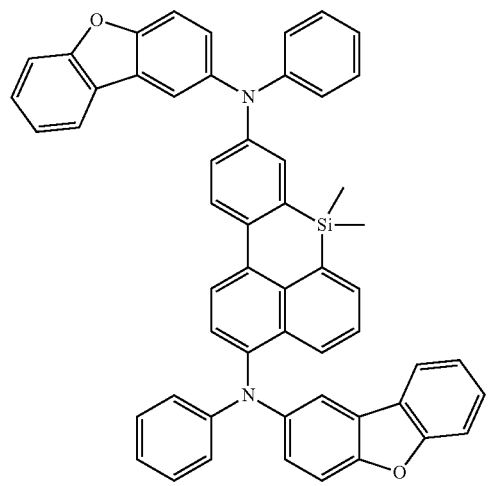
268
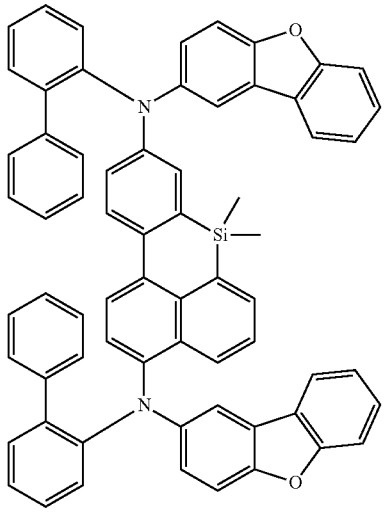
269
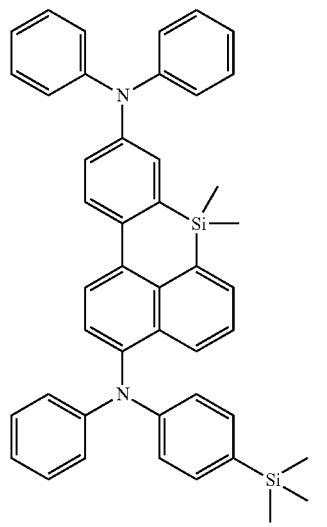
270
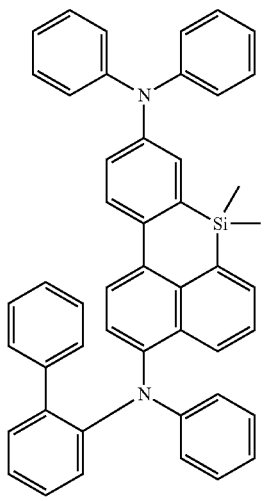
271
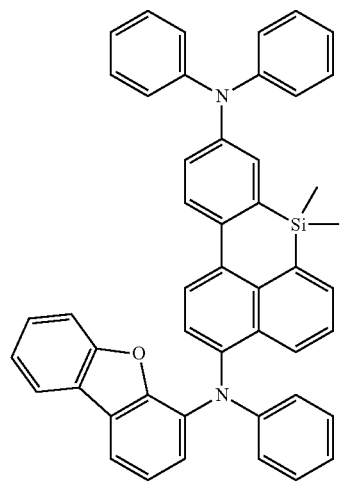
272
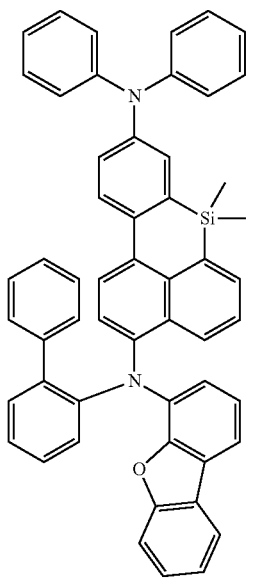

-continued
273 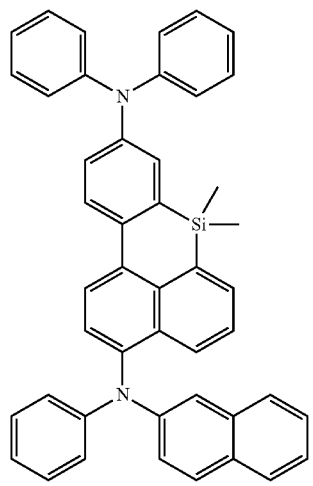
274 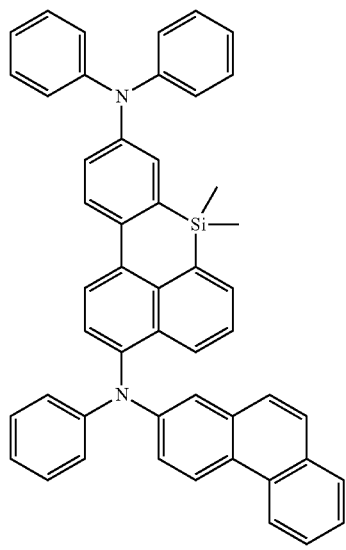
275 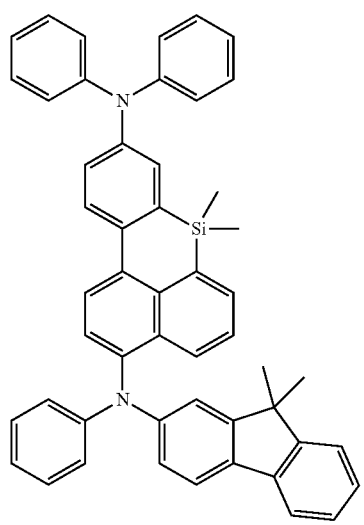
276 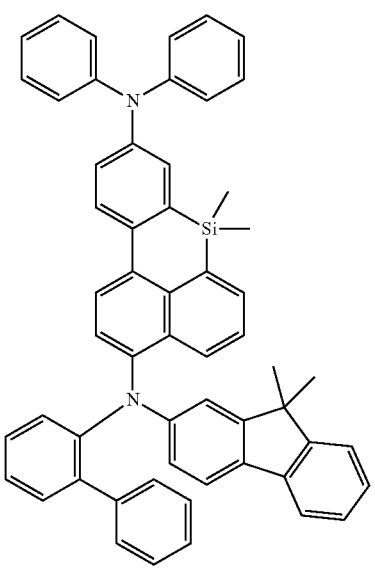
277 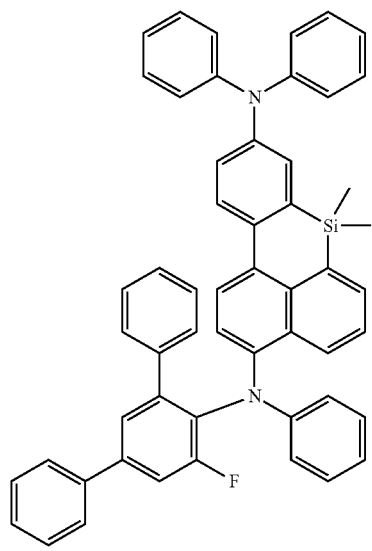
278 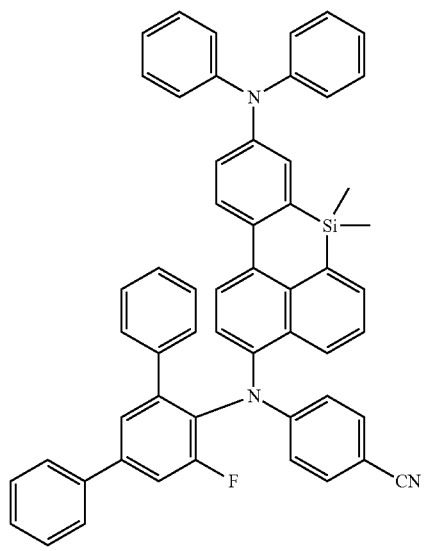

-continued
279
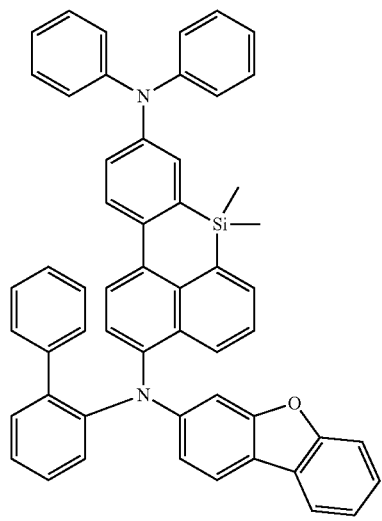
280
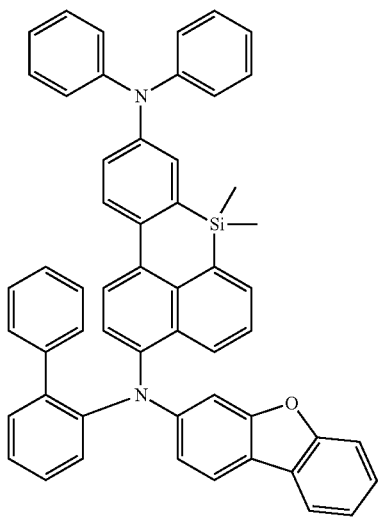
281
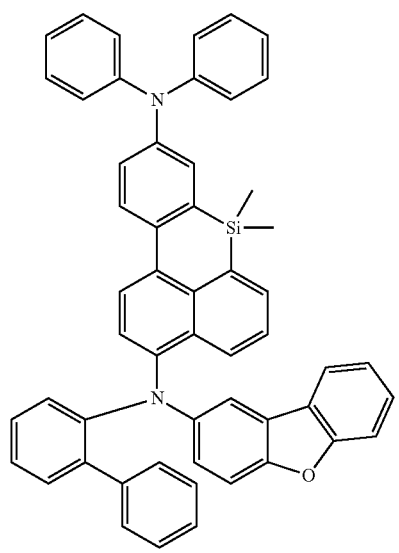
282
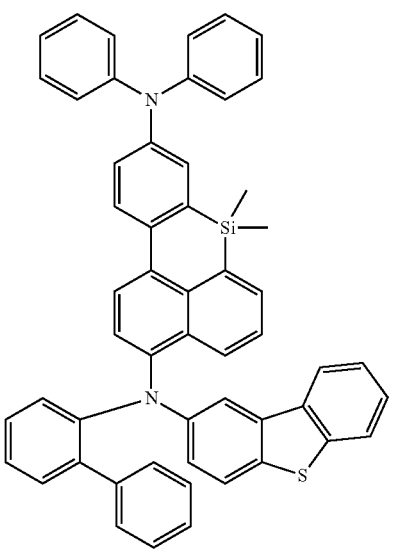
283
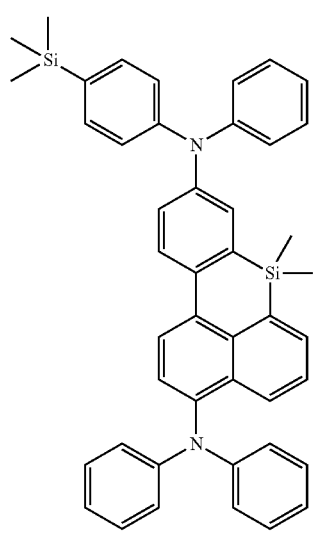
284
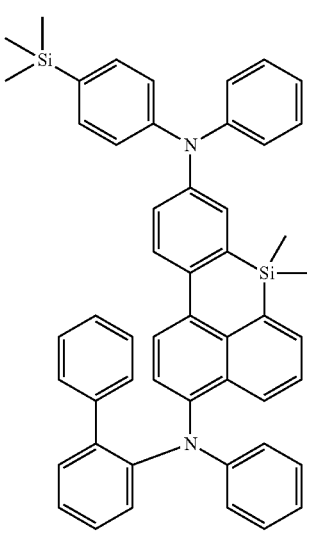

-continued
285 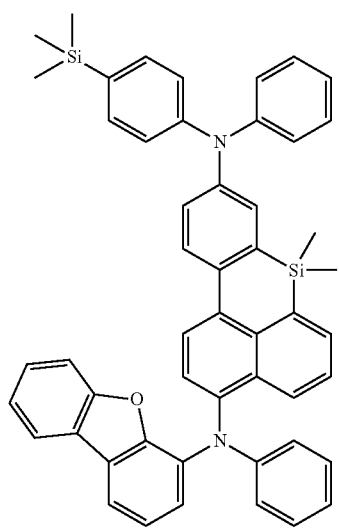
286 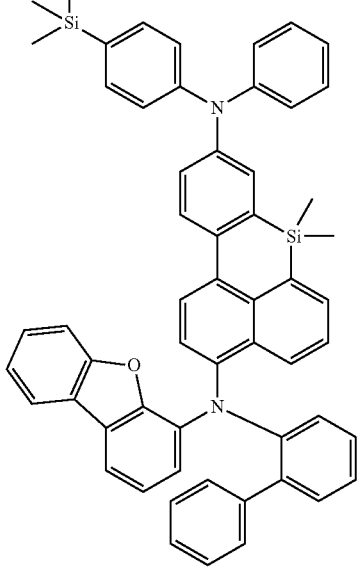
287 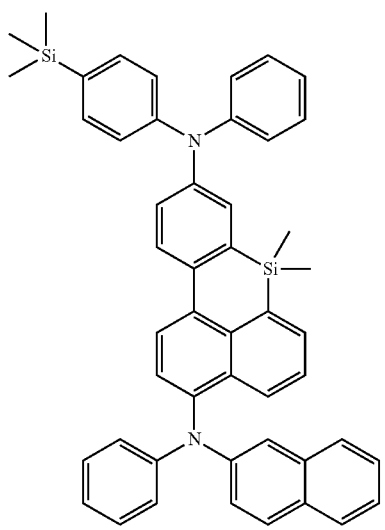
288 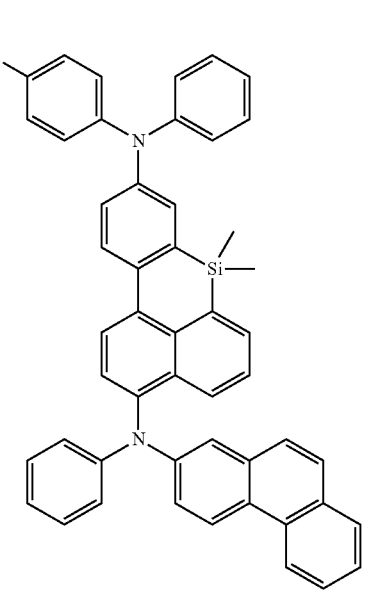

-continued
197
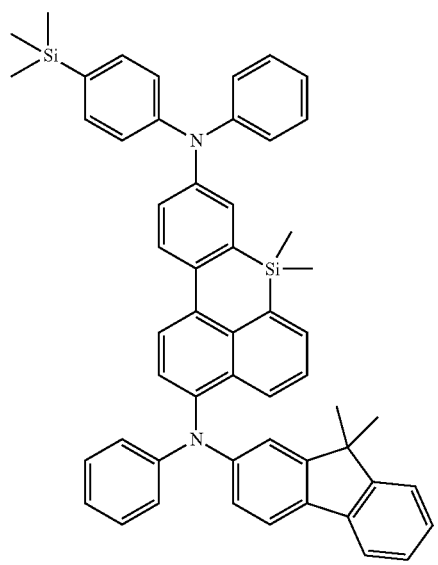
198
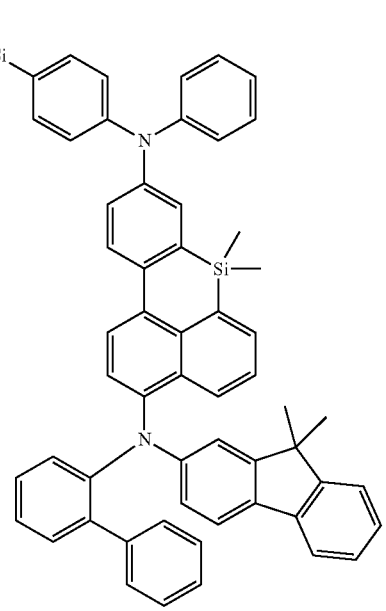
289
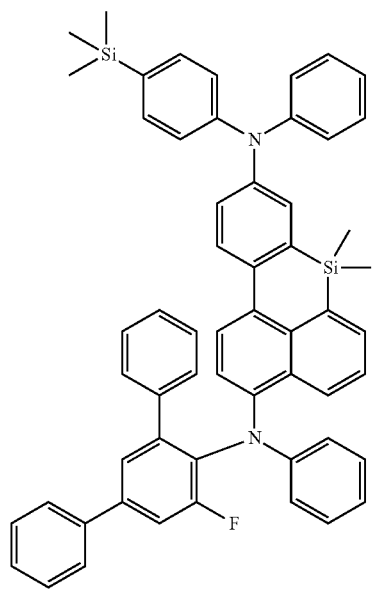
291
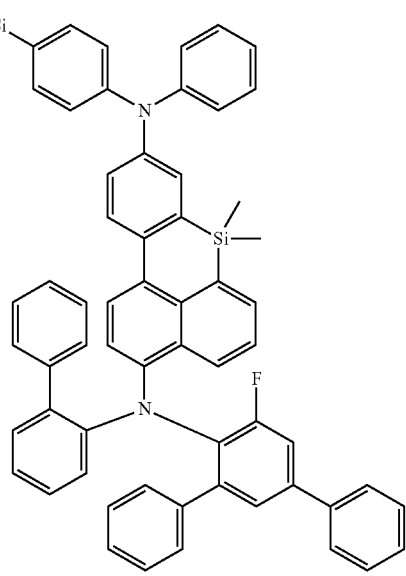
290
292

293
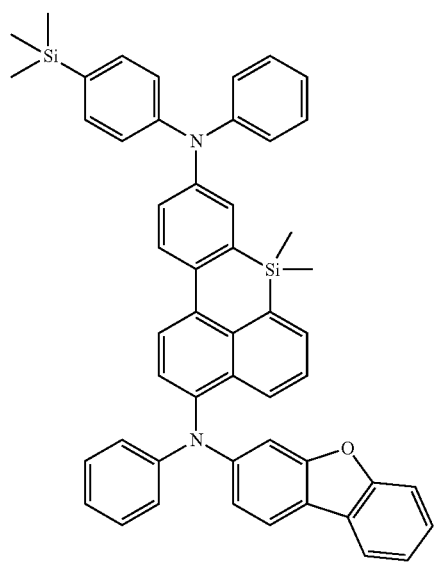
294
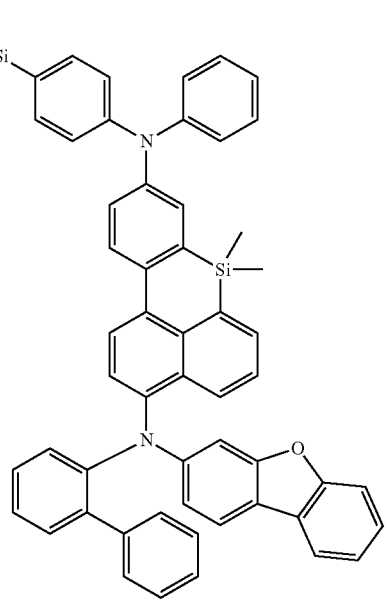
295
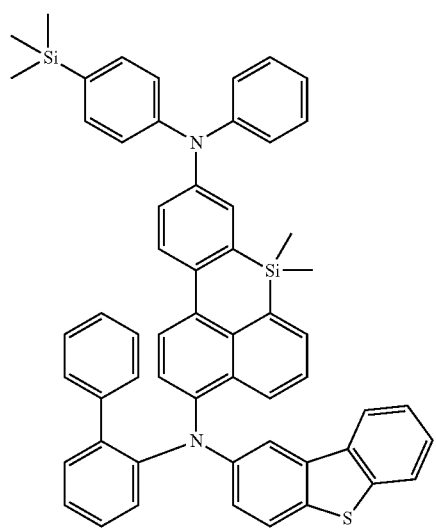
296
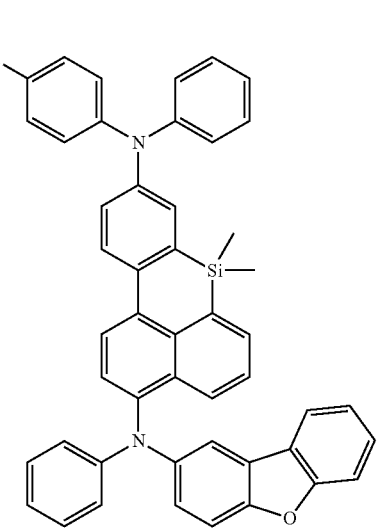

297
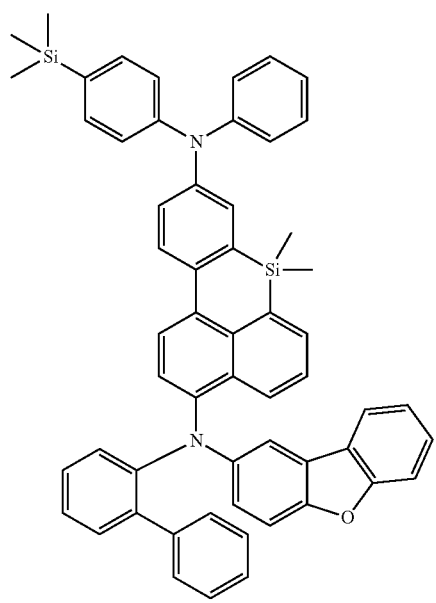
298
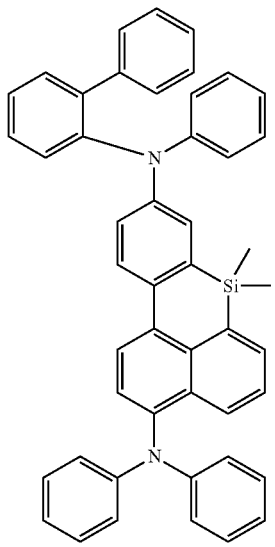
299
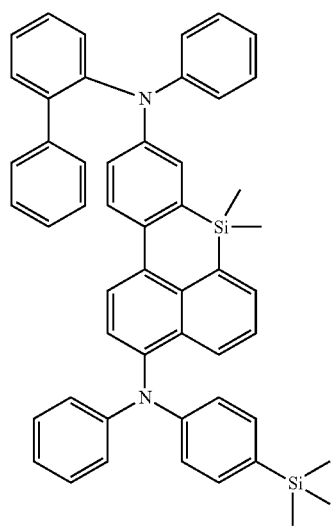
300
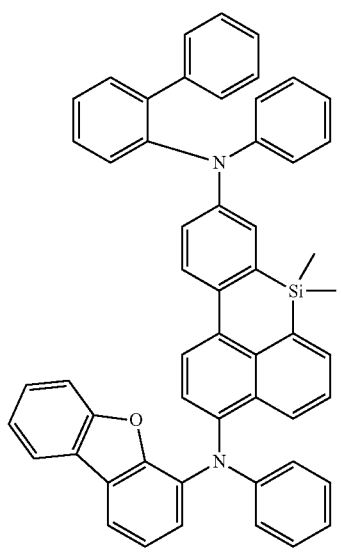

-continued
203
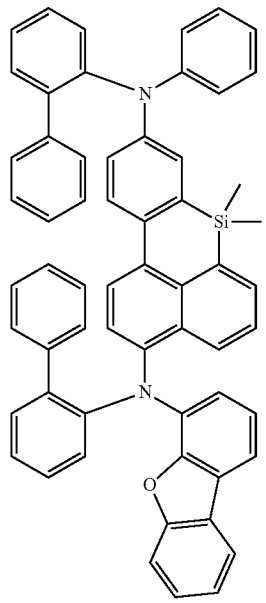
301
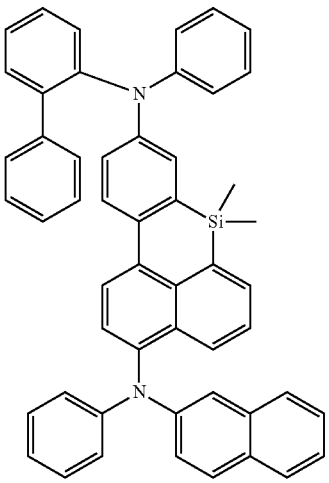
302
303
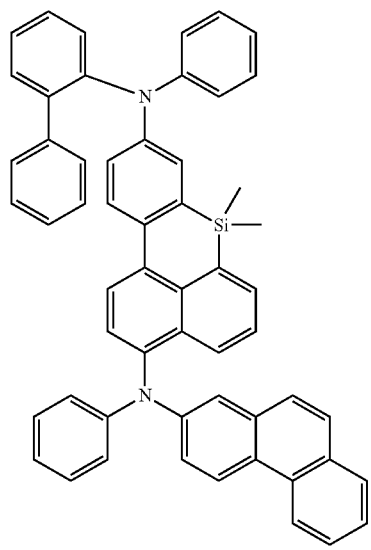
304
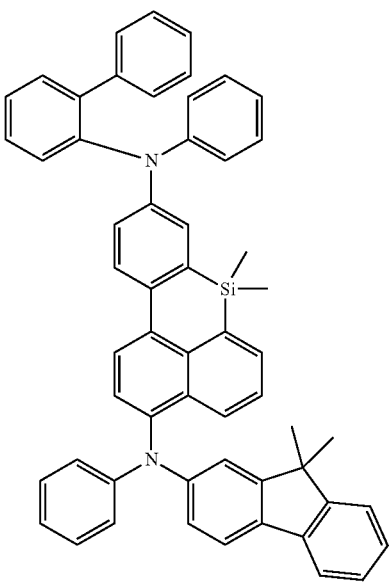

-continued
205
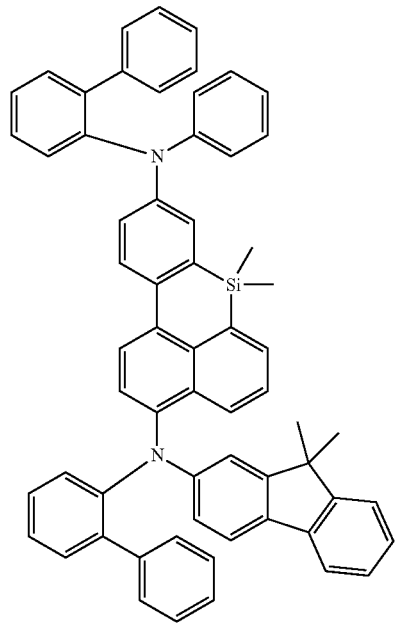
206 305
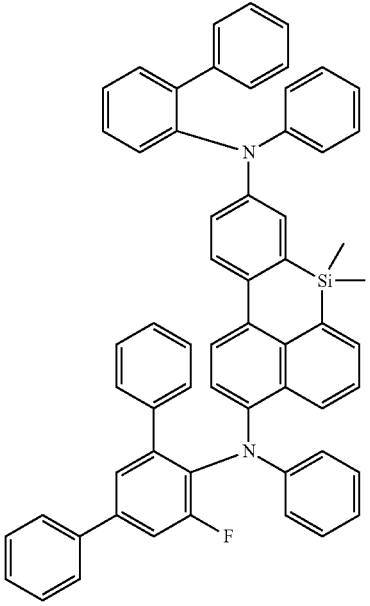
306
307
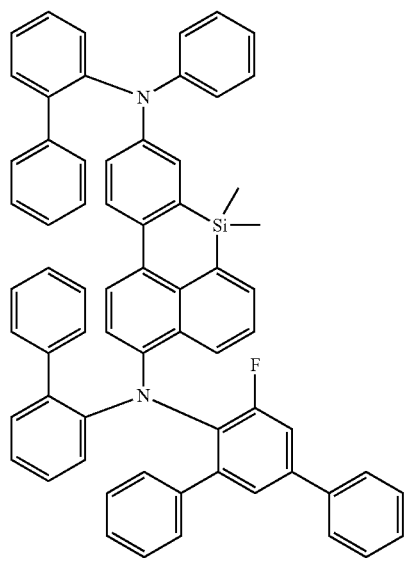
308
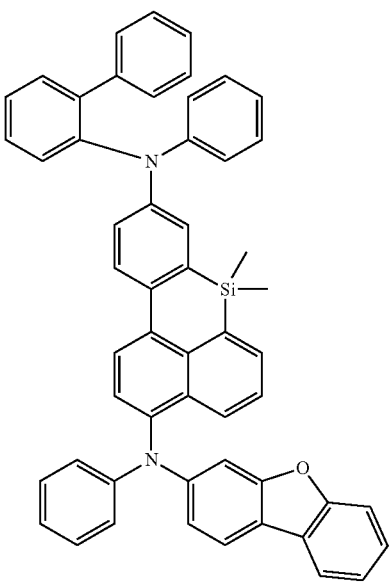

-continued
207
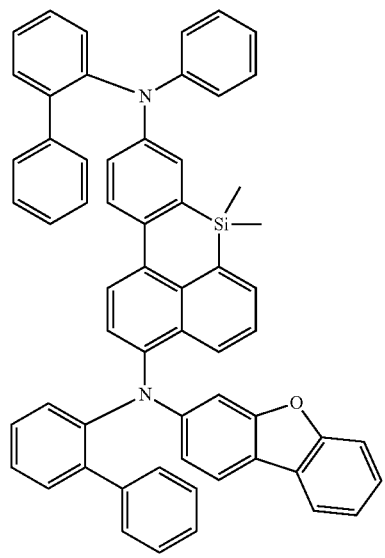
208
309
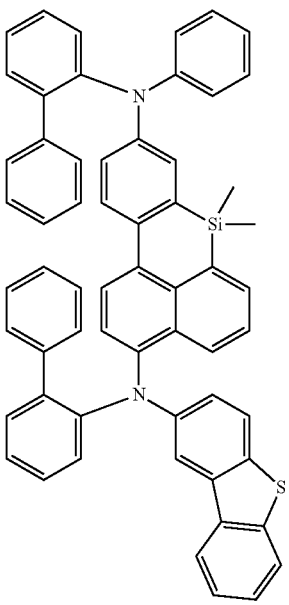
310
311
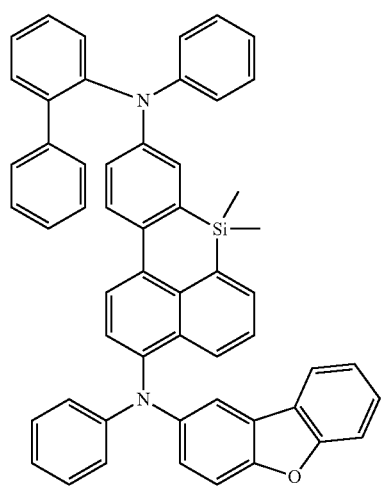
312
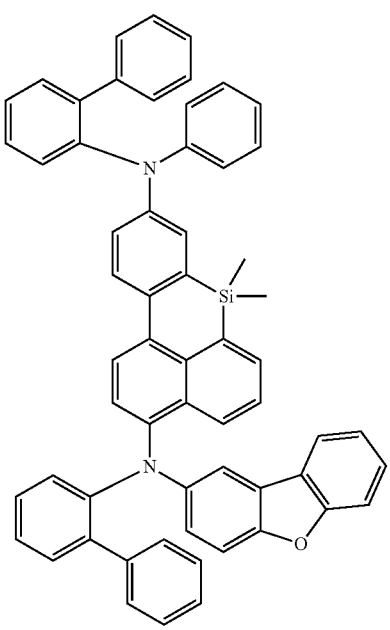

-continued
313
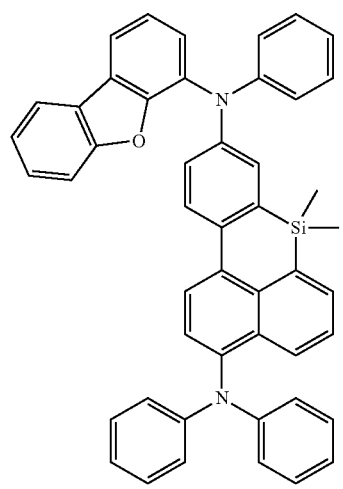
314
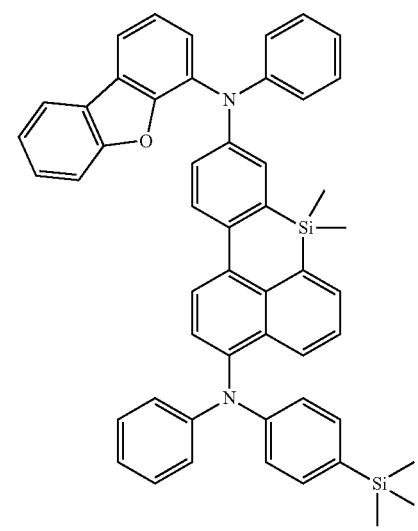
315
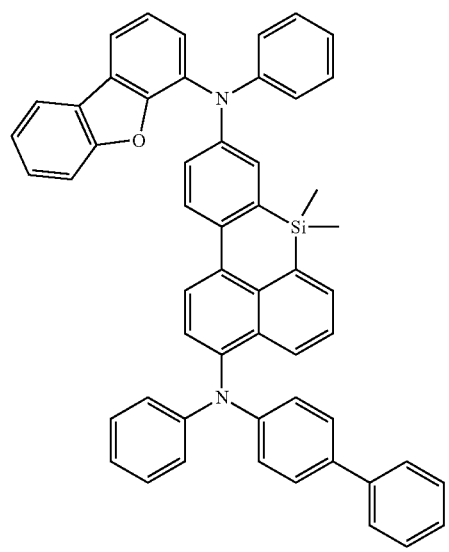
316
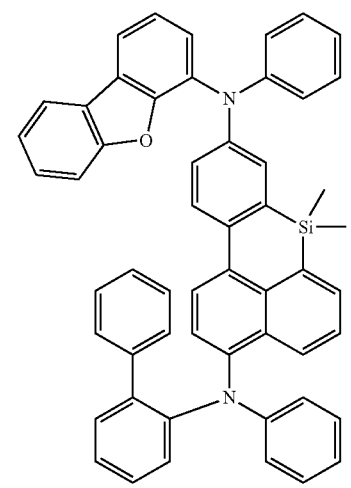
317
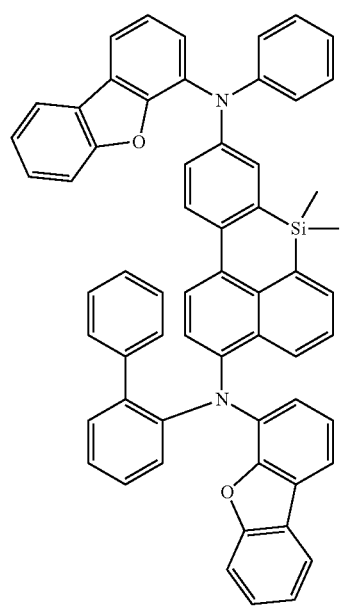
318
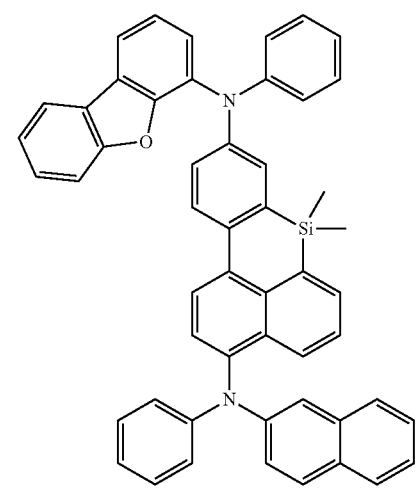

-continued
319
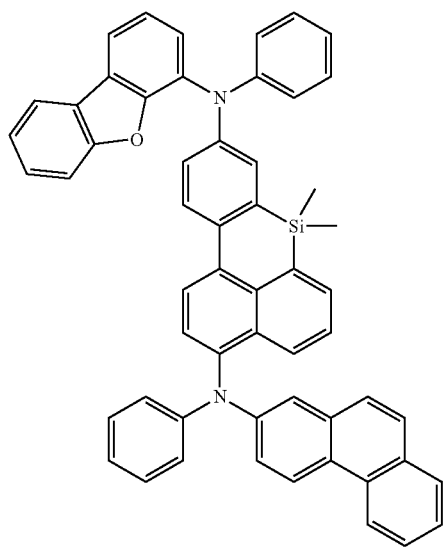
320
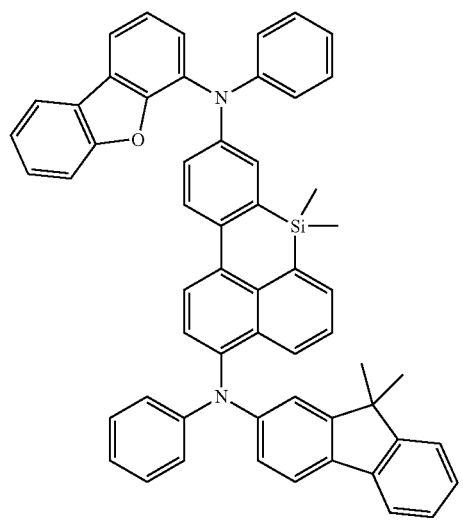
321
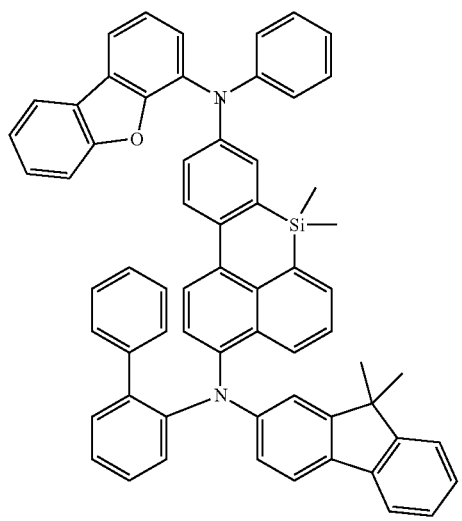
322
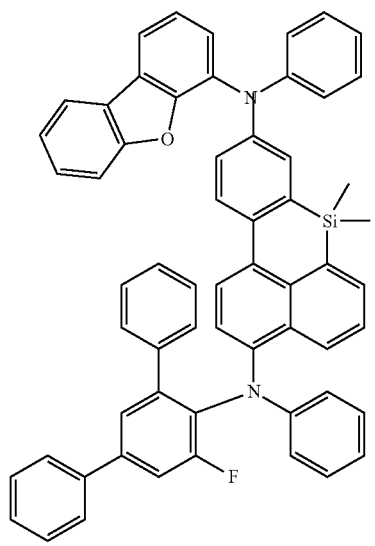
323
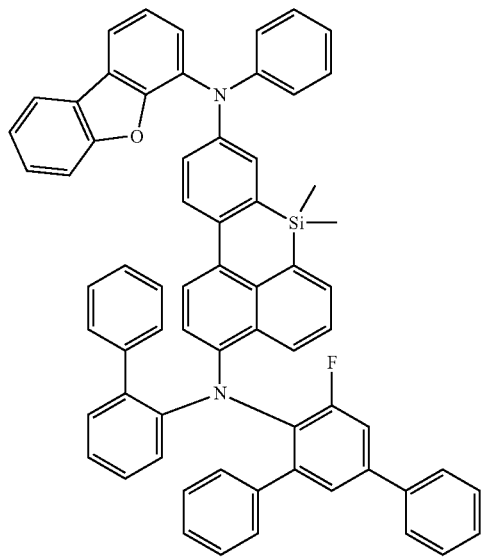
324
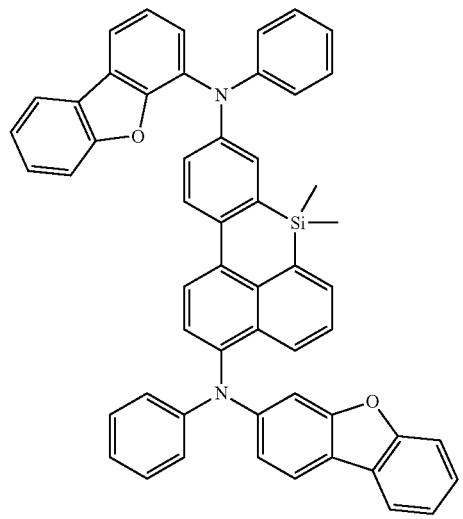

-continued
325
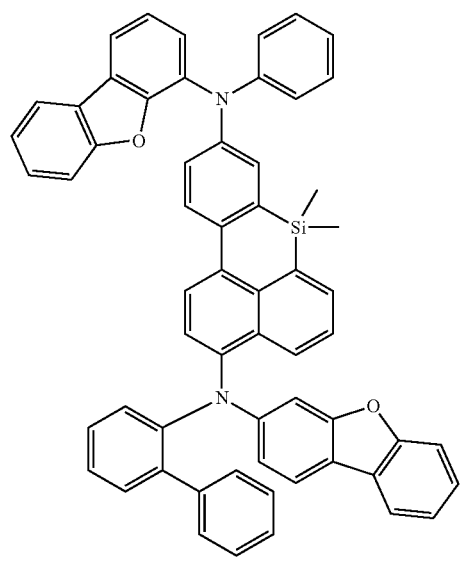
326
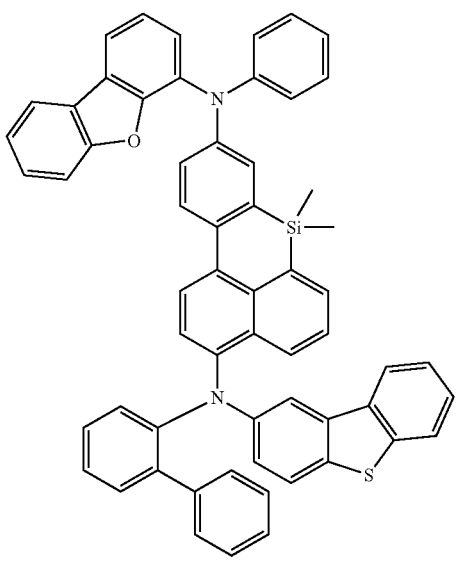
327
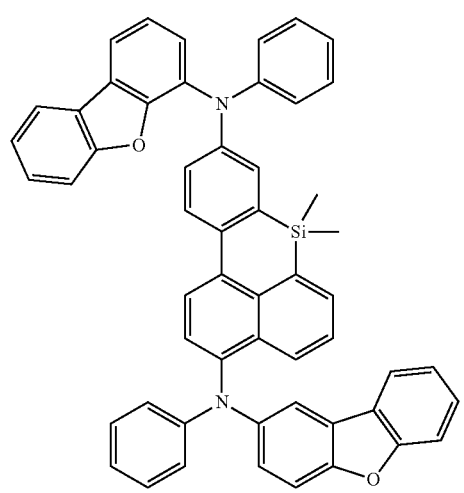
328
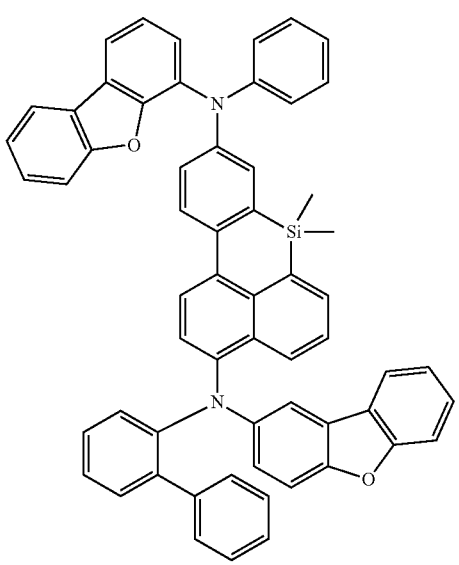
329
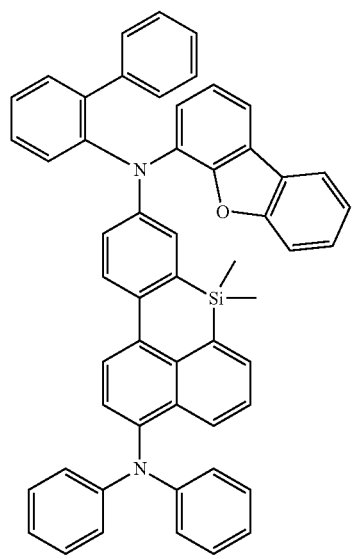
330
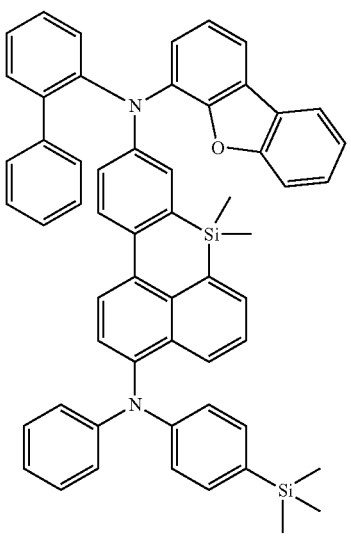

-continued
215 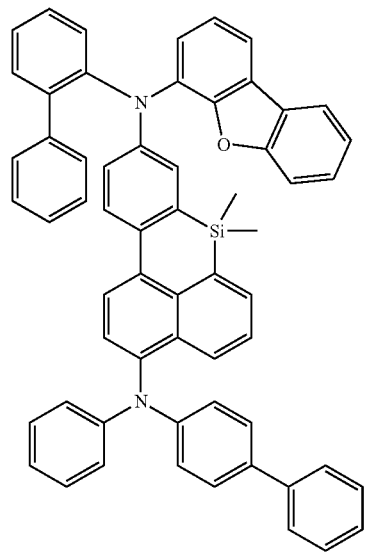
331 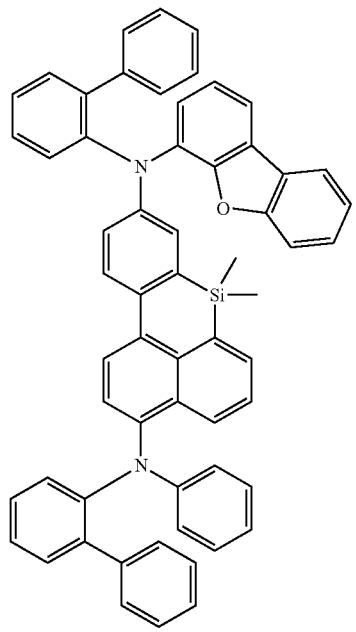
216
332
333 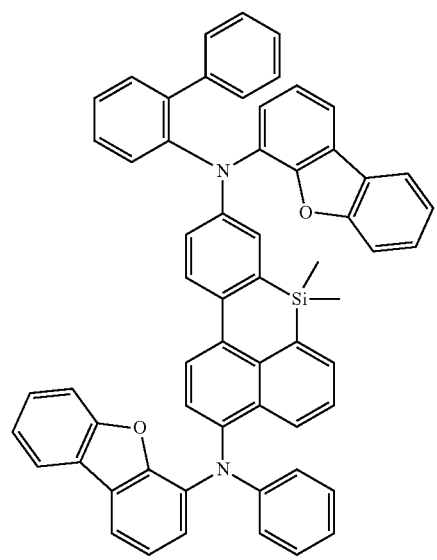
334 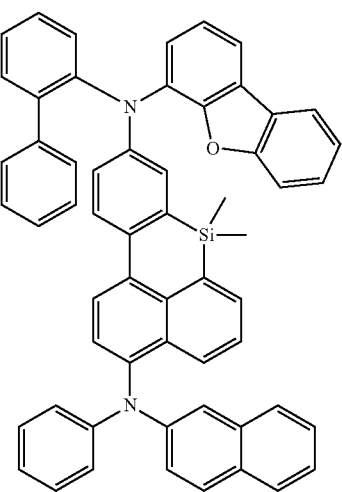

-continued
335
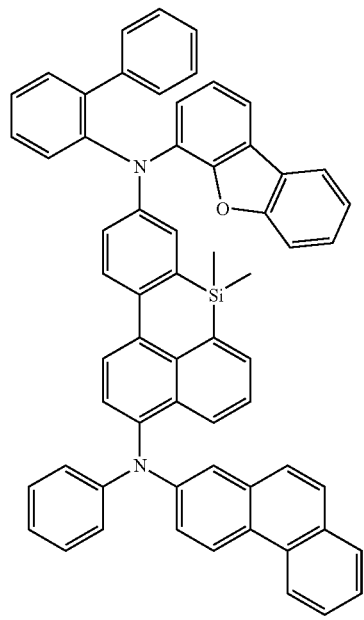
336
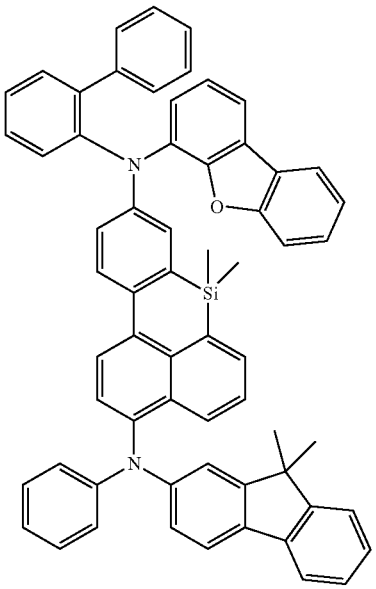
337
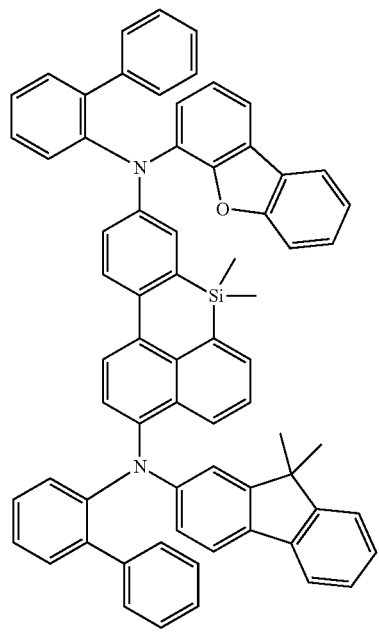
338
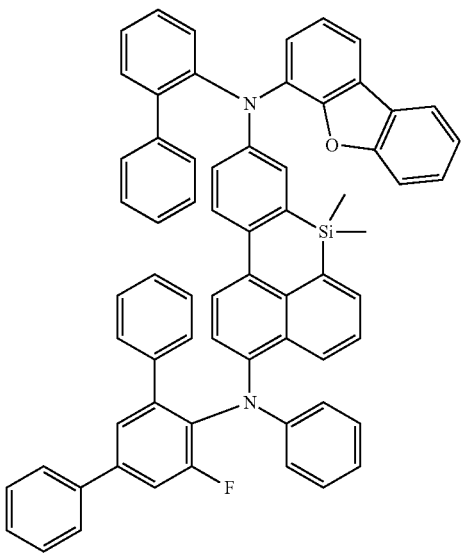

-continued
339 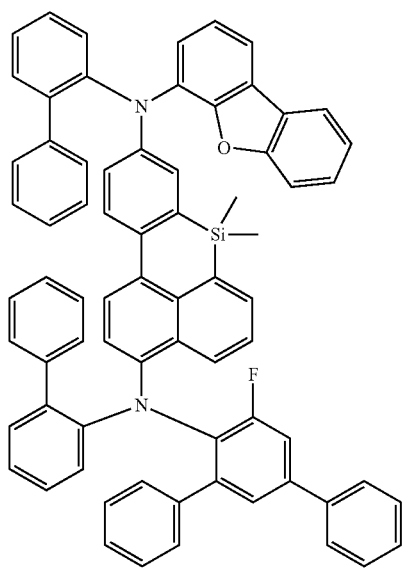
340 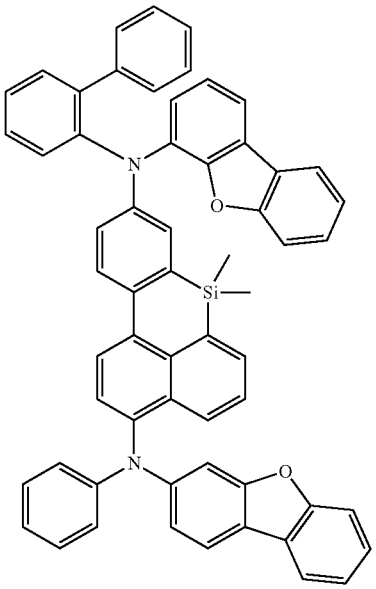
341 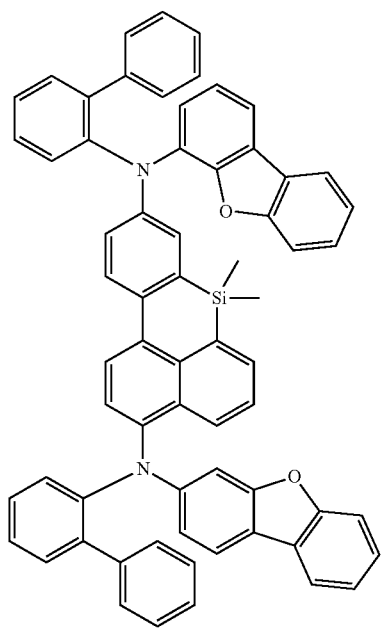
342 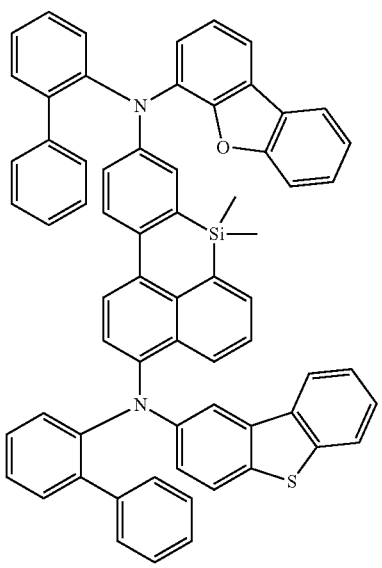

-continued
| 343 | 344 |
|---|---|
| 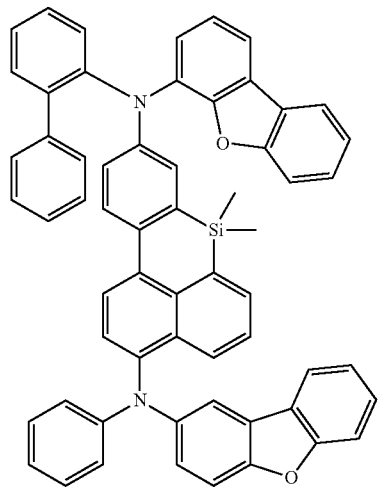 | 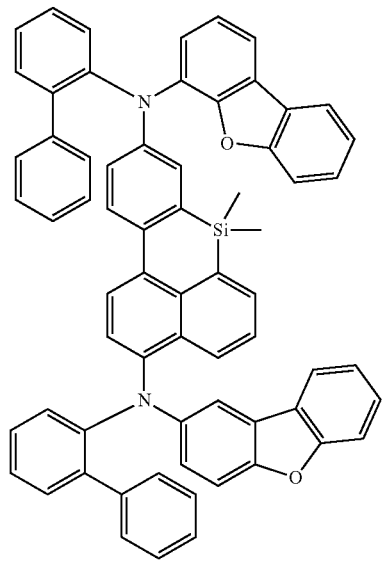 |
| 345 | 346 |
| 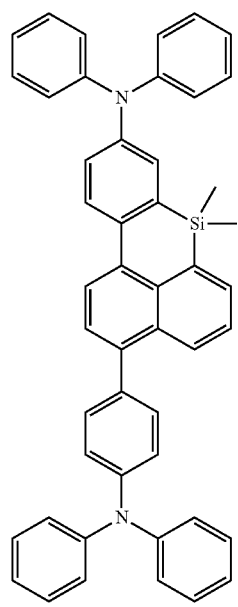 | 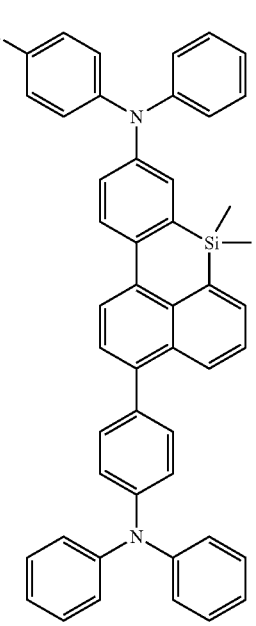 |

-continued
223
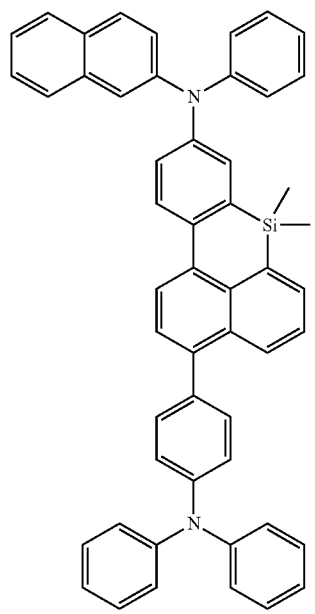
347
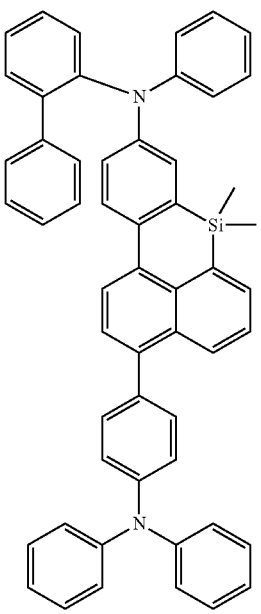
224
348
349
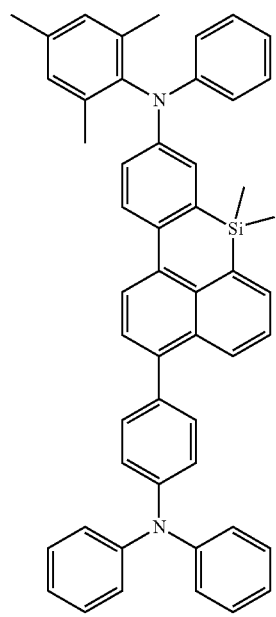
350
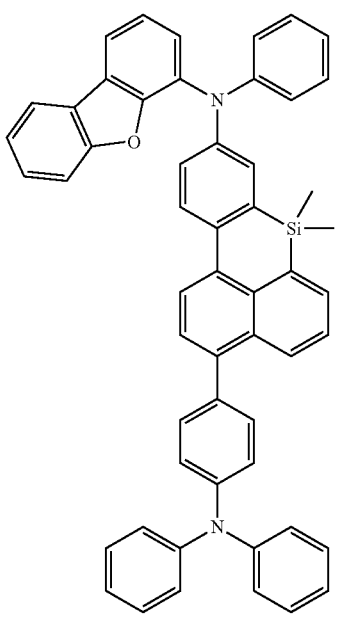

225
226
-continued
351 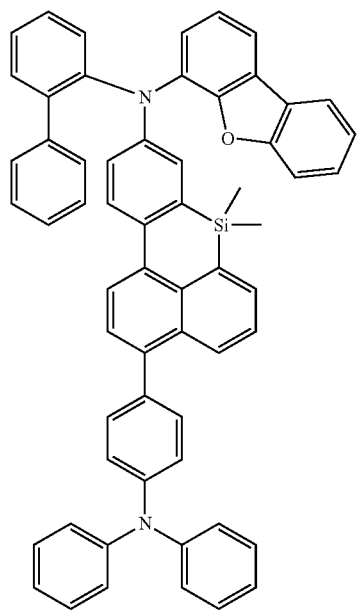
352 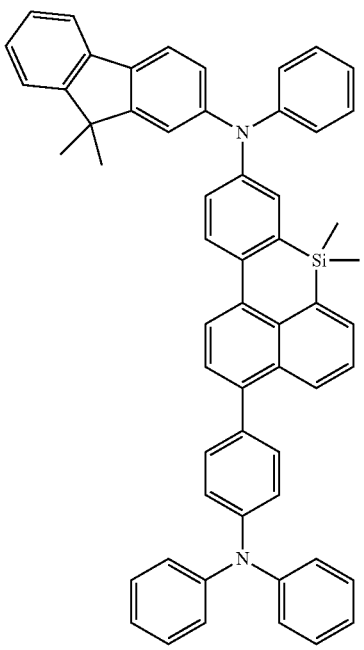
353 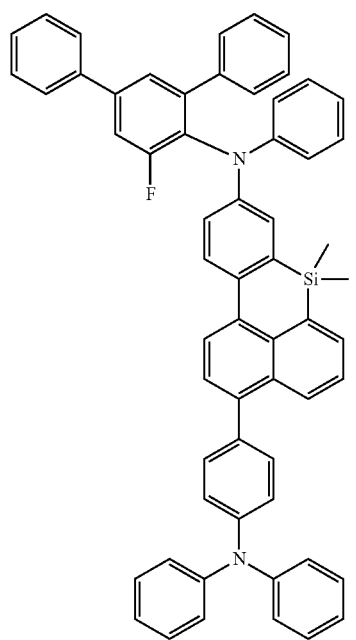
354 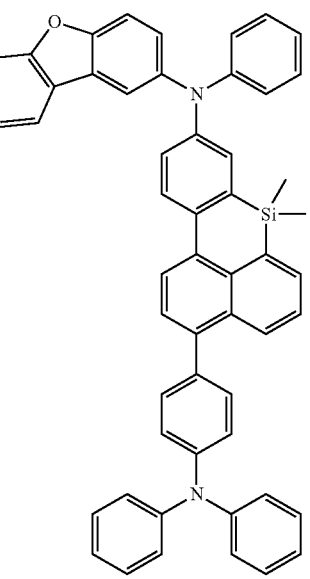

227
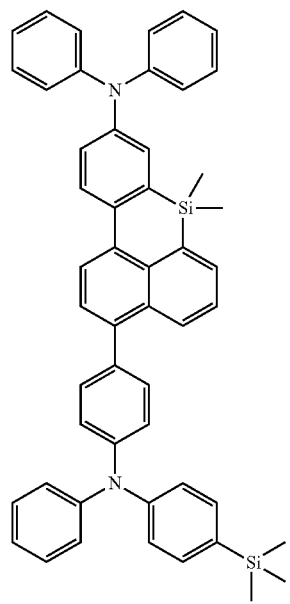
228
-continued
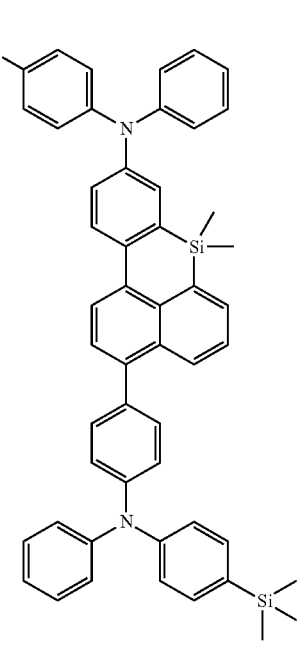
355  356
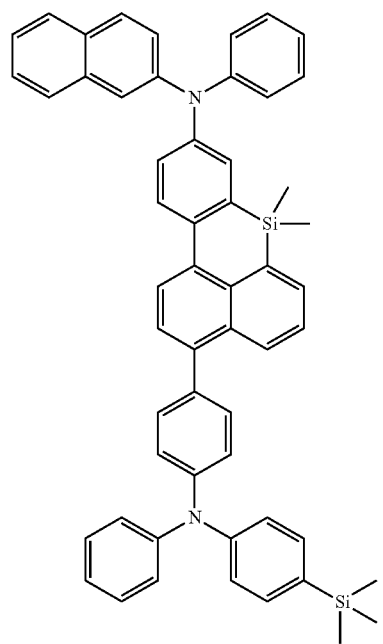
357
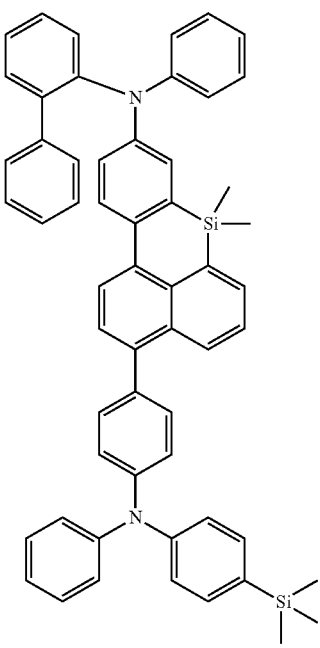
358

229
-continued
| 359 | 360 |
|---|---|
| 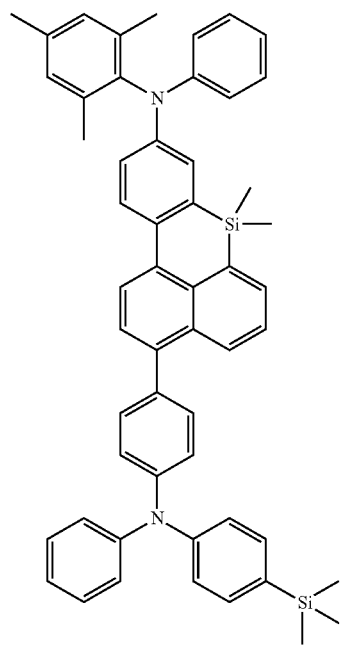 | 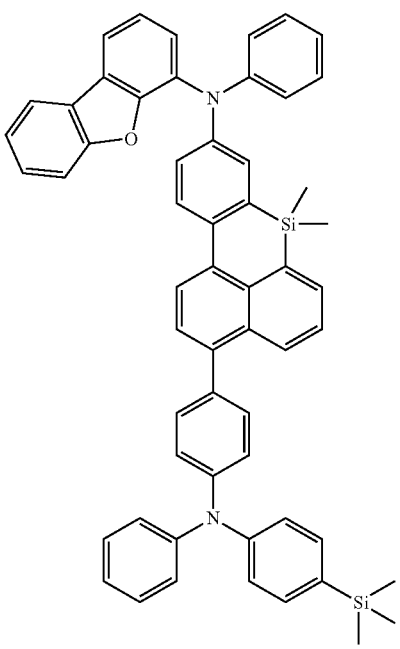 |
| 361 | 362 |
| 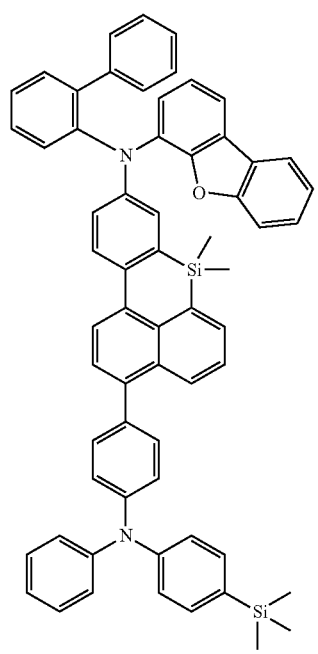 | 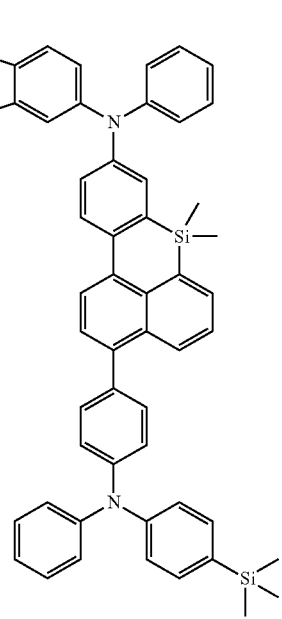 |

231 232
-continued
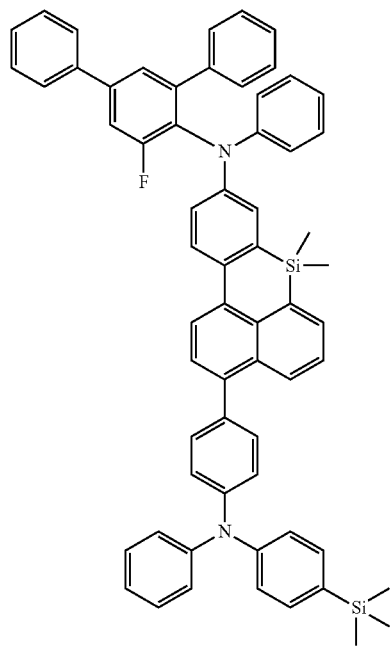
363
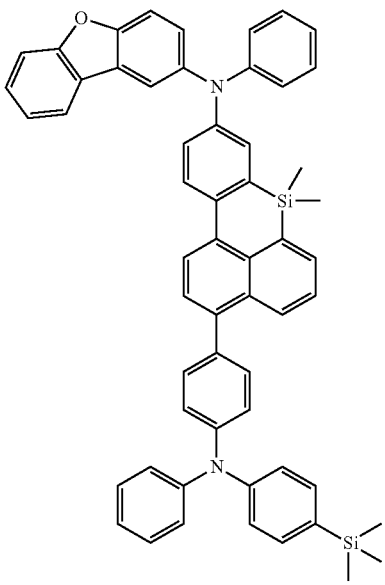
364
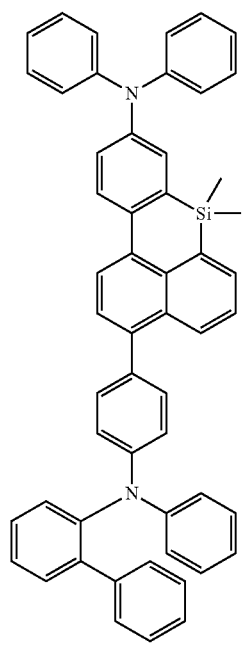
365
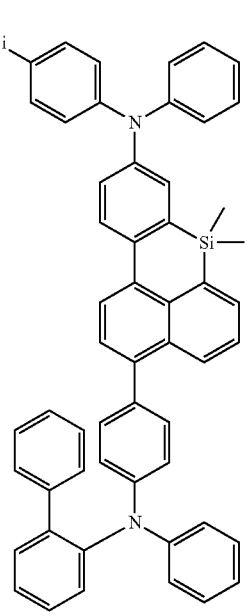
366

-continued
367 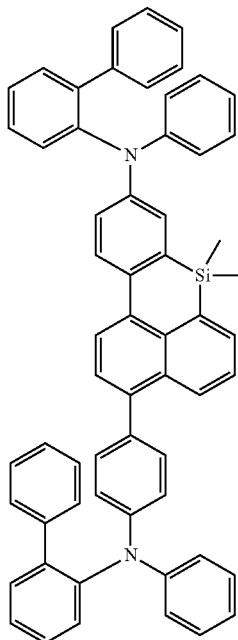
368 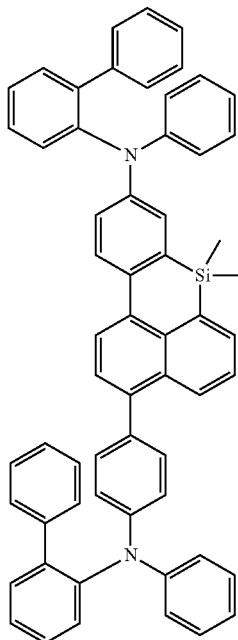
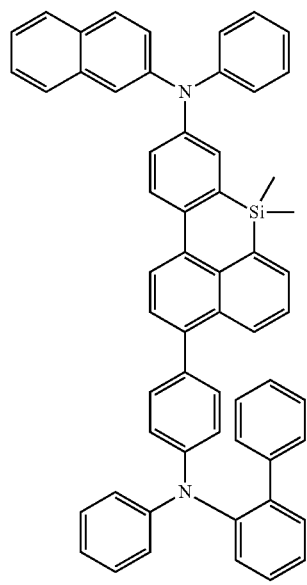
369 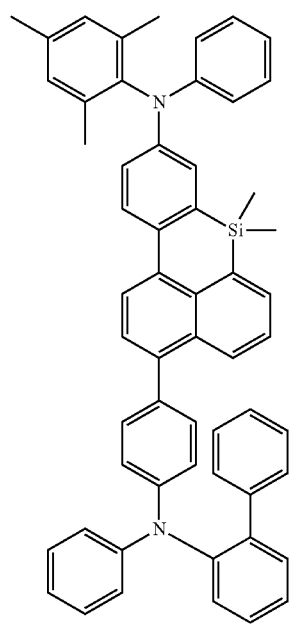
370 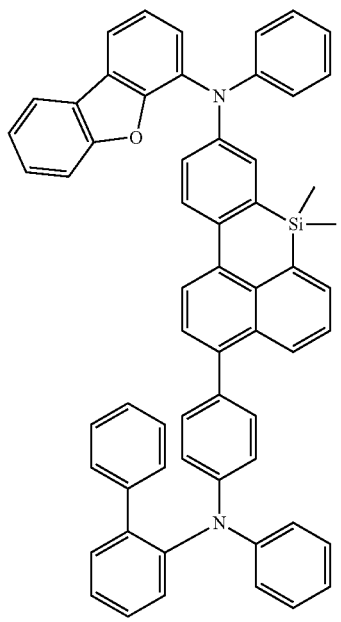

235 236
-continued
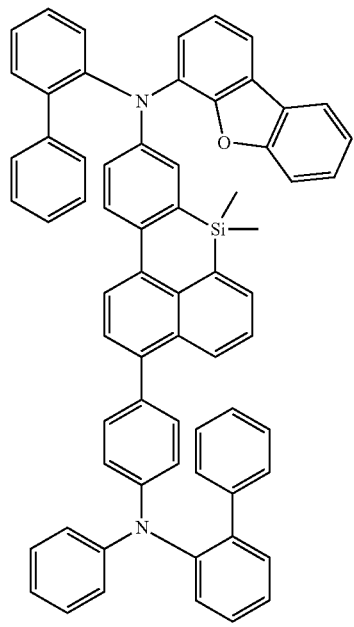
371
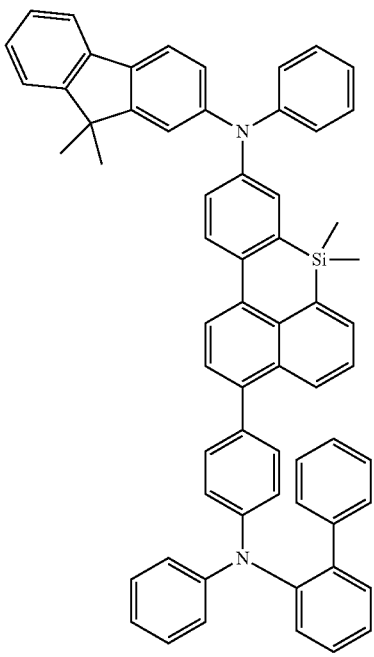
372
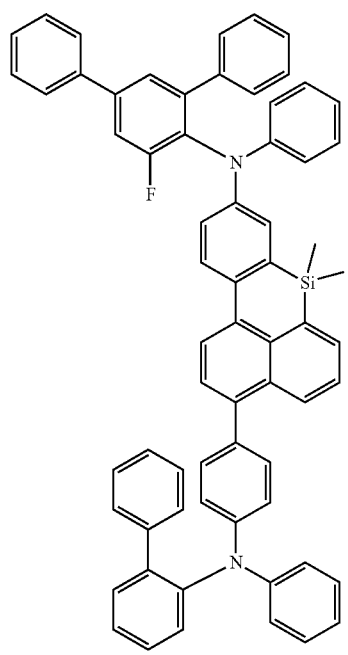
373
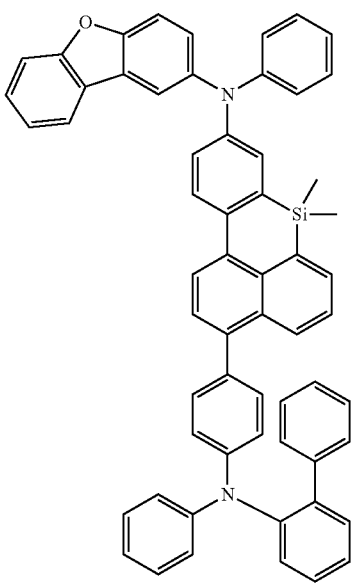
374

-continued
237
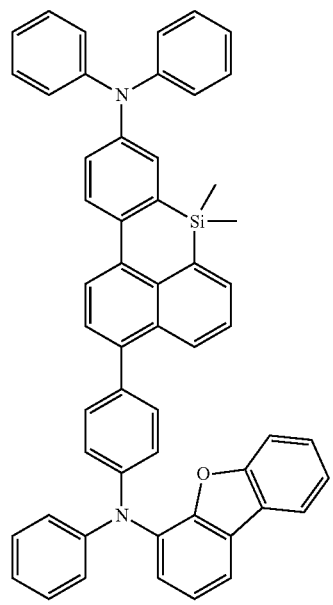
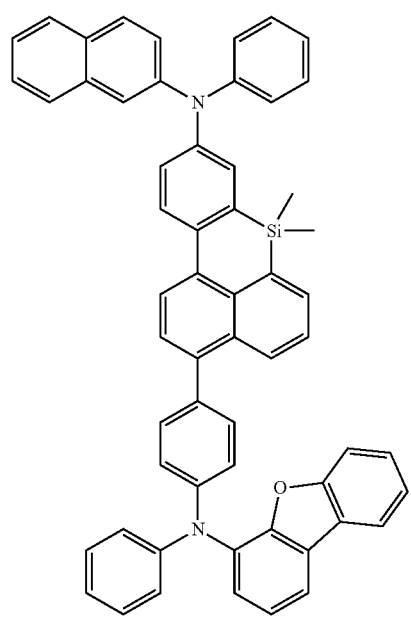
238
375
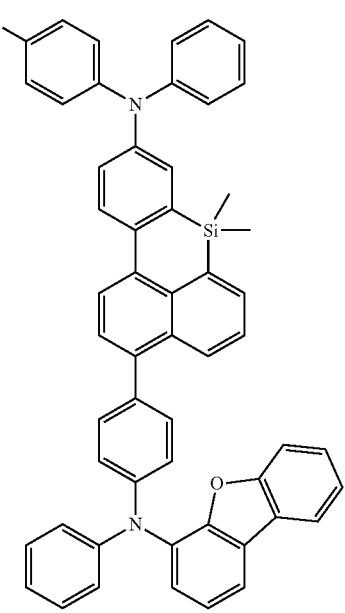
377
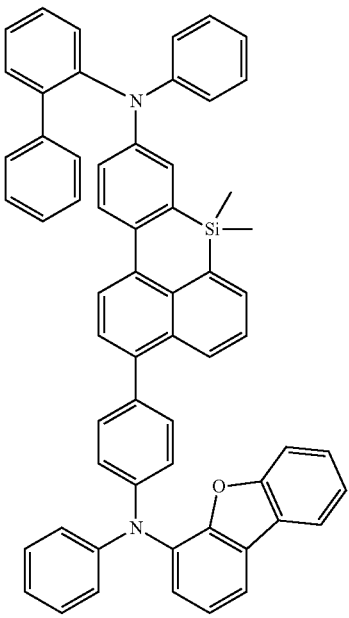
376
378

-continued
239
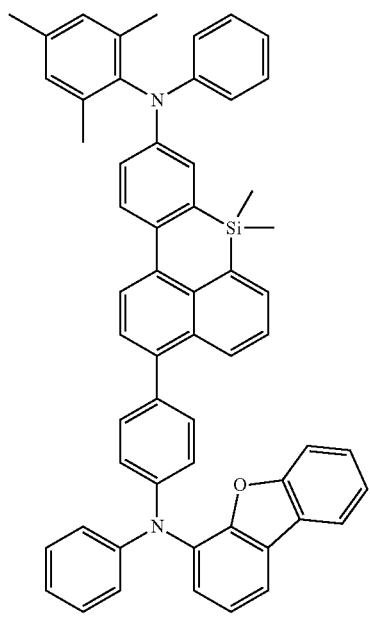
240
379
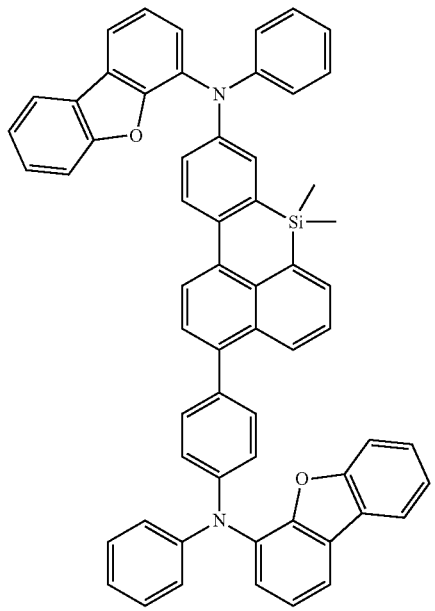
380
381
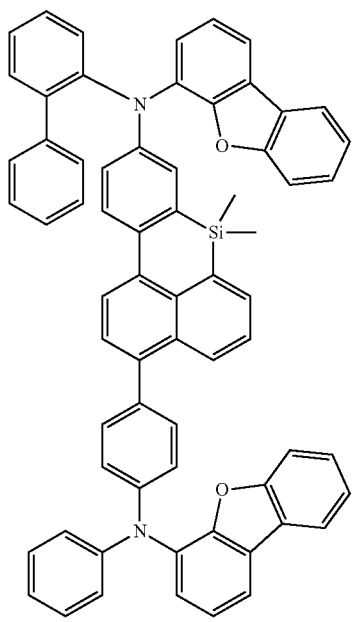
382
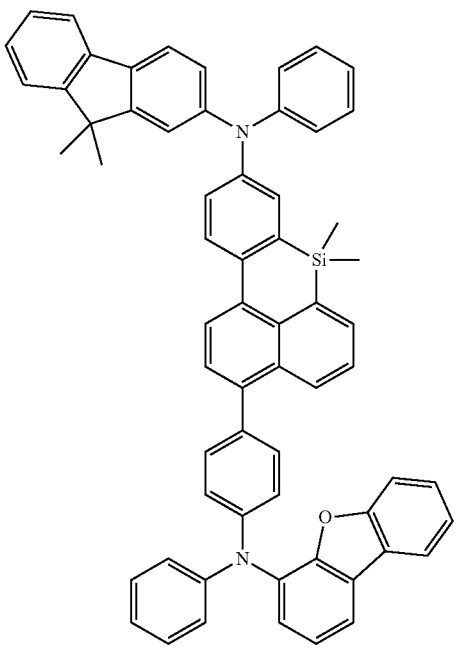

241
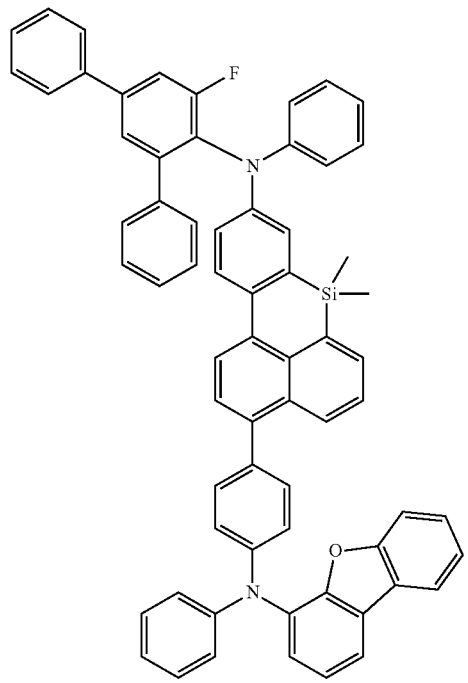
383
242
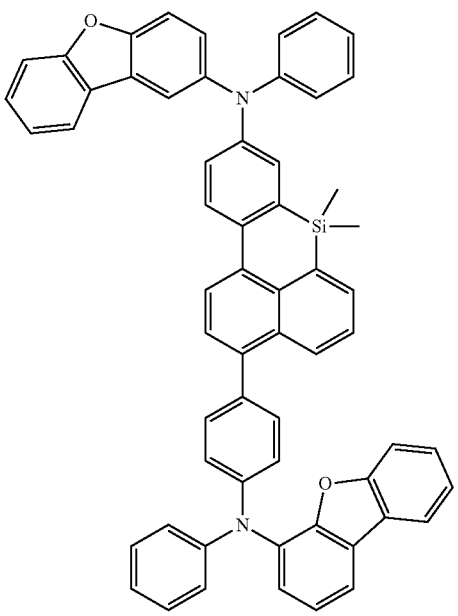
384
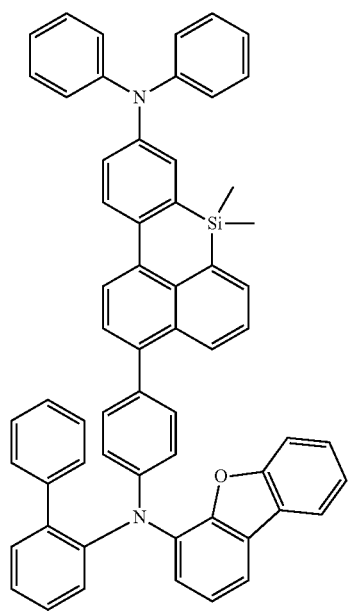
385
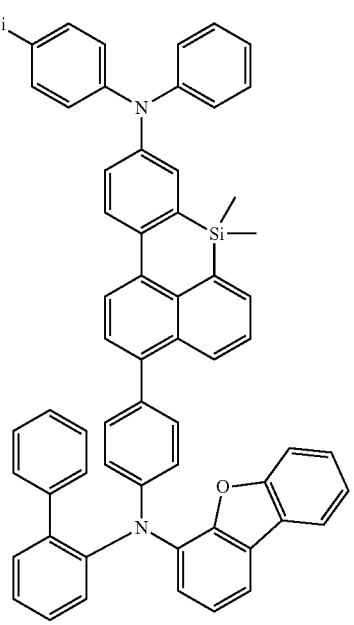
386

-continued
387
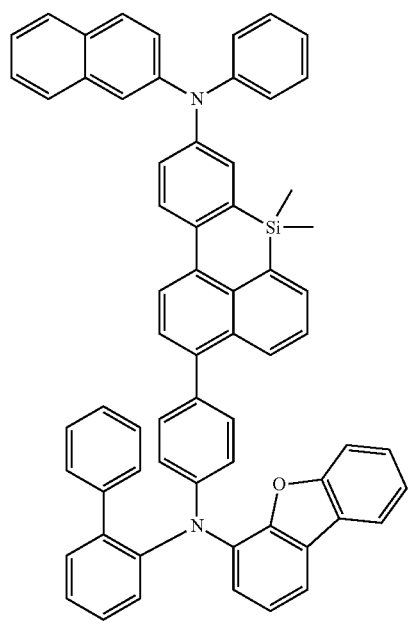
388
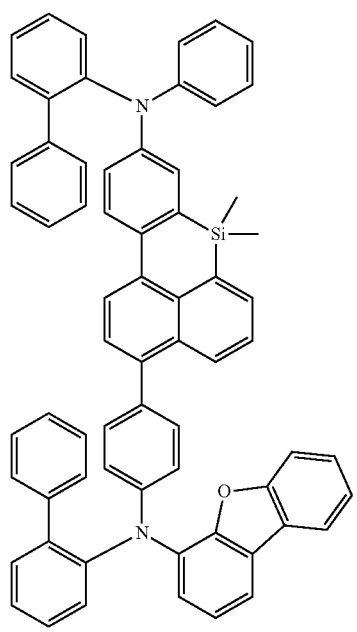
389
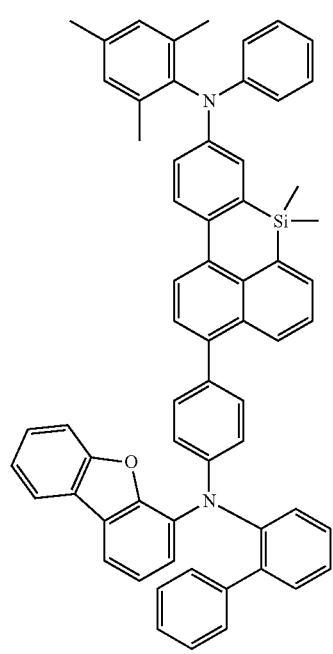
390
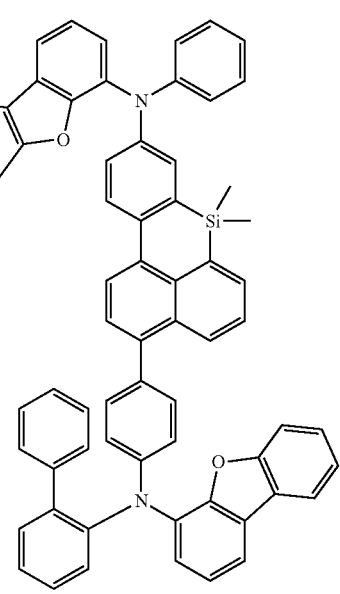

-continued
245
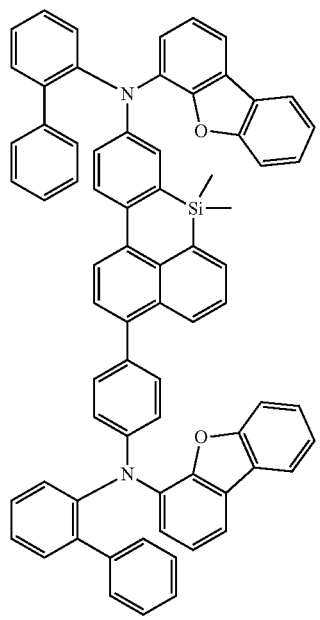
246
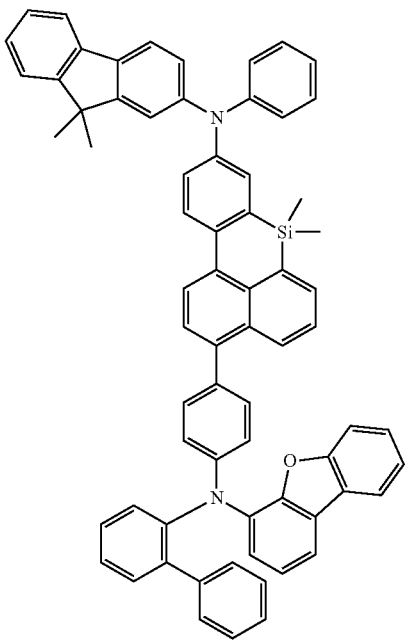
391
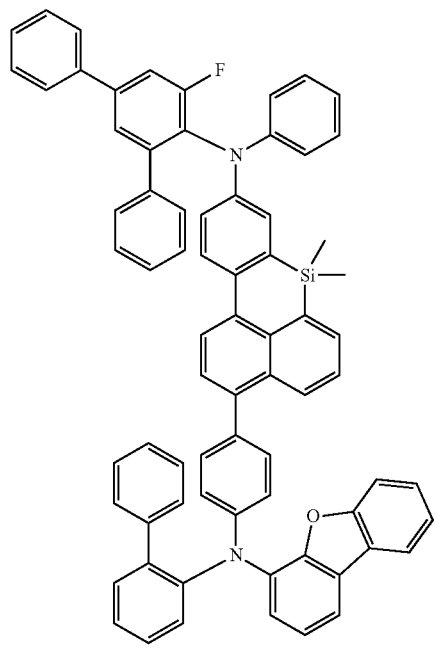
392
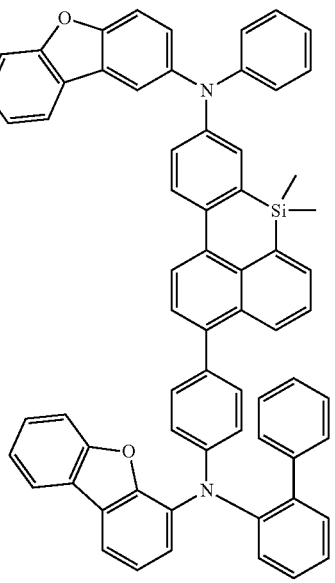
393
394

-continued
247
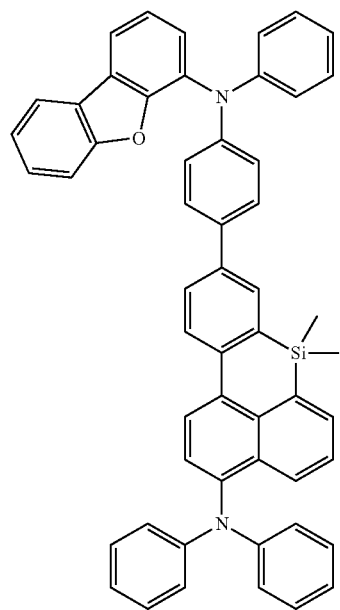
395
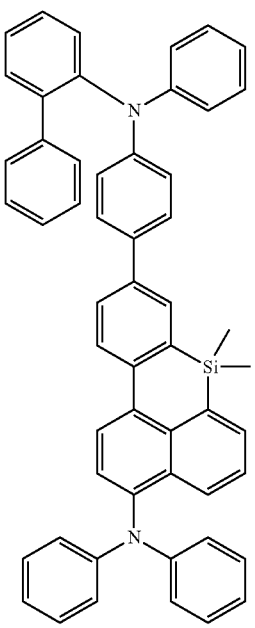
248
396
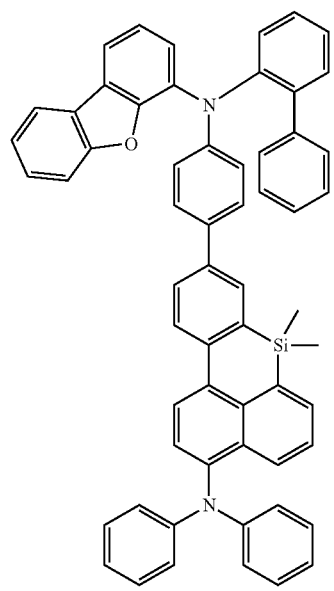
397
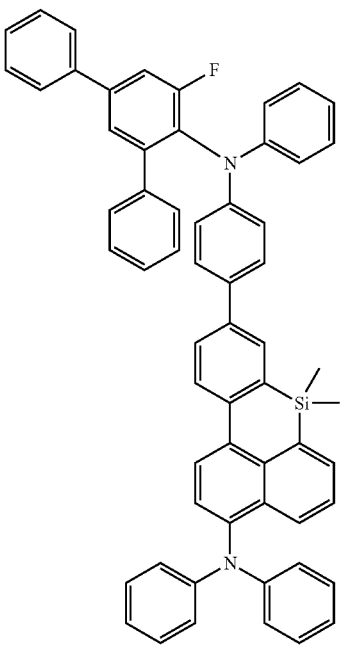
398

249
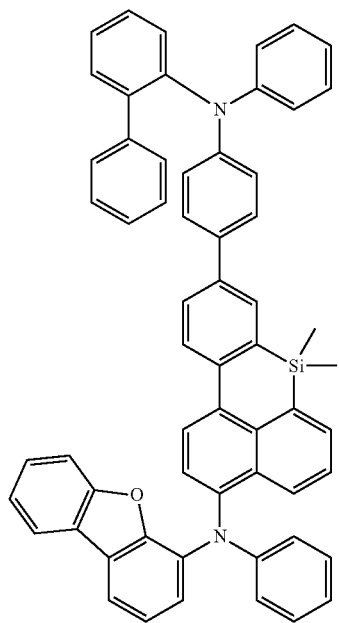
250
-continued
399
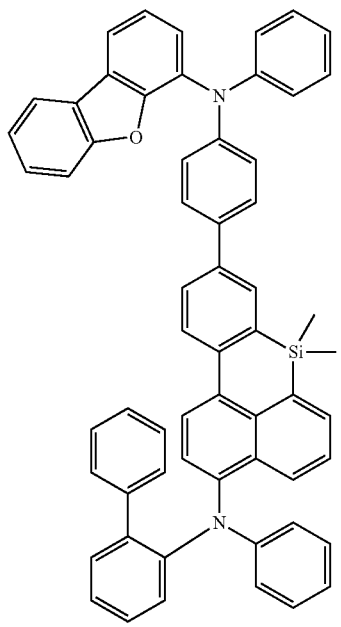
400
401
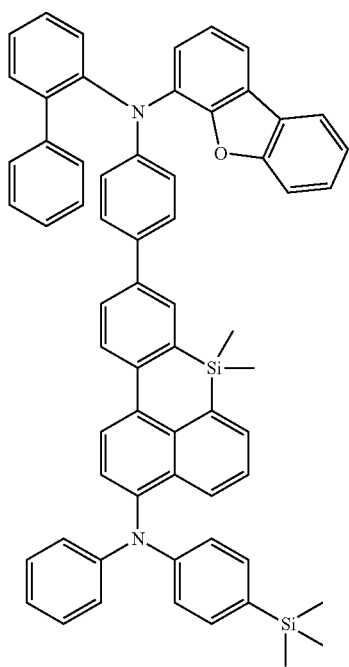
402
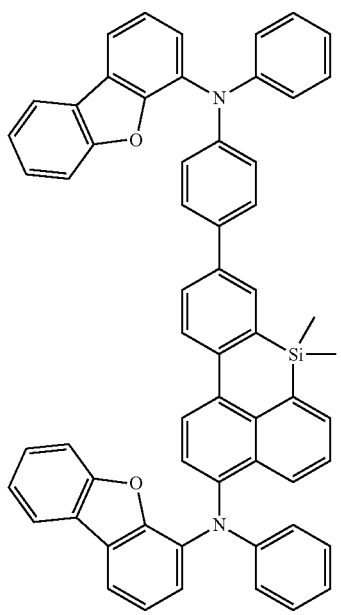

251 252
-continued
403 404
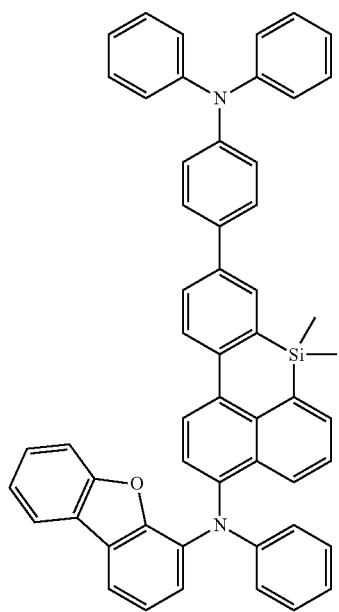
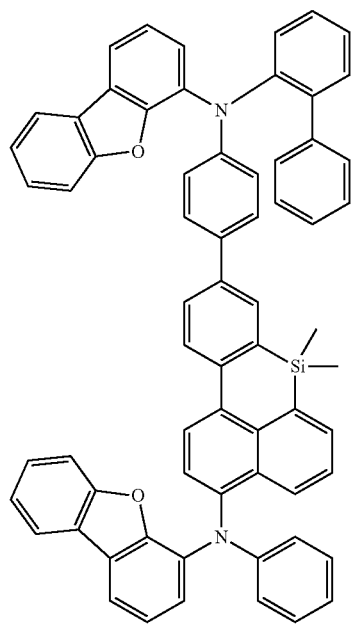
405 406
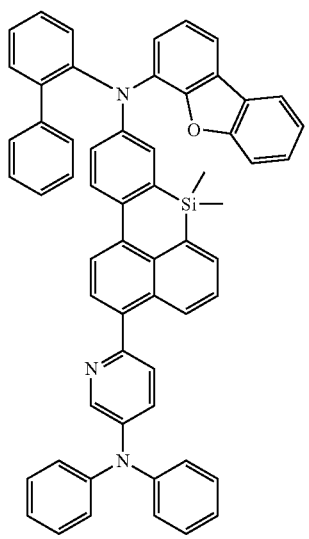
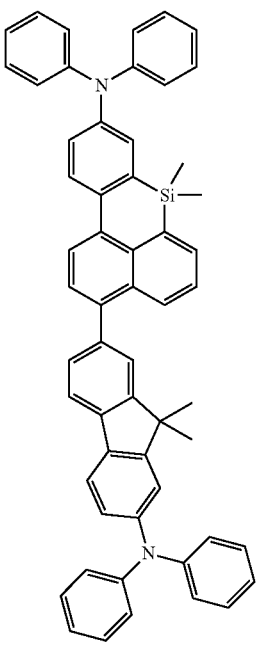

-continued
407 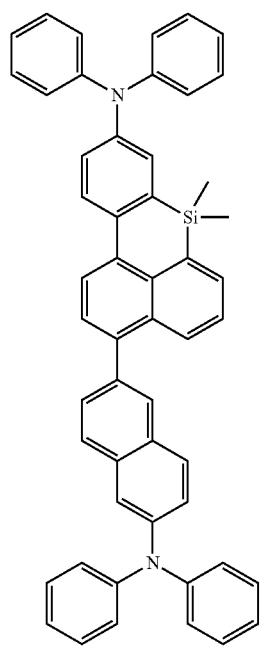
408 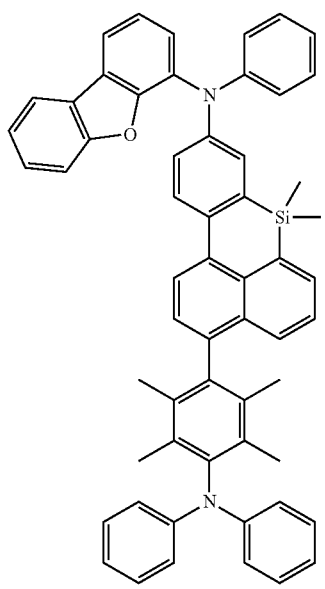
409 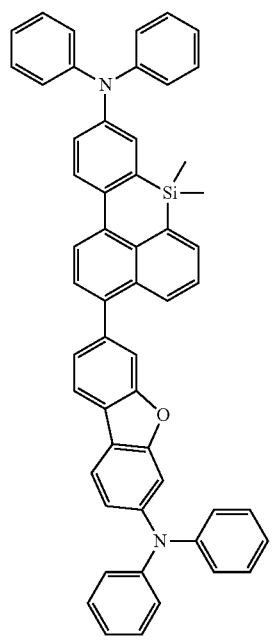
410 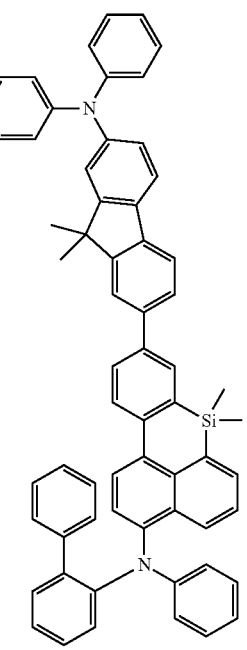

-continued
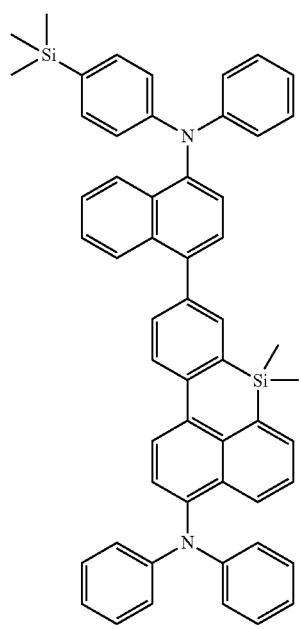
411
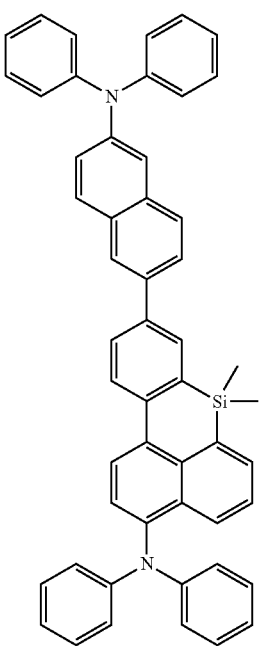
412
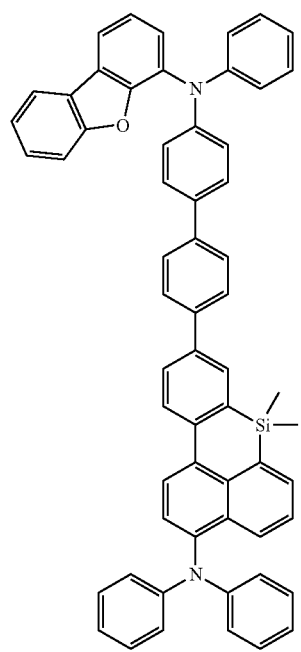
413
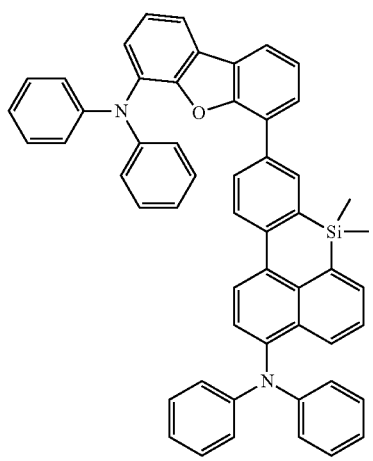
414

-continued
415
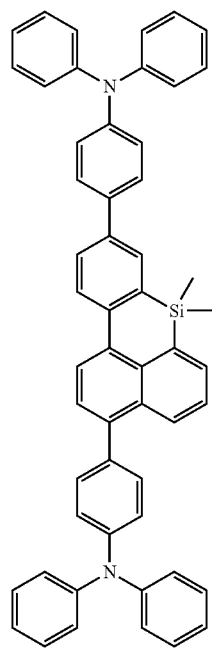
416
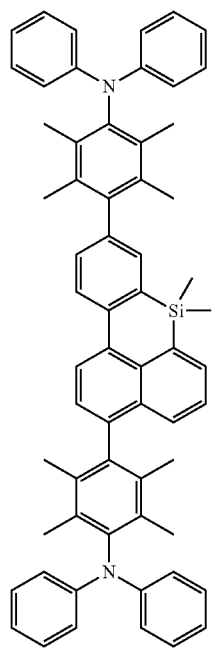
417
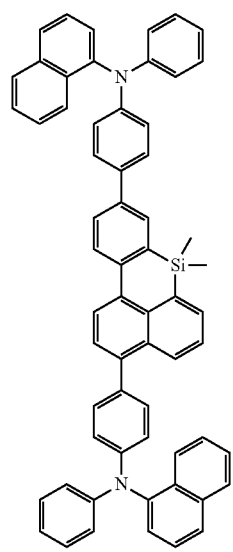
418
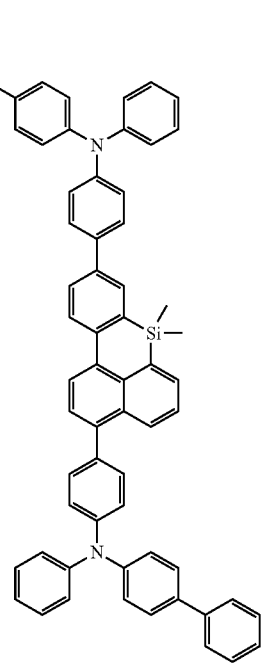

-continued
419
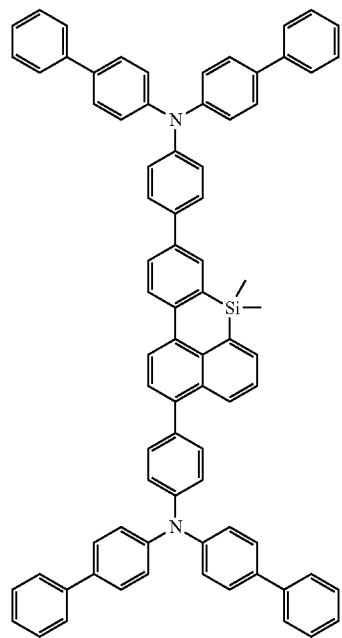
420
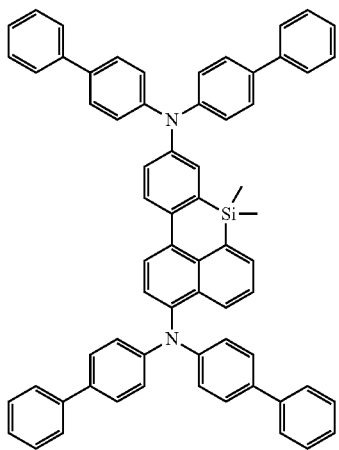
421
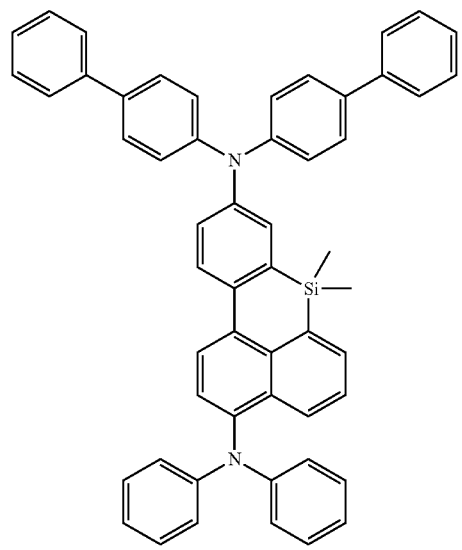
422
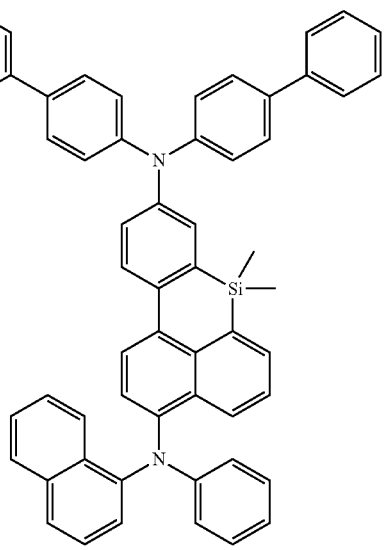

-continued
261
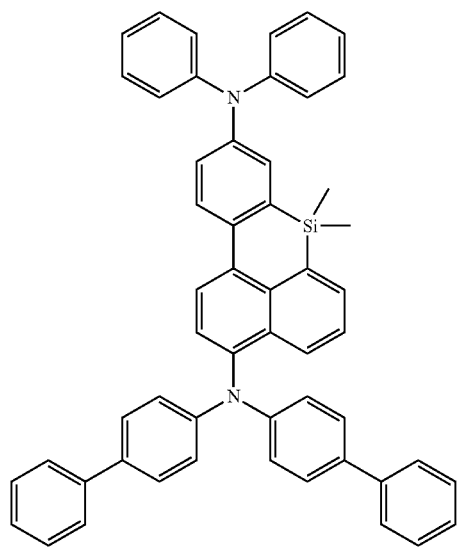
423
262
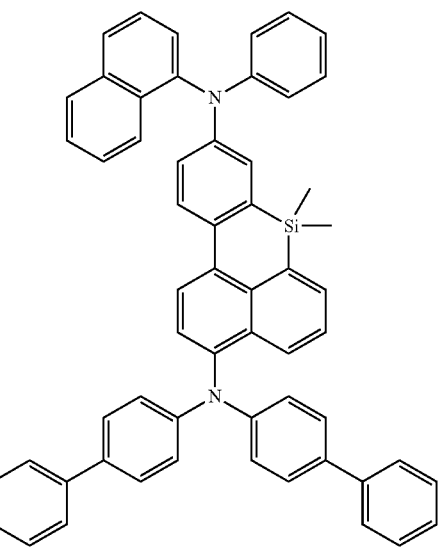
424
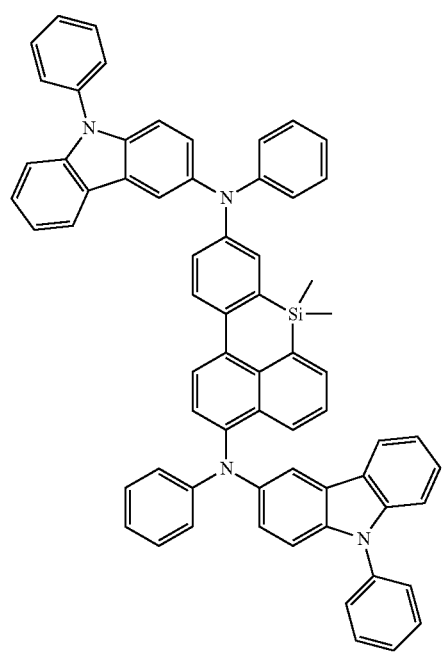
425
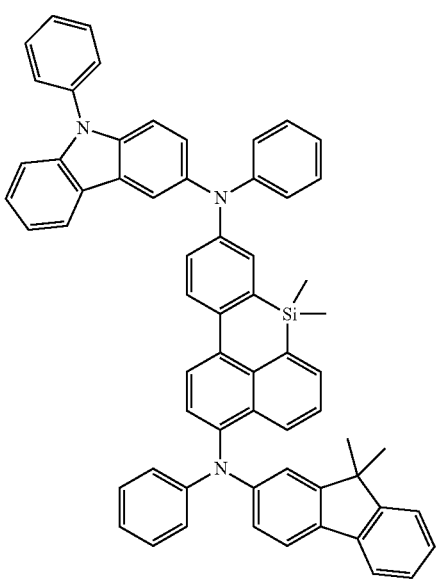
426

-continued
427 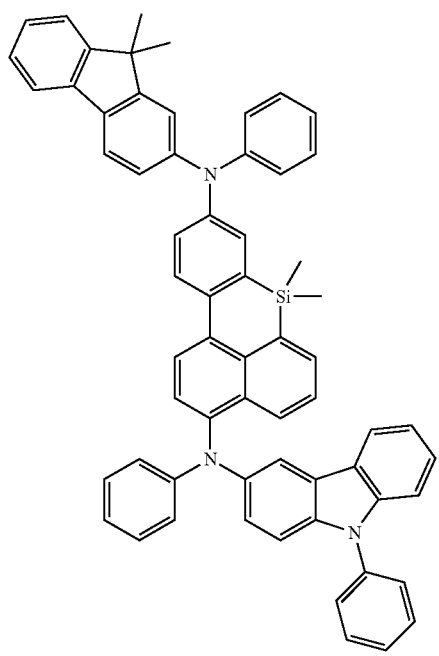
428 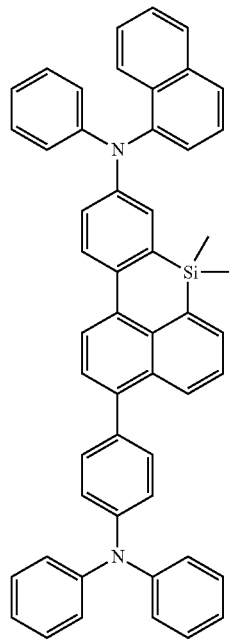
429 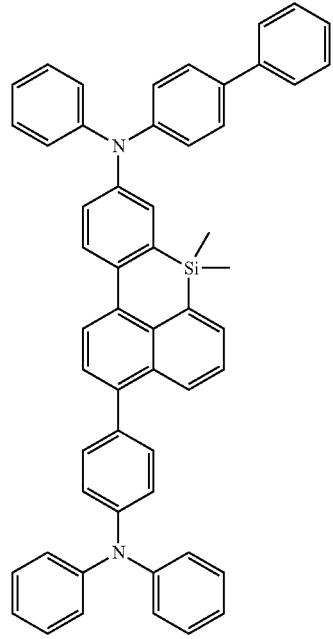
430 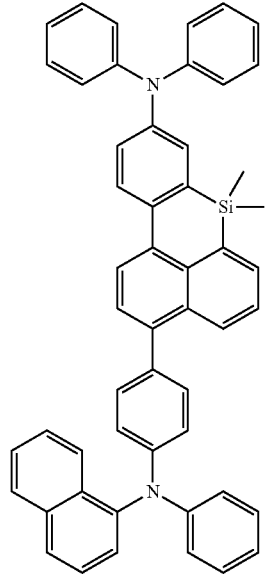

-continued
431
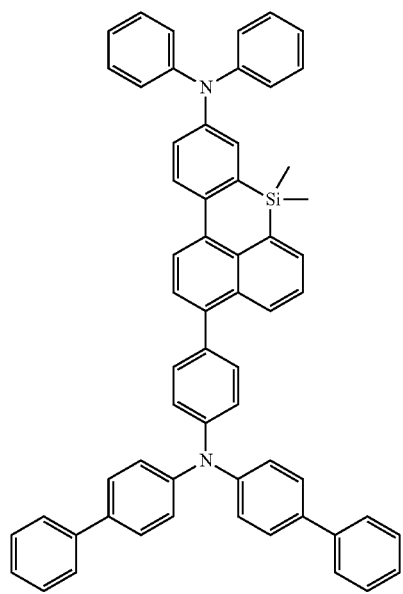
432
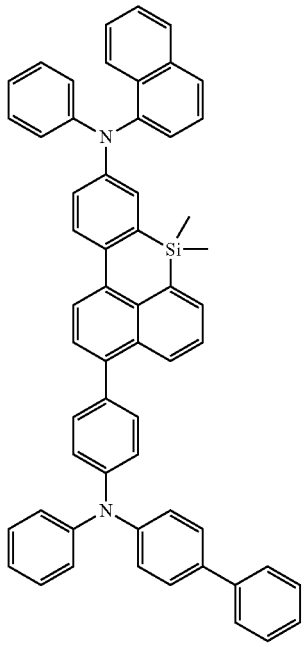
433
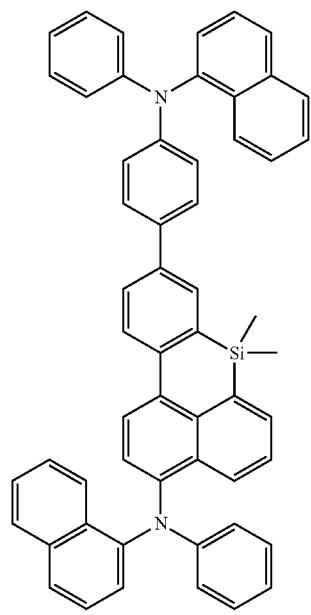
434
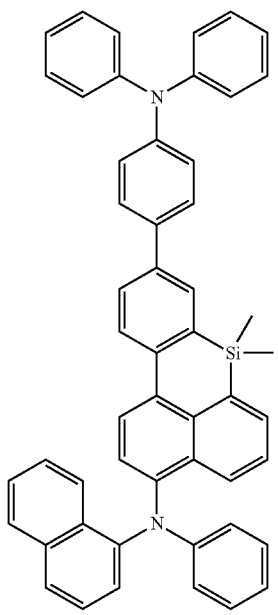

435

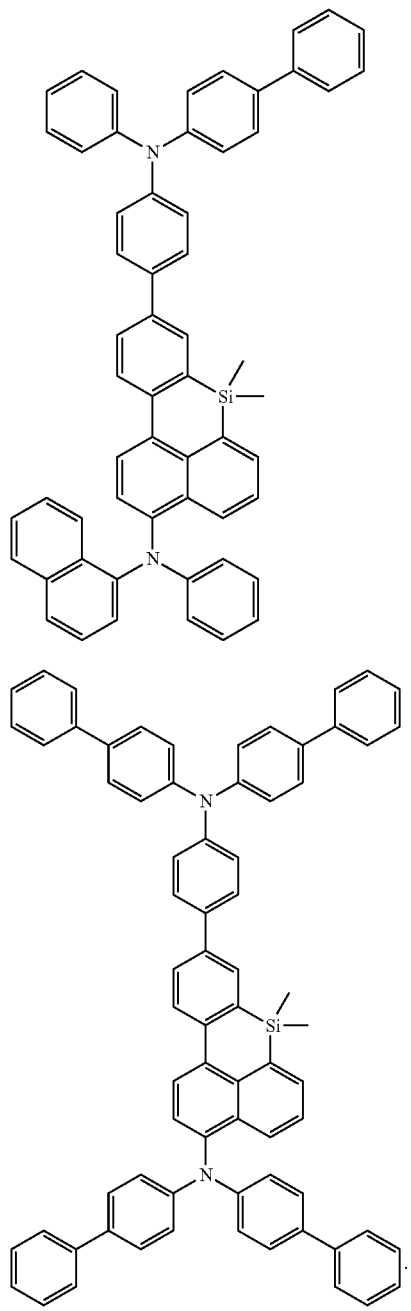

436

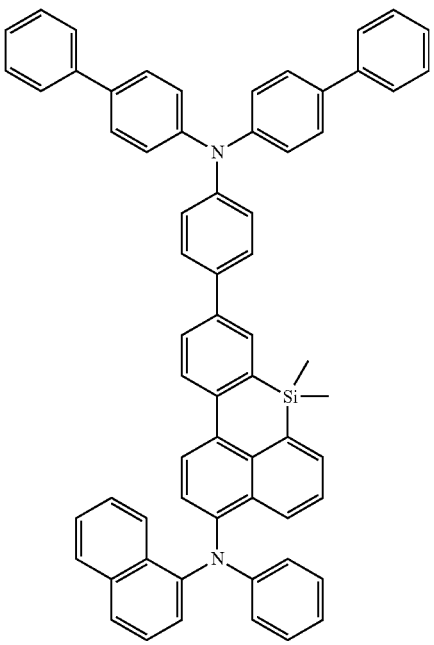

437

The amine-based compound of Formula 1 necessarily has silicon in its core. Due to the inclusion of silicon in the core of the amine-based compound of Formula 1, electron and hole transporting characteristics may be improved. Accordingly, an organic light-emitting device including the amine-based compound of Formula 1 may have improved driving voltage and lifespan.

In addition, when the amine-based compound of Formula 1 includes at least one amine substituent, the emission wavelength may be easily adjusted. Accordingly, an organic light-emitting device including the amine-based compound of Formula 1 may have high color purity.

In addition, based on improved chemical, physical, and electrical characteristics of the amine-based compound of Formula 1, an organic light-emitting device including the amine-based compound of Formula 1 may have low driving voltage, long lifespan, high efficiency, and/or high color purity.

The amine-based compound of Formula 1 may be synthesized by utilizing any suitable organic synthesis methods. The organic synthesis methods of the amine-based compound of Formula 1 may be understood by those of ordinary skill in the art by referring to the Examples that will be described later.

At least one amine-based compound of Formula 1 may be utilized between a pair of electrodes in an organic light-emitting device. For example, an emission layer and/or a hole transport region may include the amine-based compound of Formula 1. In various embodiments, an emission layer may include the amine-based compound of Formula 1, and may further include a host, wherein the amine-based compound of Formula 1 may be utilized as a dopant. In various embodiments, the hole transport region may include a hole transport layer, and the hole transport layer may include the amine-based compound of Formula 1.

Therefore, there is provided an organic light-emitting device that may include: a first electrode; a second electrode facing the first electrode; and an organic layer between the first electrode and the second electrode, the organic layer including an emission layer, wherein the organic layer includes the amine-based compound of Formula 1.

Descriptions of FIG. 1

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 according to an embodiment will be described in connection with FIG. 1.

First Electrode 110

In FIG. 1, a substrate may be additionally disposed under the first electrode 110 or above the second electrode 190. The substrate may be a glass substrate or a transparent plastic substrate, each having excellent mechanical strength, thermal stability, transparency, surface smoothness, ease of handling, and/or water-resistance.

The first electrode 110 may be, for example, formed by depositing or sputtering a material for the first electrode 110 on the substrate. When the first electrode 110 is an anode, the material for the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, the material for the first electrode 110 may be a transparent and highly conductive material, and non-limiting examples of such material may include indium tin oxide (ITO), indium zinc oxide (IZO), tin oxide ($SnO_2$), zinc oxide (ZnO), or a combination thereof, but embodiments of the present disclosure are not limited thereto. In various embodiments, when the first electrode 110 is a semi-transmissive electrode or a reflective electrode, the material for the first electrode 110 may be selected from magnesium (Mg), aluminum (Al), aluminum-lithium (Al—Li), calcium (Ca), magnesium-indium (Mg—In), magnesium-silver (Mg—Ag), and combinations thereof, but embodiments of the present disclosure are not limited thereto.

The first electrode 110 may have a single-layered structure, or a multi-layered structure including a plurality of layers. For example, the first electrode 110 may have a three-layered structure of ITO/Ag/ITO, but embodiments of the present disclosure are not limited thereto.

Organic Layer 150

The organic layer 150 may be disposed on the first electrode 110 and may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single layered structure formed of a single material, ii) a single-layered structure formed of a plurality of different materials, or iii) a multi-layered structure having a plurality of layers formed of a plurality of different materials.

The hole transport region may include at least one layer selected from a hole injection layer, a hole transport layer, an emission auxiliary layer, and an electron blocking layer.

For example, the hole transport region may have a single-layered structure formed of a plurality of different materials, or a structure of hole injection layer/hole transport layer, a structure of hole injection layer/hole transport layer/emission auxiliary layer, a structure of hole injection layer/emission auxiliary layer, a structure of hole transport layer/emission auxiliary layer, or a structure of hole injection layer/hole transport layer/electron blocking layer, wherein the layers of each structure are sequentially stacked from the first electrode 110 in each stated order, but embodiments of the present disclosure are not limited thereto.

When the hole transport region includes a hole injection layer, the hole injection layer may be formed on the first electrode 110 by utilizing one or more suitable methods such as vacuum deposition, spin coating, casting, a Langmuir-Blodgett (LB) method, ink-jet printing, laser-printing, and/or laser-induced thermal imaging (LITI).

When a hole injection layer is formed by vacuum deposition, for example, the vacuum deposition may be performed at a deposition temperature of about 100° C. to about 500° C., at a vacuum degree of about $10^{-8}$ torr to about $10^{-3}$ torr, and at a deposition rate of about 0.01 Å/sec to about 100 Å/sec, by taking into account a compound for forming the hole injection layer to be deposited and a structure of the hole injection layer to be formed.

When a hole injection layer is formed by spin coating, for example, the spin coating may be performed at a coating rate of about 2,000 rpm to about 5,000 rpm, and at a temperature of about 80° C. to about 200° C., by taking into account a compound for the hole injection layer to be deposited and a structure of the hole injection layer to be formed.

When the hole transport region includes a hole transport layer, the hole transport layer may be formed on the first electrode 110 or the hole injection layer by utilizing one or more suitable methods such as vacuum deposition, spin coating, casting, an LB method, ink-jet printing, laser-printing, and/or LITI. When the hole transport layer is formed by vacuum deposition and/or spin coating, deposition and coating conditions for the hole transport layer may be the same as the deposition and coating conditions for the hole transport layer.

The hole transport region may include, in addition to the amine-based compound of Formula 1, at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201, and a compound represented by Formula 202:

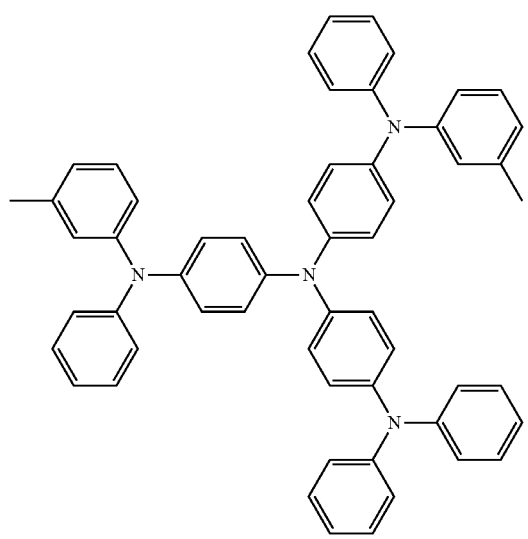
m-MTDATA
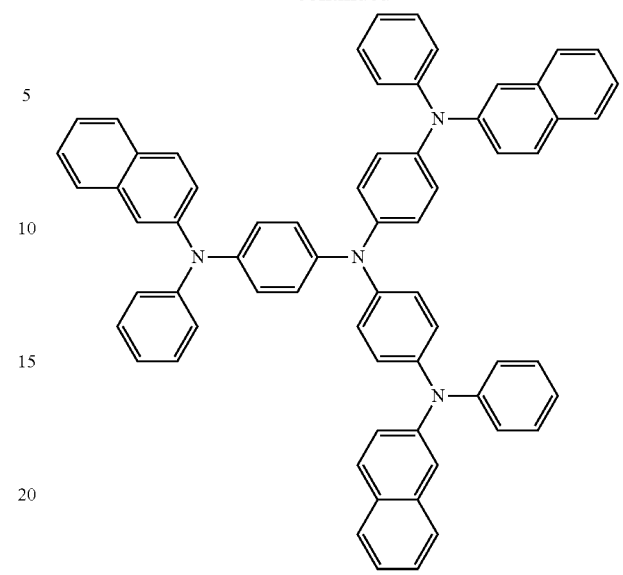
2-TNATA
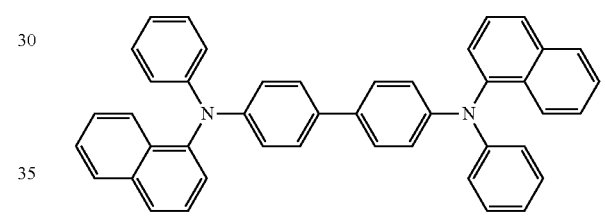
NPB
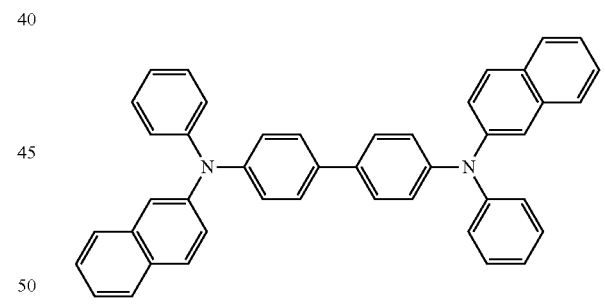
β-NPB
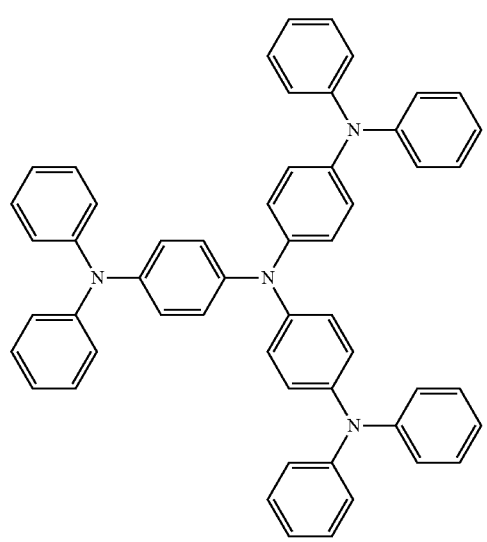
TDATA
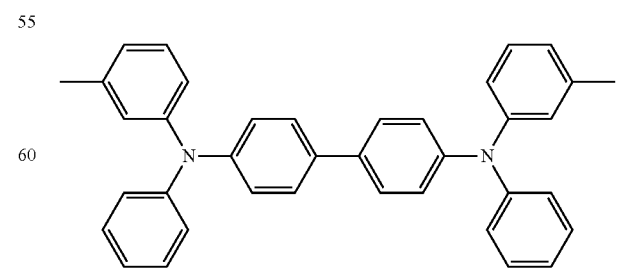
TPD

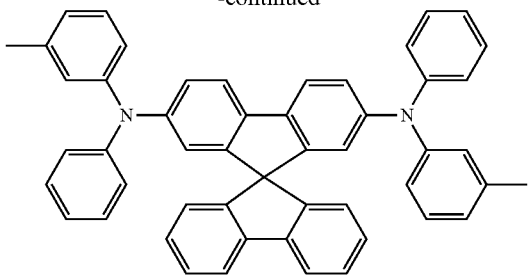

Spiro-TBD

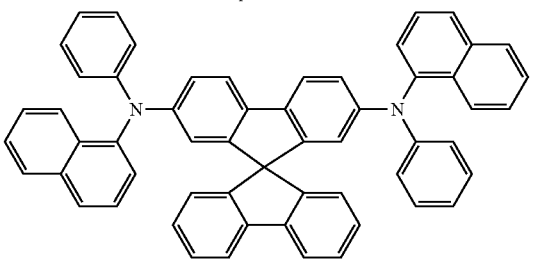

Spiro-NBD

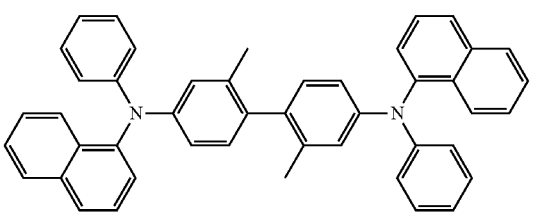

methylated NPB

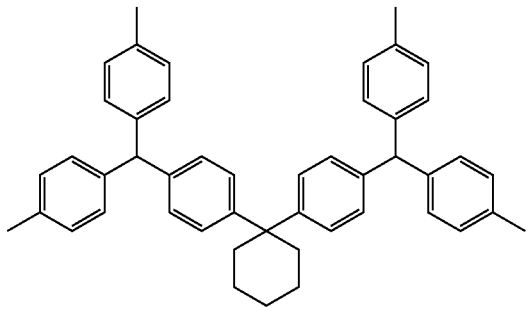

TAPC

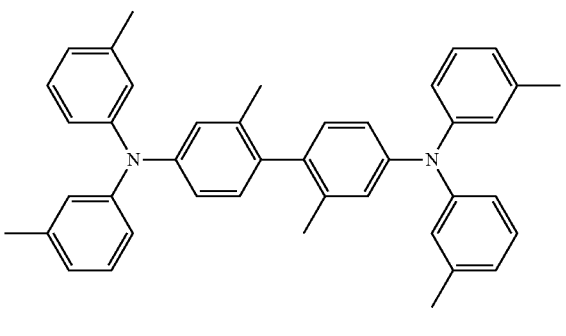

HMTPD

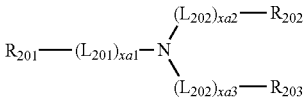

Formula 201

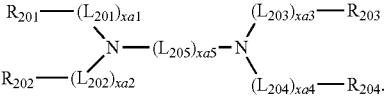

Formula 202

In Formulae 201 and 202, $L_{201}$ to $L_{205}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be selected from 0, 1, 2, and 3, xa5 may be selected from 1, 2, 3, 4, and 5, and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may each independently be selected from the group consisting of:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xa1 to xa4 may each independently be 0, 1, or 2.

In various embodiments, xa5 may be 1, 2, or 3.

In various embodiments, $R_{201}$ to $R_{204}$ may each independently be selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be the same as described herein.

The compound of Formula 201 may be represented by Formula 201A:

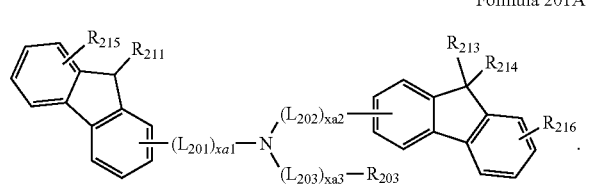

Formula 201A

For example, the compound of Formula 201 may be represented by Formula 201A-1, but embodiments of the present disclosure are not limited thereto:

Formula 201A-1

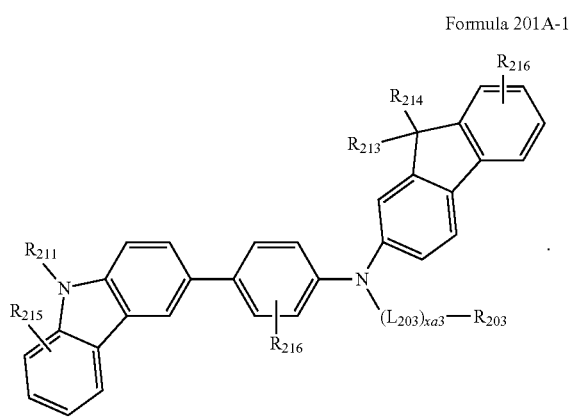

The compound of Formula 202 may be represented by Formula 202A, but embodiments of the present disclosure are not limited thereto:

Formula 202A

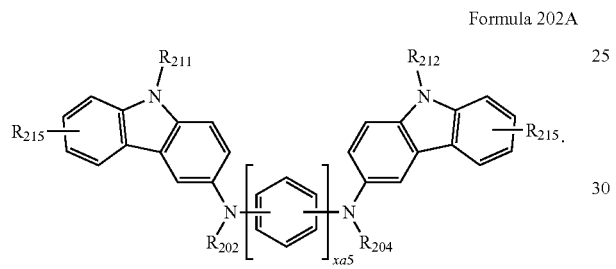

In Formulae 201A, 201A-1, and 202A, $L_{201}$ to $L_{203}$, xa1 to xa3, xa5, and $R_{202}$ to $R_{204}$ may each independently be the same as respectively described herein in connection with Formulae 201 and 202, $R_{211}$ and $R_{212}$ may each independently be the same as described herein in connection with $R_{203}$ in Formulae 201 and 202, and $R_{213}$ to $R_{216}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In Formulae 201A and 201A-1, $R_{213}$ and $R_{214}$ may be optionally linked to form a saturated or unsaturated ring.

The compound of Formula 201 and the compound of Formula 202 may each independently include Compounds HT1 to HT20, but embodiments of the present disclosure are not limited thereto:

HT1

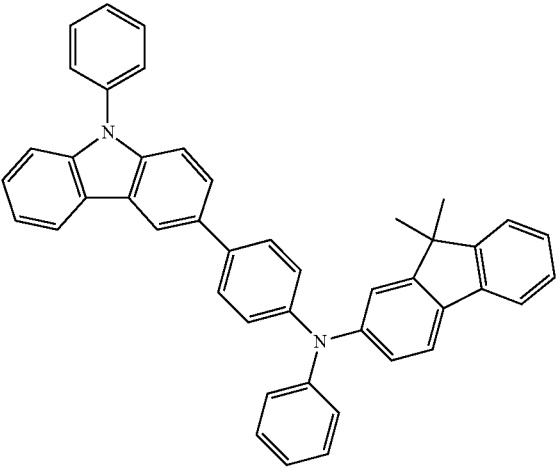

HT2

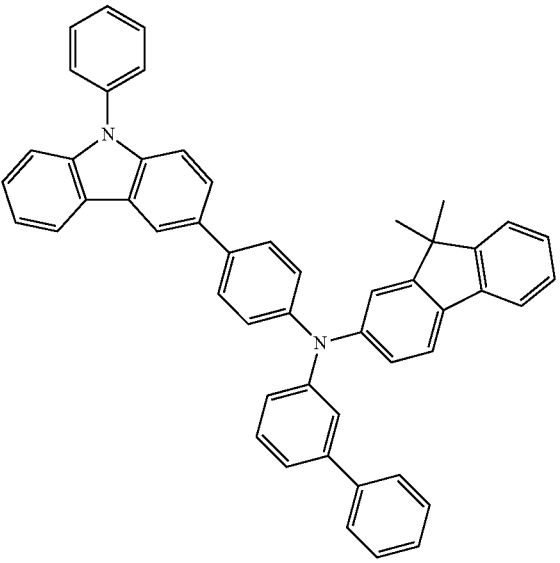

HT3
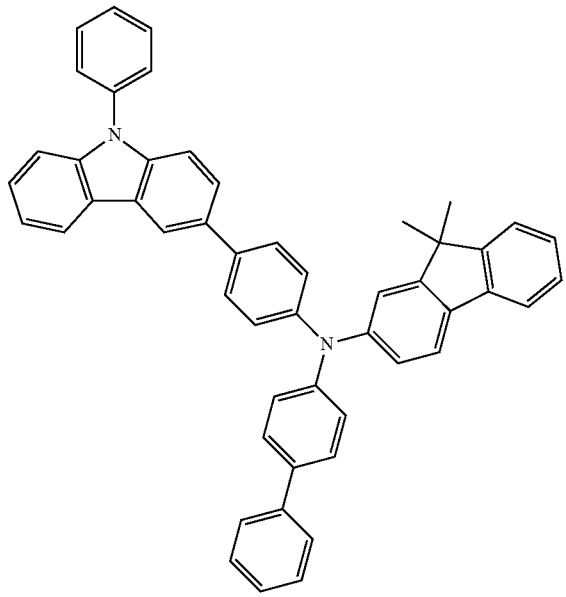
HT4
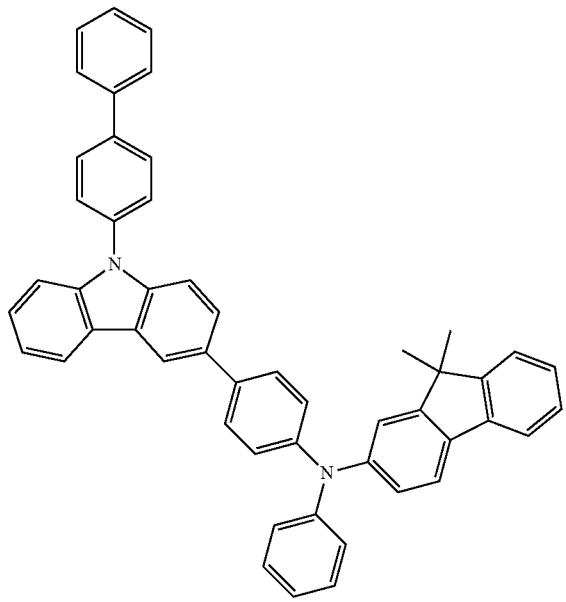
HT5
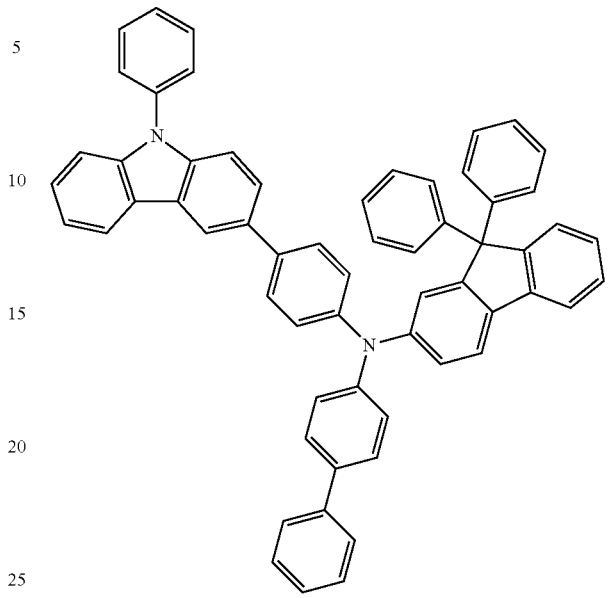
HT6
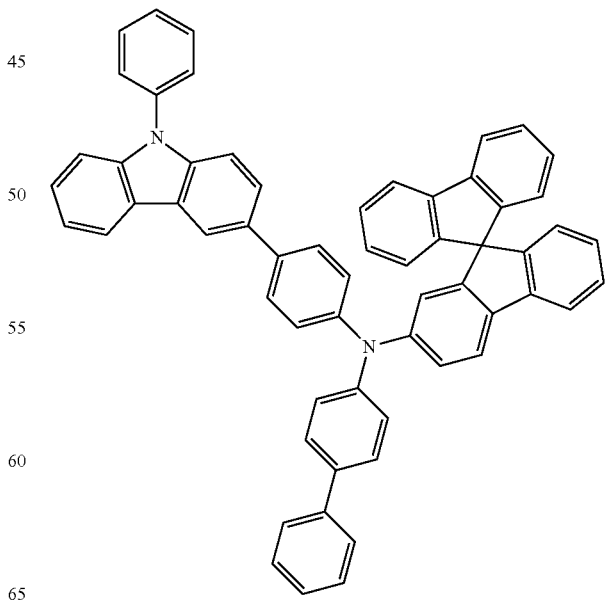

HT7
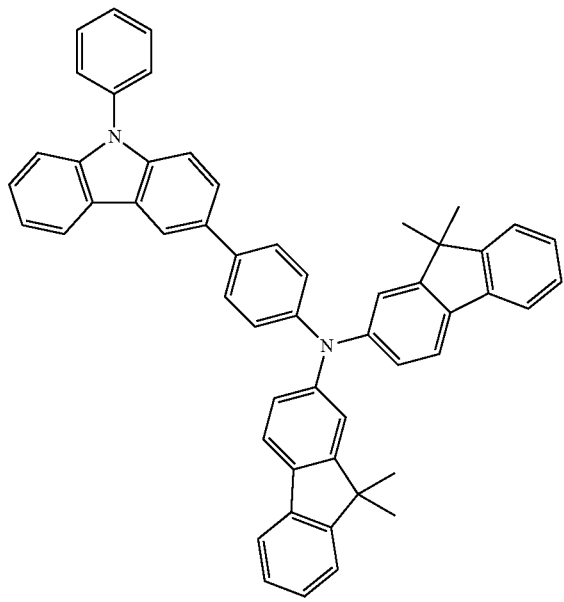
HT9
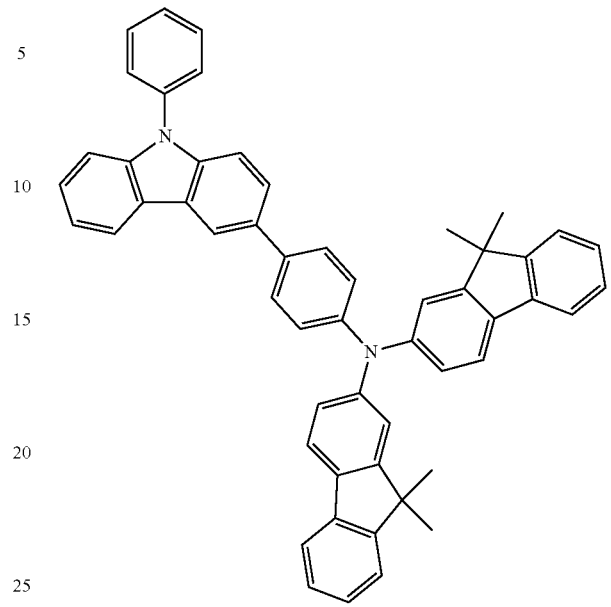
HT8
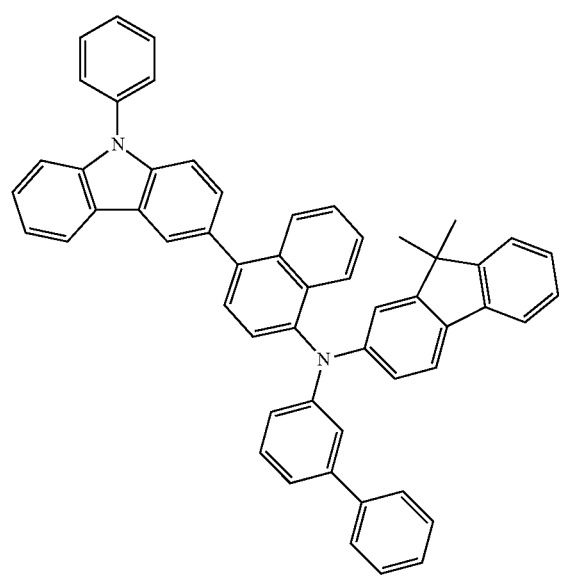
HT10
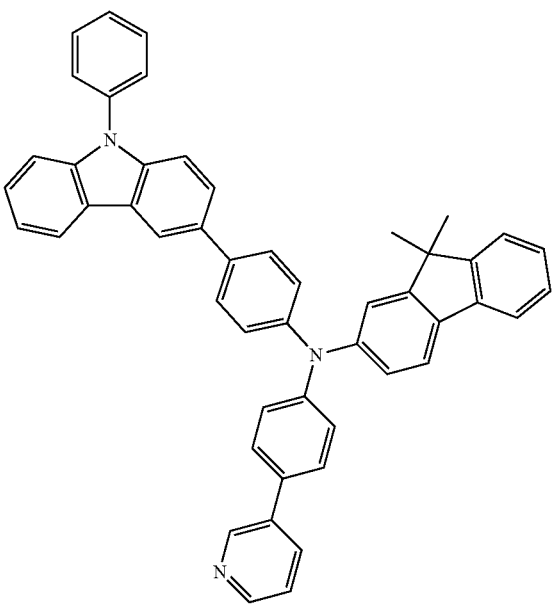

HT11
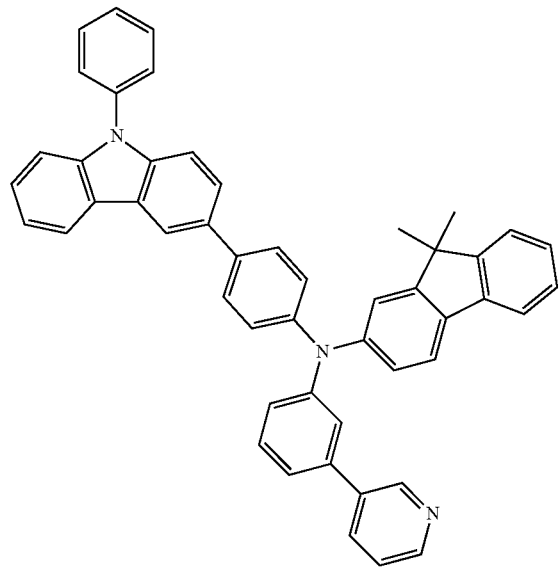
HT12
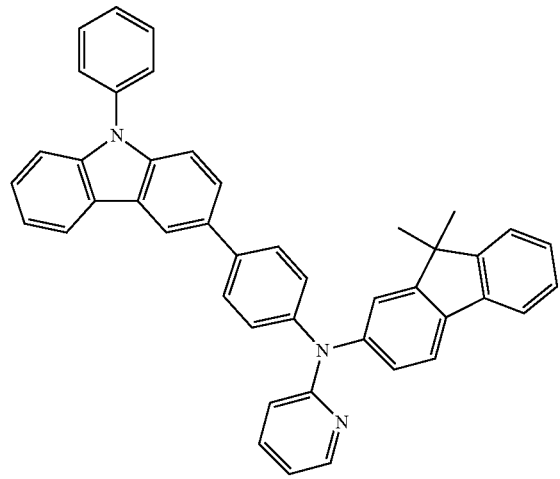
HT13
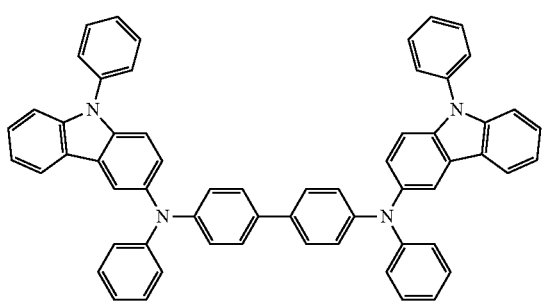
HT14
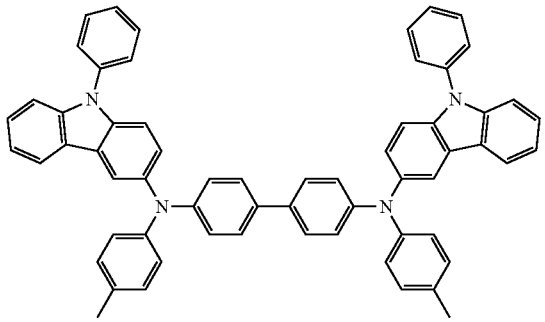
HT15
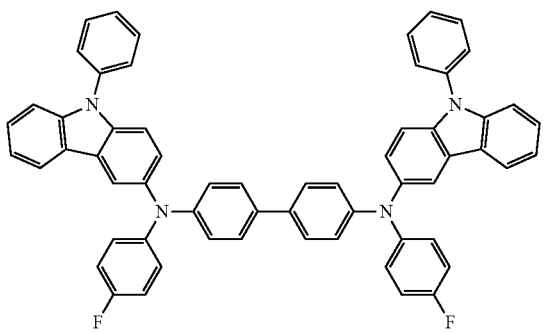
HT16
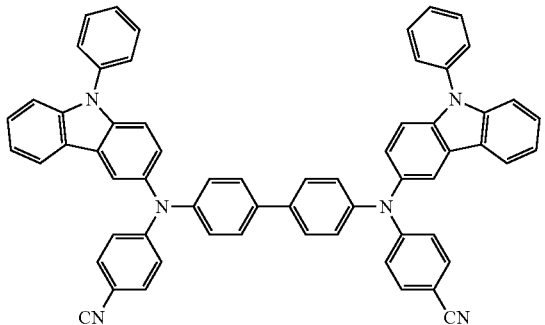
HT17
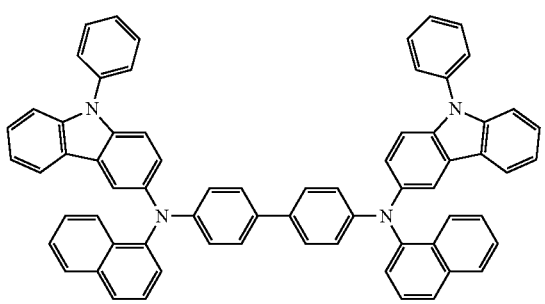

-continued

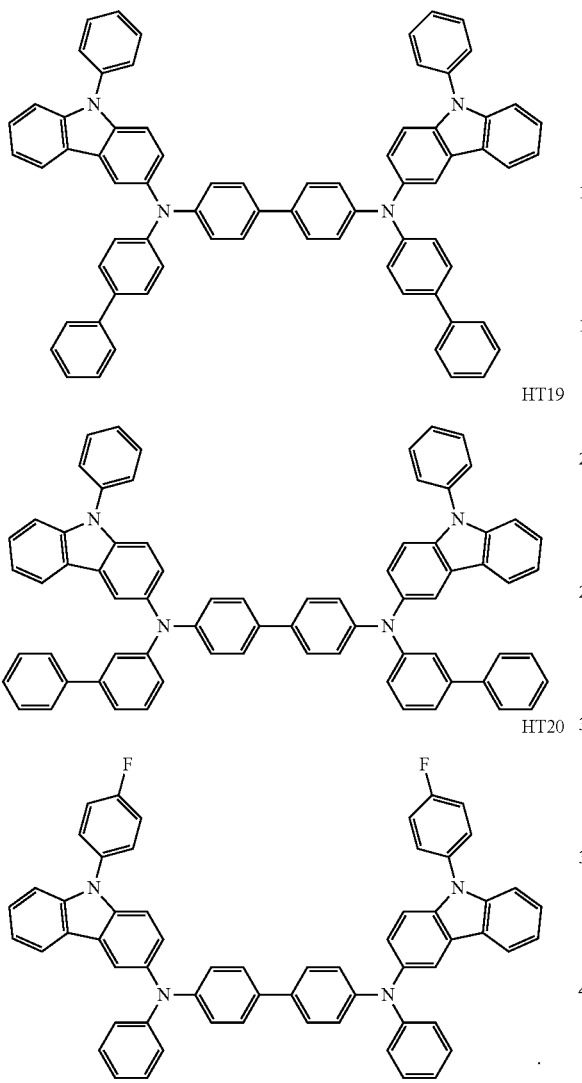

HT18

HT19

HT20

A thickness of the hole transport region may be in a range of about 100 Å to about 10,000 Å, for example, about 100 Å to about 1,000 Å. When the hole transport region includes at least one selected from a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within any of the ranges described above, satisfactory hole transport characteristics may be obtained without a substantial increase in driving voltage.

The emission auxiliary layer may increase light-emission efficiency by compensating for an optical resonance distance according to the wavelength of the light emitted by the emission layer, and the electron blocking layer may block the flow of electrons from the electron transport region. The emission auxiliary layer and the electron blocking layer may include the materials described above.

P-Dopant

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant.

In various embodiments, a lowest unoccupied molecular orbital (LUMO) of the p-dopant may be −3.5 eV or less.

The p-dopant may be one selected from a quinone derivative, a metal oxide, and a cyano group-containing compound, but embodiments of the present disclosure are not limited thereto.

For example, the p-dopant may include at least one selected from the group consisting of:

a quinone derivative, such as tetracyanoquinodimethane (TCNQ) and/or 2,3,5,6-tetrafluoro-7,7,8,8-tetracyanoquinodimethane (F4-TCNQ), a metal oxide, such as tungsten oxide and/or molybdenum oxide;

1,4,5,8,9,11-hexaazatriphenylene-hexacarbonitrile (HAT-CN); and a compound represented by Formula 221, but embodiments of the present disclosure are not limited thereto:

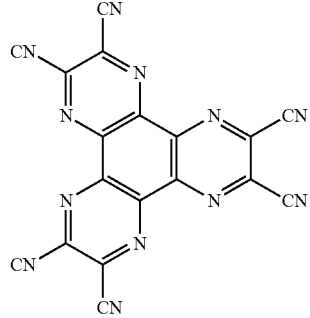

HAT-CN

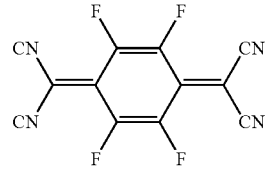

F4-TCNQ

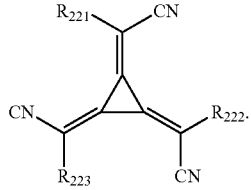

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

The emission layer may be formed on the first electrode 110 or the hole transport region by utilizing one or more suitable methods such as vacuum deposition, spin coating, casting, an LB method, ink-jet printing, laser-printing, and/or LITI. When the emission layer is formed by vacuum deposition and/or spin coating, deposition and coating conditions for the emission layer may be the same as the deposition and coating conditions for the hole transport layer.

When the organic light-emitting device 10 is a full-color organic light-emitting device, the emission layer may be patterned into a red emission layer, a green emission layer, and/or a blue emission layer, according to an individual sub-pixel. In various embodiments, the emission layer may have a stacked structure of two or more layers selected from a red emission layer, a green emission layer, and a blue emission layer, in which the two or more layers contact each other or are separated from each other. In various embodiments, the emission layer may include two or more materials selected from a red-light emission material, a green-light emission material, and a blue-light emission material, which may be mixed with each other in a single layer, to thereby emit white light. In various embodiments, the emission layer may be a white emission layer, and may further include a color converting layer and/or a color filter to turn white light into light of a desired or suitable color.

The emission layer may include a host and a dopant.

For example, the host may include at least one selected from TPBi, TBADN, ADN (herein also referred to as "DNA"), CBP, CDBP, and TCP:

TBADN

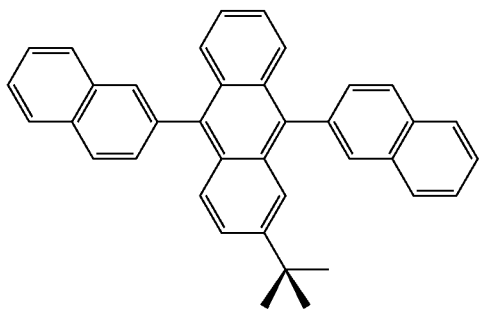

ADN

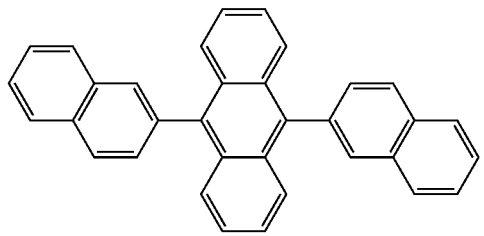

CBP

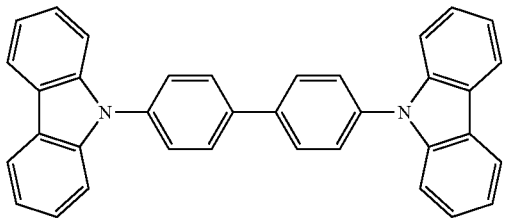

CDBP

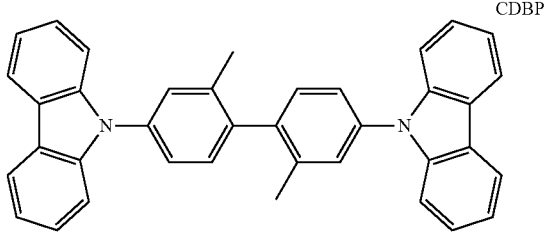

TPBi

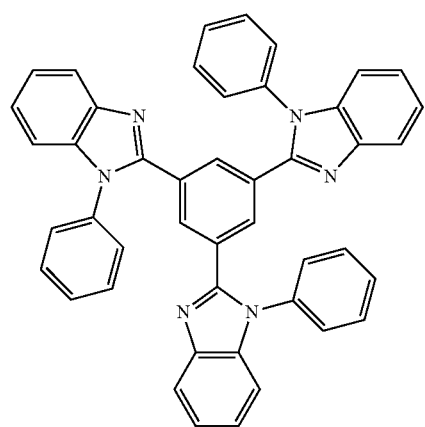

TCP

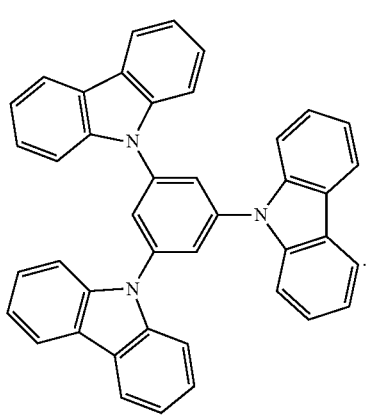

For example, the host may be represented by one selected from Formulae 2-1 to 2-4:

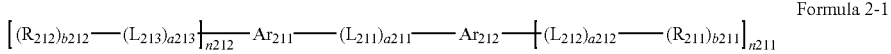

Formula 2-1

Formula 2-2

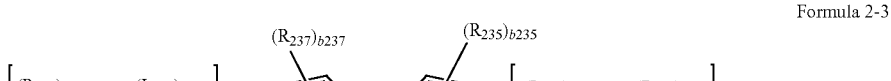

Formula 2-3

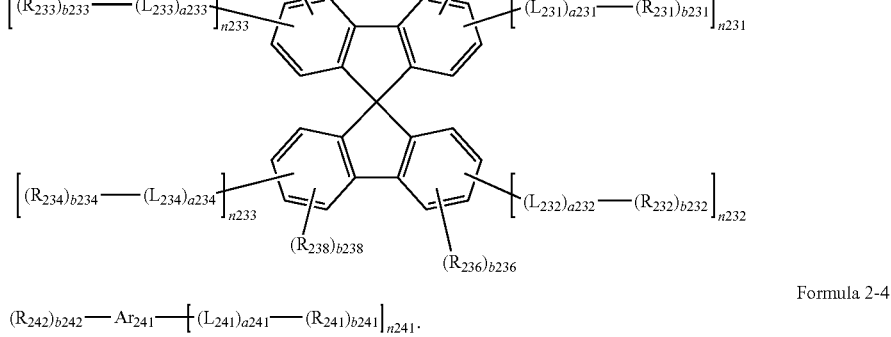

Formula 2-4

$(R_{242})_{b242}$—Ar$_{241}$—$[(L_{241})_{a241}$—$(R_{241})_{b241}]_{n241}$.

In Formulae 2-1 to 2-4,

Ar$_{211}$ and Ar$_{212}$ may each independently be selected from a naphthalene group, an anthracene group, a triphenylene group, a pyrene group, a chrysene group, and a perylene group, Ar$_{241}$ may be selected from a benzene group, a biphenyl group, and a triphenylene group, L$_{211}$ to L$_{213}$, L$_{221}$, L$_{231}$ to L$_{234}$, and L$_{241}$ may each independently be the same as described herein in connection with L$_{11}$ in Formula 1, a211 to a213, a221, a231 to a234, and a241 may each independently be selected from 0, 1, and 2, R$_{231}$ to R$_{234}$ and R$_{241}$ may each independently be the same as described herein in connection with R$_{11}$ in Formula 1 b231 to b234 and b241 may each independently be selected from 1, 2, and 3,

R$_{211}$, R$_{212}$, R$_{221}$, R$_{222}$, R$_{235}$ to R$_{238}$, and R$_{242}$ may each independently be the same as described herein in connection with R$_{101}$ in Formula 1, b211, b212, b221, b222, b235 to b238, and b242 may each independently be selected from 1, 2, and 3, n211, n212, and n221 may each independently be selected from 1, 2, and 3, n231 to n234 may each independently be selected from 0, 1, and 2, wherein the sum of n231 to n234 may be selected from 1, 2, 3, 4, 5, and 6, and n241 may be selected from 3, 4, 5, 6, 7, and 8.

For example, in Formula 2-1,

Ar$_{211}$ may be selected from an anthracene group, a triphenylene group, a pyrene group, a chrysene group, and a perylene group, and Ar$_{212}$ may be selected from a naphthalene group, an anthracene group, a triphenylene group, a pyrene group, a chrysene group, and a perylene group, but embodiments of the present disclosure are not limited thereto.

In various embodiments, in Formula 2-1,

Ar$_{211}$ and Ar$_{212}$ may each independently be selected from an anthracene group, a triphenylene group, a pyrene group, a chrysene group, and a perylene group, but embodiments of the present disclosure are not limited thereto.

In various embodiments, in Formula 2-1, Ar$_{211}$ and Ar$_{212}$ may be identical to each other, but embodiments of the present disclosure are not limited thereto.

In various embodiments, in Formula 2-1, Ar$_{211}$ and Ar$_{212}$ may each independently be an anthracene group, but embodiments of the present disclosure are not limited thereto.

For example, in Formulae 2-1 to 2-4, a211 to a213, a221, a231 to a234, and a241 may each independently be selected from 0 and 1, but embodiments of the present disclosure are not limited thereto.

For example, in Formulae 2-3 and 2-4, R$_{231}$ to R$_{234}$ and R$_{241}$ may each independently be selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), and —B($Q_{31}$)($Q_{32}$); and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with a $C_1$-$C_{20}$ alkyl group that is substituted with at least one selected from deuterium, —F, —Cl, —Br, —I, a cyano group, and a nitro group, wherein $Q_{31}$ to $Q_{33}$ may each independently be selected from a $C_1$-$C_{60}$ alkyl group, a $C_6$-$C_{60}$ aryl group, a biphenyl group, and a terphenyl group, but embodiments of the present disclosure are not limited thereto.

In various embodiments, in Formulae 2-3 and 2-4, $R_{231}$ to $R_{234}$ and $R_{241}$ may each independently be selected from the group consisting of:

a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group; and a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, and a naphthyl group, but embodiments of the present disclosure are not limited thereto.

In various embodiments, in Formulae 2-3 and 2-4, $R_{231}$ to $R_{234}$ and $R_{241}$ may each independently be selected from groups represented by Formulae 7-1 to 7-16, but embodiments of the present disclosure are not limited thereto:
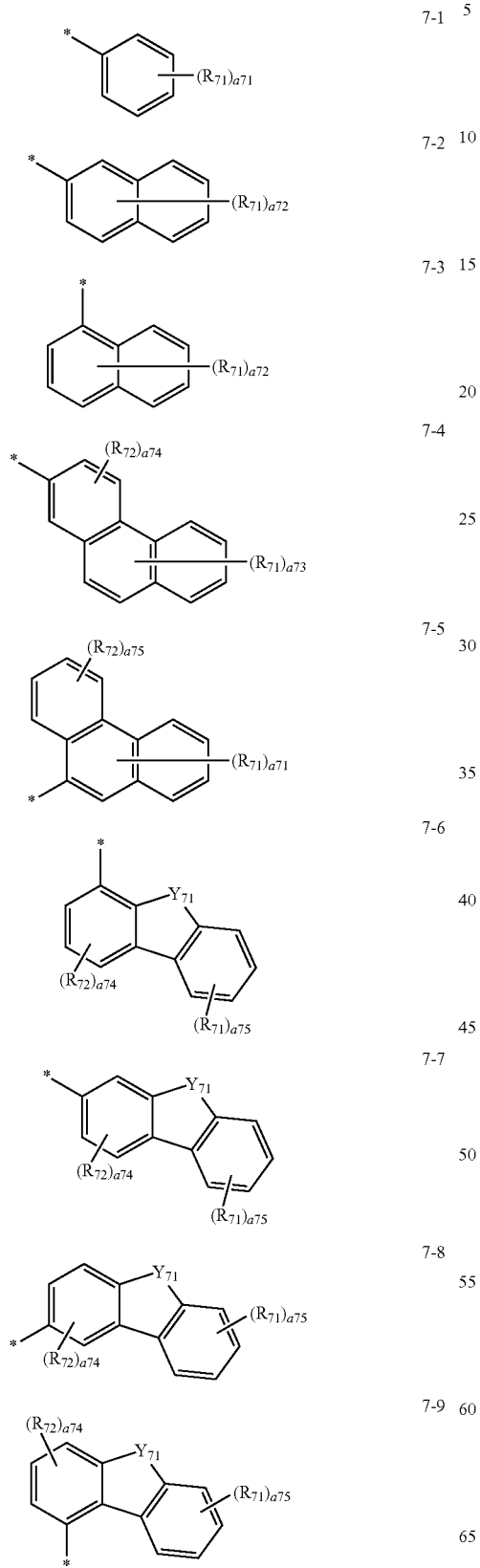
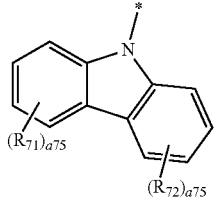
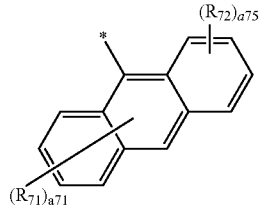
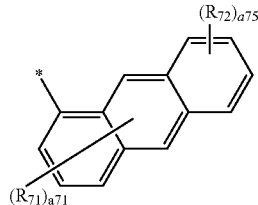
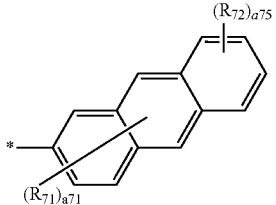
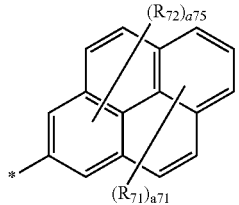
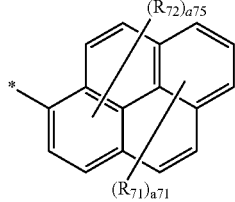
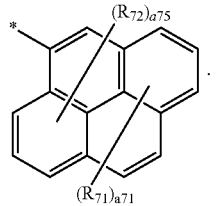
In Formulae 7-1 to 7-16,
$Y_{71}$ may be selected from $C(R_{73})(R_{74})$, $N(R_{73})$, O, and S,
$R_{71}$ to $R_{74}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, and a naphthyl group, a71 may be selected from 1, 2, 3, 4, and 5,
a72 may be selected from 1, 2, 3, 4, 5, 6, and 7,
a73 may be selected from 1, 2, 3, 4, 5, and 6,
a74 may be selected from 1, 2, and 3,
a75 may be selected from 1, 2, 3, and 4, and
* indicates a binding site to a neighboring atom.

For example, in Formulae 2-3 and 2-4, b231 to b234 and b241 may each independently be selected from 1 and 2, but embodiments of the present disclosure are not limited thereto.

For example, in Formulae 2-1 to 2-4, $R_{211}$, $R_{212}$, $R_{221}$, $R_{222}$, $R_{235}$ to $R_{238}$, and $R_{242}$ may each independently be selected from the group consisting of:

hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{31}$)($Q_{32}$), —Si($Q_{31}$)($Q_{32}$)($Q_{33}$), and —B($Q_{31}$)($Q_{32}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{31}$)($Q_{32}$), —Si($Q_{31}$)($Q_{32}$)($Q_{33}$), and —B($Q_{31}$)($Q_{32}$); and —Si($Q_1$)($Q_2$)($Q_3$), —N($Q_1$)($Q_2$), and —B($Q_1$)($Q_2$), wherein $Q_1$ to $Q_3$ and $Q_{31}$ to $Q_{33}$ may each independently be selected from a $C_1$-$C_{60}$ alkyl group, a $C_6$-$C_{60}$ aryl group, a biphenyl group, and a terphenyl group, but embodiments of the present disclosure are not limited thereto.

In various embodiments, in Formulae 2-1 to 2-4, $R_{211}$, $R_{212}$, $R_{221}$, $R_{222}$, $R_{235}$ to $R_{238}$, and $R_{242}$ may each independently be selected from the group consisting of:

hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a phenoxy group, a phenylthio group, a phenyl group, a biphenyl group, a terphenyl group, a naphthyl group, —N($Q_{31}$)($Q_{32}$), —Si($Q_{31}$)($Q_{32}$)($Q_{33}$), and —B($Q_{31}$)($Q_{32}$);

a phenoxy group, a phenylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group;

a phenoxy group, a phenylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a $C_1$-$C_{20}$ alkyl group, a $C_1$-$C_{20}$ alkoxy group, a phenoxy group, a phenylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, $-N(Q_{31})(Q_{32})$, $-Si(Q_{31})(Q_{32})(Q_{33})$, and $-B(Q_{31})(Q_{32})$; and $-Si(Q_1)(Q_2)(Q_3)$, $-N(Q_1)(Q_2)$, and $-B(Q_1)(Q_2)$, wherein $Q_1$ to $Q_3$ and $Q_{31}$ to $Q_{33}$ may each independently be selected from a $C_1$-$C_{60}$ alkyl group, a phenyl group, a biphenyl group, a terphenyl group, and a naphthyl group, but embodiments of the present disclosure are not limited thereto.

In various embodiments, in Formulae 2-1 to 2-4, $R_{211}$, $R_{212}$, $R_{221}$, $R_{222}$, $R_{235}$ to $R_{238}$, and $R_{242}$ may each independently be selected from the group consisting of:

hydrogen, deuterium, —F, —Cl, —Br, —I, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a phenoxy group, a phenylthio group, a phenyl group, a biphenyl group, a terphenyl group, a naphthyl group, $-N(Q_{31})(Q_{32})$, $-Si(Q_{31})(Q_{32})(Q_{33})$, and $-B(Q_{31})(Q_{32})$;

a phenoxy group, a phenylthio group, a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group;

a phenoxy group, a phenylthio group, a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a $C_1$-$C_{20}$ alkyl group, a $C_1$-$C_{20}$ alkoxy group, a phenoxy group, a phenylthio group, a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, a dibenzothiophenyl group, $-N(Q_{31})(Q_{32})$, $-Si(Q_{31})(Q_{32})(Q_{33})$, and $-B(Q_{31})(Q_{32})$; and $-Si(Q_1)(Q_2)(Q_3)$, $-N(Q_1)(Q_2)$, and $-B(Q_1)(Q_2)$, wherein $Q_1$ to $Q_3$ and $Q_{31}$ to $Q_{33}$ may each independently be selected from a $C_1$-$C_{60}$ alkyl group, a phenyl group, a biphenyl group, a terphenyl group, and a naphthyl group, but embodiments of the present disclosure are not limited thereto.

In various embodiments, in Formulae 2-1 to 2-4, $R_{211}$, $R_{212}$, $R_{221}$, $R_{222}$, $R_{235}$ to $R_{238}$, and $R_{242}$ may each independently be selected from hydrogen, deuterium, —F, —Cl, —Br, —I, a methyl group, an ethyl group, an n-propyl group, an iso-propyl group, an n-butyl group, an iso-butyl group, a sec-butyl group, a tert-butyl group, a methoxy group, an ethoxy group, an iso-propoxy group, an n-butoxy group, an iso-butoxy group, a sec-butoxy group, a tert-butoxy group, $-Si(CH_3)_3$, $-Si(Ph)_3$, $-N(Ph_2)_2$, $-B(Ph)_2$, and a group represented by any of Formulae 9-1 to 9-15, but embodiments of the present disclosure are not limited thereto:

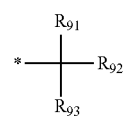

9-1

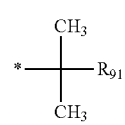

9-2

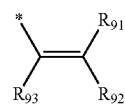

9-3

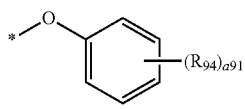

9-4

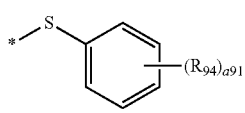

9-5

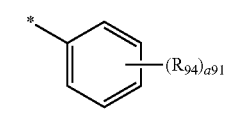

9-6

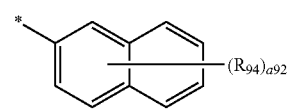

9-7

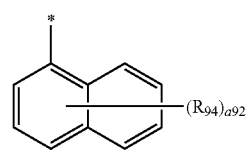

9-8

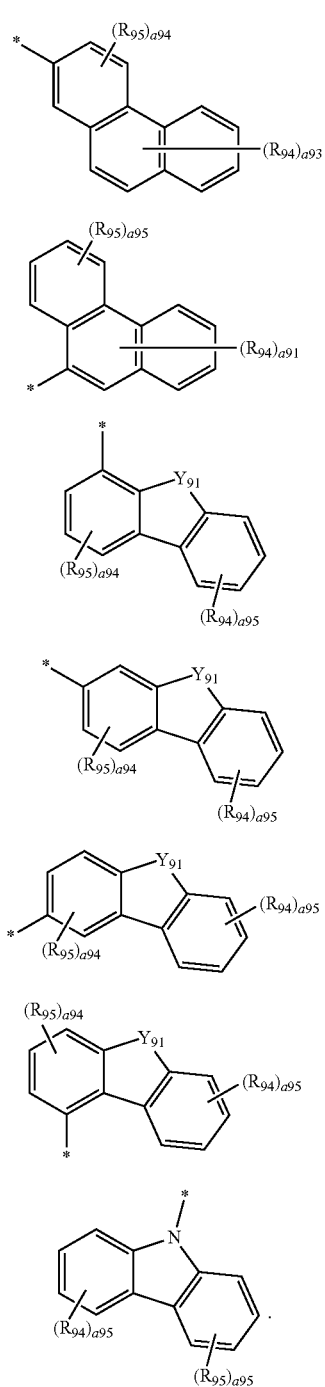

9-9

9-10

9-11

9-12

9-13

9-14

9-15

In Formulae 9-1 to 9-15, $Y_{91}$ may be selected from $C(R_{96})(R_{97})$, $N(R_{96})$, O, and S, $R_{91}$ to $R_{93}$ may each independently be selected from hydrogen, deuterium, —F, —Cl, —Br, —I, a phenoxy group, a phenylthio group, a phenyl group, a biphenyl group, a terphenyl group, and a naphthyl group, $R_{94}$ to $R_{97}$ may each independently be selected from hydrogen, deuterium, —F, —Cl, —Br, —I, a $C_1$-$C_{20}$ alkyl group, a $C_1$-$C_{20}$ alkoxy group, a phenoxy group, a phenylthio group, a phenyl group, a biphenyl group, a terphenyl group, a naphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a carbazolyl group, a dibenzofuranyl group, and a dibenzothiophenyl group, a91 may be selected from 1, 2, 3, 4, and 5, a92 may be selected from 1, 2, 3, 4, 5, 6, and 7, a93 may be selected from 1, 2, 3, 4, 5, and 6, a94 may be selected from 1, 2, and 3, a95 may be selected from 1, 2, 3, and 4, and

* indicates a binding site to a neighboring atom.

In various embodiments, in Formulae 2-1 to 2-4, $R_{211}$, $R_{212}$, $R_{221}$, $R_{222}$, $R_{235}$ to $R_{238}$, and $R_{242}$ may each independently be selected from hydrogen, deuterium, —F, —Cl, —Br, —I, a methyl group, an ethyl group, an n-propyl group, an iso-propyl group, an n-butyl group, an iso-butyl group, a sec-butyl group, a tert-butyl group, a methoxy group, an ethoxy group, an iso-propoxy group, an n-butoxy group, an iso-butoxy group, a sec-butoxy group, a tert-butoxy group, —Si(CH$_3$)$_3$, —Si(Ph)$_3$, —N(Ph$_2$)$_2$, —B(Ph)$_2$, and a group represented by any of Formulae 10-1 to 10-26, but embodiments of the present disclosure are not limited thereto:

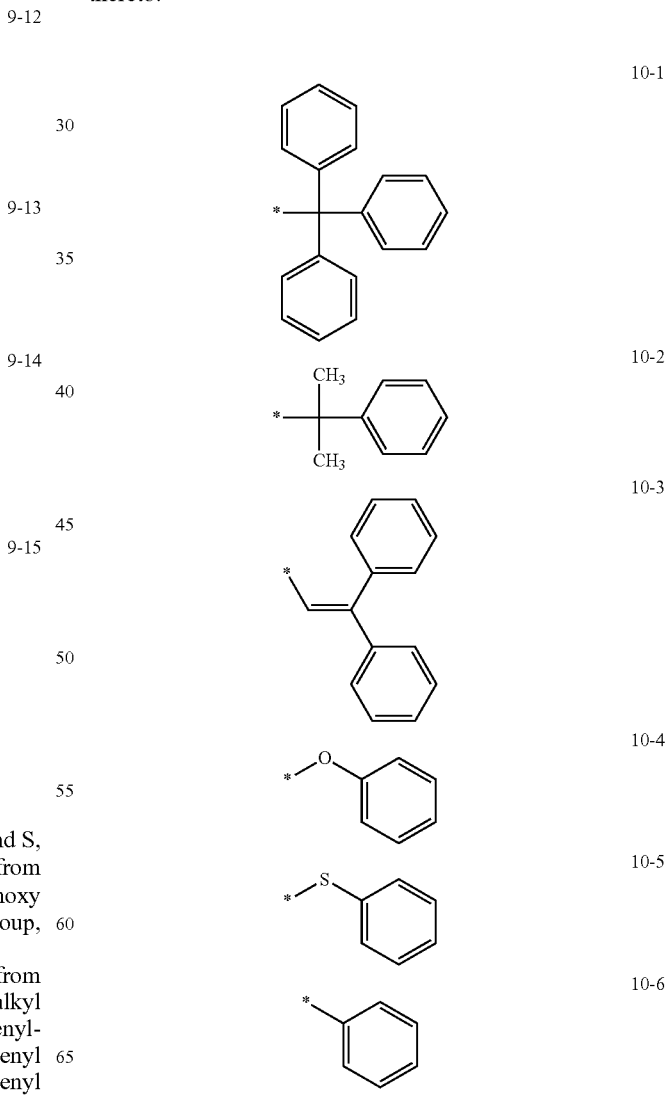

301
-continued
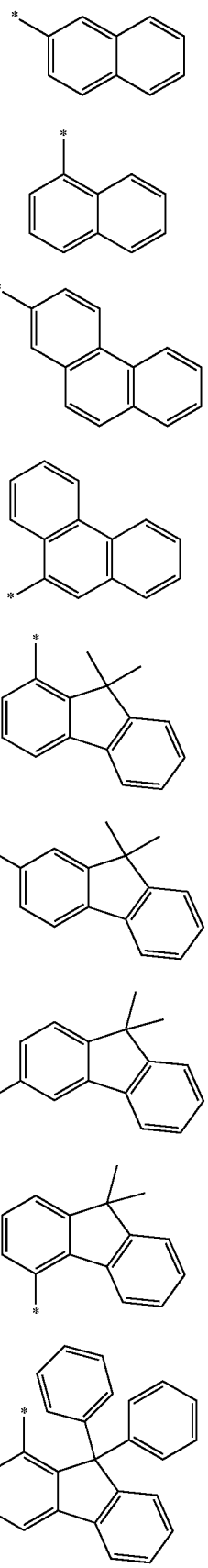
10-7
10-8
10-9
10-10
10-11
10-12
10-13
10-14
10-15
302
-continued
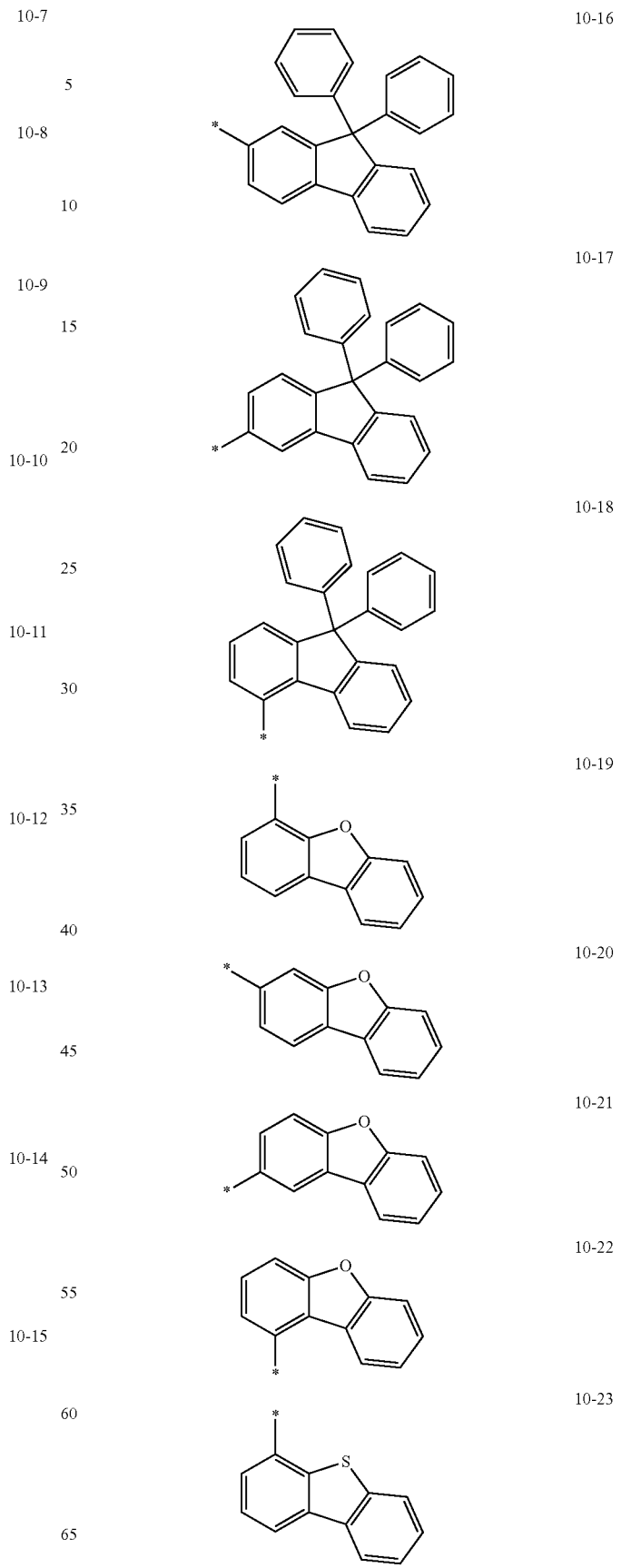
10-16
10-17
10-18
10-19
10-20
10-21
10-22
10-23

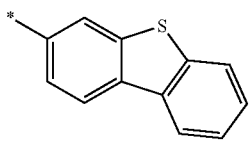

10-24

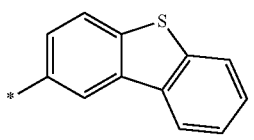

10-25

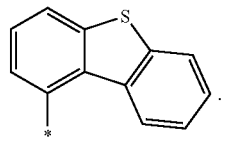

10-26

In Formulae 10-1 to 10-26, * indicates a binding site to a neighboring atom.

For example, in Formulae 2-1 to 2-4, b211, b212, b221, b222, b235 to b238, and b242 may each independently be selected from 1 and 2, but embodiments of the present disclosure are not limited thereto.

For example, the host represented by one selected from Formulae 2-1 to 2-4 may be represented by one selected from Formulae 2-11 to 2-16, but embodiments of the present disclosure are not limited thereto:

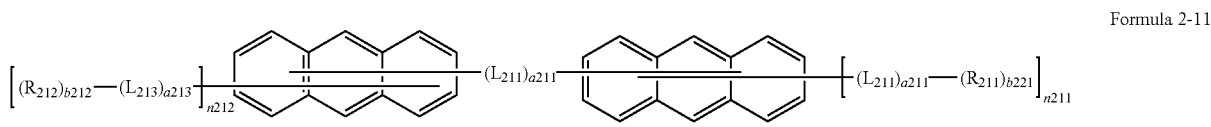

Formula 2-11

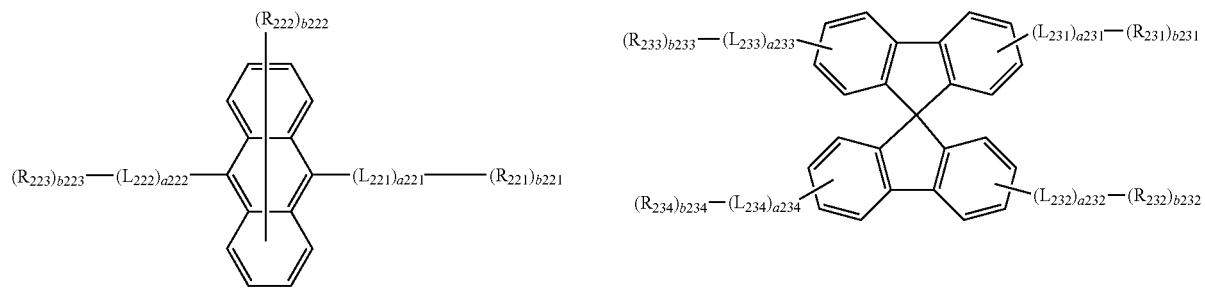

Formula 2-12        Formula 2-13

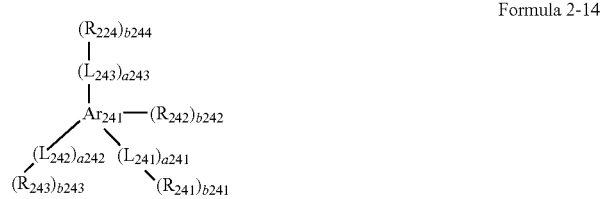

Formula 2-14

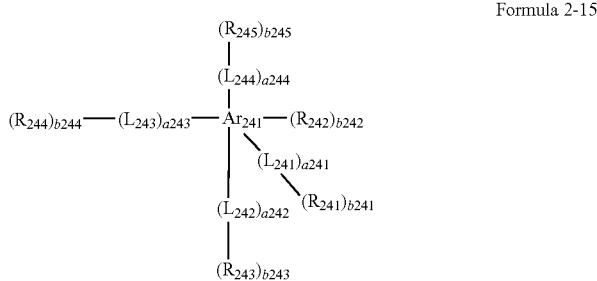

Formula 2-15

Formula 2-16

In Formulae 2-11 to 2-16, $Ar_{241}$, $L_{211}$ to $L_{213}$, $L_{221}$, $L_{231}$ to $L_{234}$, $L_{241}$, a211 to a213, a221, a231 to a234, a241, $R_{231}$ to $R_{234}$, $R_{241}$, b231 to b234, b241, $R_{211}$, $R_{212}$, $R_{221}$, $R_{222}$, $R_{235}$ to $R_{238}$, $R_{242}$, b211, b212, b221, b222, b235 to b238, b242, n211, and n212 may each independently be the same as respectively described herein in connection with Formulae 2-1 to 2-4, $R_{243}$ to $R_{247}$ may each independently be the same as described herein in connection with $R_{241}$ in Formula 2-3, b243 to b247 may each independently be the same as described herein in connection with b241 in Formula 2-4, $L_{222}$ may be the same as described herein in connection with $L_{221}$ in Formula 2-2, a222 may be the same as described herein in connection with a221 in Formula 2-2, $R_{223}$ may be the same as described herein in connection with $R_{221}$ in Formula 2-2, b223 may be the same as described herein in connection with b221 in Formula 2-2, $L_{242}$ to $L_{246}$ may each independently be the same as described herein in connection with $L_{241}$ in Formula 2-4, and a242 to a246 may each independently be the same as described herein in connection with a241 in Formula 2-4.

In various embodiments, the host represented by one selected from Formulae 2-1 to 2-4 may be represented by one selected from Formulae 2-21 to 2-29, but embodiments of the present disclosure are not limited thereto:

Formula 2-21

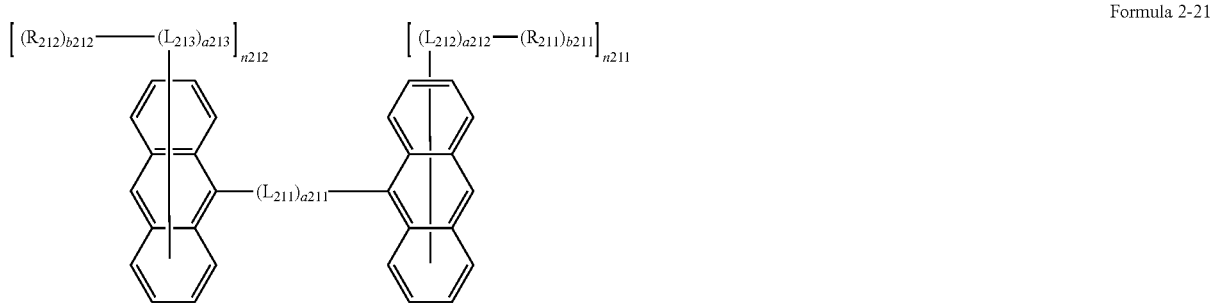

Formula 2-22

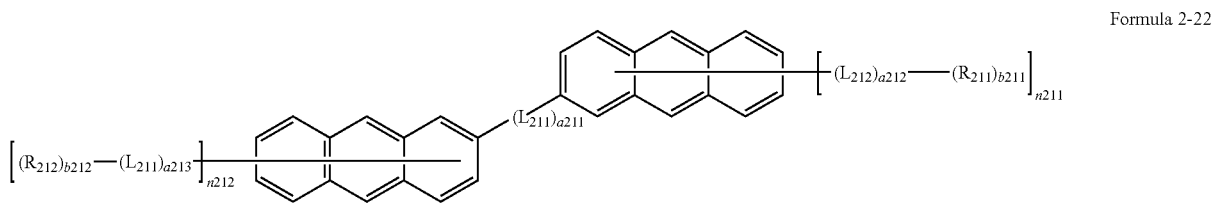

Formula 2-23

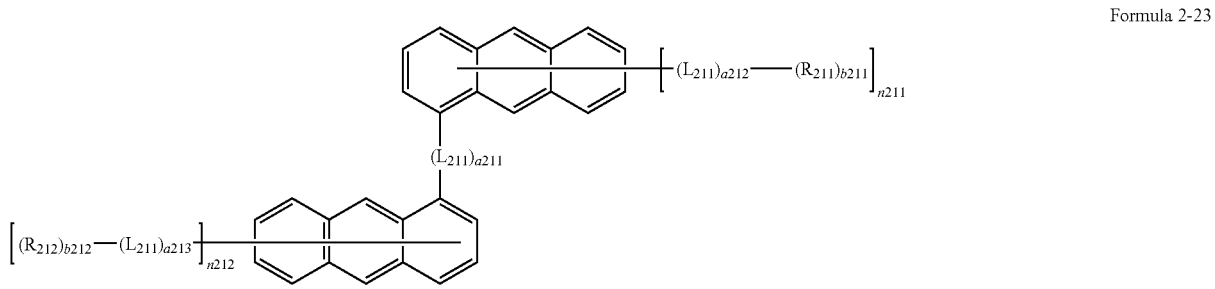

Formula 2-24                                    Formula 2-25

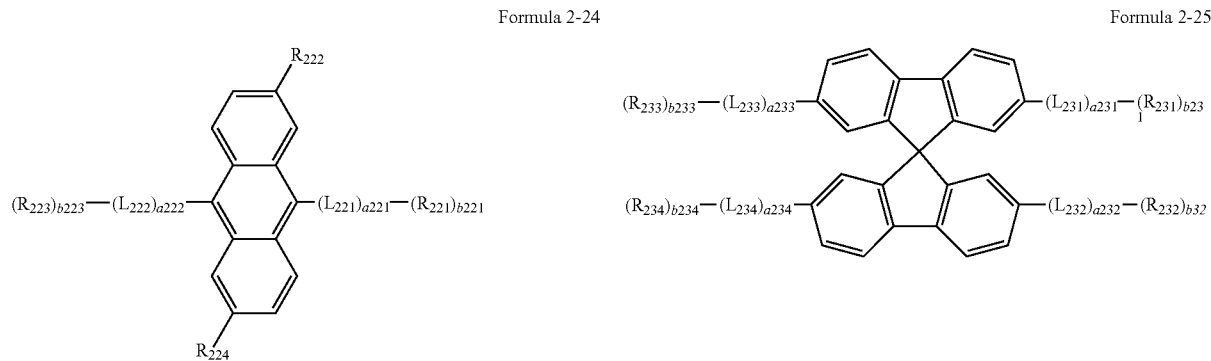

Formula 2-26

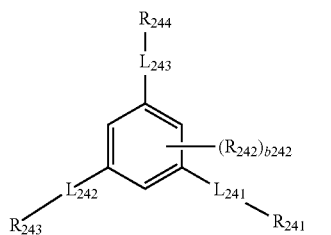

Formula 2-27

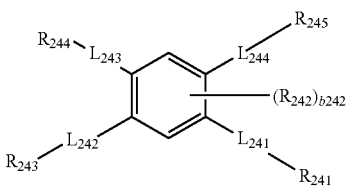

Formula 2-28

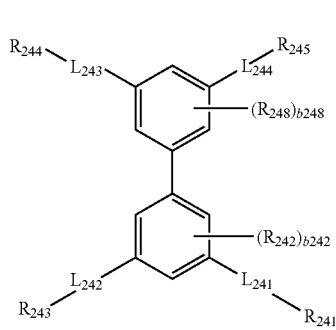

Formula 2-29

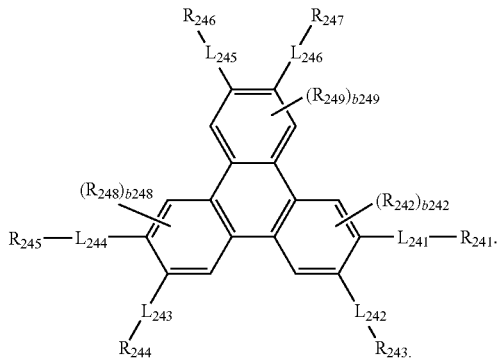

In Formulae 2-21 to 2-29, $Ar_{241}$, $L_{211}$ to $L_{213}$, $L_{221}$, $L_{231}$ to $L_{234}$, $L_{241}$, a211 to a213, a221, a231 to a234, a241, $R_{231}$ to $R_{234}$, $R_{241}$, b231 to b234, b241, $R_{211}$, $R_{212}$, $R_{221}$, $R_{222}$, $R_{235}$ to $R_{238}$, $R_{242}$, b211, b212, b221, b222, b235 to b238, b242, n211, and n212 may each independently be the same as respectively described herein in connection with Formulae 2-1 to 2-4, $R_{224}$ may be the same as described herein in connection with $R_{222}$ in Formula 2-2, $L_{222}$ may be the same as described herein in connection with $L_{221}$ in Formula 2-2, a222 may be the same as described herein in connection with a221 in Formula 2-2, $R_{223}$ may be the same as described herein in connection with $R_{221}$ in Formula 2-2, b223 may be the same as described herein in connection with b221 in Formula 2-2, $L_{242}$ to $L_{246}$ may each independently be the same as described herein in connection with $L_{241}$ in Formula 2-4, a242 to a246 may each independently be the same as described herein in connection with a241 in Formula 2-4, $R_{243}$ to $R_{247}$ may each independently be the same as described herein in connection with $R_{241}$ in Formula 2-4, $R_{248}$ and $R_{249}$ may each independently be the same as described herein in connection with $R_{242}$ in Formula 2-4, b243 to b247 may each independently be the same as described herein in connection with b241 in Formula 2-4, and b248 and b249 may each independently be the same as described herein in connection with b242 in Formula 2-4.

In various embodiments, the host represented by one selected from Formulae 2-1 to 2-4 may be selected from Compounds H-1 to H-68, but embodiments of the present disclosure are not limited thereto:

H-1

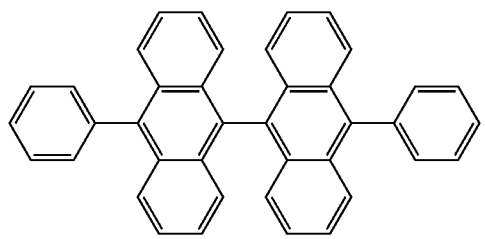

H-2

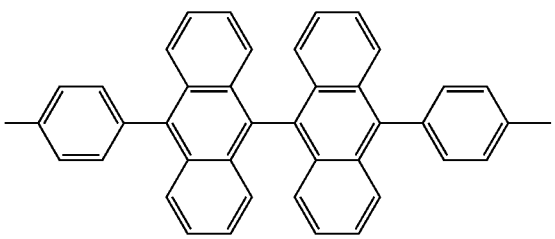

H-3

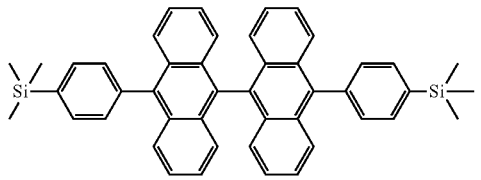

H-4

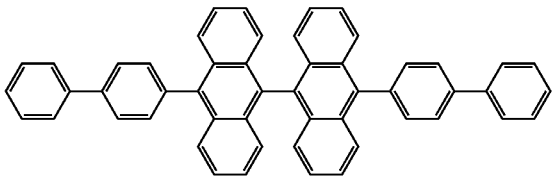

-continued
H-5
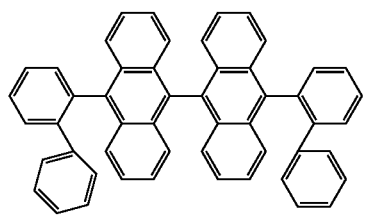
H-6
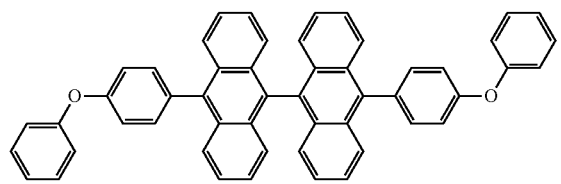
H-7
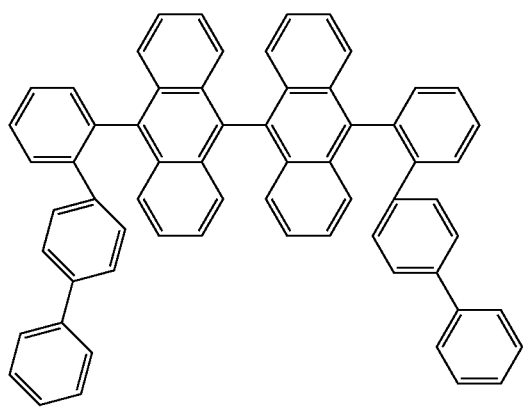
H-8
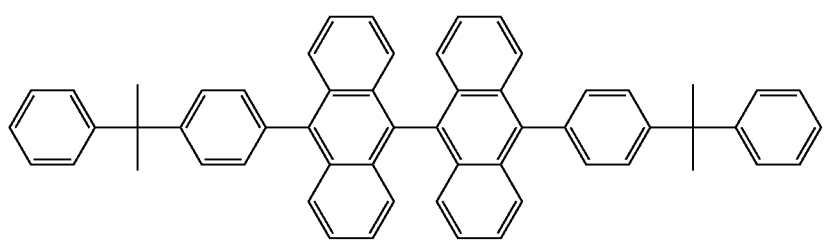
H-9
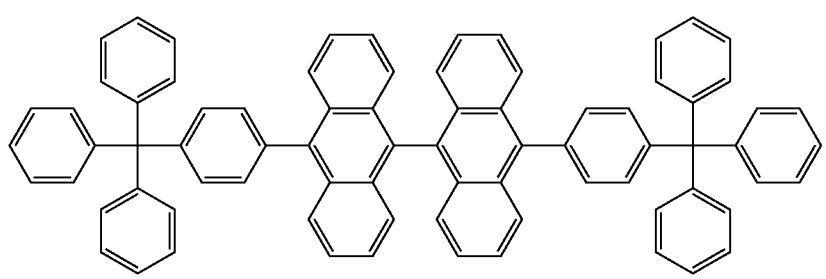
H-10
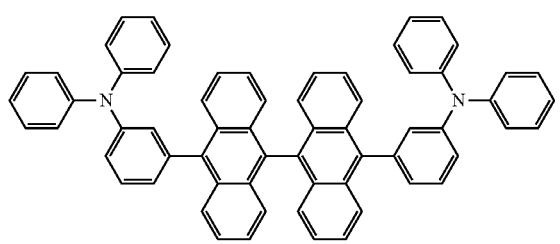
H-11
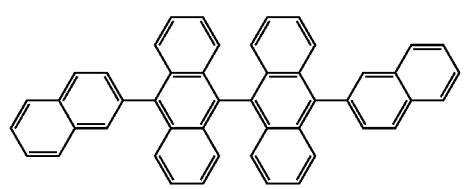

-continued
H-12
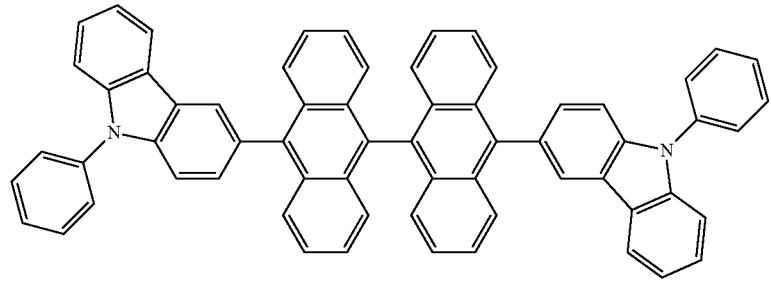
H-13
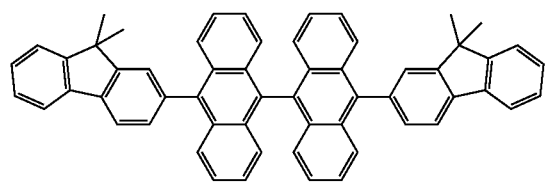
H-14
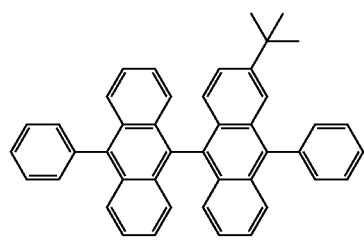
H-15
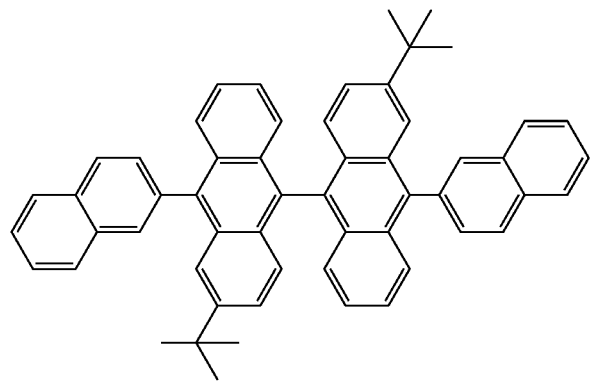
H-16
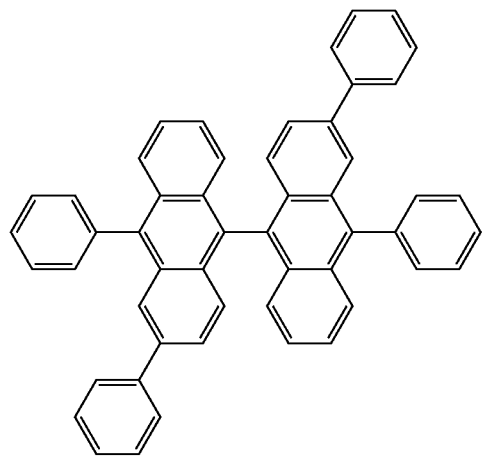
H-17
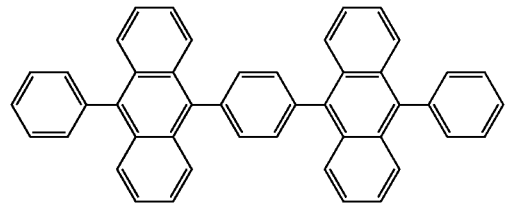
H-18
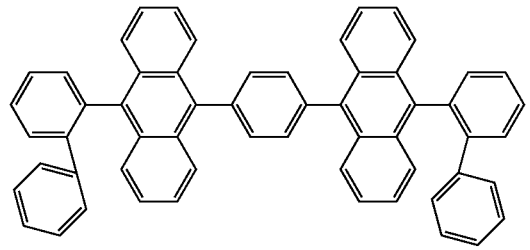
H-19
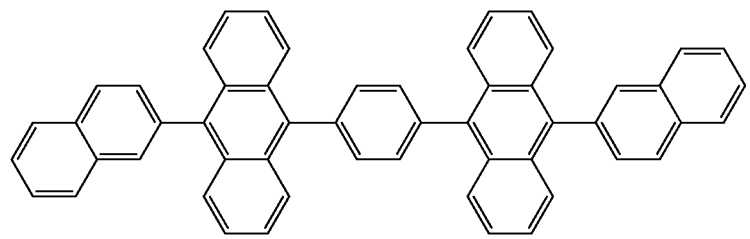

-continued
H-20
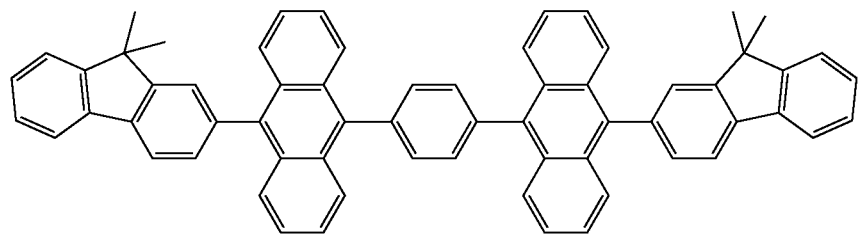
H-21
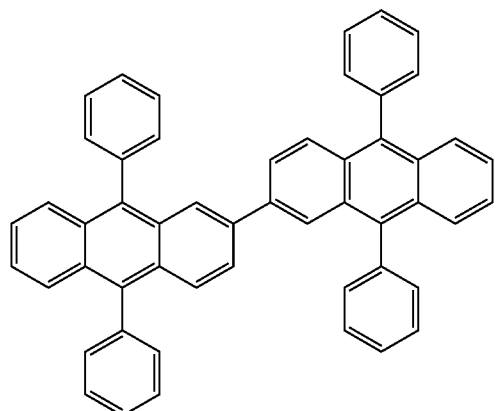
H-22
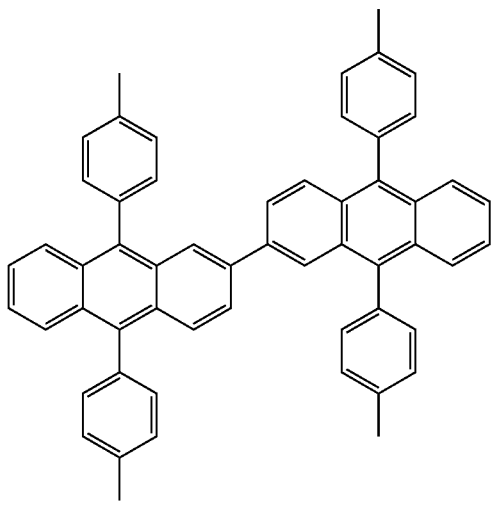
H-23
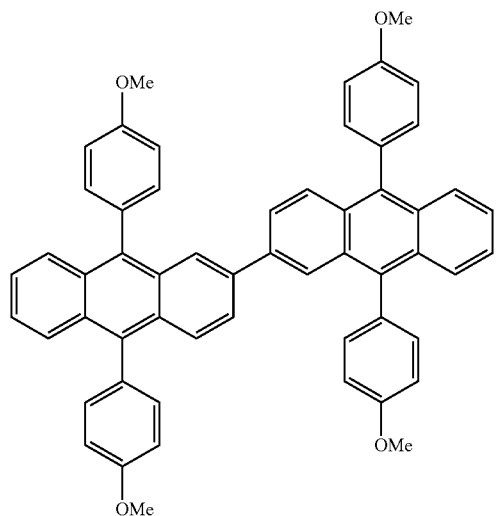
H-24
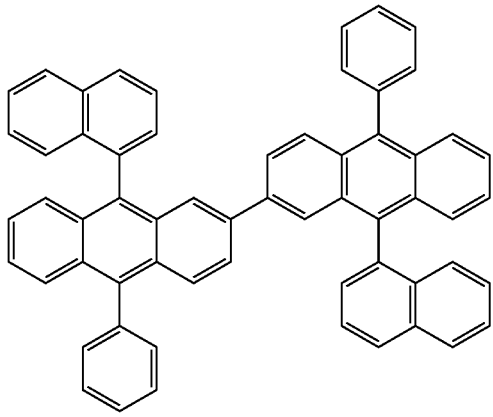

-continued
H-25
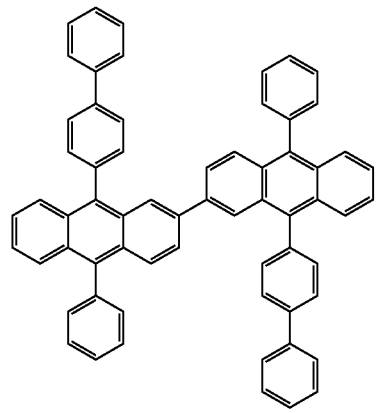
H-26
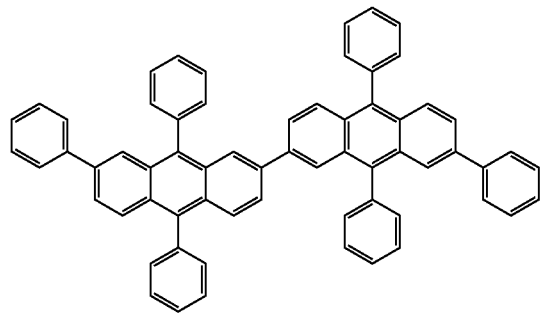
H-27
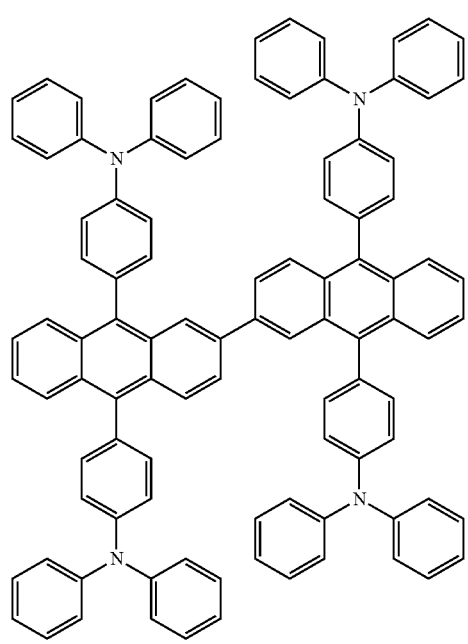
H-28
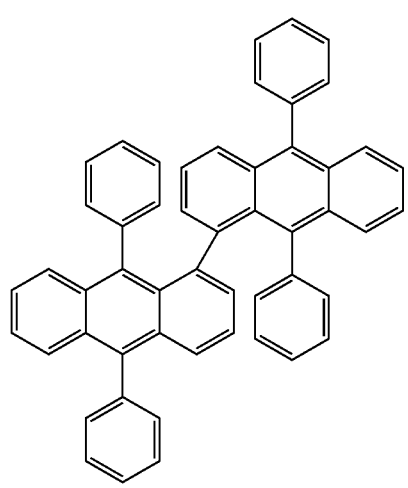
H-29
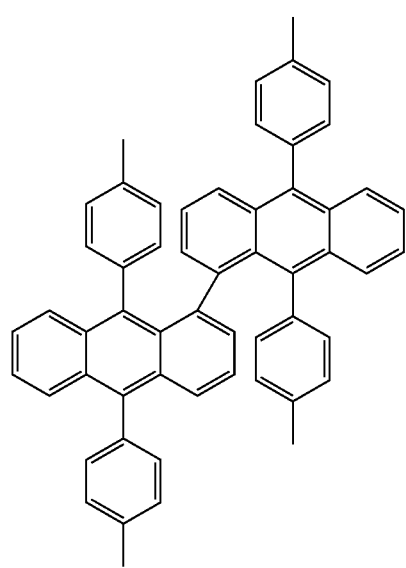
H-30
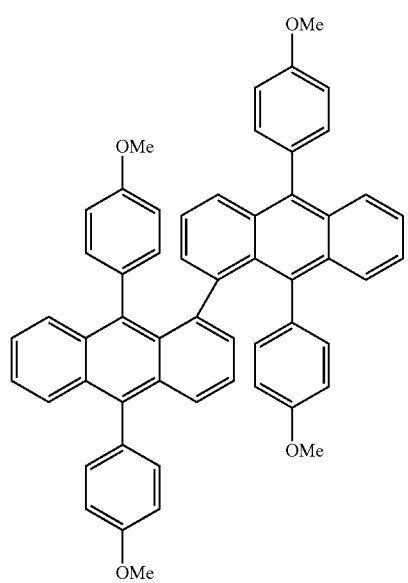

-continued
H-31
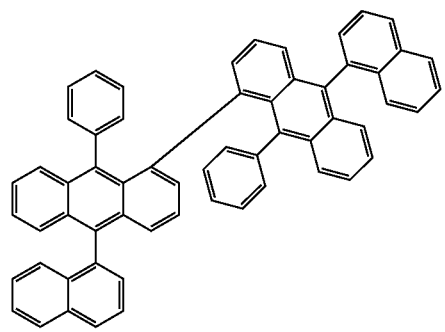
H-32
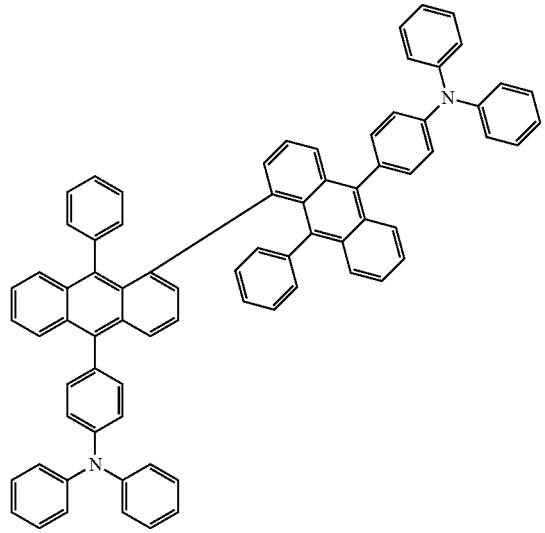
H-33
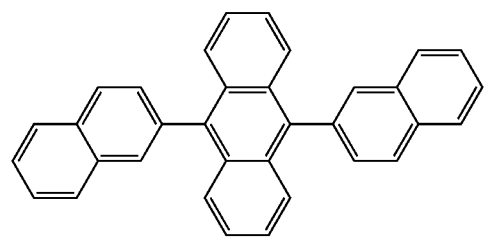
H-34
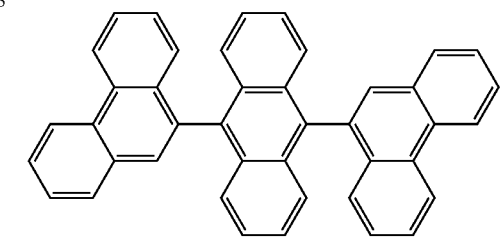
H-35
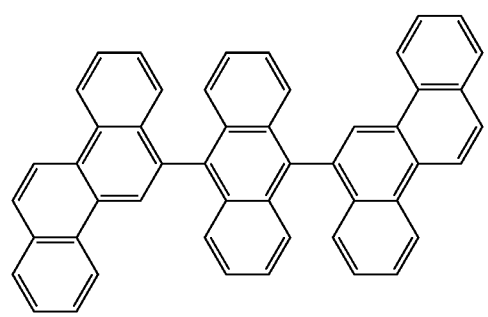
H-36
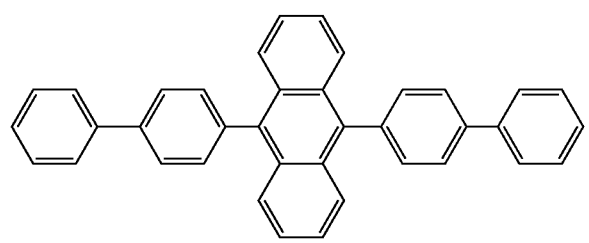
H-37
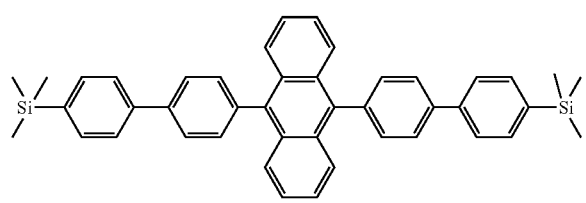
H-38
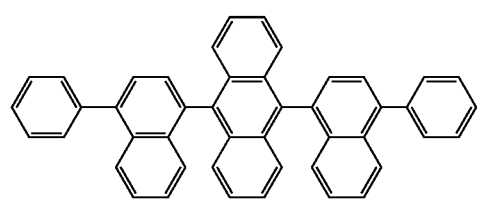

-continued
H-39
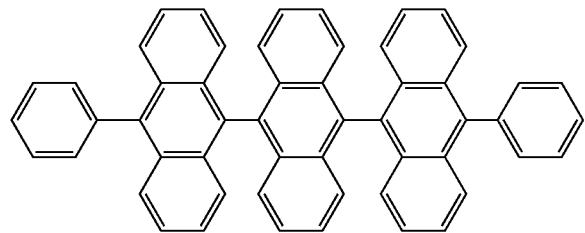
H-40
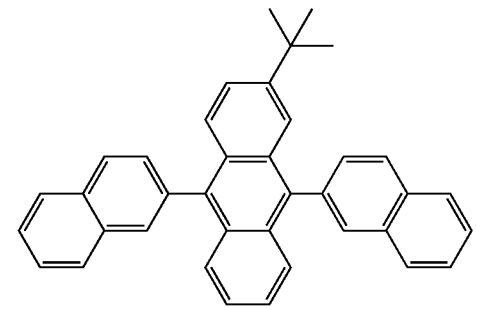
H-41
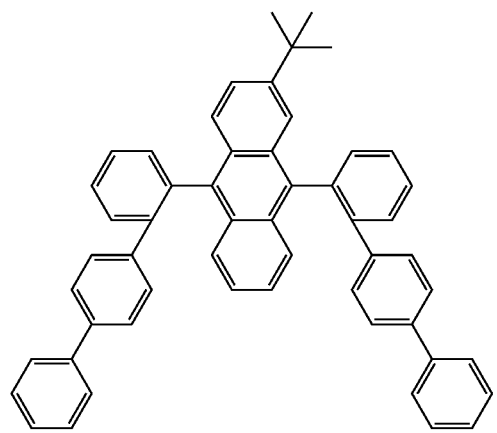
H-42
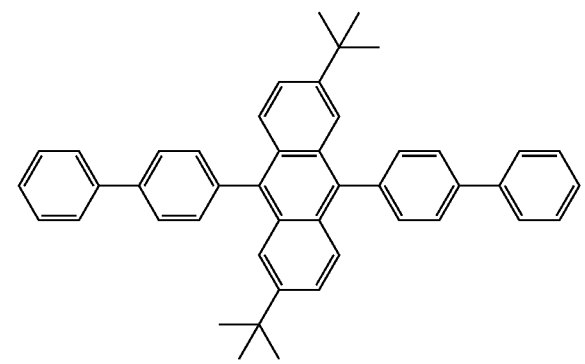
H-43
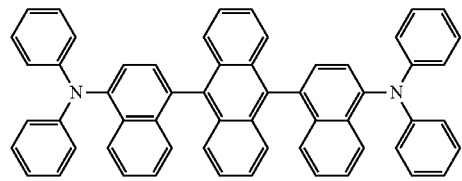
H-44
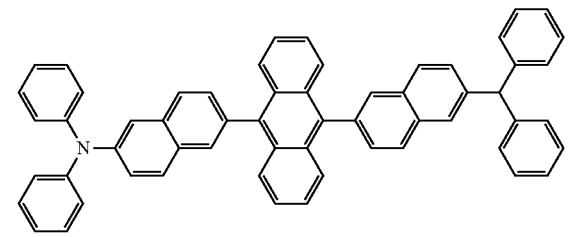
H-45
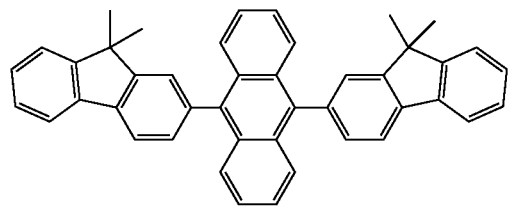
H-46
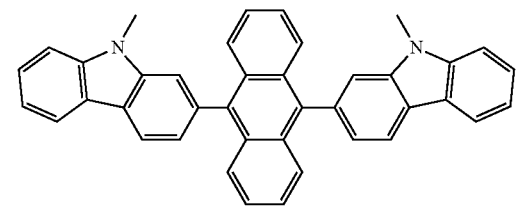
H-47
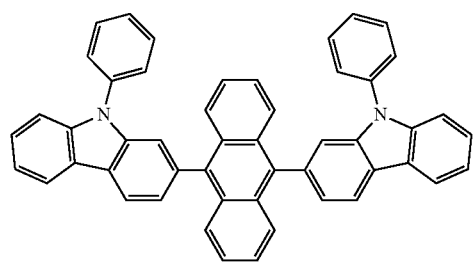
H-48
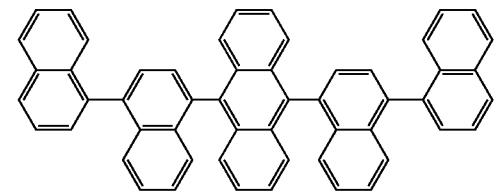

H-49
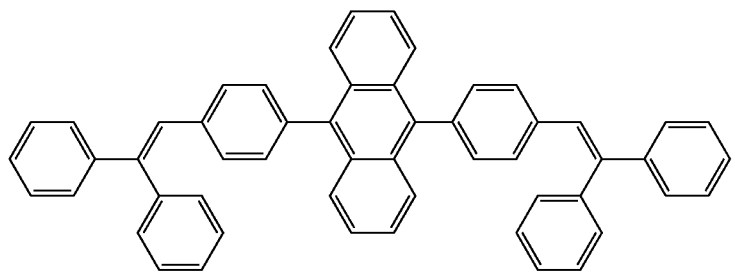
H-50
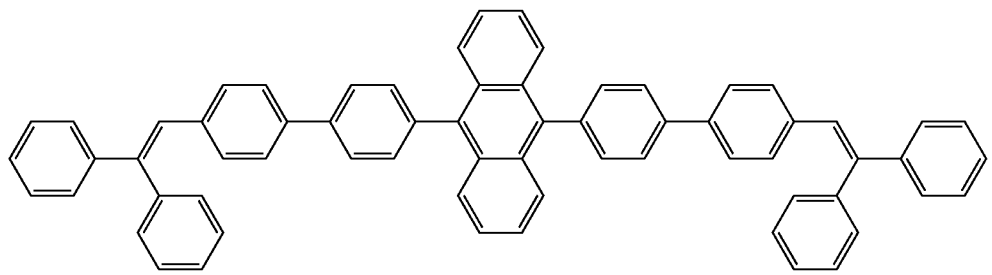
H-51
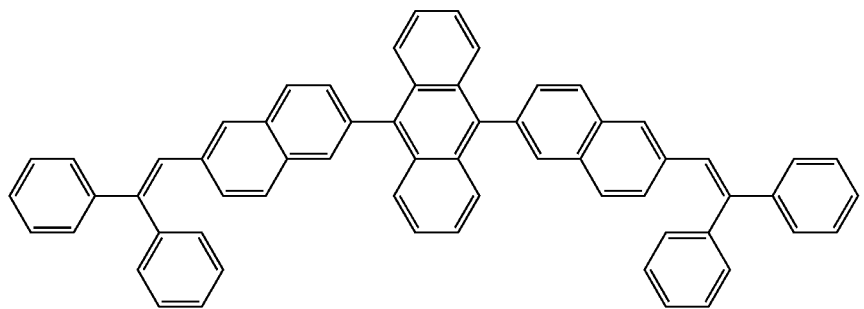
H-52
H-53
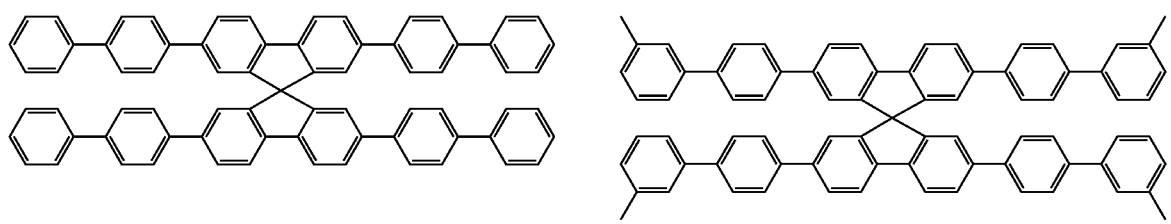
H-54
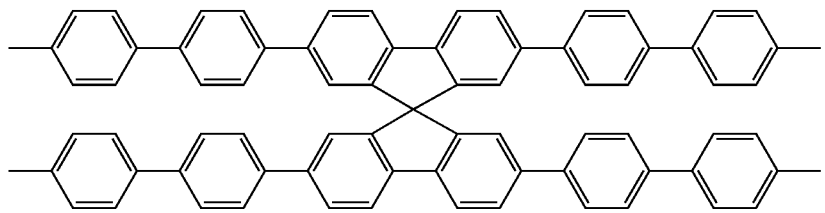
H-55
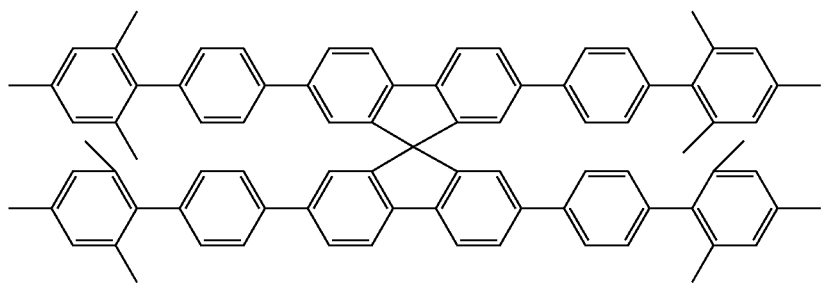

-continued
H-56
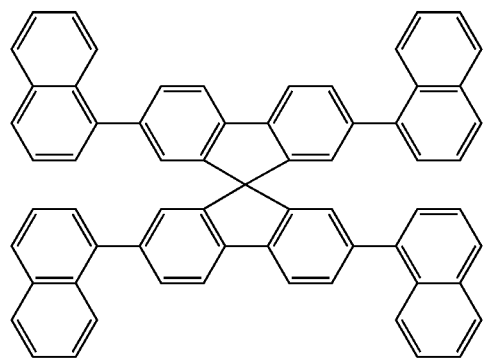
H-57
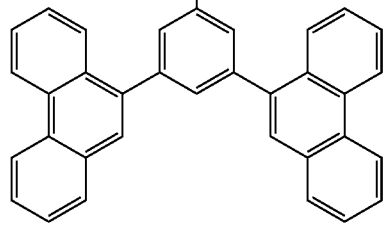
H-58
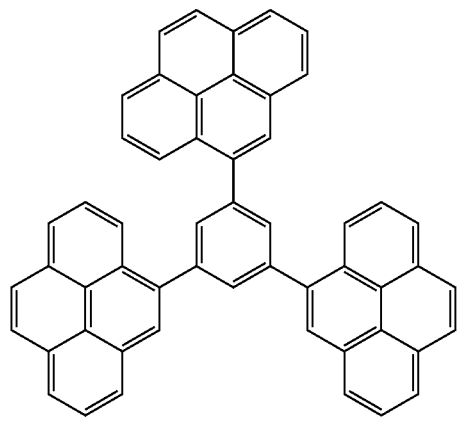
H-59
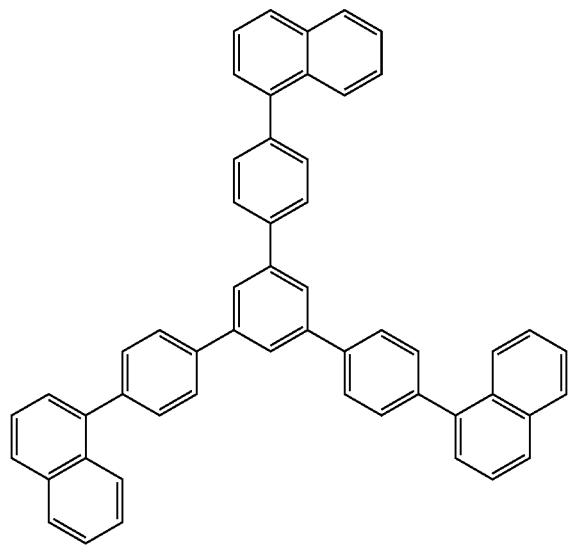
H-60
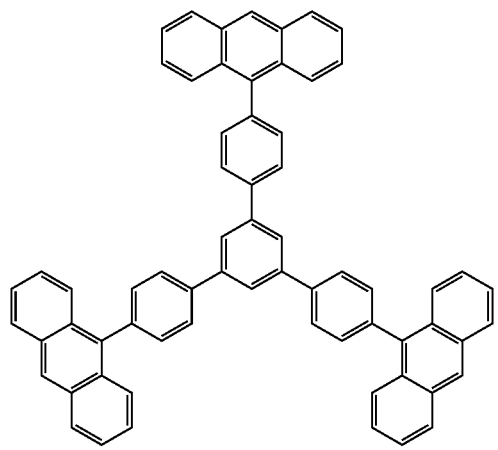
H-61
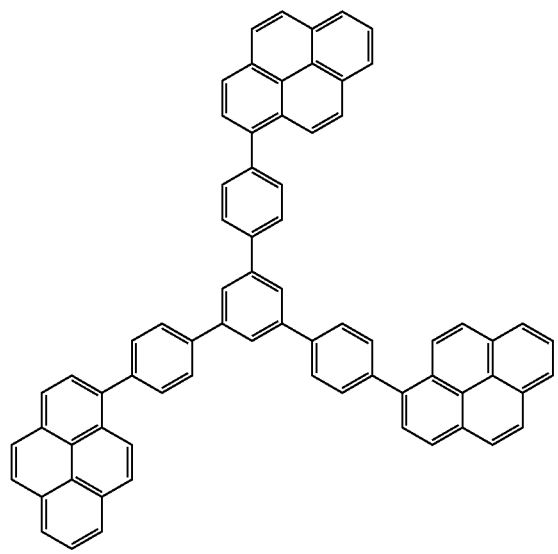

-continued
H-61
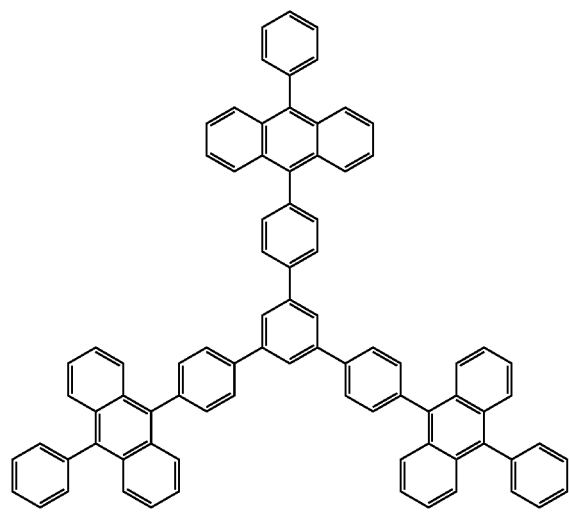
H-63
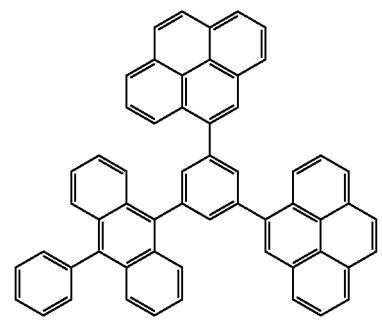
H-64
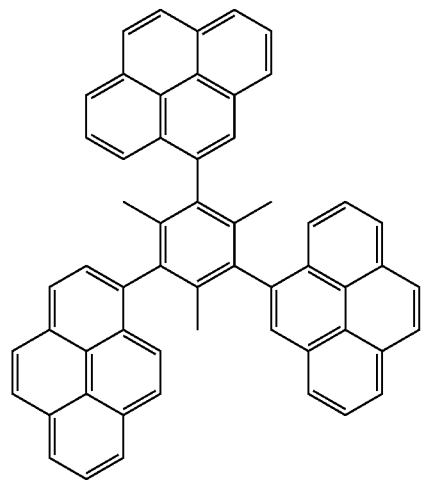
H-65
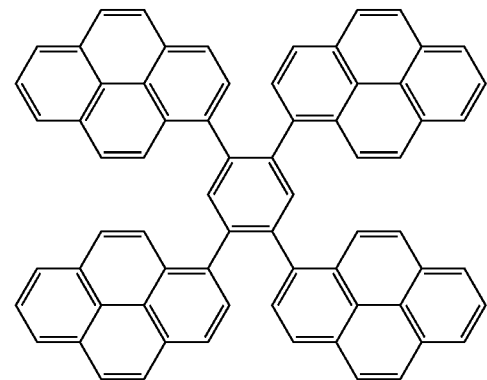
H-66
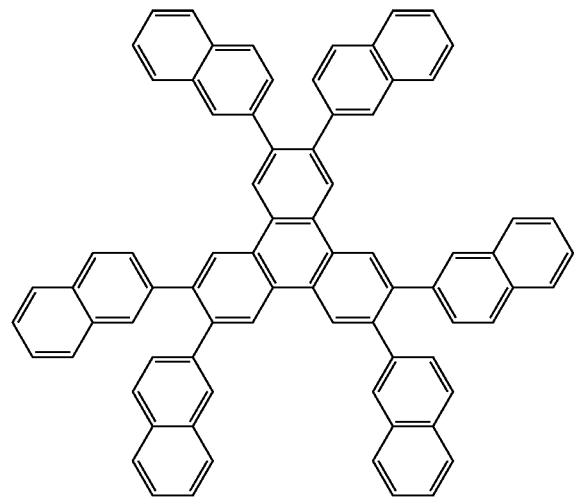
H-67
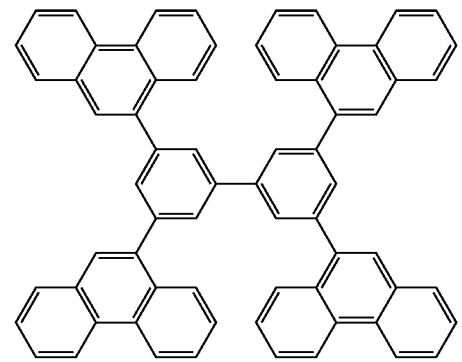

H-68

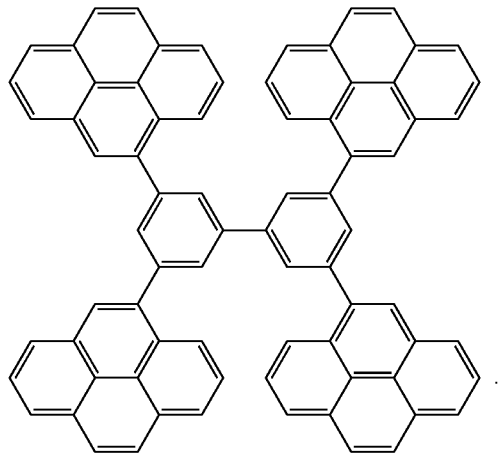

The dopant may include at least one selected from a fluorescent dopant and a phosphorescent dopant.

The phosphorescent dopant may include an organometallic complex represented by Formula 401:

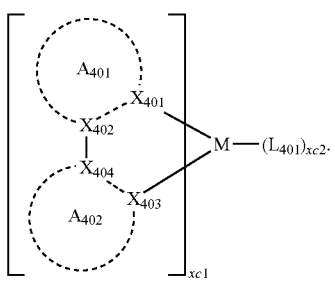

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (TM), $X_{401}$ to $X_{404}$ may each independently be nitrogen or carbon, ring $A_{401}$ and ring $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$aryloxy group, a $C_6$-$C_{60}$arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand, xc1 may be 1, 2, or 3, and xc2 may be 0, 1, 2, or 3.

$Q_{401}$ to $Q_{407}$, $Q_{411}$ to $Q_{417}$, and $Q_{421}$ to $Q_{427}$ may each independently be the same as described herein in connection with $Q_1$.

In various embodiments, $L_{401}$ may be a monovalent, divalent, or trivalent organic ligand. For example, $L_{401}$ may be a halogen ligand (for example, Cl and/or F), a diketone ligand (for example, acetylacetonate, 1,3-diphenyl-1,3-propane dionate, 2,2,6,6-tetramethyl-3,5-heptanedionate, and/or hexafluoroacetonate), a carboxylic acid ligand (for example, picolinate, dimethyl-3-pyrazolecarboxylate and/or benzoate), a carbon monoxide ligand, an isonitrile ligand, a cyano group ligand, and a phosphorus ligand (for example, phosphine and/or phosphite), but embodiments of the present disclosure are not limited thereto.

When $A_{401}$ in Formula 401 has two or more substituents, the two or more substituents of $A_{401}$ may be linked to form a saturated or unsaturated ring.

When $A_{402}$ in Formula 401 has two or more substituents, the two or more substituents of $A_{402}$ may be linked to form a saturated or unsaturated ring.

When xc1 in Formula 401 is two or more, a plurality of ligands

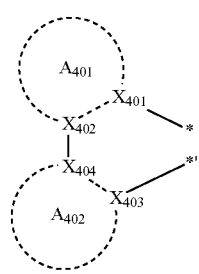

in Formula 401 may be identical to or different from each other. When xc1 in Formula 401 is two or more, $A_{401}$ and $A_{402}$ of one ligand may each be directly connected or connected through a linking group (for example, a $C_1$-$C_5$ alkylene group, —N(R')—(wherein R' is a $C_1$-$C_{10}$ alkyl group or a $C_6$-$C_{20}$ aryl group), and/or —C(=O)—) to $A_{401}$ and $A_{402}$, respectively, of another neighboring ligand.

The phosphorescent dopant may include at least one selected from Compounds PD1 to PD74, but embodiments of the present disclosure are not limited thereto:

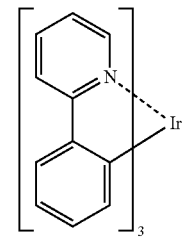

PD1

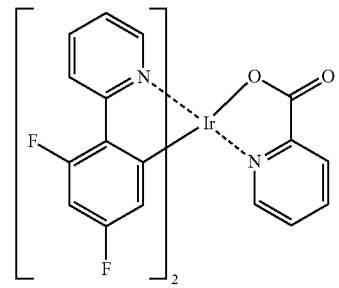

PD2

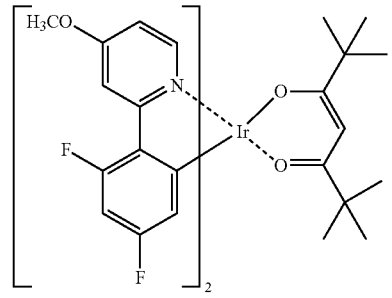

PD3

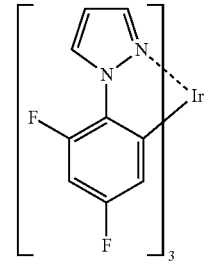

PD4

| PD5 | PD10 |
|---|---|
| 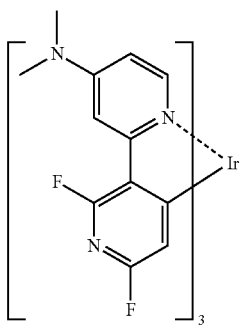 | 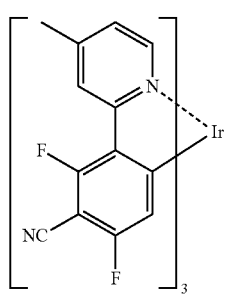 |
| PD6 | PD11 |
| 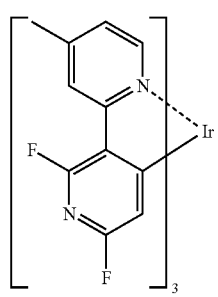 | 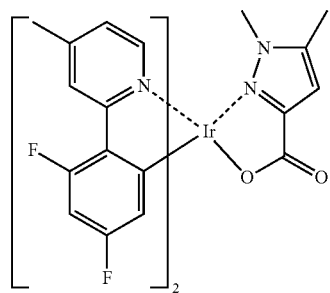 |
| PD7 | PD12 |
| 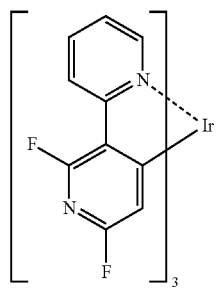 | 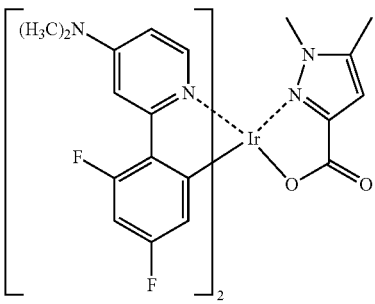 |
| PD8 | PD13 |
| 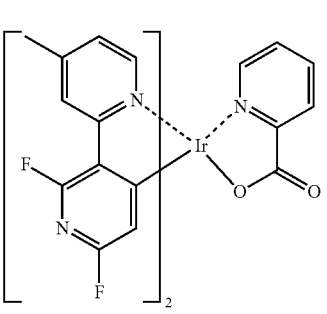 | 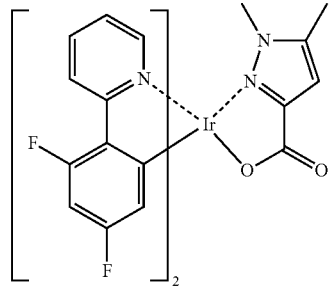 |
| PD9 | PD14 |
| 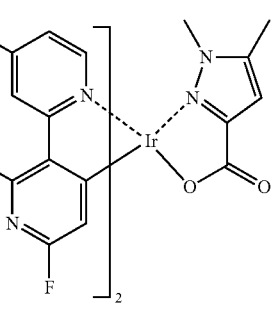 | 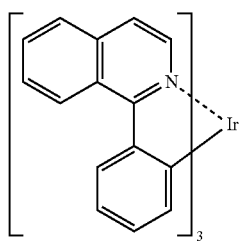 |

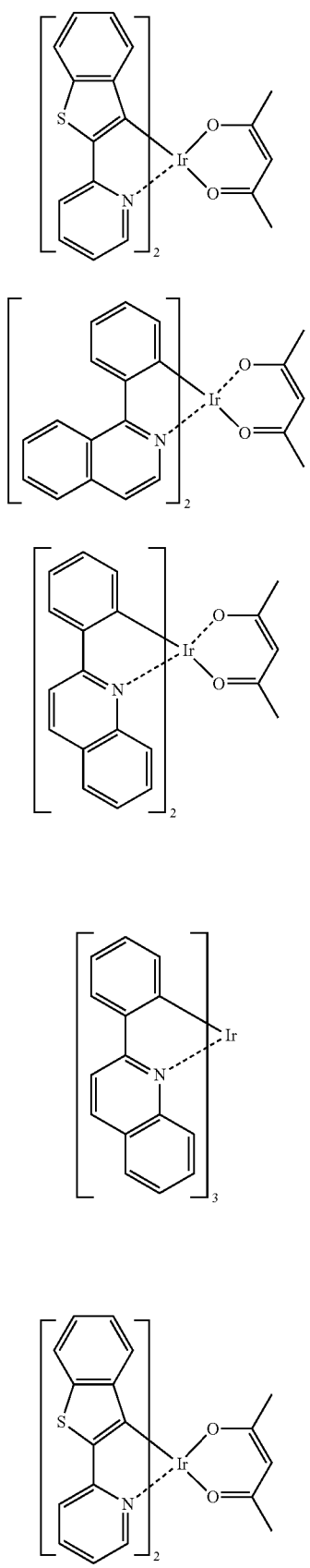
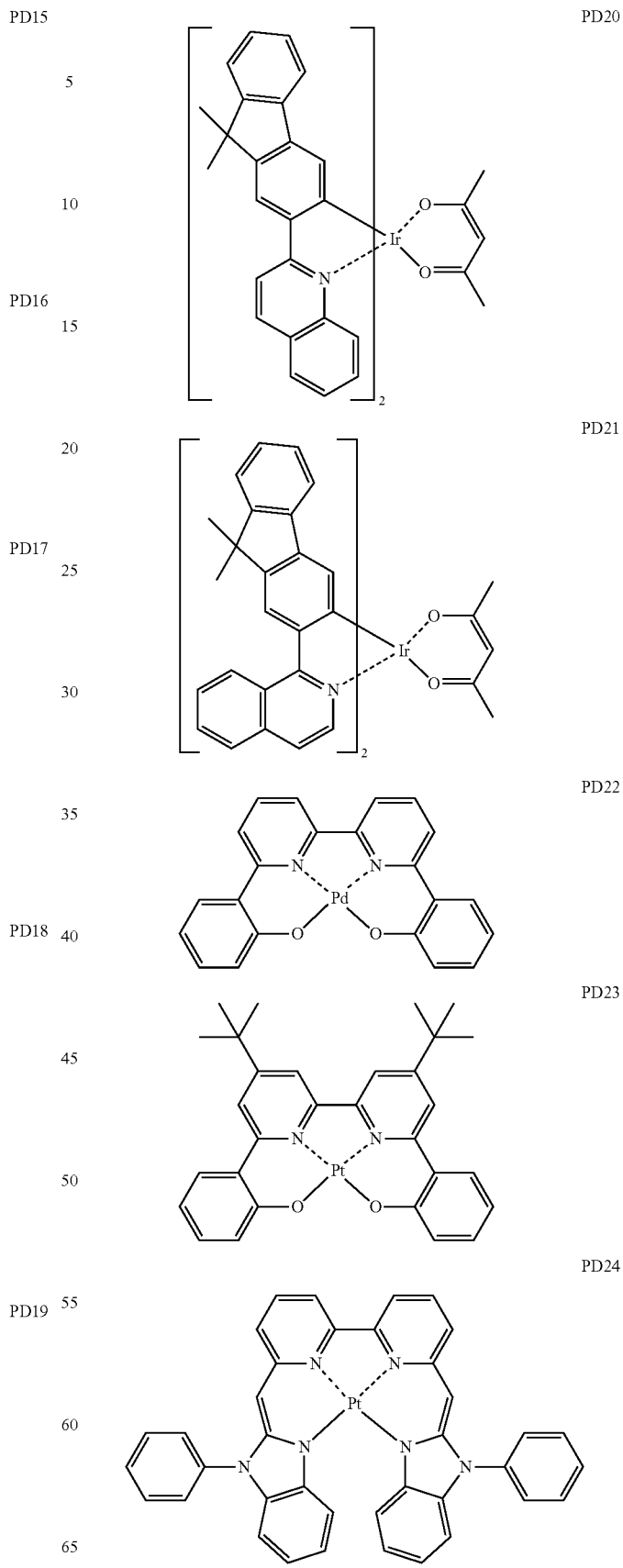

PD25 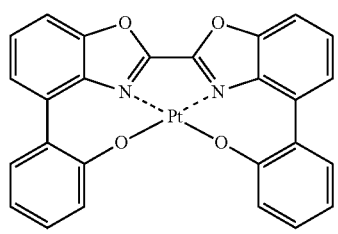
PD26 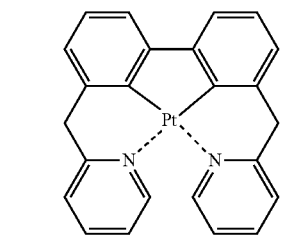
PD27 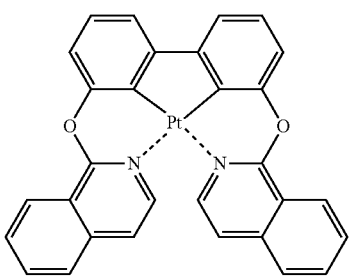
PD28 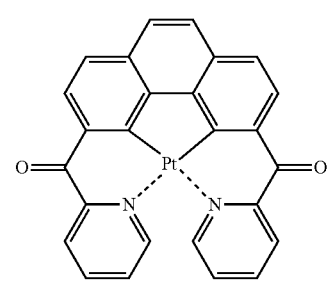
PD29 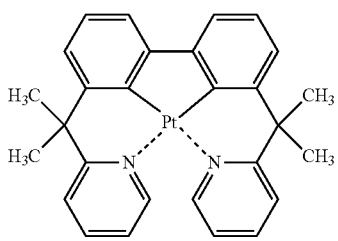
PD30 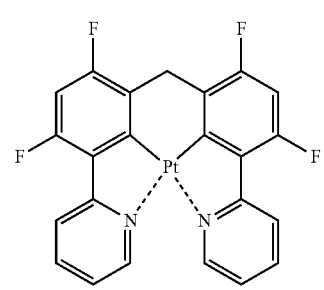
PD31 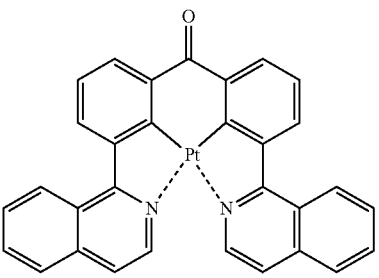
PD32 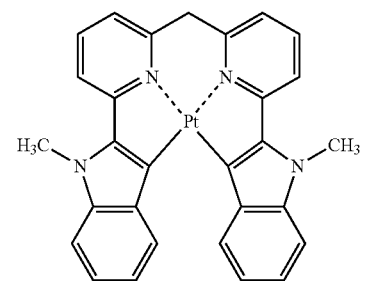
PD33 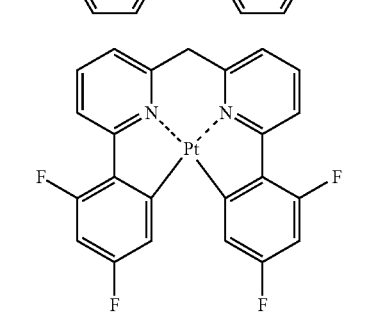
PD34 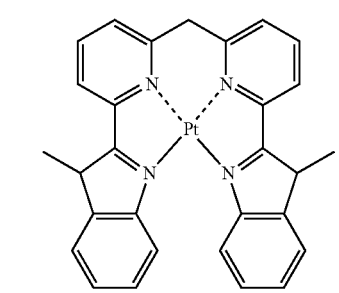
PD35 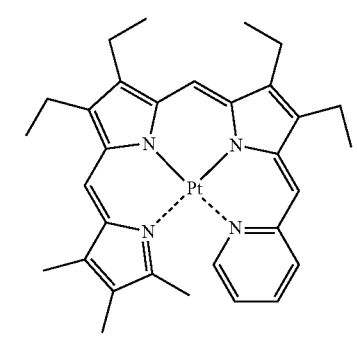

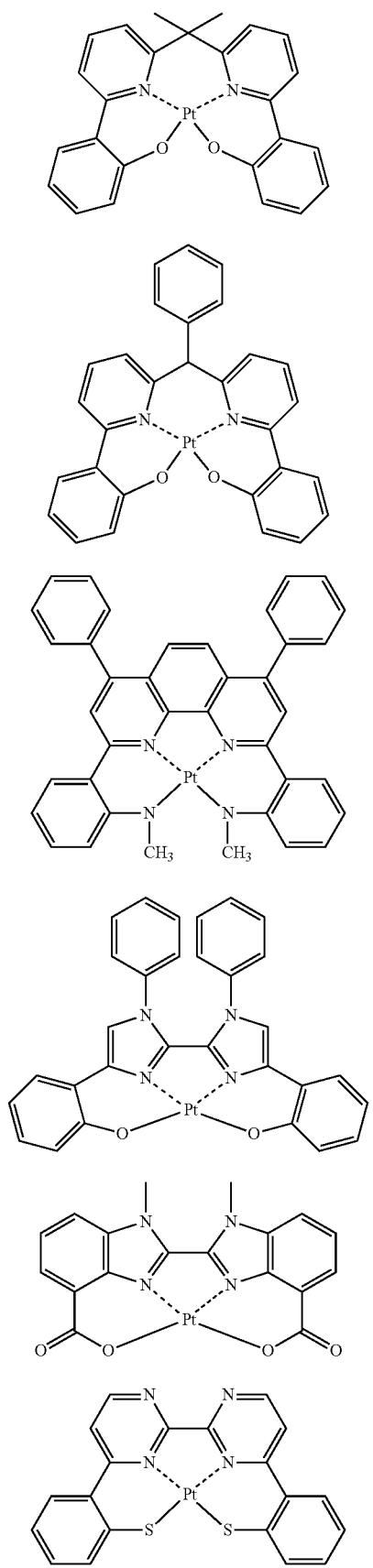

-continued
PD47
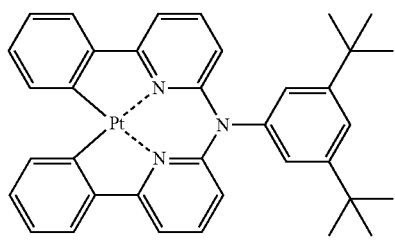
PD48
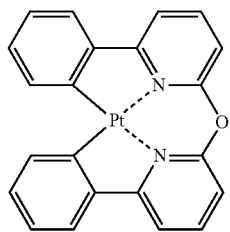
PD49
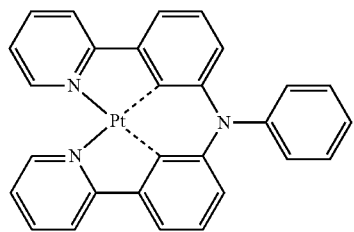
PD50
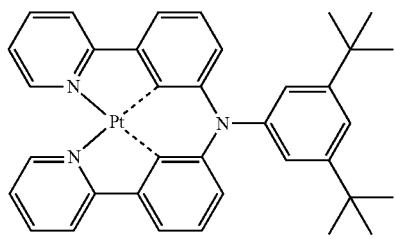
PD51
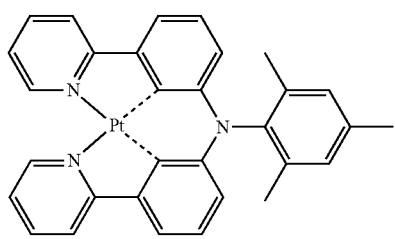
PD52
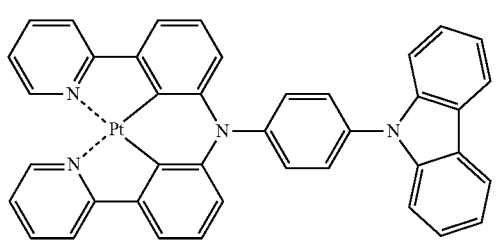
-continued
PD53
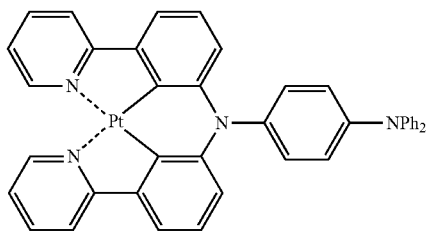
PD54
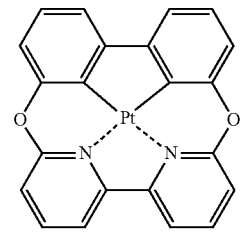
PD55
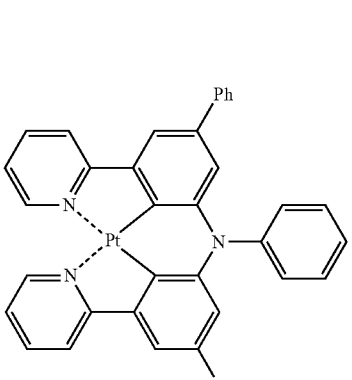
PD56
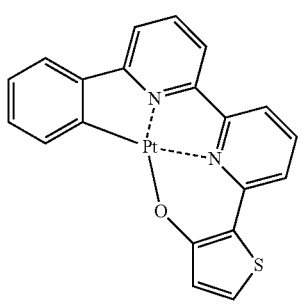
PD57
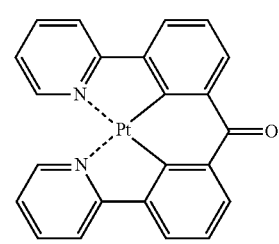

PD58
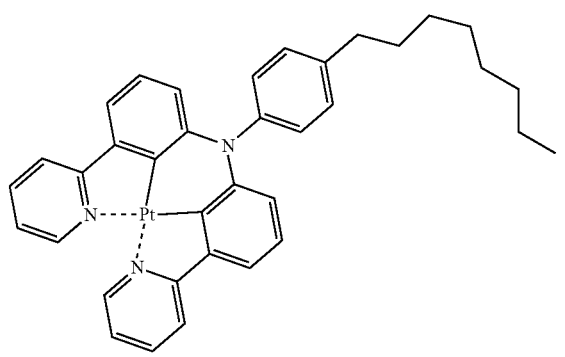
PD59
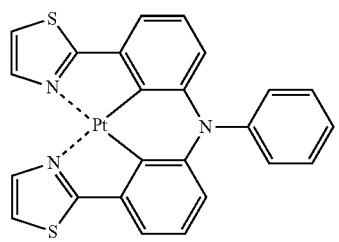
PD60
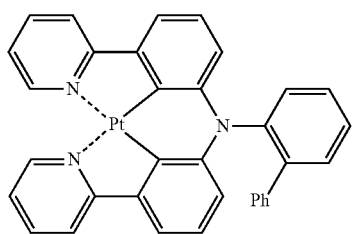
PD61
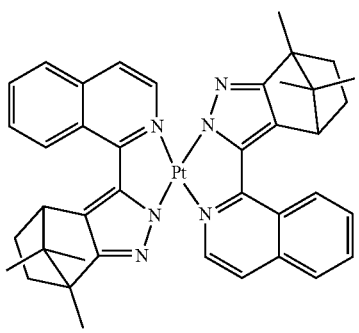
PD62
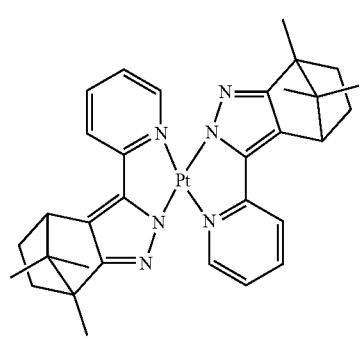
PD63
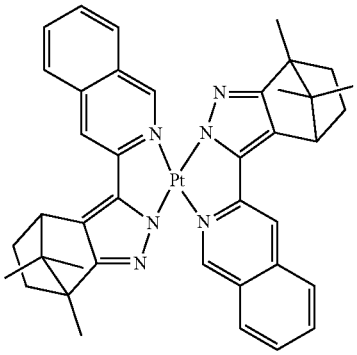
PD64
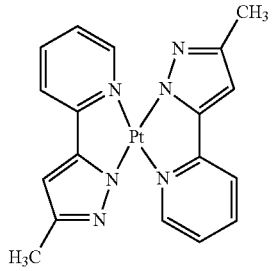
PD65
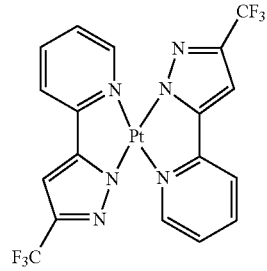
PD66
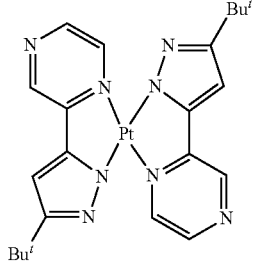
PD67
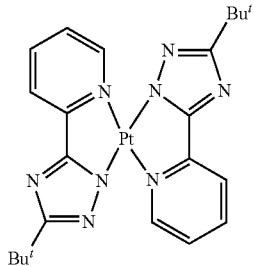

-continued
PD68
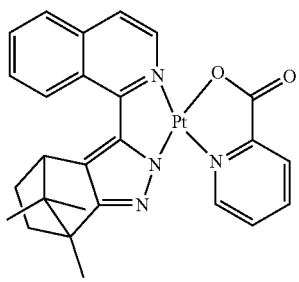
PD69
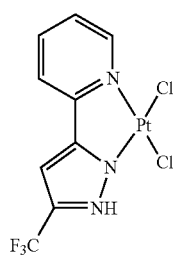
PD70
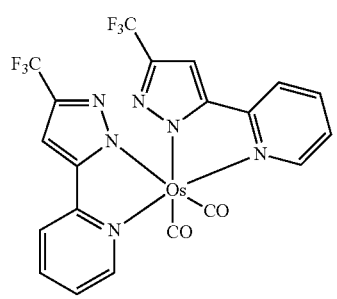
PD71
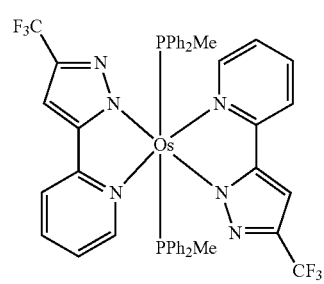
PD72
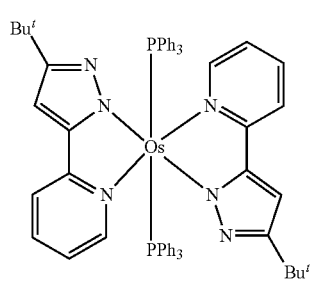
-continued
PD73
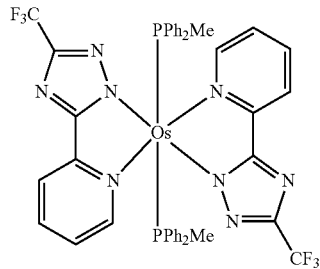
PD74
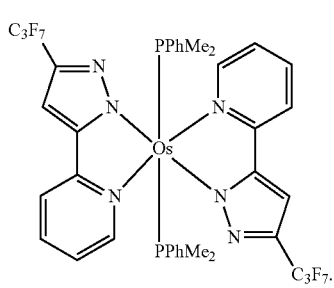
In various embodiments, the phosphorescent dopant may include PtOEP:
PtOEP
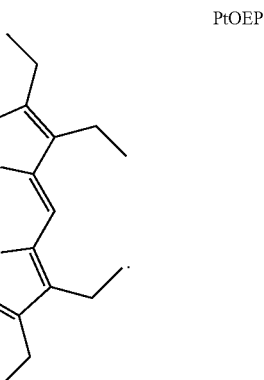
The fluorescent dopant may include at least one selected from DPAVBi, BDAVBi, TBPe, DCM, DCJTB, Coumarin 6, and C545T:

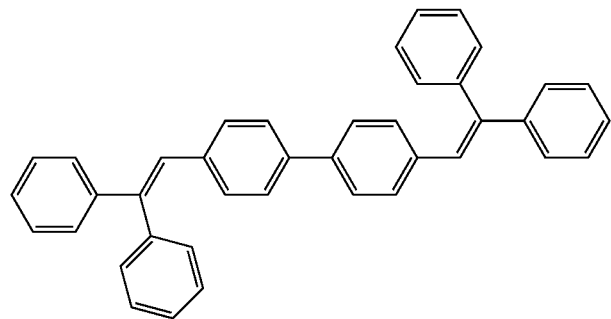

DPVBi

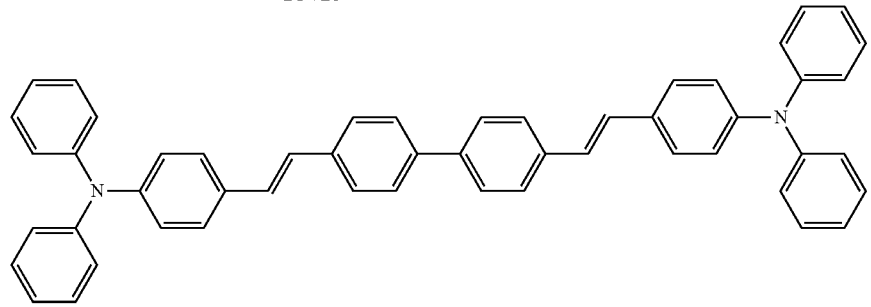

DPAVBi

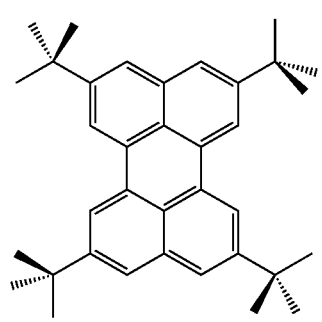

TBPe

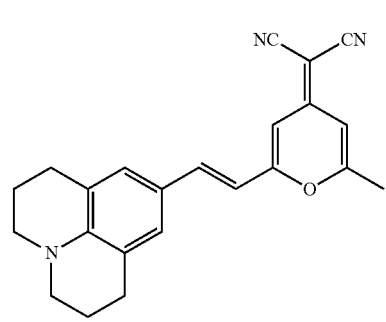

DCM

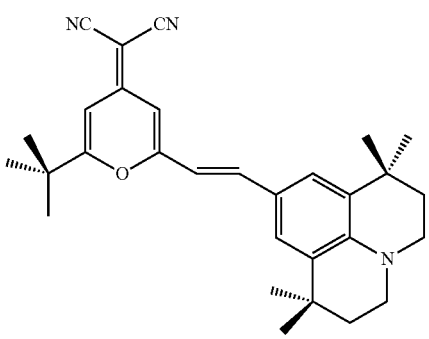

DCJTB

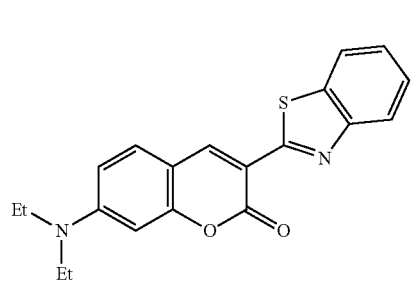

Coumarin 6

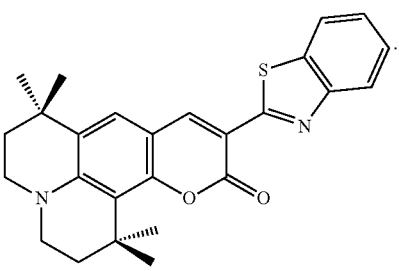

C545T

In various embodiments, the fluorescent dopant may include a compound represented by Formula 501:

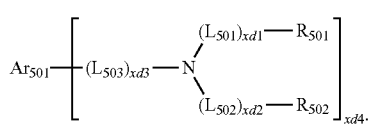

Formula 501

In Formula 501, $Ar_{501}$ may be selected from the group consisting of:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $L_{501}$ to $L_{503}$ may each independently be the same as described herein in connection with $L_{201}$ in Formulae 201 and 202

$R_{501}$ and $R_{502}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, a dibenzothio group, and a phenyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothio group, and a phenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothio group, a phenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xd1 to xd3 may each independently be selected from 0, 1, 2, and 3, and xb4 may be selected from 1, 2, 3, and 4, wherein $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The fluorescent dopant may include at least one selected from Compounds FD1 to FD8:

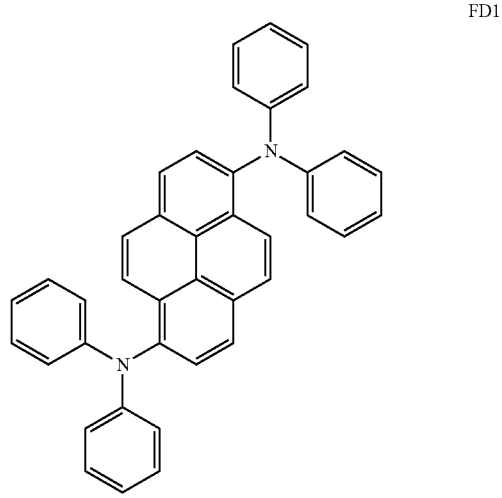

FD1

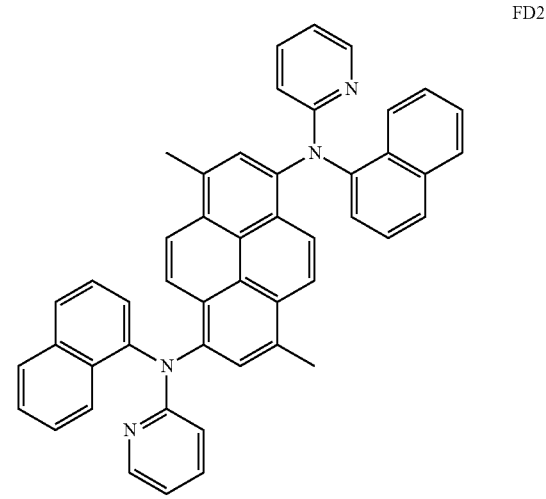

FD2

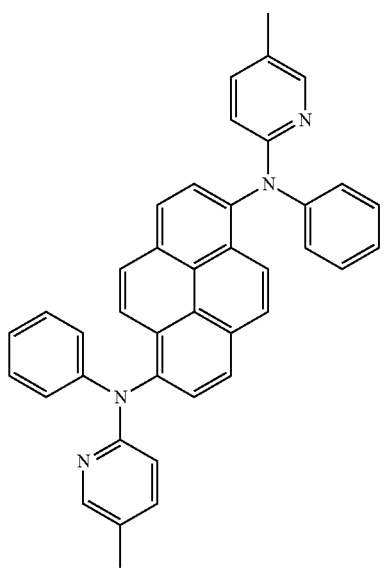
FD3
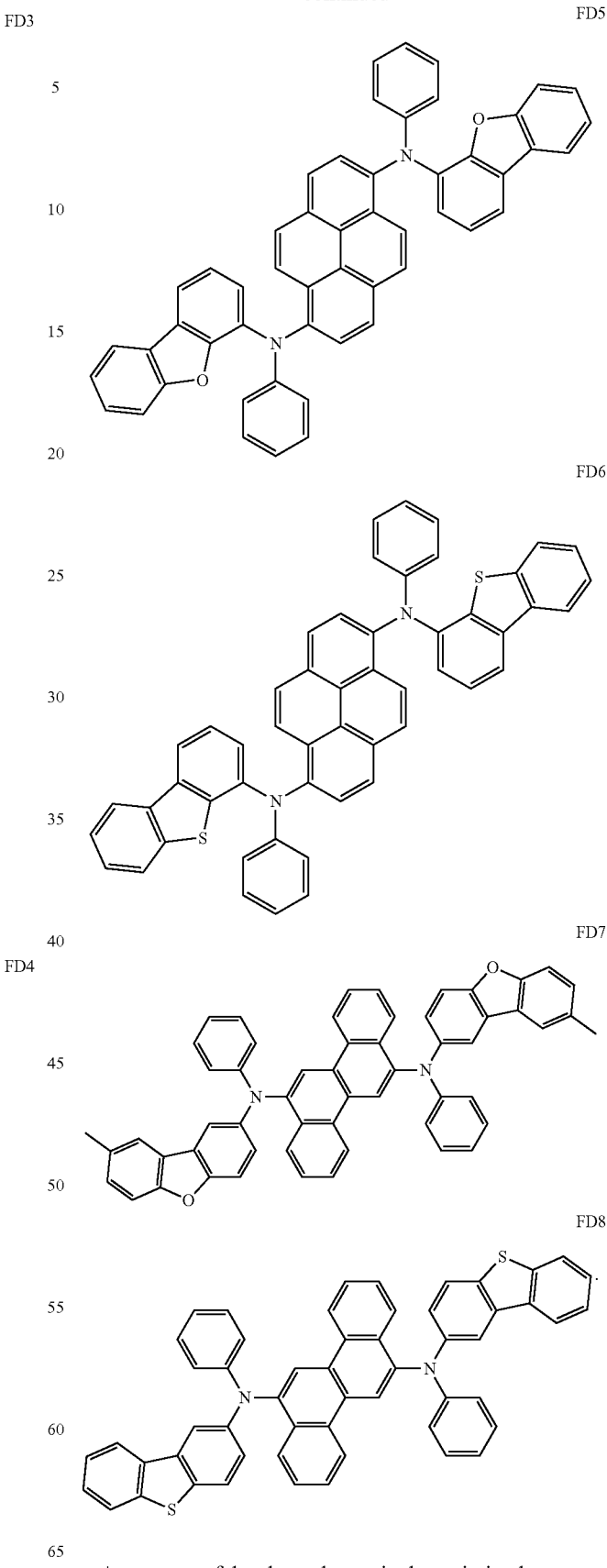
An amount of the above dopant in the emission layer may be, for example, in a range of about 0.01 to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within any of these ranges, excellent light-emission characteristics may be obtained without a substantial increase in driving voltage.

Electron Transport Region in Organic Layer 150

The electron transport region may have i) a single layered structure formed of a single material, ii) a single-layered structure formed of a plurality of different materials, or iii) a multi-layered structure having a plurality of layers formed of a plurality of different materials.

The electron transport region may include at least one layer selected from a buffer layer, a hole blocking layer, an electron control layer, an electron transport layer, and an electron injection layer, but embodiments of the present disclosure are not limited thereto.

For example, the electron transport region may have a structure of electron transport layer/electron injection layer, a structure of hole blocking layer/electron transport layer/electron injection layer, a structure of electron control layer/electron transport layer/electron injection layer, or a structure of buffer layer/electron transport layer/electron injection layer, wherein the layers of each structure are sequentially stacked form the emission layer in each stated order, but embodiments of the present disclosure are not limited thereto.

When the electron transport region includes a hole blocking layer, the hole blocking layer may be formed on the emission layer by utilizing one or more suitable methods such as vacuum deposition, spin coating, casting, an LB method, ink-jet printing, laser-printing, and/or LITI. When a hole blocking layer is formed by vacuum deposition and/or spin coating, deposition and coating conditions for the hole blocking layer may be the same as the deposition and coating conditions for the hole transport layer.

The hole blocking layer may include, for example, at least one selected from BCP and Bphen, but embodiments of the present disclosure are not limited thereto.

A thickness of a buffer layer, a hole blocking layer, or an electron control layer may be in a range of about 20 Å to about 1,000 Å, for example, about 30 Å to about 300 Å.

When the thickness of the buffer layer, the hole blocking layer, or the electron control layer is within any of the ranges described above, excellent hole block characteristics may be obtained without a substantial decrease in driving voltage.

The electron transport region may include an electron transport layer. The electron transport layer may be formed on the emission layer or the hole blocking layer by utilizing one or more suitable methods such as vacuum deposition, spin coating, casting, an LB method, ink-jet printing, laser-printing, and/or LITI. When the electron transport layer is formed by vacuum deposition and/or spin coating, deposition and coating conditions for the electron transport layer may be the same as the deposition and coating conditions for the hole transport layer.

The electron transport layer may further include at least one selected from BCP, Bphen, $Alq_3$, BAlq, TAZ, and NTAZ:

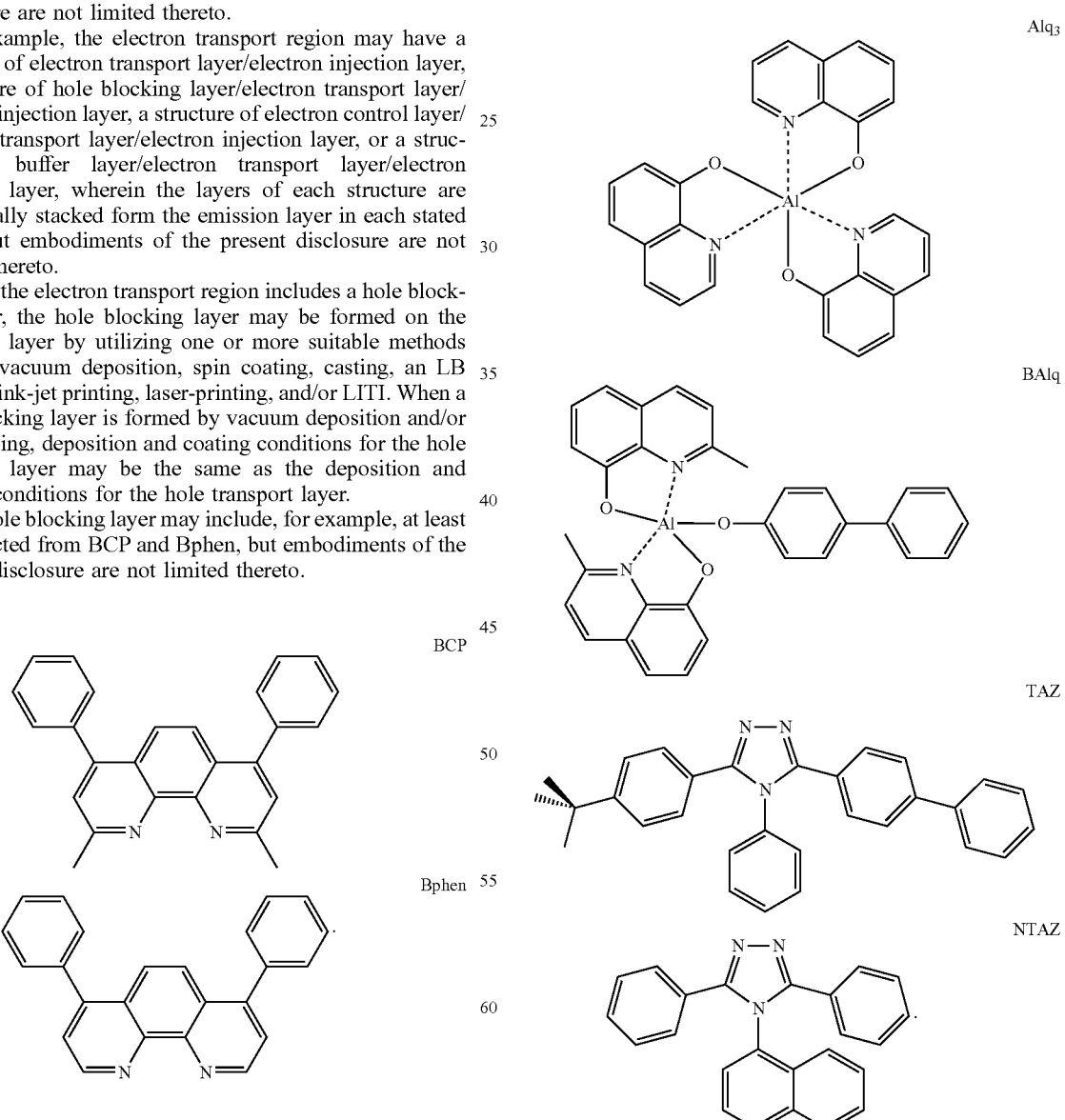

In various embodiments, the electron transport layer may include at least one of compounds represented by Formula 601:

$$Ar_{601}\text{-}[(L_{601})_{xe1}\text{-}E_{601}]_{xe2}.$$  Formula 601

In Formula 601, $Ar_{601}$ may be selected from the group consisting of:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $L_{601}$ may be the same as described herein in connection with $L_{201}$ in Formulae 201 and 202, $E_{601}$ may be selected from the group consisting of:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xe1 may be selected from 0, 1, 2, and 3, and
xe2 may be selected from 1, 2, 3, and 4, wherein $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In various embodiments, the electron transport layer may include at least one of compounds represented by Formula 602:

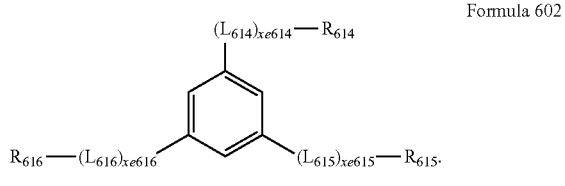

Formula 602

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, wherein at least one selected from $X_{611}$ to $X_{613}$ may be N, $L_{611}$ to $L_{616}$ may each independently be the same as described herein in connection with $L_{201}$ in Formulae 201 and 202, $R_{611}$ to $R_{616}$ may each independently be selected from a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, and xe611 to xe616 may each independently be selected from 0, 1, 2, and 3, wherein $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The compound of Formula 601 and the compound of Formula 602 may each include at least one selected from Compounds ET1 to ET15:

ET1
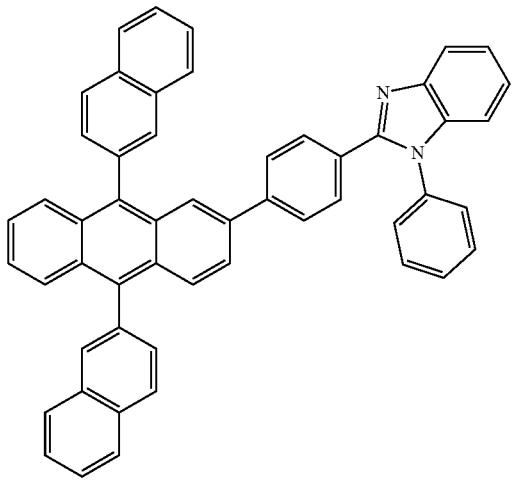

ET2
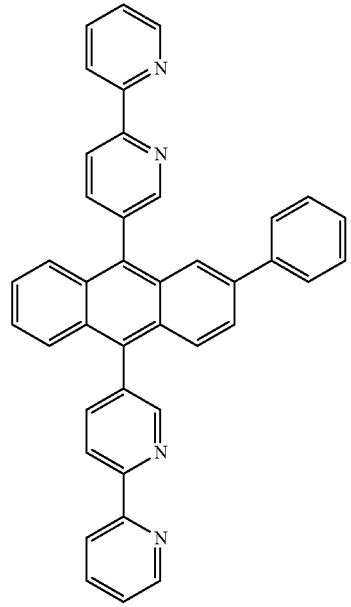

ET3
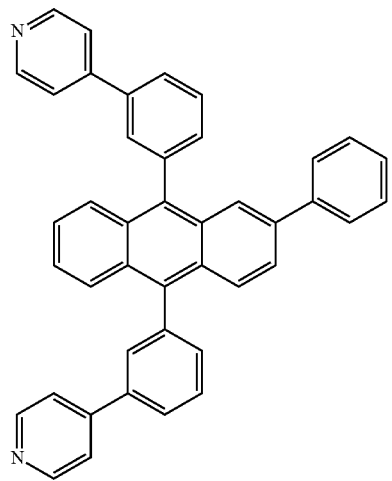

357
-continued
ET4
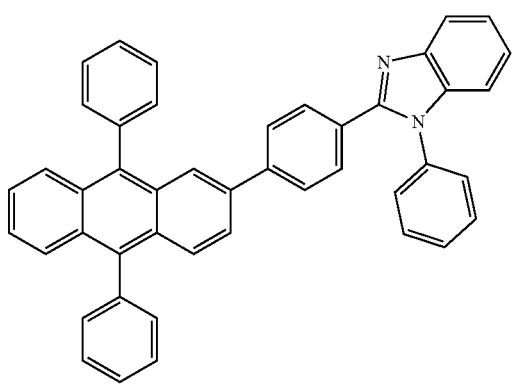
ET5
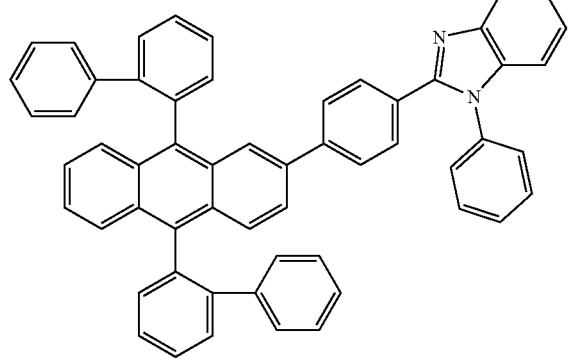
ET6
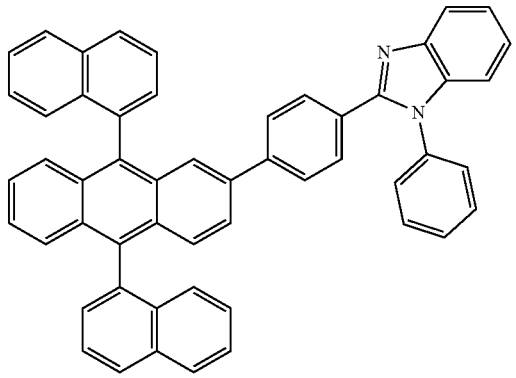
358
-continued
ET7
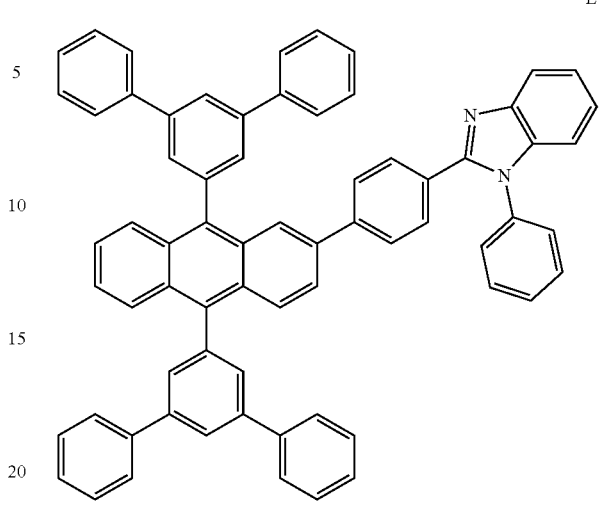
ET8
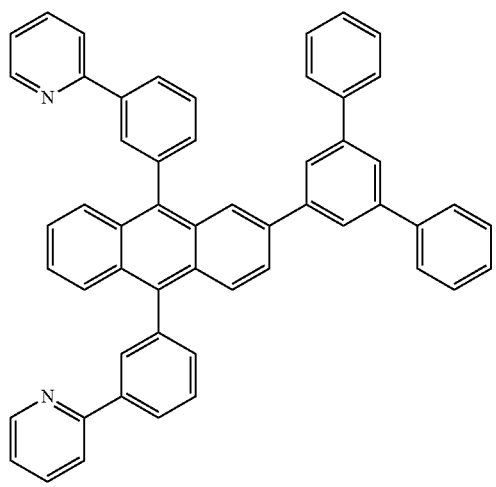
ET9
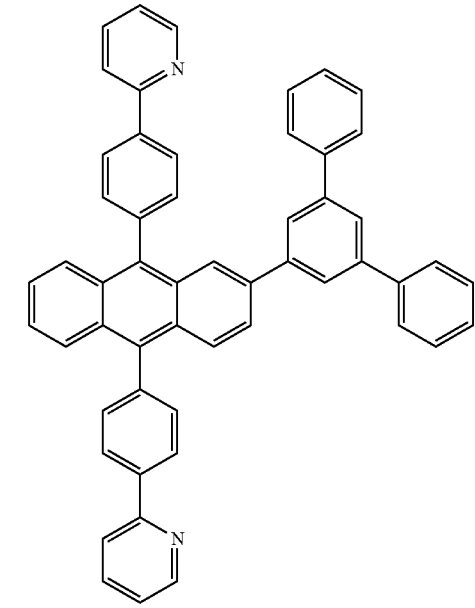

-continued

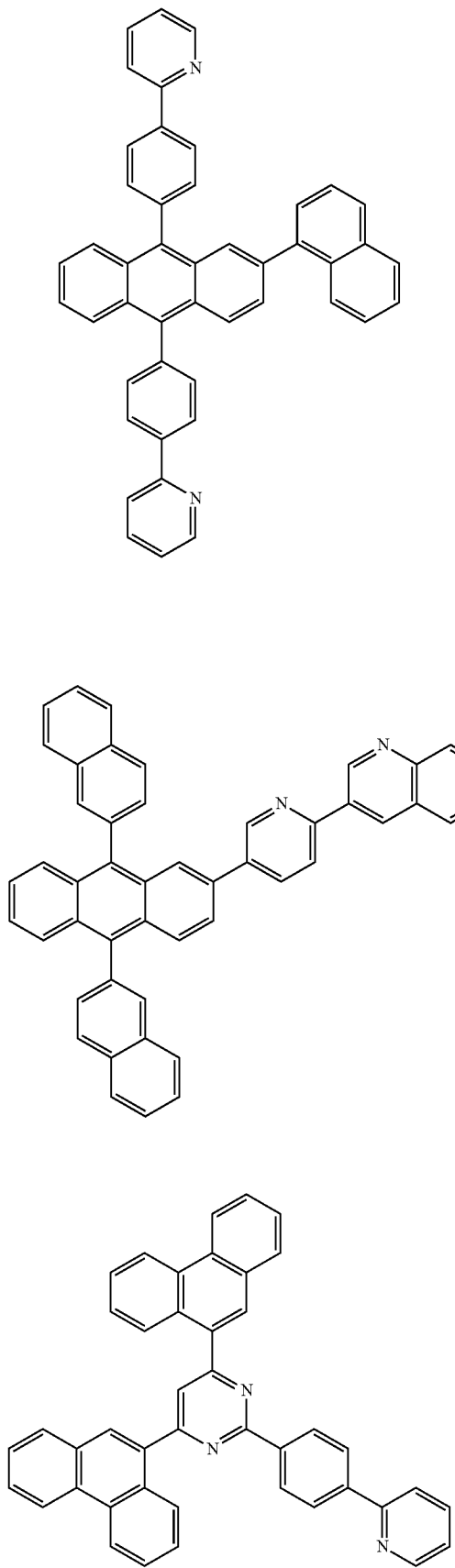

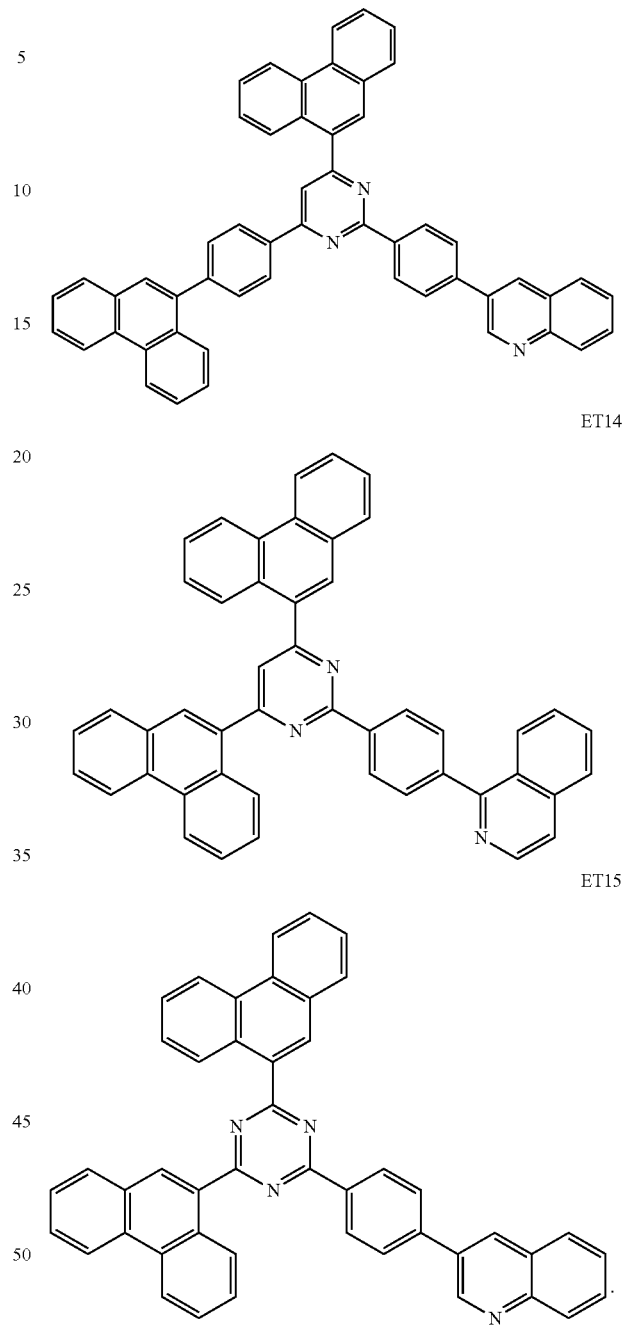

A thickness of the electron transport layer may be in a range of about 100 Å to about 1,000 Å, for example, about 150 Å to about 500 Å. When the thickness of the electron transport layer is within any of these ranges, satisfactory electron transport characteristics may be obtained without a substantial increase in driving voltage.

The electron transport layer may further include, in addition to the materials described above, a metal-containing material.

The metal-containing material may include a lithium (Li) complex. The Li complex may include, for example, Compound ET-D1 (lithium quinolate, LiQ) and/or Compound ET-D2:

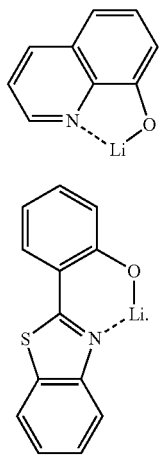

ET-D1

ET-D2

The electron transport region may include an electron injection layer that facilitates injection of electrons from the second electrode 190. The electron injection layer may directly contact the second electrode 190.

The electron injection layer may have i) a single layered structure formed of a single material, ii) a single-layered structure formed of a plurality of different materials, or iii) a multi-layered structure having a plurality of layers formed of a plurality of different materials.

The electron injection layer may be formed on the electron transport layer by utilizing one or more suitable methods such as vacuum deposition, spin coating, casting, an LB method, ink-jet printing, laser-printing, and/or LITI. When the electron injection layer is formed by vacuum deposition and/or spin coating, deposition and coating conditions for the electron injection layer may be the same as the deposition and coating conditions for the hole transport layer.

The electron injection layer may include at least one selected from LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within any of these ranges, satisfactory electron injection characteristics may be obtained without a substantial increase in driving voltage.

Second Electrode 190

The second electrode 190 may be disposed on the organic layer 150 having the structure described above according to one or more embodiments. The second electrode 190 may be a cathode, which is an electron injection electrode, and in this regard, a material for the second electrode 190 may be selected from a metal, an alloy, an electrically conductive compound, and a combination thereof, which may have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a reflective electrode, a semi-transmissive electrode, or a transmissive electrode.

The second electrode 190 may have a single-layered structure or a multi-layered structure having a plurality of layers.

Hereinabove, the organic light-emitting device 10 has been described with reference to FIG. 1, but embodiments of the present disclosure are not limited thereto.

Figure 2:
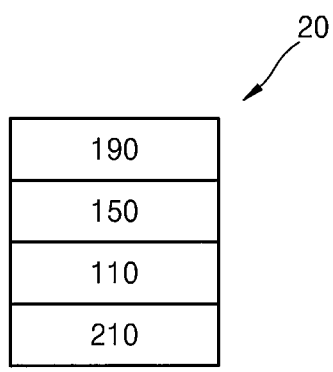
FIG. 2 is a schematic view of a structure of an organic light-emitting device according to another embodiment.
Figure 3:
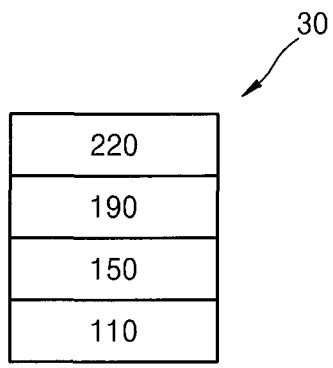
FIG. 3 is a schematic view of a structure of an organic light-emitting device according to another embodiment.
Figure 4:
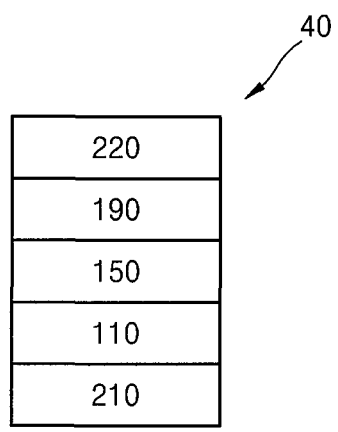
FIG. 4 is a schematic view of a structure of an organic light-emitting device according to another embodiment.

Descriptions of FIGS. 2 to 4

An organic light-emitting device 20 of FIG. 2 includes a first capping layer 210, a first electrode 110, an organic layer 150, and a second electrode 190, which are sequentially stacked in this stated order, an organic light-emitting device 30 of FIG. 3 includes a first electrode 110, an organic layer 150, a second electrode 190, and a second capping layer 220, which are sequentially stacked in this stated order, and an organic light-emitting device 40 of FIG. 4 includes a first capping layer 210, a first electrode 110, an organic layer 150, a second electrode 190, and second capping layer 220, which are sequentially stacked in this stated order.

In FIGS. 2 to 4, the first electrode 110, the organic layer 150, and the second electrode 190 may each independently be the same as respectively described herein in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external brightness efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may include the amine-based compound of Formula 1.

At least one selected from the first capping layer 210 and the second capping layer 220 may include, in addition to the amine-based compound of Formula 1, at least one selected from a carbocyclic compound, a heterocyclic compound, an amine-based compound, a porphine derivative, a phthalocyanine derivative, a naphthalocyanine derivative, an alkaline metal complex, and an alkaline earth metal complex. The carbocyclic compound, the heterocyclic compound, and the amine-based compound may be optionally substituted with a substituent containing at least one element selected from O, N, S, Se, Si, F, Cl, Br and I.

In various embodiments, at least one selected from the first capping layer 210 and the second capping layer 220 may include the amine-based compound of Formula 1.

In various embodiments, at least one selected from the first capping layer 210 and the second capping layer 220 may include the compound of Formula 201 or the compound of Formula 202.

In various embodiments, at least one selected from the first capping layer 210 and the second capping layer 220 may include a compound selected from Compounds HT13 to HT20 and Compounds CP1 to CP5, but embodiments of the present disclosure are not limited thereto:

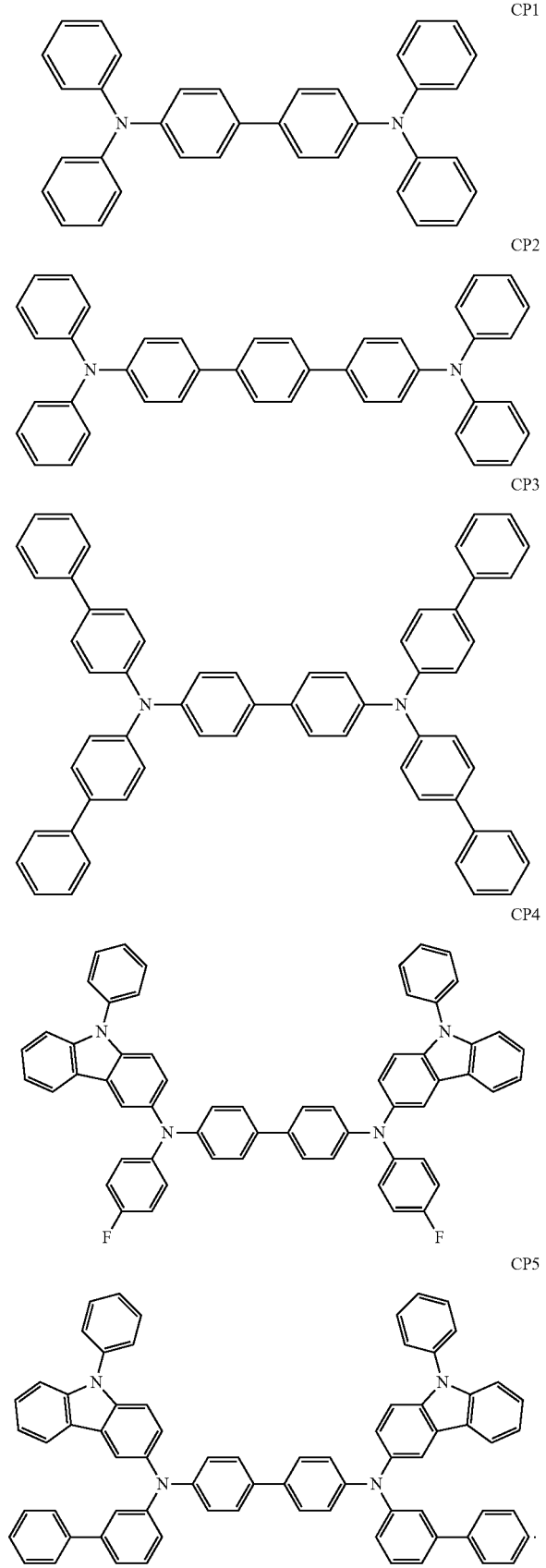 [SMILES: c1ccc(N(c2ccccc2)c2ccc(-c3ccc(N(c4ccccc4)c4ccccc4)cc3)cc2)cc1 ; c1ccc(N(c2ccccc2)c2ccc(-c3ccc(-c4ccc(N(c5ccccc5)c5ccccc5)cc4)cc3)cc2)cc1 ; c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1 ; Fc1ccc(N(c2ccc(-c3ccc(N(c4ccc(F)cc4)c4ccc5c(c4)c4ccccc4n5-c4ccccc4)cc3)cc2)c2ccc3c(c2)c2ccccc2n3-c2ccccc2)cc1 ; c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1]

Hereinabove, the organic light-emitting device has been described with reference to FIGS. 1 to 4, but embodiments of the present disclosure are not limited thereto.

Layers constituting the hole transport region, the emission layer, and layers constituting the electron transport region may each independently be formed in a certain region by utilizing one or more suitable methods such as vacuum deposition, spin coating, casting, an LB method, ink-jet printing, laser-printing, and/or LITI.

When layers constituting the hole transport region, the emission layer, and layers constituting the electron transport region are each independently formed by vacuum deposition and/or spin coating, deposition and coating conditions for the vacuum deposition may be, for example, performed at a deposition temperature of about 100° C. to about 500° C., at a vacuum degree of about $10^{-8}$ to about $10^{-3}$ torr, and at a deposition rate of about 0.01 to about 100 Å/sec, by taking into account a compound to be included in a layer to be formed and a structure of the layer to be formed.

When layers constituting the hole transport region, the emission layer, and layers constituting the electron transport region are each independently formed by spin coating, for example, the spin coating may be performed at a coating rate of about 2,000 rpm to about 5,000 rpm and at a temperature of about 80° C. to about 200° C., by taking into account a compound to be included in a layer to be formed, and a structure of the layer to be formed.

Full-Color Organic Light-Emitting Device

Figure 5:
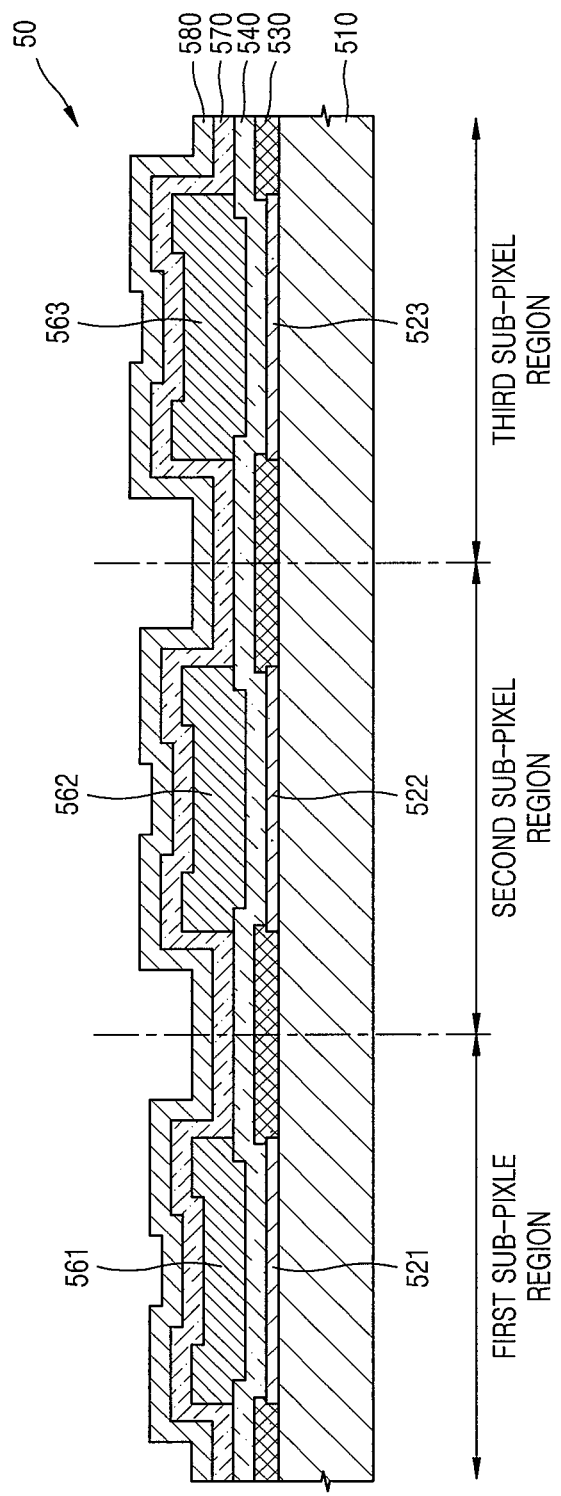
FIG. 5 is a schematic view of a structure of a full-color organic light-emitting device according to an embodiment.

FIG. 5 is a schematic cross-sectional view of a full-color organic light-emitting device according to an embodiment.

Referring to FIG. 5, an organic light-emitting device 50 includes a substrate 510 that is partitioned into a first sub-pixel region, a second sub-pixel region, and a third sub-pixel region.

A first sub-pixel may be formed in the first sub-pixel region, a second sub-pixel may be formed in the second sub-pixel region, and a third sub-pixel may be formed in the third sub-pixel region.

A plurality of first electrodes 521, 522, and 523 may respectively be disposed in the first sub-pixel region, the second sub-pixel region, and the third sub-pixel region of the substrate 510. That is, the first electrode 521 may be disposed in the first sub-pixel region, the first electrode 522 may be disposed in the second sub-pixel region, and the first electrode 523 may be disposed in the third sub-pixel region.

A hole transport region 540 may be disposed on the plurality of the first electrodes 521, 522, and 523. The hole transport region 540 may be formed as a common layer over the plurality of the first electrodes 521, 522, and 523. The hole transport region 540 may include a first hole transport region formed in the first sub-pixel region, a second hole transport region formed in the second sub-pixel region, and a third hole transport region formed in the third sub-pixel region. For example, the hole transport region 540 may include the amine-based compound of Formula 1. In more detail, the amine-based compound of Formula 1 may be in only one region selected from the first hole transport region, the second hole transport region, and the third hole transport region, or all of the first hole transport region, the second hole transport region, and the third hole transport region.

The amine-based compound of Formula 1 may be the same as described herein.

A plurality of emission layers including a first emission layer 561, a second emission layer 562, and a third emission layer 563 may be formed on the hole transport region 540. The first emission layer 561 may be formed in the first sub-pixel region and emit a first color light, the second emission layer 562 may be formed in the second sub-pixel region and emit a second color light, and the third emission layer 563 may be formed in the third sub-pixel region and emit a third color light.

The first color light may be red light, the second color light may be green light, and the third color light may be blue light. The first color light, the second color light, and the third color light may be mixed with each other to emit white light.

An electron transport region 570 may be disposed over the first, second, and third emission layers 561, 562, and 563. The electron transport region 570 may be formed as a common layer over the plurality of the emission layers 561, 562, and 563. The electron transport region 570 may include an electron transport layer and an electron injection layer that are sequentially stacked from the plurality of the emission layers 561, 562, and 563 in this stated order.

A second electrode 580 may be formed as a common layer on the electron transport region 570.

The term "common layer," as used herein, may refer to a layer formed entirely over the first sub-pixel region, the second sub-pixel region, and the third sub-pixel region, rather than being patterned according to the first sub-pixel region, the second sub-pixel region, and the third sub-pixel region.

A pixel insulating layer 530 may be formed along edges of the plurality of the first electrodes 521, 522, and 523. The pixel insulating layer 530 defines a pixel region, and may include various suitable organic insulating materials (for example, a silicon-based material), inorganic insulating materials, or organic/inorganic composite insulating materials.

The first electrodes 521, 522, and 523, the hole transport region 540, the emission layers 561, 562, and 563, the electron transport region 570, and the second electrode 580 may each independently be the same as respectively described herein in connection with FIG. 1.

The organic light-emitting device 50 may be included in a flat panel display device including a thin film transistor. The thin film transistor may include a gate electrode, source and drain electrodes, a gate insulating film, and an active layer, and one of the source and drain electrodes may electrically contact the first electrodes 521, 522, and 523 of the organic light-emitting device 50. The active layer may include crystalline silicon, amorphous silicon, organic semiconductor, oxide semiconductor, or the like, but embodiments of the present disclosure are not limited thereto.

Hereinabove, the full-color organic light-emitting device has been described with reference to FIG. 5, but embodiments of the present disclosure are not limited thereto. For example, the third emission layer 563 may be formed as a common layer that extends to the first sub-pixel region and the second sub-pixel region. In addition, the third sub-pixel region may not include the third auxiliary layer. In addition, only one of the first auxiliary layer and the second auxiliary layer may be utilized.

General Definition of Substituents

A "$C_1$-$C_{60}$ alkyl group," as used herein, may refer to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. The term "$C_1$-$C_{60}$ alkylene group," as used herein, may refer to a divalent group having substantially the same structure as the $C_1$-$C_{60}$ alkyl group.

A "$C_2$-$C_{60}$ alkenyl group," as used herein, may refer to an aliphatic saturated hydrocarbon monovalent group having 1 to 60 carbon atoms and having at least one carbon-carbon double bond at one or more positions along the hydrocarbon chain (e.g., in the middle or at either terminal end of the $C_2$-$C_{60}$ alkyl group), and non-limiting examples thereof include an ethenyl group, a propenyl group, and a butenyl group. A "$C_2$-$C_{60}$ alkenylene group," as used herein, may refer to a divalent group having substantially the same structure as the $C_2$-$C_{60}$ alkenyl group.

A "$C_2$-$C_{60}$ alkynyl group," as used herein, refers to a hydrocarbon group having at least one carbon-carbon triple bond at one or more positions along the hydrocarbon chain (e.g., in the middle or at either terminal end of the $C_2$-$C_{60}$ alkyl group), and non-limiting examples thereof include an ethynyl group and a propynyl group. A "$C_2$-$C_{60}$ alkynylene group," as used herein, may refer to a divalent group having substantially the same structure as the $C_2$-$C_{60}$ alkynyl group.

A "$C_1$-$C_{60}$ alkoxy group," as used herein, may refer to a monovalent group represented by —$OA_{101}$ (where $A_{101}$ is the $C_1$-$C_{60}$ alkyl group), and non-limiting examples thereof include a methoxy group, an ethoxy group, and an isopropyloxy group.

A "$C_3$-$C_{10}$ cycloalkyl group," as used herein, may refer to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. A "$C_3$-$C_{10}$ cycloalkylene group," as used herein, may refer to a divalent group having substantially the same structure as the $C_3$-$C_{10}$ cycloalkyl group.

A "$C_1$-$C_{10}$ heterocycloalkyl group," as used herein, may refer to a monovalent saturated monocyclic group having at least one heteroatom selected from N, O, Si, P, and S as a ring-forming atom in addition to 1 to 10 carbon atoms, and non-limiting examples thereof include a 1,2,3,4-oxatriazolidinyl group, a tetrahydrofuranyl group, and a tetrahydrpthiophenyl group. A "$C_1$-$C_{10}$ heterocycloalkylene group," as used herein, may refer to a divalent group having substantially the same structure as the $C_1$-$C_{10}$ heterocycloalkyl group.

A "$C_3$-$C_{10}$ cycloalkenyl group," as used herein, may refer to a monovalent monocyclic group that has 3 to 10 carbon atoms and at least one carbon-carbon double bond in the ring thereof and does not have aromaticity, and non-limiting examples thereof include a cyclopentenyl group, a cyclohexenyl group, and a cycloheptenyl group. A "$C_3$-$C_{10}$ cycloalkenylene group," as used herein, may refer to a divalent group having substantially the same structure as the $C_3$-$C_{10}$ cycloalkenyl group.

A "$C_1$-$C_{10}$ heterocycloalkenyl group," as used herein, may refer to a monovalent monocyclic group that has at least one heteroatom selected from N, O, Si, P, and S as a ring-forming atom in addition to 1 to 10 carbon atoms, and at least one carbon-carbon double bond in the ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. A "$C_1$-$C_{10}$ heterocycloalkenylene group," as used herein, may refer to a divalent group having substantially the same structure as the $C_1$-$C_{10}$ heterocycloalkenyl group.

A "$C_6$-$C_{60}$ aryl group," as used herein, may refer to a monovalent group having an aromatic system having 6 to 60 carbon atoms, and a "$C_6$-$C_{60}$ arylene group," as used herein, may refer to a divalent group having an aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other or may be linked with each other via a single bond.

A "$C_1$-$C_{60}$ heteroaryl group," as used herein, may refer to a monovalent group having a heterocyclic aromatic system that has at least one heteroatom selected from N, O, Si, P, and S as a ring-forming atom in addition to 1 to 60 carbon atoms. A "$C_1$-$C_{60}$ heteroarylene group," as used herein, may refer to a divalent group having a heterocyclic aromatic system that has at least one heteroatom selected from N, O, Si, P, and S as a ring-forming atom in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other or may be linked with each other via a single bond.

A "$C_6$-$C_{60}$ aryloxy group," as used herein, may refer to a group represented by —$OA_{102}$ (where $A_{102}$ is the $C_6$-$C_{60}$ aryl group), and a "$C_6$-$C_{60}$ arylthio group," as used herein, may refer to a group represented by —$SA_{103}$ (where $A_{103}$ is the $C_6$-$C_{60}$ aryl group).

A "monovalent non-aromatic condensed polycyclic group," as used herein, may refer to a monovalent group that has two or more rings condensed to each other, has only carbon atoms as ring-forming atoms (for example, 8 to 60 carbon atoms), and has non-aromaticity in the entire molecular structure. A non-limiting example of the monovalent non-aromatic condensed polycyclic group includes a fluorenyl group. A "divalent non-aromatic condensed polycyclic group," as used herein, may refer to a divalent group having substantially the same structure as the monovalent non-aromatic condensed polycyclic group.

A "monovalent non-aromatic condensed heteropolycyclic group," as used herein, may refer to a monovalent group that has two or more rings condensed to each other, has at least one heteroatom selected from N, O, Si, P, and S as a ring-forming atom in addition to carbon atoms (for example, 1 to 60 carbon atoms), and has non-aromaticity in the entire molecular structure. A non-limiting example of the monovalent non-aromatic condensed heteropolycyclic group includes a carbazolyl group. A "divalent non-aromatic condensed heteropolycyclic group," as used herein, may refer to a divalent group having substantially the same structure as the monovalent non-aromatic condensed heteropolycyclic group.

A "$C_5$-$C_{60}$ carbocyclic group," as used herein, may refer to a monocyclic or polycyclic group having 5 to 60 carbon atoms in which the ring-forming atoms include carbon atoms only. The $C_5$-$C_{60}$ carbocyclic group may be an aromatic carbocyclic group or a non-aromatic carbocyclic group. The $C_5$-$C_{60}$ carbocyclic group may be a ring, such as a benzene group, a monovalent group, such as a phenyl group, or a divalent group, such as a phenylene group. In various embodiments, depending on the number of substituents connected to the $C_5$-$C_{60}$ carbocyclic group, the $C_5$-$C_{60}$ carbocyclic group may be a trivalent group or a quadrivalent group.

A "$C_1$-$C_{60}$ heterocyclic group," as used herein, may refer to a group having substantially the same structure as the $C_5$-$C_{60}$ carbocyclic group except that as a ring-forming atom, at least one heteroatom selected from N, O, Si, P, and S is used in addition to carbon (the number of carbon in the $C_1$-$C_{60}$ heterocyclic group may be in a range of 1 to 60).

In the present specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from the group consisting of:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), and —P(=O)(Q$_{21}$)(Q$_{22}$); and —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), wherein Q$_{11}$ to Q$_{13}$, Q$_{21}$ to Q$_{23}$, and Q$_{31}$ to Q$_{33}$ may each independently be selected from hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group.

The term "Ph," as used herein, may refer to a phenyl group, the term "Me," as used herein, may refer to a methyl group, the term "Et," as used herein, may refer to an ethyl group, the term "ter-Bu" or "Bu$^t$," as used herein, may refer to a tert-butyl group, and the term "OMe," as used herein, may refer to a methoxy group.

The term "biphenyl group," as used herein, may refer to "a phenyl group substituted with a phenyl group". The term "biphenyl group," as used herein, belongs to "a substituted phenyl group" having "a C$_6$-C$_{60}$ aryl group" as a substituent.

The term "terphenyl group," as used herein, may refer to "a phenyl group substituted with a biphenyl group". The term "terphenyl group," as used herein, may refer to "a substituted phenyl group" having "a C$_6$-C$_{60}$ aryl group substituted with a C$_6$-C$_{60}$ aryl group" as a substituent.

* and *', as used herein, unless defined otherwise, each indicate a binding site to a neighboring atom in a corresponding formula.

Hereinafter, a compound according to one or more embodiments and an organic light-emitting device according to one or more embodiments will be described in more detail with reference to the Synthesis Examples and Examples. However, these examples are provided for illustrative purposes only, and should not in any sense be interpreted as limiting the scope of the present disclosure. The expression "B was utilized instead of A" used in describing the Synthesis Examples may refer to an identical number of molar equivalents of B being utilized in place of molar equivalents of A.

EXAMPLES

Synthesis Example 1: Synthesis of Compound 1

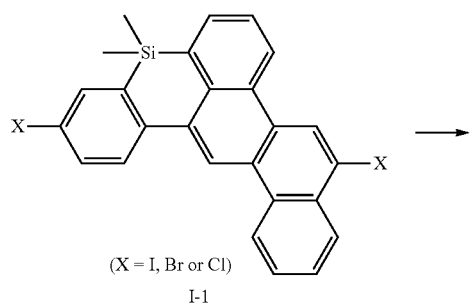

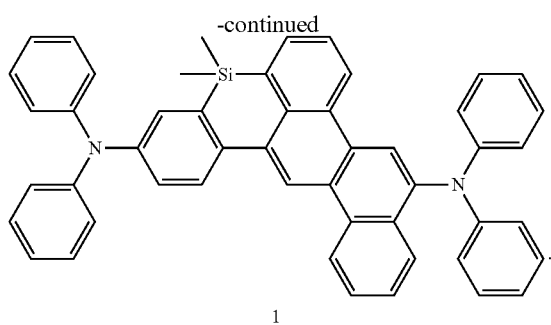

Compound I-1 (100 mmol), diphenylamine (210 mmol), Pd$_2$(dba)$_3$ (1.50 g, 1.70 mmol), PtBu$_3$ (0.30 g, 1.70 mmol), and NaOtBu (12 g, 125 mmol) were dissolved in 1.0 L of toluene, and then, the obtained reaction solution was stirred at a temperature of about 120° C. for 5 hours. After the reaction solution was cooled to room temperature, a washing process was performed thereon utilizing brine, and then, an extraction process was performed thereon three times utilizing diethylether each time. An organic layer collected therefrom was dried utilizing magnesium sulfate, and a solvent was removed therefrom by evaporation. The residue obtained therefrom was separation-purified by silica gel column chromatography, thereby completing the synthesis of 52.8 g (yield: 76%) of Compound 1. The synthesized compound was identified by LC-MS and $^1$H NMR.

C50H38N2Si: M+1 694.3 $^1$H NMR (500 MHz, CDCl$_3$) δ=9.27 (s, 1H), 9.08 (d, 1H), 8.98 (d, 1H), 8.11-8.10 (m, 2H), 7.83-7.79 (m, 2H), 7.68-7.62 (m, 2H), 7.51-7.47 (m, 3H), 7.24 (t, 8H), 7.08-7.00 (m, 12H), 0.66 (s, 6H)

Synthesis Example 2: Synthesis of Compound 2

Compound 2 (yield: 81%) was synthesized in substantially the same manner as in Synthesis Example 1, except that 9,9-dimethyll-N-phenyl-9H-fluorene-2-amine was utilized instead of diphenylamine. Compound 2 synthesized therefrom was identified by LC-MS and $^1$H NMR.

C68H54N2Si: M+1 926.4 $^1$H NMR (500 MHz, CDCl$_3$) δ=8.51 (s, 1H), 8.38 (d, 1H), 8.18 (d, 1H), 8.11-8.10 (m, 2H), 7.83-7.79 (m, 2H), 7.68-7.62 (m, 2H), 7.51-7.47 (m, 3H), 7.24 (t, 8H), 7.08-7.00 (m, 12H), 0.66 (s, 6H)

Synthesis Example 3: Synthesis of Compound 4

Compound 4 (yield: 77%) was synthesized in substantially the same manner as in Synthesis Example 1, except that N-phenyldibenzo[b,d]furan-4-amine was utilized instead of diphenylamine. Compound 4 synthesized therefrom was identified by LC-MS and $^1$H NMR.

C62H42N2O2Si: M+1 874.3 $^1$H NMR (500 MHz, CDCl$_3$) δ=9.25 (s, 1H), 9.08 (d, 1H), 8.88 (d, 1H), 8.01-8.10 (m, 2H), 7.83-7.79 (m, 2H), 7.66-7.62 (m, 2H), 7.51-7.47 (m, 3H), 7.24 (t, 8H), 7.08-7.00 (m, 12H), 0.76 (s, 6H)

Synthesis Example 4: Synthesis of Compound 15

Compound 15 (yield: 69%) was synthesized in substantially the same manner as in Synthesis Example 1, except that N-([1,1'-biphenyl]-2-yl)dibenzo[b,d]furan-4-amine was utilized instead of diphenylamine. Compound 15 synthesized therefrom was identified by LC-MS and $^1$H NMR.

C74H50N2O2Si: M+1 1026.4 $^1$H NMR (500 MHz, CDCl$_3$) δ=9.00 (s, 1H), 9.08 (d, 1H), 8.98 (d, 1H), 8.11-8.10

(m, 2H), 7.83-7.79 (m, 2H), 7.68-7.62 (m, 2H), 7.51-7.47 (m, 3H), 7.24 (t, 8H), 7.08-7.00 (m, 12H), 0.66 (s, 6H)

Synthesis Example 5: Synthesis of Compound 66

Compound 66 (yield: 85%) was synthesized in substantially the same manner as in Synthesis Example 1, except that N-phenyl-4-(trimethylsilyl)aniline was instead of diphenylamine. Compound 66 synthesized therefrom was identified by LC-MS and $^1$H NMR.

$C_{59}H_{48}N_2OSi$: M+1 856.3 $^1$H NMR (500 MHz, $CDCl_3$) δ=9.53 (s, 1H), 9.33 (d, 1H), 7.98 (d, 1H), 7.75-7.70 (m, 2H), 7.63-7.51 (m, 2H), 7.51-7.47 (m, 10H), 7.24 (t, 8H), 7.08-7.00 (m, 12H), 0.66 (s, 6H)

Synthesis Example 6: Synthesis of Compound 24

Compound 24 (yield: 69%) was synthesized in substantially the same manner as in Synthesis Example 1, except that 1.2 equivalents of N-([1,1'-biphenyl]-2-yl)dibenzo[b,d]furan-4-amine and 1.2 equivalents of diphenylamine were utilized instead of 2 equivalents of diphenylamine. Compound 24 synthesized therefrom was identified by LC-MS and $^1$H NMR.

$C_{62}H_{44}N_2OSi$: M+1 861.13 $^1$H NMR (500 MHz, $CDCl_3$) δ=9.27 (s, 1H), 9.08 (d, 1H), 8.98 (d, 1H), 8.11-8.10 (m, 2H), 7.83-7.79 (m, 2H), 7.68-7.62 (m, 2H), 7.51-7.47 (m, 3H), 7.24 (t, 8H), 7.08-7.00 (m, 12H), 0.66 (s, 6H)

Synthesis Example 7: Synthesis of Compound 65

Compound 65 (yield: 90%) was synthesized in substantially the same manner as in Synthesis Example 1, except that 1.2 equivalents of N-phenyldibenzo[b,d]furan-4-amine and 1.2 equivalents of diphenylamine were utilized instead of 2 equivalents of diphenylamine. Compound 65 synthesized therefrom was identified by LC-MS and $^1$H NMR.

$C_{56}H_{40}N_2OSi$: M+1 785.03 $^1$H NMR (500 MHz, $CDCl_3$) δ=9.27-9.08 (m, 2H), 8.98-7.79 (m, 11H), 7.68-7.62 (m, 2H), 7.51-7.47 (m, 3H), 7.24 (t, 8H), 7.08-7.00 (m, 12H), 0.66 (s, 6H)

Synthesis Example 8: Synthesis of Compound 88

Compound 88 (yield: 88%) was synthesized in substantially the same manner as in Synthesis Example 1, except that 9,9-dimethyl-N-phenyl-9H-fluorene-2-amine and N-([1,1'-biphenyl]-2-yl)dibenzo[b,d]furan-4-amine were utilized instead of diphenylamine. Compound 88 synthesized therefrom was identified by LC-MS and $^1$H NMR.

$C_{71}H_{52}N_2OSi$: M+1 977.30 $^1$H NMR (500 MHz, $CDCl_3$) δ=9.51 (s, 1H), 9.11 (d, 1H), 8.58 (d, 1H), 8.23-8.10 (m, 3H), 7.83-7.60 (m, 4H), 7.58-7.47 (m, 5H), 7.24 (t, 8H), 7.08-7.00 (m, 12H), 0.69 (s, 6H)

Synthesis Example 9: Synthesis of Compound 72

Compound 72 (yield: 70%) was synthesized in substantially the same manner as in Synthesis Example 1, except that 9,9-dimethyl-N-phenyl-9H-fluorene-2-amine and N-phenyldibenzo[b,d]furan-4-amine were utilized instead of diphenylamine. Compound 72 synthesized therefrom was identified by LC-MS and $^1$H NMR.

$C_{65}H_{48}N_2OSi$: M+1 901.20 $^1$H NMR (500 MHz, $CDCl_3$) δ=9.53 (s, 1H), 9.33 (d, 1H), 7.98 (d, 1H), 7.75-7.70 (m, 2H), 7.63-7.51 (m, 2H), 7.51-7.47 (m, 10H), 7.24 (t, 8H), 7.08-7.00 (m, 12H), 0.66 (s, 6H)

Synthesis Example 10: Synthesis of Compound 106

Compound 106 (yield: 67%) was synthesized in substantially the same manner as in Synthesis Example 1, except that 1.2 equivalents of N-phenyldibenzo[b,d]furan-2-amine and 1.2 equivalents of diphenylamine were utilized instead of 2 equivalents of diphenylamine. Compound 106 synthesized therefrom was identified by LC-MS and $^1$H NMR.

$C_{62}H_{44}N_2OSi$: M+1 861.13 $^1$H NMR (500 MHz, $CDCl_3$) δ=9.41 (s, 1H), 9.11 (d, 1H), 7.81-7.70 (m, 5H), 7.63-7.51 (m, 2H), 7.51-7.47 (m, 10H), 7.24 (t, 8H), 7.08-7.00 (m, 12H), 0.66 (s, 6H)

Synthesis Example 11: Synthesis of Compound 109

Compound 109 (yield: 70%) was synthesized in substantially the same manner as in Synthesis Example 1, except that N-phenylnaphthalene-2-amine and N-phenyl-4-(trimethylsilyl)aniline were utilized instead of diphenylamine. Compound 109 synthesized therefrom was identified by LC-MS and $^1$H NMR.

$C_{63}H_{52}N_2Si_2$: M+1 893.29 $^1$H NMR (500 MHz, $CDCl_3$) δ=9.56 (s, 1H), 9.13 (d, 1H), 8.21-7.90 (m, 5H), 7.73-7.34 (m, 13H), 7.12-7.05 (m, 12H), 0.53 (s, 6H)

Synthesis Example 12: Synthesis of Compound 124

Compound 124 (yield: 88%) was synthesized in substantially the same manner as in Synthesis Example 1, except that 9,9-dimethyl-N-phenyl-9H-fluorene-2-amine and N-phenyl-[1,1'-biphenyl]-2-amine were utilized instead of diphenylamine. Compound 124 synthesized therefrom was identified by LC-MS and $^1$H NMR.

$C_{71}H_{54}N_2Si$: M+1 963.31 $^1$H NMR (500 MHz, $CDCl_3$) δ=9.19 (s, 1H), 9.00 (d, 1H), 7.98 (d, 1H), 7.75-7.70 (m, 2H), 7.63-7.51 (m, 2H), 7.51-7.47 (m, 10H), 7.24 (t, 8H), 7.08-7.00 (m, 12H), 0.66 (s, 6H)

Synthesis Example 13: Synthesis of Compound 158

Compound 158 (yield: 70%) was synthesized in substantially the same manner as in Synthesis Example 1, except that 9,9-dimethyl-N,N-diphenyl-9H-fluorene-2-amine was utilized instead of diphenylamine. Compound 158 synthesized therefrom was identified by LC-MS and $^1$H NMR.

$C_{65}H_{50}N_2Si$: M+1 887.21 $^1$H NMR (500 MHz, $CDCl_3$) δ=9.23 (s, 1H), 9.21 (d, 1H), 8.58 (t, 1H), 8.15-7.70 (m, 2H), 7.53-7.51 (m, 2H), 7.41-7.38 (m, 10H), 7.24 (t, 8H), 7.08-7.00 (m, 12H), 0.56 (s, 6H)

Synthesis Example 14: Synthesis of Compound 199

Compound 199 (yield: 56%) was synthesized in substantially the same manner as in Synthesis Example 1, except that N-(naphthalene-2-yl)dibenzo[b,d]furan-4-amine was utilized instead of diphenylamine. Compound 199 synthesized therefrom was identified by LC-MS and $^1$H NMR.

C66H44N2O2Si: M+1 925.18 $^1$H NMR (500 MHz, CDCl$_3$) δ=9.07 (s, 1H), 9.01 (d, 1H), 8.88 (t, 2H), 8.41-8.38 (m, 4H), 7.60-7.49 (m, 9H), 7.19-7.13 (m, 5H), 7.00-6.91 (m, 6H), 0.73 (s, 6H)

Synthesis Example 15: Synthesis of Compound 212

Compound 212 (yield: 71%) was synthesized in substantially the same manner as in Synthesis Example 1, except that N-([1,1'-biphenyl]-4-yl)dibenzo[b,d]furan-2-amine was utilized instead of diphenylamine. Compound 212 synthesized therefrom was identified by LC-MS and $^1$H NMR.

C70H48N2O2Si: M+1 997.25 $^1$H NMR (500 MHz, CDCl$_3$) δ=9.25 (s, 1H), 9.17 (d, 1H), 8.77 (d, 1H), 8.31-8.27 (m, 5H), 7.43-7.40 (d, 2H), 7.38-7.32 (m, 2H), 7.21-7.27 (m, 3H), 7.04 (t, 8H), 7.08-7.00 (m, 12H), 0.69 (s, 6H)

Synthesis Example 16: Synthesis of Compound 229

Compound 229 (yield: 56%) was synthesized in substantially the same manner as in Synthesis Example 1, except that N-(4'-fluoro-[1,1': 3',1''-terphenyl]-5'-yl)phenanthrene-3-amine was utilized instead of diphenylamine. Compound 229 synthesized therefrom was identified by LC-MS and $^1$H NMR.

C86H58F2N2Si: M+1 1185.51 $^1$H NMR (500 MHz, CDCl$_3$) δ=8.99 (s, 1H), 8.90 (d, 1H), 8.74 (d, 2H), 8.68-8.55 (m, 5H), 7.71-7.57 (m, 6H), 7.48-7.41 (m, 2H), 7.24-7.16 (m, 12H), 0.74 (s, 6H)

Synthesis Example 17: Synthesis of Compound 240

Compound 240 (yield: 69%) was synthesized in substantially the same manner as in Synthesis Example 1, except that 4-methyl-N-phenylaniline was utilized instead of diphenylamine. Compound 240 synthesized therefrom was identified by LC-MS and $^1$H NMR.

C48H40N2Si: M+1 672.95 $^1$H NMR (500 MHz, CDCl$_3$) δ=8.91 (s, 1H), 8.88 (d, 1H), 8.27 (d, 1H), 8.19-7.79 (m, 4H), 7.70-7.52 (m, 5H), 7.35 (m, 8H), 7.29 (d, 2H), 7.15-6.98 (m, 12H), 0.51 (s, 6H)

Example 1

An anode was prepared by cutting an ITO glass substrate (Corning), on which an ITO layer having a thickness of 15Ω/cm$^2$ (1,200 Å) was formed, to a size of 50 mm×50 mm×0.7 mm, ultrasonically cleaning the ITO glass substrate by utilizing isopropyl alcohol and pure water for 5 minutes each, and then irradiating UV light for 30 minutes thereto, and exposing the ITO glass substrate to ozone to clean the ITO glass substrate. Then, the anode was loaded into a vacuum deposition apparatus.

2-TNATA was deposited on the anode to form a hole injection layer having a thickness of 600 Å, and then, Compound 1 was deposited on the hole injection layer to form a hole transport layer having a thickness of 300 Å. ADN (as a host) and Compound FD1 (as a dopant) were co-deposited on the hole transport layer at a weight ratio of 98:2 to form an emission layer having a thickness of 300 Å. Alq$_3$ was deposited on the emission layer to form an electron transport layer having a thickness of 300 Å, and LiF was deposited on the electron transport layer to form an electron injection layer having a thickness of 10 Å. Then, Al was deposited on the electron injection layer to form a cathode having a thickness of 3,000 Å, thereby completing the manufacturing of an organic light-emitting device.

Examples 2 to 8 and Comparative Example 1

Organic light-emitting devices were each manufactured in substantially the same manner as in Example 1, except that compounds shown in Table 1 were utilized instead of Compound 1 in forming the hole transport layer.

Example 9

An anode was prepared by cutting an ITO glass substrate (Corning), on which an ITO layer having a thickness of 15Ω/cm$^2$ (1,200 Å) was formed, to a size of 50 mm×50 mm×0.7 mm, ultrasonically cleaning the ITO glass substrate by utilizing isopropyl alcohol and pure water for 5 minutes each, and then irradiating UV light for 30 minutes thereto, and exposing the ITO glass substrate to ozone to clean the ITO glass substrate. Then, the anode was loaded into a vacuum deposition apparatus.

2-TNATA was deposited on the anode to form a hole injection layer having a thickness of 600 Å, and then, NPB was deposited on the hole injection layer to form a hole transport layer having a thickness of 300 Å. ADN (as a host) and Compound 2 were co-deposited on the hole transport layer at a weight ratio of 98:2 to form an emission layer having a thickness of 300 Å.

Alq$_3$ was deposited on the emission layer to form an electron transport layer having a thickness of 300 Å, and LiF was deposited on the electron transport layer to form an electron injection layer having a thickness of 10 Å. Then, Al was deposited on the electron injection layer to form a cathode having a thickness of 3,000 Å, thereby completing the manufacture of an organic light-emitting device.

Examples 10 to 17 and Comparative Examples 2 to 4

Organic light-emitting devices were each manufactured in substantially the same manner as in Example 9, except that compounds shown in Table 2 were utilized instead of Compound 2 in forming the emission layer.

Evaluation Example 1

The driving voltage, current density, brightness, efficiency, and half-lifespan of each of the organic light-emitting devices of Examples 1 to 17 and Comparative Examples 1 to 4 were measured utilizing a Kethley SMU 236 meter and a PR650 brightness measurement meter. The results thereof are shown in Tables 1 and 2. Here, half-lifespan results are reported as the time at which the brightness was reduced to be 50% of the initial brightness thereof after driving the organic light-emitting device.

TABLE 1

| | Hole transport layer | Driving voltage (V) | Current density (mA/cm$^2$) | Brightness (cd/m$^2$) | Efficiency (cd/A) | Emission color | Half-lifespan (hours @100 mA/cm$^2$) |
|---|---|---|---|---|---|---|---|
| Example 1 | Compound 1 | 5.66 | 50 | 3356 | 6.53 | Blue | 320 |
| Example 2 | Compound 65 | 6.01 | 50 | 3278 | 6.66 | Blue | 316 |
| Example 3 | Compound 88 | 5.97 | 50 | 3215 | 6.78 | Blue | 296 |
| Example 4 | Compound 109 | 5.52 | 50 | 3369 | 6.15 | Blue | 350 |
| Example 5 | Compound 124 | 5.90 | 50 | 3493 | 6.27 | Blue | 317 |
| Example 6 | Compound 158 | 6.05 | 50 | 3015 | 6.39 | Blue | 309 |
| Example 7 | Compound 229 | 5.49 | 50 | 3591 | 6.45 | Blue | 340 |
| Example 8 | Compound 240 | 5.81 | 50 | 3178 | 6.71 | Blue | 349 |
| Comparative Example 1 | NPB | 6.99 | 50 | 2745 | 5.27 | Blue | 266 |

TABLE 2

| | Emission layer | Driving voltage (V) | Current density (mA/cm$^2$) | Brightness (cd/m$^2$) | Efficiency (cd/A) | Emission color | Half-lifespan (hours @100 mA/cm$^2$) |
|---|---|---|---|---|---|---|---|
| Example 9 | Compound 2 | 5.98 | 50 | 3672 | 7.26 | Blue | 366 |
| Example 10 | Compound 4 | 5.59 | 50 | 3357 | 7.15 | Blue | 371 |
| Example 11 | Compound 15 | 5.29 | 50 | 3715 | 7.06 | Blue | 350 |
| Example 12 | Compound 24 | 5.99 | 50 | 3296 | 7.11 | Blue | 355 |
| Example 13 | Compound 66 | 5.74 | 50 | 3487 | 7.26 | Blue | 314 |
| Example 14 | Compound 72 | 5.63 | 50 | 3614 | 7.32 | Blue | 309 |
| Example 15 | Compound 106 | 5.51 | 50 | 3295 | 6.97 | Blue | 312 |
| Example 16 | Compound 199 | 5.72 | 50 | 3045 | 7.10 | Blue | 374 |
| Example 17 | Compound 212 | 5.36 | 50 | 3109 | 7.05 | Blue | 336 |
| Comparative Example 1 | Compound FD1 | 6.99 | 50 | 2745 | 6.92 | Blue | 266 |
| Comparative Example 2 | Compound A | 6.65 | 50 | 2560 | 7.15 | Blue | 250 |
| Comparative Example 3 | Compound B | 6.47 | 50 | 2998 | 6.11 | Blue | 251 |
| Comparative Example 4 | Compound C | 5.98 | 50 | 2799 | 7.21 | Blue | 290 |

377
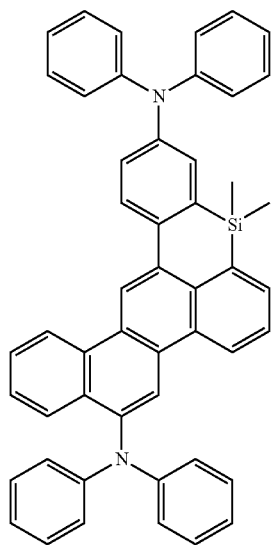
1
378
-continued
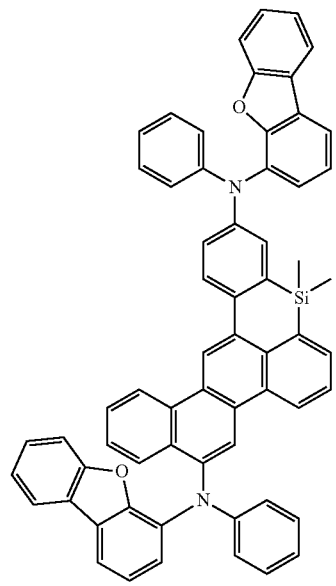
4
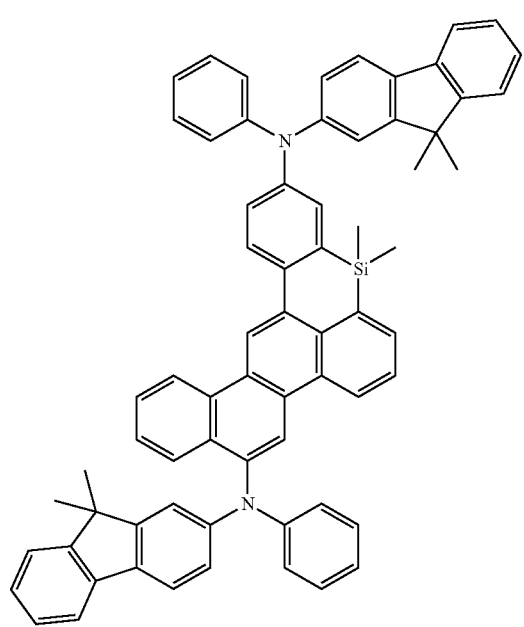
2
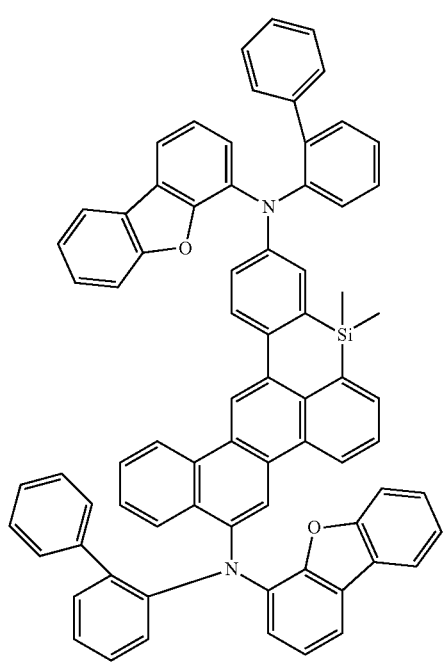
15

379
-continued
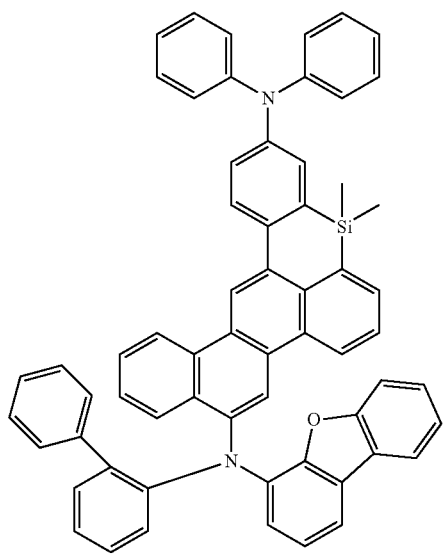
24
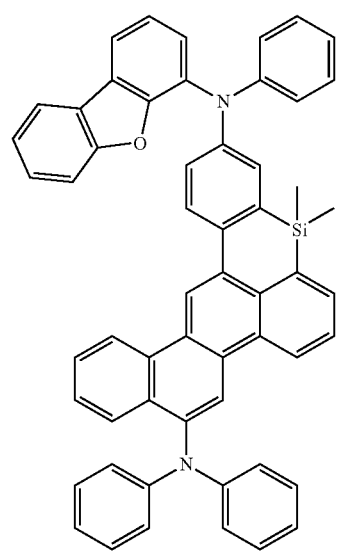
65
380
-continued
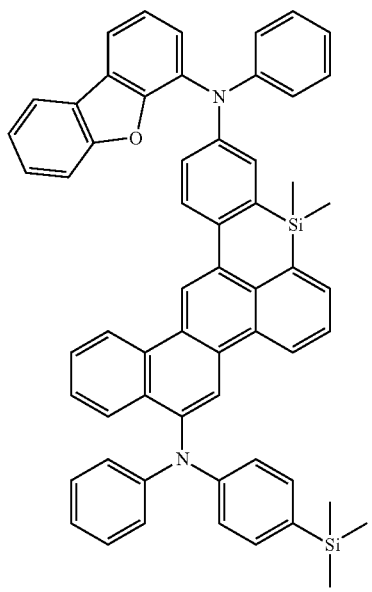
66
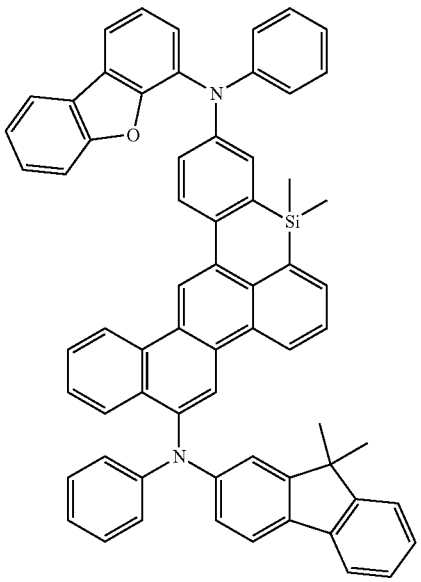
72

-continued
88
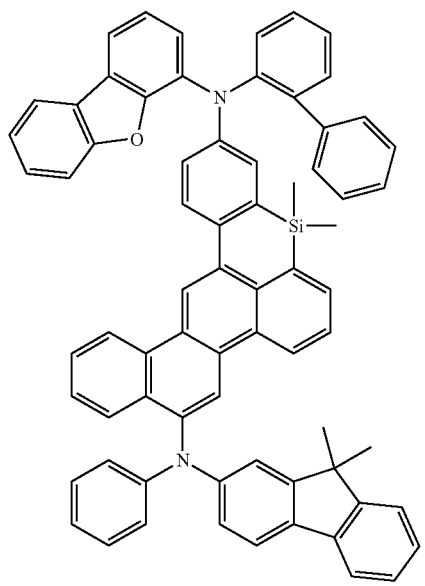
106
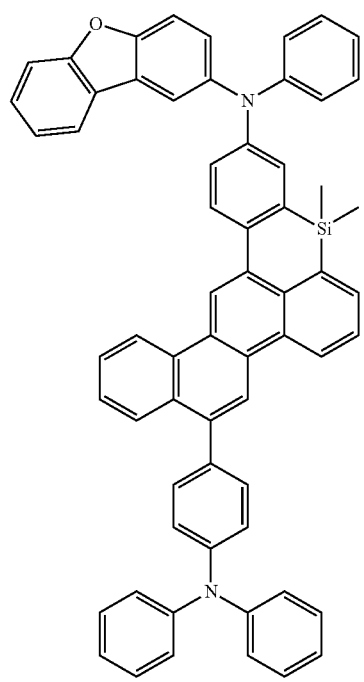
-continued
109
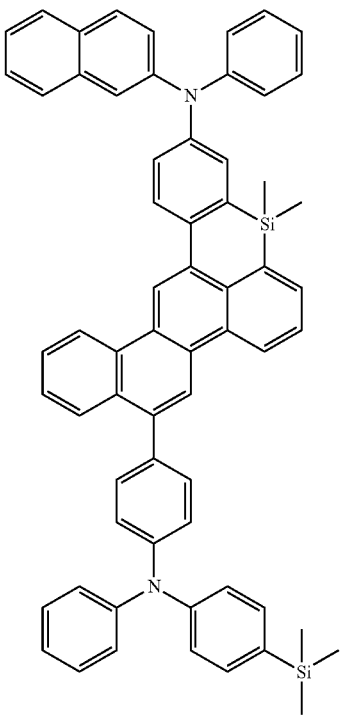
124
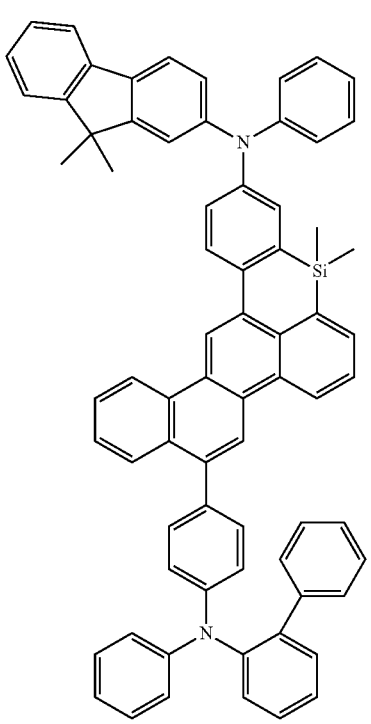

-continued
158
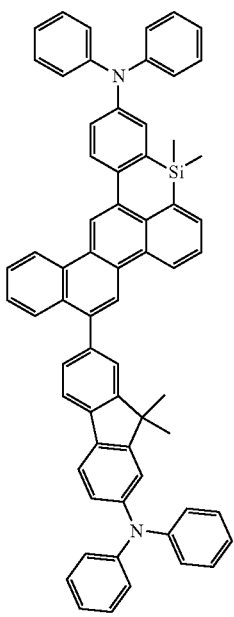
-continued
212
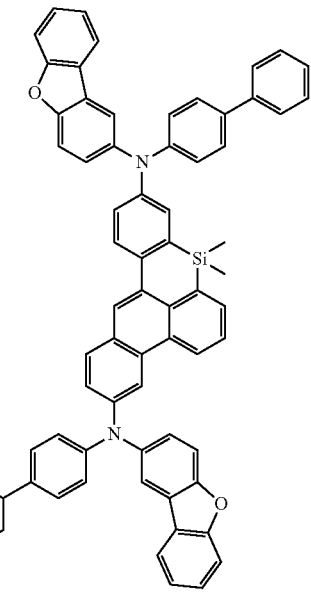
199
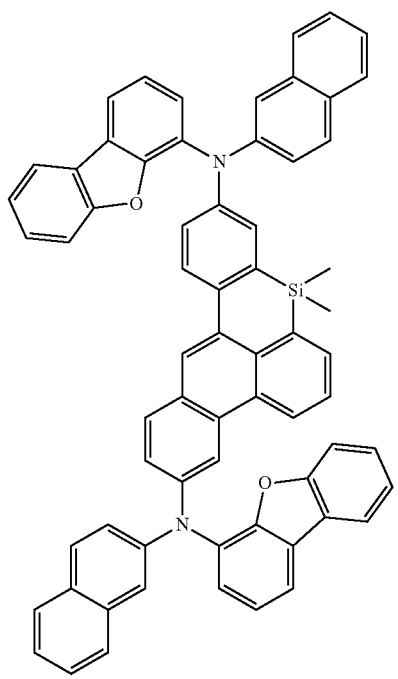
229
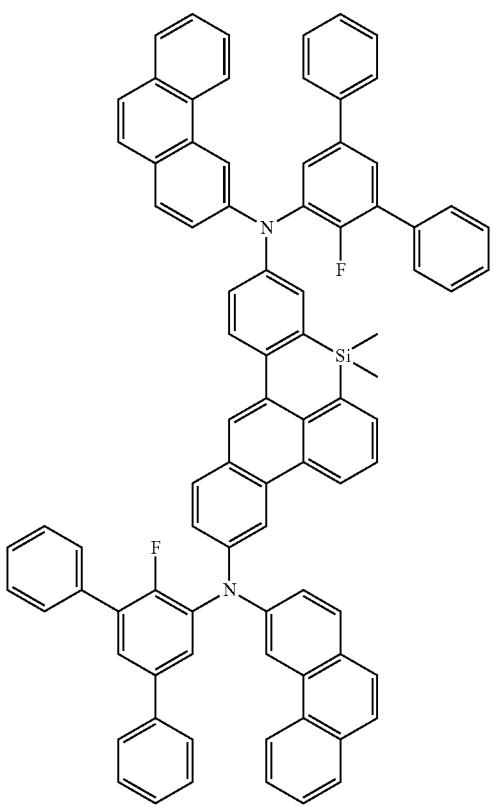

-continued

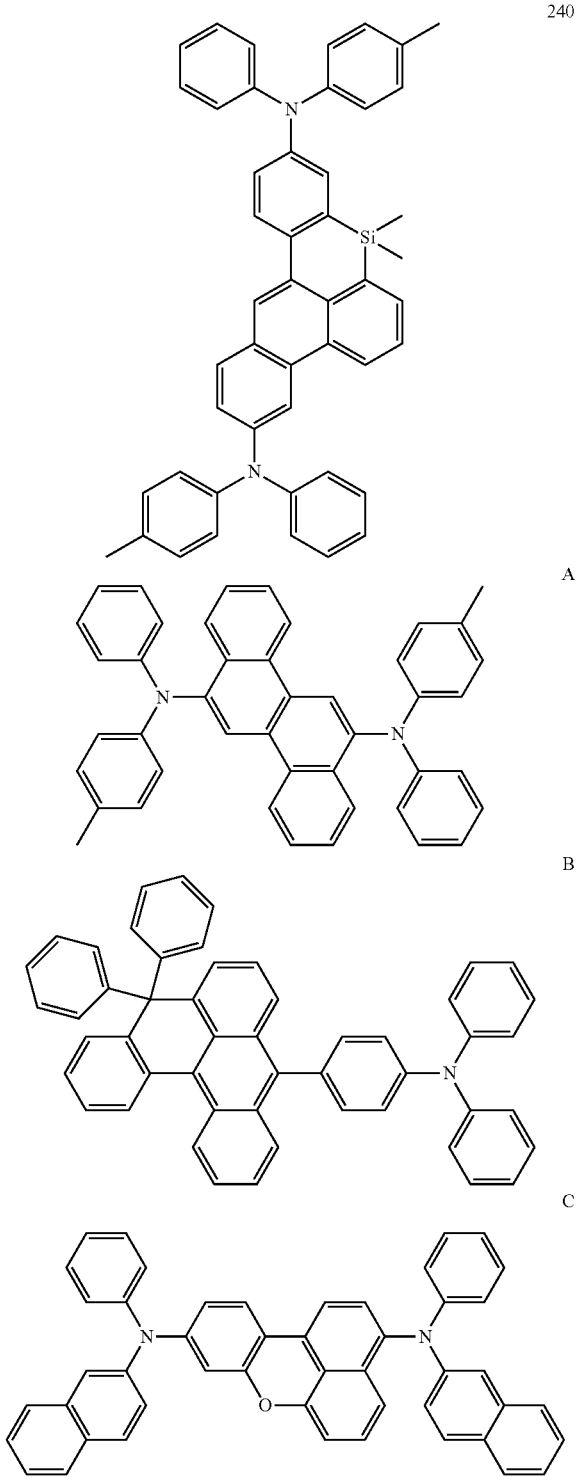

Referring to Tables 1 and 2, it was confirmed that each of the organic light-emitting devices of Examples 1 to 17 had improved characteristics, compared to the organic light-emitting devices of Comparative Examples 1 to 4.

An organic light-emitting device including an amine-based compound according to an embodiment of the present disclosure may have low driving voltage, high efficiency, high brightness, and/or long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An amine-based compound represented by Formula 1:

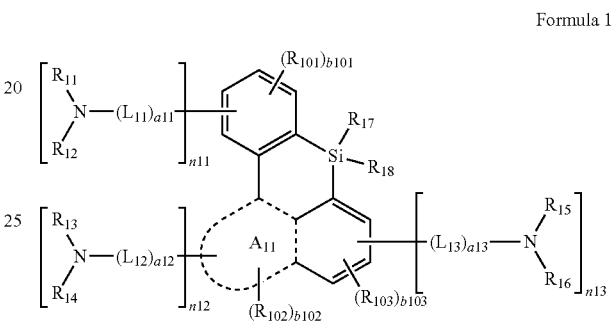

Formula 1 wherein, in Formula 1,
$A_{11}$ is selected from a $C_6$-$C_{20}$ carbocyclic group and a $C_1$-$C_{20}$ heterocyclic group,
$L_{11}$ to $L_{13}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a11 to a13 are each independently selected from 0, 1, 2, 3, 4, and 5,
$R_{11}$ to $R_{16}$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group,
n11 to n13 are each independently selected from 0, 1, and 2, wherein a sum of n11 to n13 is selected from 1, 2, 3, 4, 5, and 6,
$R_{17}$, $R_{18}$, and $R_{101}$ to $R_{103}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b101 and b103 are each independently selected from 1, 2, 3, and 4, b102 is selected from 1, 2, 3, 4, 5, 6, 7, and 8, and $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The amine-based compound of claim 1, wherein $A_{11}$ is selected from a benzene group, a naphthalene group, a fluorene group, a phenanthrene group, an anthracene group, a triphenylene group, a pyrene group, a chrysene group, a furan group, a thiophene group, a pyridine group, a pyrazine group, a pyrimidine group, a pyridazine group, a quinoline group, an isoquinoline group, a quinoxaline group, a quinazoline group, a benzofuran group, a benzothiophene group, a dibenzofuran group, and a dibenzothiophene group.

3. The amine-based compound of claim 1, wherein $A_{11}$ is selected from a benzene group, a naphthalene group, a phenanthrene group, an anthracene group, a triphenylene group, a pyrene group, and a chrysene group.

4. The amine-based compound of claim 1, wherein $L_{11}$ to $L_{13}$ are each independently selected from the group consisting of:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group.

5. The amine-based compound of claim 1, wherein $L_{11}$ to $L_{13}$ may each independently be a group selected from groups represented by Formulae 3-1 to 3-43:

3-1
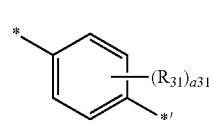

3-2
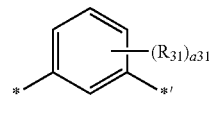

3-3
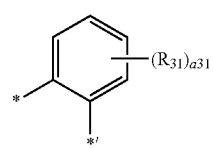

3-4
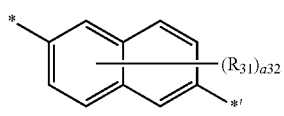

3-5
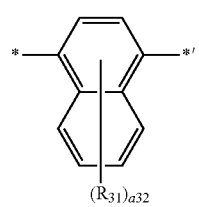

3-6
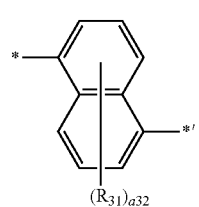

3-7
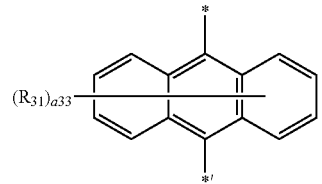

3-8
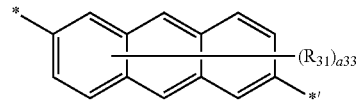

3-9
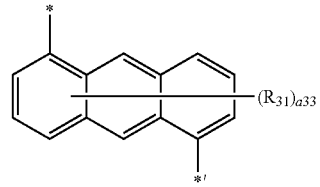

3-10
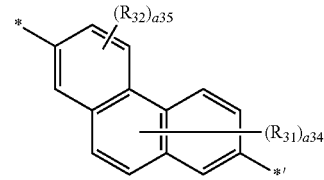

3-11
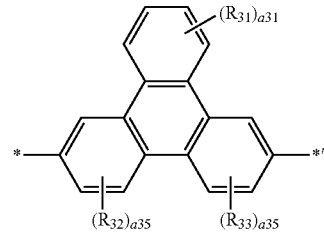

3-12
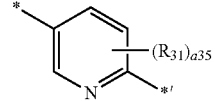

3-13
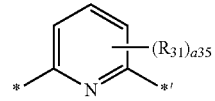

3-14
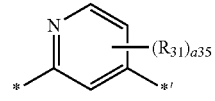

3-15
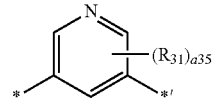

3-16
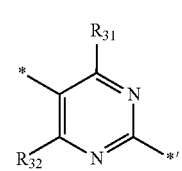

| | |
|---|---|
| 3-17 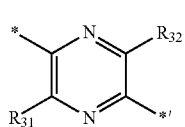 | 3-26 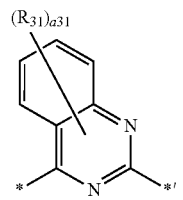 |
| 3-18 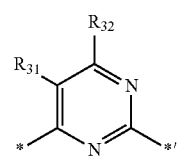 | 3-27 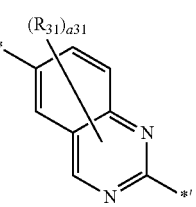 |
| 3-19 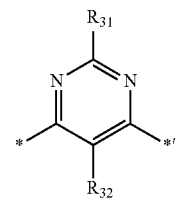 | 3-28 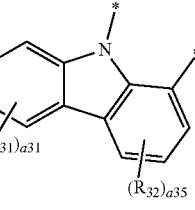 |
| 3-20 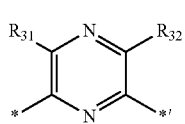 | 3-29 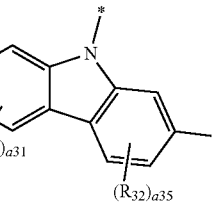 |
| 3-21 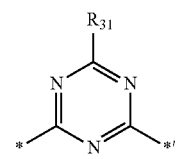 | 3-30 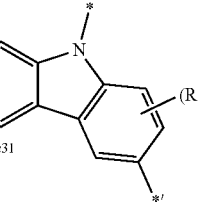 |
| 3-22 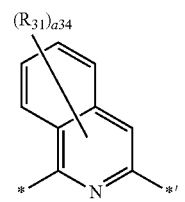 | 3-31 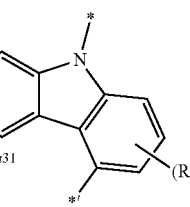 |
| 3-23 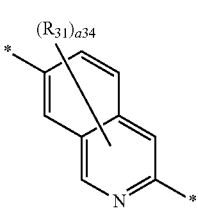 | 3-32 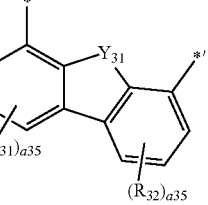 |
| 3-24 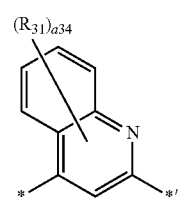 | |
| 3-25 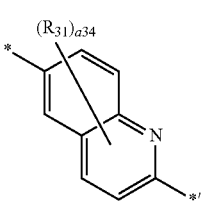 | |

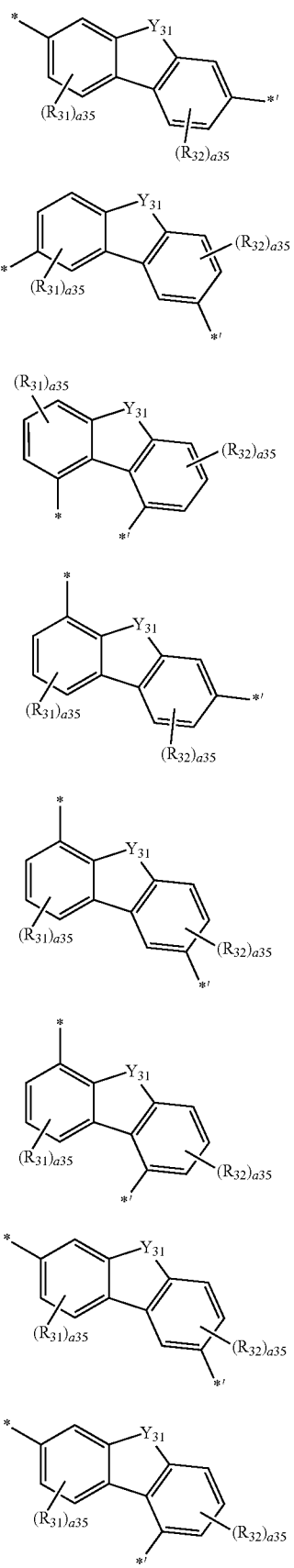
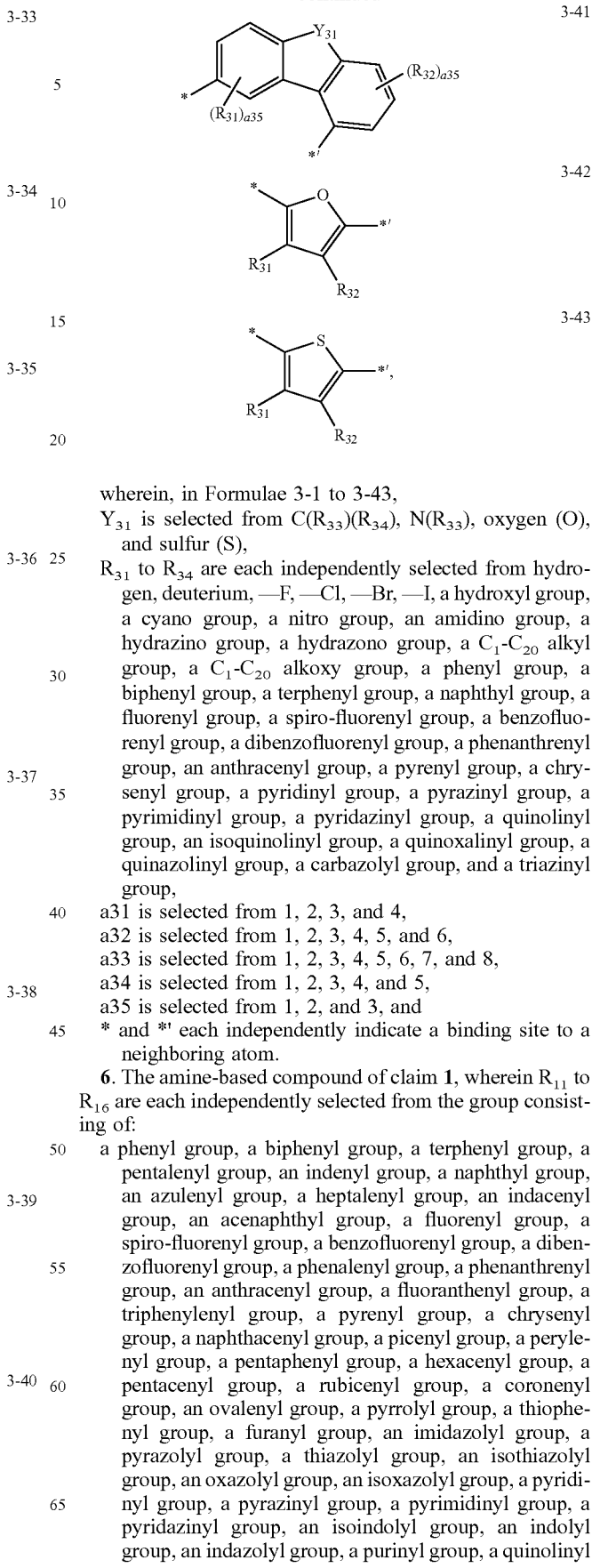

wherein, in Formulae 3-1 to 3-43, $Y_{31}$ is selected from $C(R_{33})(R_{34})$, $N(R_{33})$, oxygen (O), and sulfur (S), $R_{31}$ to $R_{34}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a31 is selected from 1, 2, 3, and 4,
a32 is selected from 1, 2, 3, 4, 5, and 6,
a33 is selected from 1, 2, 3, 4, 5, 6, 7, and 8,
a34 is selected from 1, 2, 3, 4, and 5,
a35 is selected from 1, 2, and 3, and
* and *' each independently indicate a binding site to a neighboring atom.

6. The amine-based compound of claim 1, wherein $R_{11}$ to $R_{16}$ are each independently selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), and —B($Q_{31}$)($Q_{32}$); and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, and an imidazopyrimidinyl group, each substituted with a $C_1$-$C_{20}$ alkyl group that is substituted with at least one selected from deuterium, —F, —Cl, —Br, —I, a cyano group, and a nitro group, and $Q_{31}$ to $Q_{33}$ are each independently selected from a $C_1$-$C_{60}$ alkyl group, a $C_6$-$C_{60}$ aryl group, a biphenyl group, and a terphenyl group.

7. The amine-based compound of claim 1, wherein $R_{11}$ to $R_{16}$ are each independently selected from the group consisting of:

a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, and a dibenzosilolyl group; and a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, —$CD_3$, —$CF_3$, a $C_1$-$C_{20}$ alkoxy group, a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, a dibenzosilolyl group, and —Si($Q_{31}$)($Q_{32}$)($Q_{33}$), wherein $Q_{31}$ to $Q_{33}$ are each independently selected from a methyl group, an ethyl group, a tert-butyl group, a phenyl group, a biphenyl group, a terphenyl group, and a naphthyl group.

8. The amine-based compound of claim 1, wherein $R_{11}$ to $R_{16}$ are each independently a group selected from groups represented by Formulae 5-1 to 5-32:

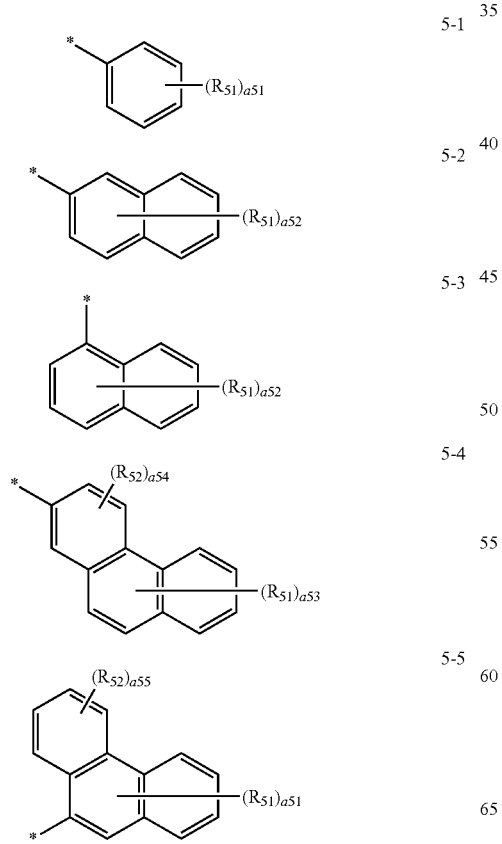

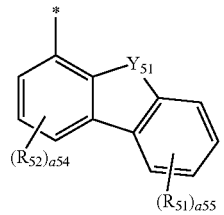

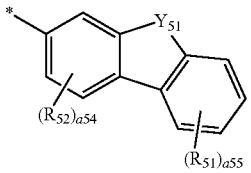

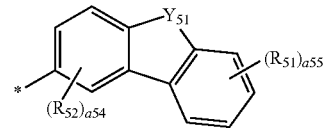

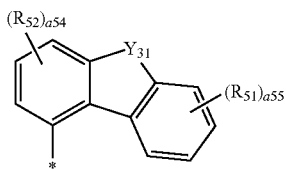

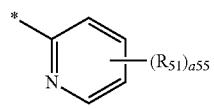

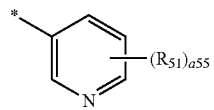

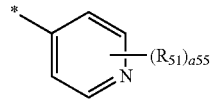

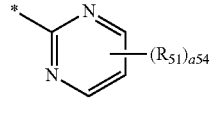

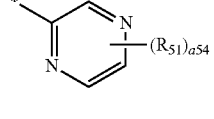

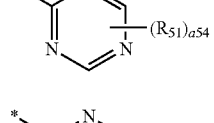

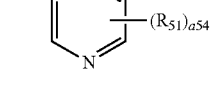

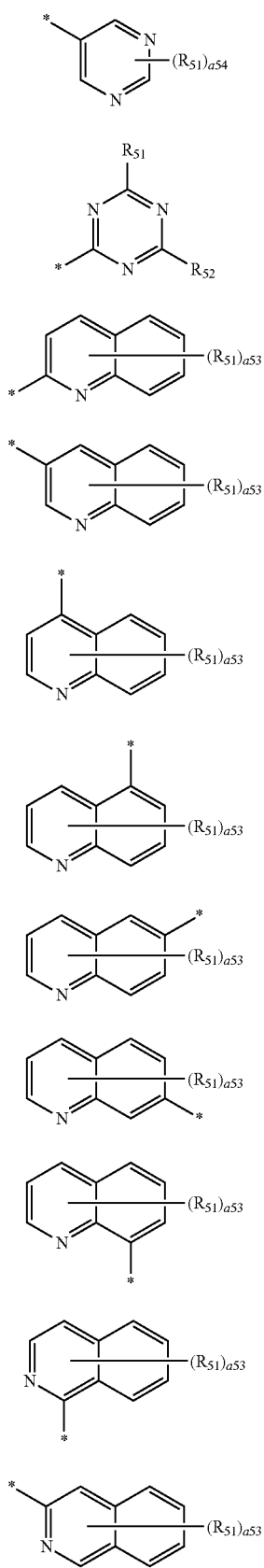
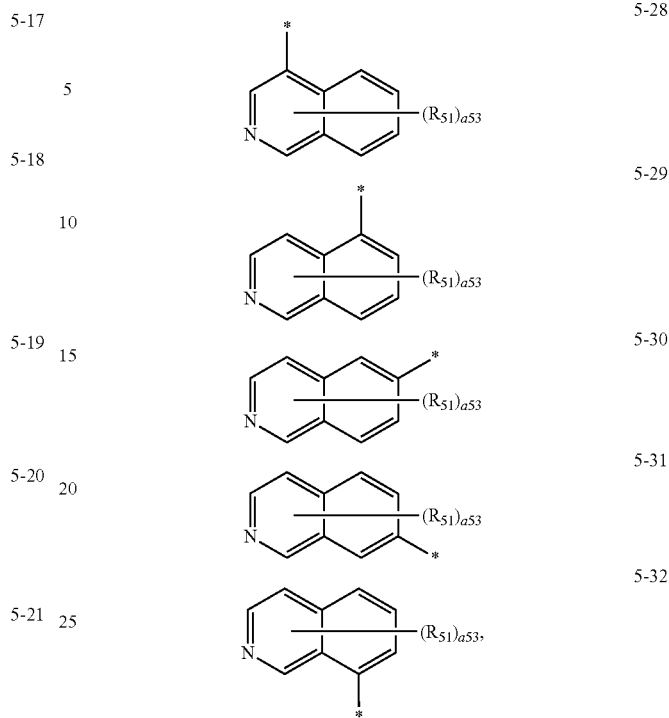

wherein, in Formulae 5-1 to 5-32, $Y_{51}$ is selected from $C(R_{53})(R_{54})$, $Si(R_{53})(R_{54})$, $N(R_{53})$, O, and S, $R_{51}$ to $R_{54}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, —$CD_3$, —$CF_3$, a $C_1$-$C_{20}$ alkoxy group, a phenyl group, a biphenyl group, a terphenyl group, a naphthyl group, a fluorenyl group, a phenanthrenyl group, a pyridinyl group, a pyrazinyl group, a pyrimidinyl group, a quinolinyl group, an isoquinolinyl group, a naphthyridinyl group, a quinoxalinyl group, a quinazolinyl group, a cinnolinyl group, a triazinyl group, a dibenzofuranyl group, a dibenzothiophenyl group, a dibenzosilolyl group, and —$Si(Q_{31})(Q_{32})(Q_{33})$, wherein $Q_{31}$ to $Q_{33}$ are each independently selected from a methyl group, an ethyl group, a tert-butyl group, a phenyl group, a biphenyl group, a terphenyl group, and a naphthyl group, a51 is selected from 1, 2, 3, 4, and 5,
a52 is selected from 1, 2, 3, 4, 5, 6, and 7,
a53 is selected from 1, 2, 3, 4, 5, and 6,
a54 is selected from 1, 2, and 3,
a55 is selected from 1, 2, 3, and 4, and
\* indicates a binding site to a neighboring atom.

9. The amine-based compound of claim 1, wherein n11 to n13 are each independently selected from 0 and 1.

10. The amine-based compound of claim 1, wherein the sum of n11 to n13 is selected from 1, 2, 3, and 4.

11. The amine-based compound of claim 1, wherein $R_{17}$, $R_{18}$, and $R_{101}$ to $R_{103}$ are each independently selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_1$-$C_{60}$ alkoxy group, a cyclopentyl group, and a cyclohexyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, and a triazinyl group, each substituted with a $C_1$-$C_{60}$ alkyl group; and —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $Q_1$ to $Q_3$ are each independently selected from a $C_1$-$C_{20}$ alkyl group, a phenyl group, a biphenyl group, a terphenyl group, and a naphthyl group.

12. The amine-based compound of claim 1, wherein $R_{17}$ and $R_{18}$ are each independently selected from a methyl group, an ethyl group, an n-propyl group, an iso-propyl group, an n-butyl group, a sec-butyl group, an iso-butyl group, a tert-butyl group, a cyclopentyl group, a cyclohexyl group, a phenyl group, a biphenyl group, a terphenyl group, and a naphthyl group.

13. The amine-based compound of claim 1, wherein $R_{101}$ to $R_{103}$ are each independently selected from hydrogen, deuterium, —F, a hydroxyl group, a cyano group, a methyl group, an ethyl group, an n-propyl group, an iso-propyl group, an n-butyl group, a sec-butyl group, an iso-butyl group, a tert-butyl group, a cyclopentyl group, a cyclohexyl group, a phenyl group, a biphenyl group, a terphenyl group, a naphthyl group, a fluorenyl group, a phenyl group substituted with a methyl group, a fluorenyl group substituted with a methyl group, a pyridinyl group, a pyrazinyl group, a pyrimidinyl group, a quinolinyl group, an isoquinolinyl group, a carbazolyl group, a triazinyl group, —Si(CH$_3$)$_3$, and —Si(Ph)$_3$.

14. The amine-based compound of claim 1, wherein the amine-based compound is represented by one selected from Formulae 1-1 to 1-3:

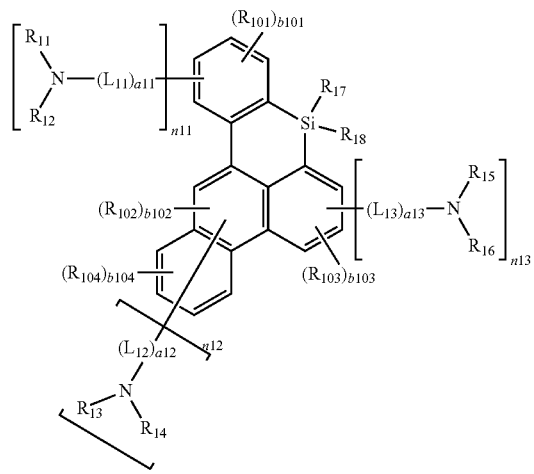

Formula 1-2

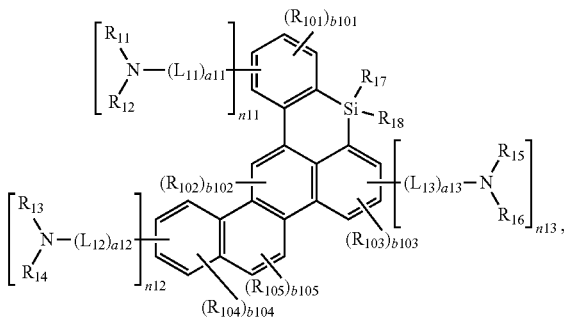

Formula 1-3 wherein, in Formulae 1-1 to 1-3

$L_{11}$ to $L_{13}$, a11 to a13, $R_{11}$ to $R_{18}$, n11 to n13, $R_{101}$ to $R_{103}$, and b101 to b103 are each independently the same as respectively described herein in connection with Formula 1, $R_{104}$ and $R_{105}$ are each independently the same as described herein in connection with $R_{101}$ in Formula 1, and b104 and b105 are each independently the same as described herein in connection with b101 in Formula 1.

15. The amine-based compound of claim 1, wherein the amine-based compound is represented by one selected from Formulae 1-11 to 1-19:

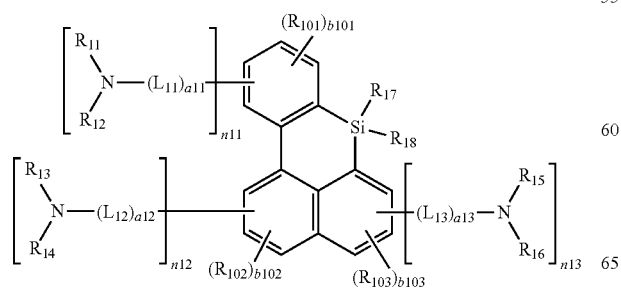

Formula 1-1

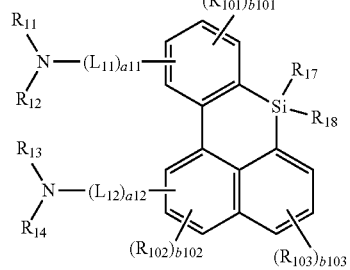

Formula 1-11

-continued
Formula 1-12
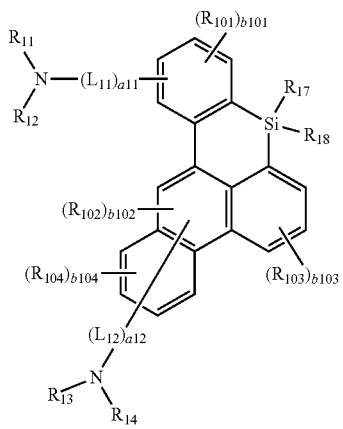
Formula 1-13
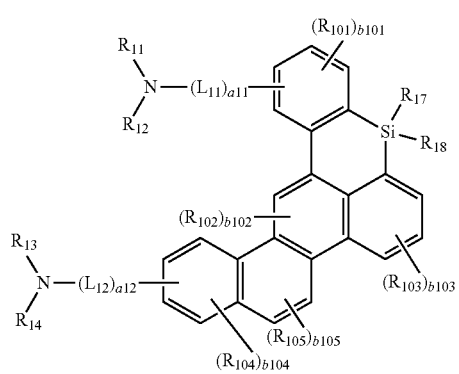
Formula 1-14
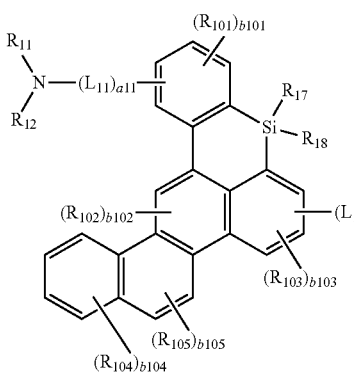
Formula 1-15
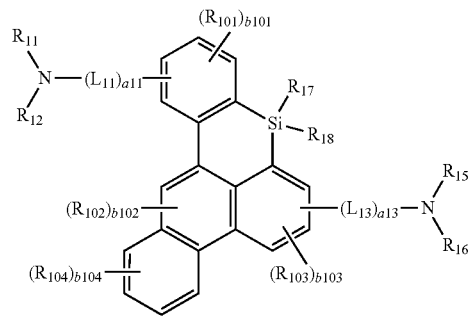
Formula 1-16
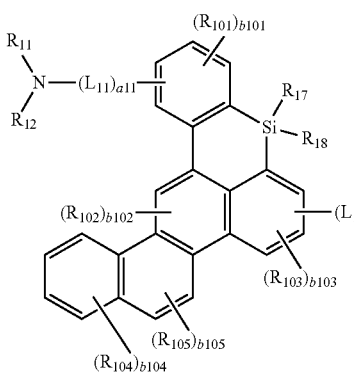
Formula 1-17
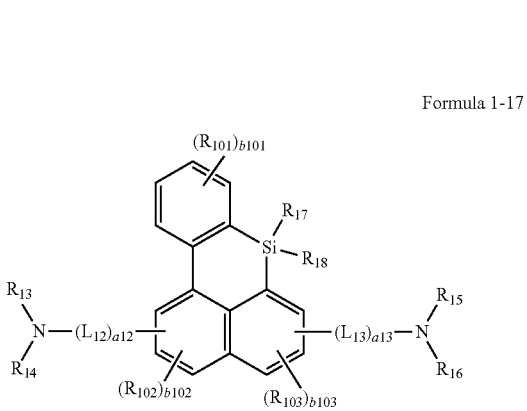
Formula 1-18
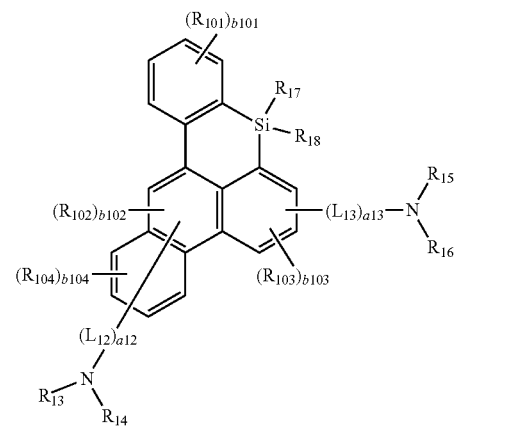

405
-continued

Formula 1-19

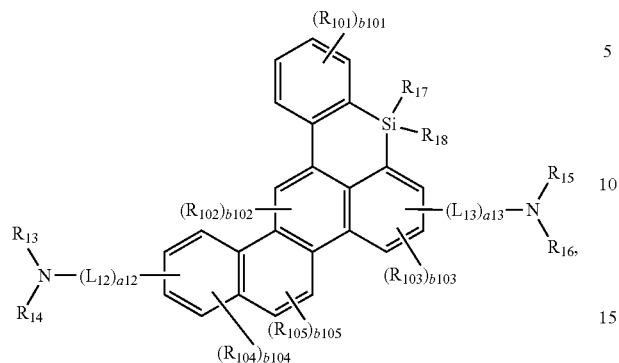

wherein, in Formulae 1-11 to 1-19, $L_{11}$ to $L_{13}$, a11 to a13, $R_{11}$ to $R_{16}$, $R_{17}$, $R_{18}$, $R_{101}$ to $R_{103}$, and b101 to b103 are each independently the same as respectively described herein in connection with Formula 1, $R_{104}$ and $R_{105}$ are each independently the same as described herein in connection with $R_{101}$ in Formula 1, and b104 and b105 are each independently the same as described herein in connection with b101 in Formula 1.

16. The amine-based compound of claim 1, wherein the amine-based compound is represented by one selected from Formulae 1-21 to 1-23:

1-21

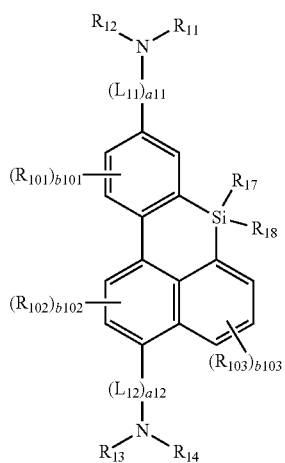

406
-continued 1-22

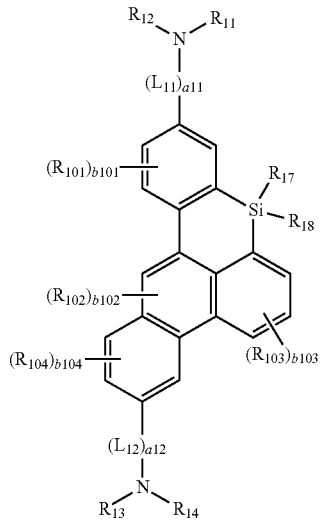

1-23

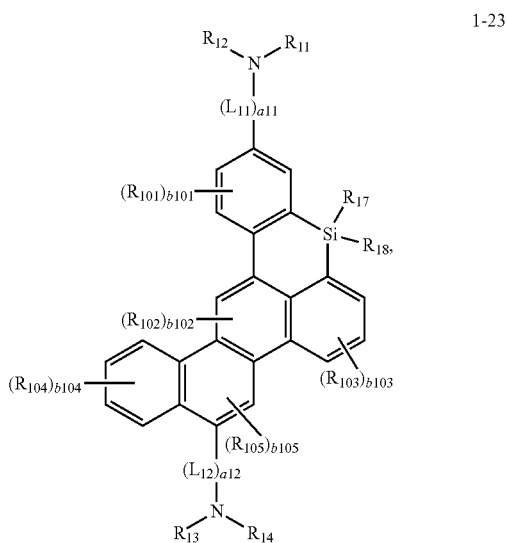

wherein, in Formulae 1-21 to 1-23, $L_{11}$, $L_{12}$, a11, a12, $R_{11}$ to $R_{14}$, $R_{17}$, $R_{18}$, $R_{101}$ to $R_{103}$, and b101 to b103 are each independently the same as respectively described herein in connection with Formula 1, $R_{104}$ and $R_{105}$ are each independently the same as described herein in connection with $R_{101}$ in Formula 1, and b104 and b105 are each independently the same as described herein in connection with b101 in Formula 1.

17. The amine-based compound of claim 1, wherein amine-based compound comprises at least one selected from Compounds 1 to 437:

407
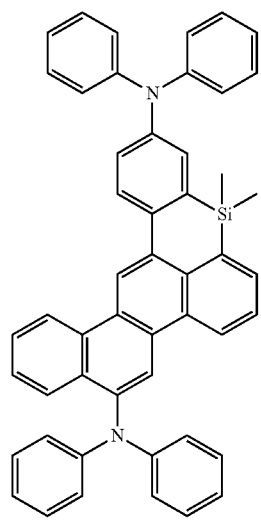
408
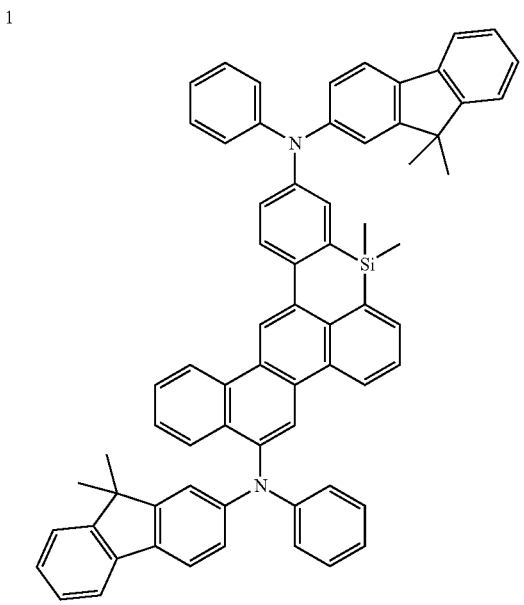
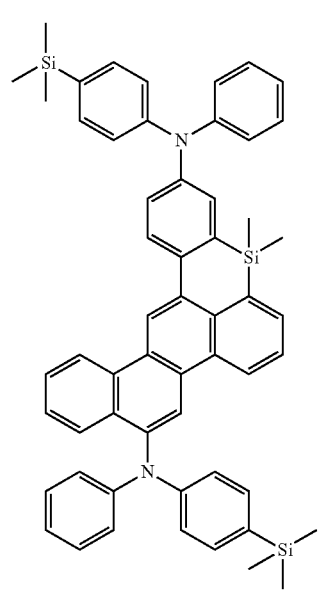
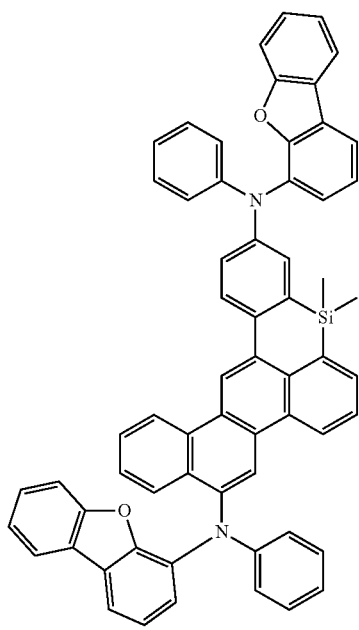

-continued
409
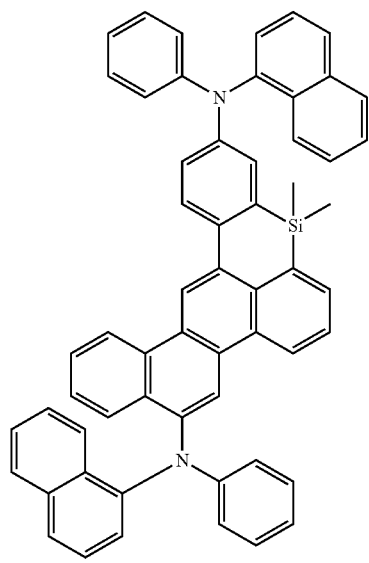
410
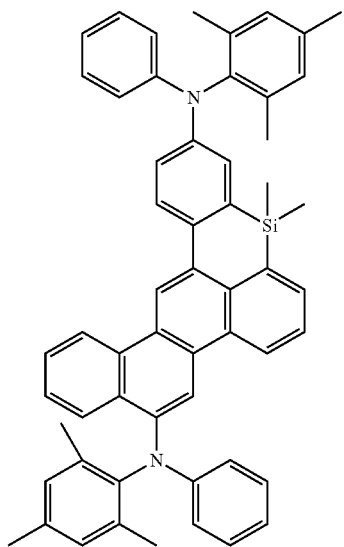
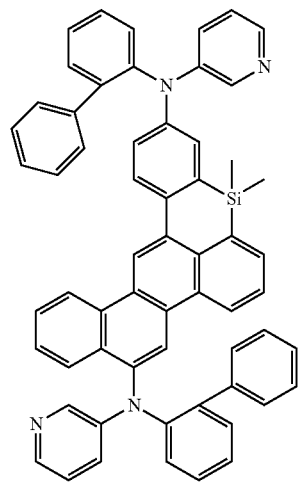
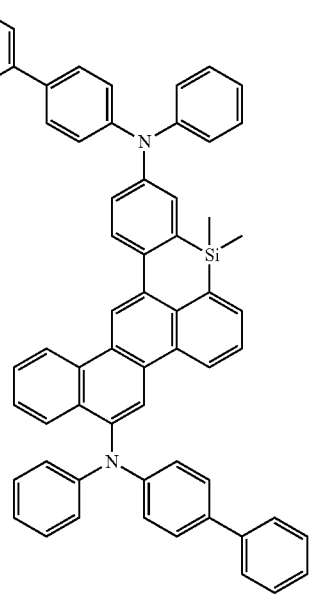

-continued
411
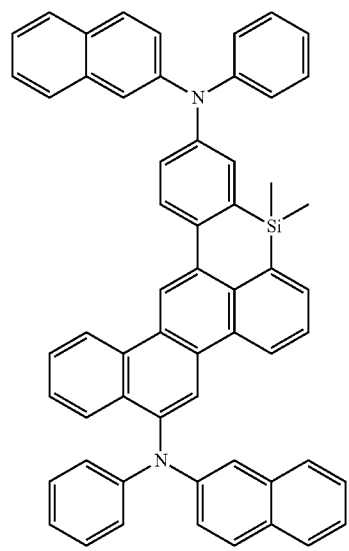
412
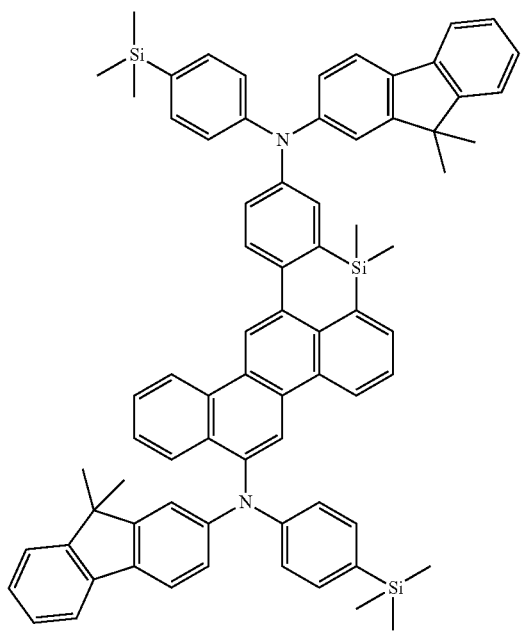
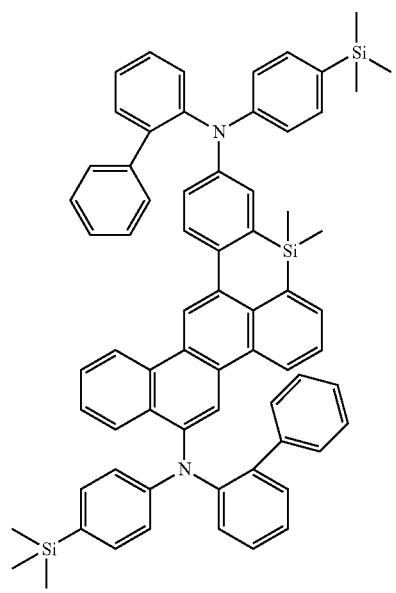
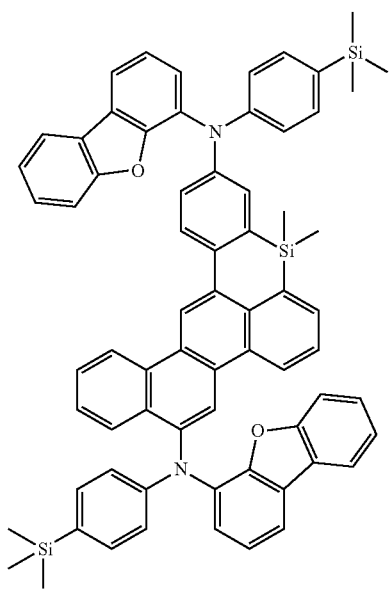

-continued
13
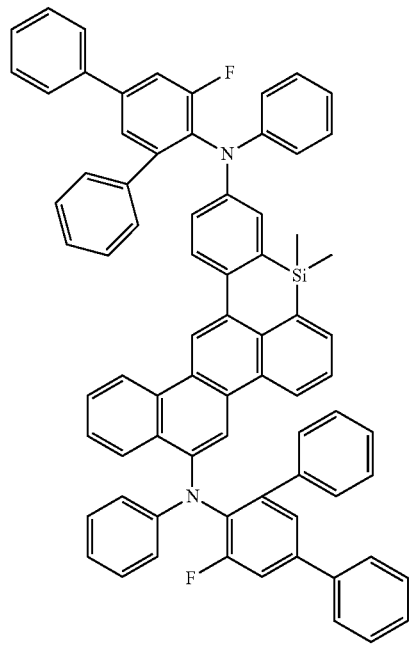
14
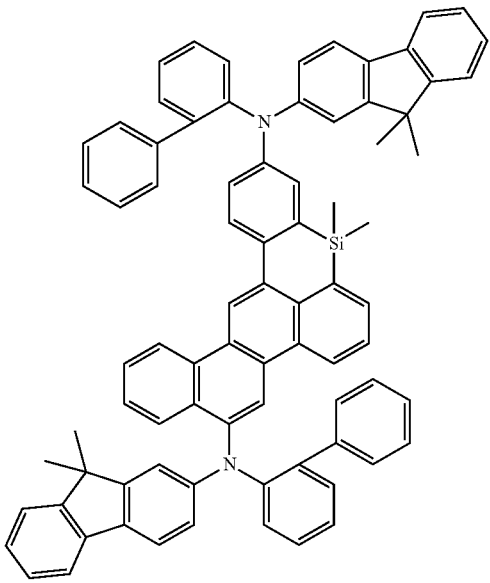
15
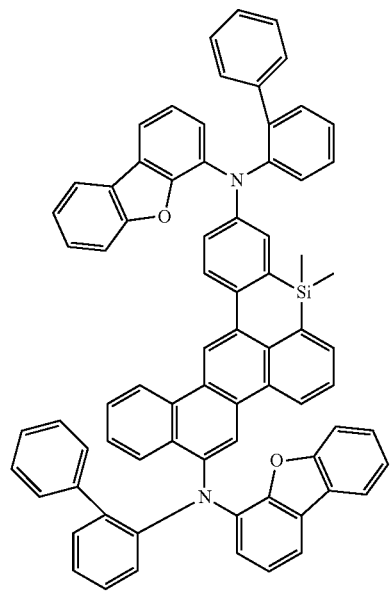
16
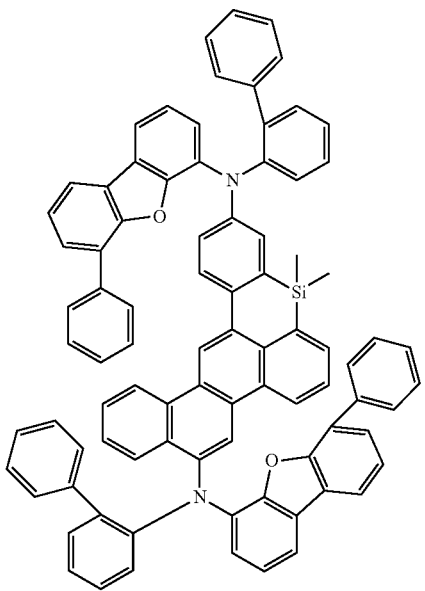

415
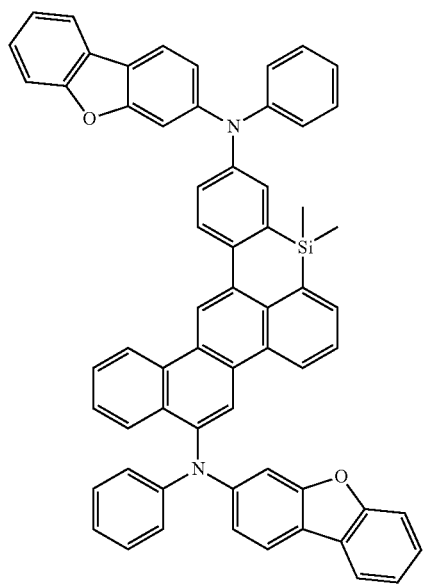
-continued
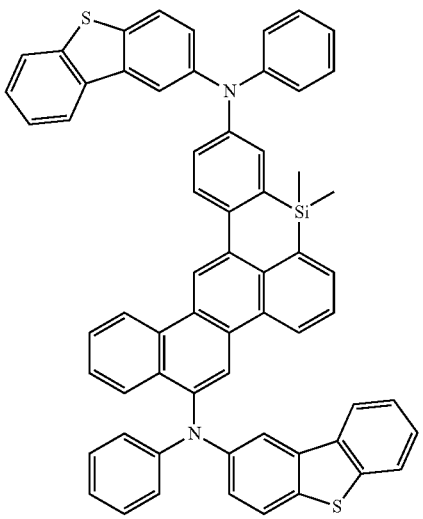
416
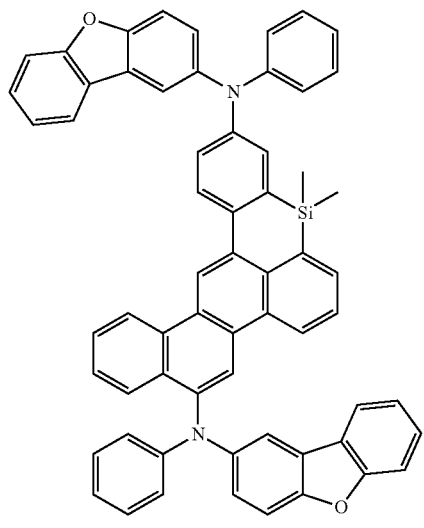
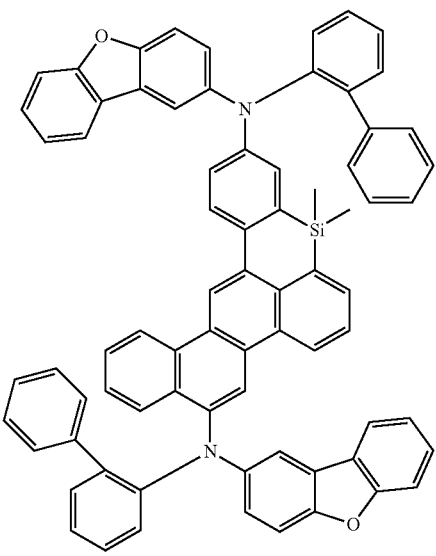

21
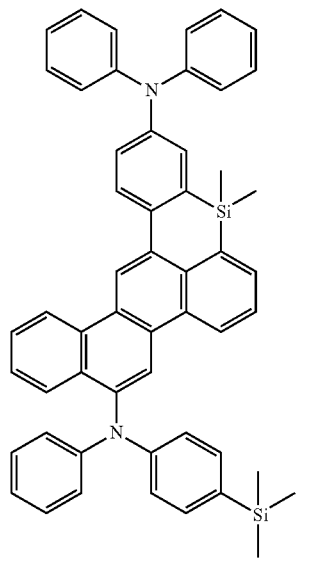
22
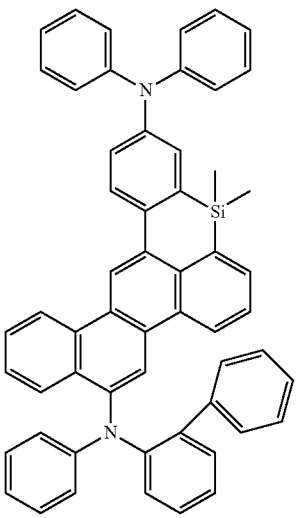
23
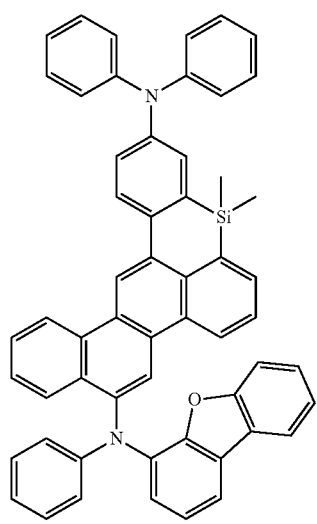
24
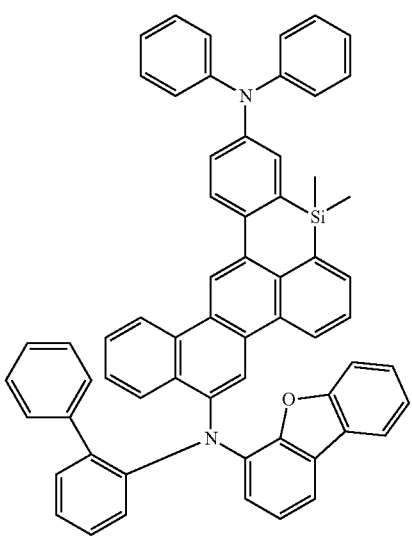
25
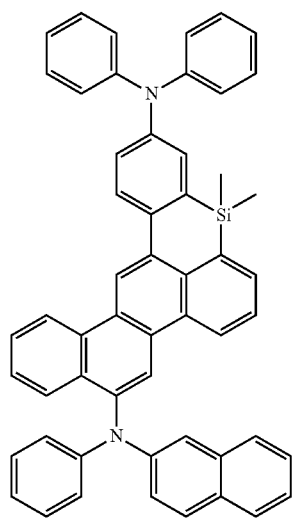
26
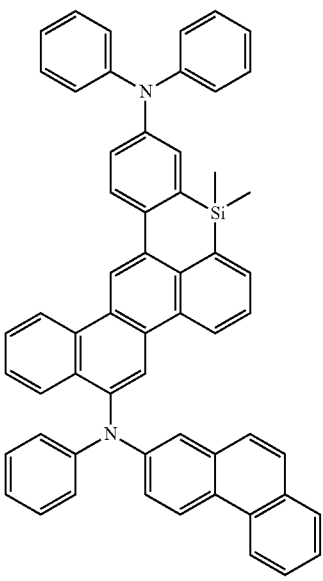

-continued
27
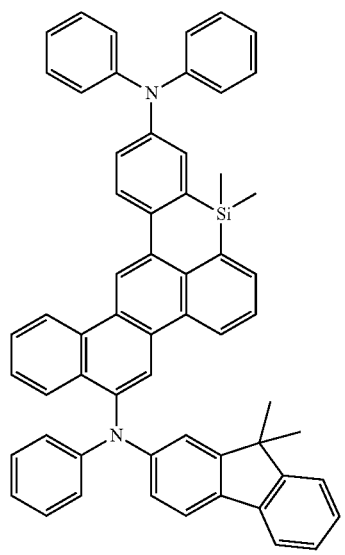
28
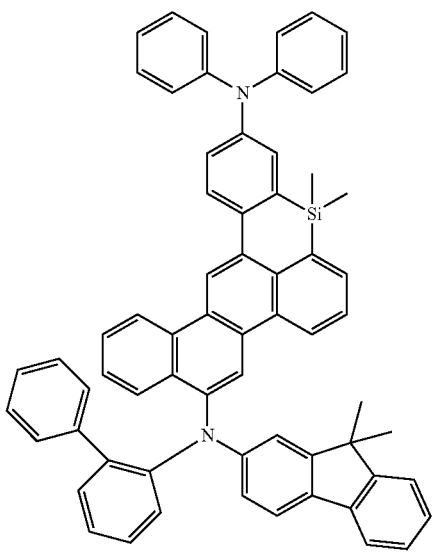
29
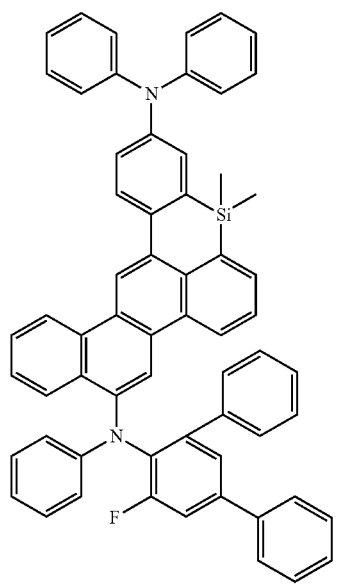
30
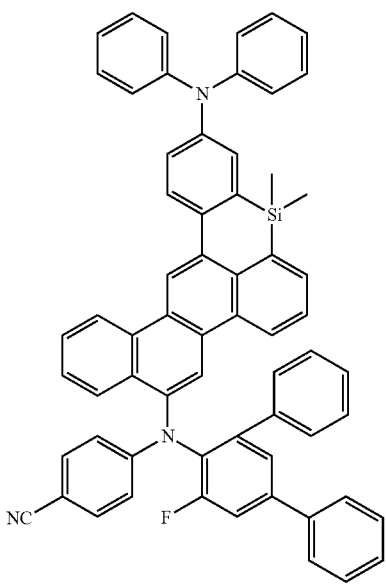

-continued
421
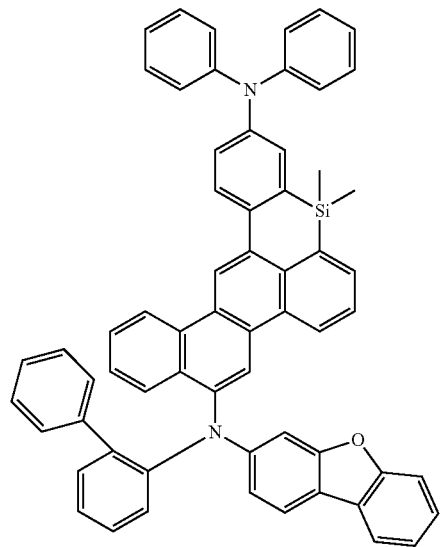
422
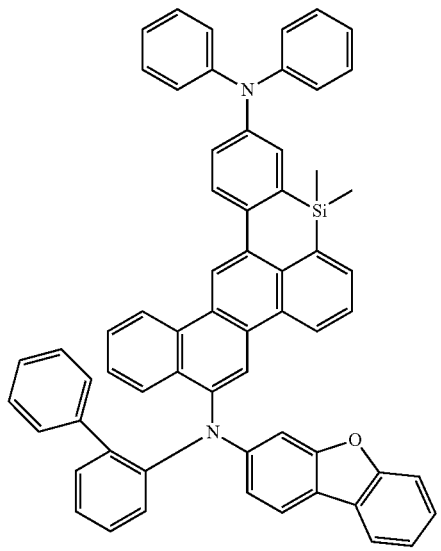
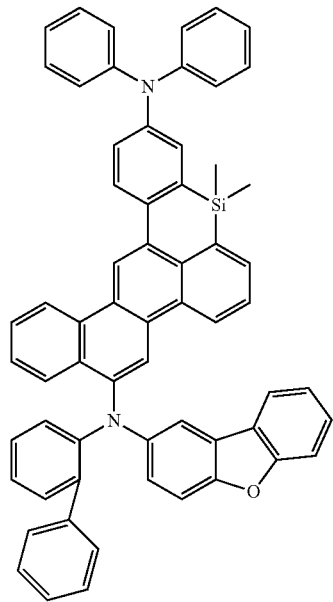
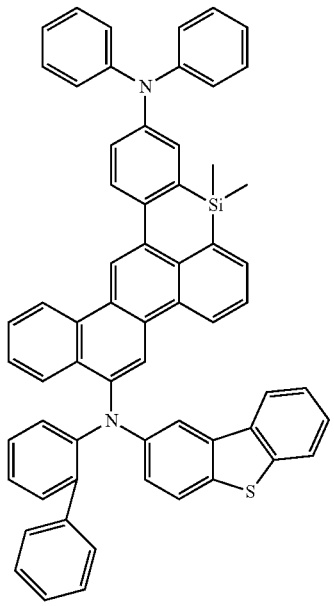

-continued
35
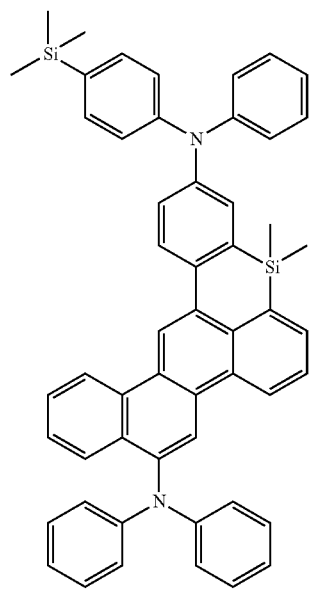
36
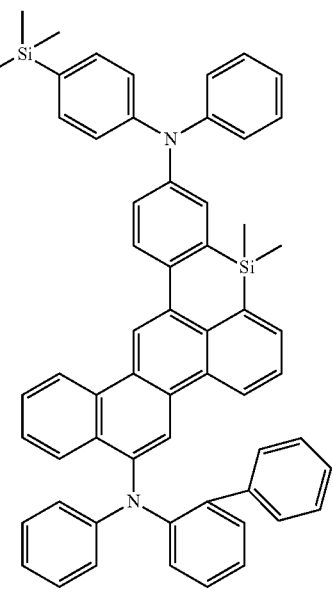
37
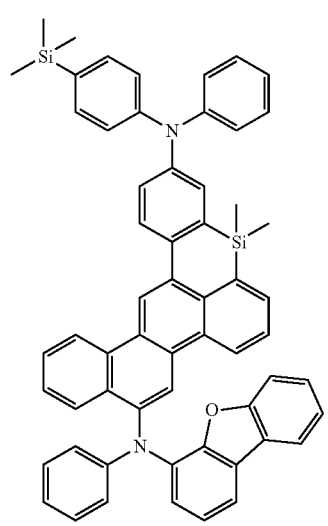
38
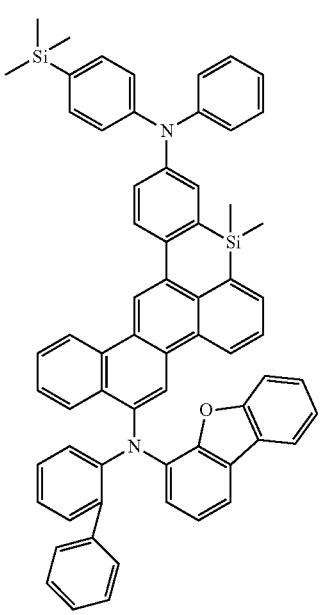

-continued
39
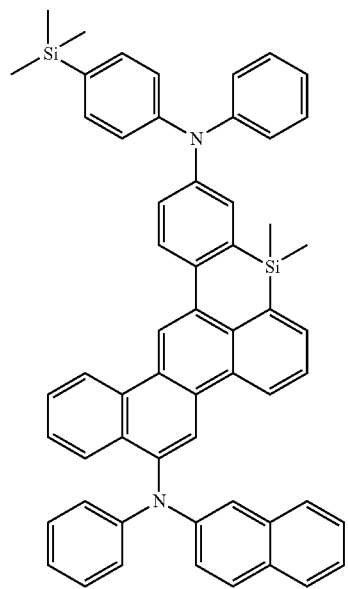
40
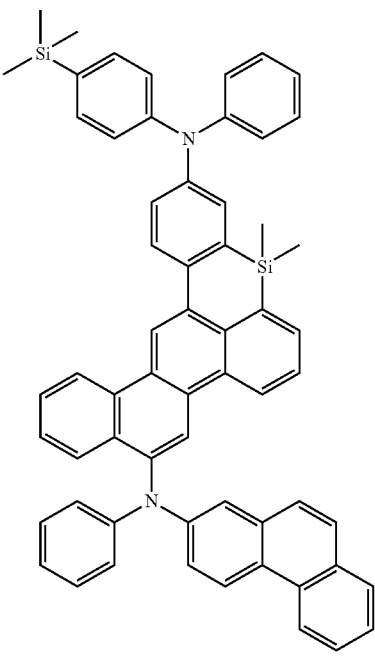
41
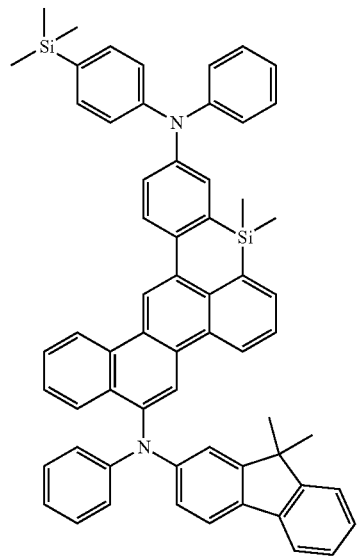
42
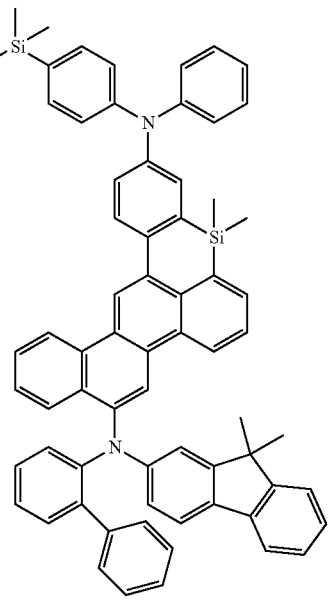

-continued
43
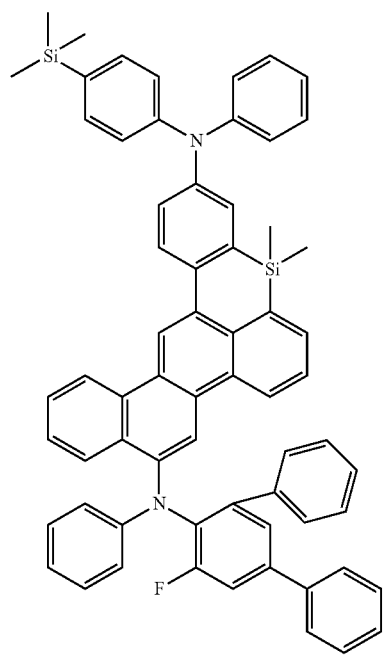
44
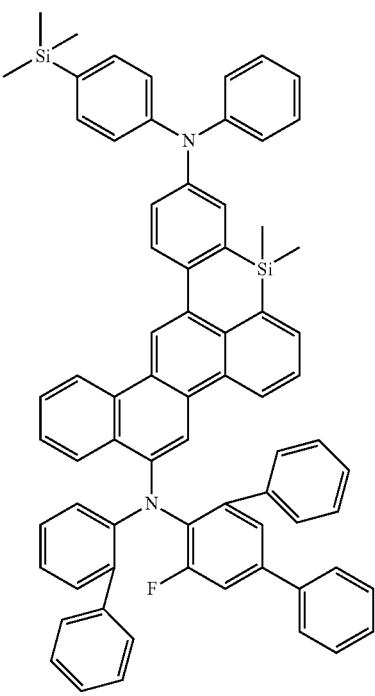
45
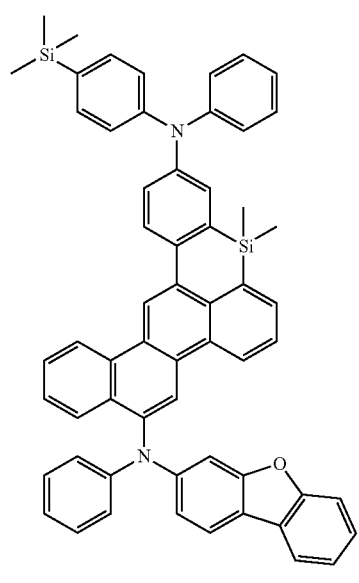
46
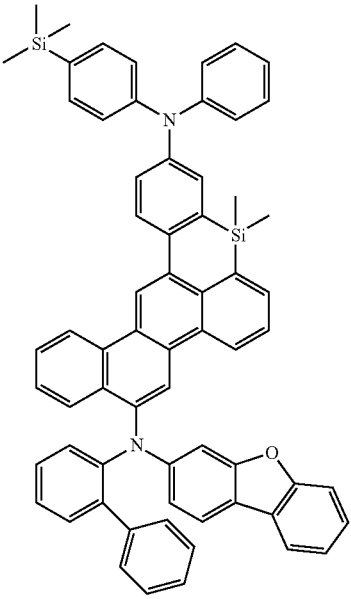

47
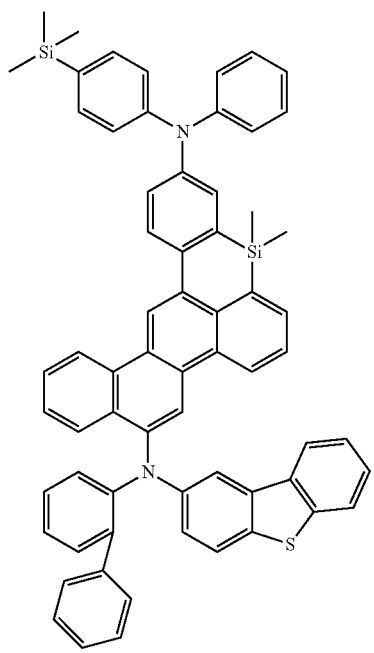
48
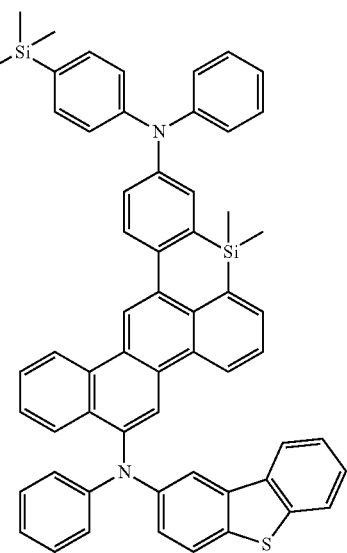
49
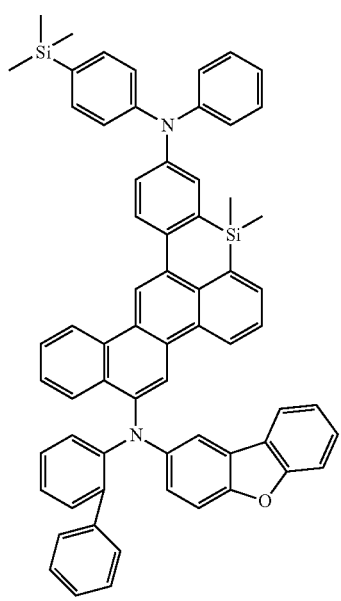
50
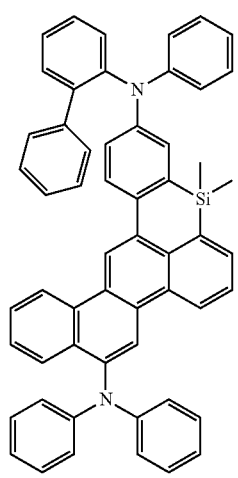

-continued
51
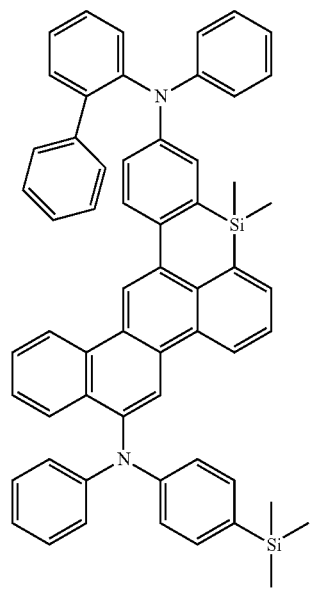
52
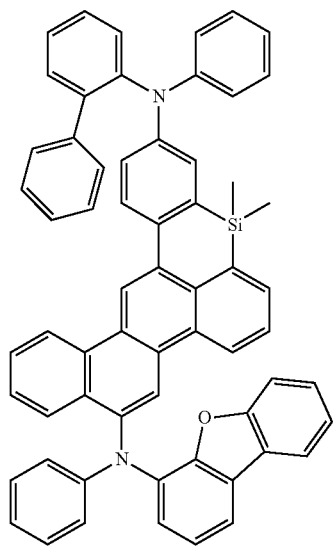
53
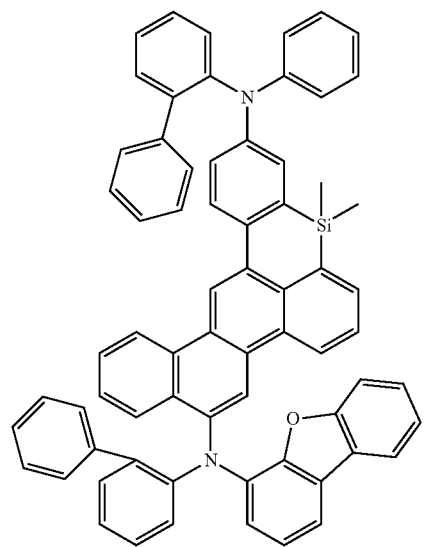
54
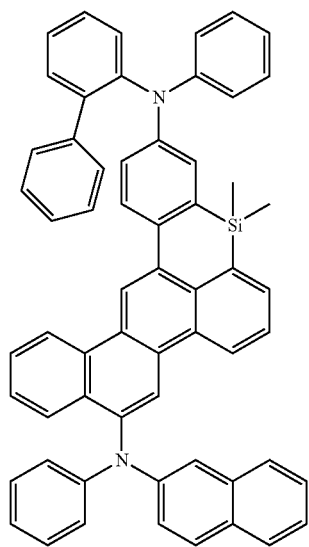

55
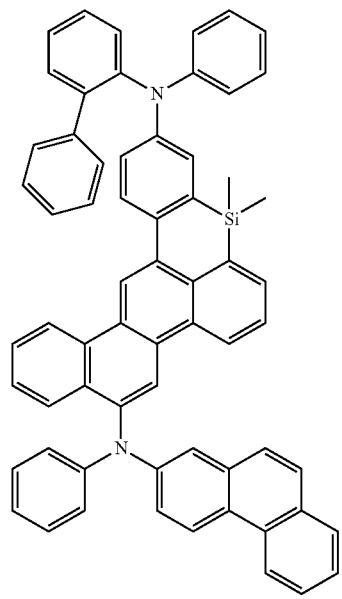
56
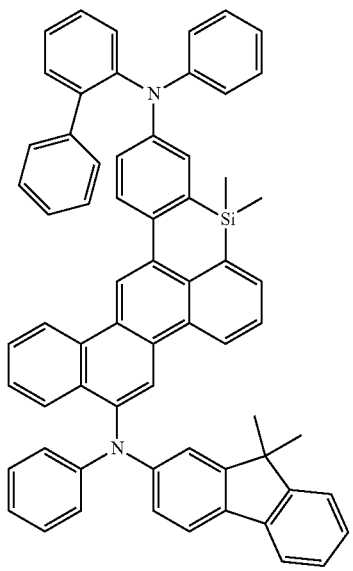
57
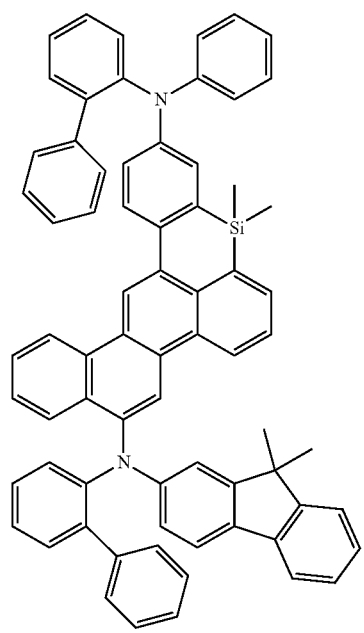
58

-continued
59
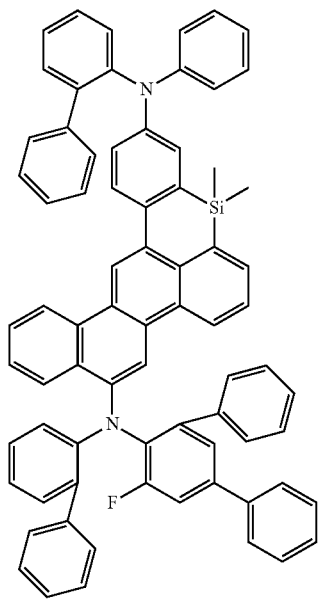
60
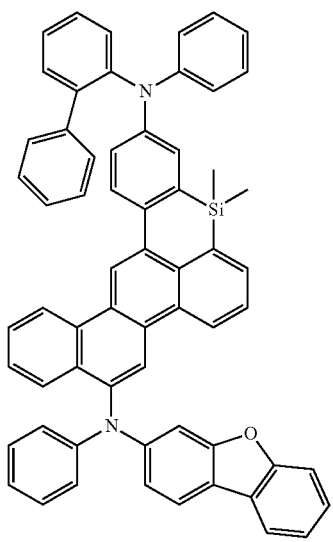
61
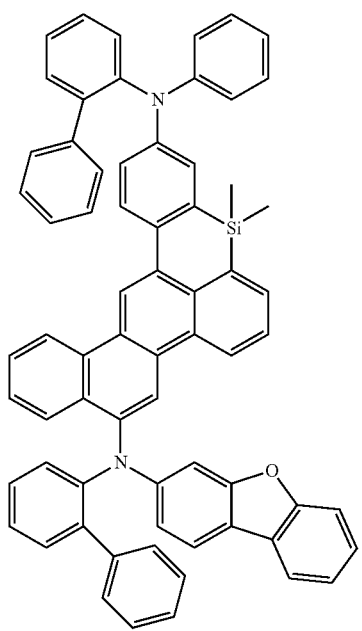
62
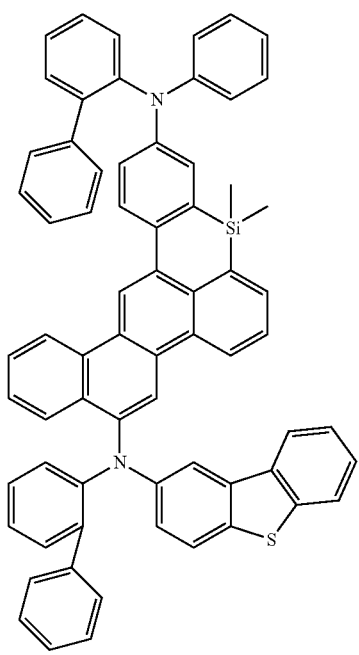

-continued
63
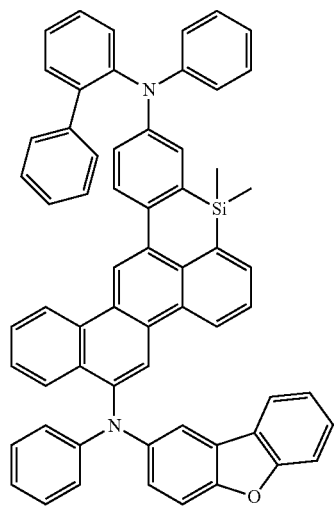
64
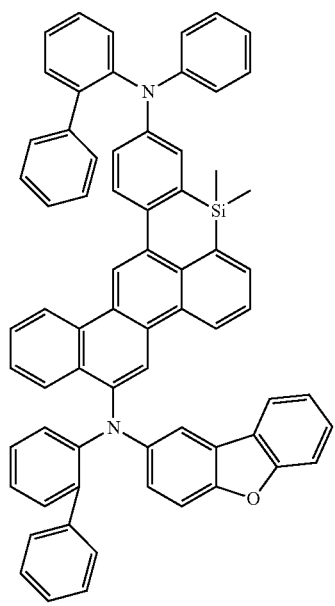
65
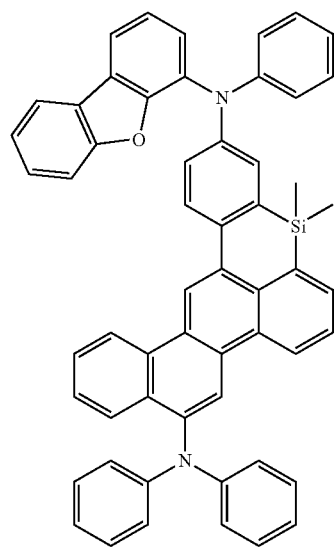
66
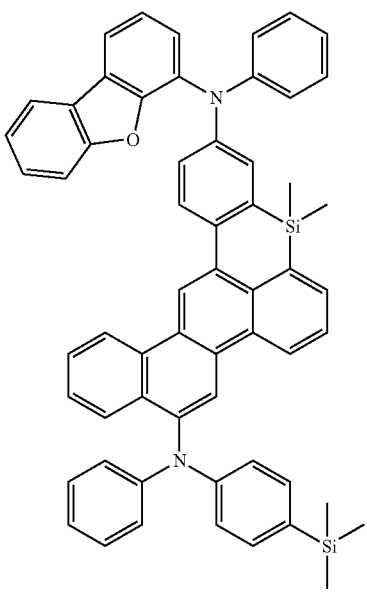

67
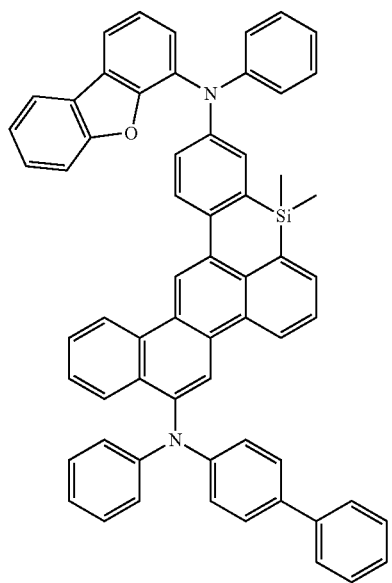
68
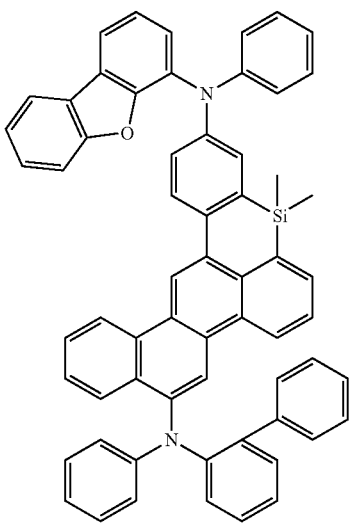
69
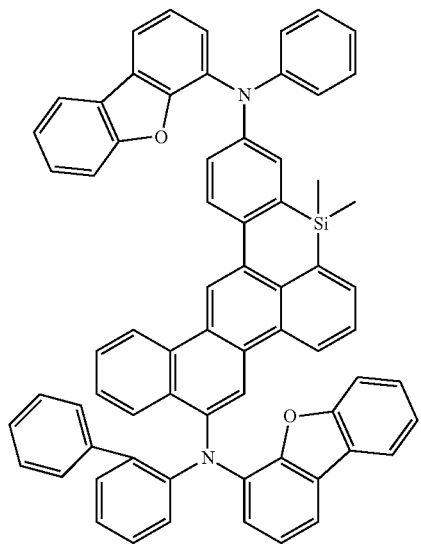
70
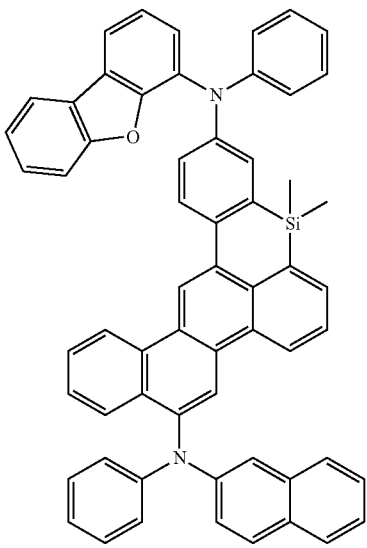

-continued
441
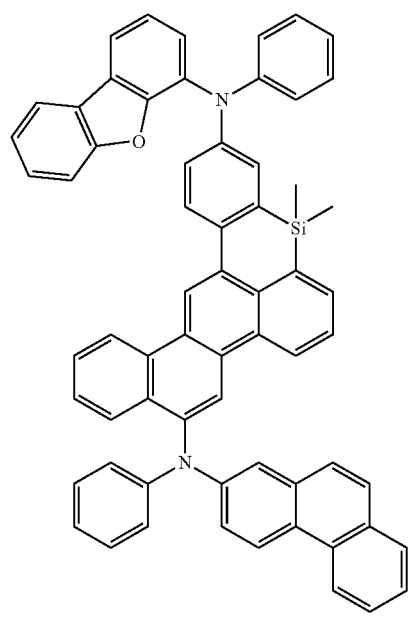
442
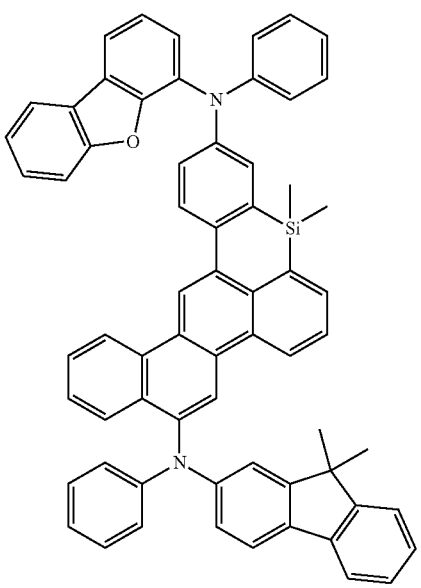
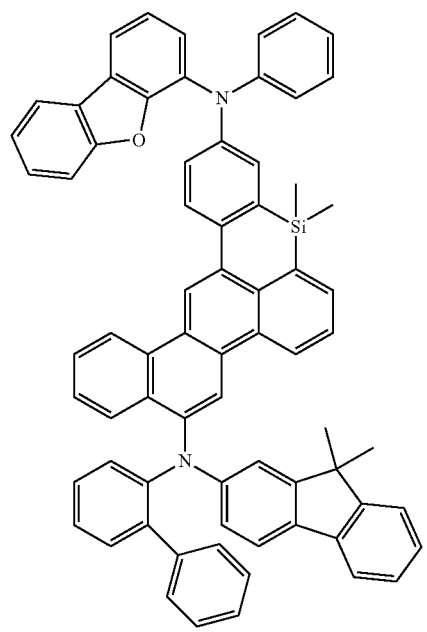
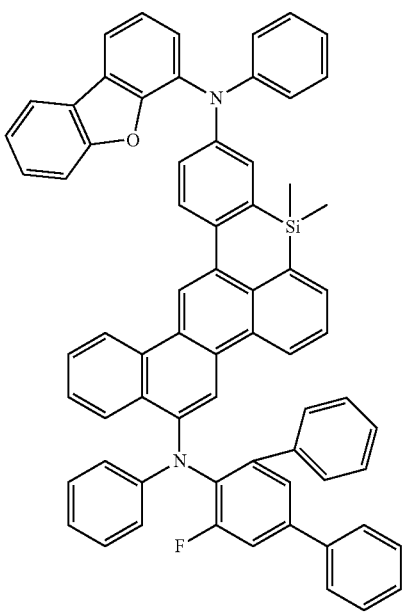

443
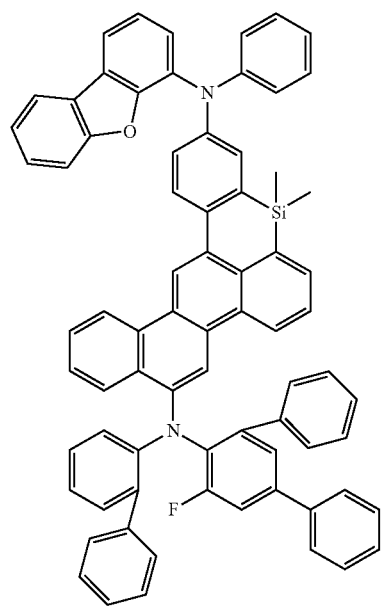
444
-continued
75
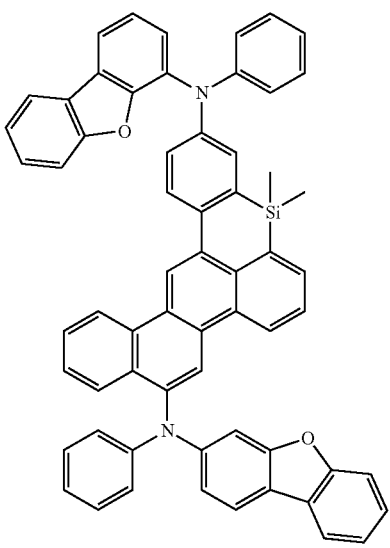
76
77
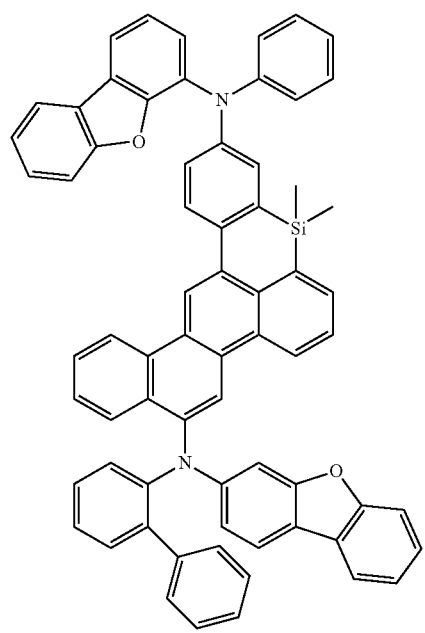
78
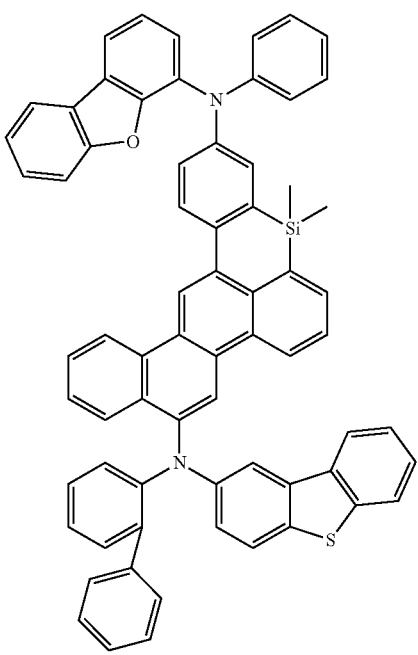

445
446
-continued
79
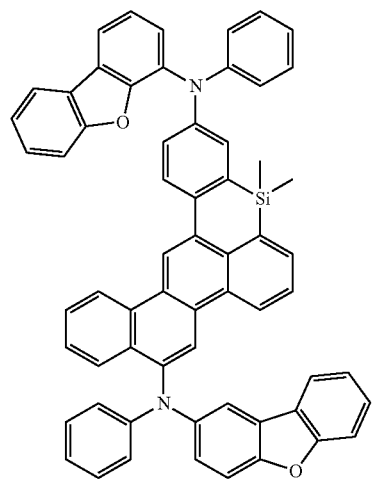
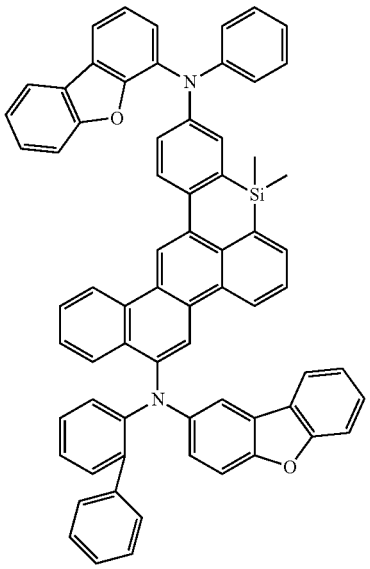
80
81
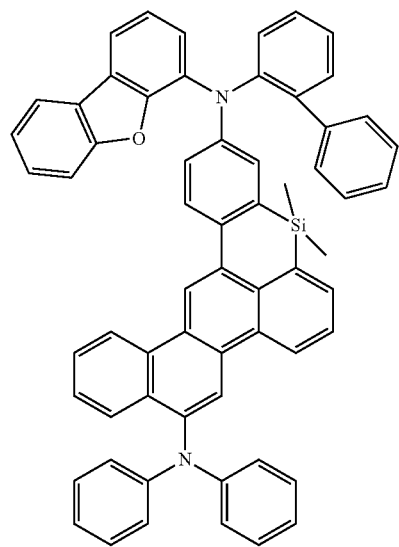
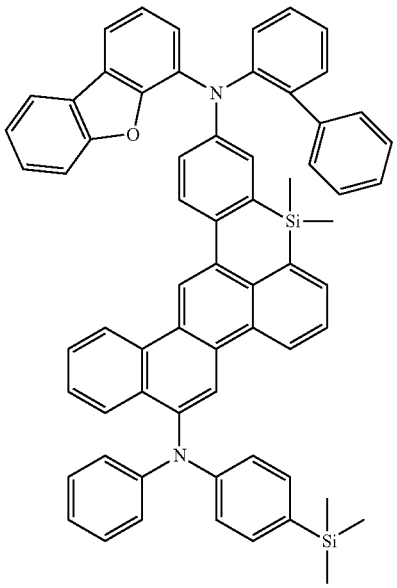
82

-continued
83
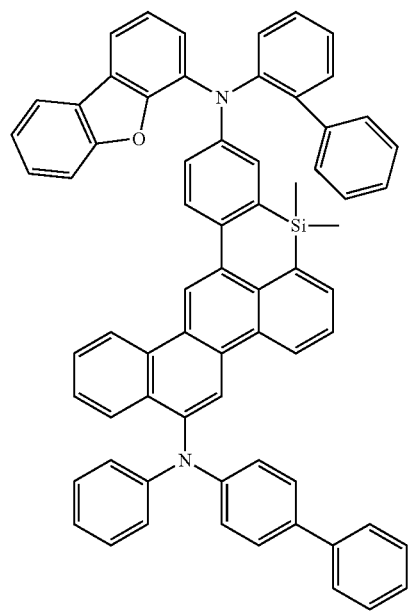
84
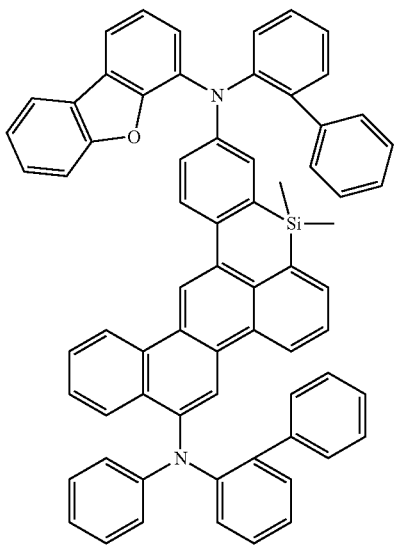
85
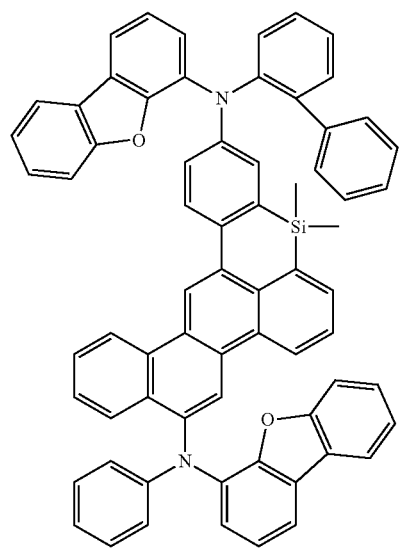
86
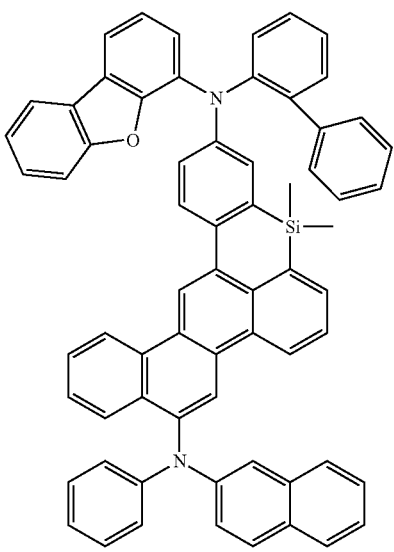

449
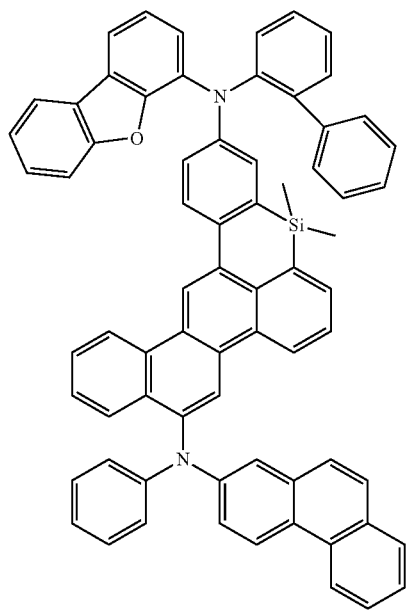
87
450
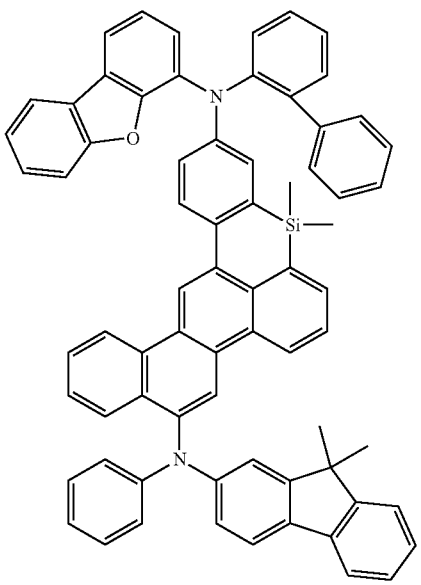
88
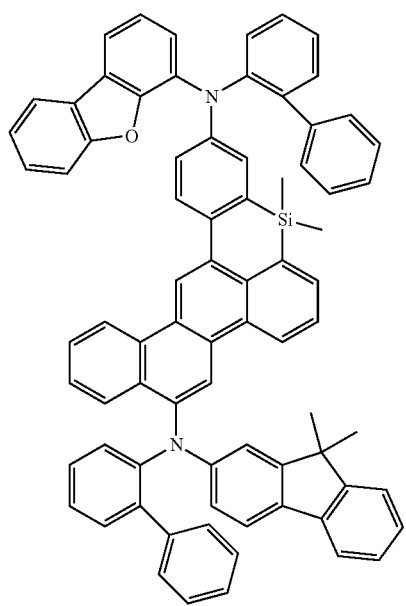
89
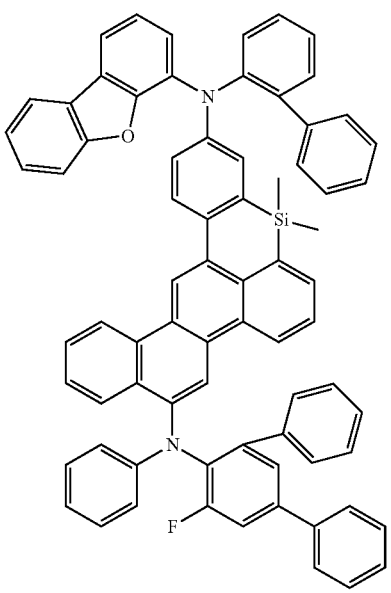
90

-continued
451
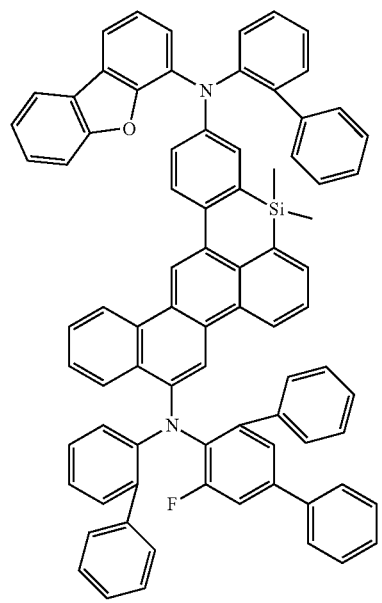
91
452
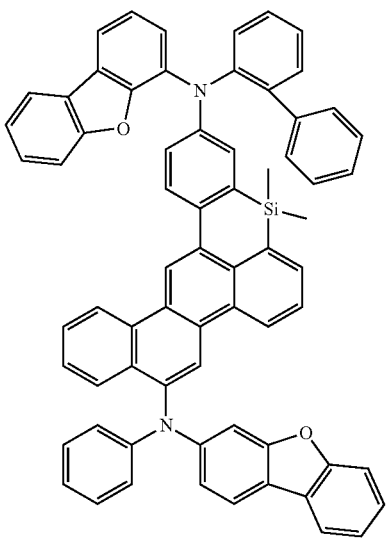
92
93
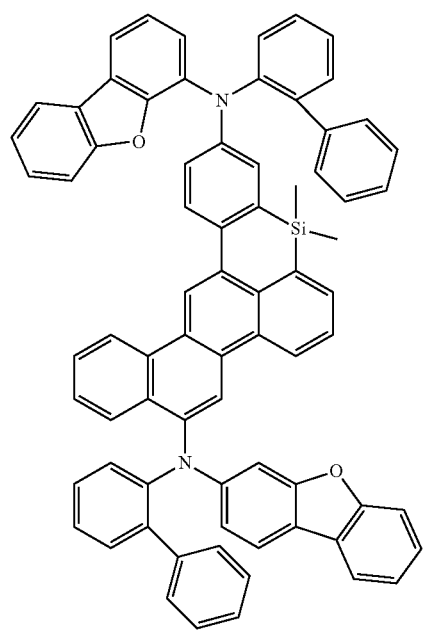
94
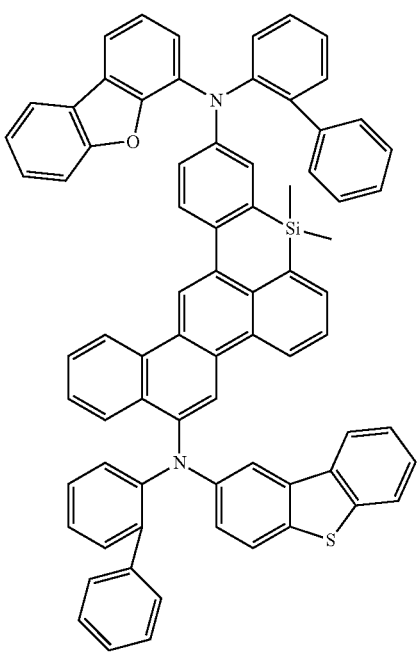

95
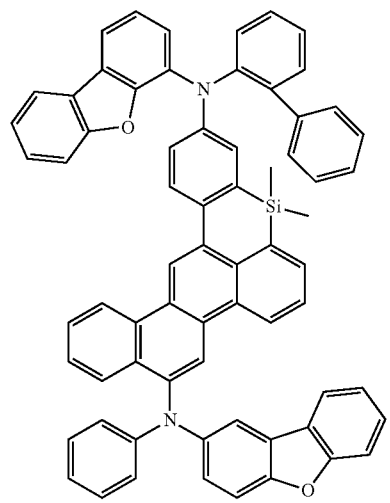
96
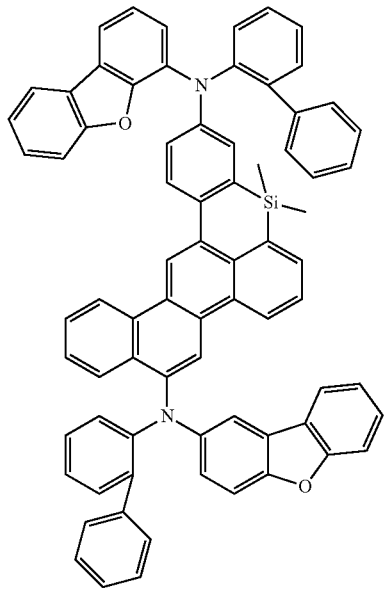
97
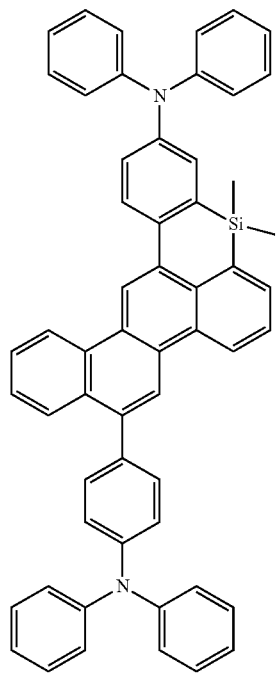
98
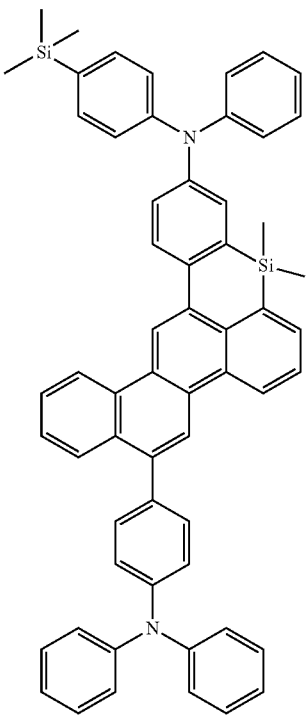

-continued
99
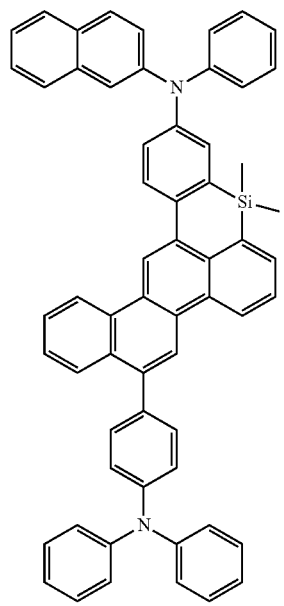
100
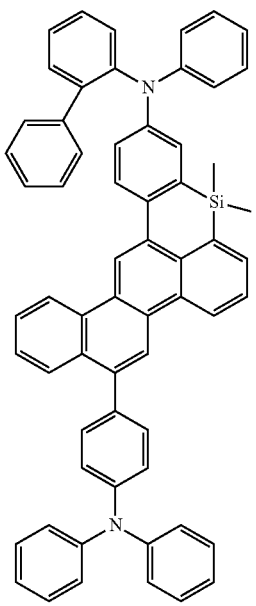
101
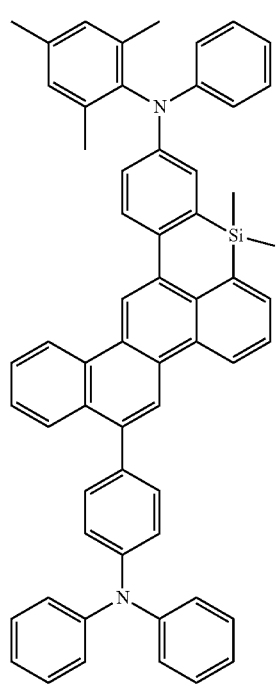
102
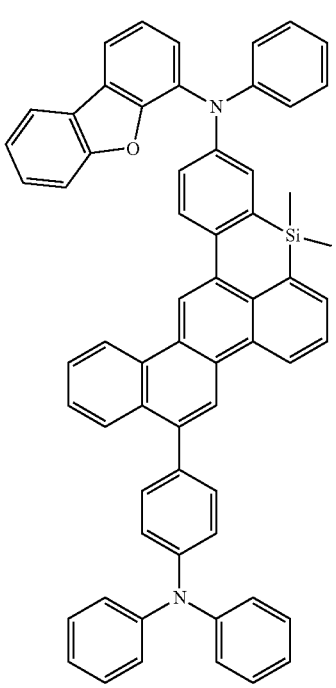

457 458
-continued
103 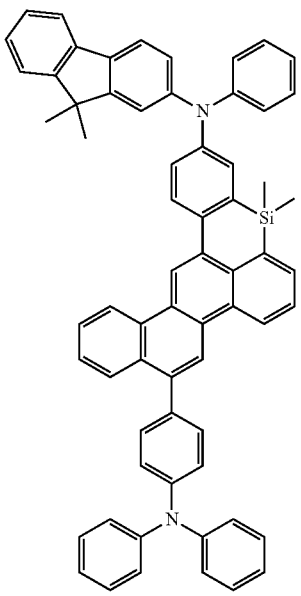 104
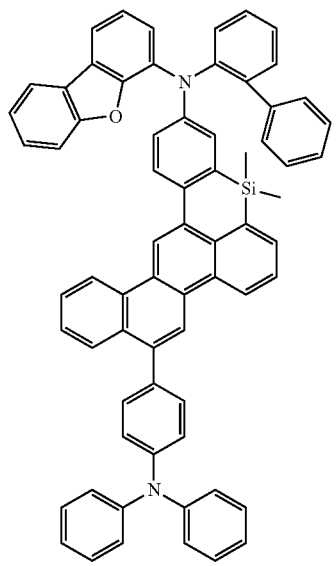
105 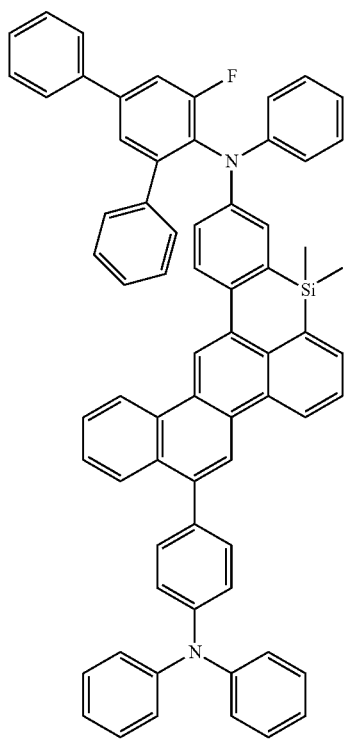 106 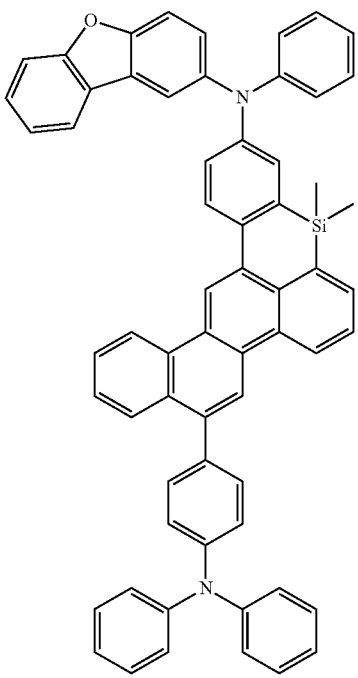

-continued
107
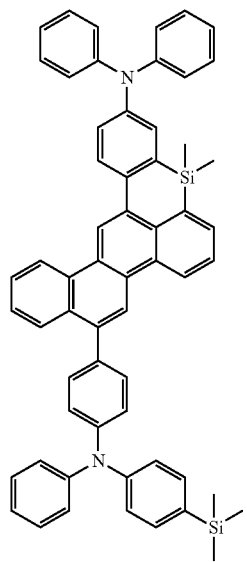
108
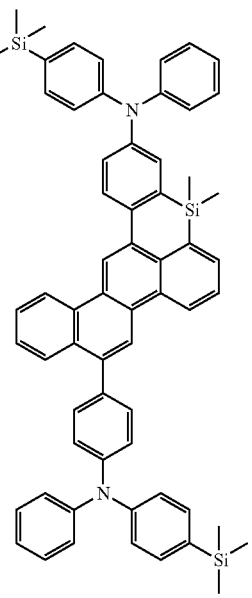
109
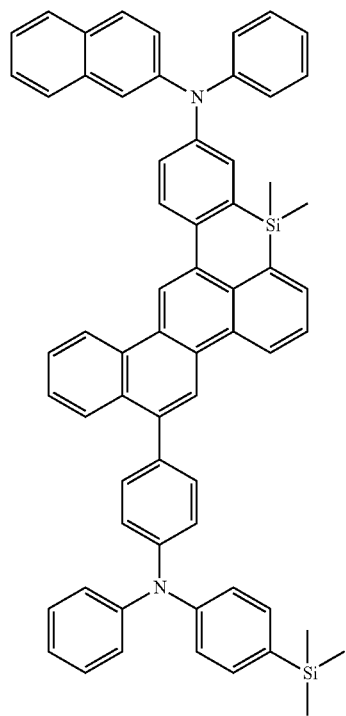
110
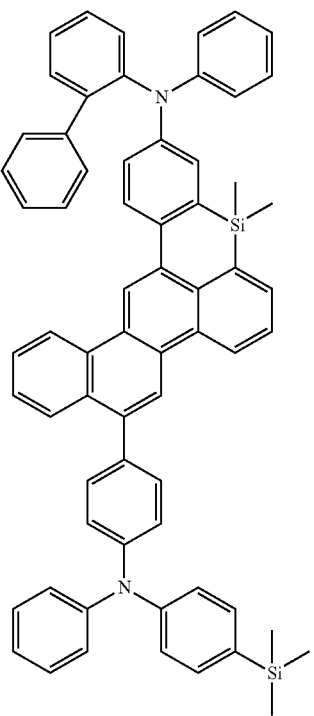

461 462
-continued
| 111 | 112 |
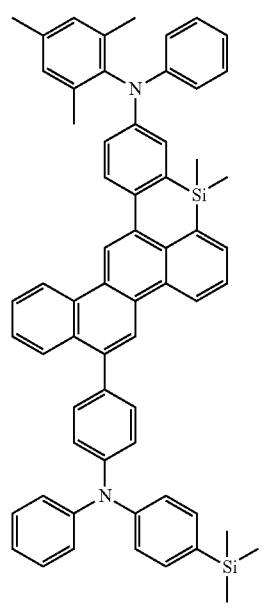
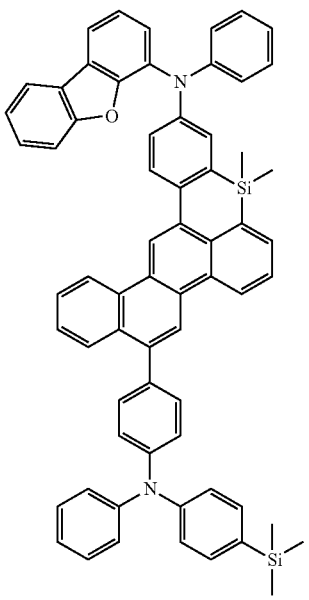
| 113 | 114 |
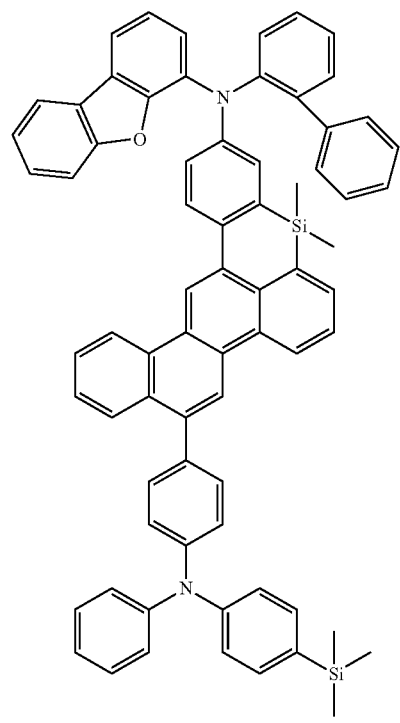
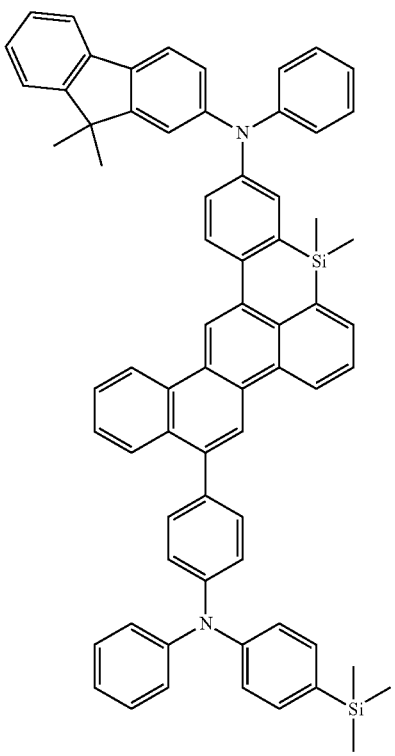

-continued
116
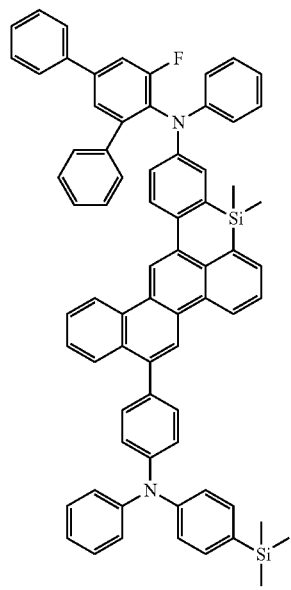
115
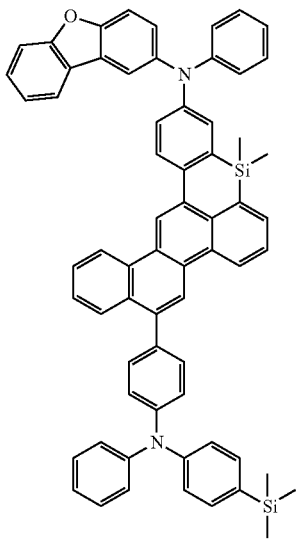
117
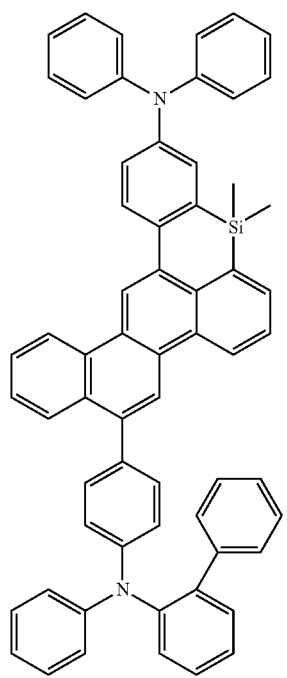
118
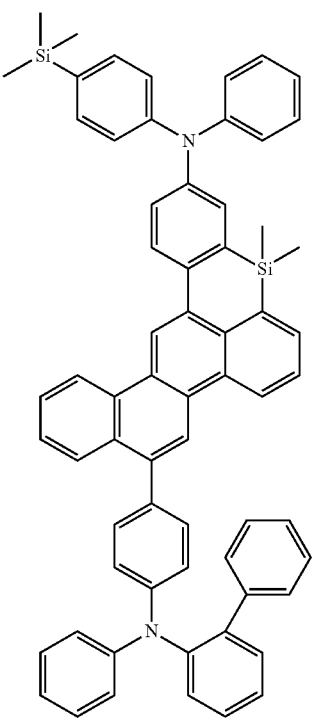

-continued
119
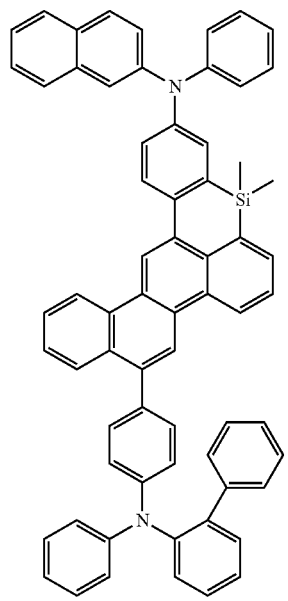
120
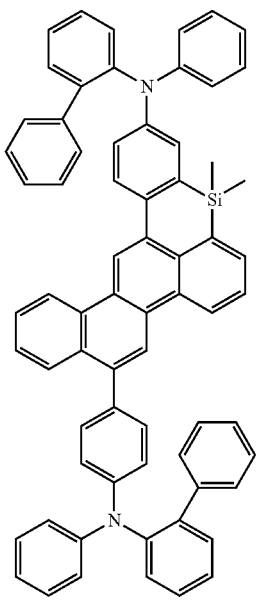
121
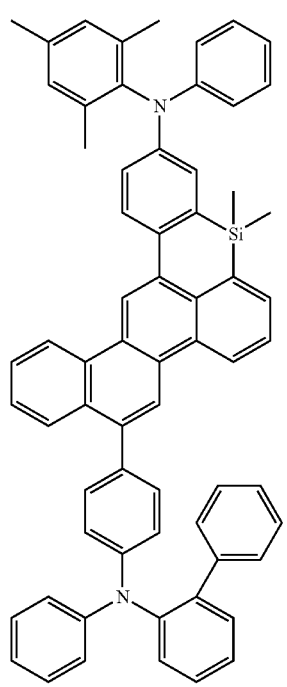
122
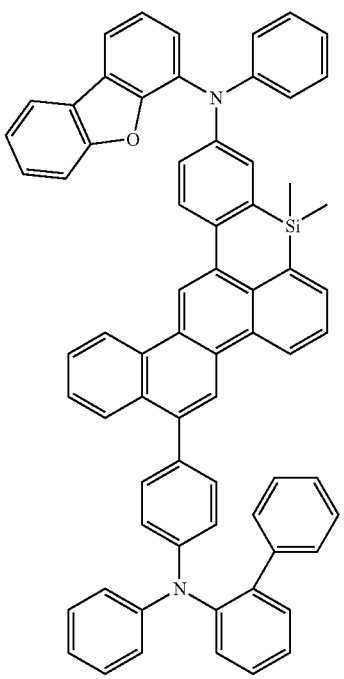

-continued
467
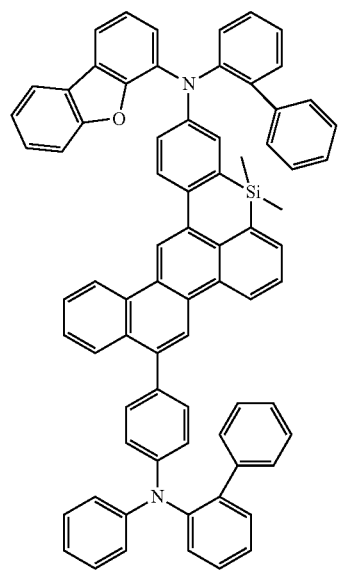
468
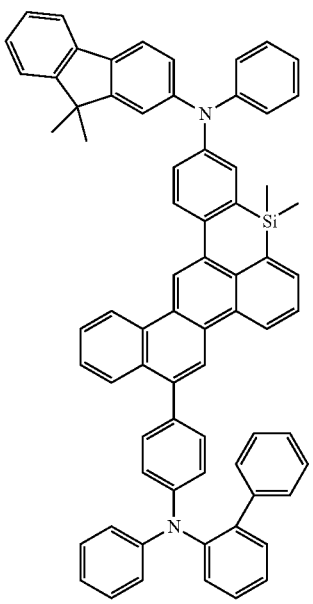
123
124
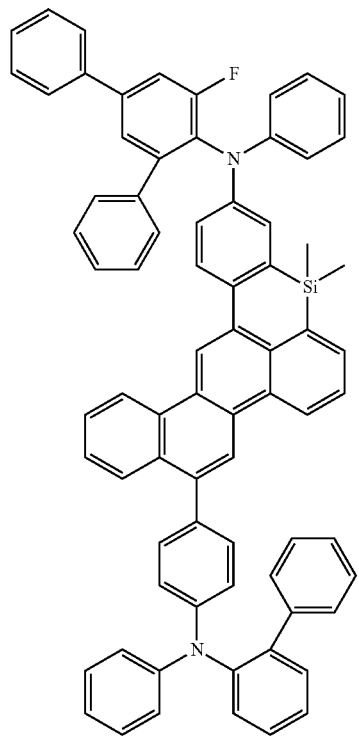
125
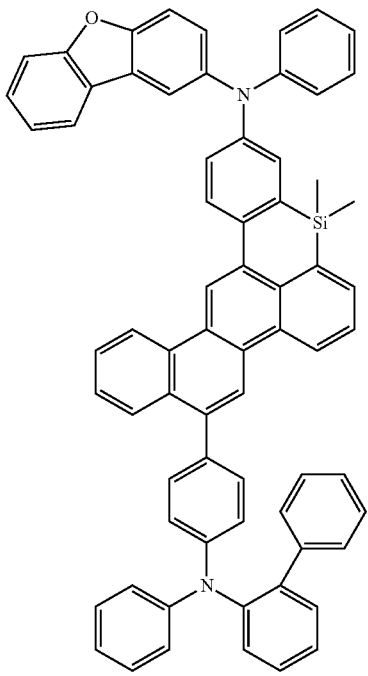
126

-continued
127
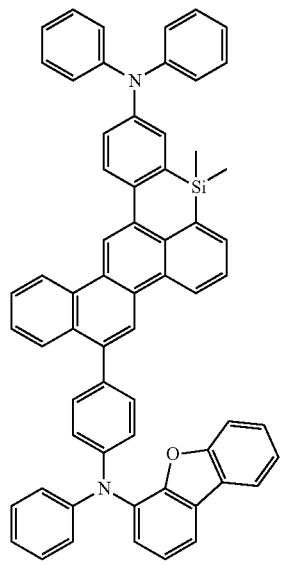
128
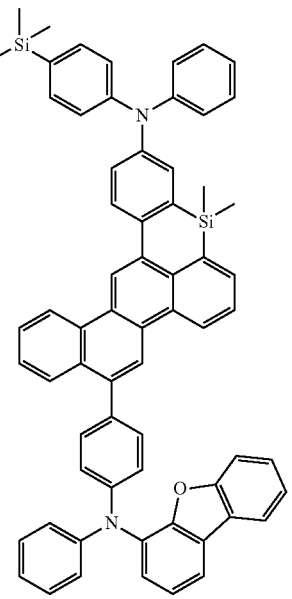
129
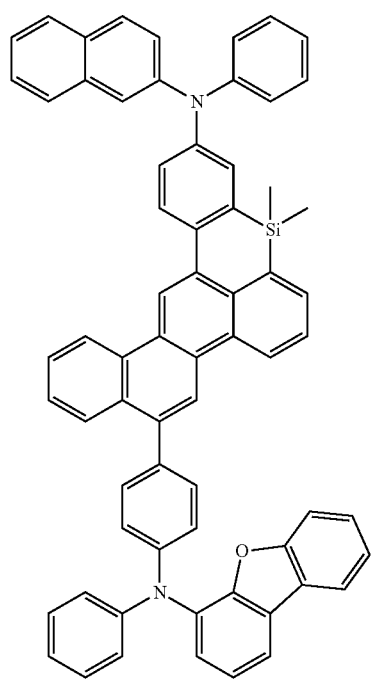
130
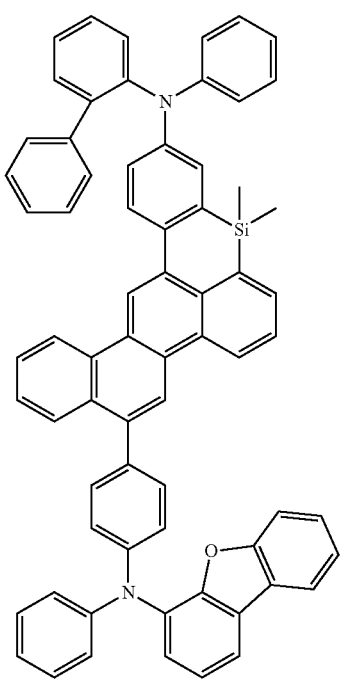

-continued
471
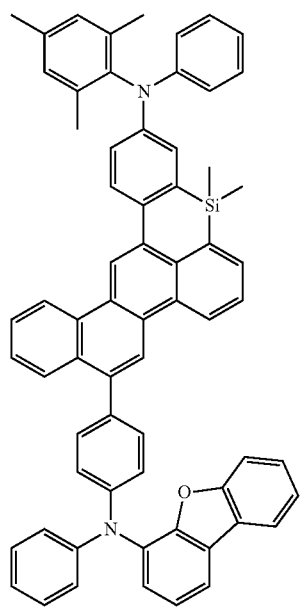
472
131
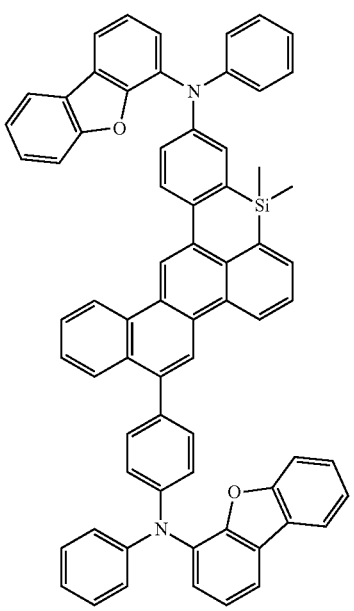
132
133
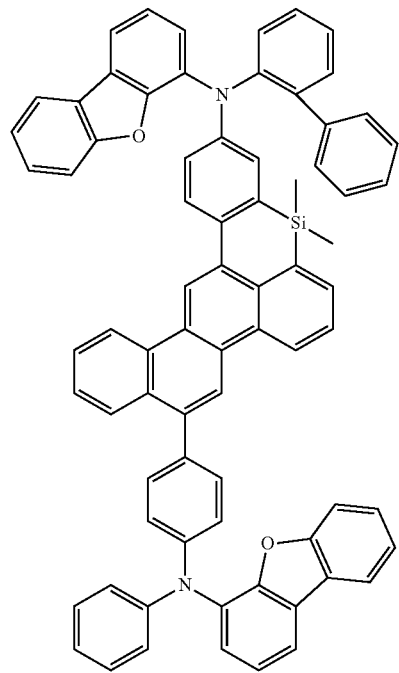
134
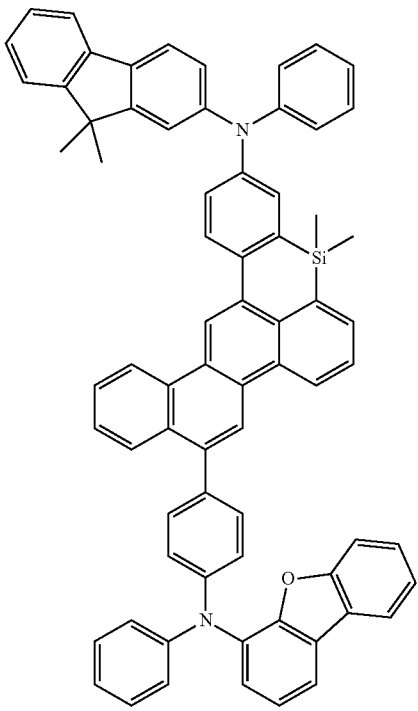

-continued
136
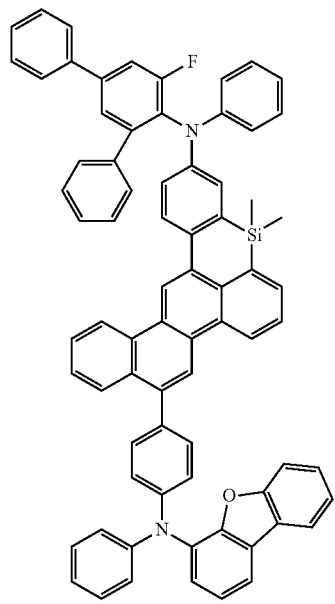
135
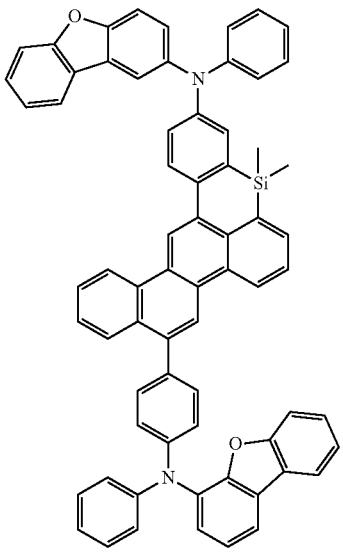
137
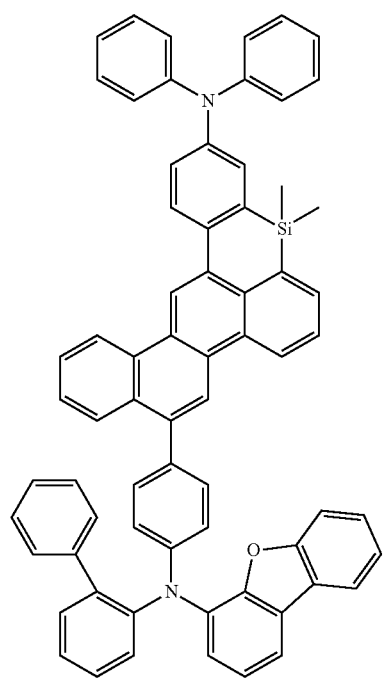
138
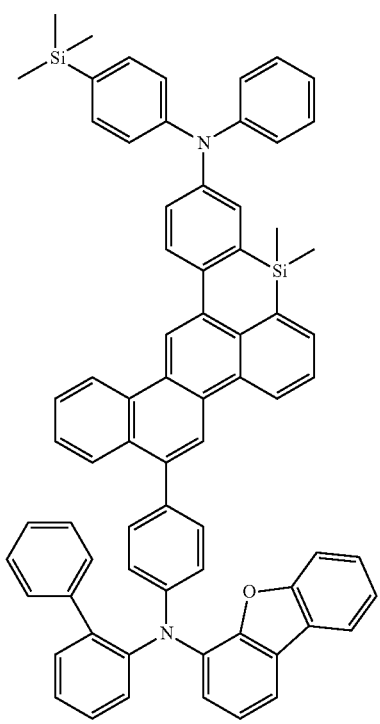

-continued
139
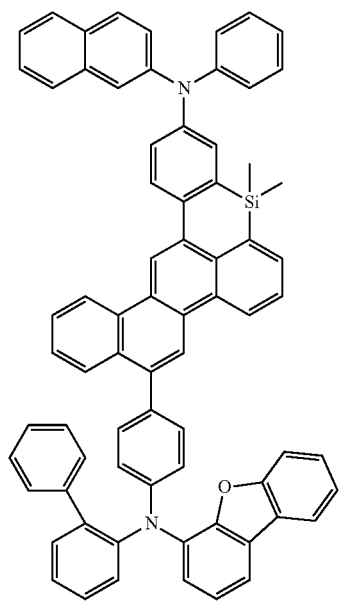
140
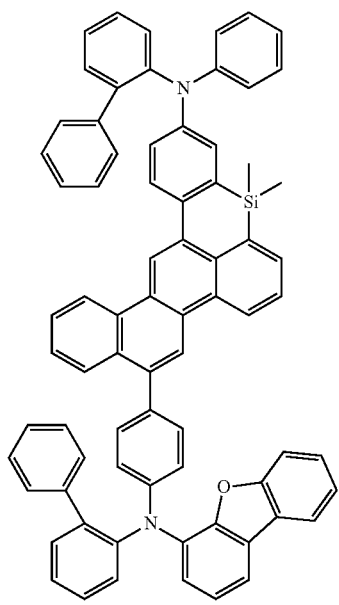
141
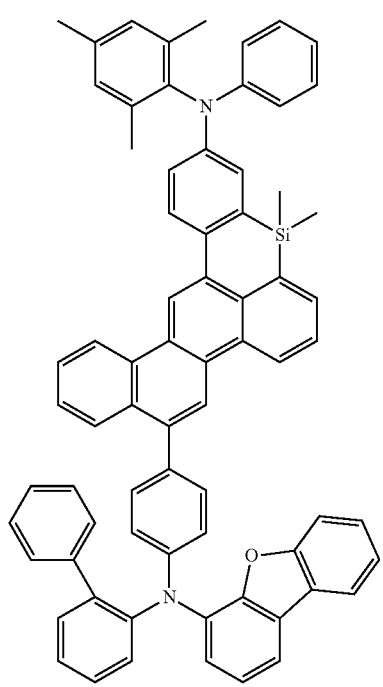
142
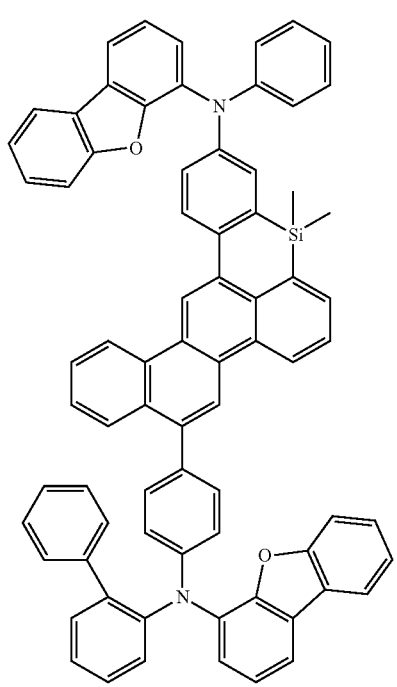

-continued
143
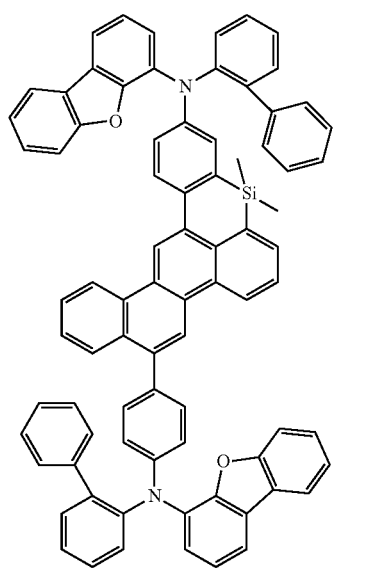
144
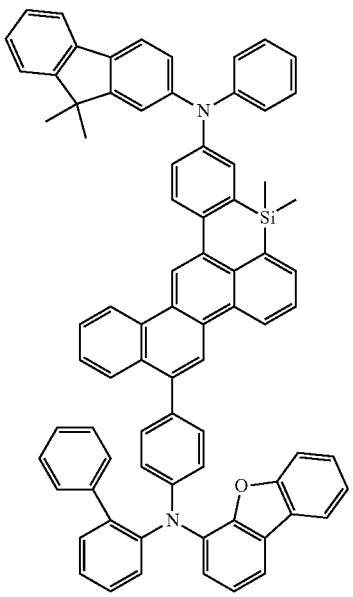
145
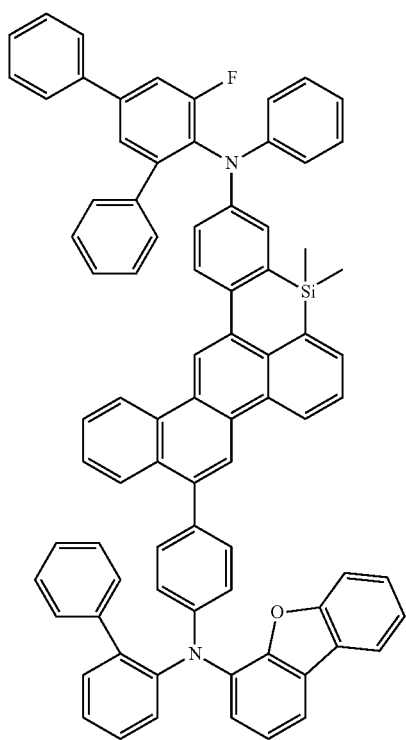
146
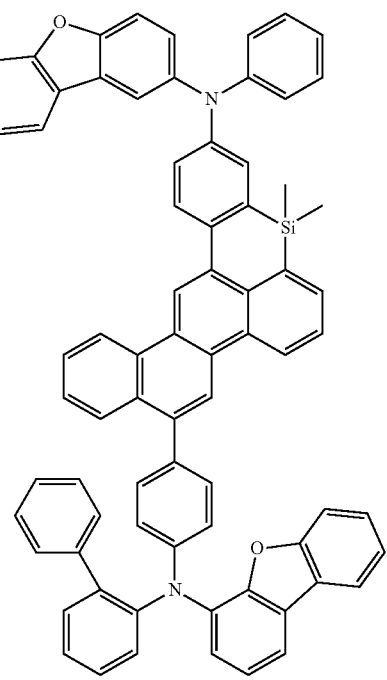

-continued
147
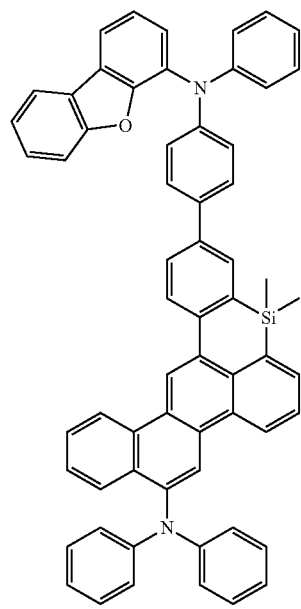
148
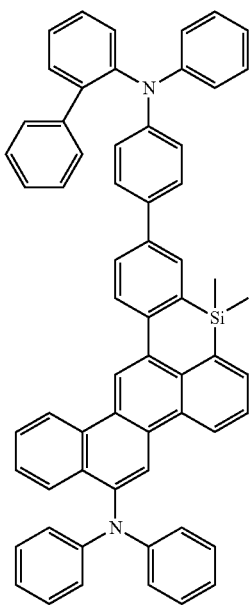
149
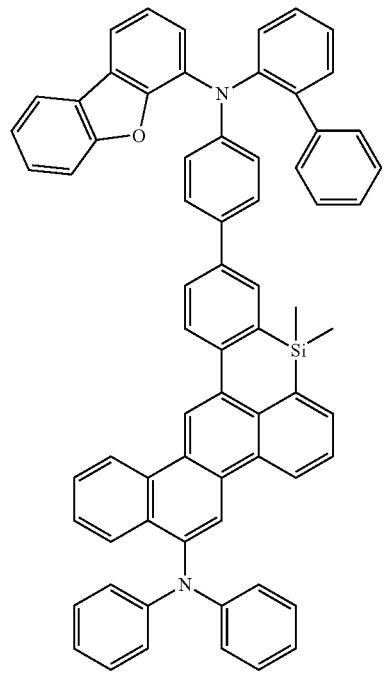
150
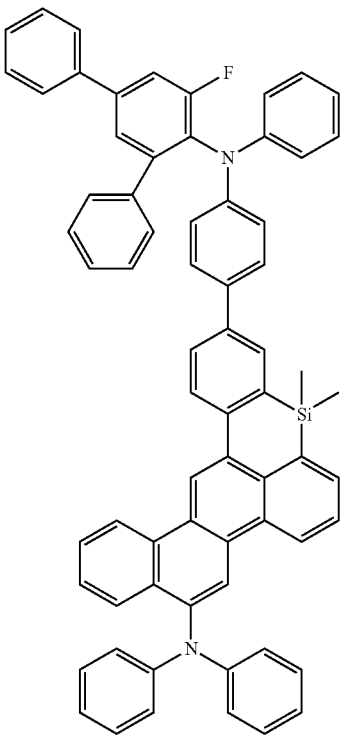

481
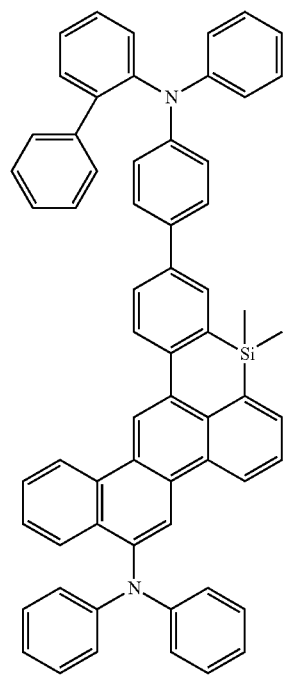
482
-continued
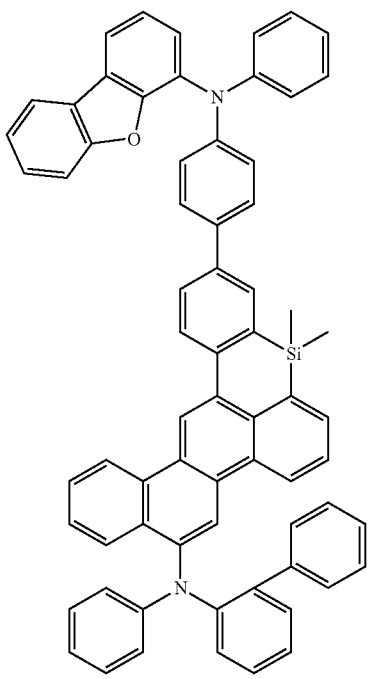
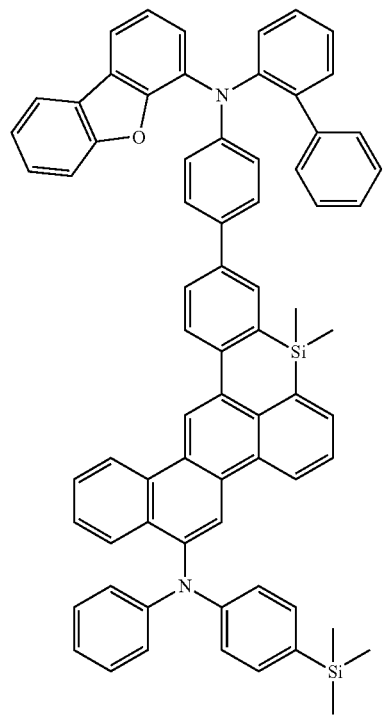
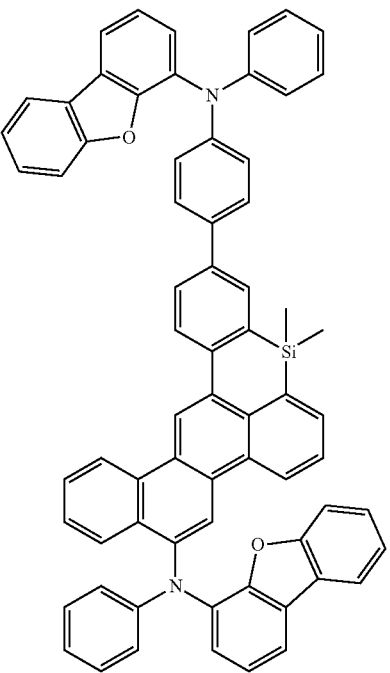

483
484
-continued
155
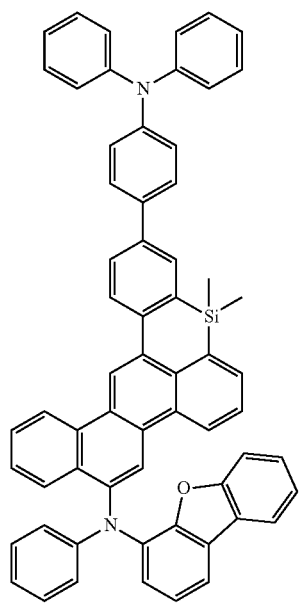
156
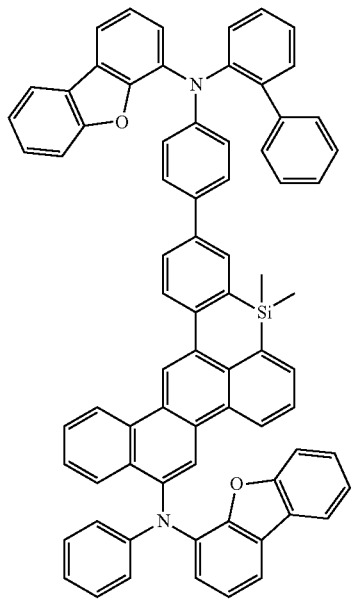
157
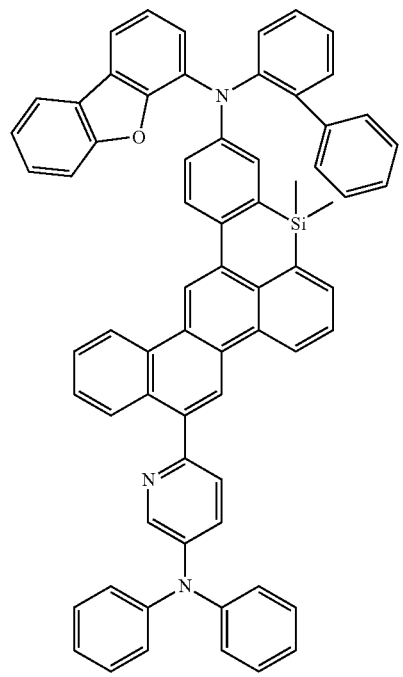
158
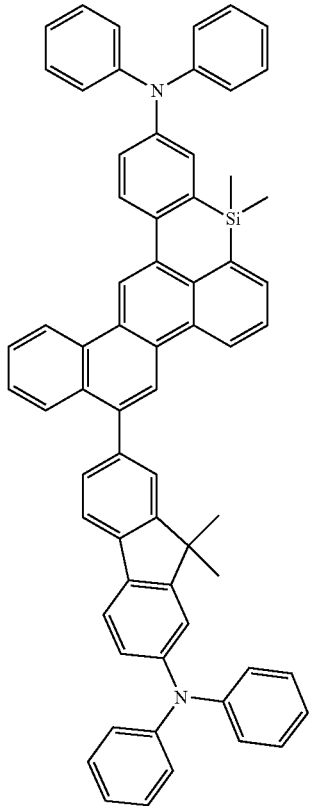

-continued
159
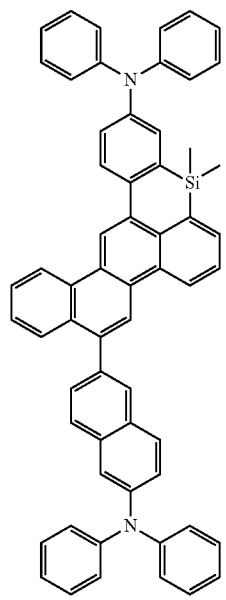
160
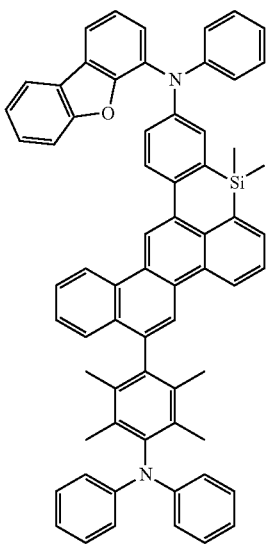
161
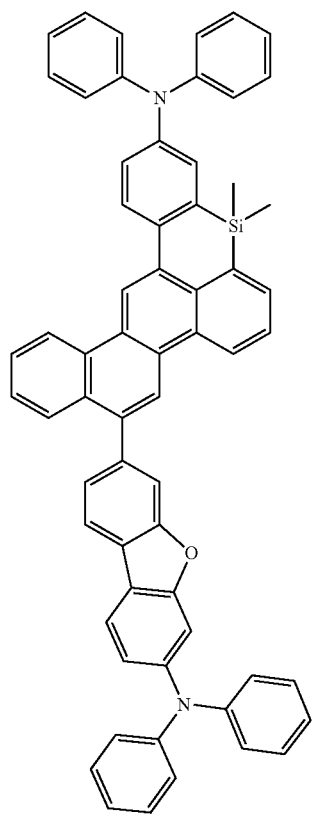
162
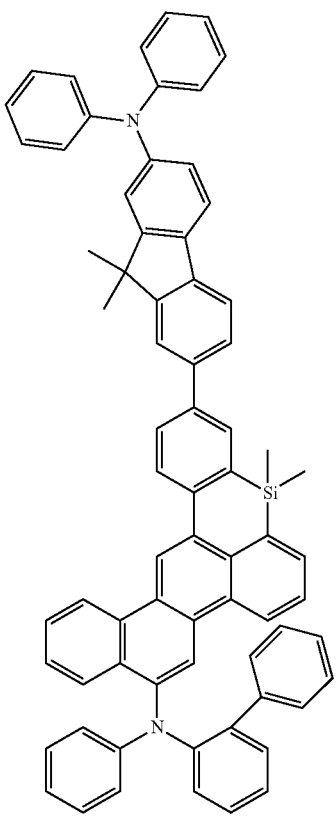

-continued
487
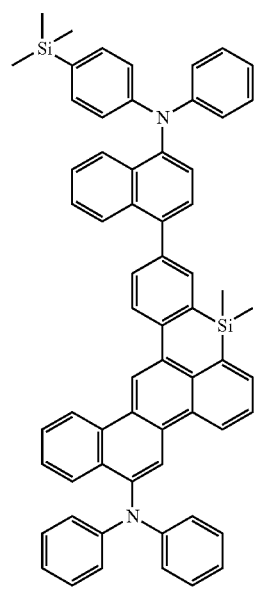
488
163
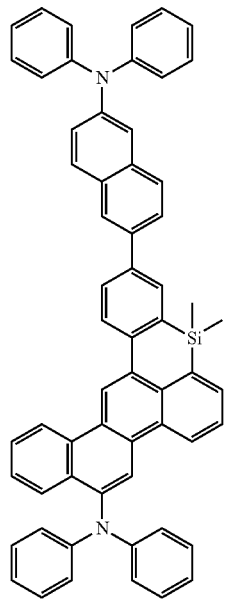
164
165
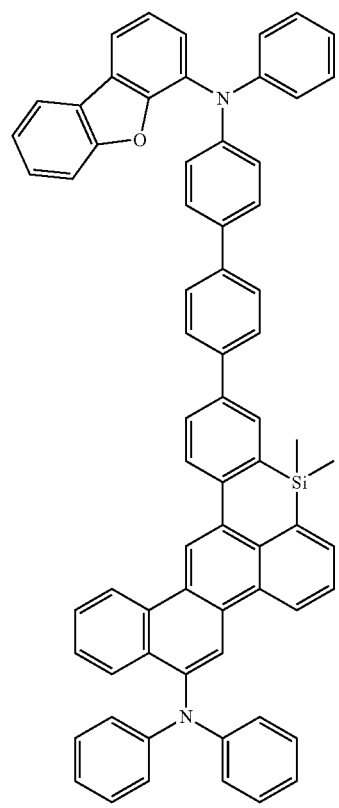
166

-continued
489 167 490 168
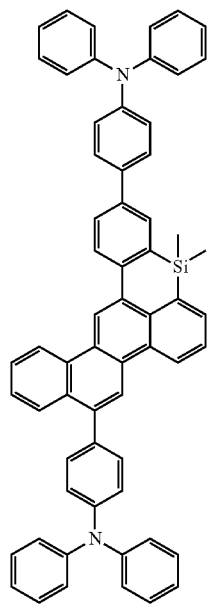 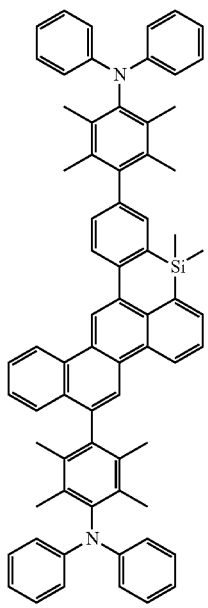
169 170
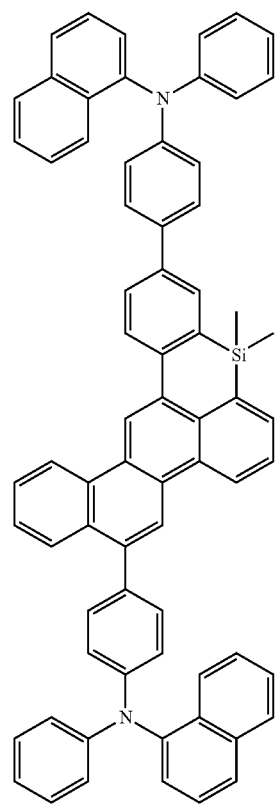 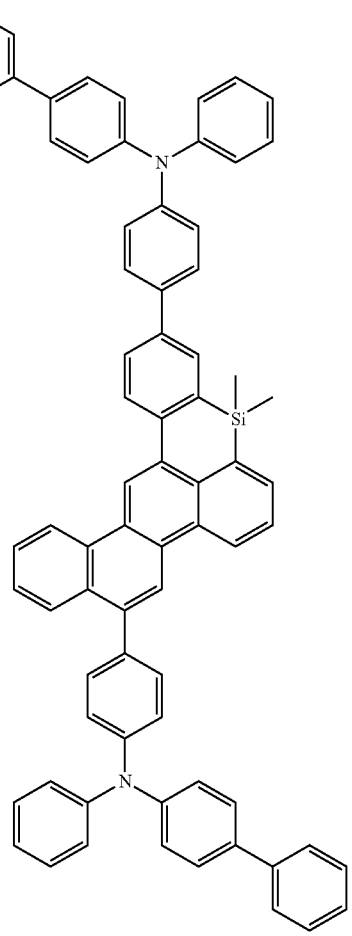

491
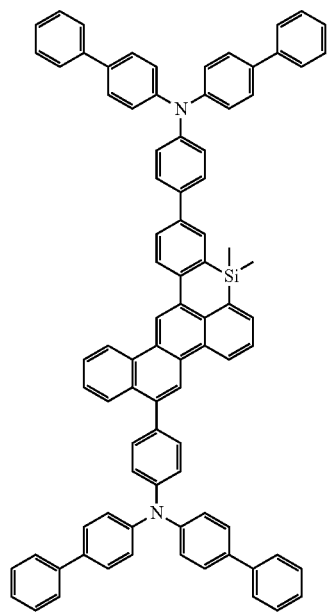
171
492
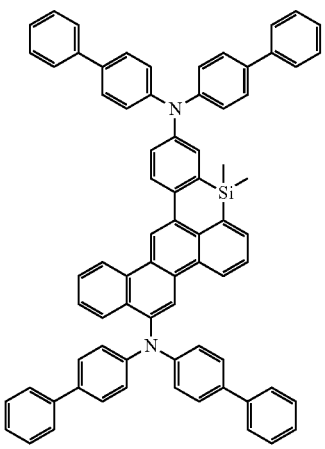
-continued
173
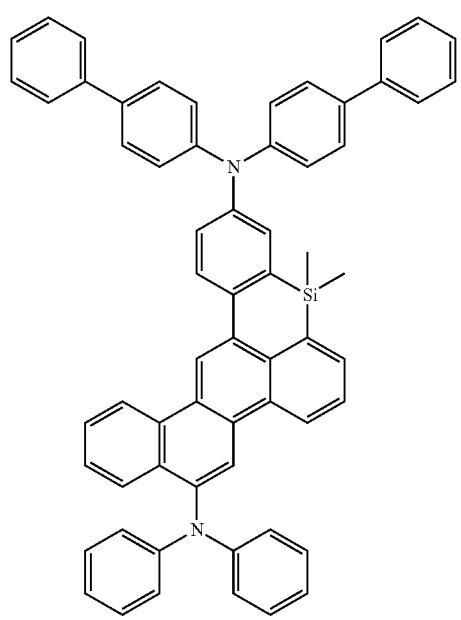
172
174
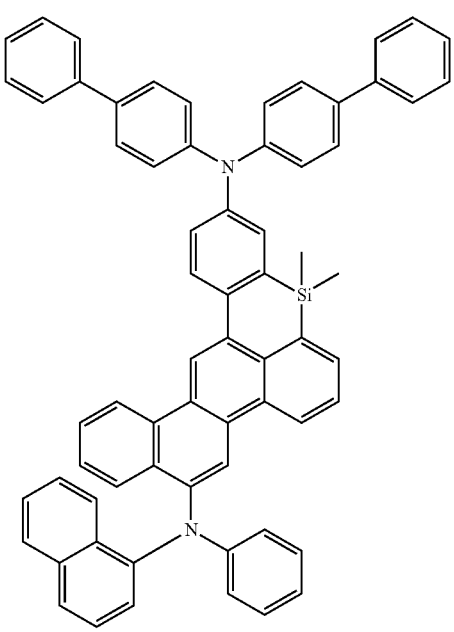

493
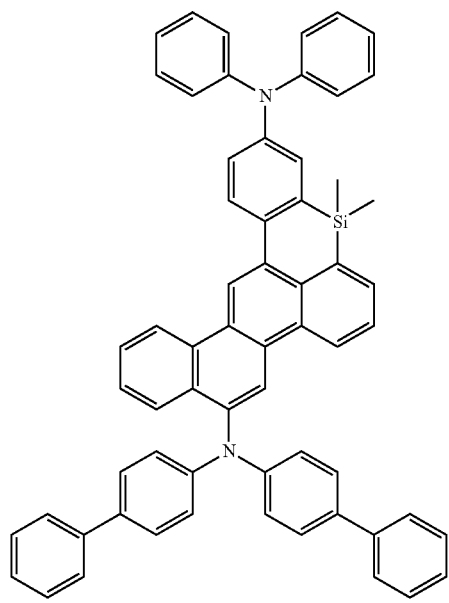
494
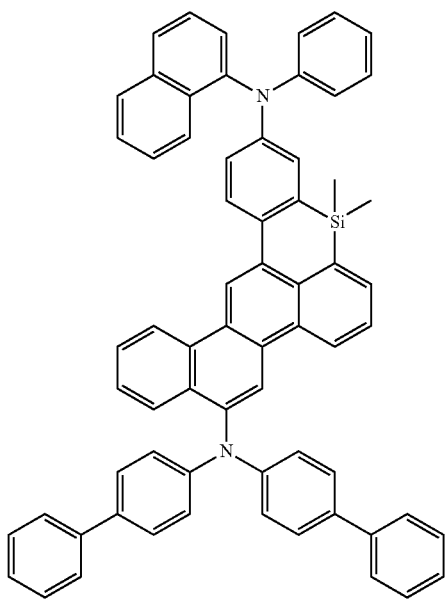
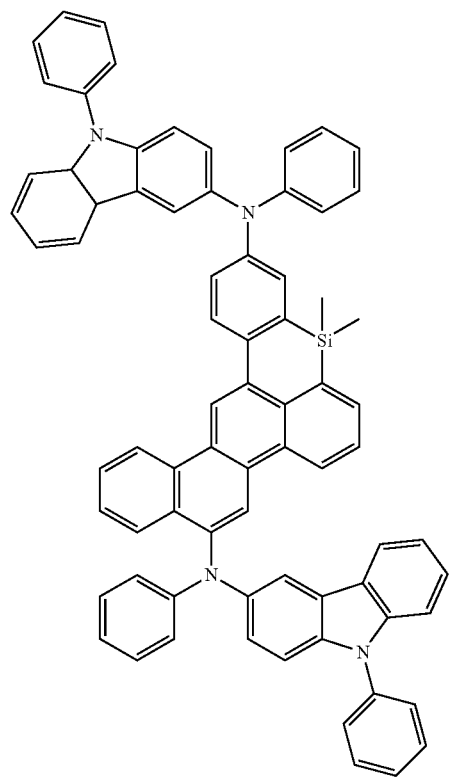
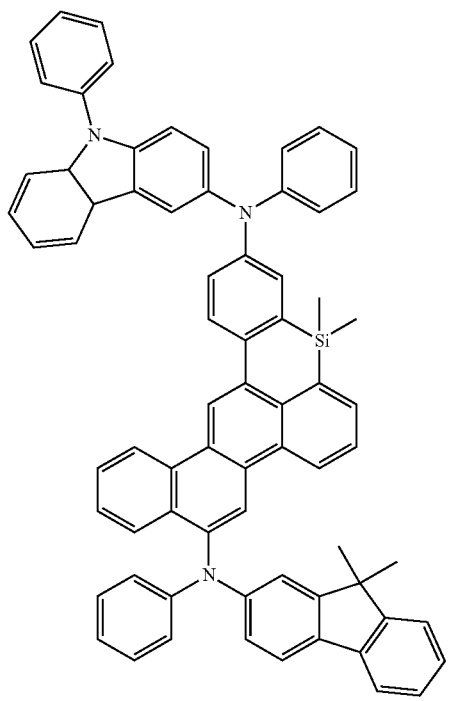

-continued
179
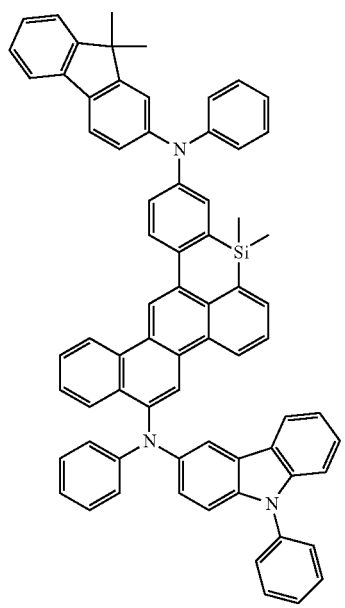
180
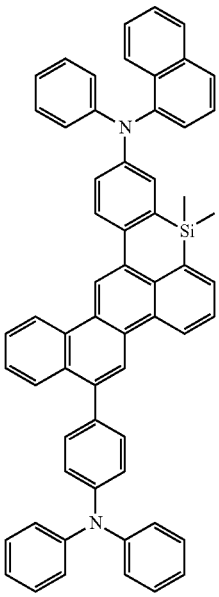
181
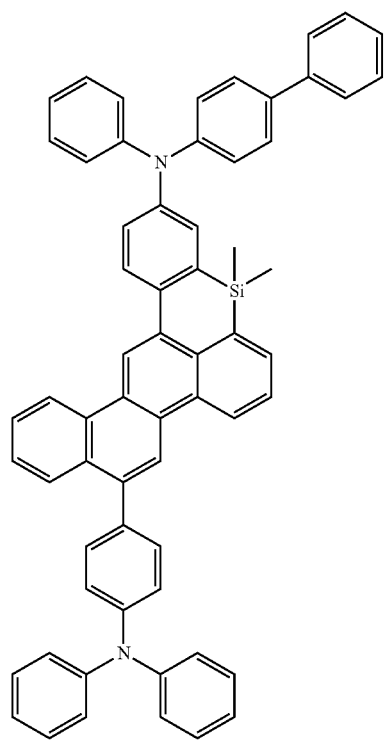
182
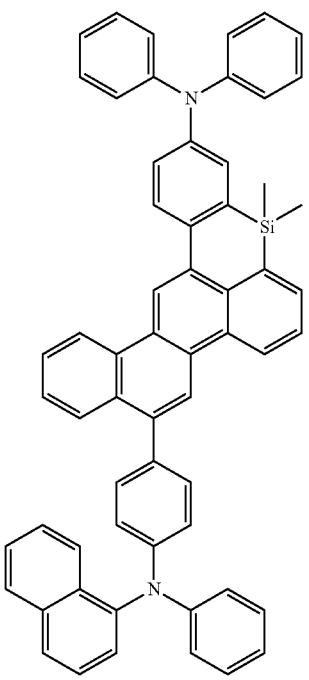

-continued
183
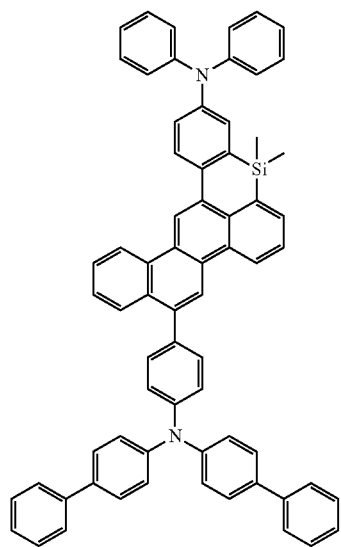
184
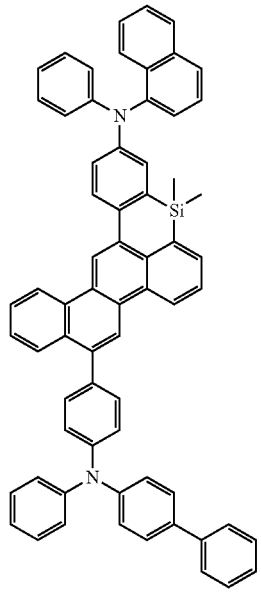
185
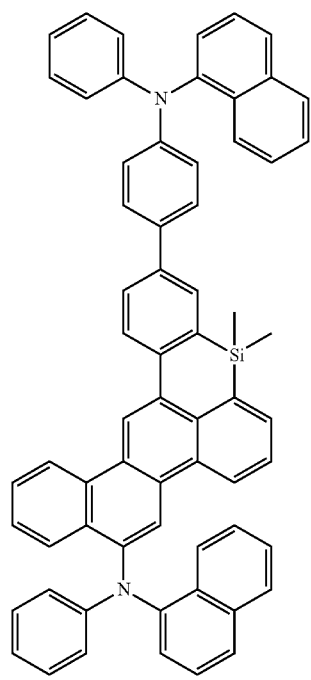
186
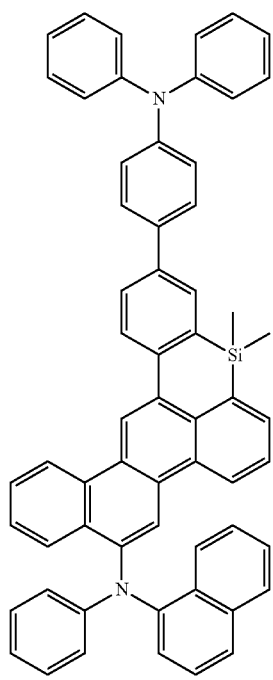

499
500
-continued
187 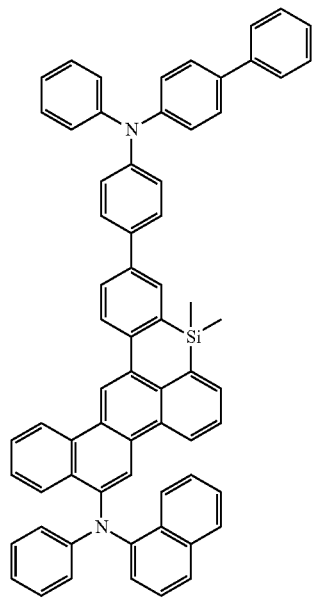
188 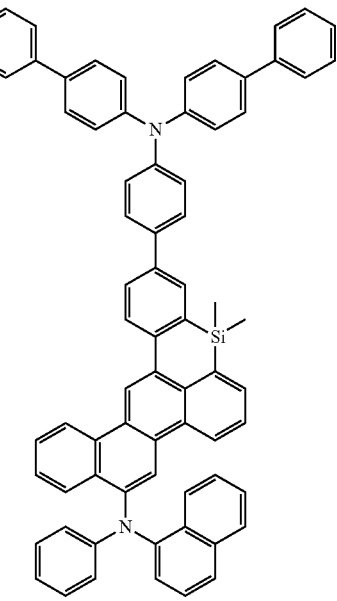
189 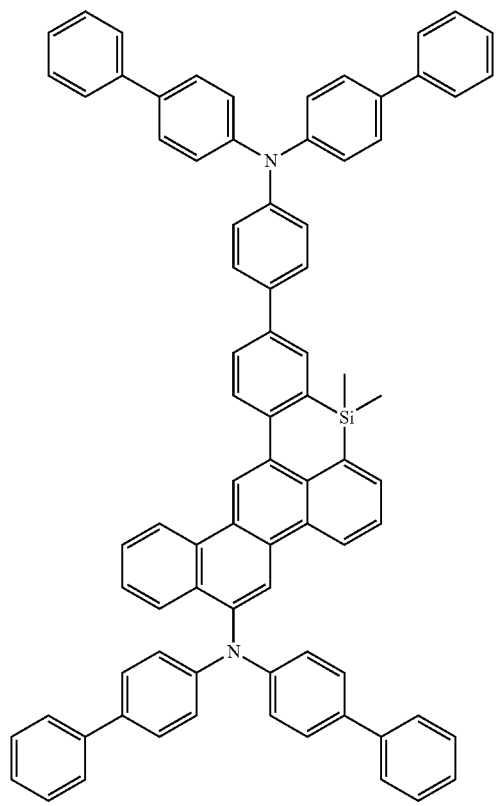

-continued
190
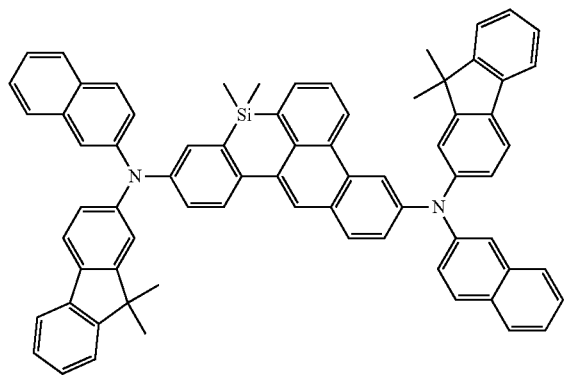
191
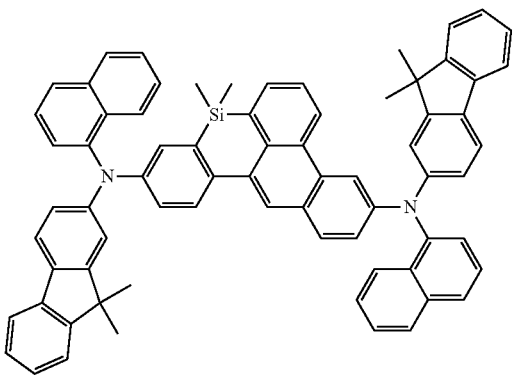
192
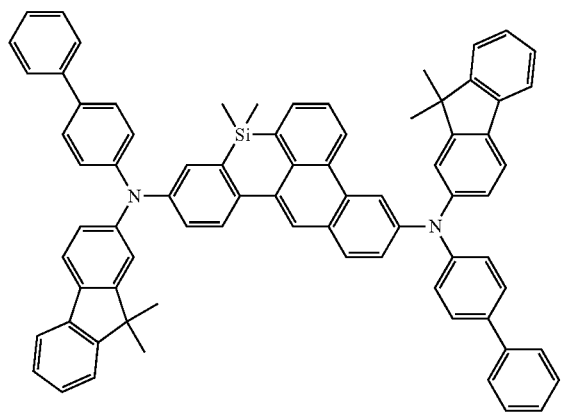
193
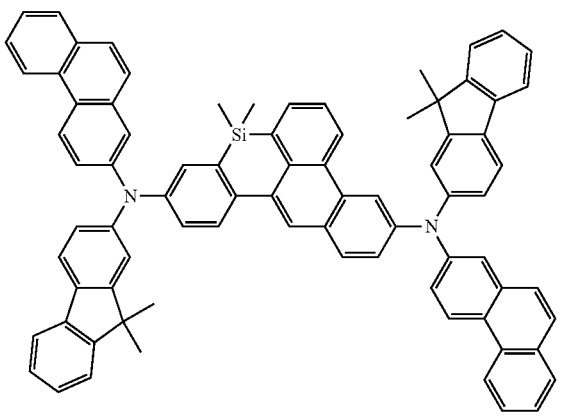
194
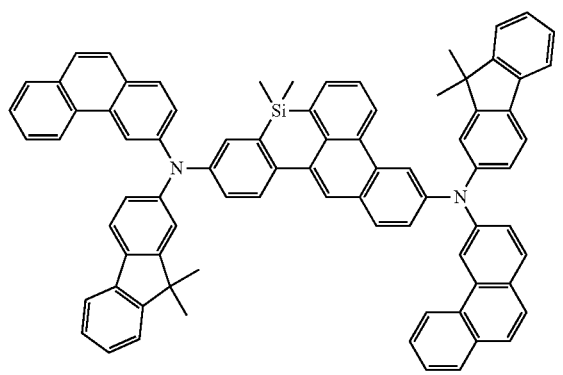
195
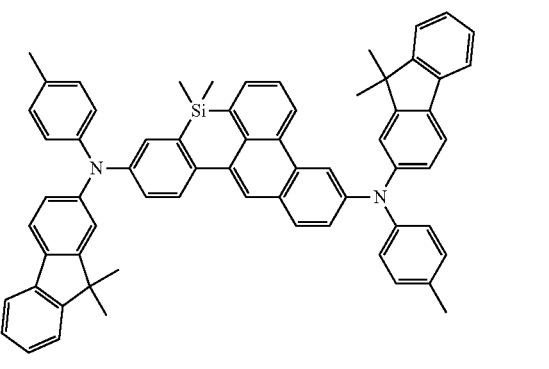

196
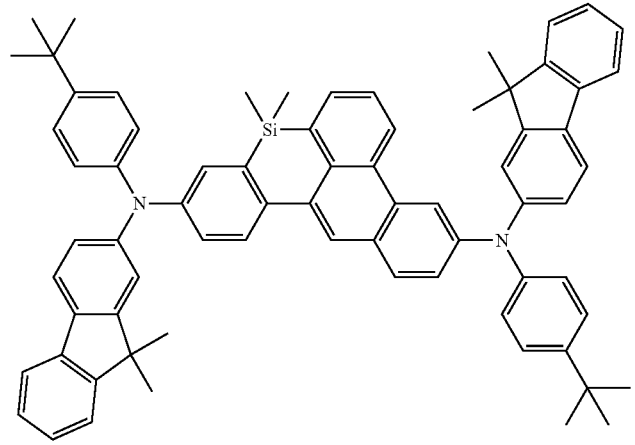
197
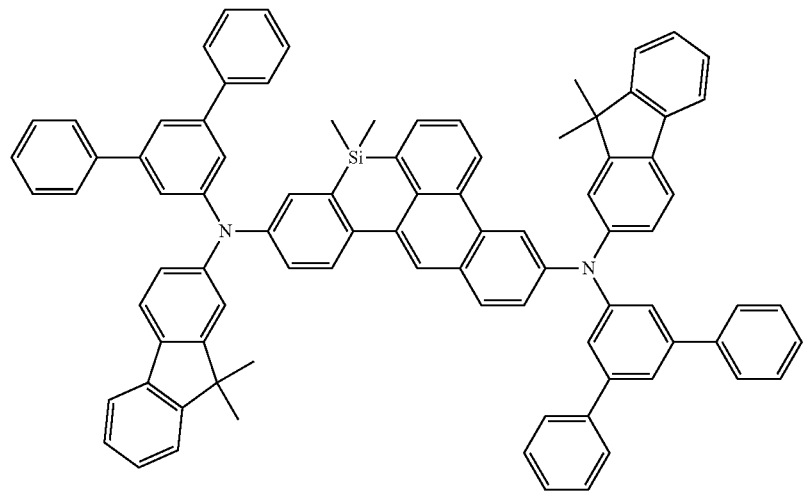
198
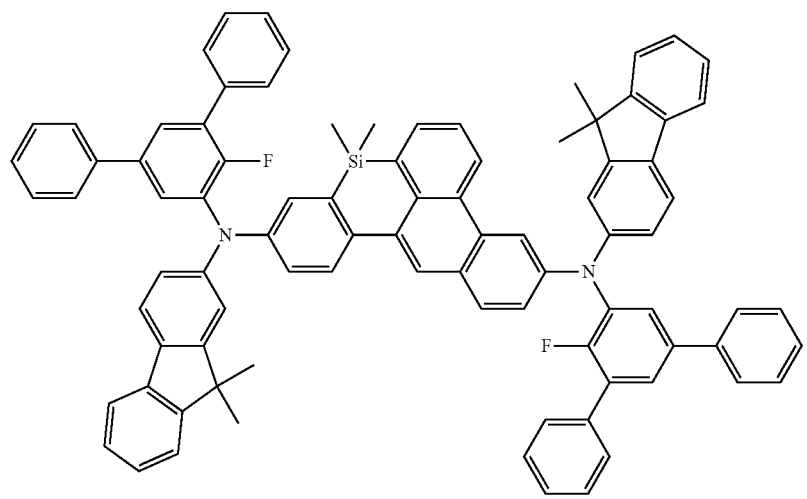

-continued
199
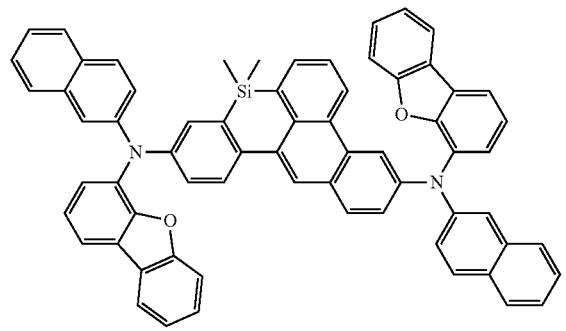
200
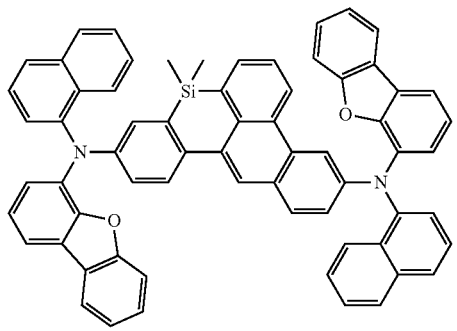
201
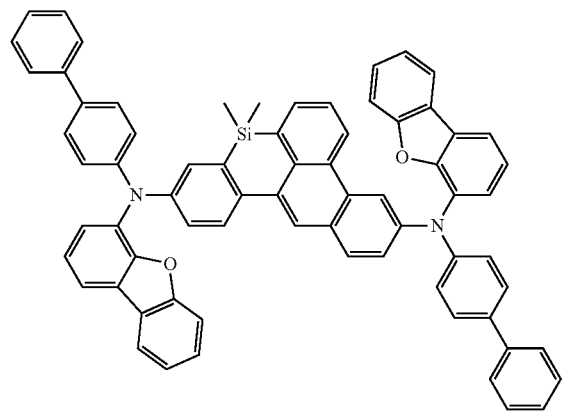
202
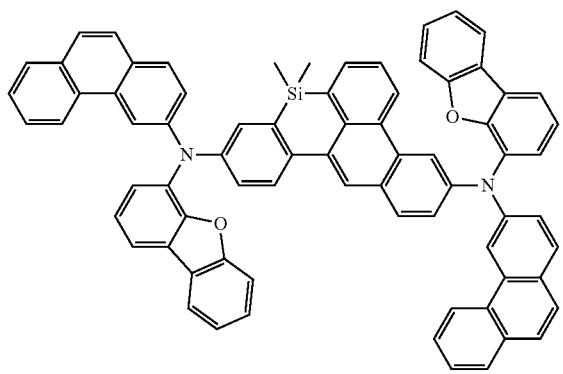
203
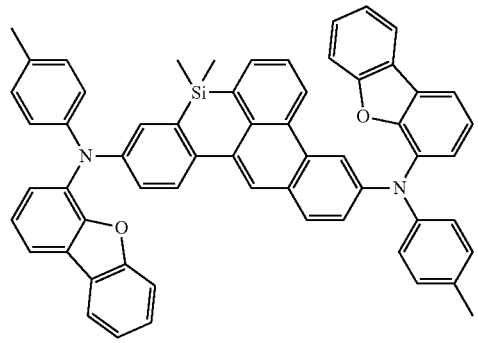
204
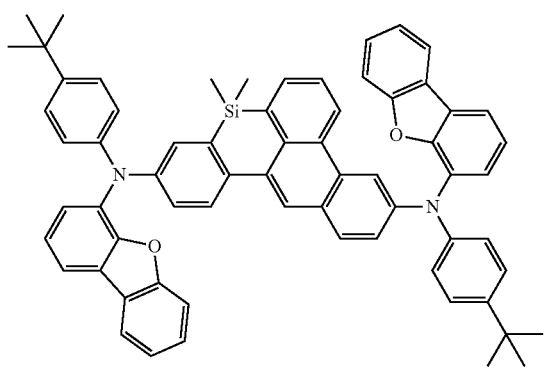
205
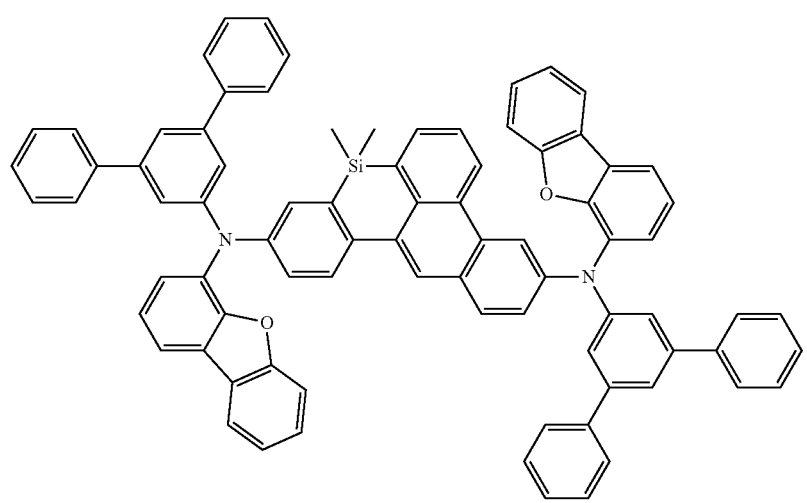

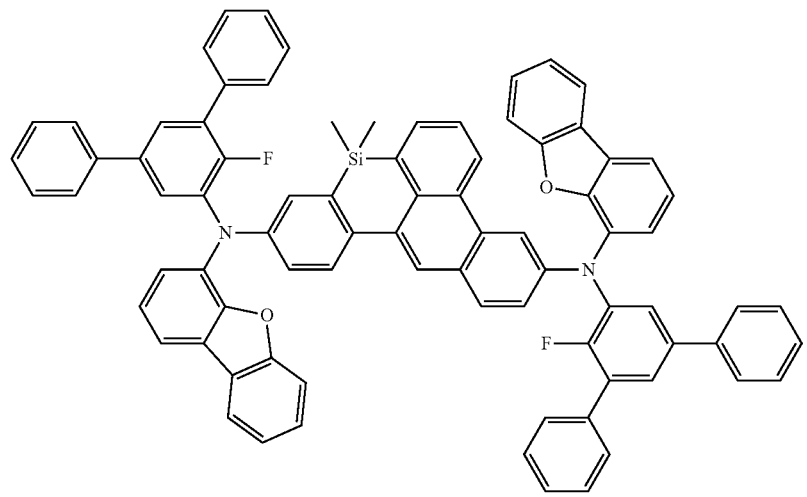
206
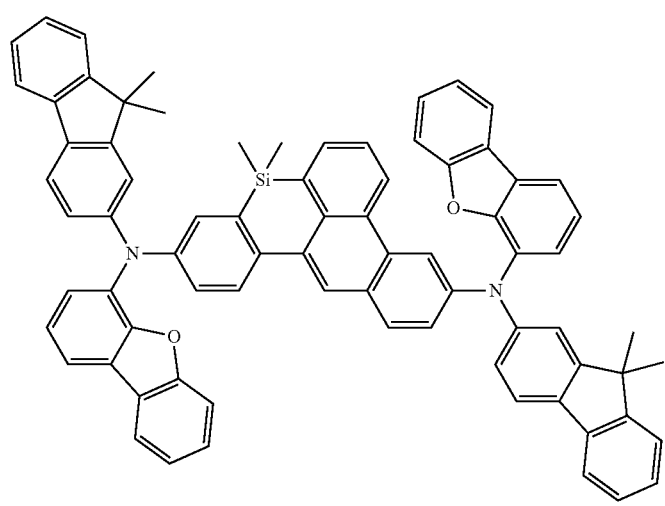
207
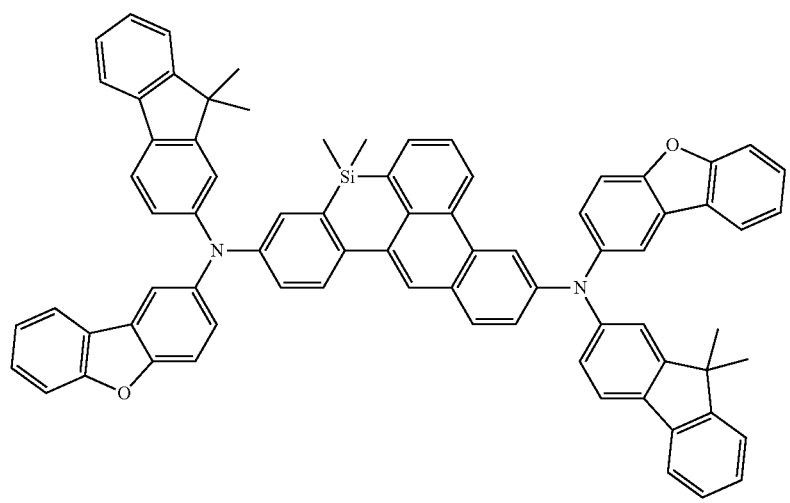
208

-continued
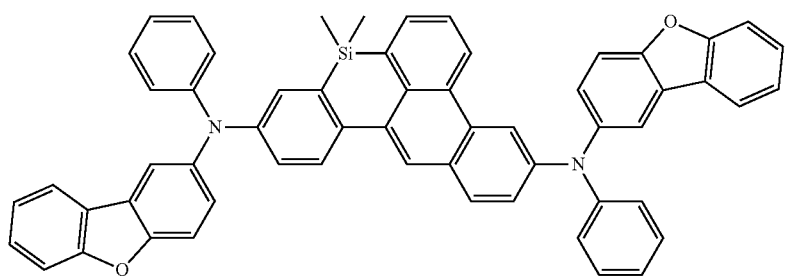
209
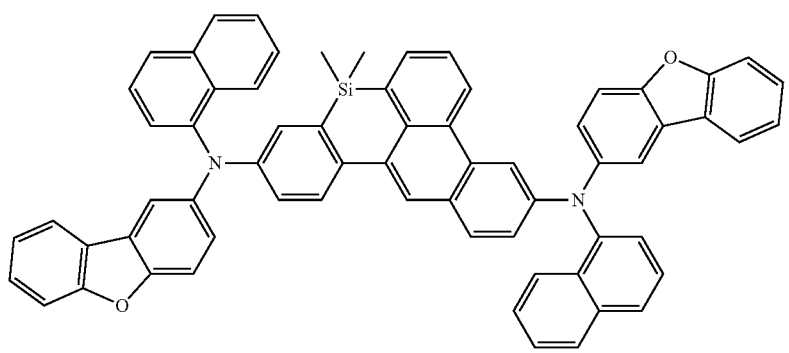
210
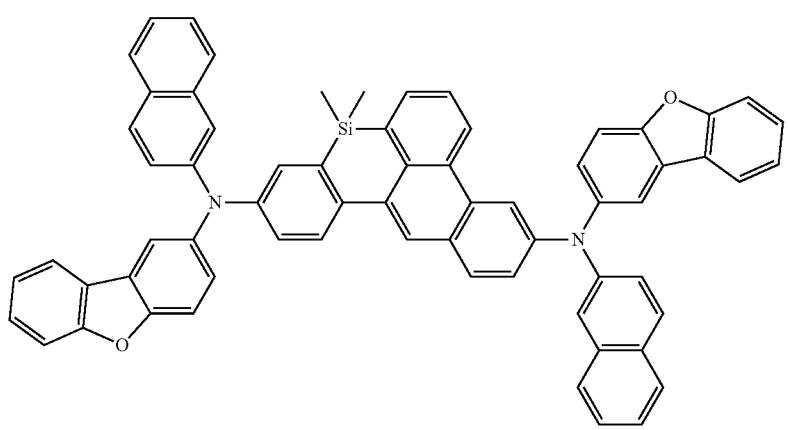
211
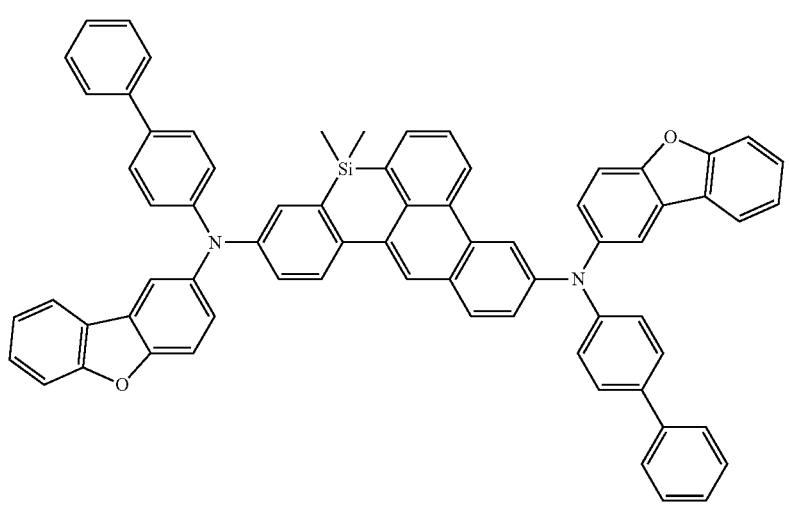
212

-continued
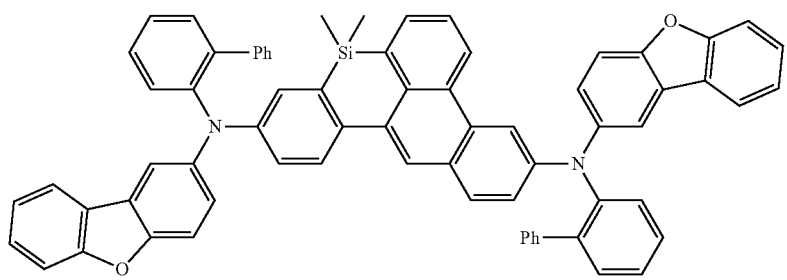
213
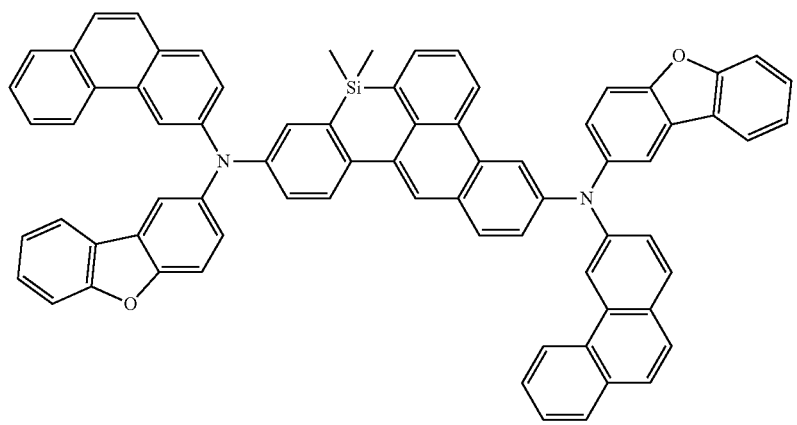
214
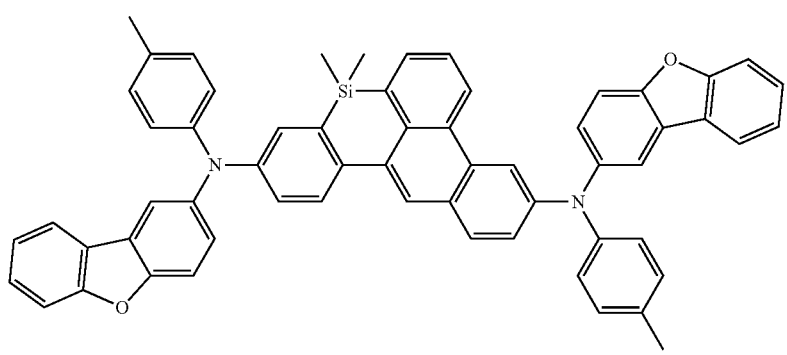
215
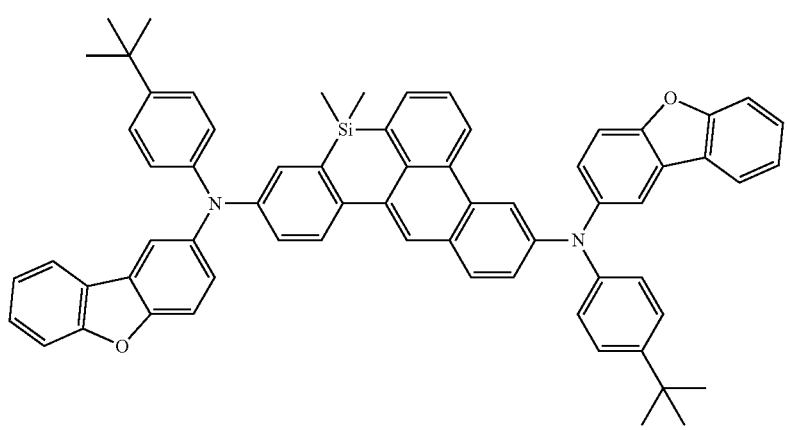
216

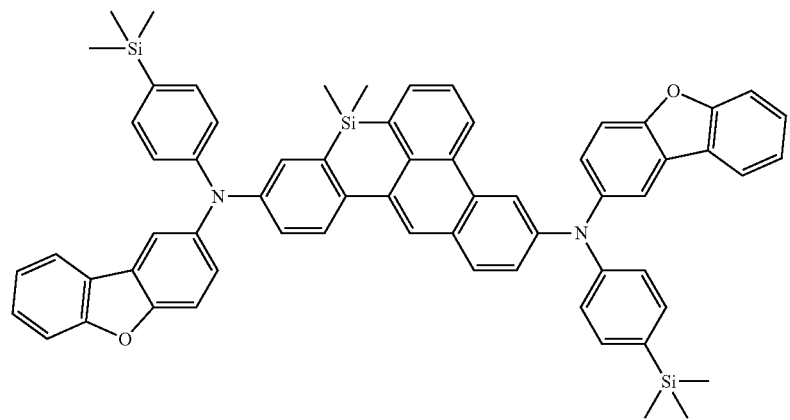
217
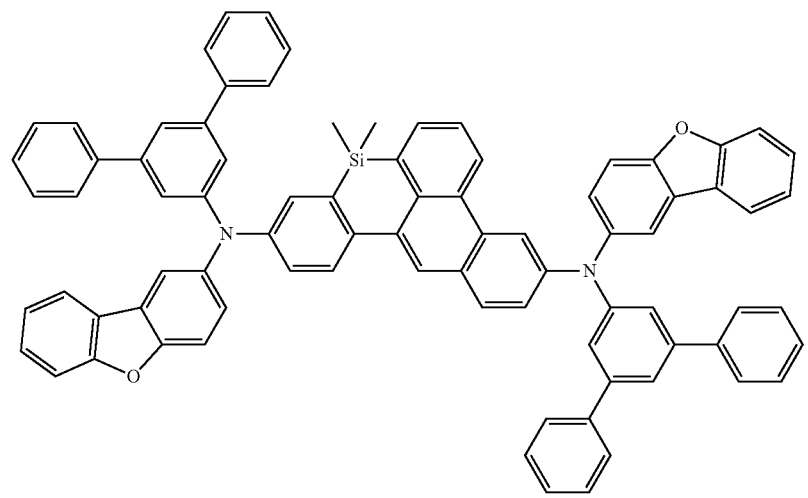
218
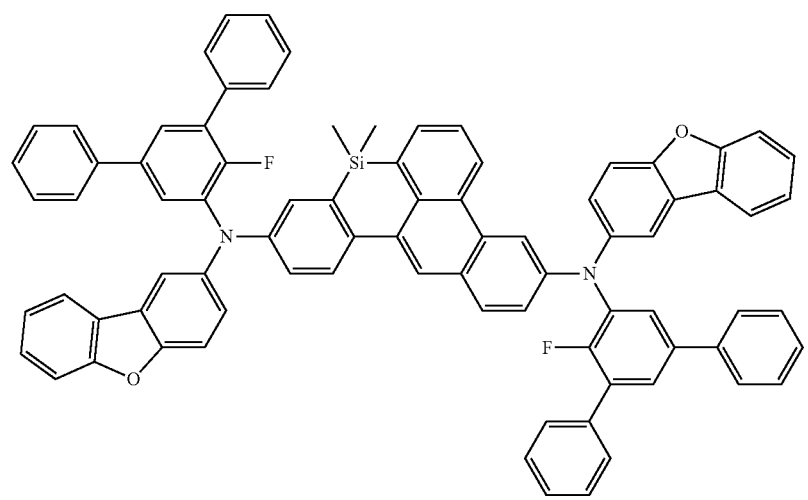
219

-continued
220
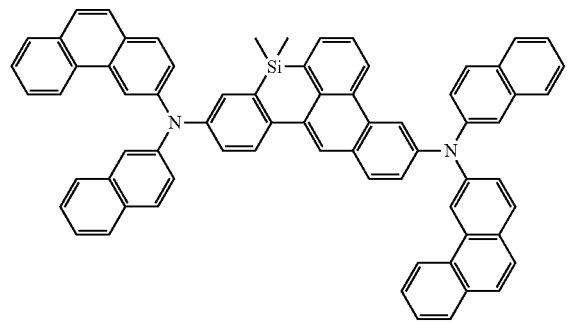
221
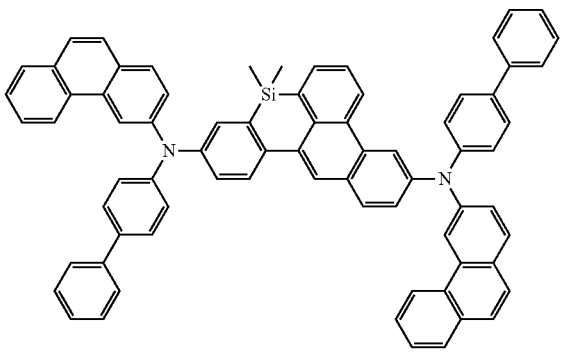
222
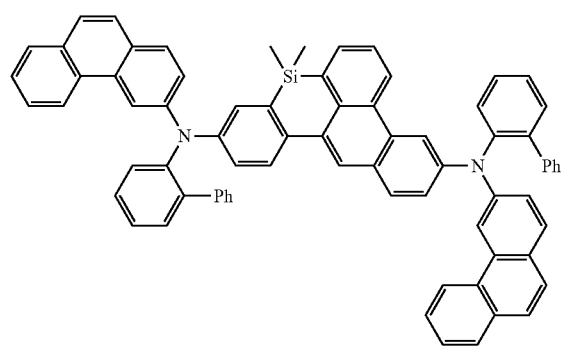
223
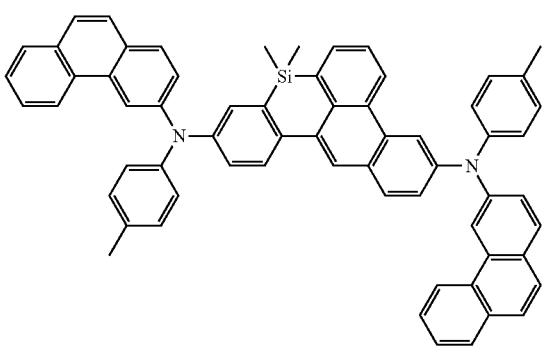
224
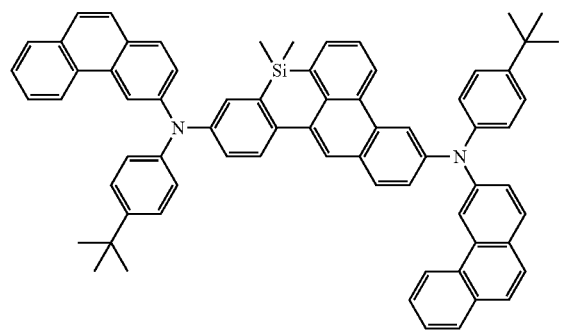
225
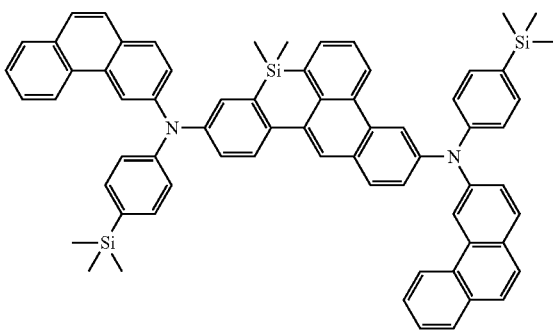
226
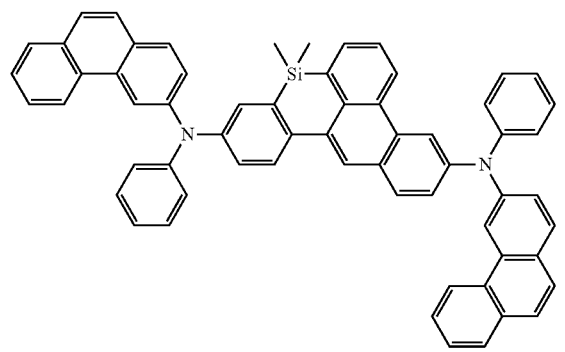
227
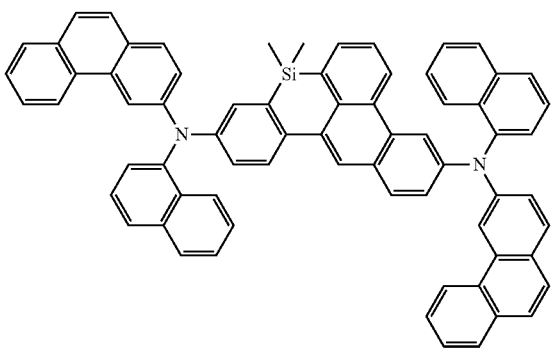

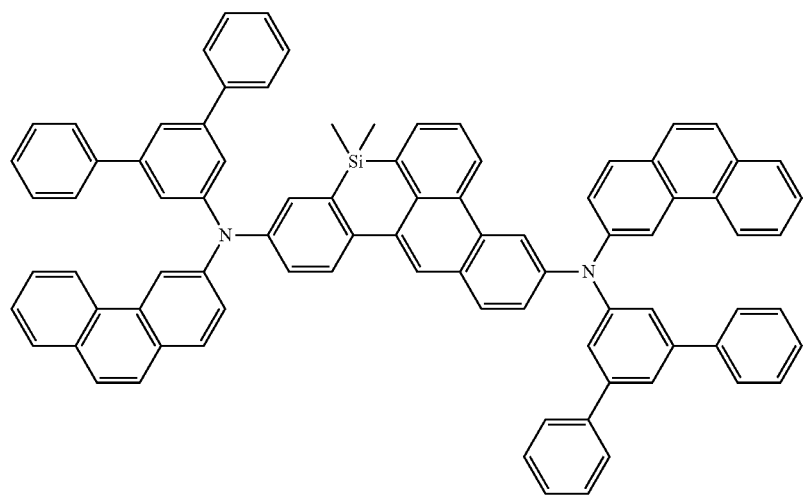
228
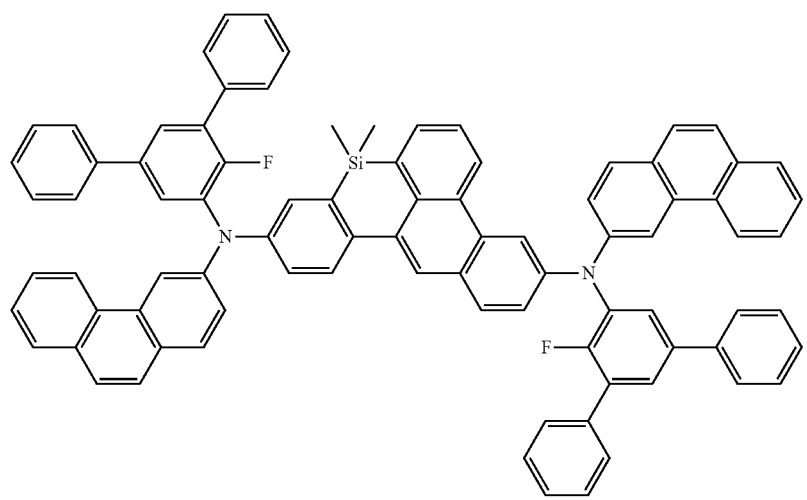
229
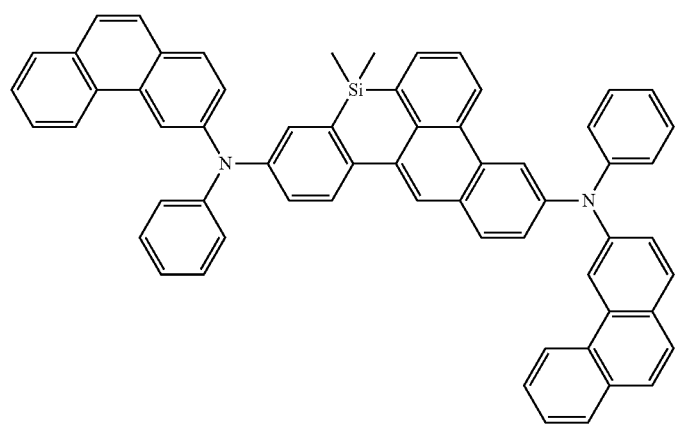
230

-continued
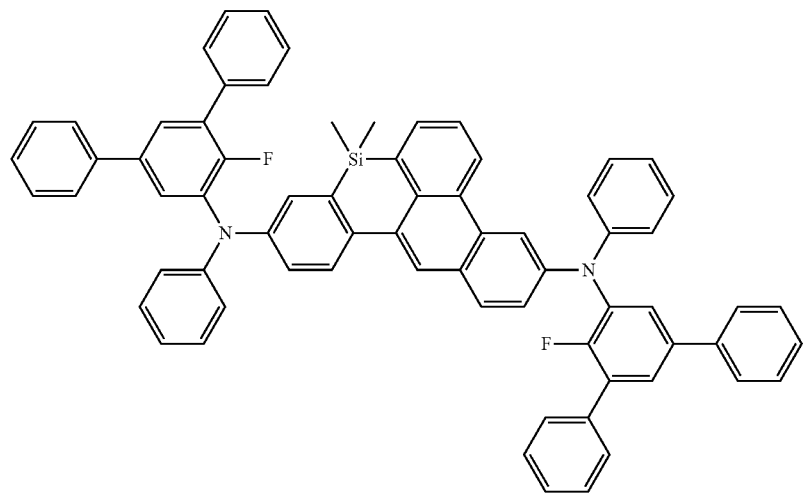
231
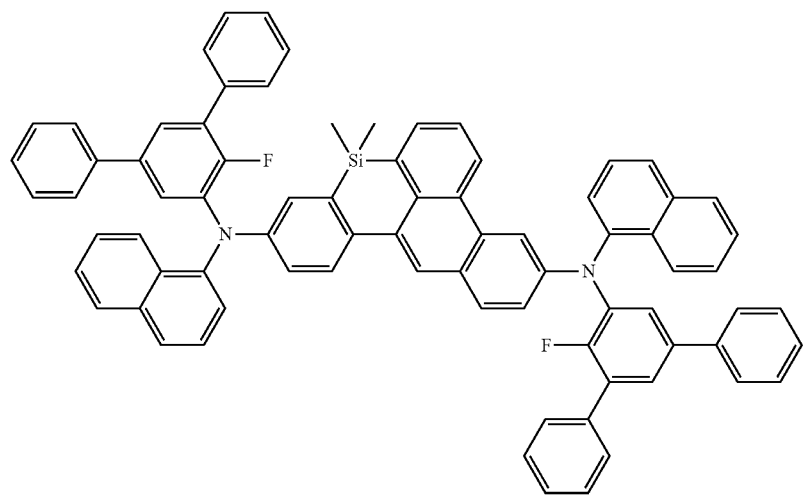
232
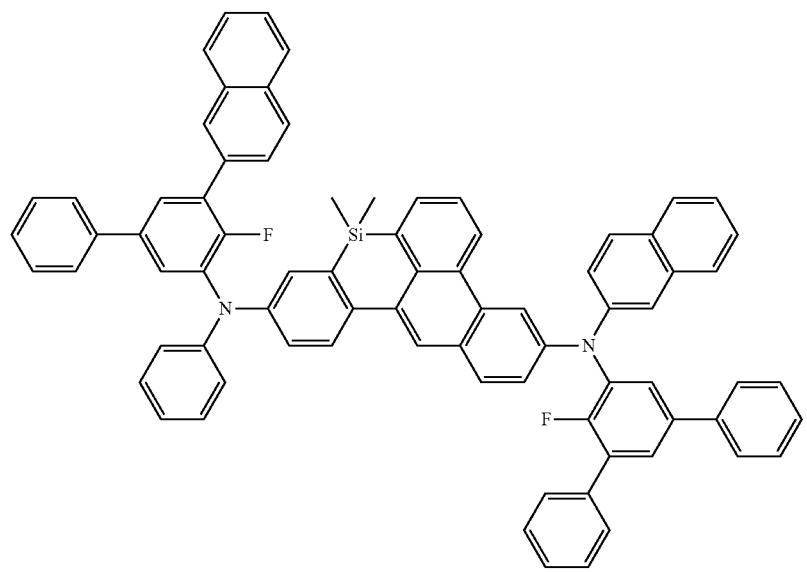
233

234
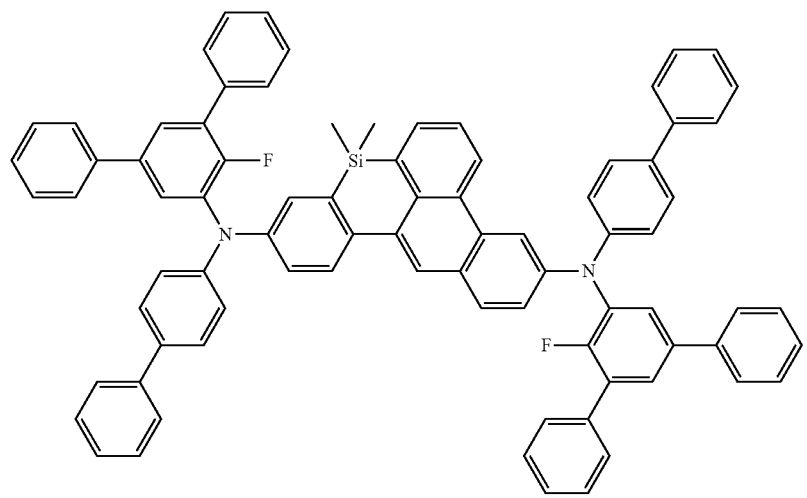
235
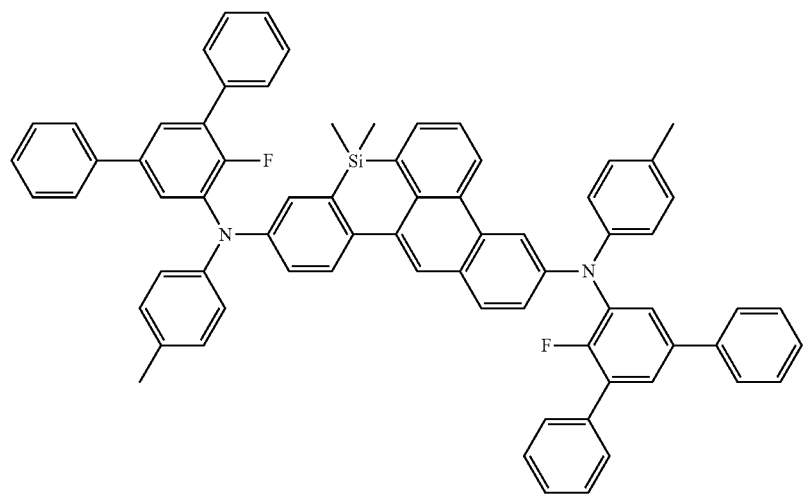
236
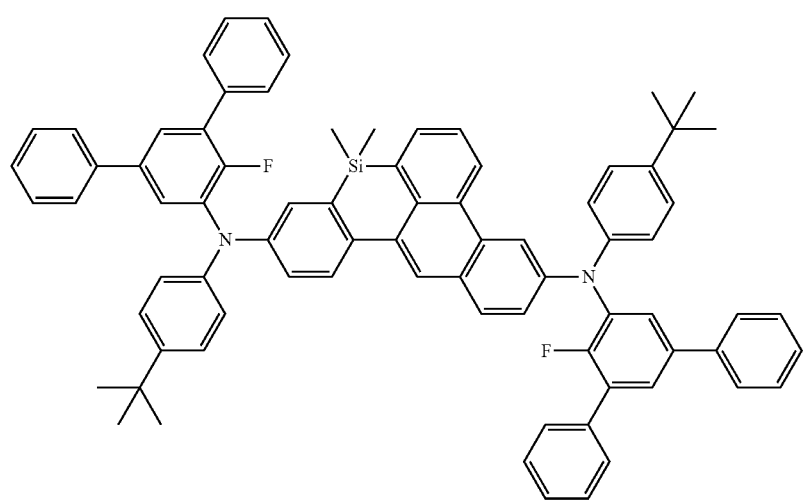

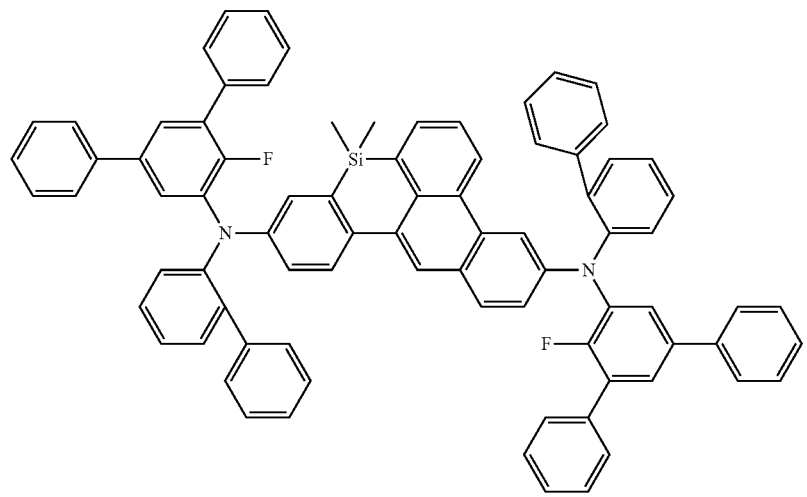
237
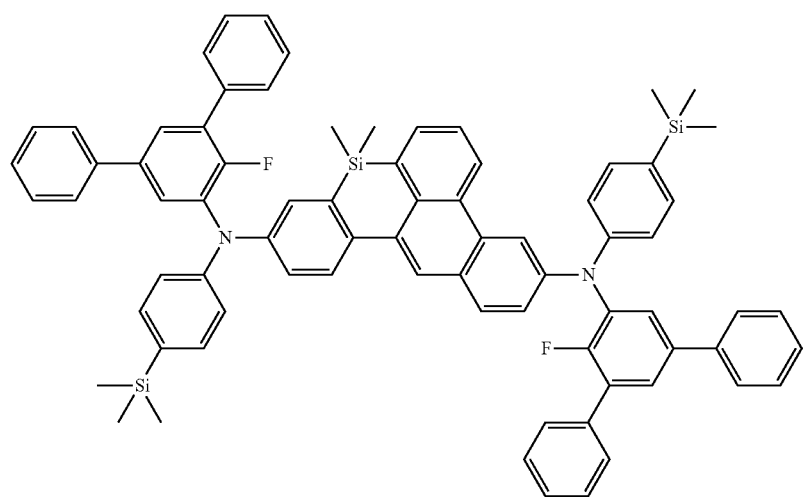
238
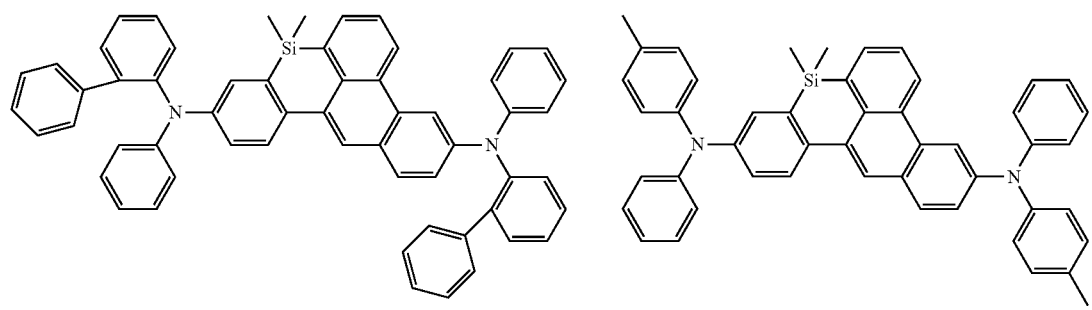
239 240

-continued
241
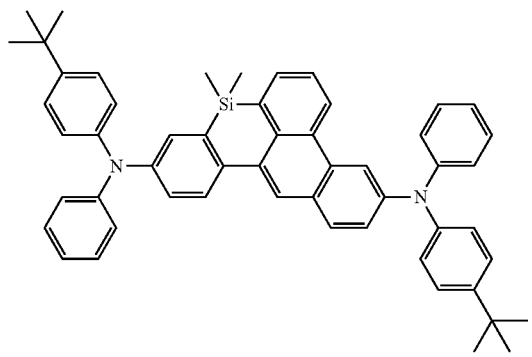
242
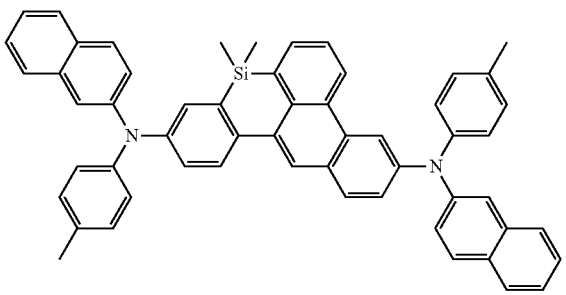
243
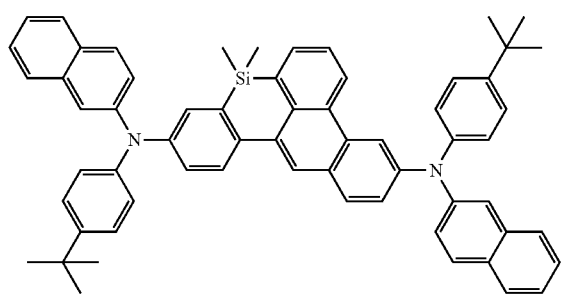
244
245
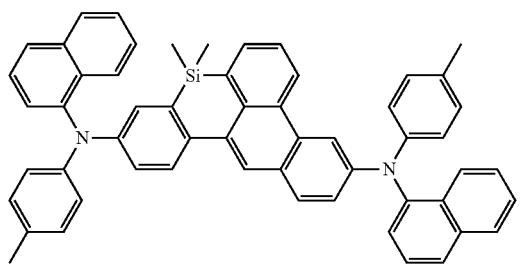
246
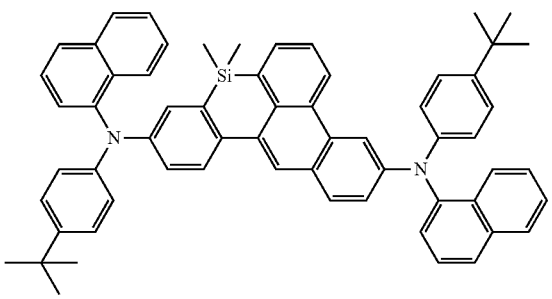
247
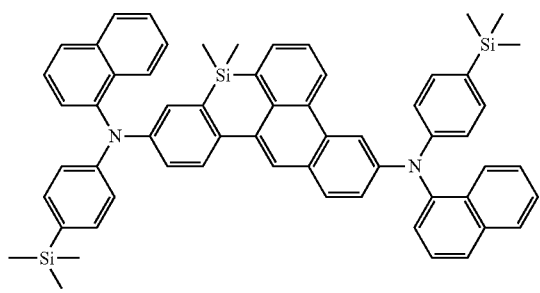
248
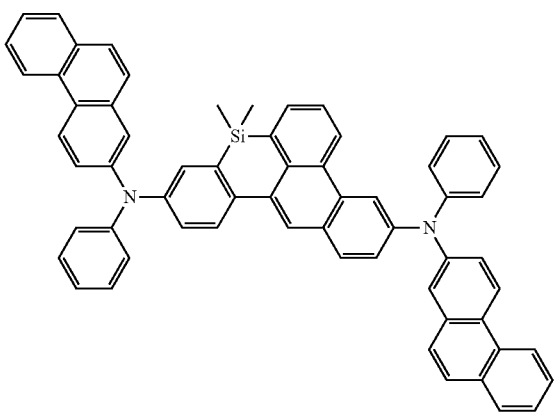

527
249
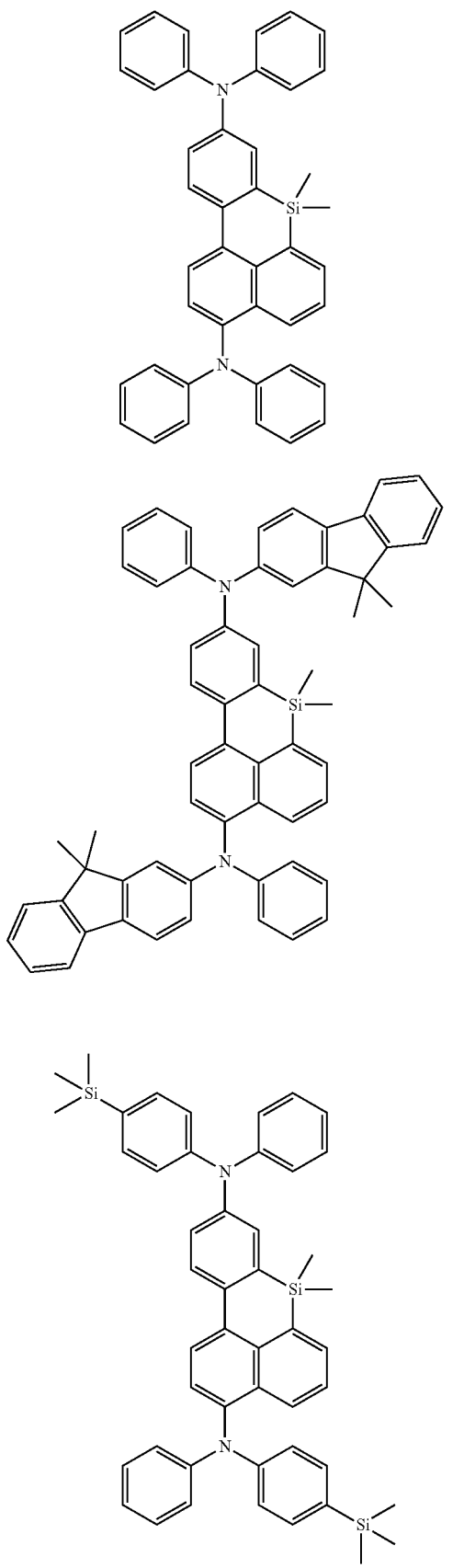
250
251
528
-continued
252
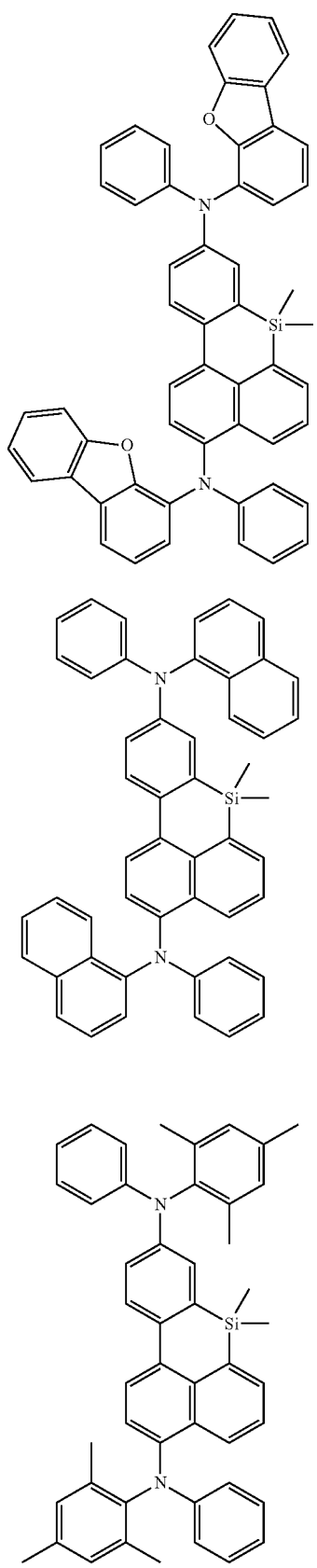
253
254

529
-continued
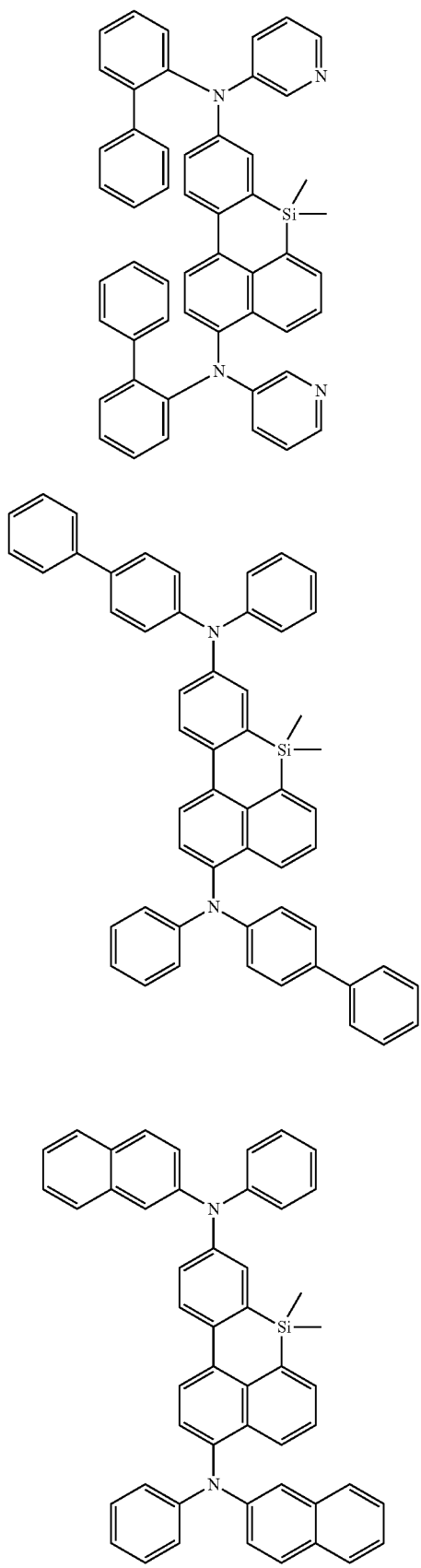
530
-continued
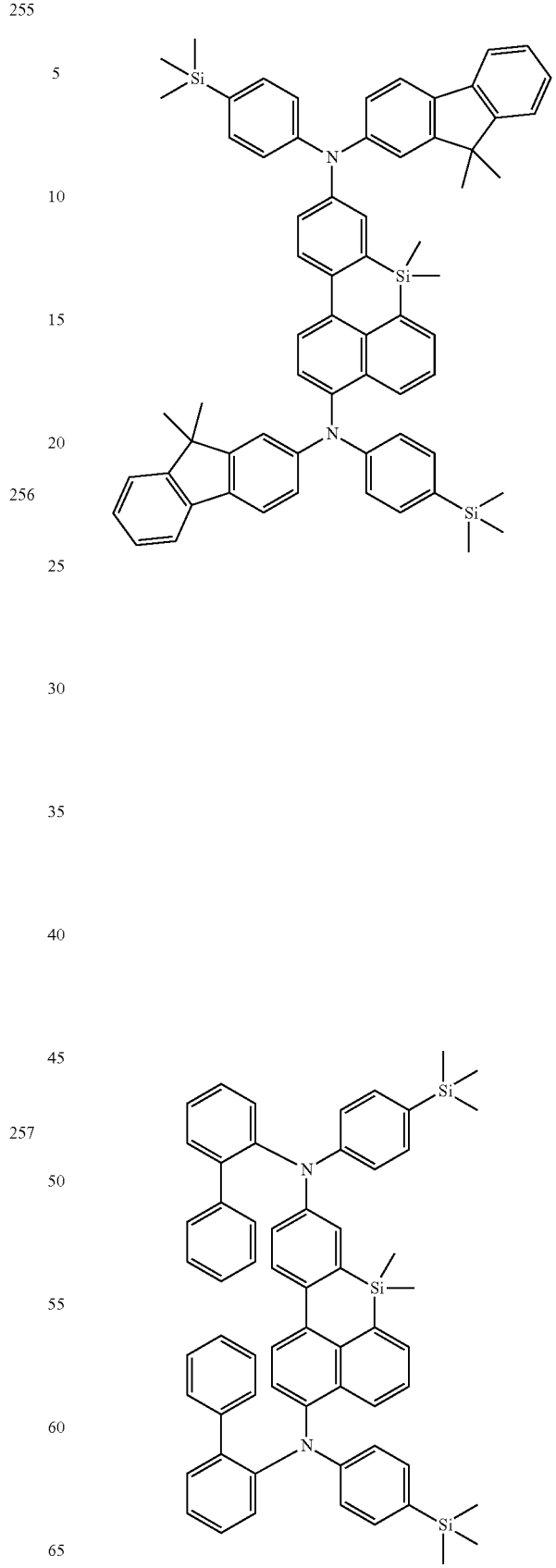

531-continued
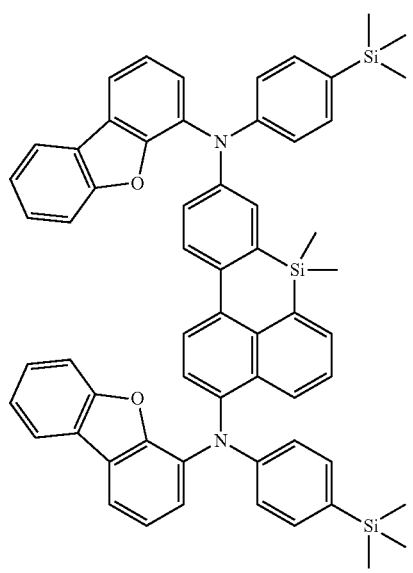
260
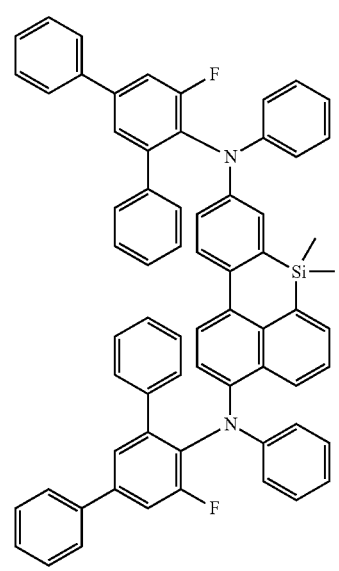
261
532-continued
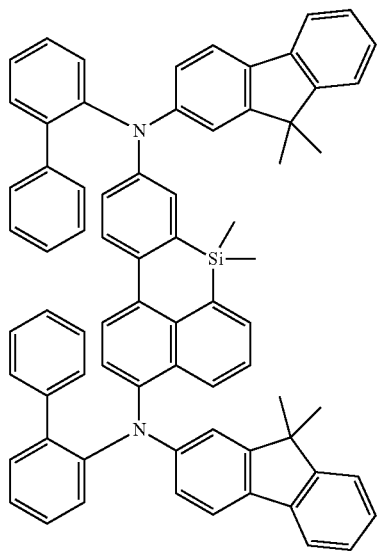
262
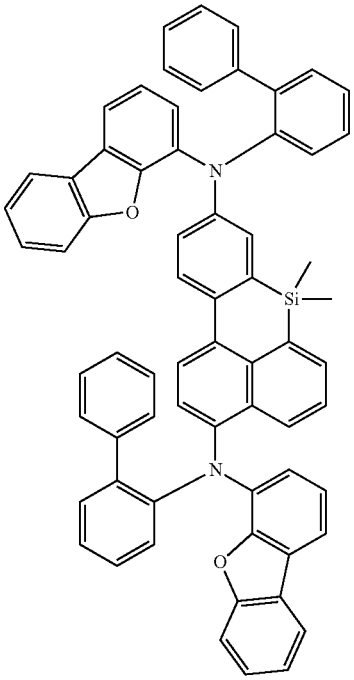
263

533
-continued
534
-continued
264
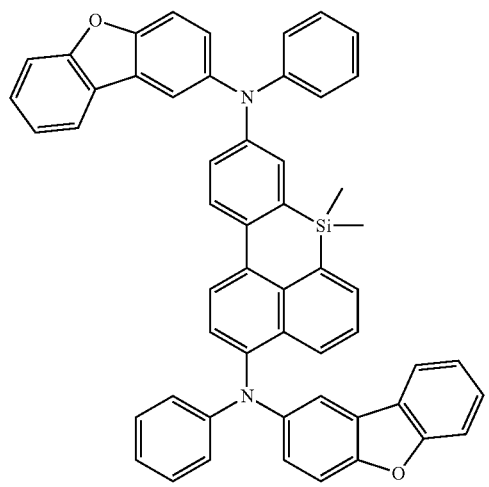
265
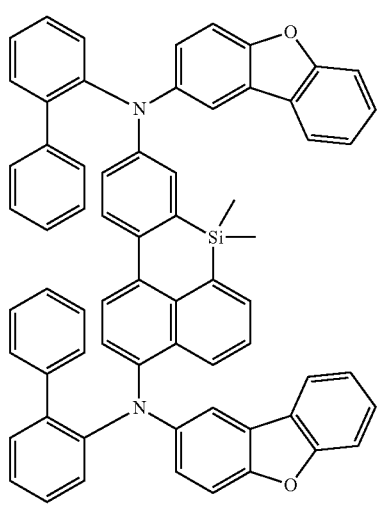
266
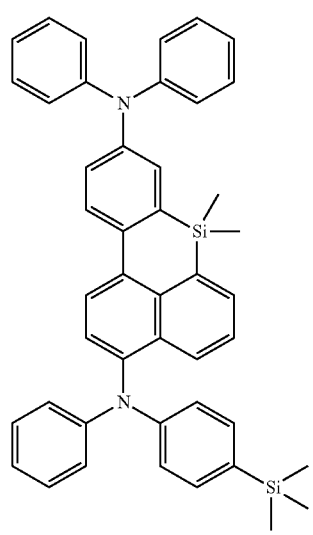
267
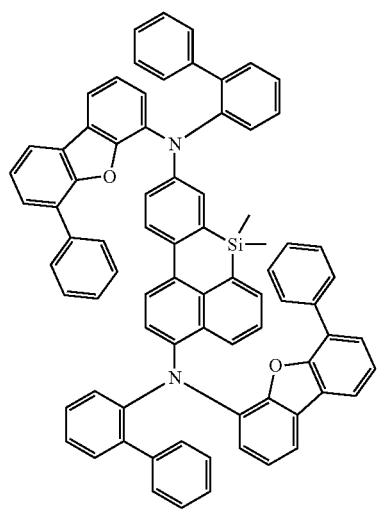
268
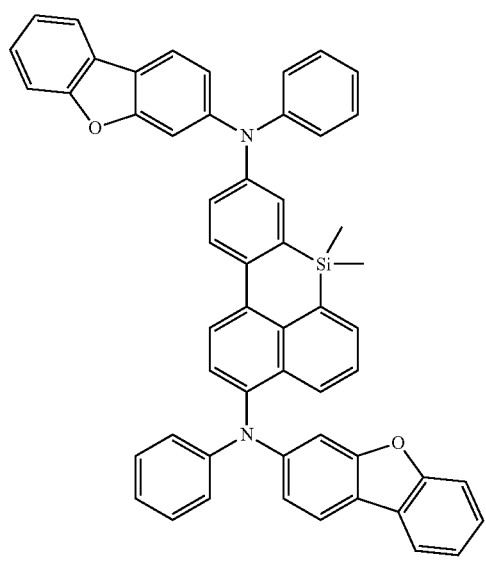
269
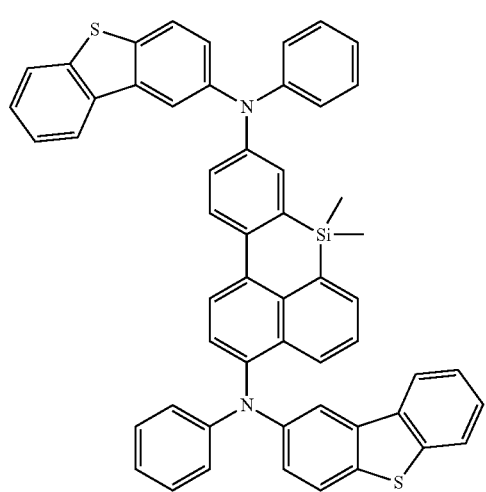

535
-continued
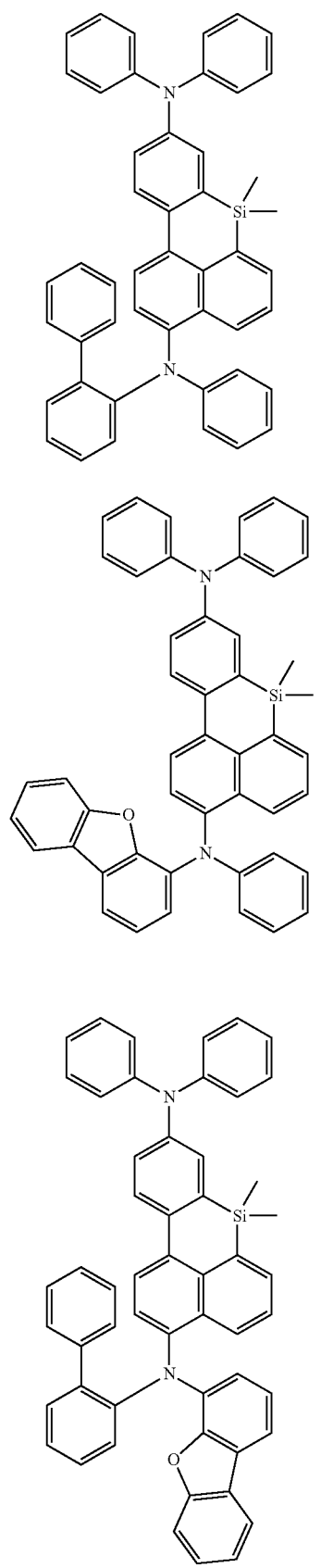
270
271
272
536
-continued
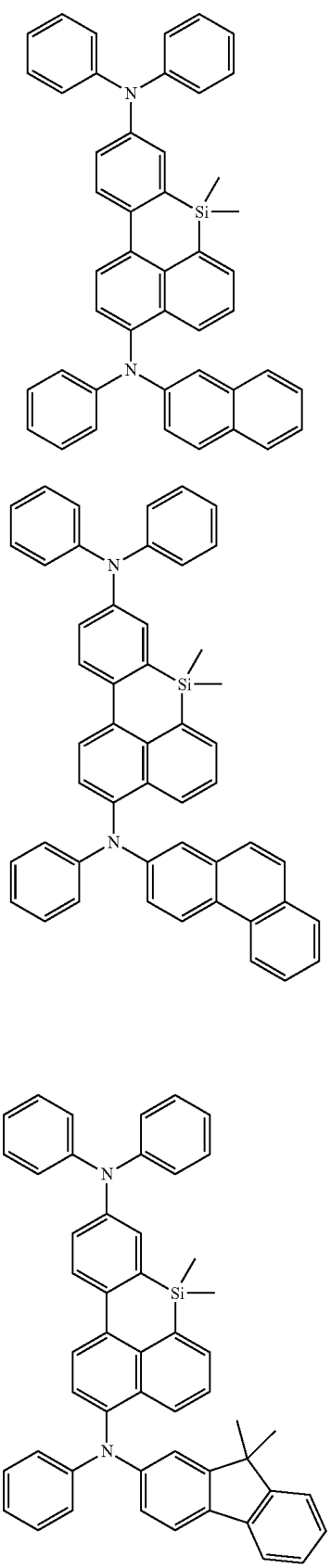
273
274
275

537
-continued
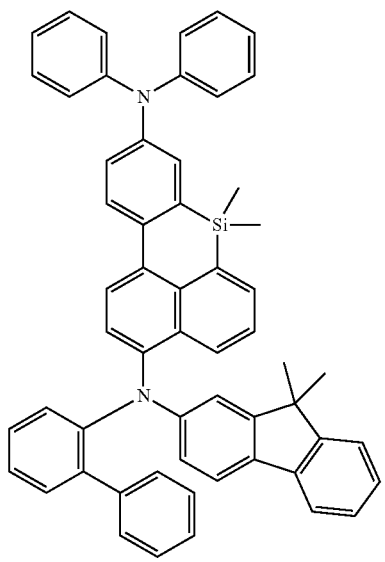
276
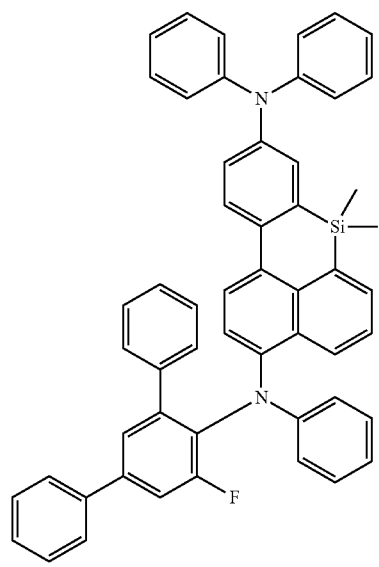
277
538
-continued
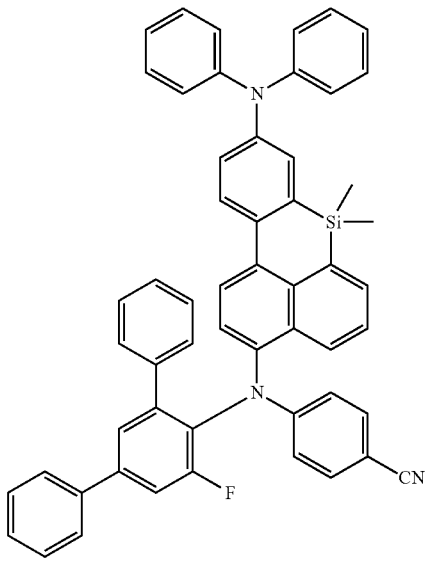
278
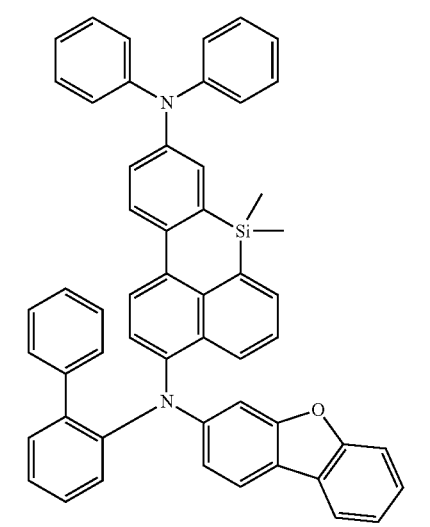
279
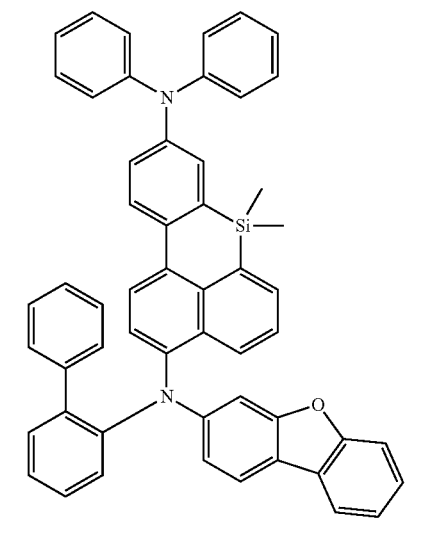
280

539
-continued
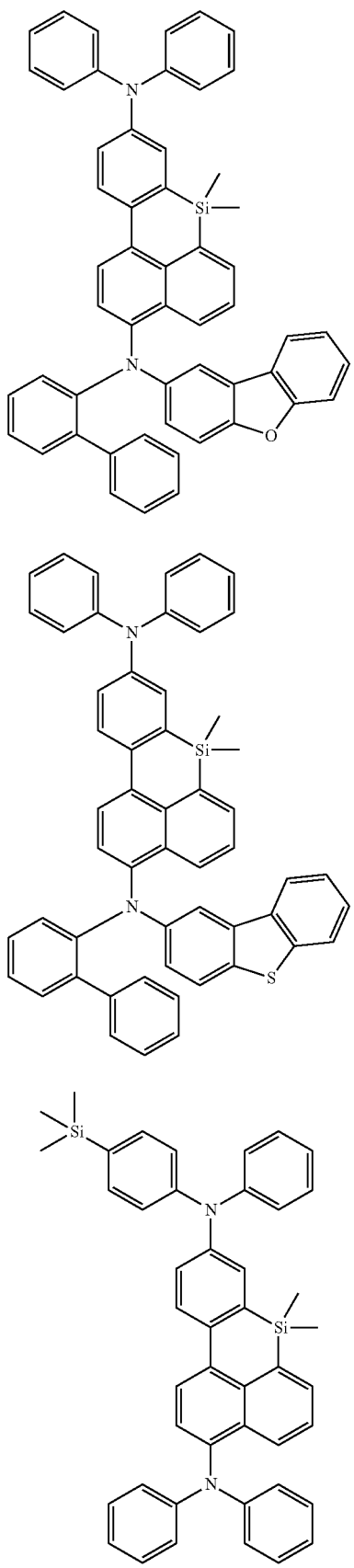
540
-continued
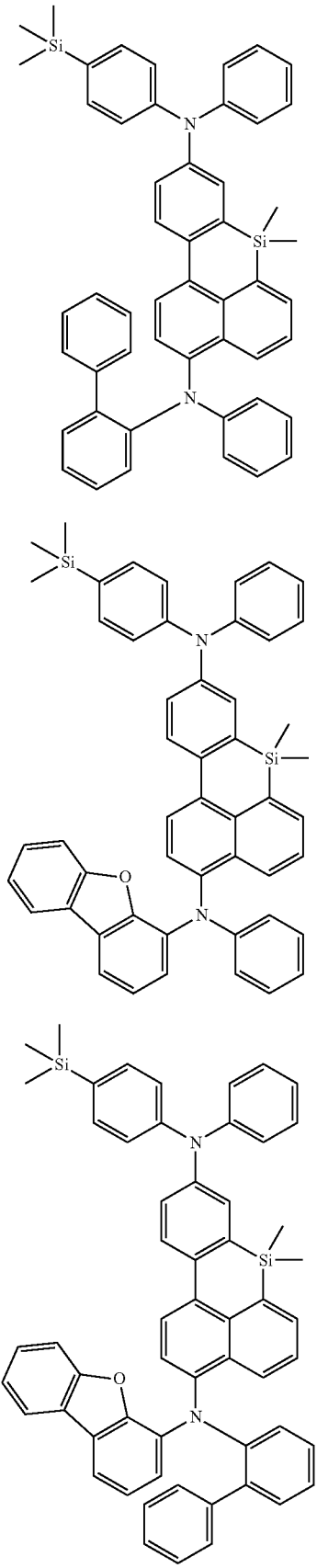

541
-continued
542
-continued
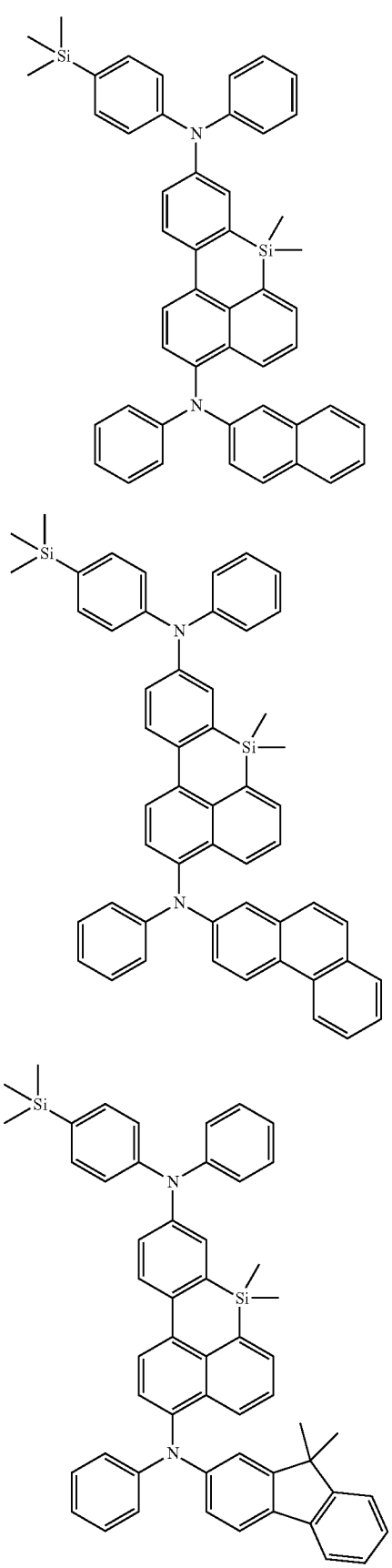
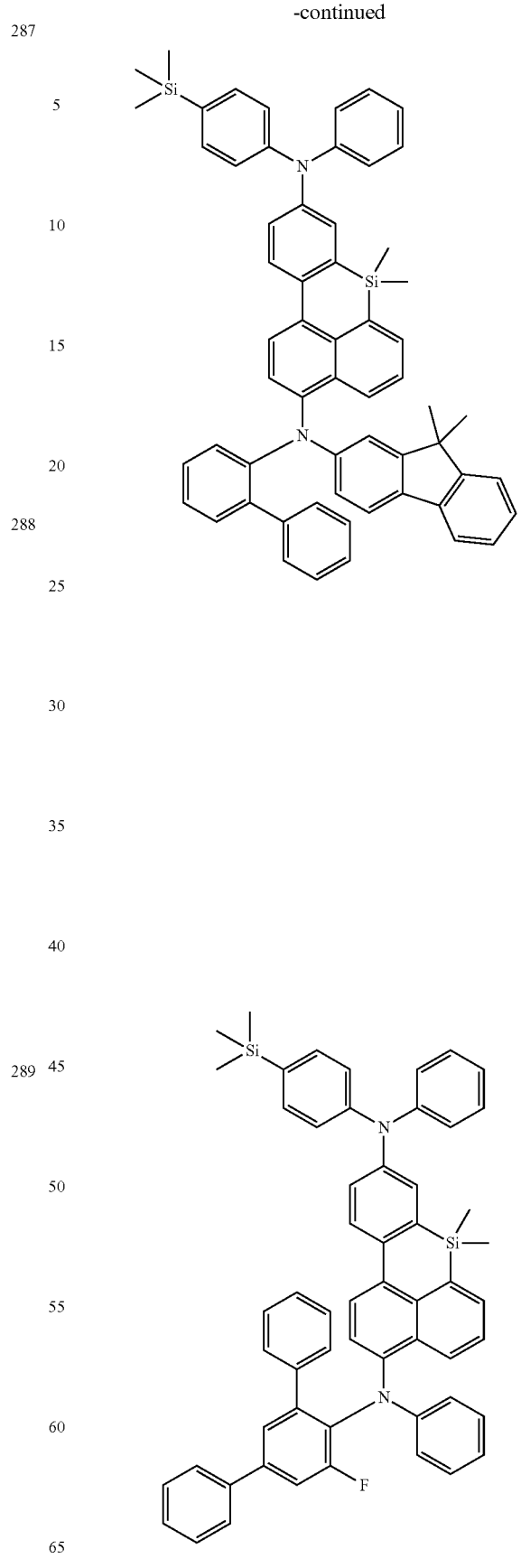

543
-continued
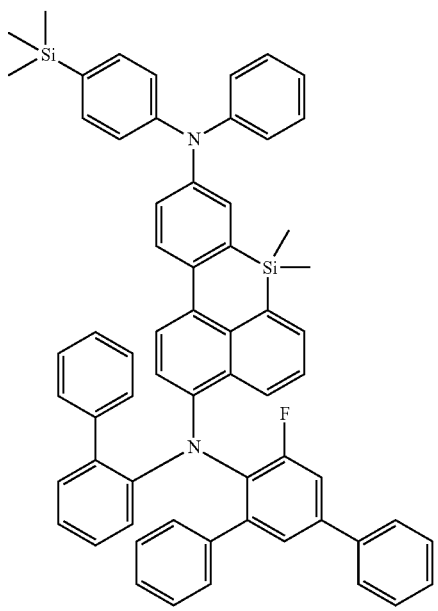
292
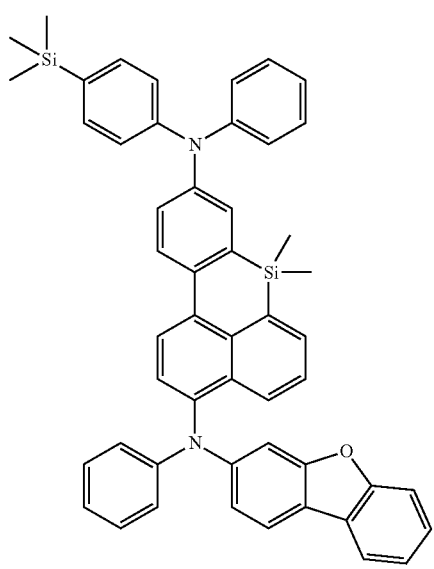
293
544
-continued
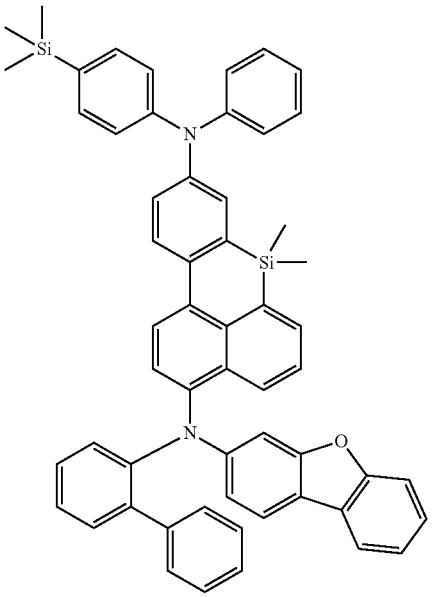
294
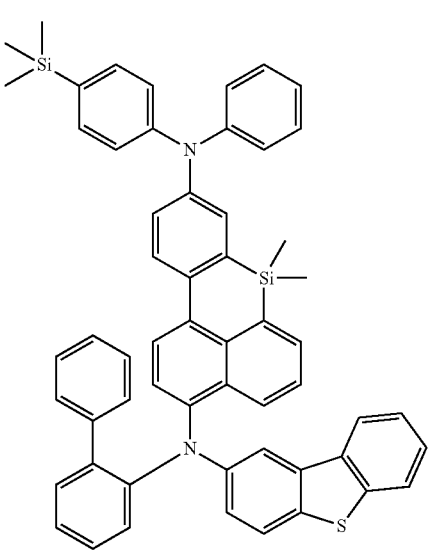
295
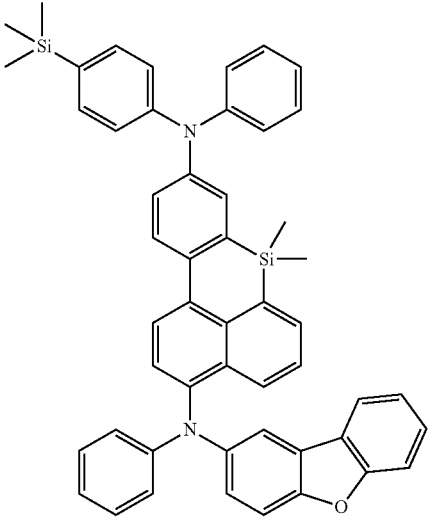
296

297
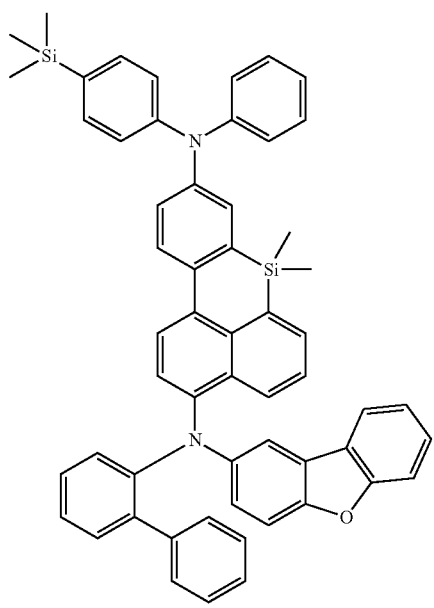
298
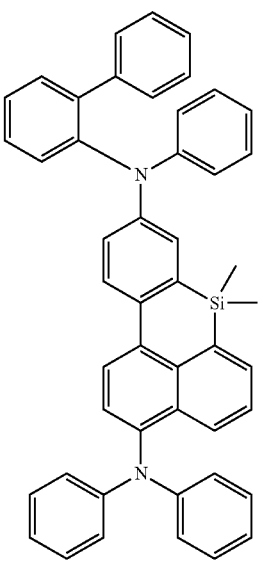
299
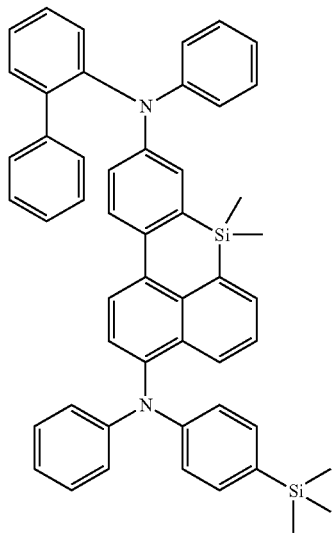
300
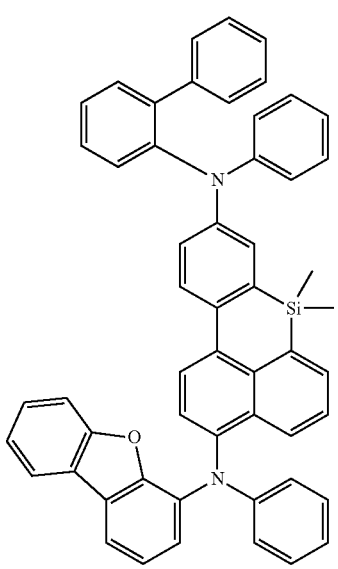

547
-continued
548
-continued
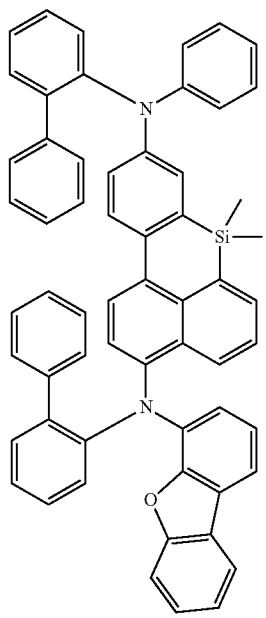
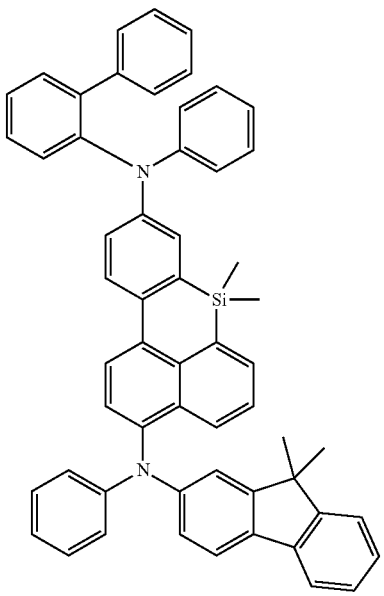

306
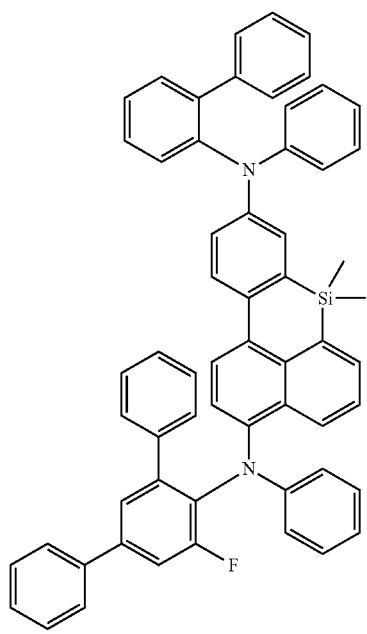
307
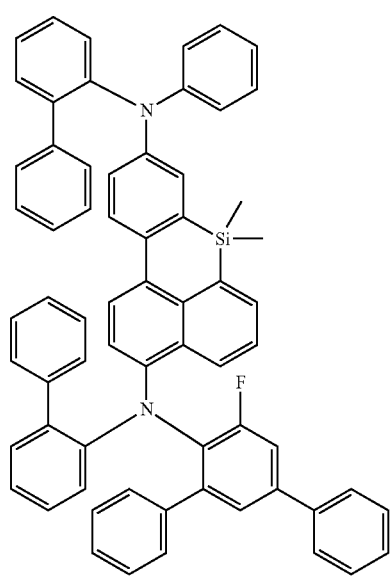
308
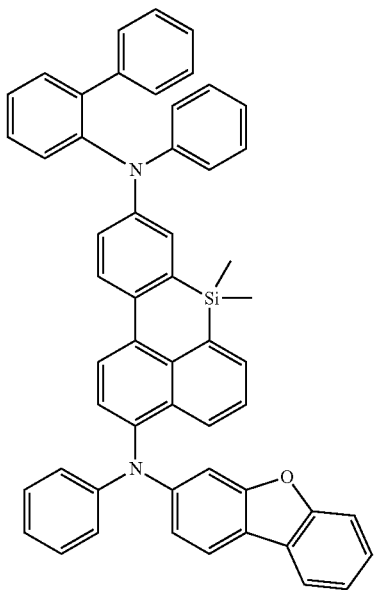
309
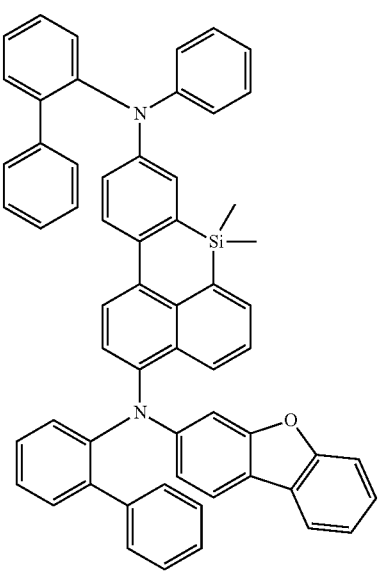

551
-continued
552
-continued
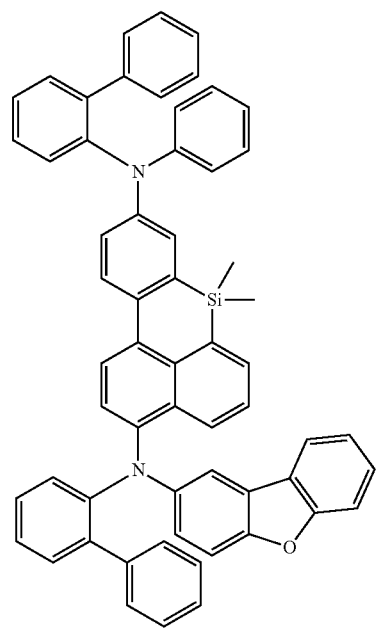
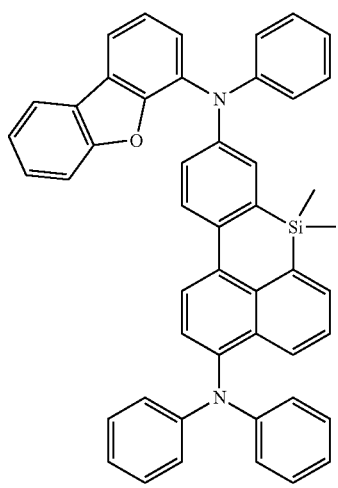
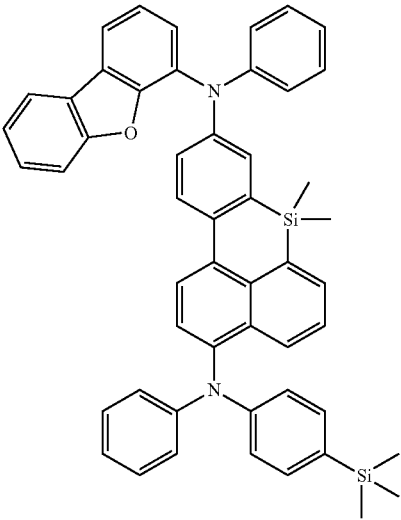

553
-continued
315
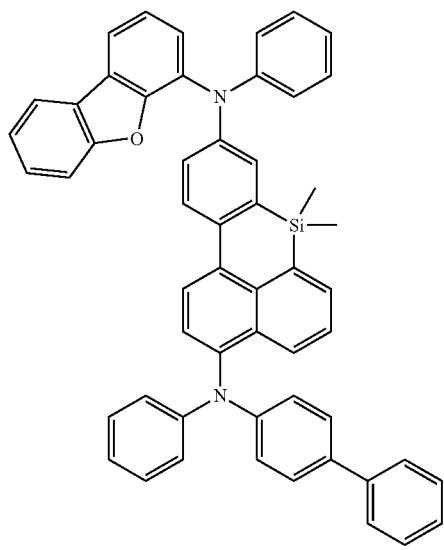
316
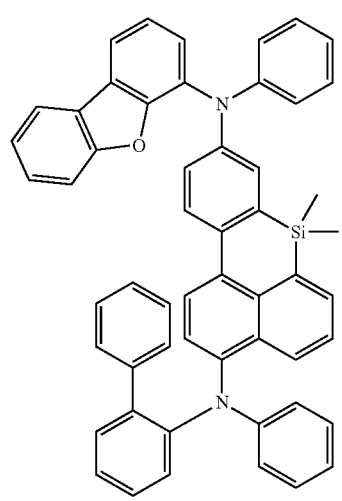
317
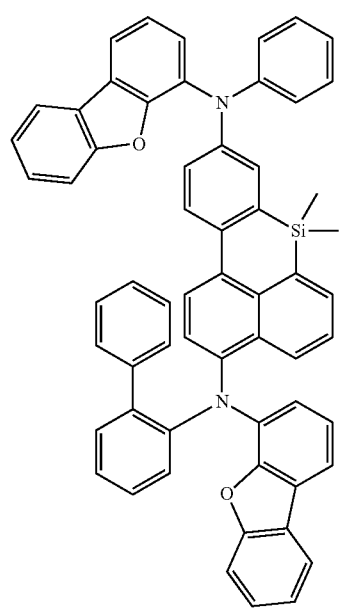
554
-continued
318
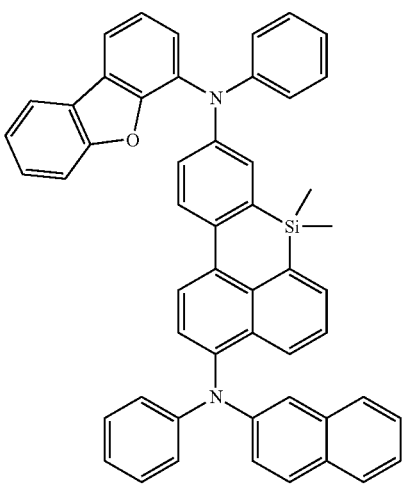
319
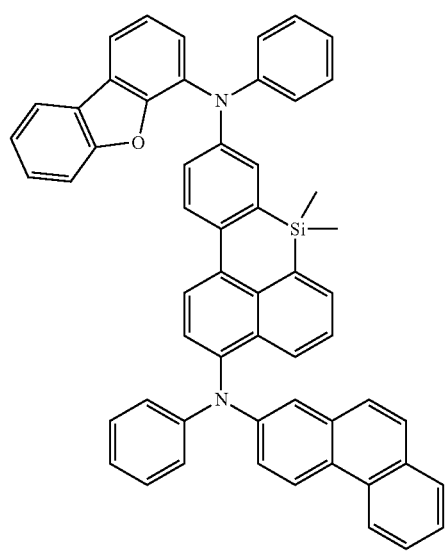
320
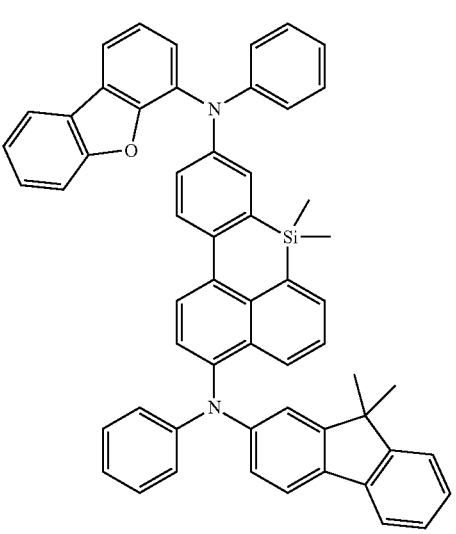

555
-continued
321
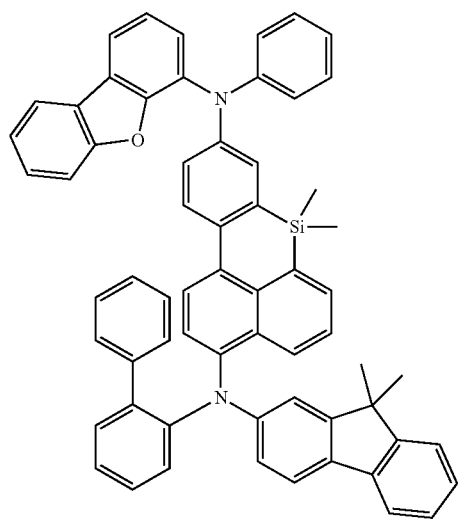
322
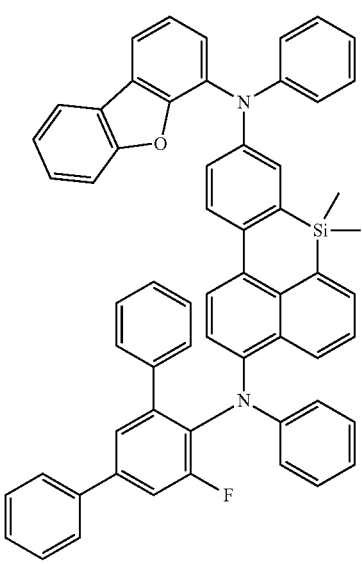
323
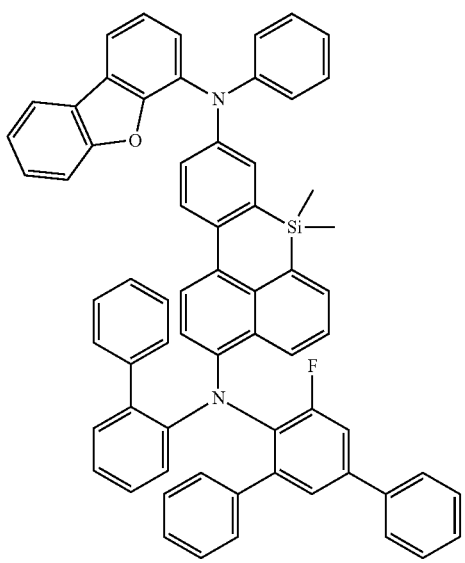
556
-continued
324
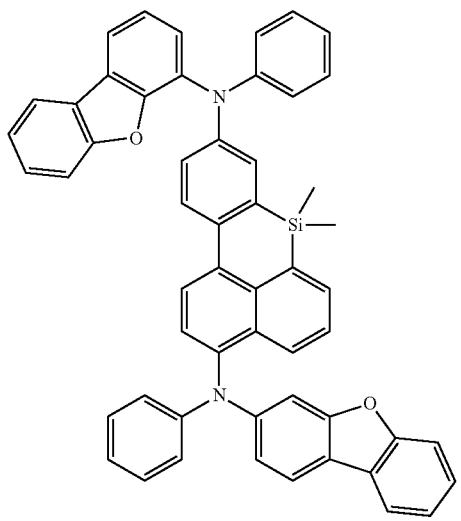
325
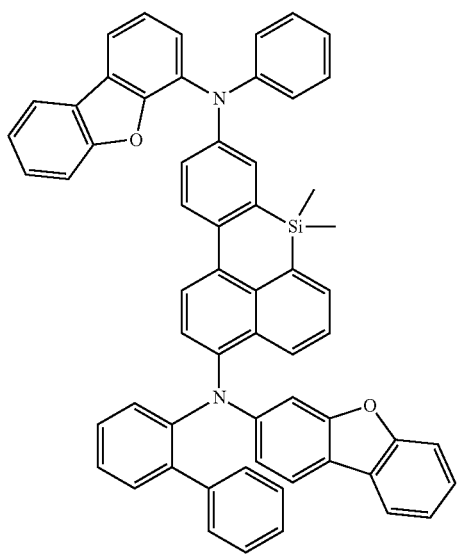
326
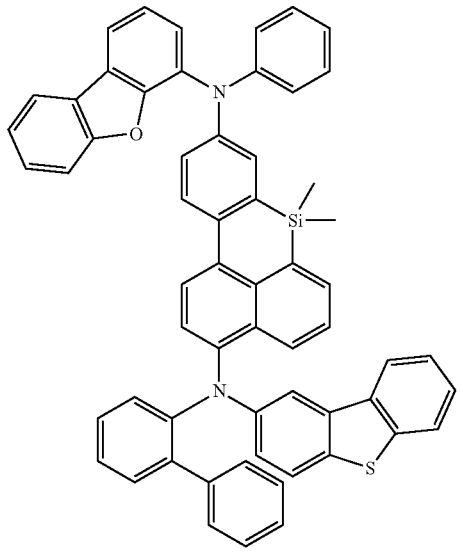

557
-continued
327
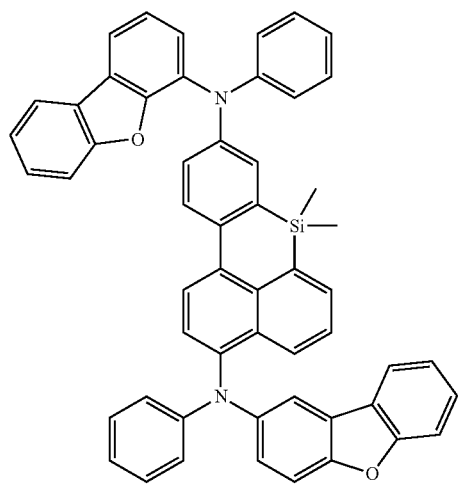
328
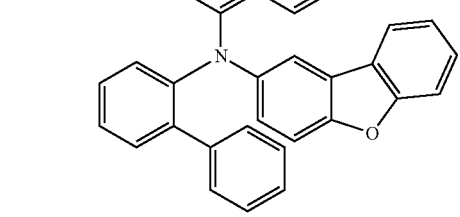
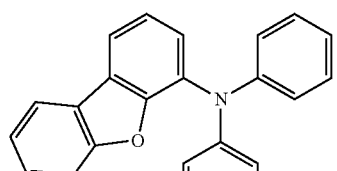
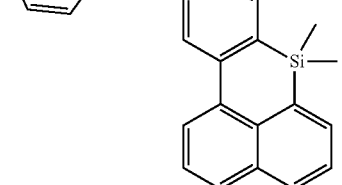
329
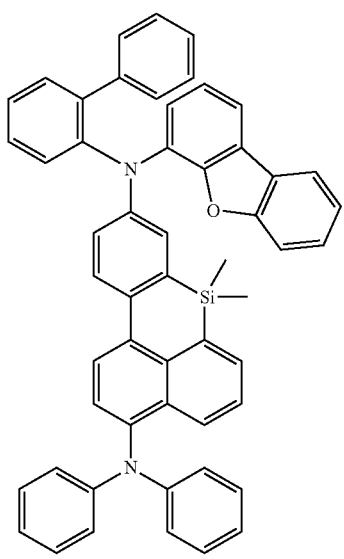
558
-continued
330
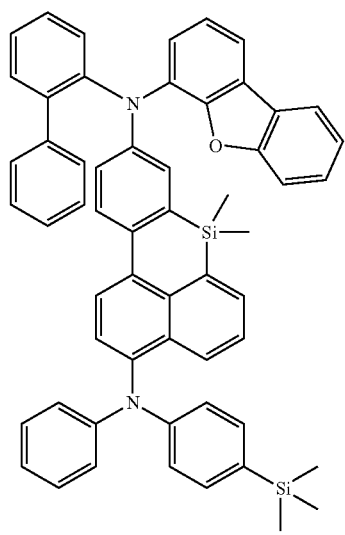
331
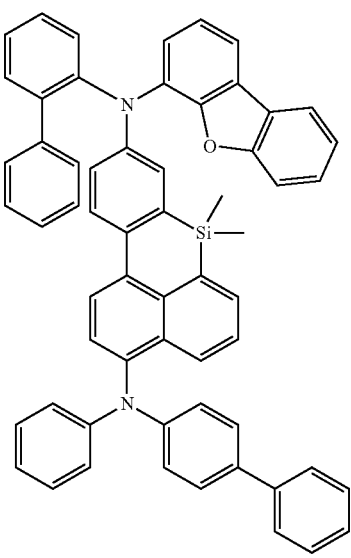

559
-continued
332
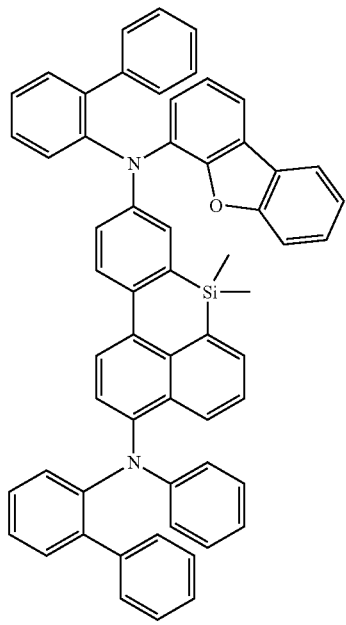
333
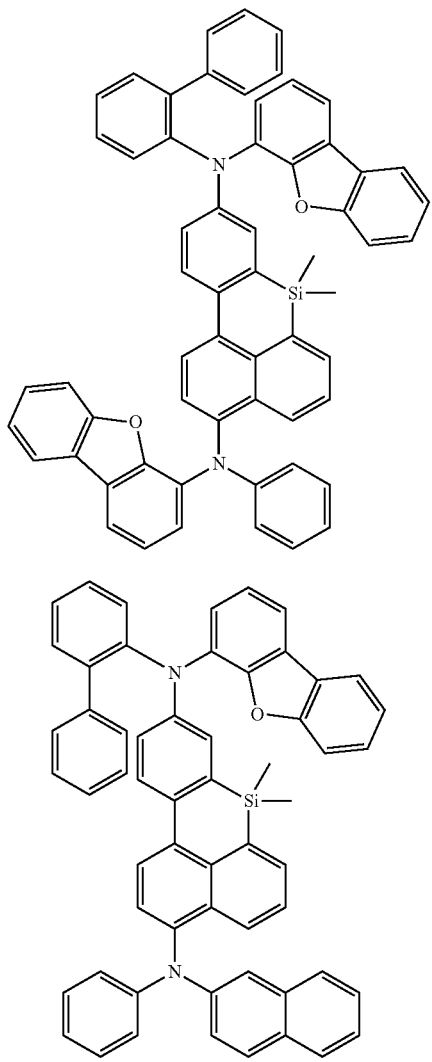
560
-continued
335
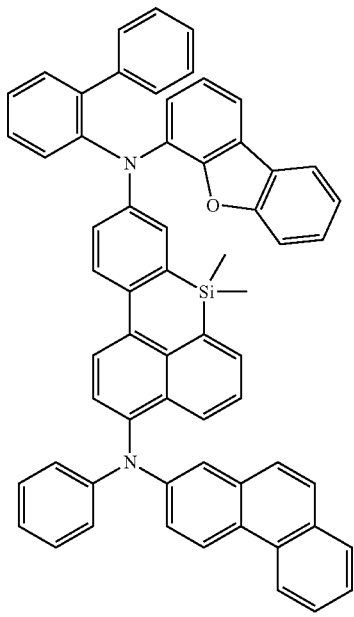
336
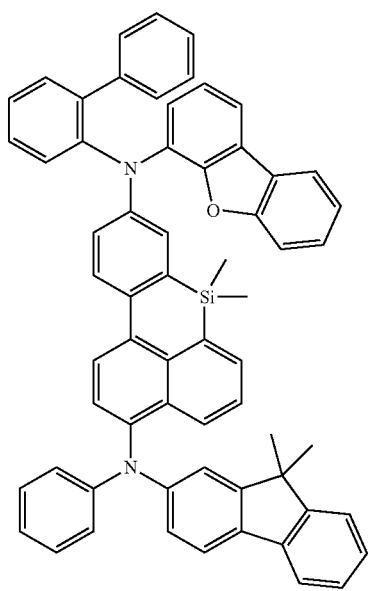

337
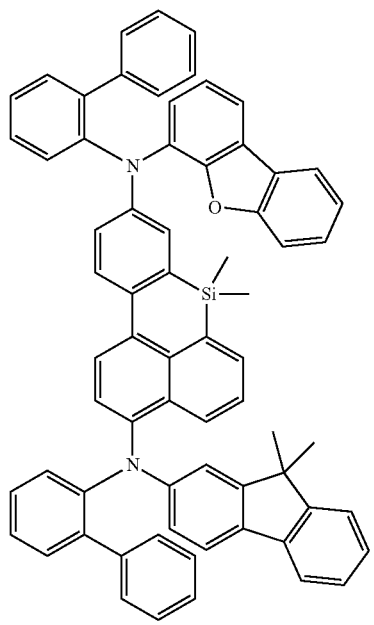
338
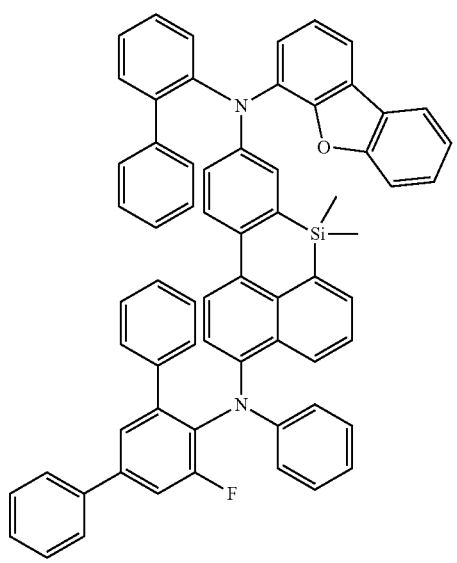
339
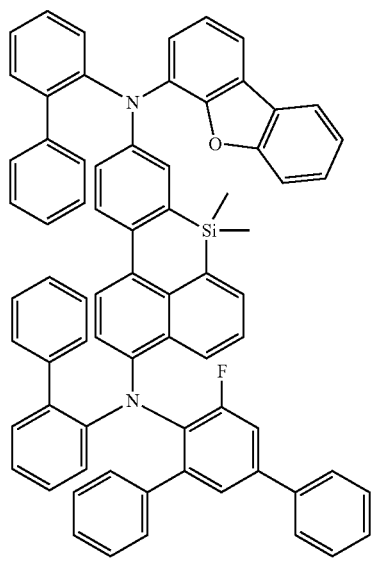
340
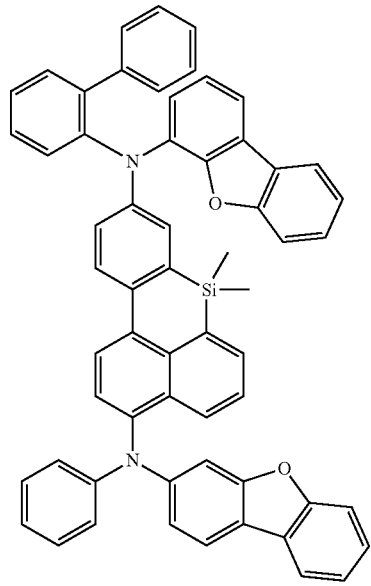

563
-continued
341
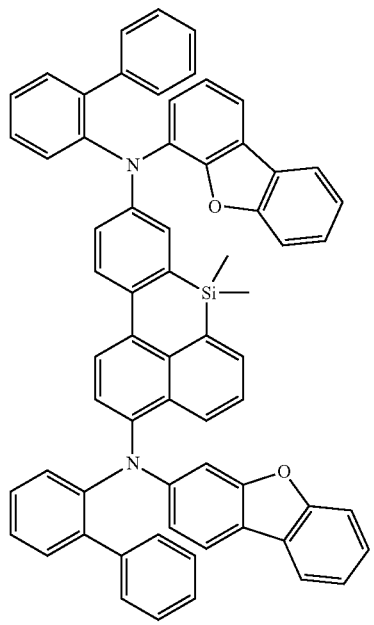
342
564
-continued
344
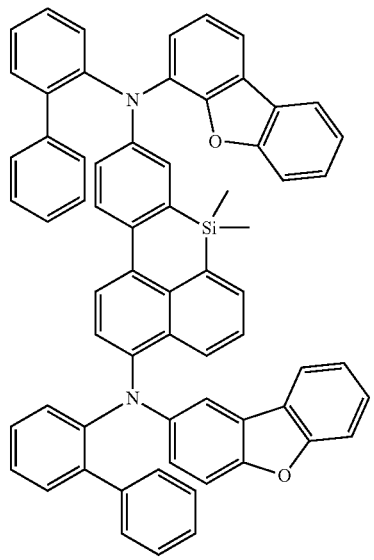
345
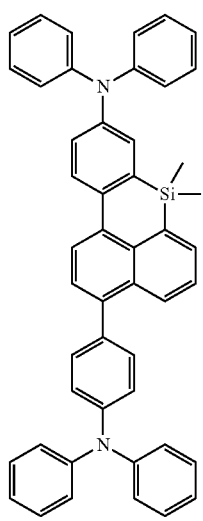
343

565
-continued
346
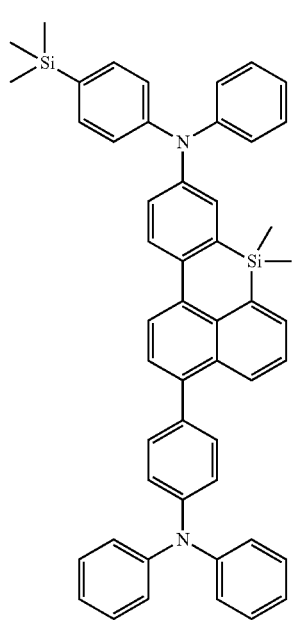
347
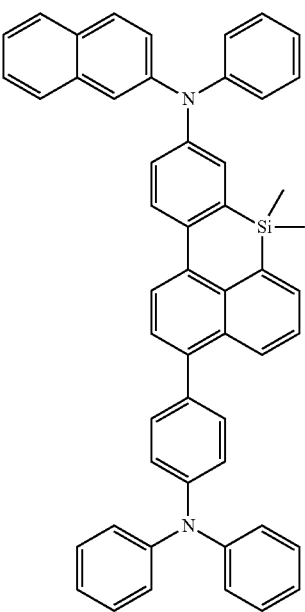
566
-continued
348
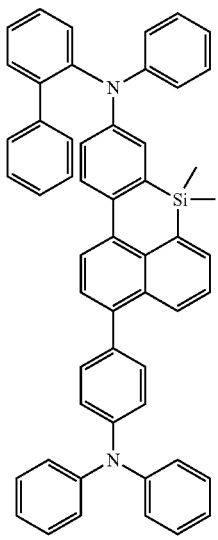
349
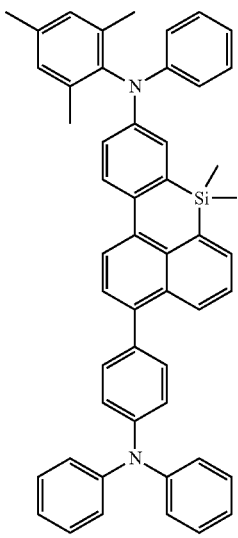

567
-continued
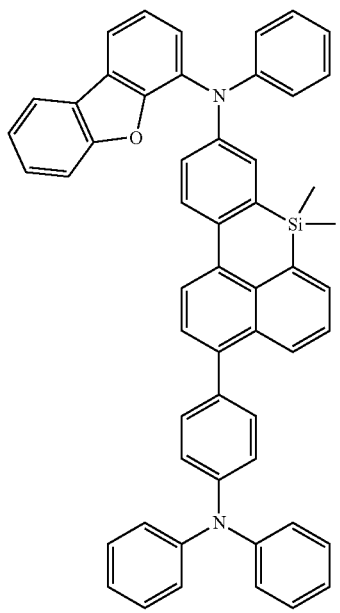
350
568
-continued
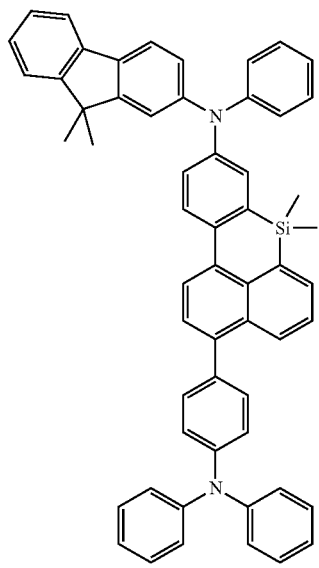
352
351
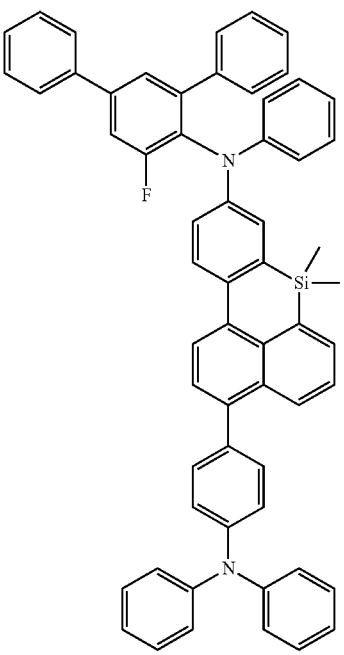
353

569
-continued
354
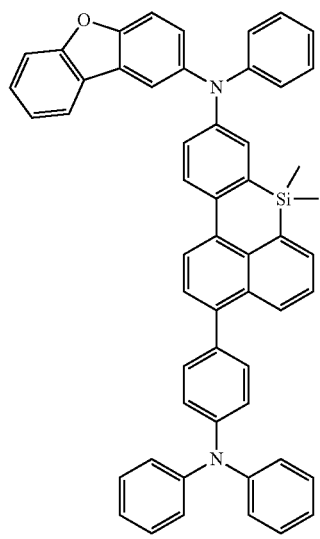
355
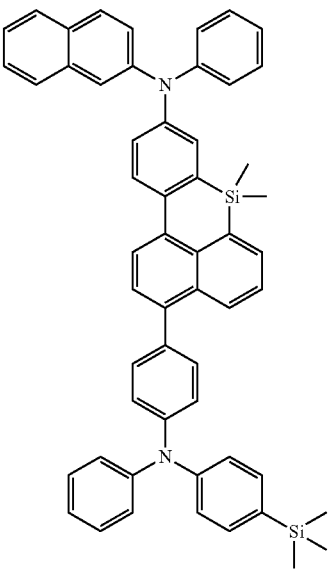
570
-continued
356
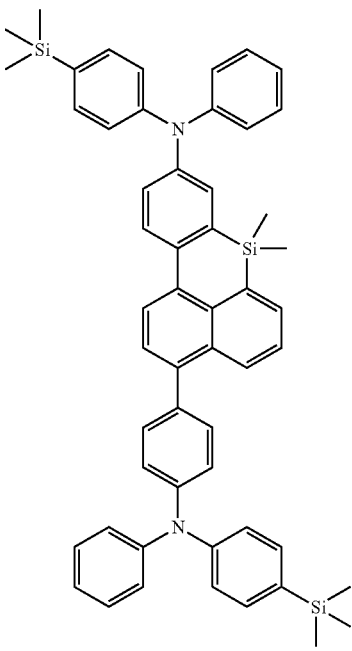
357

571
-continued
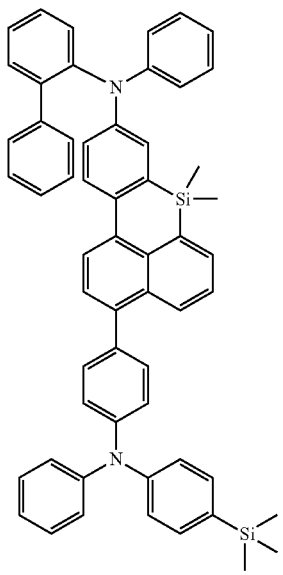
358
572
-continued
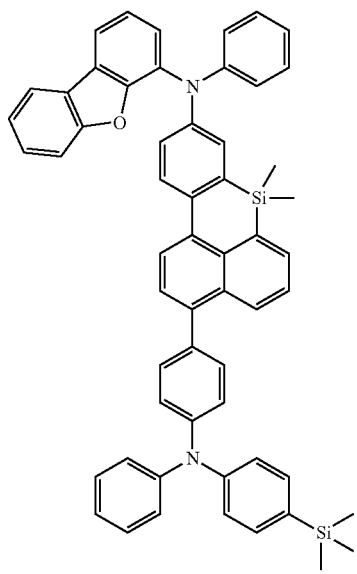
360
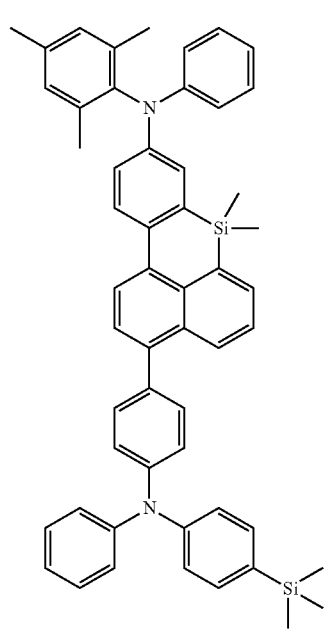
359
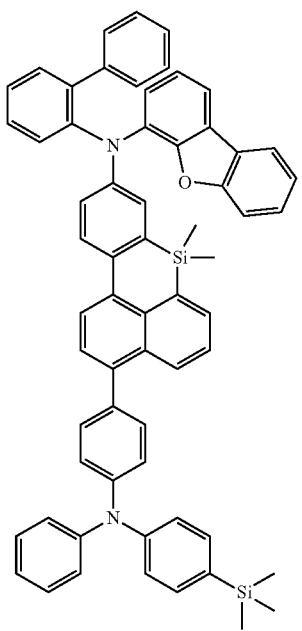
361

573
-continued
362
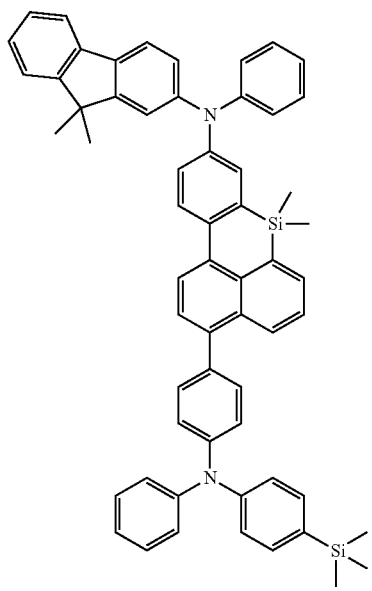
363
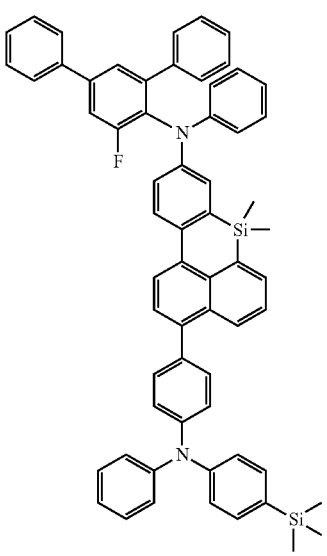
574
-continued
364
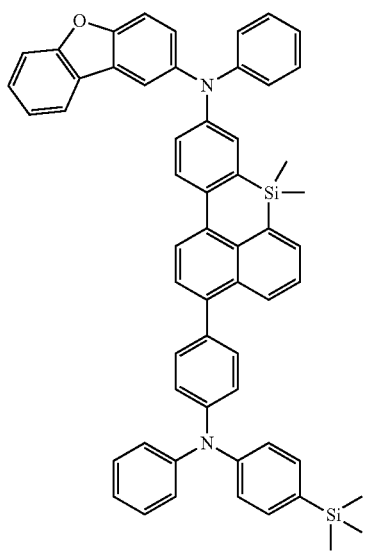
365
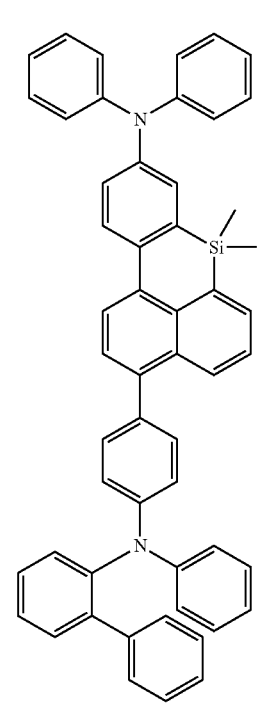

575
-continued
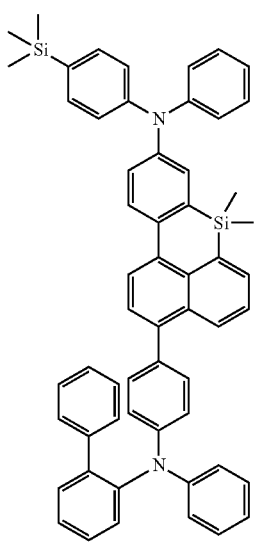
366
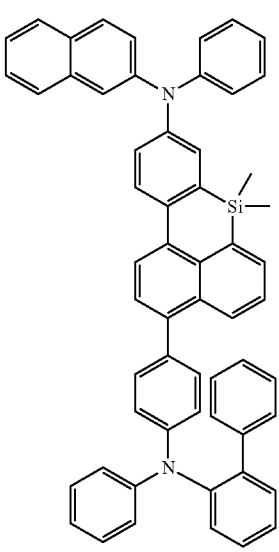
367
576
-continued
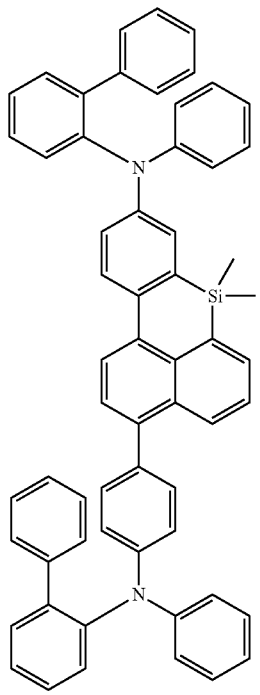
368
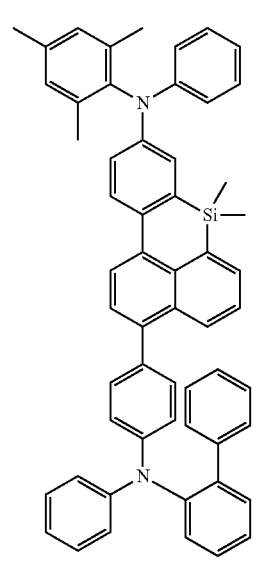
369

577
-continued
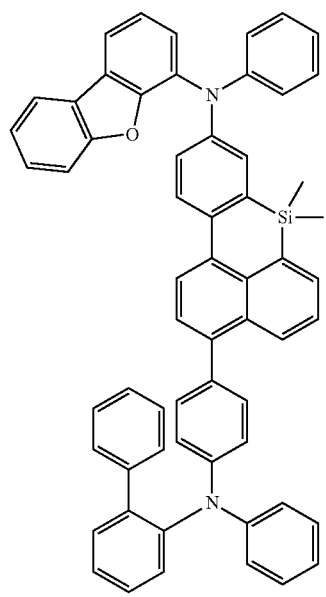
370
578
-continued
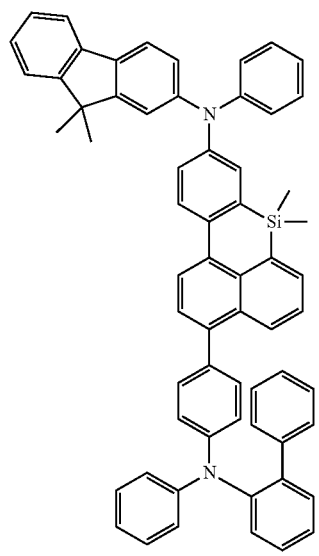
372
371
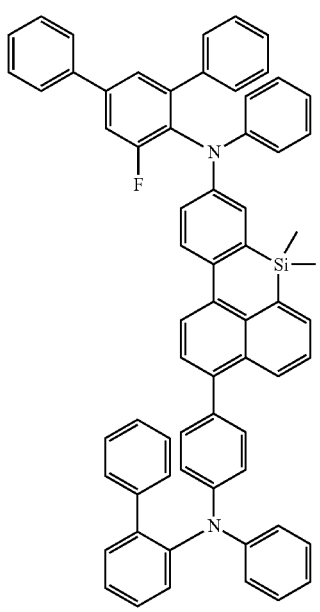
373

579
-continued
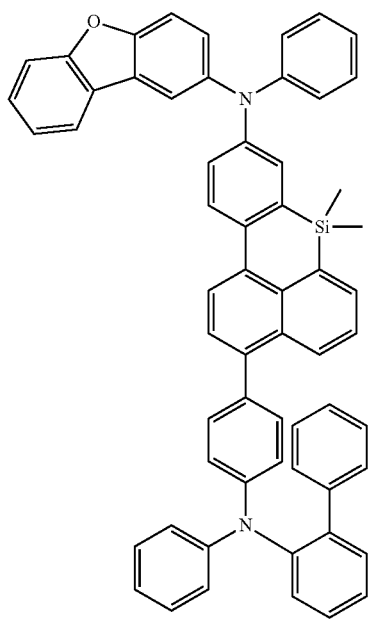
374
580
-continued
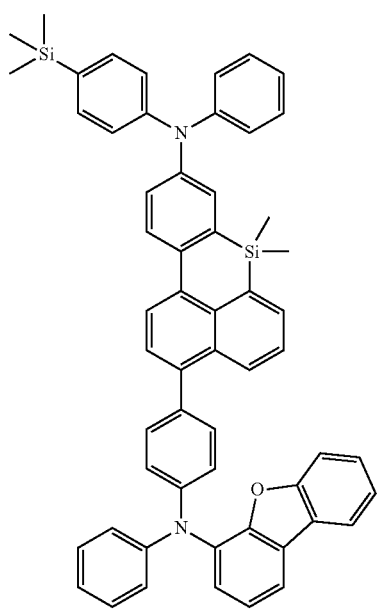
376
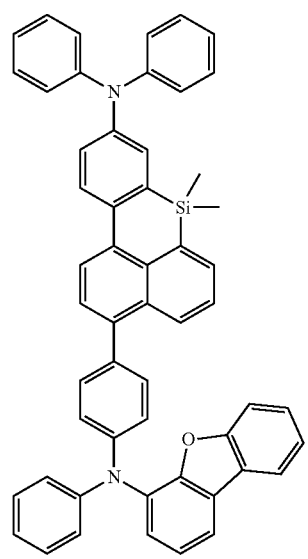
375
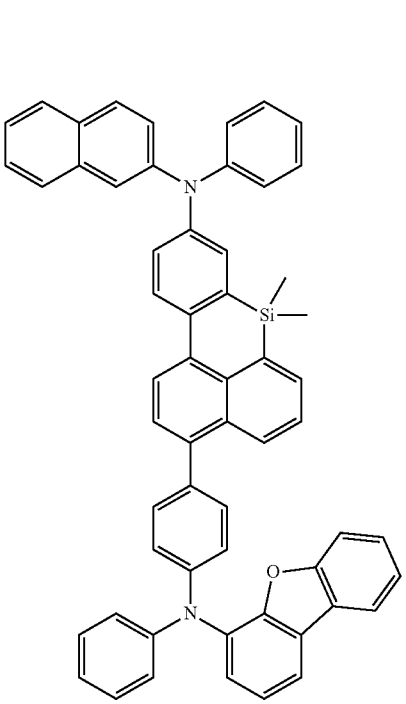
377

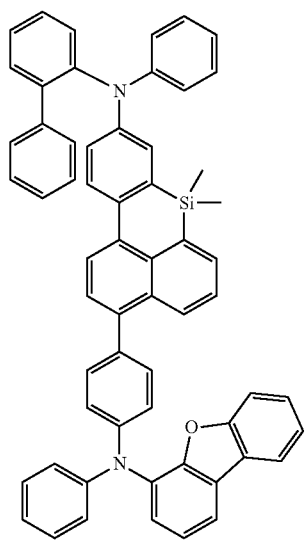
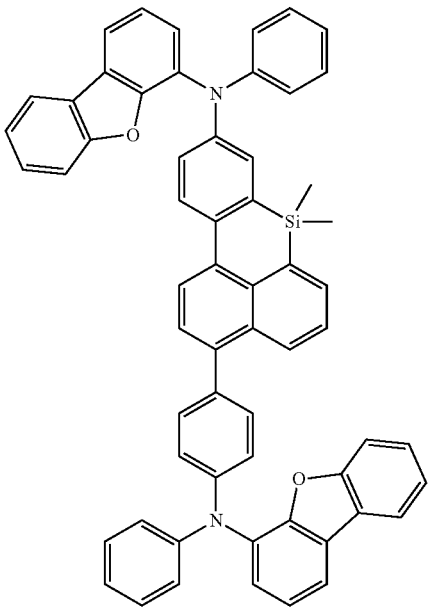
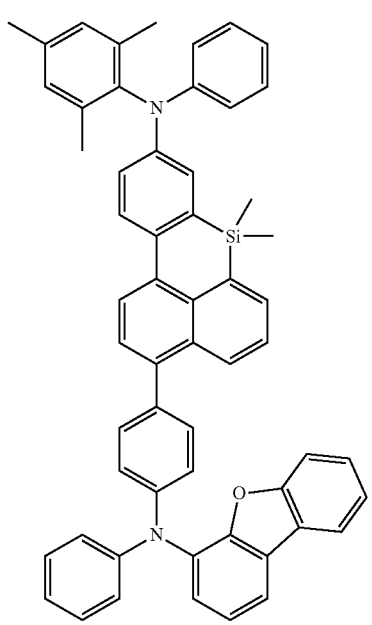
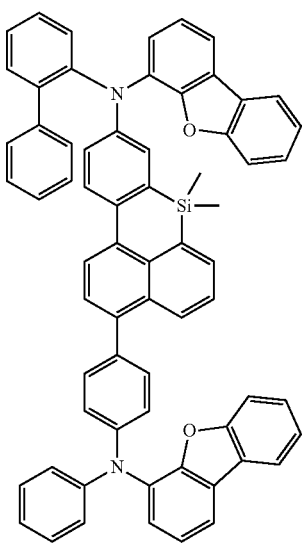

583
-continued
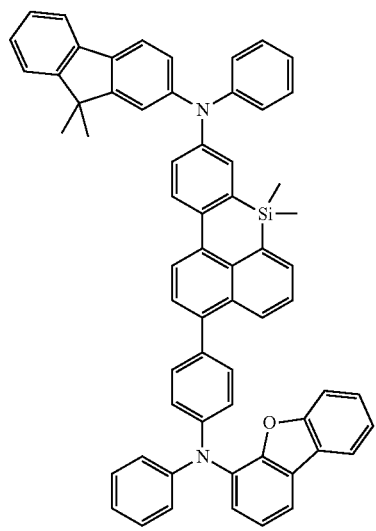
382
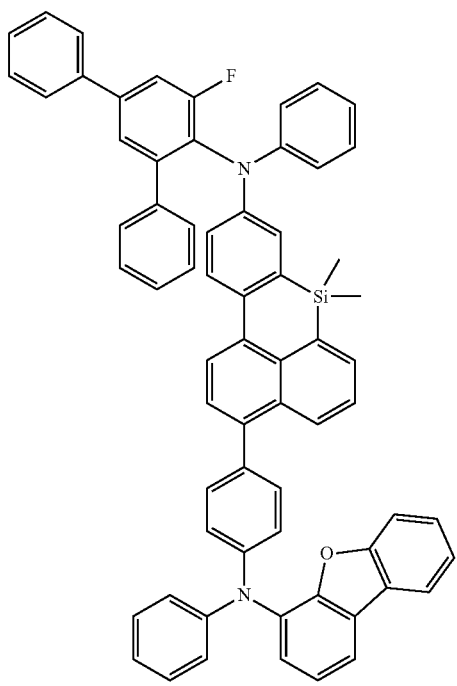
383
584
-continued
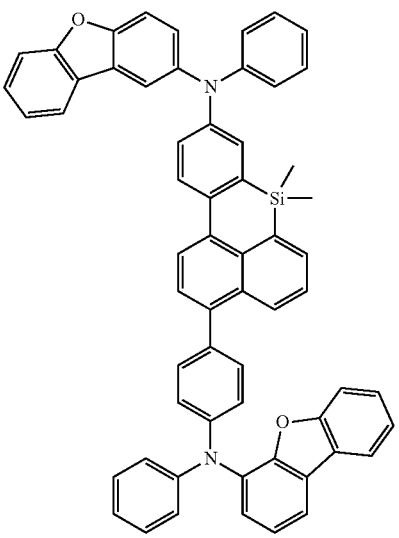
384
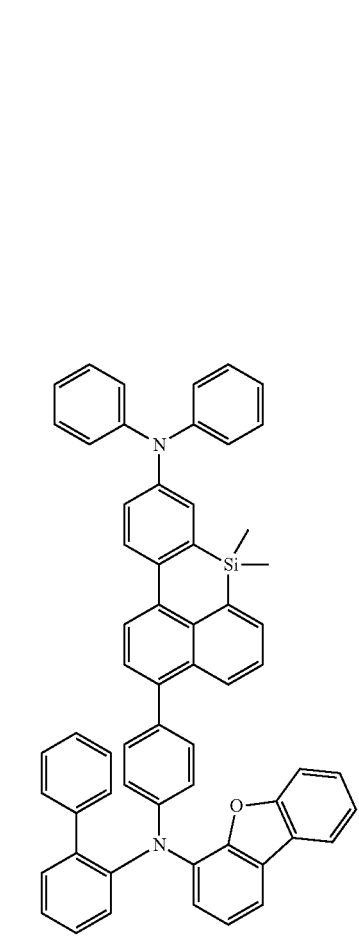
385

585
-continued
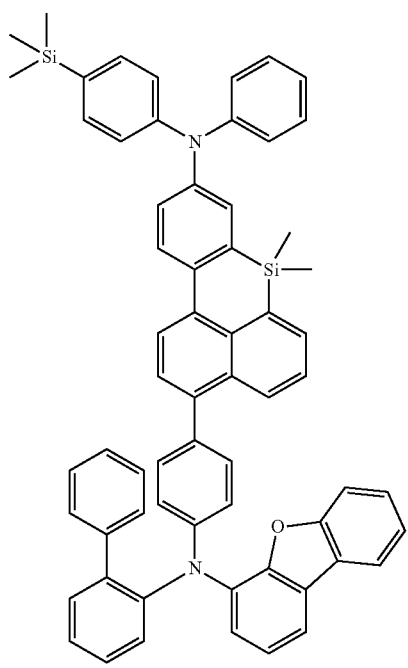
386
586
-continued
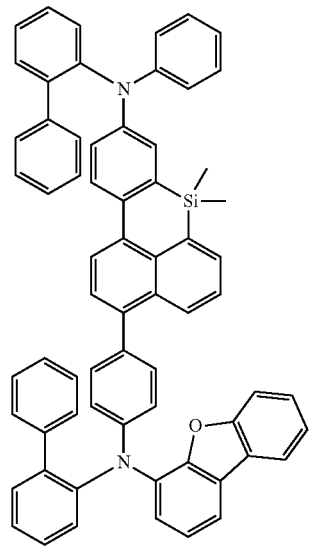
388
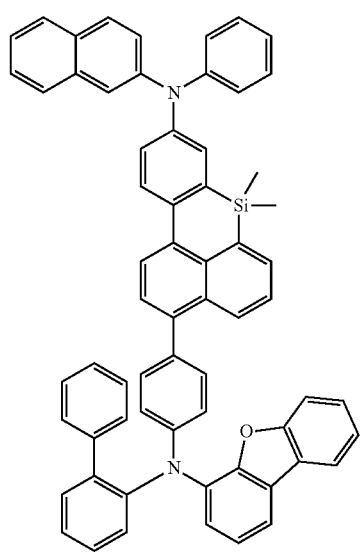
387
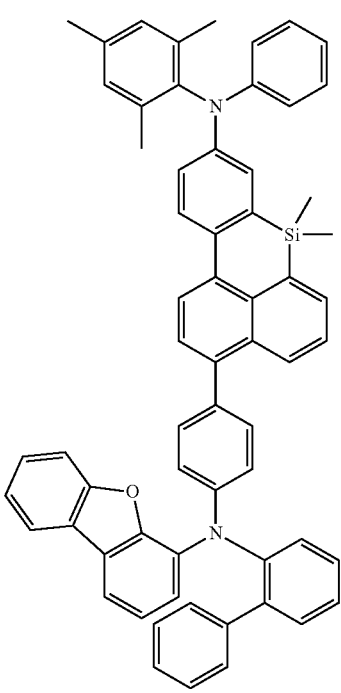
389

587
-continued
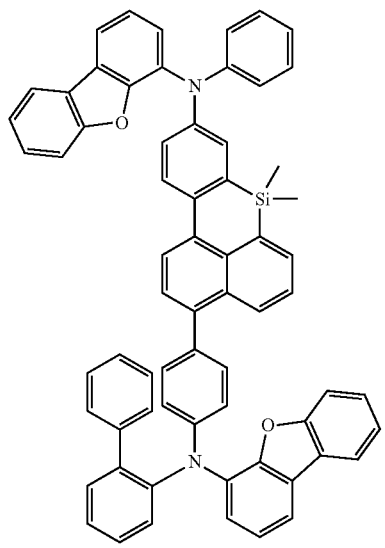
390
588
-continued
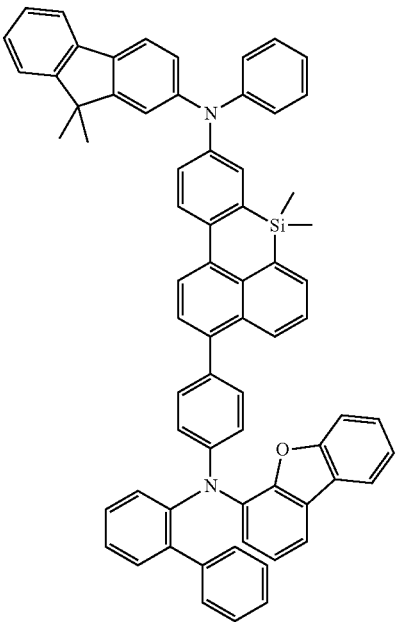
392
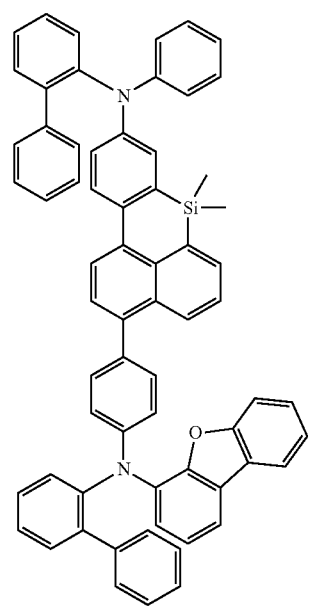
391
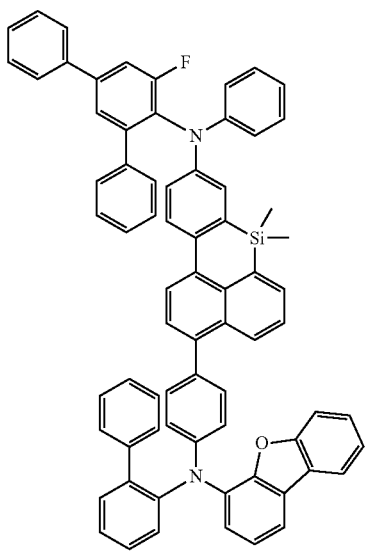
393

589
-continued
394
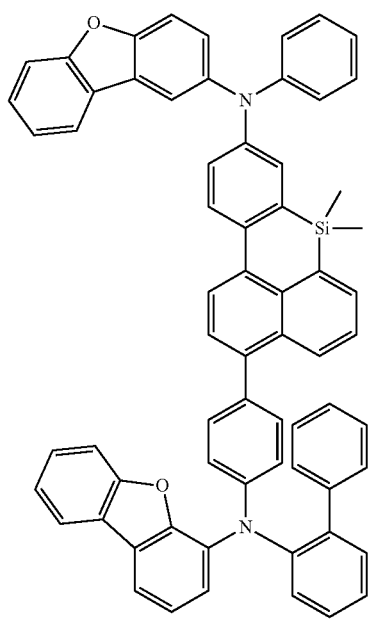
395
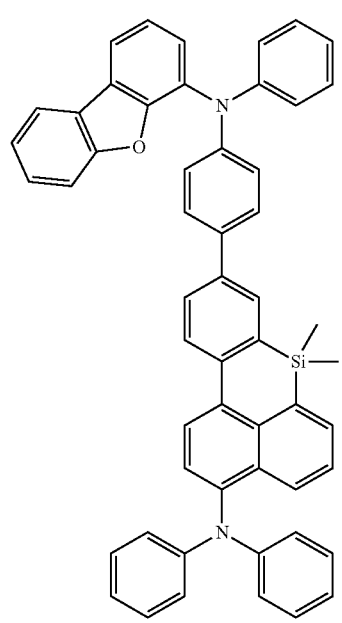
590
-continued
396
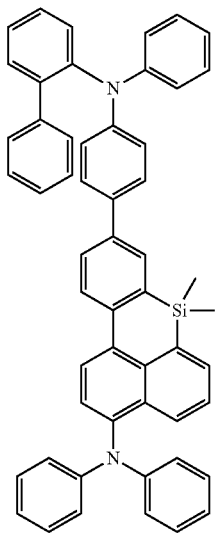
397
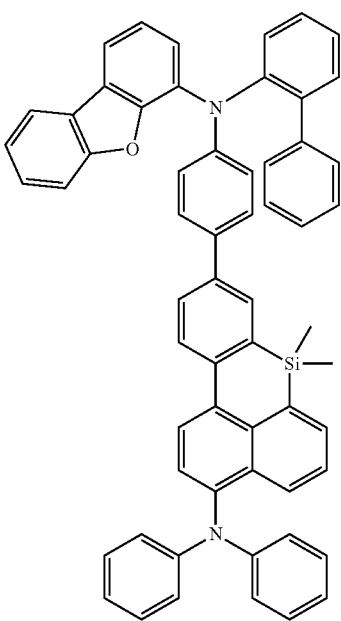

591
-continued
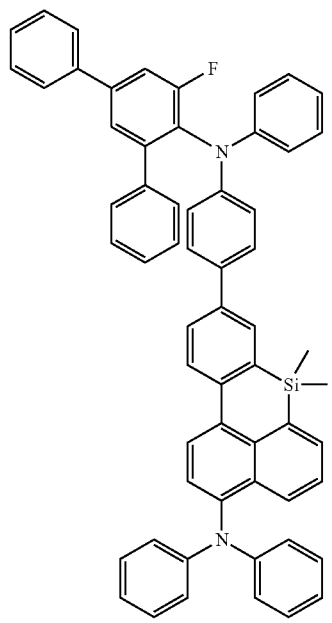
398
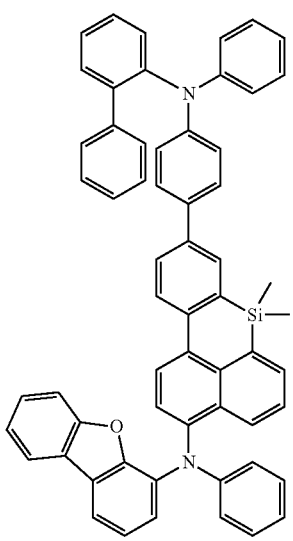
399
592
-continued
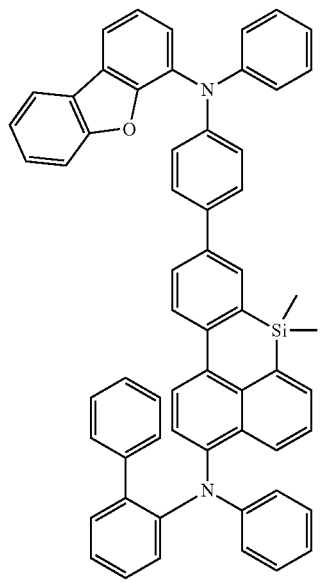
400
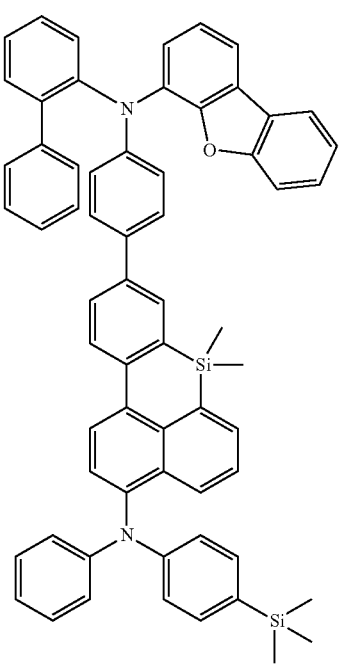
401

593
-continued
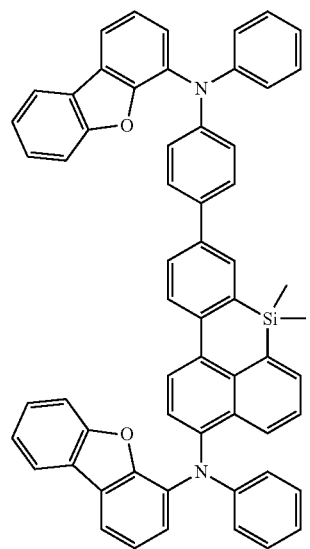
402
594
-continued
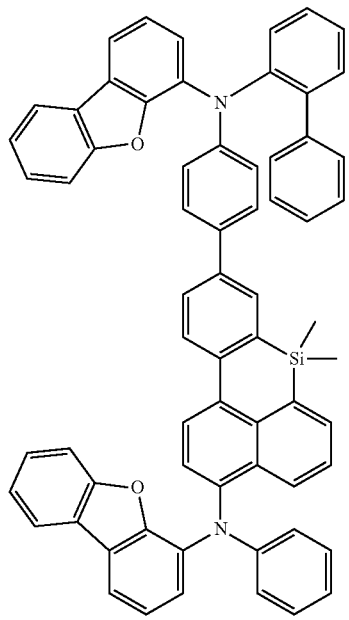
404
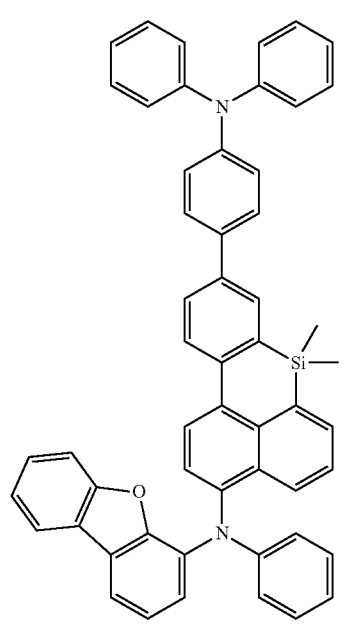
403
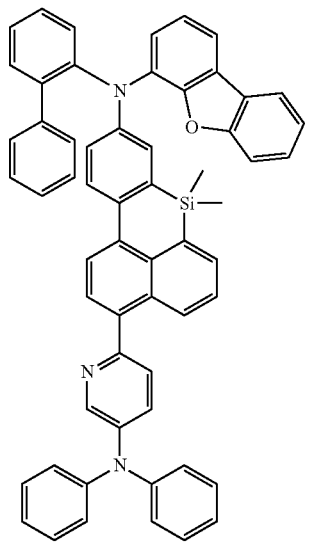
405

595
-continued
406
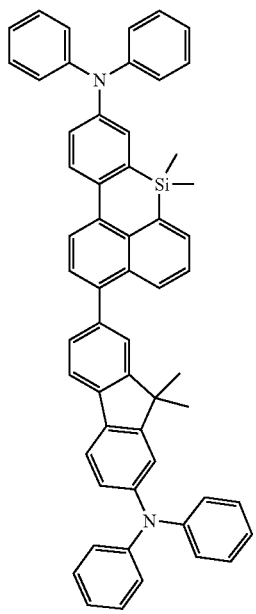
407
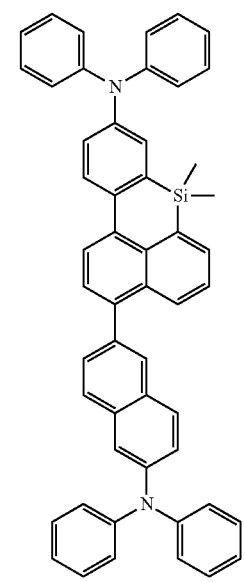
408
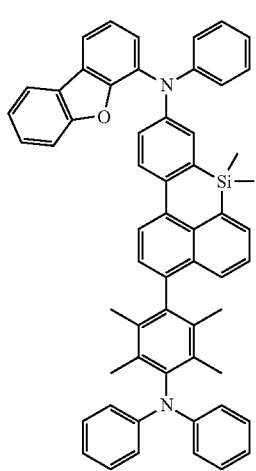
596
-continued
409
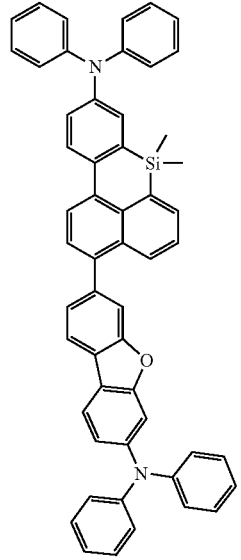
410
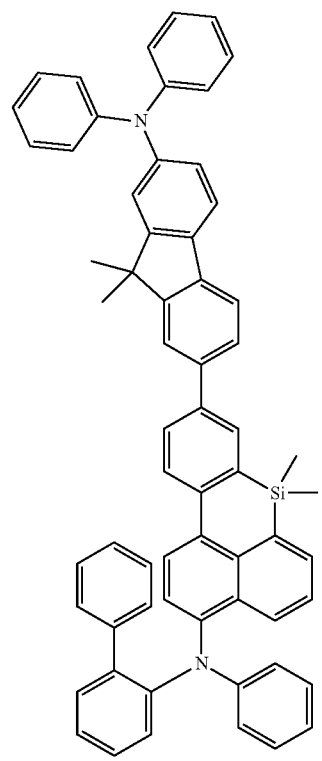

597
-continued
411
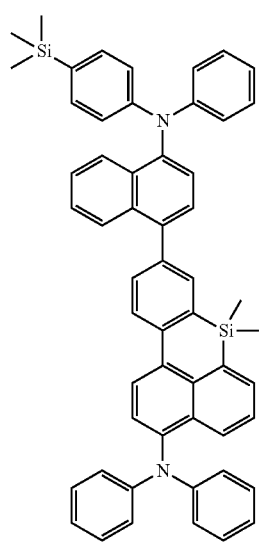
412
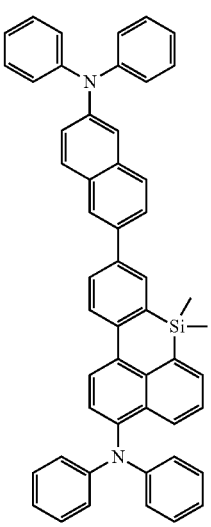
598
-continued
413
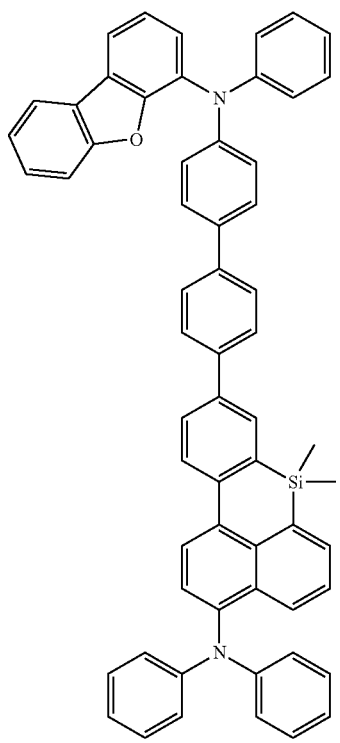
414
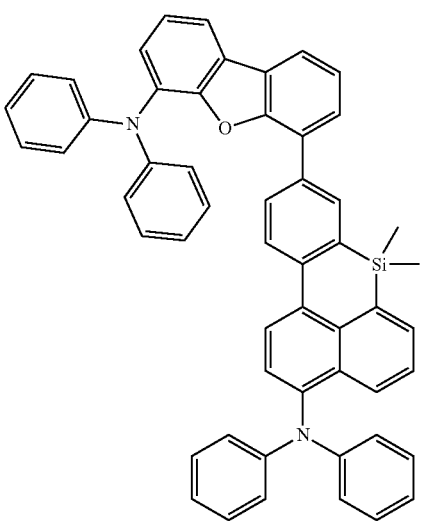

599
-continued
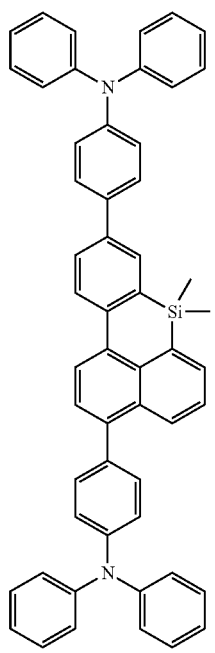
415
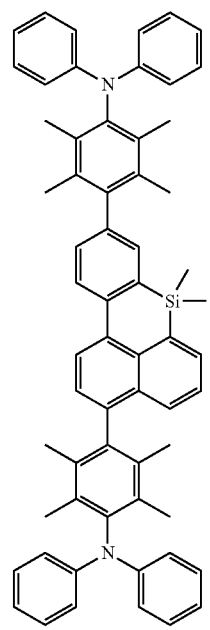
416
600
-continued
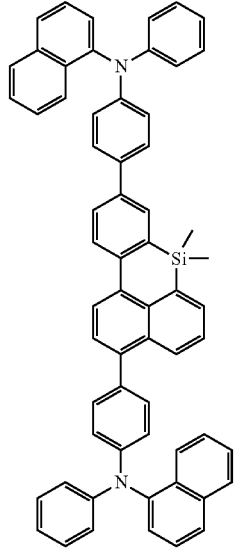
417
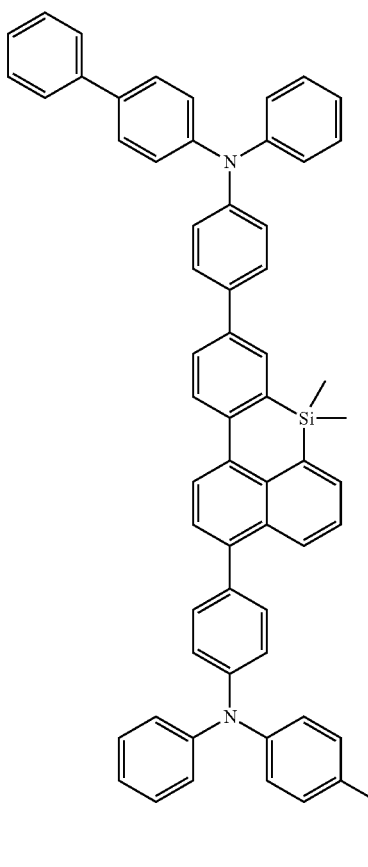
418

601
-continued
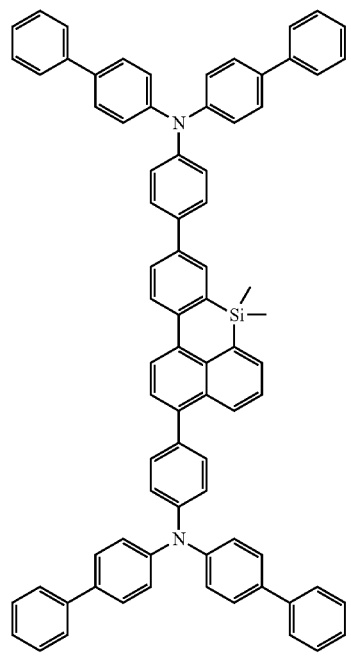
419
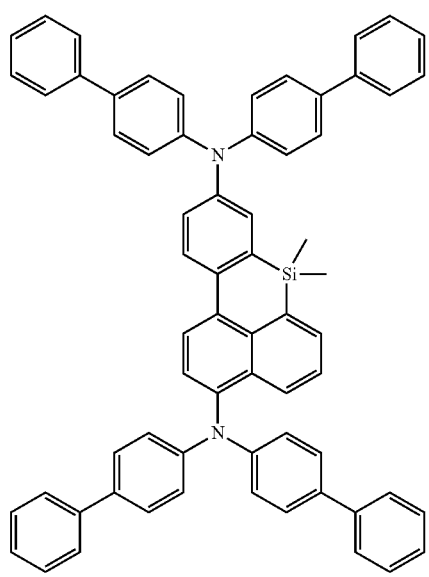
420
602
-continued
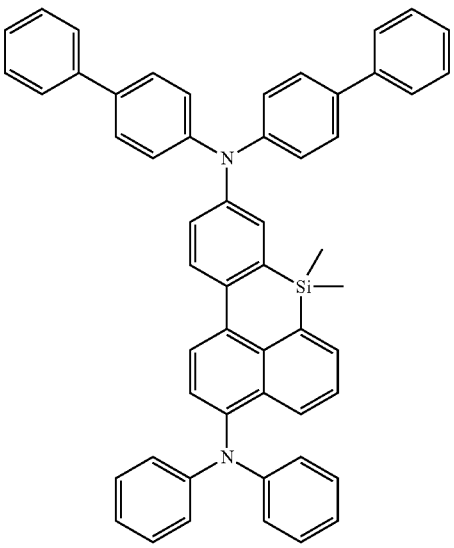
421
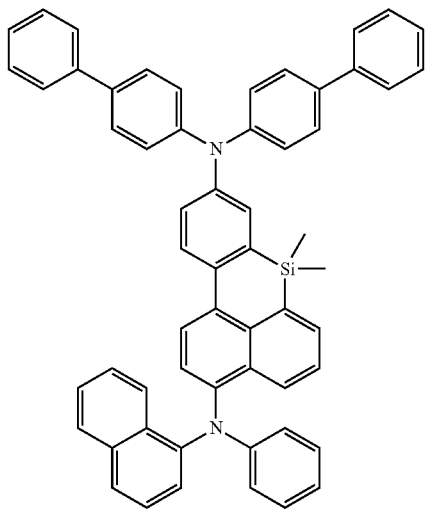
422

603
-continued
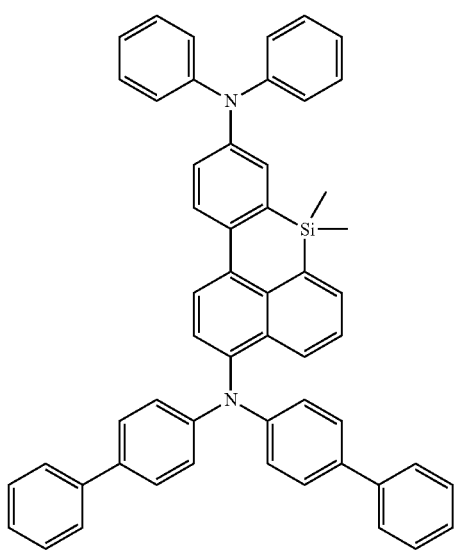
423
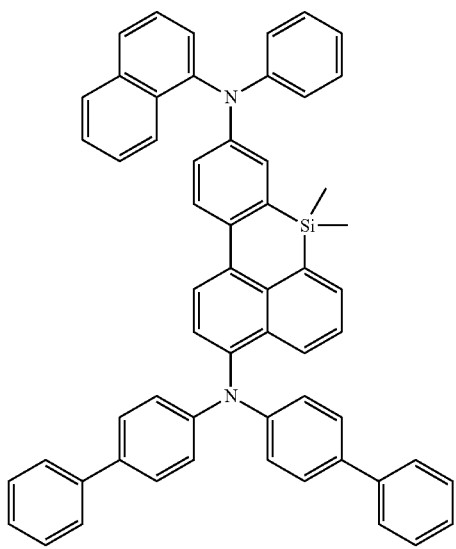
424
604
-continued
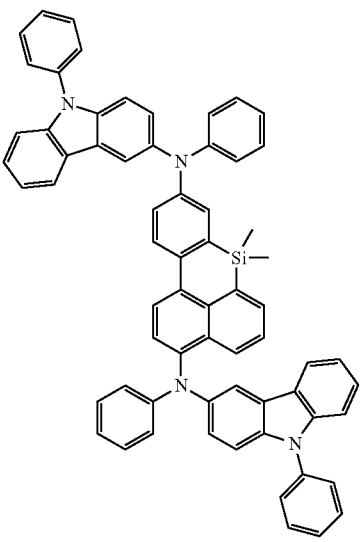
425
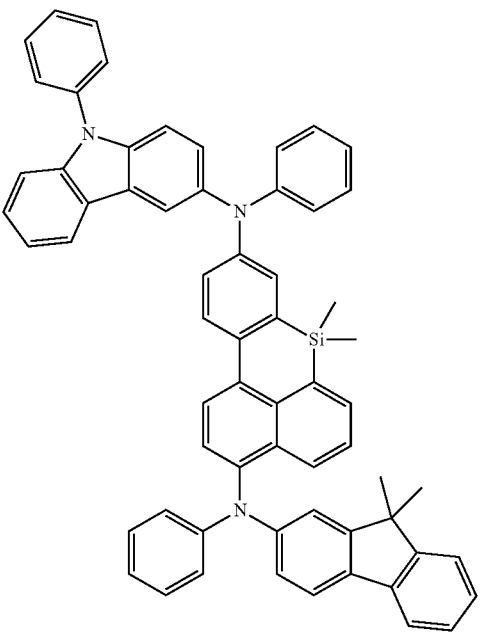
426

605
-continued
427
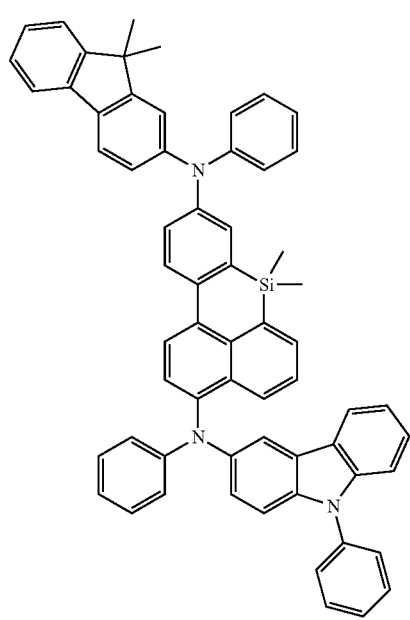
606
-continued
429
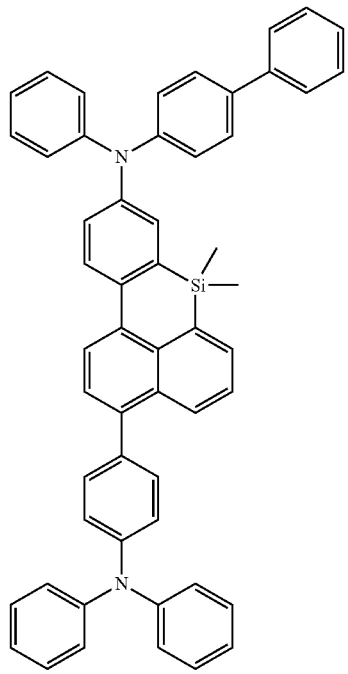
428
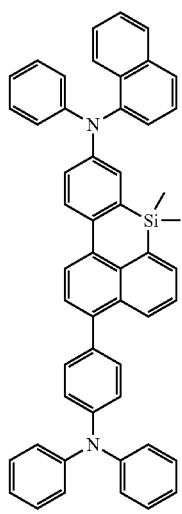
430
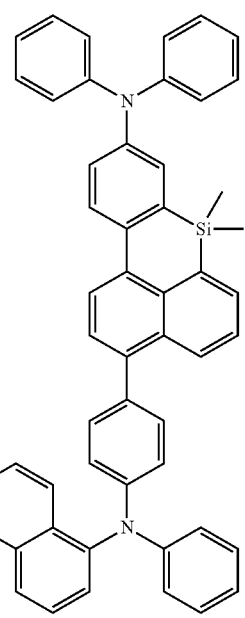

607
-continued
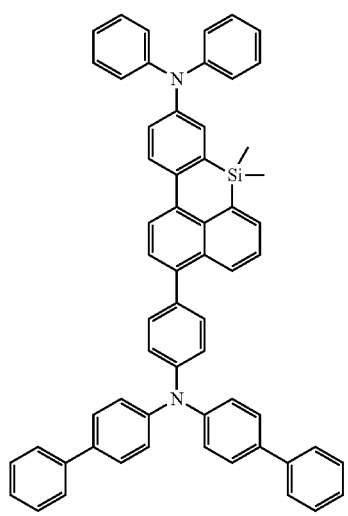
431
608
-continued
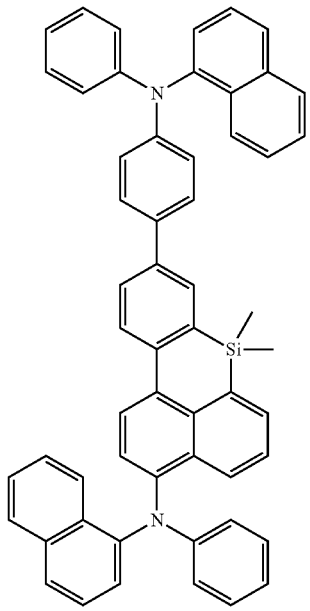
433
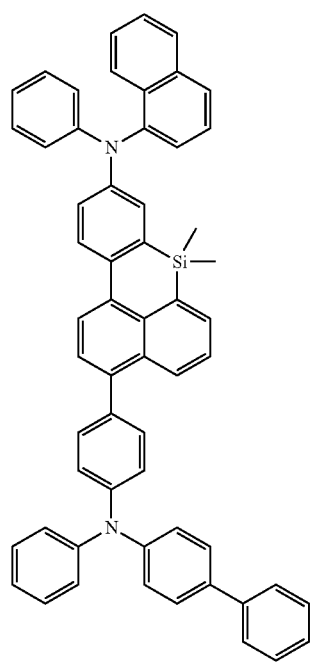
432
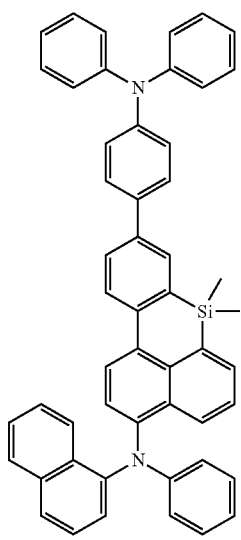
434

435

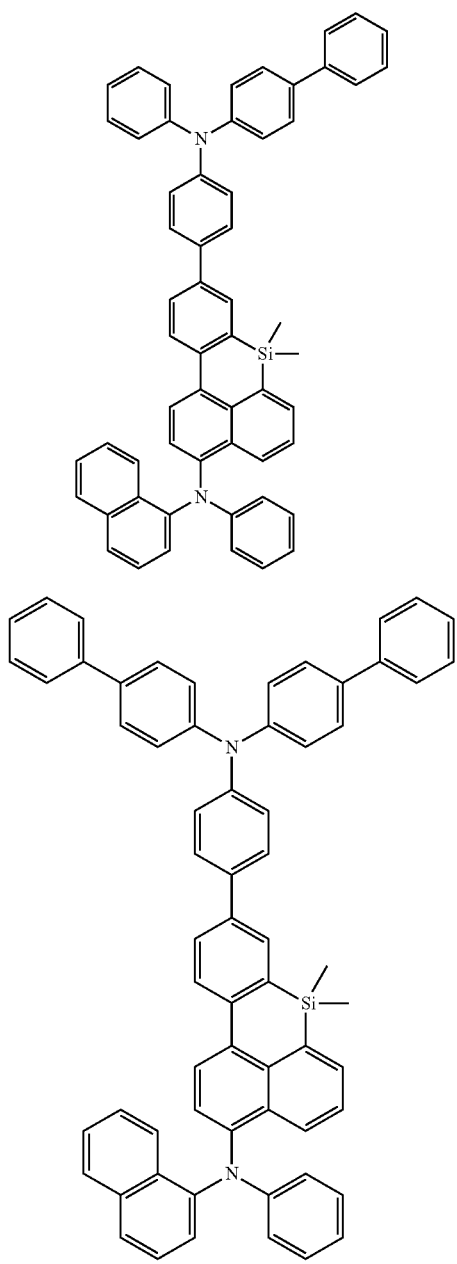

436

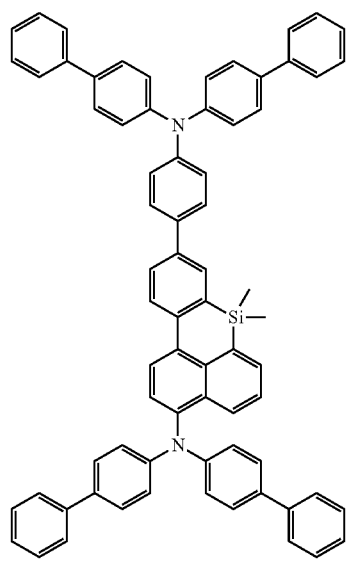

437

18. An organic light-emitting device comprising:

a first electrode;

a second electrode facing the first electrode; and an organic layer between the first electrode and the second electrode, the organic layer comprising an emission layer, wherein the organic layer comprises the amine-based compound of claim 1.

19. The organic light-emitting device of claim 18, wherein the emission layer comprises the amine-based compound, and further comprises a host, wherein the amine-based compound is a dopant.

20. The organic light-emitting device of claim 18, wherein the organic layer comprises a hole transport region between the first electrode and the emission layer, wherein the hole transport region comprises a hole transport layer, and the hole transport layer comprises the amine-based compound.

* * * * *